US008945571B2

(12) United States Patent
Mössner et al.

(10) Patent No.: US 8,945,571 B2
(45) Date of Patent: Feb. 3, 2015

(54) TARGETED IMMUNOCONJUGATES

(75) Inventors: Ekkehard Mössner, Kreuzlingen (CH); Ralf Jörg Hosse, Bonstetten (CH); Pablo Umaña, Wädenswil (CH); Michela Silacci-Melkko, Zürich (CH)

(73) Assignee: Roche GlycArt AG (CH)

( * ) Notice: Subject to any disclaimer, the term of this patent is extended or adjusted under 35 U.S.C. 154(b) by 572 days.

(21) Appl. No.: 12/857,882

(22) Filed: Aug. 17, 2010

(65) Prior Publication Data

US 2011/0064751 A1 Mar. 17, 2011

Related U.S. Application Data

(60) Provisional application No. 61/234,584, filed on Aug. 17, 2009.

(30) Foreign Application Priority Data

May 10, 2010 (EP) .................................... 10162410

(51) Int. Cl.

| | |
|---|---|
| ***A61K 39/395*** | (2006.01) |
| ***C12N 15/00*** | (2006.01) |
| ***C12N 5/10*** | (2006.01) |
| ***C12P 21/08*** | (2006.01) |
| ***C07K 16/46*** | (2006.01) |
| ***C07H 21/04*** | (2006.01) |
| ***C07K 16/00*** | (2006.01) |
| ***A61K 47/48*** | (2006.01) |
| ***C07K 16/18*** | (2006.01) |
| ***C07K 16/40*** | (2006.01) |
| *A61K 39/00* | (2006.01) |

(52) U.S. Cl.

CPC ........... *C07K 16/00* (2013.01); *A61K 47/48423* (2013.01); *A61K 47/48538* (2013.01); *A61K 47/48646* (2013.01); *C07K 16/18* (2013.01); *C07K 16/40* (2013.01); *C07K 16/468* (2013.01); *A61K 2039/505* (2013.01); *C07K 2317/73* (2013.01); *C07K 2317/74* (2013.01); *C07K 2317/92* (2013.01)

USPC .................... 424/179.1; 435/69.6; 435/320.1; 435/325; 530/391.7; 536/23.4; 536/23.53

(58) Field of Classification Search

None

See application file for complete search history.

(56) References Cited

U.S. PATENT DOCUMENTS

| | | | | |
|---|---|---|---|---|
| 5,650,150 | A | 7/1997 | Gillies | |
| 6,632,927 | B2 | 10/2003 | Adair et al. | |
| 2002/0146750 | A1 * | 10/2002 | Hoogenboom et al. | 435/7.23 |
| 2003/0040606 | A1 | 2/2003 | Leung | |
| 2003/0175269 | A1 | 9/2003 | Black et al. | |
| 2004/0132066 | A1 | 7/2004 | Balint et al. | |
| 2006/0223096 | A1 * | 10/2006 | Umana et al. | 435/6 |
| 2009/0304580 | A1 * | 12/2009 | Goldenberg et al. | 424/1.49 |

FOREIGN PATENT DOCUMENTS

| | | | |
|---|---|---|---|
| WO | WO 93/06213 | A1 | 4/1993 |
| WO | WO 98/39363 | A2 | 9/1998 |
| WO | WO 99/29732 | A2 | 6/1999 |
| WO | WO 01/62298 | A2 | 8/2001 |
| WO | WO 2006/119897 | A2 | 11/2001 |
| WO | WO02/02143 | * | 1/2002 |
| WO | WO 2007/128563 | A1 | 11/2007 |
| WO | WO 2009/017823 | A2 | 2/2009 |
| WO | WO2009/008998 | * | 7/2009 |
| WO | WO 2010/059315 | | 5/2010 |

OTHER PUBLICATIONS

Gafner et al (International Journal of Cancer, vol. 119, pp. 2205-2212).*

Ebbinghaus et al (Current Pharmaceutical Design, 2004, vol. 10, pp. 1537-1549).*

Borsi et al (International Journal of Cancer, 2002, vol. 102, pp. 75-85).*

Cheng et al (Clinical Cancer Research, 2003, vol. 9, pp. 2590-1595).*

Becker, J., et al., "An antibody-interleukin 2 fusion protein overcomes tumor.heterogeneity by induction of a cellular immune response," *Proc. Natl. Acad. Sci. USA 93*:7826-7831, National Academy of Sciences, United States (1996).

Brack, S., et al., "Tumor-targeting properties of novel antibodies specific to the large isoform of tenascin-C," *Clin. Cancer Res.* 12:3200-3208, American Association for Cancer Research, United States (2006).

Brutlag, D., et al., "Improved sensitivity of biological sequence database searches," *Comput. Appl. Biosci.* 6:237-245, Oxford University Press, United Kingdom (1990).

Carter, P., et al., "Humanization of an anti-p185HER2 antibody for human cancer therapy," *Proc. Natl. Acad. Sci. USA 89*:4285-4289, National Academy of Sciences, United States (1992).

Chothia, C. and A. Lesk, "Canonical structures for the hypervarable regions of immunoglobins," *J. Mol. Biol.* 196:901-917, Academic Press, United States (1987).

Clackson, T., et al., "Making antibody fragments using phage library displays," *Nature 352*:624-628, Nature Publishing Group, United Kingdom (1991).

Griffith, G. and S. Isaaz, "Granzymes A and B are targeted to the lytic granules of lymphocytes by the mannose-6-phosphate receptor," *J. Cell. Bio.* 120:885-896, Rockefellar University Press, United States (1993).

(Continued)

*Primary Examiner* — Karen Canella

(74) *Attorney, Agent, or Firm* — Sterne, Kessler, Goldstein & Fox P.L.L.C.

(57) ABSTRACT

The present invention relates to immunoconjugates. In particular embodiments, the present invention relates to immunoconjugates comprising at least one single-chain effector moiety and two or more antigen binding moieties. In addition, the present invention relates to nucleic acid molecules encoding such immunoconjugates, vectors and host cells comprising such nucleic acid molecules. The invention further relates to methods for producing the immunoconjugates of the invention, and to methods of using these immunoconjugates in the treatment of disease.

24 Claims, 84 Drawing Sheets

(56) References Cited

OTHER PUBLICATIONS

Harvill, E. and S. Morrison, "An IgG3-IL2 fusion protein activates complement, binds Fc gamma RI, generates LAK activity and shows enhanced binding to high affinity IL-2R," *Immunotechnol.* 1:95-105, Elsevier, Netherlands (1995).
Heeley, R., et al., "Mutations flanking the polyglutamine repeat in the mandatory domain of rat glucocorticoid receptor lead to an increase in affinity for hormone," *Endocr. Res.* 28:217-229, Informa Healthcare, United Kingdom (2002).
Hoogenboom, H., et al., "Multi-subunit proteins on the surface of filamentous phage: methodologies for displaying antibody (Fab) heavy and light chains," *Nucleic Acids Res.* 19:4133-4137, Oxford University Press, United Kingdom (1991).
Hudson, P. and C. Souriau, "Engineered antibodies," *Nat. Med.* 9:129-134, Nature Publishing, United Kingdom (2003).
Jakobovits, A., et al., "Germ-line transmission and expression of a human-derived yeast artificial chromosome," *Nature 362*:255-258, Nature Publishing Group, United Kingdom (1993).
Jun, L., et al., "Chemical conjugation of a novel antibody-interleukin 2 immunoconjugate against c-erbB-2 product," *Chin. Med. J. 113*:151-153, Chinese Medical Association and Pergamon Press, China (2000).
Kabat, E., et al. (eds), Sequences of Proteins of Immunological Interest 80-2008, National Institutions of Health, Bethesda, United States (1983).
Kozbor, D., et al., "A human hybrid myeloma for production of human monoclonal antibodies," *J Immunol.* 133:3001-3005, The American Association of Immunologists, Inc., United States (1984).
Liljeblad, M., et al., "Analysis of agalactor-IgG in rheumatoid arthritis using surface plasmon resonance," *Glyco. J.* 17:323-329, Springer, Germany (2000).
Marks, J., et al., "By-Passing Immunization: Building High Affinity Human Antibodies by Chain Shuffling," *Nature Biotech.* 10:779-783, Nature Publishing Group, United Kingdom (1992).
Marks, J., et al., "By-passing immunization: Human antibodies from V-gene libraries displayed on phage," *J. Mol. Bio.* 222:581-597, Elsevier B.V., United Kingdom (1991).
McCafferty, J., et al., "Phage antibodies: filamentous phage displaying antibody variable domains," *Nature 348*:552-554, Nature Publishing Group, United Kingdom (1990).
Merchant, A., et al., "An efficient route to human bispecific IgG," *Nature Biotech.* 16:677-681, Nature Publishing Group, United Kingdom (1998).
Morrison, S. and V. Oi, "Genetically Engineered Antibody Molecules," *Adv. Immunol.* 44:65-92, Academic Press Inc., United Kingdom (1988).
Morrison, S., et al., "Chimeric human antibody molecules: Mouse antigen-binding domains with human constant region domains," *Proc. Natl. Acad. Sci.* 81:6851-6855, National Academy of Sciences, United States (1984).
Nakamura K. and A. Kubo, "Biodistribution of iodine-125 labeled monoclonal antibody/Interleukin-2 immunoconjugate in athymic mice bearing human tumor xenografts," *Cancer 80*:2650-2655, American Cancer Society, United States (1997).
Padlan, E., "A possible procedure for reducting the immunogenicity of antibody variable domains while preserving their ligand-binding properties," *Mol. Immunol.* 28:489-498, Pergamon Press, United Kingdom (1991).
Padlan, E., "Anatomy of the antibody molecule," *Mol. Immunol.* 31:169-217, Pergamon Press, United Kingdom (1994).
Presta, L., et al., "Humanization of an antibody directed against IgE," *J. Immunol.* 151:2623-2632, The American Association of Immunologists, United States (1993).
Savage, P. et al., "A recombinant single chain antibody interleukin-2 fusion protein," *Br. J. Cancer 67*:304-310, Nature Publishing Group, United Kingdom (1993).
Sims, M., et al., "A humanized CD18 antibody can block function without cell destruction," *J. Immunol.* 151:2296-2308, The American Association of Immunologists, United States (1993).
Verhoeyen, M., et al., "Reshaping human antibodies: grafting antilysozyme activity," *Science 239*:1534-1536, American Association for the Advancement of Science, United States (1988).
Waterhouse, P., et al., "Combinatorial infection and in vivo recombination: a strategy for making large phage antibody repertoires," *Nucl. Acids Res.* 21:2265-2666, Oxford Journals, United Kingdom (1993).
Xiang, J., et al., "Single chain antibody variable region-targeted interleukin-2 stimulates T cell killing of human colorectal carcinoma cells," *Immunol. Cell Biol.* 72:275-285, Nature Publishing Group, United Kingdom (1994).
Xiang, J., "Targeting cytokines to tumors to induce active antitumor immune responses by recombinant fusion proteins," *Hum. Antibodies 9*:23-36, IOS Press, Antibodies (1999).
Yang, J., et al., "A genetically engineered single-chain FV/TNF molecule possesses the anti-tumor immunoreactivity of FV as well as the cytotoxic activity of tumor necrosis factor," *Mol. Immunol.* 32:873-881, Pergamon Press, United Kingdom (1995).
International Search Report cited in PCT Appl. No. PCT/EP2010/06180, dated Mar. 4, 2011, 8 pgs.

* cited by examiner

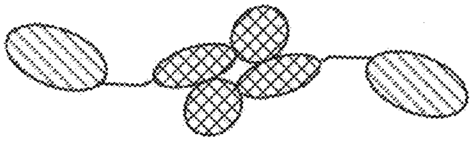
FIG.1A
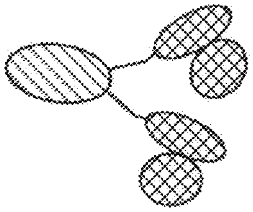
FIG.1D
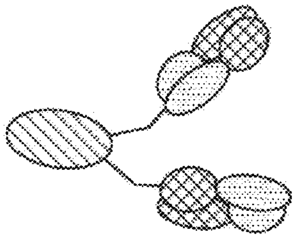
FIG.1B
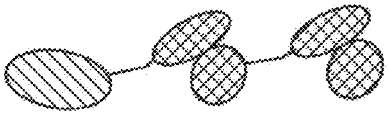
FIG.1E
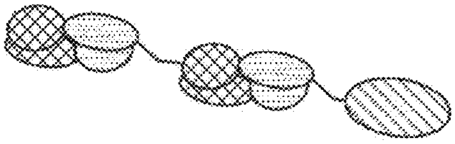
FIG.1C
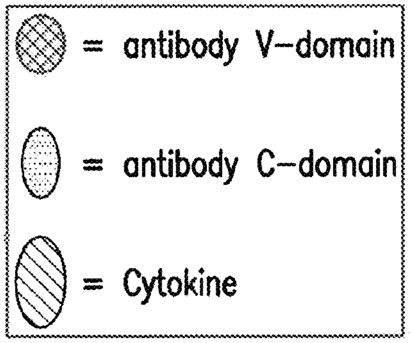

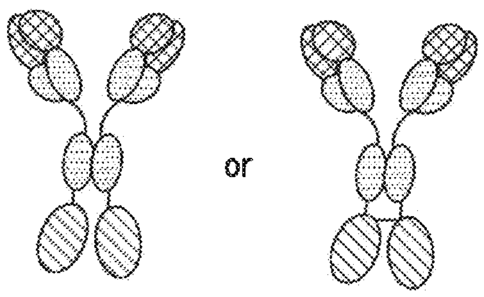
FIG.2A
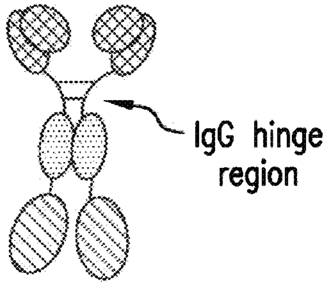
FIG.2D
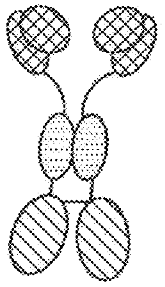
FIG.2B
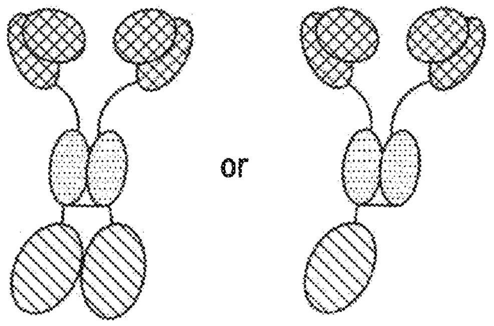
FIG.2E
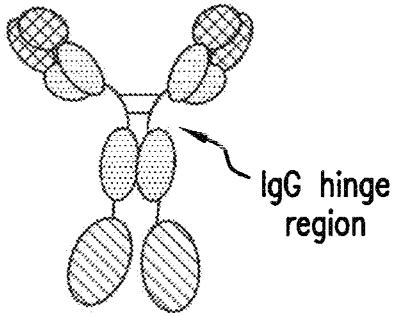
FIG.2C
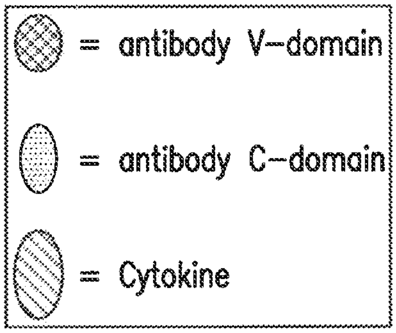

Kinetics parameters:

| | $k_{on}$(1/Ms) | $k_{off}$(1/s) | $K_D$(M) |
|---|---|---|---|
| IL-2 | 7.45E+5 | 3.69E-4 | 4.95E-10 |

Published $K_D$ = ~1nM

Kinetics parameters:

| | $K_D$ apparent (M) |
|---|---|
| TNC A1 | 4.8E-9 |
| IL-2R | 7.4E-9 |

| | $K_D$ apparent (M) |
|---|---|
| TNC A1 | 1.15E−8 |
| IL−2R | 2.5E−9 |

Summary

| Format | Tenascin C domain A1 | IL-2 Receptor |
|---|---|---|
| | $K_D$ apparent (M) | $K_D$ apparent (M) |
| F16 IgG | 2.6E-9 | - |
| F16 Fab | 5.0E-8 | - |
| IL-2 | - | 4.95E-10 |
| F16 dia IL2 | 5E-9 | 8.1E-10 |
| Fab-IL2-Fab | 4.8E-9 | 7.4E-9 |
| scFv-IL2-scFv | 1.15E-8 | 2.5E-9 |

FIG. 17 clone: 19G1, format: Fab, antigen: hu FAP
$k_{on}$: 7.6 x $10^5$ $k_{off}$: 5.8 x $10^{-5}$ $K_D$: 76 pM clone: 19G1, format: Fab, antigen: mu FAP
$k_{on}$: 4.4 x $10^5$ $k_{off}$: 1.1 x $10^{-3}$ $K_D$: 2.6 nM clone: 20G8, format: Fab, antigen: hu FAP
$k_{on}$: 7.5 x $10^5$ $k_{off}$: 5.2 x $10^{-5}$ $K_D$: 69 pM clone: 20G8, format: Fab, antigen: mu FAP
$k_{on}$: 3.5 x $10^5$ $k_{off}$: 9.9 x $10^{-4}$ $K_D$: 2.8 nM clone: 4B9, format: Fab, antigen: hu FAP
$k_{on}$: 7.3 x $10^5$ $k_{off}$: 1.2 x $10^{-4}$ $K_D$: 157 pM clone: 4B9, format: Fab, antigen: mu FAP
$k_{on}$: 4.4 x $10^5$ $k_{off}$: 1.5 x $10^{-3}$ $K_D$: 3.3 nM clone: 5B8, format: Fab, antigen: hu FAP
$k_{on}$: 5.1 x $10^5$ $k_{off}$: 3.5 x $10^{-4}$ $K_D$: 690 pM clone: 5B8, format: Fab, antigen: mu FAP
$k_{on}$: 3.4 x $10^5$ $k_{off}$: 1.1 x $10^{-3}$ $K_D$: 3.2 pM clone: 5F1, format: Fab, antigen: hu FAP
$k_{on}$: 6.2 x $10^5$ $k_{off}$: 1.5 x $10^{-4}$ $K_D$: 243 pM clone: 5F1, format: Fab, antigen: mu FAP
$k_{on}$: 4.3 x $10^5$ $k_{off}$: 1.8 x $10^{-3}$ $K_D$: 4.1 pM clone: 14B3, format: Fab, antigen: hu FAP
$k_{on}$: 4.8 x $10^5$ $k_{off}$: 1.8 x $10^{-4}$ $K_D$: 377 pM clone: 14B38, format: Fab, antigen: mu FAP
$k_{on}$: 3.6 x $10^5$ $k_{off}$: 1.4 x $10^{-3}$ $K_D$: 3.8 nM clone: 16F1, format: Fab, antigen: hu FAP
$k_{on}$: 5.9 x $10^5$ $k_{off}$: 1.2 x $10^{-4}$ $K_D$: 193 pM clone: 16F1, format: Fab, antigen: mu FAP
$k_{on}$: 4.3 x $10^5$ $k_{off}$: 1.4 x $10^{-3}$ $K_D$: 3.4 nM clone: 16F8, format: Fab, antigen: hu FAP
$k_{on}$: 6.8 x $10^5$ $k_{off}$: 2.1 x $10^{-4}$ $K_D$: 301 pM clone: 16F8, format: Fab, antigen: mu FAP
$k_{on}$: 3.8 x $10^5$ $k_{off}$: 1.4 x $10^{-3}$ $K_D$: 3.8 nM clone: 03C9, format: Fab, antigen: hu FAP
$k_{on}$: 7.5 x $10^5$ $k_{off}$: 1.2 x $10^{-4}$ $K_D$: 160 pM clone: 03C9, format: Fab, antigen: mu FAP
$k_{on}$: 5.1 x $10^5$ $k_{off}$: 1.9 x $10^{-3}$ $K_D$: 3.7 nM clone: 28H1, format: Fab, antigen: hu FAP
$k_{on}$: 5.7 x $10^5$ $k_{off}$: 1.1 x $10^{-4}$ $K_D$: 200 pM clone: 28H1, format: Fab, antigen: mu FAP
$k_{on}$: 2.0 x $10^5$ $k_{off}$: 1.8 x $10^{-6}$ $K_D$: 9 pM clone: 28H1, format: Fab, antigen: cyno FAP
$k_{on}$: 1.6 x $10^5$ $k_{off}$: 5.8 x $10^{-4}$ $K_D$: 3.6 nM clone: 22A3, format: Fab, antigen: hu FAP
$k_{on}$: 4.0 x $10^5$ $k_{off}$: 1.4 x $10^{-5}$ $K_D$: 34 pM clone: 22A3, format: Fab, antigen: mu FAP
$k_{on}$: 4.6 x $10^5$ $k_{off}$: 3.0 x $10^{-4}$ $K_D$: 655 pM clone: 22A3, format: Fab, antigen: cyno FAP
$k_{on}$: 3.8 x $10^5$ $k_{off}$: 2.0 x $10^{-4}$ $K_D$: 522 pM clone: 29B11, format: Fab, antigen: hu FAP
$k_{on}$: 6.4 x $10^5$ $k_{off}$: 2.2 x $10^{-5}$ $K_D$: 35 pM clone: 29B11, format: Fab, antigen: mu FAP
$k_{on}$: 5.8 x $10^5$ $k_{off}$: 2.5 x $10^{-4}$ $K_D$: 436 pM clone: 29B11, format: Fab, antigen: cyno FAP $k_{on}$: 4.8 x $10^5$ $k_{off}$: 1.1 x $10^{-5}$ $K_D$: 23 pM clone: 23C10, format: Fab, antigen: hu FAP $k_{on}$: 5.0 x $10^5$ $k_{off}$: 7.8 x $10^{-4}$ $K_D$: 1.6 nM clone: 23C10, format: Fab, antigen: mu FAP
$k_{on}$: 3.2 x $10^5$ $k_{off}$: 4.0 x $10^{-5}$ $K_D$: 125 pM clone: 23C10, format: Fab, antigen: cyno FAP
$k_{on}$: 5.6 x $10^5$ $k_{off}$: 5.6 x $10^{-4}$ $K_D$: 990 pM clone: 2B10_C3B6, format: Fab, antigen: hu TNC A2
$k_{on}$: 7.8 x $10^5$  $k_{off}$: 1.5 x $10^{-4}$  $K_D$: 191 pM clone: 2B10_6A12, format: Fab, antigen: hu TNC A2
$k_{on}$: 7.4 x $10^5$  $k_{off}$: 2.1 x $10^{-4}$  $K_D$: 290 pM clone: 2B10_01F7, format: Fab, antigen: hu TNC A2
$k_{on}$: 6.1 x $10^5$ $k_{off}$: 3.4 x $10^{-5}$ $K_D$: 56 pM clone: 2B10_6H10, format: Fab, antigen: hu TNC A2
$k_{on}$: 6.5 x $10^5$ $k_{off}$: 5.3 x $10^{-4}$ $K_D$: 810 pM 4-12% Bis-Tris gel run with MOPS buffer Anti-FAP 3F2 Fab-IL2-Fab Anti–FAP 3F2 Fab–IL2–Fab Anti-FAP 4G8 Fab-IL2-Fab Anti-FAP 4G8 Fab-IL2-Fab Anti–FAP 3D9 Fab–IL2–Fab Anti-FAP 3D9 Fab-IL2-Fab Anti-TNC A2 2B10 Fab-IL2-Fab

TARGETED IMMUNOCONJUGATES

CROSS REFERENCE TO RELATED APPLICATIONS

This application claims the benefit of U.S. Prov. Appl. No. 61/234,584, filed Aug. 17, 2009, and European Appl. No. 10162410, filed May 10, 2010, each of which is incorporated herein by reference in its entirety.

REFERENCE TO SEQUENCE LISTING SUBMITTED ELECTRONICALLY VIA EFS-WEB

The content of the electronically submitted sequence listing (Name: 19750640001_Sequence_Listing.ascii.txt; Size: 431,626 bytes; Date of Creation: Aug. 16, 2010) filed with this application is incorporated herein by reference in its entirety.

BACKGROUND OF THE INVENTION

1. Field of the Invention

The present invention generally relates to antigen-specific immunoconjugates for selectively delivering effector moieties that influence cellular activity. In addition, the present invention relates to nucleic acid molecules encoding such immunoconjugates, and vectors and host cells comprising such nucleic acid molecules. The invention further relates to methods for producing the immunoconjugates of the invention, and to methods of using these immunoconjugates in the treatment of disease.

2. Background Art

The selective destruction of an individual cell or a specific cell type is often desirable in a variety of clinical settings. For example, it is a primary goal of cancer therapy to specifically destroy tumor cells, while leaving healthy cells and tissues intact and undamaged. A multitude of signal transduction pathways in the cell are linked to the cell's survival and/or death. Accordingly, the direct delivery of a pathway factor involved in cell survival or death can be used to contribute to the cell's maintenance or destruction.

Cytokines are cell signaling molecules that participate in regulation of the immune system. When used in cancer therapy, cytokines can act as immunomodulatory agents that have anti-tumor effects and which can increase the immunogenicity of some types of tumors. However, rapid blood clearance and lack of tumor specificity require systemic administration of high doses of the cytokine in order to achieve a concentration of the cytokine at the tumor site sufficient to activate an immune response or have an anti-tumor effect. These high levels of systemic cytokine can lead to severe toxicity and adverse reactions.

One way to deliver a signal transduction pathway factor, such as a cytokine, to a specific site in vivo (e.g., a tumor or tumor microenvironment) is to conjugate the factor to an immunoglobulin specific for the site. Early strategies aimed at delivering signal transduction pathway factors, such as cytokines, to a specific site in vivo included immunoglobulin heavy chains conjugated to various cytokines, including lymphotoxin, tumor necrosis factor-α (TNF-α), interleukin-2 (IL-2), and granulocyte macrophage-colony stimulating factor (GM-CSF). The immunoglobulin heavy chains were either chemically conjugated to a cytokine or the immunogobulin-cytokine conjugate was expressed as a fusion protein. See Nakamura K. and Kubo, A. *Cancer Supplement* 80:2650-2655 (1997); Jun, L. et al., *Chin. Med. J.* 113:151-153 (2000); and Becker J. C., et al., *Proc. Natl. Acad. Sci. USA* 93:7826-7831 (1996). Researchers observed that, not only were they able to target cytokines to specific sites in vivo, they were also able to take advantage of the fact that monoclonal antibodies have longer serum half-lives than most other proteins. Due to the systemic toxicity associated with high doses of certain unconjugated cytokines, i.e. IL-2, the ability of an immunoglobulin-cytokine fusion protein to maximize immunostimulatory activities at the site of a tumor whilst keeping systemic side effects to a minimum at a lower dose led researchers to believe that immunoglobulin-cytokine immunoconjugates were optimal therapeutic agents. However, one of the major limitations in the clinical utility of immunoglobulins as delivery agents is their inadequate uptake and poor distribution in tumors, partially due to the large size of the immunoglobulin molecule. See Xiang, J. et al., *Immunol. Cell Biol.* 72:275-285 (1994). Additionally, it has been suggested that immunoglobulin-cytokine immunoconjugates can activate complement and interact with Fc receptors. This inherent immunoglobulin feature has been viewed unfavorably because therapeutic immunoconjugates may be targeted to cells expressing Fc receptors rather than the preferred antigen-bearing cells.

One approach to overcoming these problems is the use of engineered immunoglobulin fragments. Numerous studies have detailed the characteristics of immunoglobulin fragment-cytokine immunoconjugates. See Savage, P. et al., *Br. J. Cancer* 67:304-310 (1993); Harvill, E. T. and Morrison S. L., *Immunotechnol.* 1:95-105 (1995); and Yang J. et al., *Mol. Immunol.* 32:873-881 (1995). In general, there are two common immunoglobulin fragment-cytokine fusion protein constructs, the $F(ab')_2$-cytokine expressed in mammalian cells and the scFv-cytokine expressed in *Escherichia coli*. See Xiang, *J. Hum. Antibodies* 9:23-36 (1999). Both the tumor-binding reactivity of the immunoglobulin parent molecule and the functional activity of the cytokine are maintained in most of these types of immunoconjugates. Recent preclinical studies have shown that these fusion proteins are able to target cytokines to tumors expressing the tumor-associated antigen in vivo, and to inhibit both primary and metastatic tumors in an immune competent animal model.

Examples of immunoglobulin fragment-cytokine immunoconjugates include the scFv-IL-2 immunoconjugate as set forth in PCT publication WO 2001/062298 A2; the immunoglobulin heavy chain fragment-GM-CSF immunoconjugate as set forth in U.S. Pat. No. 5,650,150; the immunoconjugate as set forth in PCT publication WO 2006/119897 A2, wherein scFv-IL-12 first subunit shares only disulfide bond(s) with IL-12 second subunit-scFv, and the immunoconjugate as described in PCT publication WO 99/29732 A2, wherein Ig heavy chain fragment-IL-12 first subunit shares only disulfide bond(s) with Ig heavy chain fragment-IL-12 second subunit. While these second generation immunoconjugates have some improved properties as compared to the first generation immunoglobulin-cytokine conjugates, development of more and even safer specific therapeutic agents is desirable for greater effectiveness against tumor cells and a decrease in the number and severity of the side effects of these products (e.g., toxicity, destruction of non-tumor cells, etc.). Additionally, it is desirable to identify ways to further stabilize immunoconjugates while maintaining acceptable therapeutic activity levels.

The present invention provides immunoconjugates that exhibit improved efficacy, high specificity of action, reduced toxicity, and improved stability in blood relative to known immunoconjugates.

BRIEF SUMMARY OF THE INVENTION

One aspect of the present invention is directed to immunoconjugates that exhibit improved efficacy, high specificity of action, reduced toxicity and improved stability as compared to known immunoconjugates. The immunoconjugates of the present invention can be used to selectively deliver effector moieties to a target site in vivo. In another embodiment, the immunoconjugate delivers a cytokine to a target site, wherein the cytokine can exert a localized biological effect, such as a local inflammatory response, stimulation of T cell growth and activation, and/or activation of B and/or NK cells.

One aspect of the present invention relates to an immunoconjugate that comprises at least a first effector moiety and at least a first and a second antigen binding moiety independently selected from the group consisting of an Fv and an Fab, wherein a first effector moiety shares an amino- or carboxy-terminal peptide bond with a first antigen binding moiety and a second antigen binding moiety shares an amino- or carboxy-terminal peptide bond with either i) the first effector moiety or ii) the first antigen binding moiety.

Another aspect of the present invention is an immunoconjugate that comprises at least a first single-chain effector moiety joined at its amino-terminal amino acid to one or more scFv molecules and wherein the first-single-chain effector moiety is joined at its carboxy-terminal amino acids to one or more scFv molecules.

Another aspect of the present invention is an immunoconjugate that comprises at least a first single-chain effector moiety and first and second antigen binding moieties, wherein each of the first and second antigen binding moieties comprises an scFv molecule joined at its carboxy-terminal amino acid to a constant region comprising a immunoglobulin constant domain independently selected from the group consisting of: IgG CH1, IgG $C_{kappa}$, and IgE CH4, and wherein the first antigen binding moiety is joined at its constant region carboxy-terminal amino acid to the amino-terminal amino acid of one of the effector moieties, and wherein the first and second antigen binding moieties are covalently linked through at least one disulfide bond.

Another aspect of the present invention is an immunoconjugate that comprises at least a first single-chain effector moiety and first and second antigen binding moieties, wherein each of the first and second antigen binding moieties comprises an scFv molecule joined at its carboxy-terminal amino acid to an IgG1 CH3 domain, and wherein the first antigen binding moiety is joined at its carboxy-terminal amino acid to the amino-terminal amino acid of one of the effector moieties, and wherein the first and second antigen binding moieties are covalently linked through at least one disulfide bond.

Another aspect of the present invention is directed to an immunoconjugate that comprises first and second single-chain effector moieties and first and second antigen binding moieties, wherein each of the antigen binding moieties comprises an Fab molecule joined at its heavy or light chain carboxy-terminal amino acid to an IgG1 CH3 domain, and wherein each of the IgG1 CH3 domains is joined at its carboxy-terminal amino acid to the amino-terminal amino acid of one of the effector moieties, and wherein the first and second antigen binding moieties are covalently linked through at least one disulfide bond.

In one embodiment, the immunoconjugate comprises the polypeptide sequence of SEQ ID NO: 95. In another embodiment, the immunoconjugate comprises the polypeptide sequence of SEQ ID NO: 104. In another embodiment, the immunoconjugate comprises the polypeptide sequence of SEQ ID NO: 105. In another embodiment, the immunoconjugate comprises the polypeptide sequence of SEQ ID NO: 106. In another embodiment, the immunoconjugate comprises the polypeptide sequence of SEQ ID NO: 107. In another embodiment, the immunoconjugate comprises the polypeptide sequence of SEQ ID NO: 96. In a further embodiment, the immunoconjugate comprises the polypeptide sequence of SEQ ID NO: 96 and a polypeptide sequence selected from the group consisting of SEQ ID NOs: 95 and 104-107. In another embodiment, the immunoconjugate comprises a polypeptide having a sequence that is at least about 80%, 85%, 90%, 95%, 96%, 97%, 98%, or 99% identical to a sequence selected from the group consisting of SEQ ID NOs: 95, 96, and 104-107.

In one embodiment, the immunoconjugate comprises a polypeptide sequence encoded by a polynucleotide sequence that is at least about 80%, 85%, 90%, 95%, 96%, 97%, 98%, or 99% identical to SEQ ID NO: 108. In another embodiment, the immunoconjugate comprises a polypeptide sequence that is encoded by the polynucleotide sequence of SEQ ID NO: 108. In one embodiment, the immunoconjugate comprises a polypeptide sequence encoded by a polynucleotide sequence that is at least about 80%, 85%, 90%, 95%, 96%, 97%, 98%, or 99% identical to SEQ ID NO: 117. In another embodiment, the immunoconjugate comprises a polypeptide sequence that is encoded by the polynucleotide sequence of SEQ ID NO: 117. In one embodiment, the immunoconjugate comprises a polypeptide sequence encoded by a polynucleotide sequence that is at least about 80%, 85%, 90%, 95%, 96%, 97%, 98%, or 99% identical to SEQ ID NO: 118. In another embodiment, the immunoconjugate comprises a polypeptide sequence that is encoded by the polynucleotide sequence of SEQ ID NO: 118. In one embodiment, the immunoconjugate comprises a polypeptide sequence encoded by a polynucleotide sequence that is at least about 80%, 85%, 90%, 95%, 96%, 97%, 98%, or 99% identical to SEQ ID NO: 119. In another embodiment, the immunoconjugate comprises a polypeptide sequence that is encoded by the polynucleotide sequence of SEQ ID NO: 119. In one embodiment, the immunoconjugate comprises a polypeptide sequence encoded by a polynucleotide sequence that is at least about 80%, 85%, 90%, 95%, 96%, 97%, 98%, or 99% identical to SEQ ID NO: 120. In another embodiment, the immunoconjugate comprises a polypeptide sequence that is encoded by the polynucleotide sequence of SEQ ID NO: 120. In one embodiment, the immunoconjugate comprises a polypeptide sequence encoded by a polynucleotide sequence that is at least about 80%, 85%, 90%, 95%, 96%, 97%, 98%, or 99% identical to SEQ ID NO: 109. In another embodiment, the immunoconjugate comprises a polypeptide sequence that is encoded by the polynucleotide sequence of SEQ ID NO: 109.

In one embodiment, the immunoconjugate comprises a heavy chain variable region that is at least about 80%, 85%, 90%, 95%, 96%, 97%, 98%, 99%, or 100% identical to the sequence of either SEQ ID NO: 13 or SEQ ID NO: 15. In another embodiment, the immunoconjugate comprises a light chain variable region sequence that is at least about 80%, 85%, 90%, 95%, 96%, 97%, 98%, 99%, or 100% identical to the sequence of either SEQ ID NO: 9 or SEQ ID NO: 11. In a further embodiment, the immunoconjugate comprises a heavy chain variable region sequence that is at least about 80%, 85%, 90%, 95%, 96%, 97%, 98%, 99%, or 100% identical to the sequence of either SEQ ID NO: 13 or SEQ ID NO: 15, and a light chain variable region sequence that is at least about 80%, 85%, 90%, 95%, 96%, 97%, 98%, 99%, or 100% identical to the sequence of either SEQ ID NO: 9 or SEQ ID NO: 11.

In one embodiment, the immunoconjugate comprises a heavy chain variable region sequence encoded by a polynucleotide sequence that is at least about 80%, 85%, 90%, 95%, 96%, 97%, 98%, or 99% identical to either SEQ ID NO:

14 or SEQ ID NO: 16. In another embodiment, the immunoconjugate comprises a heavy chain variable region sequence that is encoded by the polynucleotide sequence of either SEQ ID NO: 14 or SEQ ID NO: 16. In one embodiment, the immunoconjugate comprises a light chain variable region sequence encoded by a polynucleotide sequence that is at least about 80%, 85%, 90%, 95%, 96%, 97%, 98%, or 99% identical to either SEQ ID NO: 10 or SEQ ID NO: 12. In another embodiment, the immunoconjugate comprises a light chain variable region sequence that is encoded by the polynucleotide sequence of either SEQ ID NO: 10 or SEQ ID NO: 12.

In one embodiment, the immunoconjugate comprises a polypeptide sequence that is at least about 80%, 85%, 90%, 95%, 96%, 97%, 98%, 99%, or 100% identical to the sequence of SEQ ID NO: 99. In another embodiment, the immunoconjugate comprises a polypeptide sequence that is at least about 80%, 85%, 90%, 95%, 96%, 97%, 98%, 99%, or 100% identical to the sequence of either SEQ ID NO: 100 or SEQ ID NO: 215. In another embodiment, the immunoconjugate comprises a polypeptide sequence that is at least about 80%, 85%, 90%, 95%, 96%, 97%, 98%, 99%, or 100% identical to the sequence of either SEQ ID NO: 101 or SEQ ID NO: 235. In a further embodiment, the immunoconjugate comprises a polypeptide sequence that is at least about 80%, 85%, 90%, 95%, 96%, 97%, 98%, 99%, or 100% identical to the sequence of SEQ ID NO: 100, and a polypeptide sequence that is at least about 80%, 85%, 90%, 95%, 96%, 97%, 98%, 99%, or 100% identical to the sequence of SEQ ID NO: 101. In a further embodiment, the immunoconjugate comprises a polypeptide sequence that is at least about 80%, 85%, 90%, 95%, 96%, 97%, 98%, 99%, or 100% identical to the sequence of SEQ ID NO: 215, and a polypeptide sequence that is at least about 80%, 85%, 90%, 95%, 96%, 97%, 98%, 99%, or 100% identical to the sequence of SEQ ID NO: 235.

In one embodiment, the immunoconjugate comprises a polypeptide sequence encoded by a polynucleotide sequence that is at least about 80%, 85%, 90%, 95%, 96%, 97%, 98%, or 99% identical to SEQ ID NO: 112. In another embodiment, the immunoconjugate comprises a polypeptide sequence that is encoded by the polynucleotide sequence of SEQ ID NO: 112. In one embodiment, the immunoconjugate comprises a polypeptide sequence encoded by a polynucleotide sequence that is at least about 80%, 85%, 90%, 95%, 96%, 97%, 98%, or 99% identical to either SEQ ID NO: 113 or SEQ ID NO: 216. In another embodiment, the immunoconjugate comprises a polypeptide sequence that is encoded by the polynucleotide sequence of either SEQ ID NO: 113 or SEQ ID NO: 216. In one embodiment, the immunoconjugate comprises a polypeptide sequence encoded by a polynucleotide sequence that is at least about 80%, 85%, 90%, 95%, 96%, 97%, 98%, or 99% identical to either SEQ ID NO: 114 or SEQ ID NO: 236. In another embodiment, the immunoconjugate comprises a polypeptide sequence that is encoded by the polynucleotide sequence of either SEQ ID NO: 114 or SEQ ID NO: 236.

In one embodiment, the immunoconjugate comprises a heavy chain variable region sequence that is at least about 80%, 85%, 90%, 95%, 96%, 97%, 98%, 99%, or 100% identical to a sequence selected from the group of SEQ ID NO: 7, SEQ ID NO: 179, SEQ ID NO: 183, SEQ ID NO: 187, SEQ ID NO: 191, SEQ ID NO:195, SEQ ID NO: 199, SEQ ID NO: 203 and SEQ ID NO: 207. In another embodiment, the immunoconjugate comprises a light chain variable region sequence that is at least about 80%, 85%, 90%, 95%, 96%, 97%, 98%, 99%, or 100% identical to a sequence selected from the group of SEQ ID NO: 3, SEQ ID NO: 5, SEQ ID NO: 177, SEQ ID NO: 181, SEQ ID NO:185, SEQ ID NO: 189, SEQ ID NO: 193, SEQ ID NO: 197, SEQ ID NO: 201 and SEQ ID NO: 205. In a further embodiment, the immunoconjugate comprises a heavy chain variable region sequence that is at least about 80%, 85%, 90%, 95%, 96%, 97%, 98%, 99%, or 100% identical to a sequence selected from the group of SEQ ID NO: 7, SEQ ID NO: 179, SEQ ID NO: 183, SEQ ID NO: 187, SEQ ID NO: 191, SEQ ID NO:195, SEQ ID NO: 199, SEQ ID NO: 203 and SEQ ID NO: 207 and a light chain variable region sequence that is at least about 80%, 85%, 90%, 95%, 96%, 97%, 98%, 99%, or 100% identical to a sequence selected from the group of SEQ ID NO: 3, SEQ ID NO: 5, SEQ ID NO: 177, SEQ ID NO: 181, SEQ ID NO:185, SEQ ID NO: 189, SEQ ID NO: 193, SEQ ID NO: 197, SEQ ID NO: 201 and SEQ ID NO: 205.

In one embodiment, the immunoconjugate comprises a heavy chain variable region sequence encoded by a polynucleotide sequence that is at least about 80%, 85%, 90%, 95%, 96%, 97%, 98%, or 99% identical to a sequence selected from the group of SEQ ID NO: 8, SEQ ID NO: 180, SEQ ID NO: 184, SEQ ID NO: 188, SEQ ID NO: 192, SEQ ID NO: 196, SEQ ID NO: 200, SEQ ID NO: 204 and SEQ ID NO: 208. In another embodiment, the immunoconjugate comprises a heavy chain variable region sequence that is encoded by a polynucleotide sequence selected from the group of SEQ ID NO: 8, SEQ ID NO: 180, SEQ ID NO: 184, SEQ ID NO: 188, SEQ ID NO: 192, SEQ ID NO: 196, SEQ ID NO: 200, SEQ ID NO: 204 and SEQ ID NO: 208. In one embodiment, the immunoconjugate comprises a light chain variable region sequence encoded by a polynucleotide sequence that is at least about 80%, 85%, 90%, 95%, 96%, 97%, 98%, or 99% identical to a sequence selected from the group of SEQ ID NO: 4, SEQ ID NO: 6, SEQ ID NO: 178, SEQ ID NO: 182, SEQ ID NO: 186, SEQ ID NO: 190, SEQ ID NO: 194, SEQ ID NO: 198, SEQ ID NO: 202 and SEQ ID NO: 206. In another embodiment, the immunoconjugate comprises a light chain variable region sequence that is encoded by a polynucleotide sequence selected from the group of SEQ ID NO: 4, SEQ ID NO: 6, SEQ ID NO: 178, SEQ ID NO: 182, SEQ ID NO: 186, SEQ ID NO: 190, SEQ ID NO: 194, SEQ ID NO: 198, SEQ ID NO: 202 and SEQ ID NO: 206.

In one embodiment, the immunoconjugate comprises a polypeptide sequence that is at least about 80%, 85%, 90%, 95%, 96%, 97%, 98%, 99%, or 100% identical to a sequence selected from the group of SEQ ID NO: 239, SEQ ID NO: 241 and SEQ ID NO: 243. In another embodiment, the conjugate comprises a polypeptide sequence that is at least about 80%, 85%, 90%, 95%, 96%, 97%, 98%, 99%, or 100% identical to a sequence selected from the group of SEQ ID NO: 245, SEQ ID NO: 247 and SEQ ID NO:249. In a further embodiment, the immunoconjugate comprises a polypeptide sequence that is at least about 80%, 85%, 90%, 95%, 96%, 97%, 98%, 99%, or 100% identical to a sequence selected from the group of SEQ ID NO: 239, SEQ ID NO: 241 and SEQ ID NO: 243, and a polypeptide sequence that is at least about 80%, 85%, 90%, 95%, 96%, 97%, 98%, 99%, or 100% identical to a sequence selected from the group of SEQ ID NO: 245, SEQ ID NO: 247 and SEQ ID NO:249.

In one embodiment, the immunoconjugate comprises a polypeptide sequence encoded by a polynucleotide sequence that is at least about 80%, 85%, 90%, 95%, 96%, 97%, 98%, or 99% identical to a sequence selected from the group of SEQ ID NO: 240, SEQ ID NO: 242 and SEQ ID NO: 244. In another embodiment, the immunoconjugate comprises a polypeptide sequence that is encoded by a polynucleotide sequence selected from the group of SEQ ID NO: 240, SEQ ID NO: 242 and SEQ ID NO: 244. In one embodiment, the immunoconjugate comprises a polypeptide sequence encoded by a polynucleotide sequence that is at least about 80%, 85%, 90%, 95%, 96%, 97%, 98%, or 99% identical to a sequence selected from the group of SEQ ID NO: 246, SEQ ID NO: 248 and SEQ ID NO: 250. In another embodiment, the immunoconjugate comprises a polypeptide sequence that is encoded by the polynucleotide sequence selected from the group of SEQ ID NO: 246, SEQ ID NO: 248 and SEQ ID NO: 250.

In one embodiment, the immunoconjugate comprises a heavy chain variable region sequence that is at least about 80%, 85%, 90%, 95%, 96%, 97%, 98%, 99%, or 100% identical to a sequence selected from the group consisting of: SEQ ID NO: 21, SEQ ID NO: 25, SEQ ID NO: 27, SEQ ID NO: 31, SEQ ID NO: 35, SEQ ID NO: 39, SEQ ID NO: 43, SEQ ID NO: 47, SEQ ID NO: 51, SEQ ID NO: 69, SEQ ID NO: 73, SEQ ID NO: 77, SEQ ID NO: 81, SEQ ID NO: 85, SEQ ID NO: 89, SEQ ID NO: 93, SEQ ID NO: 123, SEQ ID NO: 127, SEQ ID NO: 131, SEQ ID NO: 135, SEQ ID NO: 139, SEQ ID NO: 143, SEQ ID NO: 147, SEQ ID NO: 151, SEQ ID NO: 155, SEQ ID NO: 159, SEQ ID NO: 163, SEQ ID NO: 167, SEQ ID NO: 171 and SEQ ID NO: 175. In another embodiment, the immunoconjugate comprises a light chain variable region sequence that is at least about 80%, 85%, 90%, 95%, 96%, 97%, 98%, 99%, or 100% identical to a sequence selected from the group consisting of: SEQ ID NO: 17, SEQ ID NO: 19, SEQ ID NO: 23, SEQ ID NO: 29, SEQ ID NO: 33, SEQ ID NO: 37, SEQ ID NO: 41, SEQ ID NO: 45, SEQ ID NO: 49, SEQ ID NO: 67, SEQ ID NO: 71, SEQ ID NO: 75, SEQ ID NO: 79, SEQ ID NO: 83, SEQ ID NO: 87, SEQ ID NO: 91, SEQ ID NO: 121, SEQ ID NO: 125, SEQ ID NO: 129, SEQ ID NO: 133, SEQ ID NO: 137, SEQ ID NO: 141, SEQ ID NO: 145, SEQ ID NO: 149, SEQ ID NO: 153, SEQ ID NO: 157, SEQ ID NO: 161, SEQ ID NO: 165, SEQ ID NO: 169 and SEQ ID NO: 173. In a further embodiment, the immunoconjugate comprises a heavy chain variable region sequence that is at least about 80%, 85%, 90%, 95%, 96%, 97%, 98%, 99%, or 100% identical to a sequence selected from the group consisting of: SEQ ID NO: 21, SEQ ID NO: 25, SEQ ID NO: 27, SEQ ID NO: 31, SEQ ID NO: 35, SEQ ID NO: 39, SEQ ID NO: 43, SEQ ID NO: 47, SEQ ID NO: 51, SEQ ID NO: 69, SEQ ID NO: 73, SEQ ID NO: 77, SEQ ID NO: 81, SEQ ID NO: 85, SEQ ID NO: 89, SEQ ID NO: 93, SEQ ID NO: 123, SEQ ID NO: 127, SEQ ID NO: 131, SEQ ID NO: 135, SEQ ID NO: 139, SEQ ID NO: 143, SEQ ID NO: 147, SEQ ID NO: 151, SEQ ID NO: 155, SEQ ID NO: 159, SEQ ID NO: 163, SEQ ID NO: 167, SEQ ID NO: 171 and SEQ ID NO: 175, and a light chain variable region sequence that is at least about 80%, 85%, 90%, 95%, 96%, 97%, 98%, 99%, or 100% identical to a sequence selected from the group consisting of: SEQ ID NO: 17, SEQ ID NO: 19, SEQ ID NO: 23, SEQ ID NO: 29, SEQ ID NO: 33, SEQ ID NO: 37, SEQ ID NO: 41, SEQ ID NO: 45, SEQ ID NO: 49, SEQ ID NO: 67, SEQ ID NO: 71, SEQ ID NO: 75, SEQ ID NO: 79, SEQ ID NO: 83, SEQ ID NO: 87, SEQ ID NO: 91, SEQ ID NO: 121, SEQ ID NO: 125, SEQ ID NO: 129, SEQ ID NO: 133, SEQ ID NO: 137, SEQ ID NO: 141, SEQ ID NO: 145, SEQ ID NO: 149, SEQ ID NO: 153, SEQ ID NO: 157, SEQ ID NO: 161, SEQ ID NO: 165, SEQ ED NO: 169 and SEQ ID NO: 173.

In one embodiment, the immunoconjugate comprises a heavy chain variable region sequence that is encoded by a polynucleotide sequence that is at least about 80%, 85%, 90%, 95%, 96%, 97%, 98%, or 99% identical to a sequence selected from the group consisting of: SEQ ID NO: 22, SEQ ID NO: 26, SEQ ID NO: 28, SEQ ID NO: 32, SEQ ID NO: 36, SEQ ID NO: 40, SEQ ID NO: 44, SEQ ID NO: 48, SEQ ID NO: 52, SEQ ID NO: 70, SEQ ID NO: 74, SEQ ID NO: 78, SEQ ID NO: 82, SEQ ID NO: 86, SEQ ID NO: 90, SEQ ID NO: 94, SEQ ID NO: 124, SEQ ID NO: 128, SEQ ID NO: 132, SEQ ID NO: 136, SEQ ID NO: 140, SEQ ID NO: 144, SEQ ID NO: 148, SEQ ID NO: 152, SEQ ID NO: 156, SEQ ID NO: 160, SEQ ID NO: 164, SEQ ID NO: 168, SEQ ID NO: 172 and SEQ ID NO: 176. In another embodiment, the immunoconjugate comprises a heavy chain variable region sequence that is encoded by a polynucleotide sequence selected from the group consisting of: SEQ ID NO: 22, SEQ ID NO: 26, SEQ ID NO: 28, SEQ ID NO: 32, SEQ ID NO: 36, SEQ ID NO: 40, SEQ ID NO: 44, SEQ ID NO: 48, SEQ ID NO: 52, SEQ ID NO: 70, SEQ ID NO: 74, SEQ ID NO: 78, SEQ ID NO: 82, SEQ ID NO: 86, SEQ ID NO: 90, SEQ ID NO: 94, SEQ ID NO: 124, SEQ ID NO: 128, SEQ ID NO: 132, SEQ ID NO: 136, SEQ ID NO: 140, SEQ ID NO: 144, SEQ ID NO: 148, SEQ ID NO: 152, SEQ ID NO: 156, SEQ ID NO: 160, SEQ ID NO: 164, SEQ ID NO: 168, SEQ ID NO: 172 and SEQ ID NO: 176. In one embodiment, the immunoconjugate comprises a light chain variable region sequence that is encoded by a polynucleotide sequence that is at least about 80%, 85%, 90%, 95%, 96%, 97%, 98%, or 99% identical to a sequence selected from the group consisting of: SEQ ID NO: 18, SEQ ID NO: 20, SEQ ID NO: 24, SEQ ID NO: 30, SEQ ID NO: 34, SEQ ID NO: 38, SEQ ID NO: 42, SEQ ID NO: 46, SEQ ID NO: 50, SEQ ID NO: 68, SEQ ID NO: 72, SEQ ID NO: 76, SEQ ID NO: 80, SEQ ID NO: 84, SEQ ID NO: 88, SEQ ID NO: 92, SEQ ID NO: 122, SEQ ID NO: 126, SEQ ID NO: 130, SEQ ID NO: 134, SEQ ID NO: 138, SEQ ID NO: 142, SEQ ID NO: 146, SEQ ID NO: 150, SEQ ID NO: 154, SEQ ID NO: 158, SEQ ID NO: 162, SEQ ID NO: 166, SEQ ID NO: 170 and SEQ ID NO: 174. In another embodiment, the immunoconjugate comprises a light chain variable region sequence that is encoded by a polynucleotide sequence selected from the group consisting of: SEQ ID NO: 18, SEQ ID NO: 20, SEQ ID NO: 24, SEQ ID NO: 30, SEQ ID NO: 34, SEQ ID NO: 38, SEQ ID NO: 42, SEQ ID NO: 46, SEQ ID NO: 50, SEQ ID NO: 68, SEQ ID NO: 72, SEQ ID NO: 76, SEQ ID NO: 80, SEQ ID NO: 84, SEQ ID NO: 88, SEQ ID NO: 92, SEQ ID NO: 122, SEQ ID NO: 126, SEQ ID NO: 130, SEQ ID NO: 134, SEQ ID NO: 138, SEQ ID NO: 142, SEQ ID NO: 146, SEQ ID NO: 150, SEQ ID NO: 154, SEQ ID NO: 158, SEQ ID NO: 162, SEQ ID NO: 166, SEQ ID NO: 170 and SEQ ID NO: 174.

In one embodiment, the immunoconjugate comprises a polypeptide sequence that is at least about 80%, 85%, 90%, 95%, 96%, 97%, 98%, 99%, or 100% identical to a sequence selected from the group of SEQ ID NO: 209, SEQ ID NO: 211, SEQ ID NO: 213, SEQ ID NO: 217, SEQ ID NO: 219, SEQ ID NO: 221, SEQ ID NO: 223, SEQ JD NO: 225 and SEQ ID NO: 227. In another embodiment, the immunoconjugate comprises a polypeptide sequence that is at least about 80%, 85%, 90%, 95%, 96%, 97%, 98%, 99%, or 100% identical to a sequence selected from the group of SEQ ID NO: 229, SEQ ID NO: 231, SEQ ID NO: 233 and SEQ ID NO: 237. In a further embodiment, the immunoconjugate comprises a polypeptide sequence that is at least about 80%, 85%, 90%, 95%, 96%, 97%, 98%, 99%, or 100% identical to a sequence selected from the group of SEQ ID NO: 211, SEQ ID NO: 219, and SEQ ID NO: 221, and a polypeptide sequence that is at least about 80%, 85%, 90%, 95%, 96%, 97%, 98%, 99%, or 100% identical to the sequence of SEQ ID NO: 231. In a further embodiment, the immunoconjugate comprises a polypeptide sequence that is at least about 80%, 85%, 90%, 95%, 96%, 97%, 98%, 99%, or 100% identical to a sequence selected from the group of SEQ ID NO: 209, SEQ ID NO: 223, SEQ ID NO: 225 and SEQ ID NO: 227, and a polypeptide sequence that is at least about 80%, 85%, 90%, 95%, 96%, 97%, 98%, 99%, or 100% identical to the sequence of SEQ ID NO: 229. In a further embodiment, the immunoconjugate comprises a polypeptide sequence that is at least about 80%, 85%, 90%, 95%, 96%, 97%, 98%, 99%, or 100% identical to the sequence of SEQ ID NO: 213, and a polypeptide sequence that is at least about 80%, 85%, 90%, 95%, 96%, 97%, 98%, 99%, or 100% identical to the sequence of SEQ ID NO: 233. In a further embodiment, the immunoconjugate comprises a polypeptide sequence that is at least about 80%, 85%, 90%, 95%, 96%, 97%, 98%, 99%, or 100% identical to the sequence of SEQ ID NO: 217, and a polypeptide sequence that is at least about 80%, 85%, 90%, 95%, 96%, 97%, 98%, 99%, or 100% identical to the sequence of SEQ ID NO: 237.

In one embodiment, the immunoconjugate comprises a polypeptide sequence encoded by a polynucleotide sequence that is at least about 80%, 85%, 90%, 95%, 96%, 97%, 98%, or 99% identical to a sequence selected from the group of SEQ ID NO: 210, SEQ ID NO: 212, SEQ ID NO: 214, SEQ ID NO: 218, SEQ ID NO: 220, SEQ ID NO: 222, SEQ ID NO: 224, SEQ ID NO: 226 and SEQ ID NO: 228. In another embodiment, the immunoconjugate comprises a polypeptide sequence that is encoded by a polynucleotide sequence selected from the group of SEQ ID NO: 210, SEQ ID NO: 212, SEQ ID NO: 214, SEQ ID NO: 218, SEQ ID NO: 220, SEQ ID NO: 222, SEQ ID NO: 224, SEQ ID NO: 226 and SEQ ID NO: 228. In one embodiment, the immunoconjugate comprises a polypeptide sequence encoded by a polynucleotide sequence that is at least about 80%, 85%, 90%, 95%, 96%, 97%, 98%, or 99% identical to a sequence selected from the group of SEQ ID NO: 230, SEQ ID NO: 232, SEQ ID NO: 234 and SEQ ID NO: 238. In another embodiment, the immunoconjugate comprises a polypeptide sequence that is encoded by a polynucleotide sequence selected from the group of SEQ ID NO: 230, SEQ ID NO: 232, SEQ ID NO: 234 and SEQ ID NO: 238.

In one embodiment; the immunoconjugate comprises a heavy chain variable region sequence that is at least about 80%, 85%, 90%, 95%, 96%, 97%, 98%, 99%, or 100% identical to the sequence of either SEQ ID NO: 257 or SEQ ID NO: 261. In another embodiment, the immunoconjugate comprises a light chain variable region sequence that is at least about 80%, 85%, 90%, 95%, 96%, 97%, 98%, 99%, or 100% identical to the sequence of either SEQ ID NO: 259 or SEQ ID NO: 271. In a further embodiment, the immunoconjugate comprises a heavy chain variable region sequence that is at least about 80%, 85%, 90%, 95%, 96%, 97%, 98%, 99%, or 100% identical to to the sequence of either SEQ ID NO: 257 or SEQ ID NO: 261, and a light chain variable region sequence that is at least about 80%, 85%, 90%, 95%, 96%, 97%, 98%, 99%, or 100% identical to the sequence of either SEQ ID NO: 259 or SEQ ID NO: 271.

In one embodiment, the immunoconjugate comprises a heavy chain variable region sequence encoded by a polynucleotide sequence that is at least about 80%, 85%, 90%, 95%, 96%, 97%, 98%, or 99% identical to the sequence of either SEQ ID NO: 258 or SEQ ID NO: 262. In another embodiment, the immunoconjugate comprises a heavy chain variable region sequence that is encoded by the polynucleotide sequence of either SEQ ID NO: 258 or SEQ ID NO: 262. In one embodiment, the immunoconjugate comprises a light chain variable region sequence encoded by a polynucleotide sequence that is at least about 80%, 85%, 90%, 95%, 96%, 97%, 98%, or 99% identical to the sequence of either SEQ ID NO: 260 or SEQ ID NO: 272. In another embodiment, the immunoconjugate comprises a light chain variable region sequence that is encoded by the polynucleotide sequence of either SEQ ID NO: 260 or SEQ ID NO: 272.

In one embodiment, the immunoconjugate comprises a polypeptide sequence that is at least about 80%, 85%, 90%, 95%, 96%, 97%, 98%, 99%, or 100% identical to the sequence of either SEQ ID NO: 251 or SEQ ID NO: 255. In another embodiment, the immunoconjugate comprises a polypeptide sequence that is at least about 80%, 85%, 90%, 95%, 96%, 97%, 98%, 99%, or 100% identical to the sequence of either SEQ ID NO: 253 or SEQ ID NO: 265. In a further embodiment, the immunoconjugate comprises a polypeptide sequence that is at least about 80%, 85%, 90%, 95%, 96%, 97%, 98%, 99%, or 100% identical to the sequence of either SEQ ID NO: 251 or SEQ ID NO: 255, and a polypeptide sequence that is at least about 80%, 85%, 90%, 95%, 96%, 97%, 98%, 99%, or 100% identical to the sequence of either SEQ ID NO: 253 or SEQ ID NO: 265.

In one embodiment, the immunoconjugate comprises a polypeptide sequence encoded by a polynucleotide sequence that is at least about 80%, 85%, 90%, 95%, 96%, 97%, 98%, or 99% identical to the sequence of either SEQ ID NO: 252 or SEQ ID NO: 256. In another embodiment, the immunoconjugate comprises a polypeptide sequence that is encoded by the polynucleotide sequence of either SEQ ID NO: 252 or SEQ ID NO: 256. In one embodiment, the immunoconjugate comprises a polypeptide sequence encoded by a polynucleotide sequence that is at least about 80%, 85%, 90%, 95%, 96%, 97%, 98%, or 99% identical to either SEQ ID NO: 254 or SEQ ID NO: 266. In another embodiment, the immunoconjugate comprises a polypeptide sequence that is encoded by the polynucleotide sequence of either SEQ ID NO: 254 or SEQ ID NO: 266.

In another embodiment, the immunoconjugate comprises at least one effector moiety, wherein the effector moiety is a cytokine. In a specific embodiment, the effector moiety is a cytokine selected from the group consisting of: interleukin-2 (IL-2), granulocyte macrophage-colony stimulating factor (GM-CSF), interferon-α (INF-α), interleukin-12 (IL-12), interleukin-8 (IL-8), macrophage inflammatory protein-1α (MIP-1α), macrophage inflammatory protein-1β (MIP-1β), and transforming growth factor-β (TGF-β). In another embodiment, at least one antigen binding moiety is specific for one of the following antigenic determinants: the Extra Domain B of fibronectin (EDB), the A1 domain of tenascin (TNC-A1), the A2 domain of tenascin (TNC-A2), the Fibroblast Activated Protein (FAP); and the Melanoma Chondroitin Sulfate Proteoglycan (MCSP).

In another embodiment, the immunoconjugate of the invention binds to an effector moiety receptor with a dissociation constant ($K_D$) that is at least about 1, 1.5, 2, 2.5, 3, 3.5, 4, 4.5, 5, 5.5, 6, 6.5, 7, 7.5, 8, 8.5, 9, 9.5 or 10 times greater than that for a control effector moiety. In another embodiment, the immunoconjugate inhibits an increase in tumor volume in vivo by at least about 10%, 20%, 30%, 40%, 50%, 60%, 70%, 80%, 90%, 100% or more at the end of an administration period. In another embodiment, the immunoconjugate prolongs the survival of mammals with malignant tumors by at least about 10%, 20%, 30%, 40%, 50%, 60%, 70%, 80%, 90% when administered to a mammal in need thereof, relative to a control effector moiety or an effector moiety in a "diabody" immunoconjugate molecule.

Another aspect of the present invention is directed to isolated polynucleotides encoding immunoconjugates of the invention or fragments thereof. Another aspect of the present invention is directed to an expression vector comprising an expression cassette comprising the polynucleotide sequences of the invention.

Another aspect of the present invention is directed to host cells that express the immunoconjugates of the invention or fragments thereof.

Another aspect of the present invention is directed to methods for producing the immunoconjugates of the invention or fragments thereof, wherein the method comprises culturing host cells transformed with expression vectors encoding for the immunoconjugates of the invention or fragments thereof under conditions suitable for the expression, of the same.

Another aspect of the present invention is directed to methods for promoting proliferation and differentiation in an activated T lymphocyte cell, comprising contacting an activated T lymphocyte cell with an effective amount of the immunoconjugates of the invention.

Another aspect of the present invention is directed to methods for promoting proliferation and differentiation in an activated B lymphocyte cell, comprising contacting an activated B lymphocyte cell with an effective amount of the immunoconjugates of the invention.

Another aspect of the present invention is directed to methods for promoting proliferation and differentiation in a natural killer (NK) cell, comprising contacting a NK cell with an effective amount of the immunoconjugates of the invention.

Another aspect of the present invention is directed to methods for promoting proliferation and differentiation in a granulocyte, a monocyte or a dendritic cell, comprising contacting a granulocyte, a monocyte or a dendritic cell with an effective amount of the immunoconjugates of the invention.

Another aspect of the present invention is directed to methods for promoting cytotoxic T lymphocyte (CTL) differentiation, comprising contacting a T lymphocyte cell with an effective amount of the immunoconjugates of the invention.

Another aspect of the present invention is directed to methods for inhibiting viral replication, comprising contacting a virus-infected cell with an effective amount of the immunoconjugates of the invention.

Another aspect of the present invention is directed to methods for upregulating the expression of major histocompatibility complex I (MHC I), comprising contacting a target cell with an effective amount of the immunoconjugates of the invention.

Another aspect of the present invention is directed to methods for inducing cell death, comprising administering to a target cell an effective amount of the immunoconjugates of the invention.

Another aspect of the present invention is directed to methods for inducing chemotaxis in a target cell, comprising administering to a target cell an effective amount of the immunoconjugate of the invention.

Another aspect of the present invention is directed to a method of treating a disease in an individual, comprising the steps of administering to an individual a therapeutically effective amount of a composition comprising the immunoconjugate of the invention and a pharmaceutical carrier.

BRIEF DESCRIPTION OF THE DRAWINGS/FIGURES

FIG. 1. Schematic overview of the various immunoconjugate fusion formats. All constructs in FIG. 1 comprise two antibody scFv fragments (in the antigen binding moiety), and one or two cytokine molecules (as the effector moieties) connected to it. Panels A to E show different connectivities and stoichiometries of the antigen binding moieties and effector moieties. Panel A) depicts a "diabody"-IL-2 fusion. The "diabody" assembles non-covalently from two identical polypeptide chains. Panel B shows an immunoconjugate comprising a heavy chain of an Fab molecule fused at its carboxy-terminus to a cytokine which, in turn, is fused at its carboxy-terminus to a second Fab heavy chain. A light chain is coexpressed with the heavy chain Fab-cytokine-heavy chain Fab polypeptide to form the immunoconjugate. Alternatively, the two light chains can be fused to the cytokine, and the heavy chains are coexpressed. In panel C, the two Fab heavy chains are fused directly to each other. The cytokine shares an amino-terminal peptide bond with the second antigen binding moiety heavy chain. The two molecular formats of panels B and C can be varied such that the Fab chain is replaced by an scFv fragment, as in panels D and E.

FIG. 2. Schematic overview of additional immunoconjugates that comprise two antigen binding moieties and at least one or more effector moieties. Panel A shows a Fab molecule fused through its carboxy-terminus to an IgG CH3 domain. In order to achieve covalent antigen binding moiety homodimerization, an artificial disulfide bond can be introduced at the carboxy-terminus of the IgG CH3 domain (immunoconjugate on the right within panel A. The IgG1 CH3 domain shown in panel A can be substituted with an IgE CH4 domain. The Fab moieties in panel A are replaced by scFv fragments in panel B. For the immunoconjugate of panel C, the natural IgG hinge was fused C-terminal to the Fab molecules. Since the carboxy-terminus region of the hinge could impose some geometric constraints on the assembly of constant domains that are fused C-terminal to the IgG hinge region, an artificial linker can be introduced between the carboxy-terminal region of the hinge and the amino-terminus of the IgG CH3 domain. The hinge region can also be introduced between a scFv fragment and an immunoglobulin constant domain, as shown in panel D. In panels A to D, an IgG1 CH3 or IgE CH4 domain is used to homodimerize the constructs. Panel E depicts an immunoconjugate in which dimerization is achieved via a $CH1/C_{kappa}$ heterodimerization interaction. The immunoconjugate of panel D can have one or two cytokines per immunoconjugate.

FIG. 3 presents the results of an efficacy experiment with two different interleukin-2 immunoconjugate molecular formats specific for tumor stroma. The F9 teratocarcinoma was subcutaneously injected into 129SvEv mice, and tumor size was measured using a caliper. The "diabody"-IL-2 molecule was compared at two different concentrations to the Fab-interleukin-2-Fab (Fab-IL2-Fab) immunoconjugate, wherein the concentrations reflected similar numbers of immunoconjugate molecules. The Fab-IL2-Fab immunoconjugate is labeled as "Fab-L19", the unconjugated interleukin-2 control is labeled as "Unconj rIL-2," the "diabody"-IL-2 molecule is labeled as "diabody" in FIG. 3. The L19 antibody, directed against Extra Domain B of fibronectin (EDB), was used to generate the antigen binding moieties in both the diabody and the Fab-L19 immunoconjugates. The amount of immunoconjugate injected per mouse (in μg) is indicated in the figure legend.

FIG. 4 presents the results of a survival experiment with two different interleukin-2 immunoconjugate molecular formats specific for tumor stroma. Human gastric tumor cell-line LS174T was intrasplenically injected into SCID-beige mice. The Fab-IL2-Fab immunoconjugate is labeled as "Fab-L19", the unconjugated interleukin-2 control is labeled as "Unconj rIL-2", the "diabody"-IL-2 molecule is labeled as "diabody" in FIG. 4. The anti-EDB antibody, L19, was used to generate the antigen binding moieties in both the diabody and the Fab-L19 immunoconjugates. The amount of immunoconjugate injected per mouse (in μg) is indicated in the figure legend, and reflects same numbers of immunoconjugate molecules.

FIG. 5 shows immunohistochemical images of human uterus tissue at 100× and 400× magnification. The 2B10 variable region generated by the methods described in Example 3 binds to the A2 domain of human tenascin (TNC-A2). The 2B10 variable region in a Fab fragment was fused to a FLAG fragment (SHD2B10-FLAG). Healthy and cancerous human uterine tissue samples were prepared for immunohistochemical staining. Subsequently, the samples were incubated with the SHD2B10-FLAG Fab fragment. The samples were then washed and incubated with a fluorescent antibody specific for the FLAG epitope. Cancerous tissue samples exhibited higher expression levels of TNC-A2 as compared to the healthy tissue samples.

FIG. 6 shows the expression levels of TNC-A2 in various human tissue samples in terms of % of immunofluorescence surface area. Various human tissue samples from healthy individuals and cancer patients were incubated with the SHD2B10-FLAG Fab fragment as described in FIG. 5.

FIG. 7 shows the expression levels of Fibroblast Activated Protein (FAP) in various human tissue samples in terms of % of immunofluorescence surface area. Various human tissue samples from healthy individuals and cancer patients were incubated with a commercial antibody against FAP (Abeam). The top portion of each bar on the graph represents tumor expression of FAP, while the bottom portion of each bar on the graph represents normal FAP expression.

FIG. 8 presents BIACORE data showing the affinity of a known IgG antibody, L19, for EDB.

FIG. 9 presents BIACORE data showing the affinity of an Fab-IL-2-Fab immunoconjugate specific for EDB. The Fab fragments in the immunoconjugate were derived from the L19 antibody.

FIG. 10 presents BIACORE data showing the affinity of a "diabody"-IL2 fusion protein specific for EDB. The diabody scFv fragment was derived from the L19 antibody. The "diabody"-IL2 fusion protein includes an 8 amino acid linker located between the scFv fragment and the IL-2 molecule.

FIG. 11 presents BIACORE data showing the affinity of a "diabody"-IL2 fusion protein specific for EDB. The diabody scFv fragment was derived from the L19 antibody. The "diabody"-IL2 fusion protein includes a 12 amino acid linker between the scFv fragment and the IL-2 molecule FIG. 12 presents BIACORE data showing the affinity of a known IgG antibody, F16, for immobilized domain A1 of tenascin (TNC-A1). FIG. 12 also presents BIACORE data showing the affinity of an Fab fragment of the F16 antibody for TNC-A1. Dissociation constants ($K_D$) calculated for the F16 IgG and Fab molecules are indicated in the figure.

FIG. 13 presents BIACORE data showing the affinity of IL-2 for immobilized IL-2 receptor. Heterodimerization of the β and γ chains of IL-2R was achieved by fusing the respective chains to the "knob-into-holes" variants of the Fc portion of a human IgG1 as described in Merchant, A. M. et al., *Nat. Biotech.* 16:677-681 (1998). The $K_D$ value calculated from the BIACORE data is indicated in the figure.

FIG. 14 presents BIACORE data showing the affinity of a "diabody"-IL-2 fusion protein for TNC-A1 and IL-2 receptor. The scFv molecule in the diabody is derived from the F16 antibody. The $K_D$ values calculated from the BIACORE data are indicated in the figure.

FIG. 15 presents BIACORE data showing the affinity of an Fab-IL-2-Fab immunoconjugate for TNC-A1 and IL-2, receptor. The Fab molecules in the immunoconjugate were derived from the F16 antibody. The $K_D$ values calculated from the BIACORE data are indicated in the figure.

FIG. 16 presents BIACORE data showing the affinity of an scFv-IL-2-scFv immunoconjugate for TNC-A1 and IL-2 receptor. The scFv molecules in the immunoconjugate were derived from the F16 antibody. The $K_D$ values calculated from the BIACORE data are indicated in the figure.

FIG. 17 is a summary table of the $K_D$ values obtained from the BIACORE studies presented in FIGS. 12-16.

FIG. 18 presents the results of an efficacy experiment comparing the "diabody"-IL-2 molecule targeting the EDB domain of fibronectin to the Fab-interleukin-2-Fab immunoconjugate (labeled as "Fab-SH2B10", comprising the heavy and light chain variable regions of SEQ ID NOs: 3 and 7, respectively) targeting the A2 domain of tenascin C. The unconjugated interleukin-2 control is labeled as "Unconj rIL-2," the "diabody"-IL-2 molecule is labeled as "L19 diabody" in FIG. 18. The anti-EDB antibody, L19, was used to generate the antigen binding moiety in the diabody immunoconjugate. The teratocarcinoma cell-line F9 was subcutaneously injected into immunocompetent mice of the 129 strain. The amount of inununoconjugate injected per mouse (in μg) is indicated in the figure legend. Treatment was started at day 6 and 5 injections were performed in total until day 11 of the experiment.

FIG. 19 shows the induction of proliferation of NK-92 cells by anti-FAP, or anti-tenascin C, Fab-IL2-Fab immunoconjugates (generated using the $V_H$ and $V_L$ sequences of the 3F2, 3D9, 4B3 (anti-FAP), 2F11, and 2B10 constructs (anti-tenascin C)) compared to unconjugated human IL-2. Cell proliferation was measured using the CellTiter Glo system after two days of incubation.

FIG. 20 presents the results of an ELISA assay measuring induction of IFN-γ production by various interleukin-12 containing immunoconjugates compared either to unconjugated cytokines, or to immunoconjugates that contain the p35 and p40 domains of IL-12 in separate molecules. Panel A shows the results on fibronectin coated plates. Panel B shows the results in solution.

FIG. 21 shows Surface Plasmon Resonance (SPR)-based kinetic analyses of affinity-matured anti-FAP Fab fragments. Processed kinetic data sets are presented for clone 19G1 binding to human (hu) FAP (A) and murine (mu) FAP (B), for clone 20G8 binding to hu FAP (C), mu FAP (D) and for clone 4B9 binding to hu FAP (E) and mu FAP (F). Smooth lines represent a global fit of the data to a 1:1 interaction model.

FIG. 22 shows SPR-based kinetic analyses of affinity-matured anti-FAP Fab fragments. Processed kinetic data sets are presented for clone 5B8 binding to hu FAP (A) and mu FAP (B), for clone 5F1 binding to hu FAP (C), mu FAP (D) and for clone 14B3 binding to hu FAP (E) and mu FAP (F). Smooth lines represent a global fit of the data to a 1:1 interaction model.

FIG. 23 shows SPR-based kinetic analyses of affinity-matured anti-FAP Fab fragments. Processed kinetic data sets are presented for clone 16F1 binding to hu FAP (A) and mu FAP (B), for clone 16F8 binding to hu FAP (C), mu FAP (D) and for clone O3C9 binding to hu FAP (E) and mu FAP (F). Smooth lines represent a global fit of the data to a 1:1 interaction model.

FIG. 24 shows SPR-based kinetic analyses of affinity-matured anti-FAP Fab fragments. Processed kinetic data sets are presented for clone O2D7 binding to hu FAP (A) and mu FAP (B), for clone 28H1 binding to hu FAP (C), mu FAP (D), Cynomolgus (cyno) FAP (E) and for clone 22A3 binding to hu FAP (F), mu FAP (G) and cyno (H). Smooth lines represent a global fit of the data to a 1:1 interaction model.

FIG. 25 shows SPR-based kinetic analyses of affinity-matured anti-FAP Fab fragments. Processed kinetic data sets are presented for clone 29B11 binding to hu FAP (A), mu FAP (B), cyno FAP (C) and for clone 23C10 binding to hu FAP (D), mu FAP (E) and cyno FAP (F). Smooth lines represent a global fit of the data to a 1:1 interaction model.

FIG. 26 shows SPR-based kinetic analyses of affinity-matured anti-TNC A2 Fab fragments binding to human (hu) TNC A2. Processed kinetic data sets are presented for clone 2B10_C3B6 (A), clone 2B10_6A12 (B), clone 2B10_C3A6 (C), clone 2B10_O7D8 (D), clone 2B10_O1F7 (E) and clone 2B10_6H10 (F). Smooth lines represent a global fit of the datato a 1:1 interaction model.

FIG. 27 gives an overview of the three purification steps performed for the purification of 3F2-based Fab-IL2-Fab.

FIG. 28 shows results from the purification of 3F2-based Fab-IL2-Fab (A and B) and results from the purification of 4G8-based Fab-IL2-Fab (C and D). (A, C) 4-12% Bis-Tris and 3-8% Tris Acetate SDS-PAGE with fractions during the purification procedure and the end product. (B, D) Analytical size exclusion chromatography after the three applied purification steps.

FIG. 29. shows results from the purification of the 2B10 Fab-IL2-Fab immunoconjugate. (A) 4-12% Bis-Tris SDS-PAGE with fractions during the purification procedure and the end product. (B) Analytical size exclusion chromatography after the three applied purification steps.

FIG. 30 shows the stability assessment of anti-fibronectin EDB L19-based Fab-IL2-Fab. L19 Fab-IL2-Fab was formulated in 20 mM histidine HCl, 140 mM NaCl, pH 6.0 at a concentration of 6.3 mg/ml and stored for 4 weeks at room temperature and at 4° C. Samples were analyzed every week for (A) concentration by UV spectroscopy (after centrifugation to pellet potential precipitated material) and (B) aggregate content by analytical size exclusion chromatography.

Figure 35A:
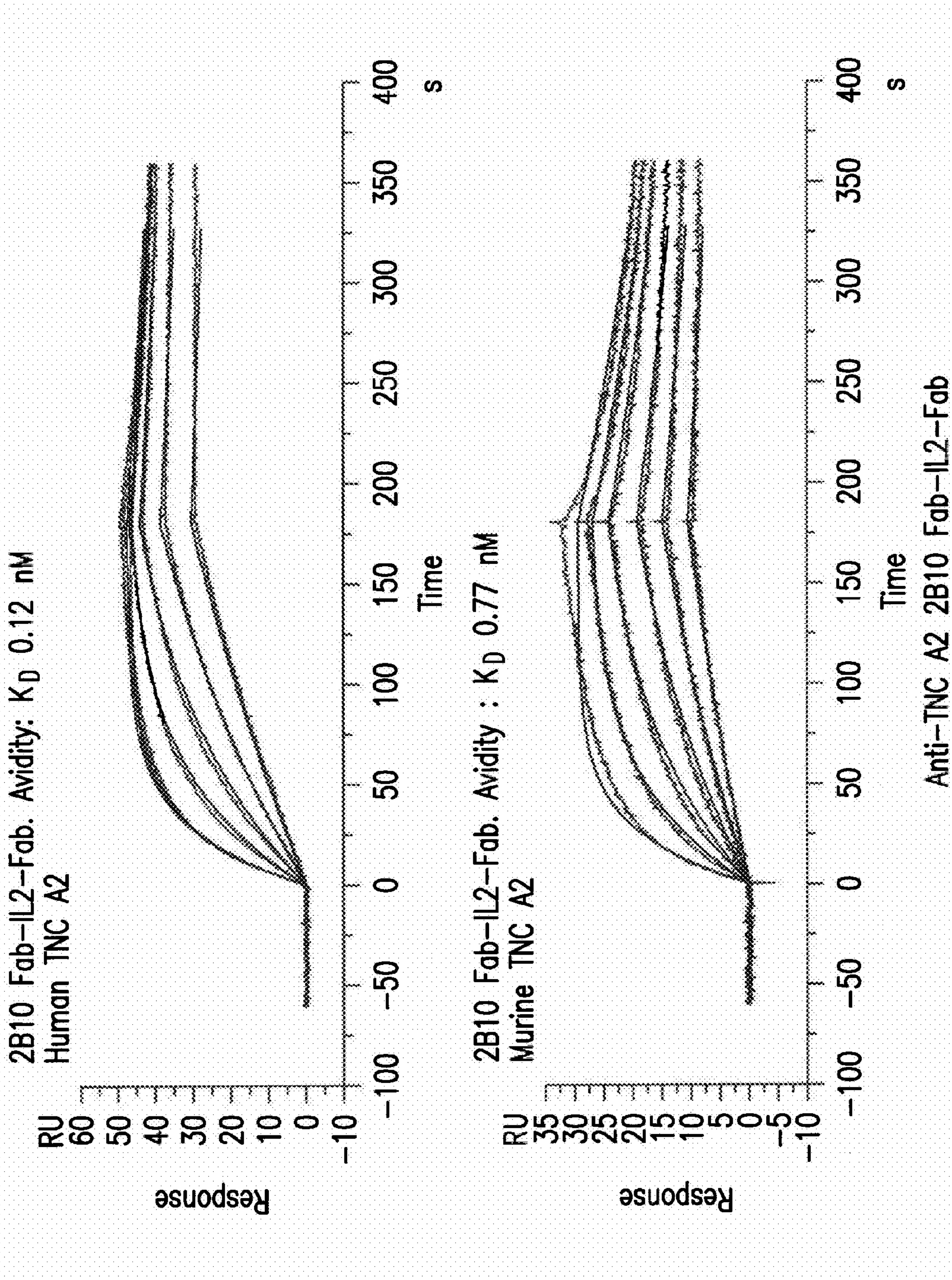
Figure 35B:
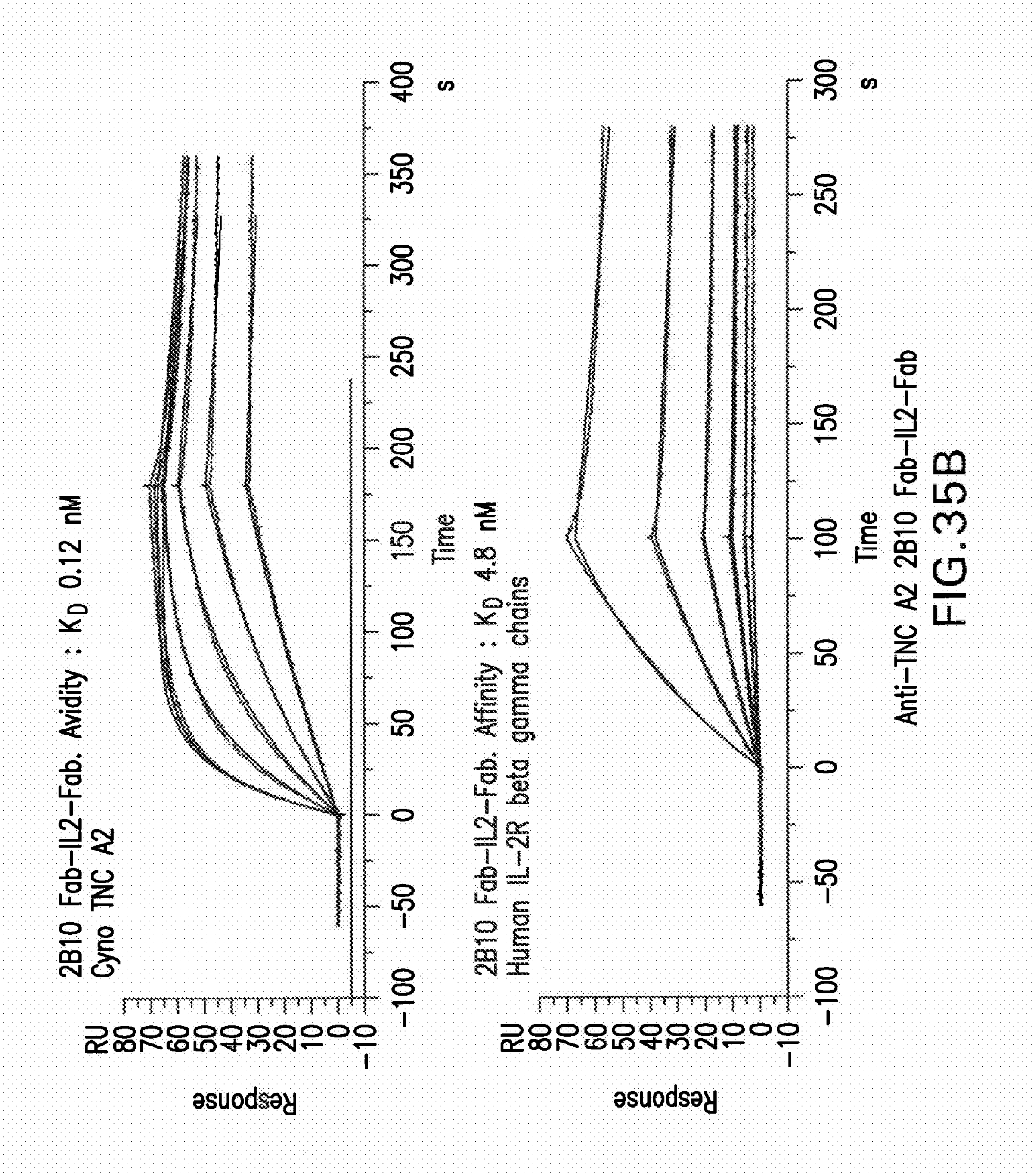

FIGS. 35A and 35B show SPR-based kinetic analyses of TNC A2-targeted 2B10 Fab-IL2-Fab constructs for human chimeric TNC A2 fusion proteins (35A), murine chimeric TNC A2 fusion proteins (35A) and Cynomolgus (cyno) chimeric TNC A2 fusion proteins (35B) and human EL-2 receptor-β/γ (IL2R bg) (35B) as determined by Surface Plasmon Resonance. Smooth lines represent a global fit of the data to a 1:1 interaction model.

Figure 36:
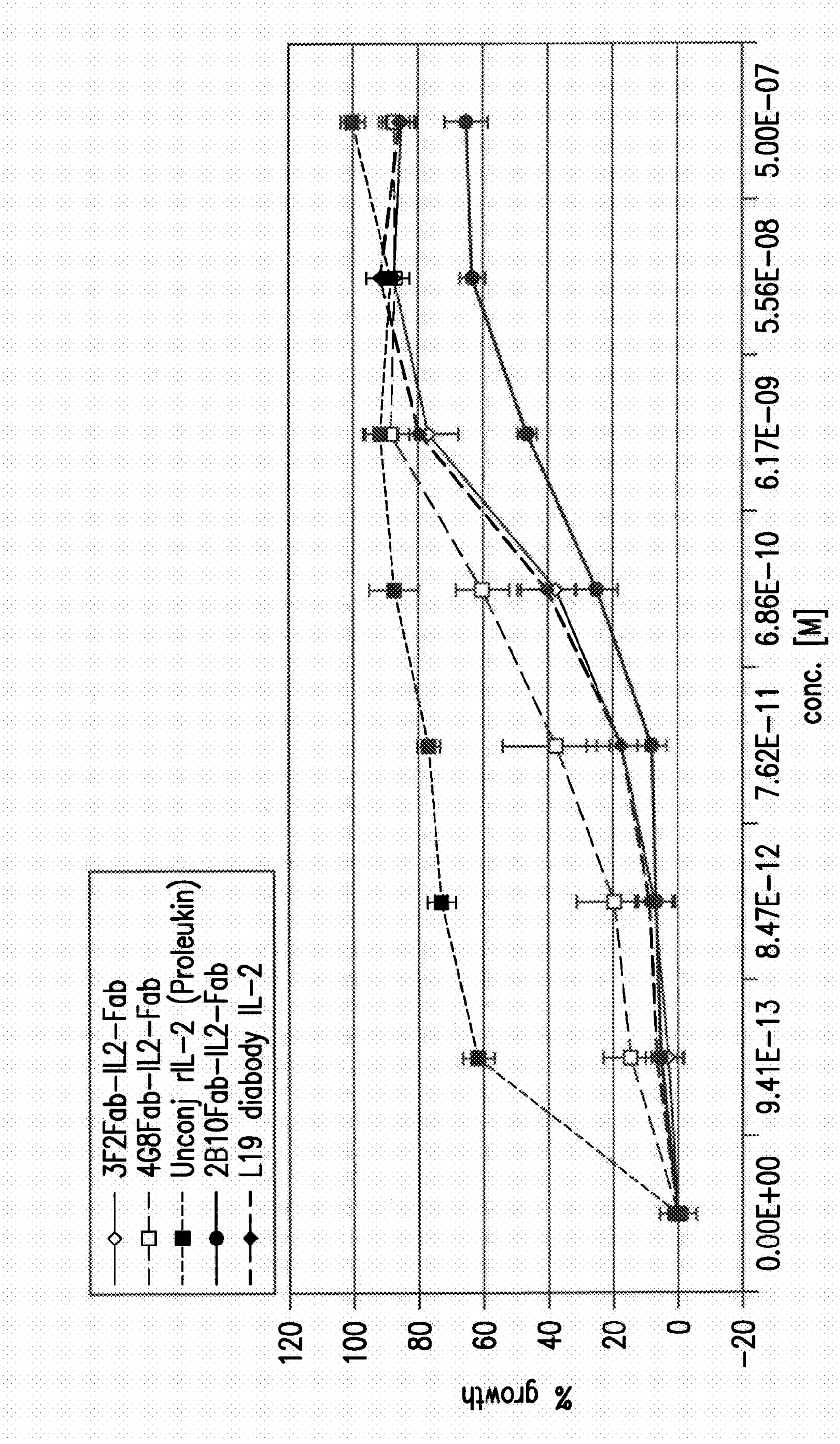
Figure 37A:
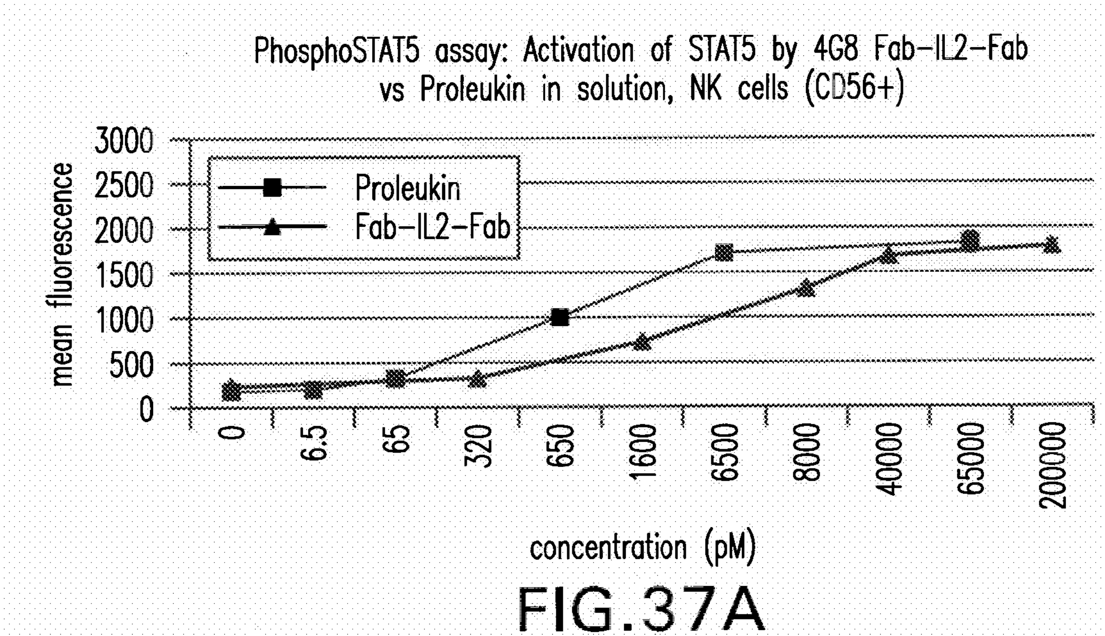
Figure 37B:
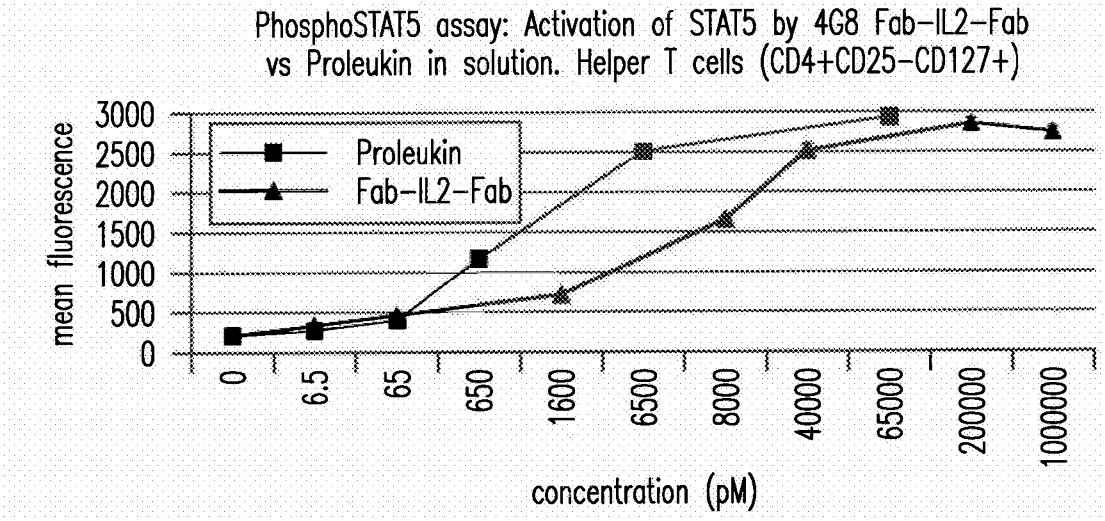
Figure 37C:
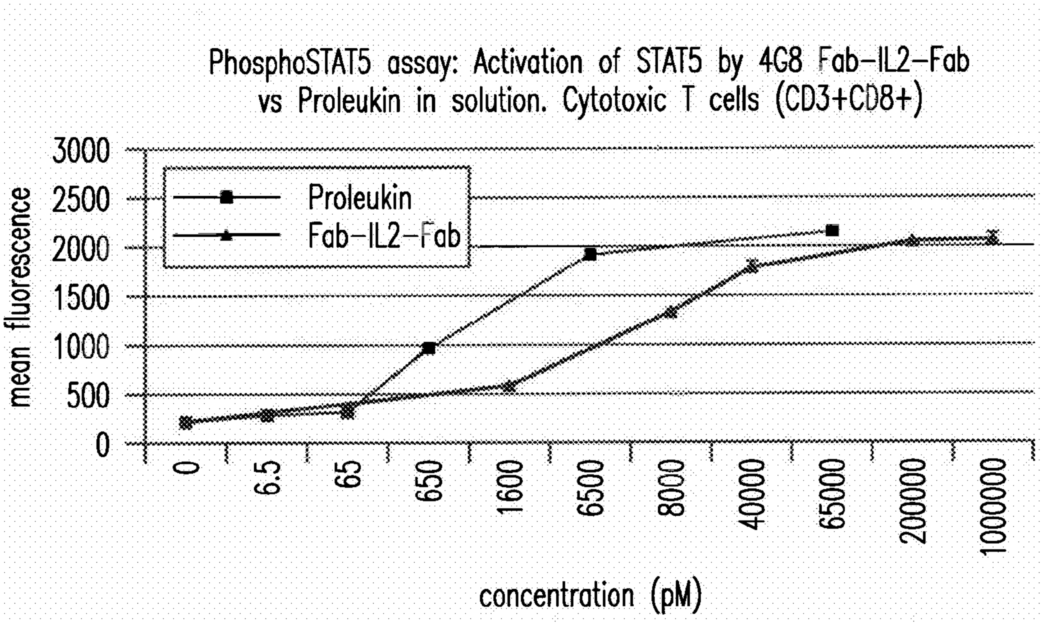
Figure 37D:
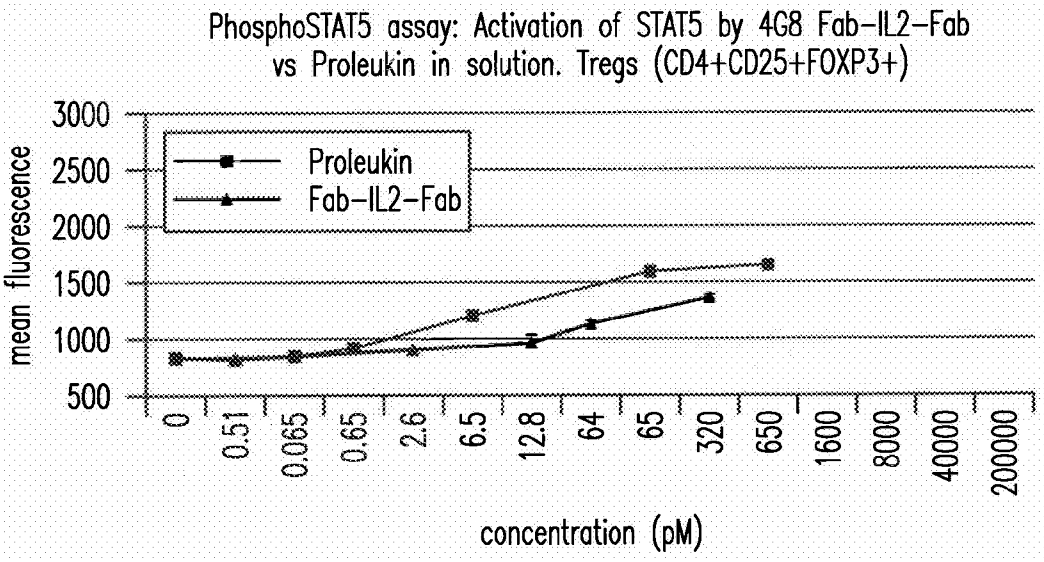

FIG. 36 illustrates the efficacy of targeted IL-2 Fab-IL2-Fab immunoconjugates recognizing TNC A2 (2B10) or FAA (3F2 and 4G8) in inducing proliferation of NK92 cells in comparison to IL-2 (Proleukin) and the L19 diabody recognizing fibronectin-EDB. The x-axis is normalized to the number of IL-2 molecules, as the diabody has two IL-2 effector moieties while the Fab-IL2-Fab constructs contain only one IL-2 effector moiety. Cell proliferation was measured using the CellTiter Glo system after two days of incubation.

FIG. 37 shows the induction of STAT5 phosphorylation as a consequence of IL-2 mediated IL-2 receptor signaling following incubation with a FAP-targeted 4G8-based IL-2 Fab-IL2-Fab immunoconjugate recognizing FAP on different effector cell populations including (A) $CD56^+$ NK cells, (B) $CD4^+CD25^-CD127^+$ helper T cells, (C) $CD3^+$, $CD8^+$ cytoxic T cells and (D) $CD4^+CD25^+FOXP3^+$ regulatory T cells (Tregs) from human PBMCs in solution.

FIG. 38 illustrates the efficacy of targeted IL-2 Fab-IL2-Fab immunoconjugates recognizing TNC A1 (2F11), TNC A2 (2B 10) or FAP (3F2, 4B3 and 3D9) in inducing IFN-γ release and proliferation of NK92 cells in comparison to IL-2, when the immunoconjugates are either present in solution or immobilized via FAP or TNC A2 coated on microtiter plates.

Figure 39:
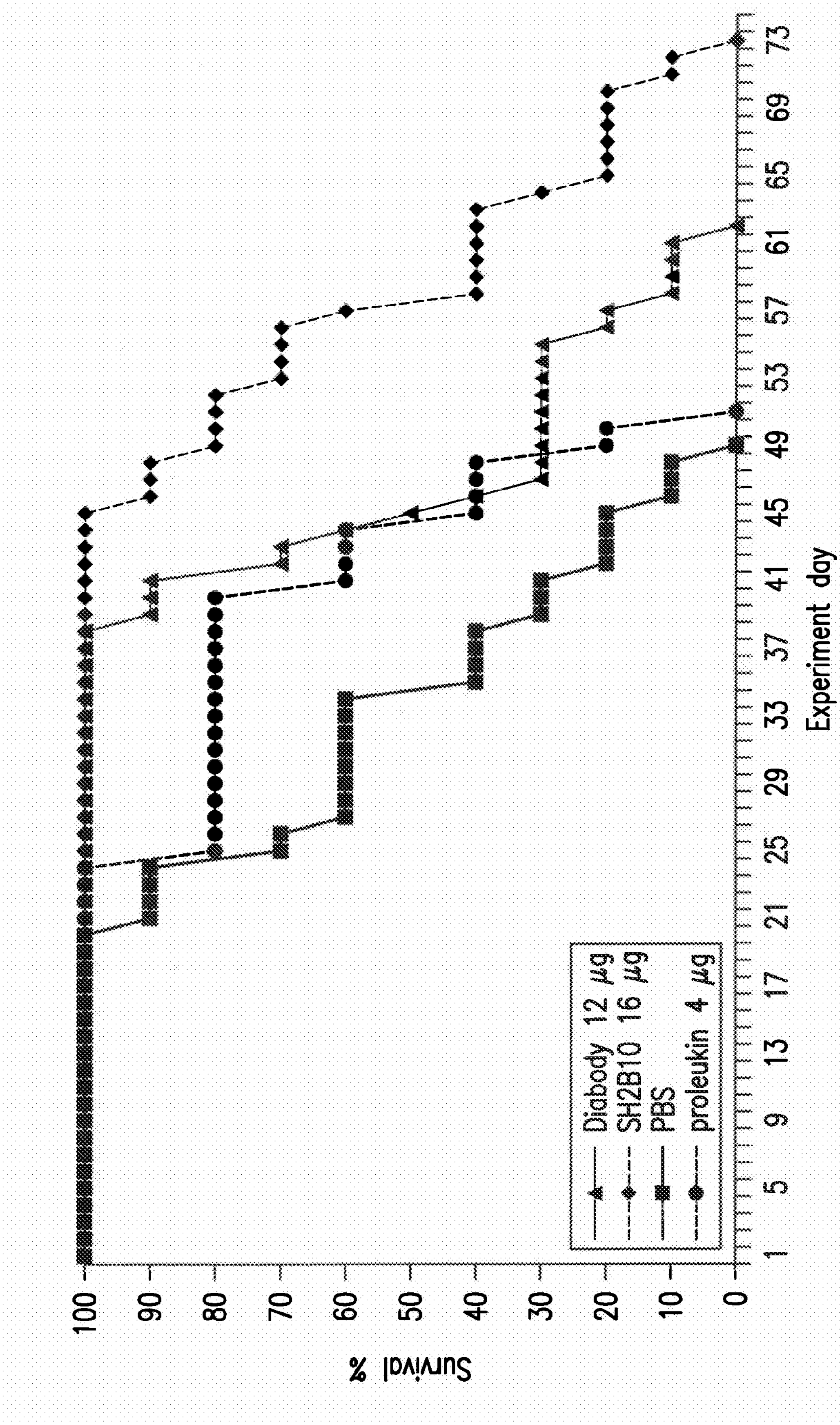

FIG. 39 presents the results of a survival experiment with two different IL-2 immunoconjugate molecular formats specific for tumor stroma. Human colon tumor cell line LS174T was intrasplenically injected into SCID mice. The TNC A2-targeted 2B10 Fab-IL2-Fab immunoconjugate is labeled as "SH2B10", the unconjugated IL-2 control is labeled as "proleukin", the fibronectin EDB-targeted diabody-IL-2 molecule is labeled as "diabody". The amount of immunoconjugate injected per mouse (in μg) is indicated in the figure legend, and reflects same numbers of immunoconjugate molecules.

Figure 40:
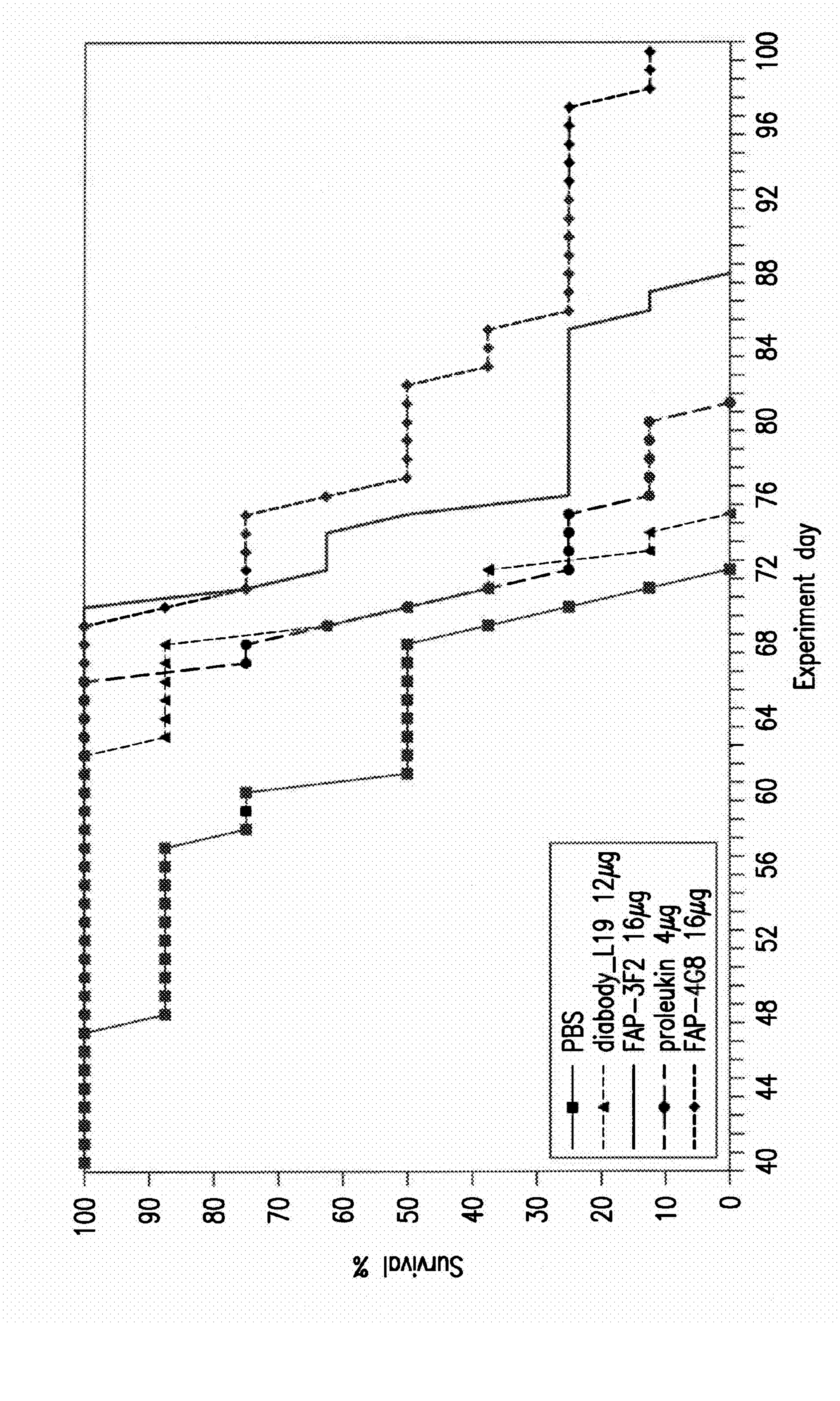

FIG. 40 presents the results of a survival experiment with two different IL-2 immunoconjugate molecular formats specific for tumor stroma. Human renal cell line ACHN was intrarenally injected into SCID mice. The FAP-targeted 3F2 or 4G8 Fab-IL2-Fab immunoconjugates are labeled as "FAP-3F2" and "FAP-4G8", the unconjugated IL-2 control is labeled as "proleukin", the fibronectin EDB-targeted diabody-IL-2 molecule is labeled as "diabody". The amount of immunoconjugates injected per mouse (in μg) is indicated in the figure legend, and reflects same numbers of immunoconjugate molecules.

Figure 41:
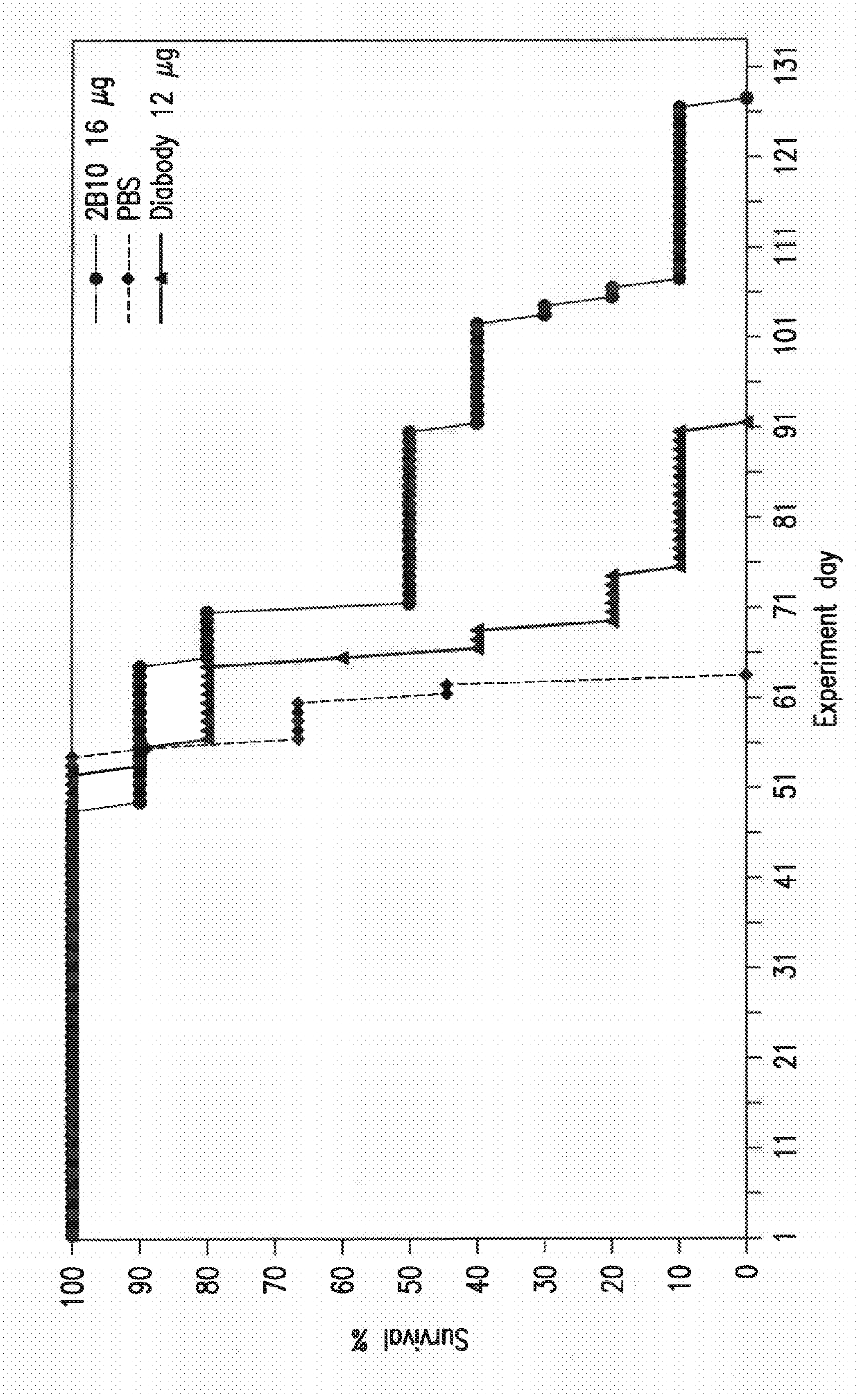

FIG. 41 presents the results of a survival experiment with two different IL-2 immunoconjugate molecular formats specific for tumor stroma. Human NSCLC cell line A549 was injected i.v. into SCID mice. The TNC A2-targeted 2B10 Fab-IL2-Fab immunoconjugate is labeled as "2B10", the fibronectin EDB-targeted diabody-IL-2 molecule is labeled as "diabody". The amount of immunoconjugate injected per mouse (in μg) is indicated in the figure legend, and reflects same numbers of immunoconjugate molecules.

Figure 42A:
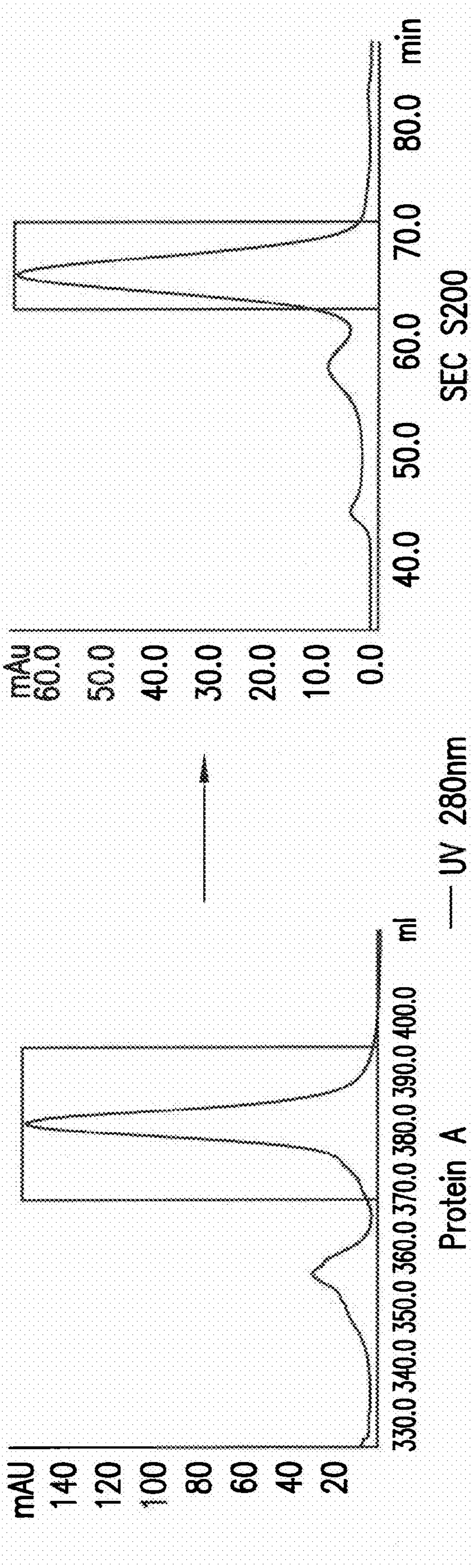
Figure 42B:
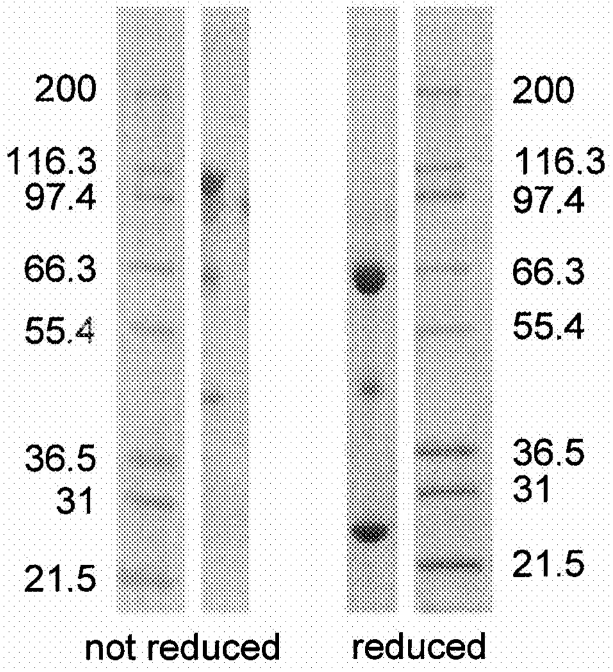

FIG. 42 presents (A) an overview of the purification procedure of the Fab-GM-CSF-Fab immunoconjugate with L19 (Fibronectin Ectodomain-B binder) as Fab, and (B) an SDS-PAGE (reduced, non-reduced) of the purified Fab-GM-CSF-Fab immunoconjugate.

Figure 43:
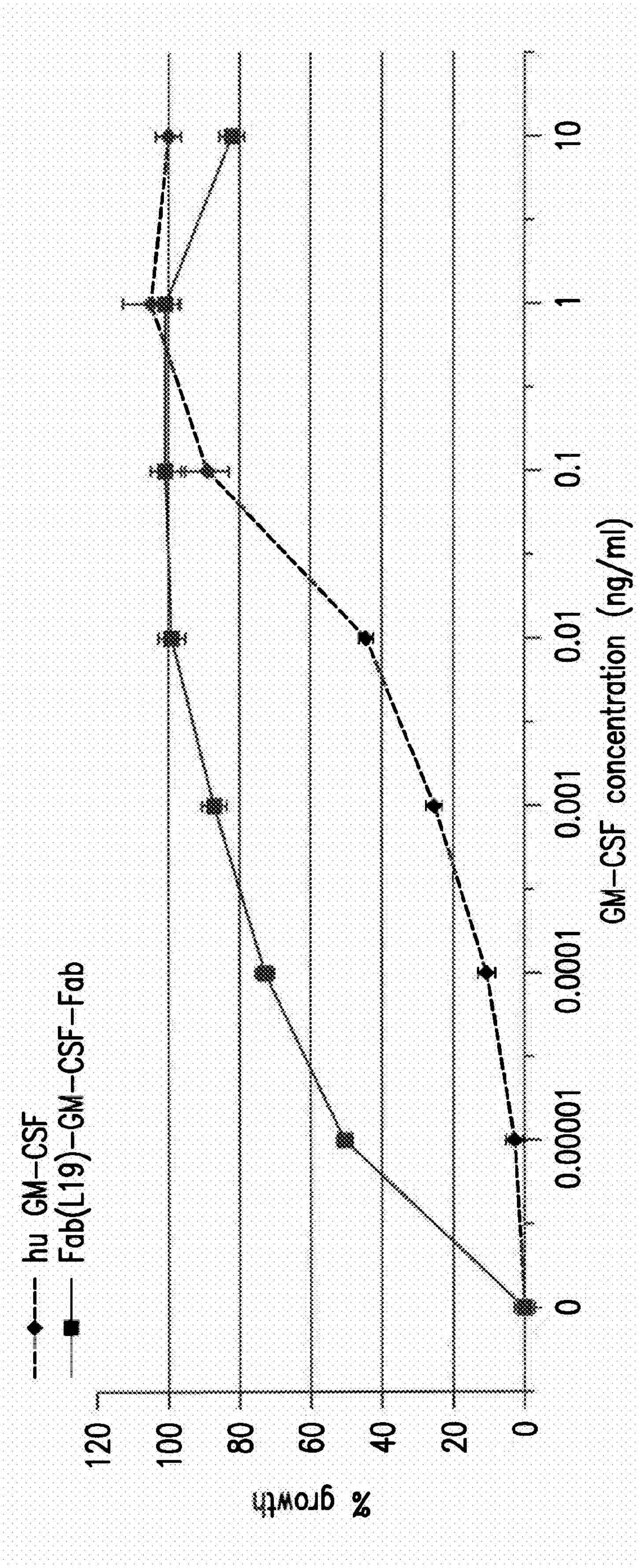

FIG. 43 presents the results of a GM-CSF-dependent proliferation assay comparing the effect of GM-CSF and the purified Fab-GM-CSF-Fab immunoconjugate with L19 (Fibronectin Ectodomain-B binder) as Fab on TF-1 cells.

Figure 44A:
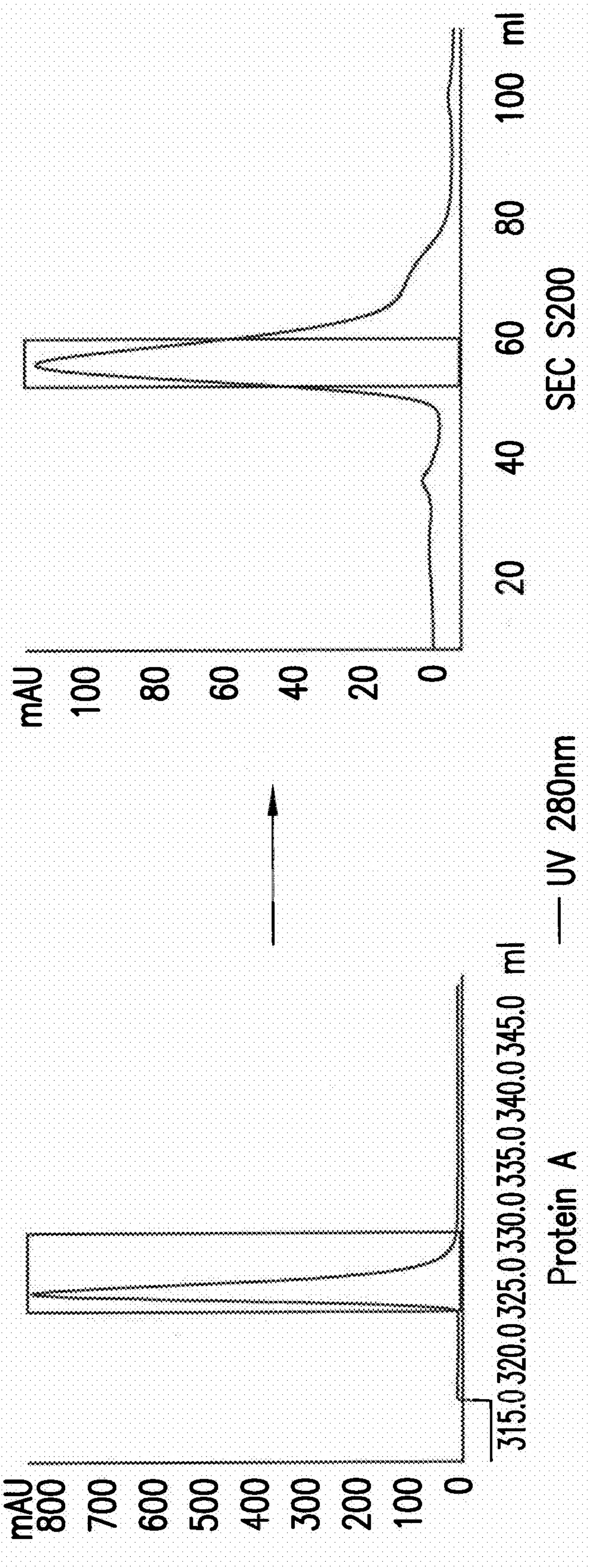
Figure 44B:
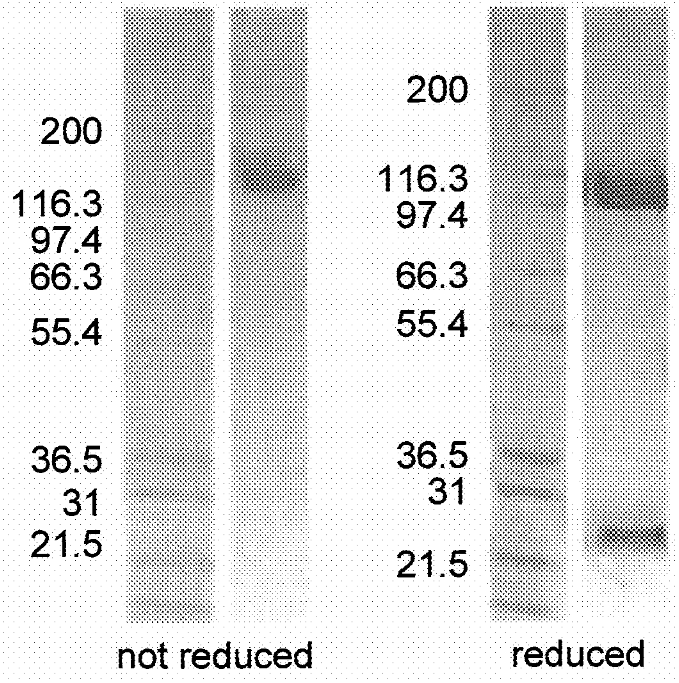

FIG. 44 presents (A) an overview of the purification procedure of the Fab-IL12-Fab immunoconjugate with 4G8 (FAP binder) as Fab, and (B) an SDS-PAGE (reduced, non-reduced) of the purified Fab-IL12-Fab immunoconjugate.

Figure 45A:
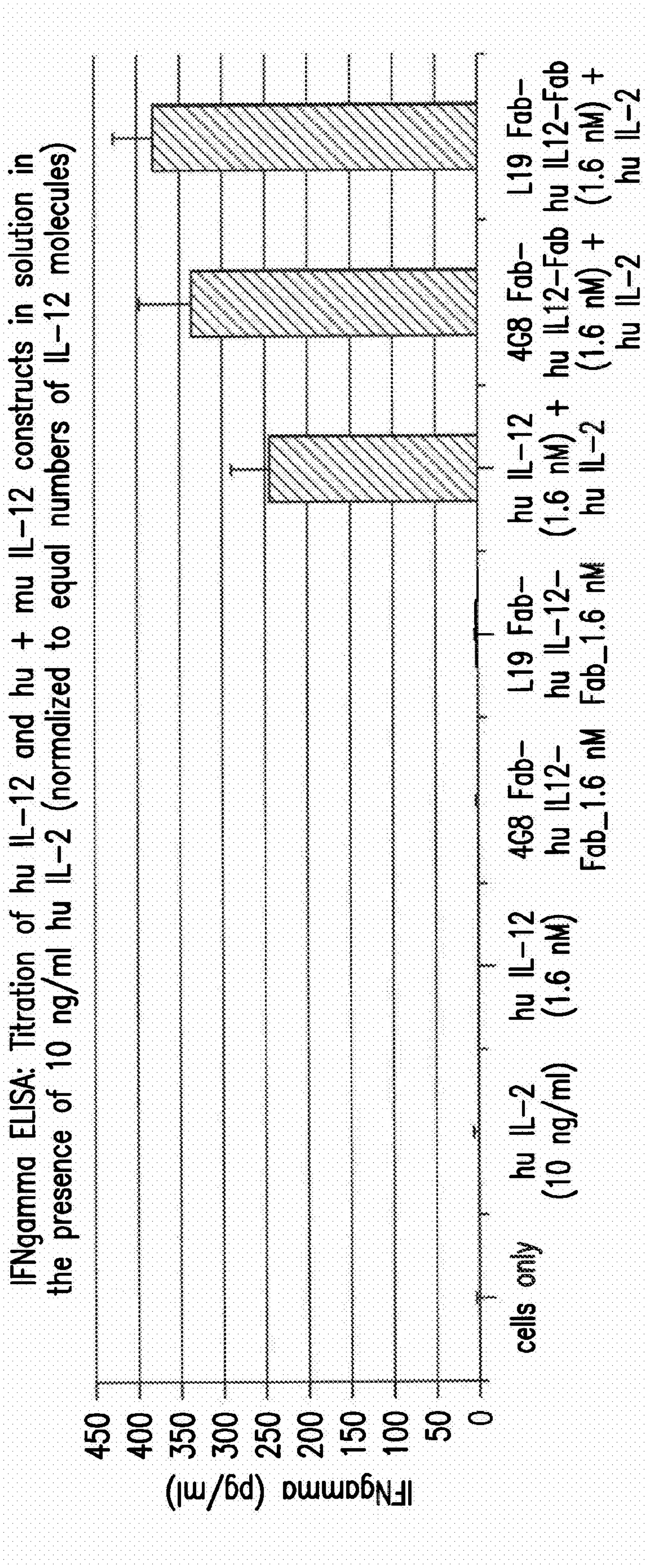
Figure 45B:
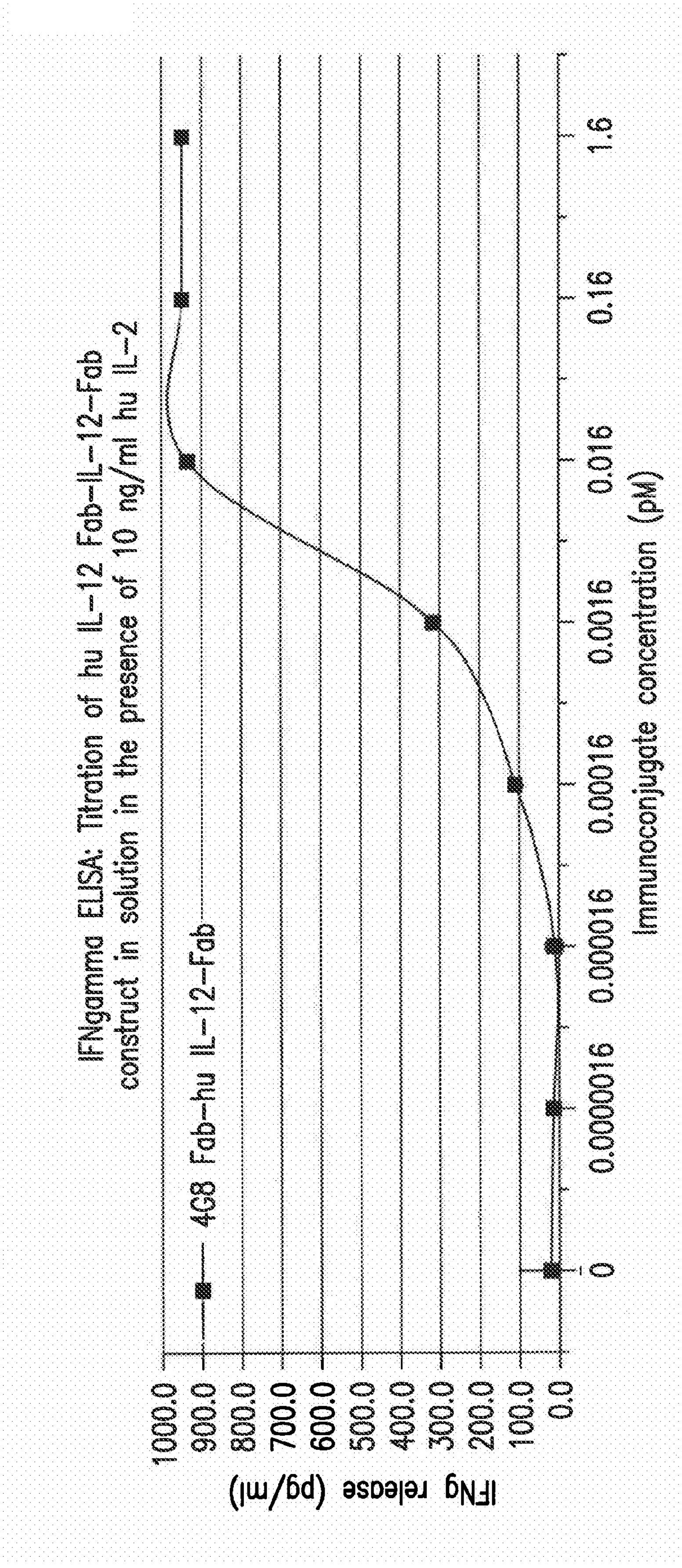

FIG. 45 presents the results of an assay testing IL-12 induced IFN-γ release, comparing the effect of IL-12 and the purified Fab-IL12-Fab immunoconjugate with 4G8 (FAP binder) as Fab, using PBMCs isolated from fresh human blood of a healthy donor.

Figure 46A:
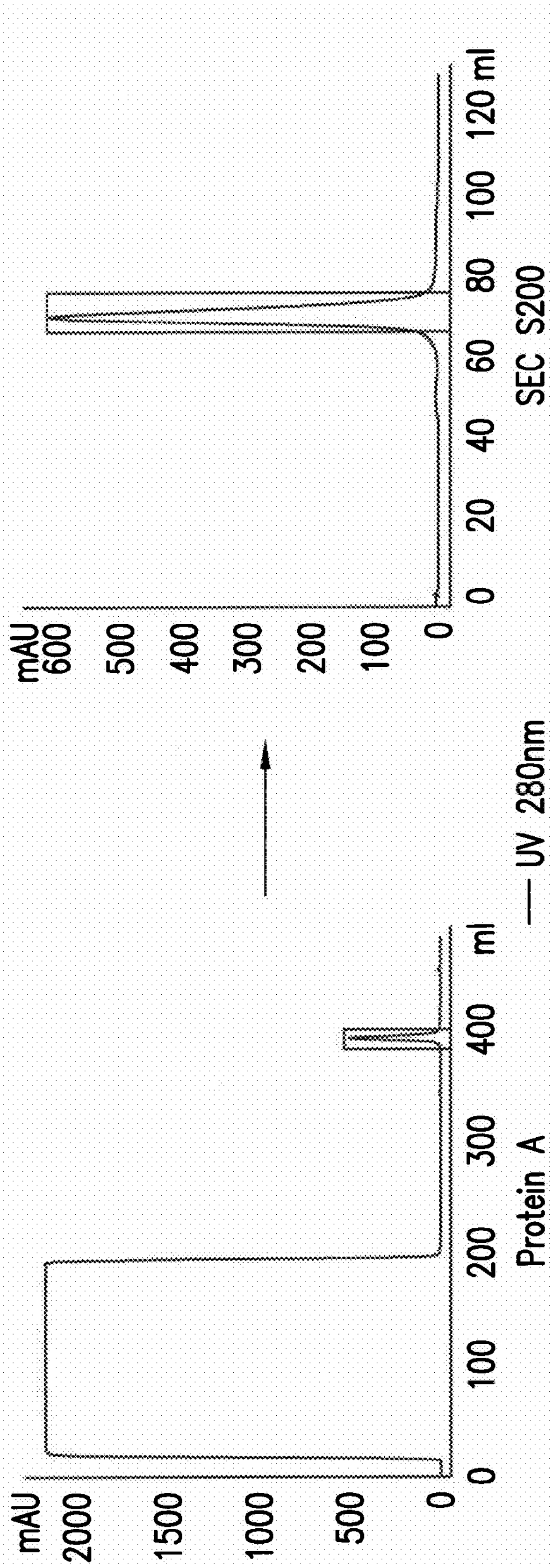
Figure 46B:
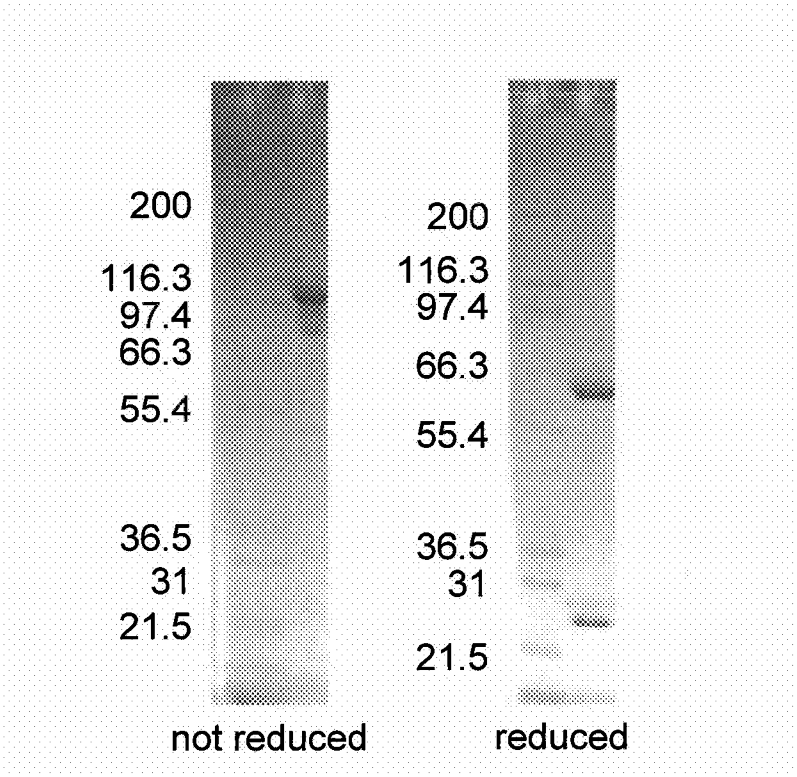

FIG. 46 presents (A) an overview of the purification procedure of the Fab-IFNα2-Fab immunoconjugate with L19 (Fibronectin Ectodomain-B binder) as Fab, and (B) an SDS-PAGE (reduced, non-reduced) of the purified Fab-IFNα2-Fab immunoconjugate.

Figure 47A:
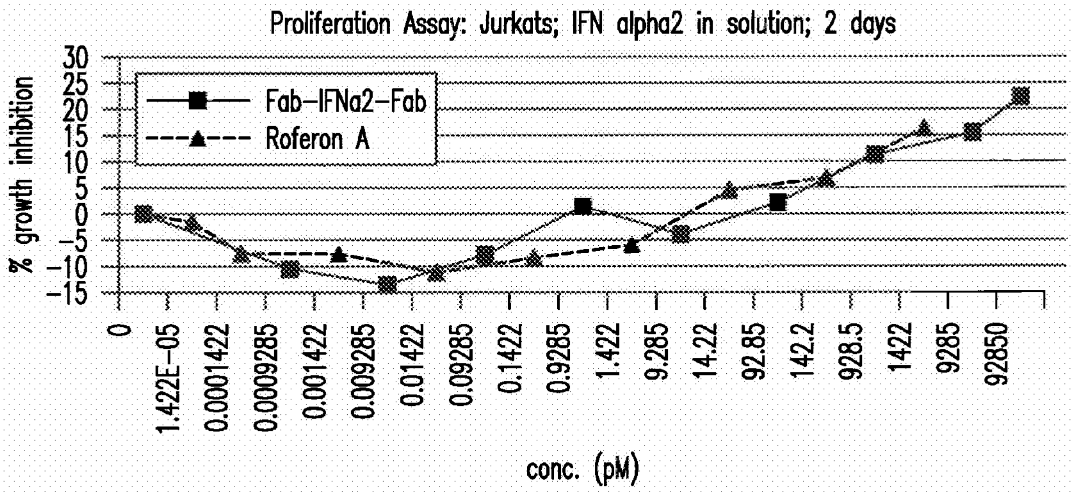
Figure 47B:
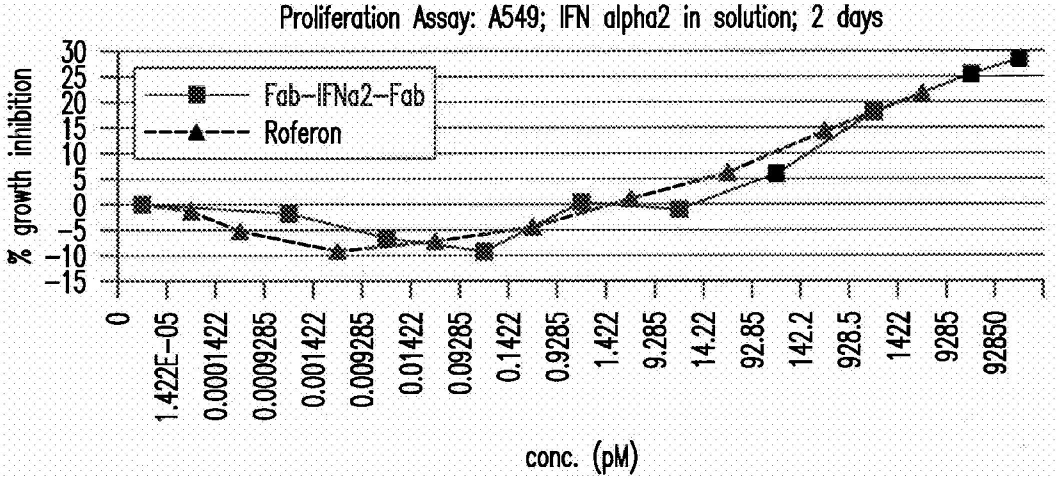

FIG. 47 presents the results of an assay testing IFN-α-induced proliferation inhibition of (A) Jurkat T cells and (B) A549 tumor cells comparing the effect of IFN-α (Roferon A, Roche) and the purified Fab-IFNα2-Fab immunoconjugate with L19 (Fibronectin Ectodomain-B binder) as Fab.

Figure 48A:
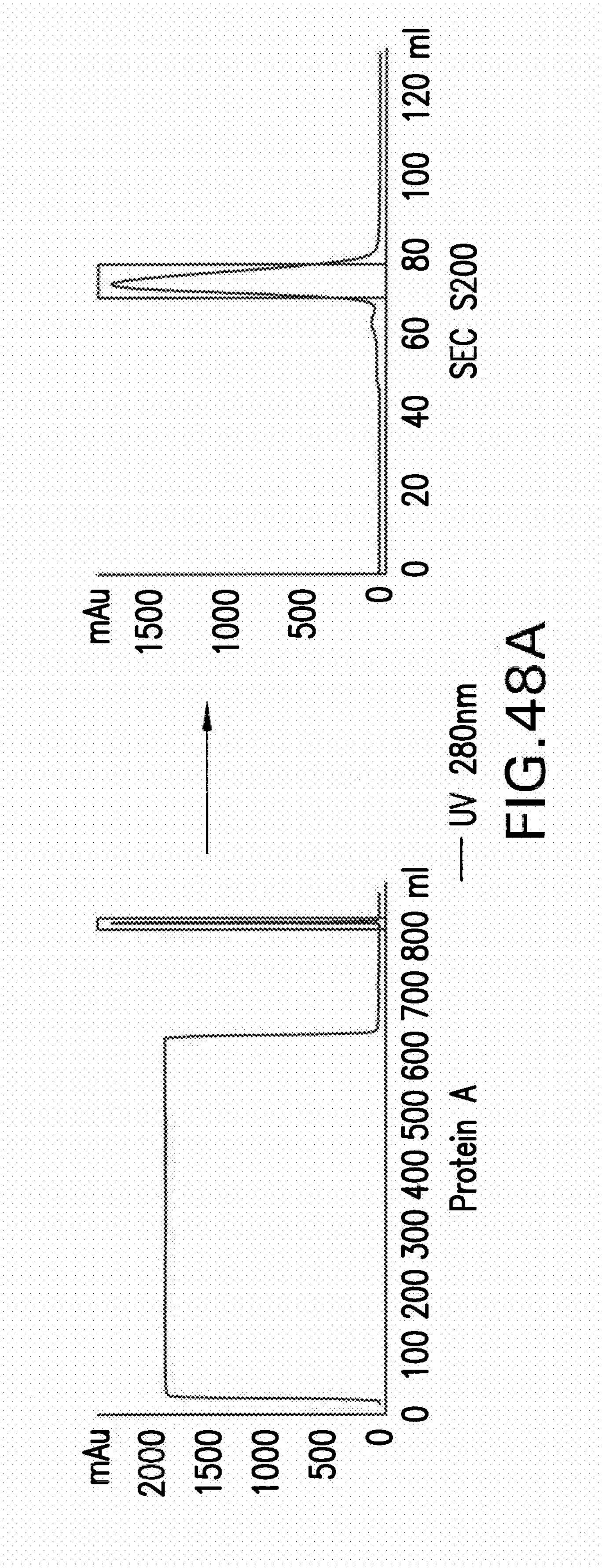
Figure 48B:
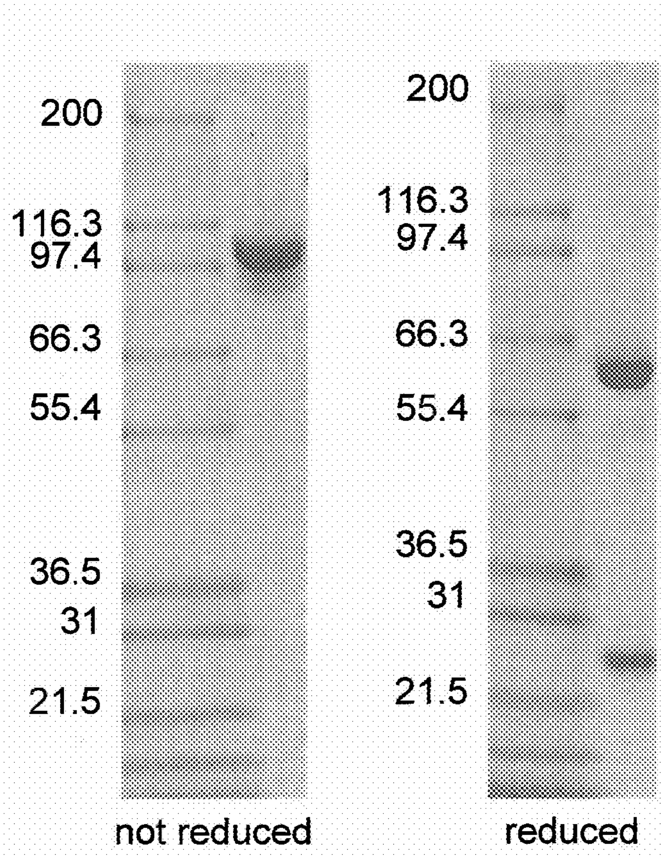

FIG. 48 shows (A) the elution profiles from the purification of the MCSP-targeted MHLG based Fab-IL2-Fab and (B) the results from the analytical characterization of the same Fab-IL2-Fab by SDS-PAGE (NuPAGE Novex Bis-Tris Mini Gel, Invitrogen, MOPS running buffer, reduced and non-reduced).

Figure 49A:
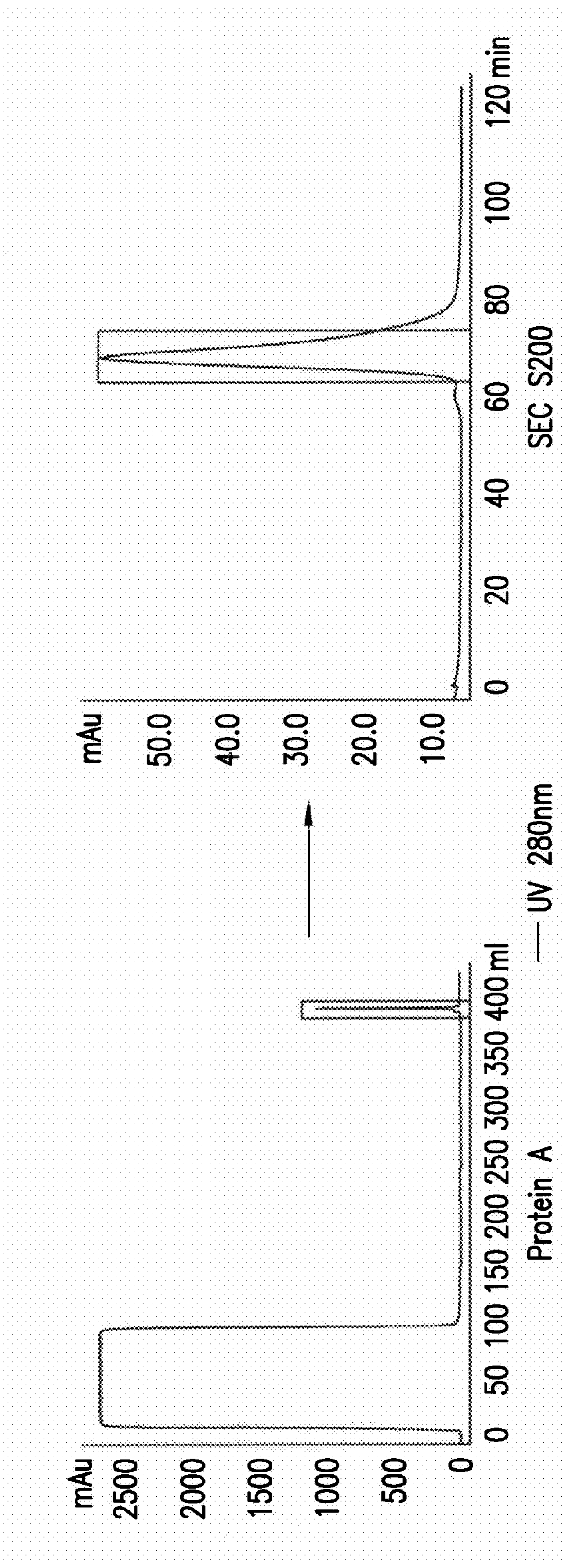
Figure 49B:
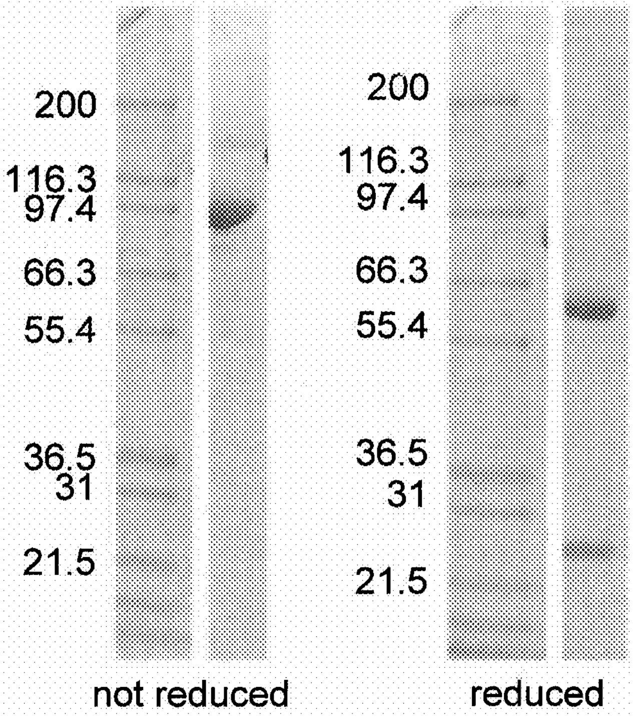

FIG. 49 shows (A) the elution profiles from the purification of the MCSP-targeted MHLG1 based Fab-IL2-Fab and (B) the results from the analytical characterization of the same Fab-IL2-Fab by SDS-PAGE (NuPAGE Novex Bis-Tris Mini Gel, Invitrogen, MOPS running buffer, reduced and non-reduced).

Figure 50:
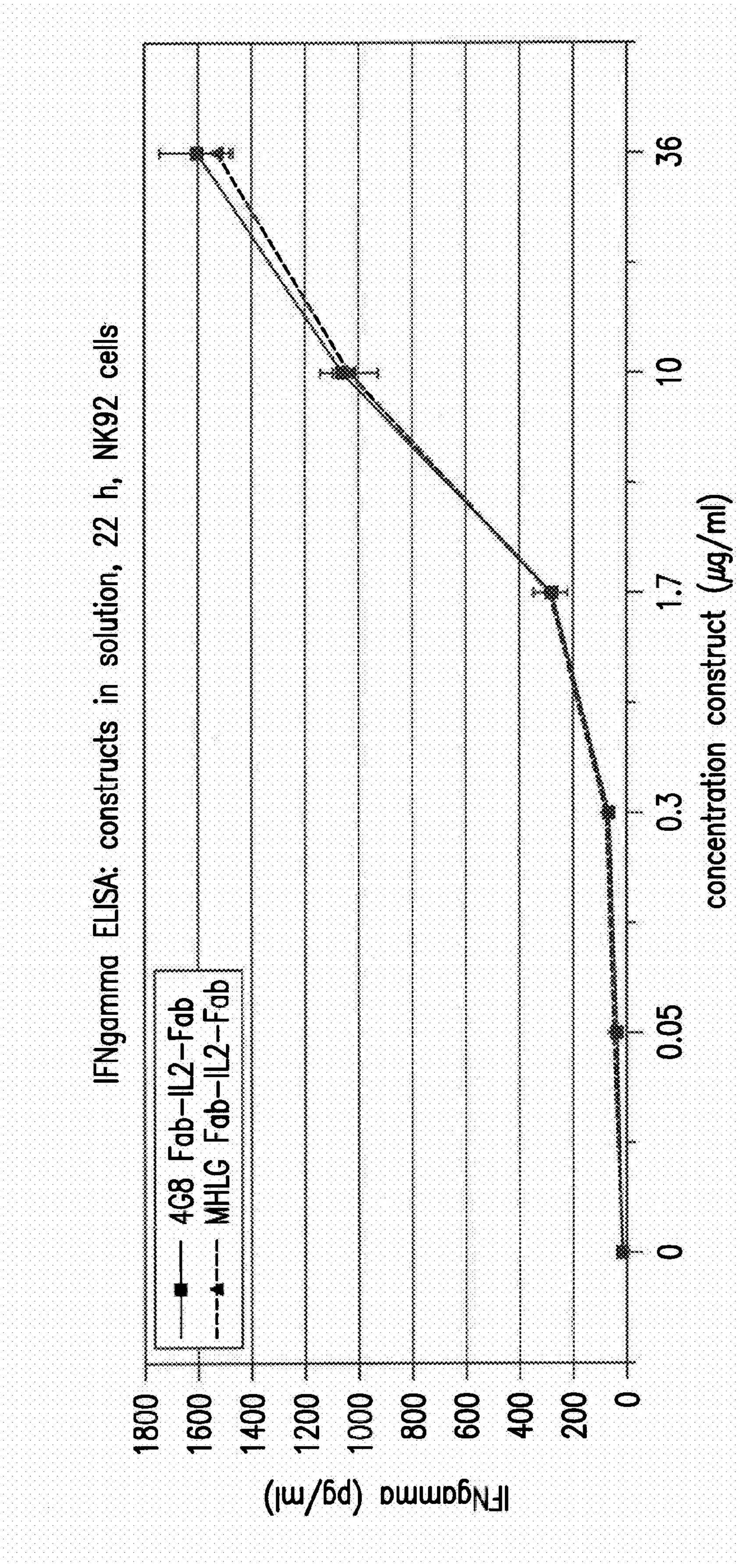

FIG. 50 presents the results of an assay testing IL-2 induced IFN-γ release comparing the effect of the purified Fab-IL2-Fab immunoconjugate with 4G8 (FAP binder) as Fab, and the purified Fab-IL2-Fab immunoconjugate with MHLG KV9 (MCSP binder) as Fab, using IL-2 starved NK92 cells.

Figure 51:
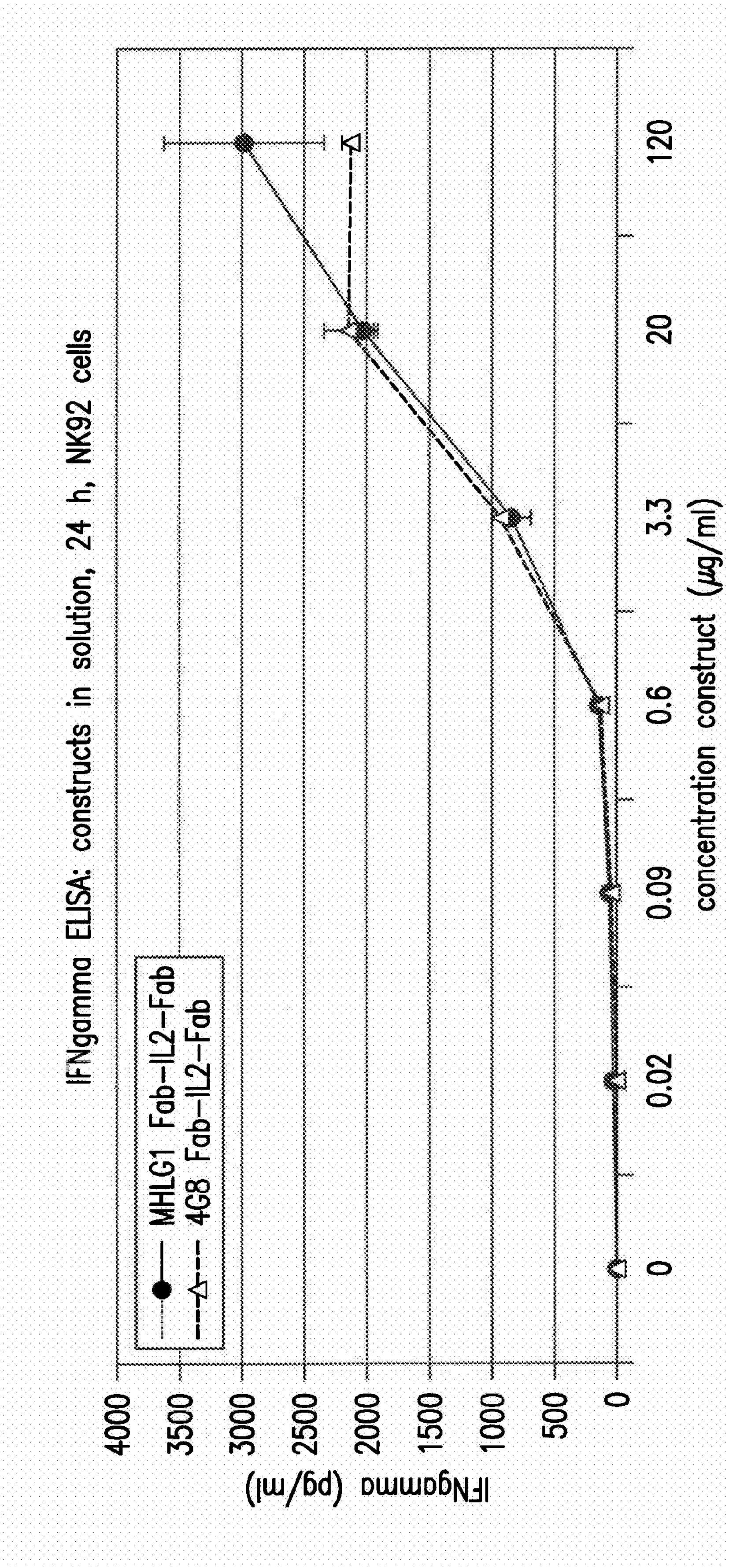

FIG. 51 presents the results of an assay testing IL-2 induced IFN-γ release comparing the effect of the purified Fab-IL2-Fab immunoconjugate with 4G8 (FAP binder) as Fab, and the purified Fab-IL12-Fab immunoconjugate with MHLGI KV9 (MCSP binder) as Fab, using IL-2 starved NK92 cells.

Figure 52:
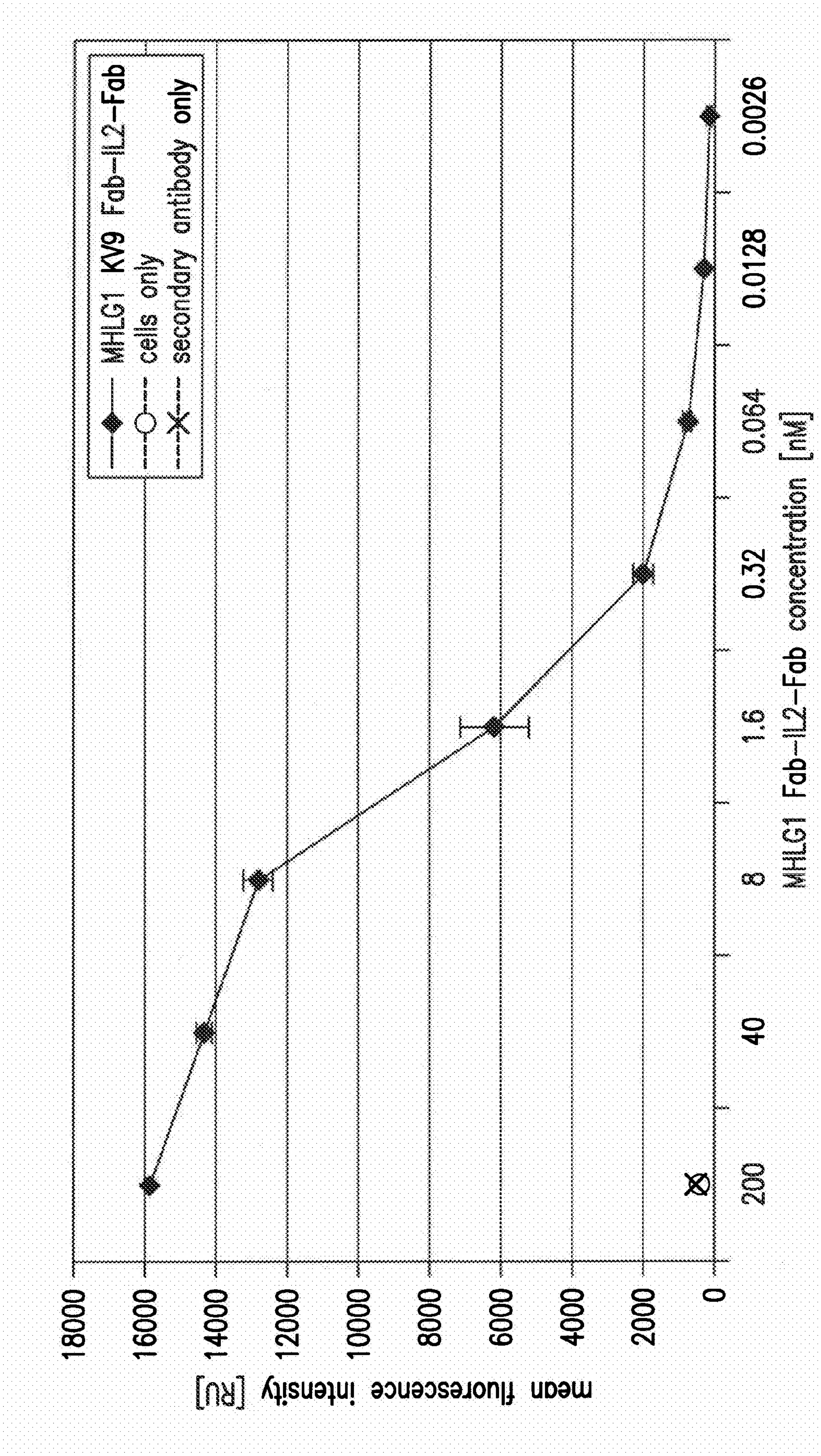

FIG. 52 shows the binding of MCSP-targeted MHLG1 KV9 Fab-IL2-Fab immunoconjugate to Colo38 cells, as determined by flow cytometry. Secondary antibody alone or cells only are shown as negative controls.

Figure 53A:
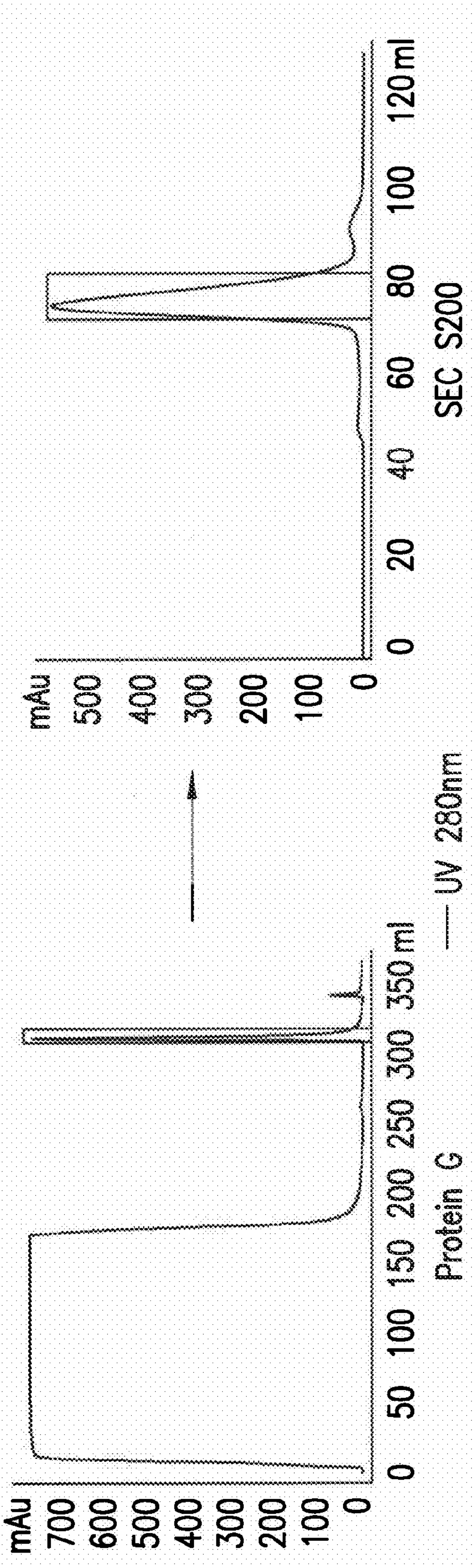
Figure 53B:
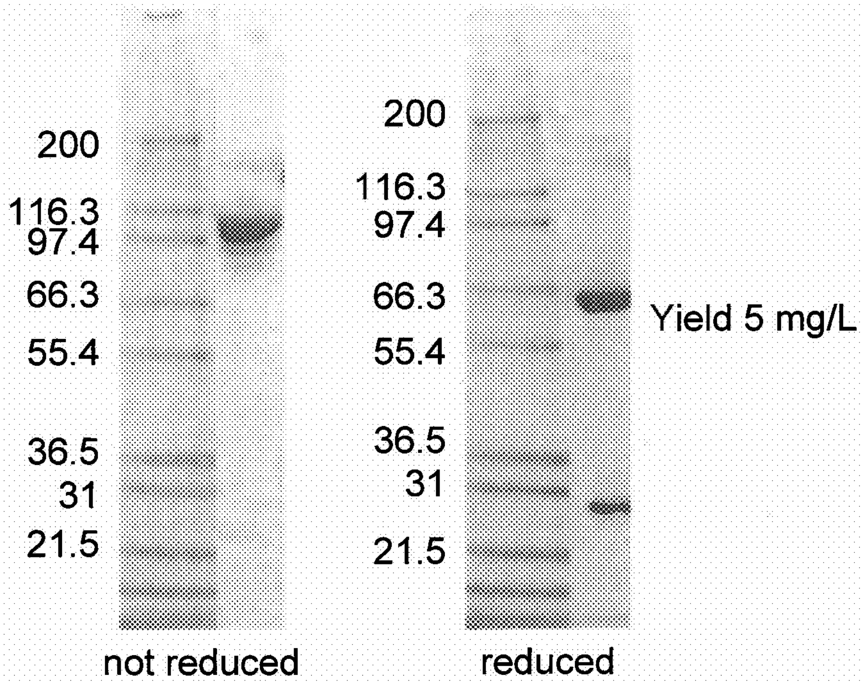

FIG. 53 presents (A) an overview of the purification procedure of the 2B10 Fab-IL2-Fab immunoconjugate with 2B10 (TNC A2 binder) as Fab, and (B) an SDS-PAGE (reduced, non-reduced) of the purified 2B10 Fab-IL2-Fab immunoconjugate.

DETAILED DESCRIPTION OF THE INVENTION

Definitions

Unless defined otherwise, all technical and scientific terms used herein generally have the same meaning as commonly understood by one of ordinary skill in the art. Generally, the nomenclature used herein and the laboratory procedures in cell culture, molecular genetics, nucleic acid chemistry and hybridization described below are those well known and commonly employed in the art. Standard techniques and procedures are generally performed according to conventional methods in the art and various general references (see generally, Sambrook et al. Molecular Cloning: A Laboratory Manual, 2nd ed. (1989) Cold Spring Harbor Laboratory Press, Cold Spring Harbor, N.Y., which is incorporated herein by reference), which are provided throughout this document.

As used herein, the term "immunoconjugate" refers to a polypeptide molecule that includes at least one effector moiety and at least one antigen binding moiety. In one embodiment, the immunoconjugate comprises at least one single-chain effector moiety, and at least two antigen binding moieties. The antigen binding molecule can be joined to the effector moiety by a variety of interactions and in a variety of configurations as described herein.

As used herein, the term "effector moiety" refers to a polypeptide, e.g., a protein or glycoprotein, that influences cellular activity, for example, through signal transduction or other cellular pathways. Accordingly, the effector moiety of the invention can be associated with receptor-mediated signaling that transmits a signal from outside the cell membrane to modulate a response in a cell bearing one or more receptors for the effector moiety. In one embodiment, an effector moiety can elicit a cytotoxic response in cells bearing one or more receptors for the effector moiety. In another embodiment, an effector moiety can elicit a proliferative response in cells bearing one or more receptors for the effector moiety. In another embodiment, an effector moiety can elicit differentiation in cells bearing receptors for the effector moiety. In another embodiment, an effector moiety can alter expression (i.e., upregulate or downregulate) of an endogenous cellular protein in cells bearing receptors for the effector moiety. Non-limiting examples of effector moieties include cytokines, growth factors, hormones, enzymes, substrates, and cofactors. The effector moiety can be associated with an antigen binding moiety in a variety of configurations to form an immunoconjugate.

As used herein, the term "cytokine" refers to a molecule that mediates and/or regulates a biological or cellular function or process (e.g., immunity, inflammation, and hematopoiesis). The term "cytokine" as used herein includes "lymphokines," "chemokines," "monokines," and "interleukins." Examples of useful cytokines include, but are not limited to, GM-CSF, IL-1α, IL-1β, IL-2, IL-3, IL-4, IL-5, IL-6, IL-7, IL-8, IL-10, IL-12, IFN-α, IFN-β, IFN-γ, MIP-1α, MIP1β, TGF-β, TNF-α, and TNF-β.

As used herein, the term "single-chain" refers to a molecule comprising amino acid monomers linearly linked by peptide bonds. In one embodiment, the effector moiety is a single-chain effector moiety. Non-limiting examples of single-chain effector moieties include cytokines, growth factors, hormones, enzymes, substrates, and cofactors. When the effector moiety is a cytokine and the cytokine of interest is normally found as a multimer in nature, each subunit of the multimeric cytokine is sequentially encoded by the single-chain of the effector moiety. Accordingly, non-limiting examples of useful single-chain effector moieties include GM-CSF, IL-1α, IL-1β, IL-2, IL-3, IL-4, IL-5, IL-6, IL-7, IL-8, IL-10, IL-12, IFN-α, IFN-β, IFN-γ, MIP1α, MIP-1β, TGF-β, TNF-α, and TNF-β.

As used herein, the term "control effector moiety" refers to an unconjugated effector moiety. For example, when comparing an IL-2 immunoconjugate of the present invention with a control effector moiety, the control effector moiety is free, unconjugated IL-2. Likewise, e.g., when comparing an IL-12 immunoconjugate of the present invention with a control effector moiety, the control effector moiety is free, unconjugated IL-12 (e.g., existing as a heterodimeric protein wherein the p40 and p35 subunits share only disulfide bond(s)).

As used herein, the term "effector moiety receptor" refers to a polypeptide molecule capable of binding specifically to an effector moiety. For example, where IL-2 is the effector moiety, the effector moiety receptor that binds to a IL-2 (e.g., an immunoconjugate comprising IL-2) is the IL-2 receptor. Similarly, e.g., where IL-12 is the effector moiety of an immunoconjugate, the effector moiety receptor is the IL-12 receptor. Where an effector moiety specifically binds to more than one receptor, all receptors that specifically bind to the effector moiety are "effector moiety receptors" for that effector moiety.

As used herein, the term "antigen binding moiety" refers to a polypeptide molecule that specifically binds to an antigenic determinant. In one embodiment, an antigen binding moiety is able to direct the entity to which it is attached (e.g., an effector moiety or a second antigen binding moiety) to a target site, for example to a specific type of tumor cell or tumor stroma bearing the antigenic determinant. Antigen binding moieties include antibodies and fragments thereof as further defined herein. By "specifically binds" is meant that the binding is selective for the antigen and can be discriminated from unwanted or non-specific interactions. In one embodiment, the immunoconjugate comprises at least one, typically two or more antigen binding moieties with constant regions as further defined herein and known in the art. Useful heavy chain constant regions include any of the five isotypes: α, δ, ϵ, γ, or μ. Useful light chain constant regions include any of the two isotypes: κ and λ.

As used herein, the term "antigenic determinant" is synonymous with "antigen" and "epitope," and refers to a site (e.g., a contiguous stretch of amino acids or a conformational configuration made up of different regions of non-contiguous amino acids) on a polypeptide macromolecule to which an antigen binding moiety binds, forming an antigen binding moiety-antigen complex.

As used herein, the term "control antigen binding moiety" refers to an antigen binding moiety as it would exist free of other antigen binding moieties and effector moieties. For example, when comparing an Fab-IL2-Fab immunoconjugate of the invention with a control antigen binding moiety, the control antigen binding moiety is free Fab, wherein the Fab-IL2-Fab immunoconjugate and the free Fab molecule can both specifically bind to the same antigen determinant.

As used herein, the terms "first" and "second" with respect to antigen binding moieties, effector moieties, etc., are used for convenience of distinguishing when there is more than one of each type of moiety. Use of these terms is not intended to confer a specific order or orientation of the immunoconjugate unless explicitly so stated.

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table I as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE 1

| CDR Definitions[1] | | | |
|---|---|---|---|
| CDR | Kabat | Chothia | AbM[2] |
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table 1 is according to the numbering conventions set forth by Kabat et al. (see below).
[2]"AbM" with a lowercase "b" as used in Table 1 refers to the CDRs as defined by Oxford Molecular's "AbM" antibody modeling software.

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antigen binding moiety of the invention are according to the Kabat numbering system. The polypeptide sequences of the sequence listing (i.e., SEQ ID NOs: 3, 5, 7, 9, 11, 13, 15, 17, 19, 21, 23, 25, 27, 29, 31, 33, 35, 37, 39, 41, 43, 45, 47, 49, 51, 67, 69, 71, 73, 75, 77, 79, 81, 83, 85, 87, 89, 91, 93, 95, 96, 97, etc.) are not numbered according to the Kabat numbering system. However, it is well within the ordinary skill of one in the art to convert the numbering of the sequences of the Sequence Listing to Kabat numbering.

Immunoconjugates

Immunoconjugates are polypeptide molecules that comprise at least one effector moiety and at least one antigen binding moiety. In one embodiment, the effector moiety is a single-chain effector moiety. In one embodiment, the immunoconjugate comprises at least two antigen binding moieties. The antigen binding moieties and effector moieties of the immunoconjugate include those that are described in detail herein above and below and in the accompanying figures. The antigen binding moiety of the immunoconjugate can be directed againt a variety of target molecules (e.g., an antigenic determinant on a protein molecule expressed on a tumor cell or tumor stroma). Non-limiting examples of antigen binding moieties are described herein. In one embodiment, the at least one antigen binding moiety is directed to an antigenic determinant of one or more of the polypeptides represented in Table 5, herein below. Immunoconjugates of the invention typically exhibit one or more of the following properties: high specificity of action, reduced toxicity and/or improved stability, particularly as compared to known immunoconjugates of different configurations targeting the same antigenic determinants and carrying the same effector moities.

In one embodiment, the immunoconjugate comprises at least a first effector moiety and at least a first and a second antigen binding moiety. In a preferred embodiment, the first effector moiety is a single chain effector moiety. In a preferred embodiment, the first and second antigen binding moeity are independently selected from the group consisting of an Fv and an Fab. In a specific embodiment, the first effector moiety shares an amino- or carboxy-terminal peptide bond with a first antigen binding moiety and a second antigen binding moiety shares an amino- or carboxy-terminal peptide bond with either i) the first effector moiety or ii) the first antigen binding moiety. In another embodiment, the immunoconjugate consists essentially of a first single-chain effector moiety and first and second antigen binding moieties.

In one embodiment, a first effector moiety, shares a carboxy-terminal peptide bond with a first antigen binding moiety and further shares an amino-terminal peptide bond with a second antigen binding moiety. In another embodiment, a first antigen binding moiety shares a carboxy-terminal peptide bond with a first effector moiety, preferably a single chain effector moiety, and further shares an amino-terminal peptide bond with a second antigen binding moiety. In another embodiment, a first antigen binding moiety shares an amino-terminal peptide bond with a first effector moiety, preferably a single chain effector moiety, and further shares a carboxy-terminal peptide with a second antigen binding moiety.

In one embodiment, an effector moiety, preferably a single chain effector moiety, shares a carboxy-terminal peptide bond with a first heavy chain variable region and further shares an amino-terminal peptide bond with a second heavy chain variable region. In another embodiment, an effector moiety, preferably a single chain effector moiety, shares a carboxy-terminal peptide bond with a first light chain variable region and further shares an amino-terminal peptide with a second light chain variable region. In another embodiment, a first heavy or light chain variable region is joined by a carboxy-terminal peptide bond to a first effector moiety, preferably a single chain effector moiety, and is further joined by an amino-terminal peptide bond to a second heavy or light chain variable region. In another embodiment, a first heavy or light chain variable region is joined by an amino-terminal peptide bond to a first effector moiety preferably a single chain effector moiety, and is further joined by a carboxy-terminal peptide bond to a second heavy or light chain variable region.

In one embodiment, an effector moiety, preferably a single chain effector moiety, shares a carboxy-terminal peptide bond with a first Fab heavy or light chain and further shares an amino-terminal peptide bond with a second Fab heavy or light chain. In another embodiment, a first Fab heavy or light chain shares a carboxy-terminal peptide bond with a first single-chain effector moiety and further shares an amino-terminal peptide bond with a second Fab heavy or light chain. In other embodiments, a first Fab heavy or light chain shares an amino-terminal peptide bond with a first single-chain effector moiety and further shares a carboxy-terminal peptide bond with a second Fab heavy or light chain.

In one embodiment, the immunoconjugate comprises at least a first effector moiety sharing an amino-terminal peptide bond to one or more scFv molecules and wherein the first effector moiety further shares a carboxy-terminal peptide bond with one or more scFv molecules. In a preferred embodiment, the effector moiety is a single chain effector moiety.

In another embodiment, the immunoconjugate comprises at least a first effector moiety, preferably a single chain effector moiety, and first and second antigen binding moieties, wherein each of the antigen binding moieties includes an scFv molecule joined at its carboxy-terminal amino acid to a constant region that includes an immunoglobulin constant domain, and wherein the first antigen binding moiety is joined at its constant region carboxy-terminal amino acid to the amino-terminal amino acid of the first effector moiety, and wherein the first and second antigen binding moieties are covalently linked through at least one disulfide bond. In a preferred embodiment, the constant region is independently selected from the group consisting of IgG CH1, IgG CH2, IgG CH3, IgG $C_{kappa}$, IgG $C_{lambda}$ and IgE $CH_4$ domains. In one embodiment, the immunoglobulin domain of the first antigen binding moiety is covalently linked to the immunoglobulin domain of the second antigen binding moiety through a disulfide bond. In one embodiment, at least one disulfide bond is located carboxy-terminal of the immunoglobulin domains of the first and second antigen binding moieties. In another embodiment, at least one disulfide bond is located amino-terminal of the immunoglobulin domains of the first and second antigen binding moieties. In another embodiment, at least two disulfide bonds are located amino-terminal of the immunoglobulin domains of the first and second antigen binding moieties.

In a specific embodiment, the immunoconjugate comprises first and second antigen binding moieties, each comprising an scFv molecule joined at its carboxy-terminal amino acid to a constant region that comprises an IgG CH1 domain, wherein the first antigen binding moiety is joined at its constant region carboxy-terminal amino acid to the amino-terminal amino acid of the first effector moiety, preferably a single chain effector moiety, and wherein the first and second antigen binding moieties are covalently linked through at least one disulfide bond. The second antigen binding moiety of the immunoconjugate can be further joined at its carboxy-terminal amino acid to the amino-terminal amino acid of a second effector moiety. In one embodiment, the second effector moiety is a single chain effector moiety.

In a specific embodiment, the immunoconjugate comprises first and second antigen binding moieties each comprising an scFv molecule joined at its carboxy-terminal amino acid to a constant region that comprises an IgG $C_{kappa}$ domain, wherein the first antigen binding moiety is joined at its constant region carboxy-terminal amino acid to the amino-terminal amino acid of the first effector moiety, preferably a single chain effector moiety, and wherein the first and second antigen binding moieties are covalently linked through at least one disulfide bond. The second antigen binding moiety of the immunoconjugate can be further joined at its carboxy-terminal amino acid to the amino-terminal amino acid of a second effector moiety. In one embodiment, the second effector moiety is a single chain effector moiety.

In another specific embodiment, the immunoconjugate comprises first and second antigen binding moieties, each comprising an scFv molecule joined at its carboxy-terminal amino acid to a constant region that comprises an IgE CH4 domain, wherein the first antigen binding moiety is joined at its constant region carboxy-terminal amino acid to the amino-terminal amino acid of the first effector moiety, preferably a single chain effector moiety, and wherein the first and second antigen binding moieties are covalently linked through at least one disulfide bond. The second antigen binding moiety of the immunoconjugate can be further joined at its carboxy-terminal amino acid to the amino-terminal amino acid of a second effector moiety. In one embodiment, the second effector moiety is a single chain effector moiety.

In another specific embodiment, the immunoconjugate comprises first and second antigen binding moieties each, comprising an scFv molecule joined at its carboxy-terminal amino acid to an IgE CH3 domain, wherein the first antigen binding moiety is joined at its carboxy-terminal amino acid to the amino-terminal amino acid of the first effector moiety, preferably a single chain effector moiety, and wherein the first and second antigen binding moieties are covalently linked through at least one disulfide bond. The second antigen binding moiety of the immunoconjugate can be further joined at its carboxy-terminal amino acid to the amino-terminal amino acid of a second effector moiety. In one embodiment, the second effector moiety is a single chain effector moiety.

In another embodiment, the immunoconjugate comprises first and second effector moieties, and first and second antigen binding moieties, wherein each of the antigen binding moieties comprises an Fab molecule joined at its heavy or light chain carboxy-terminal amino acid to an IgG1 CH3 domain, and wherein each of the IgG1 CH3 domains is joined at its respective carboxy-terminal amino acid to the amino-terminal amino acid of one of the effector moieties, and wherein the first and second antigen binding moieties are covalently linked through at least one disulfide bond. In a preferred embodiment, the first and/or second effector moiety is a single chain effector moiety. In a further embodiment, the IgG1 CH3 domains of the antigen binding moieties may be joined by disulfide bond. In another embodiment, at least one disulfide bond is located carboxy-terminal of the IgG1 CH3 domains of the first and second antigen binding moieties. In another embodiment, at least one disulfide bond is located amino-terminal of the IgG1 CH3 domains of the first and second antigen binding moieties. In another embodiment, at least two disulfide bonds are located amino-terminal of the IgG1 CH3 domains of the first and second antigen binding moieties.

In another embodiment, the immunoconjugate comprises one or more proteolytic cleavage sites located between effector moieties and antigen binding moieties.

Components of the immunoconjugate (e.g., antigen binding moieties and/or effector moieties) may be linked directly or through various linkers (e.g., peptide linkers comprising one or more amino acids, typically about 2-10 amino acids) that are described herein or are known in the art.

In a particular embodiment, the immunoconjugate has improved stability in solution, particularly compared to known immunoconjugate preparations. In one embodiment, the immunoconjugate binds to an antigenic determinant with a dissociation constant ($K_D$) that is at least about 2, 3, 4, 5, 6, 7, 8, 9, 10, 11, 12, 13, 14, 15, 16, 17, 18, 19, 20, 21, 22, 23, 24, or 25 times lower than that for a control antigen binding moiety. In a more specific embodiment, the immunoconjugate binds to an antigenic determinant with a $K_D$ that is about 10 times lower than that for a control antigen binding moiety. In one embodiment, the immunoconjugate binds to an antigenic determinant with a $K_D$ that is lower than about 10 nM, lower than about 1 nM, or lower than about 0.1 nM.

In another embodiment, the immunoconjugate has a superior safety profile compared to known immunoconjugate preparations. The immunoconjugate preferably elicits fewer and less severe side effects, such as toxicity, destruction of non-tumor cells, etc. The decrease in side effects may be attributed to the reduced binding affinity of the immunoconjugates of the invention towards effector moiety receptors. In one embodiment, the immunoconjugate binds to an effector moiety receptor with a $K_D$ that is at least about 2, 3, 4, 5, 6, 7, 8, 9, 10, 11, 12, 13, 14, 15, 16, 17, 18, 19, 20, 21, 22, 23, 24, or 25 times greater than that for a control effector moiety. In a more specific embodiment, the immuonconjugate binds to an effector moiety receptor with a $K_D$ that is about 2 times greater than that for a control effector moiety. In another embodiment, the immuonconjugate binds to an effector moiety receptor with a $K_D$ that is about 10 times greater than that for a control effector moiety. In another embodiment, the immunoconjugate binds to an effector moiety receptor with a $K_D$ that is at least 2, 3, 4, 5, 6, 7, 8, 9, or 10 times greater than that for a corresponding effector moiety in a "diabody" immunoconjugate molecule. In another embodiment, the immunoconjugate binds to an effector moiety receptor with a dissociation constant $K_D$ that is about 10 times greater than that for a corresponding effector moiety in a "diabody" immunoconjugate.

In another embodiment, the immunoconjugate has superior efficacy, particularly compared to known immunoconjugate preparations. In one embodiment, the immunoconjugate is better able to inhibit increases in tumor volume in vivo and/or better able to prolong survival in mammals with malignant tumors. In one embodiment, the immunoconjugate inhibits an increase in tumor volume in vivo by at least about 10%, 15%, 20%, 25%, 30%, 35%, 40%, 45%, 50%, 55%, 60%, 65%, 70%, 75%, 80%, 85%, 90%, 95%, or 100% by the end of an administration period of about at least 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. In one embodiment, the immunoconjugate inhibits an increase in tumor volume in vivo by at least 50%, 55%, 60%, 65%, 70%, or 75% by the end of a 13 day administration period. In another embodiment, the immunoconjugate prolongs the survival of mammals with malignant tumors by at least 5%, 10%, 15%, 20%, 25%, 30%, 35%, 40%, 45%, 50%, 55%, 60%, 65%, 70%, 75%, 80%, 85%, 90% or 95% when administered to a mammal in need thereof, relative to a control effector moiety. In another embodiment, the immunoconjugate prolongs the survival of mammals with malignant tumors by at least 30%, 32% or 35% when administered to a mammal in need thereof, relative to a control effector moiety. In another embodiment, the immunoconjugate prolongs the survival of mammals with malignant tumors by about 30% when administered to a mammal in need thereof, relative to a control effector moiety. In another embodiment, the immunoconjugate prolongs the survival of mammals with malignant tumors by at least 10%, 15%, 20%, 25%, 30%, 35%, 40%, 45%, 50%, 55%, 60%, 65%, 70%, 75%, 80%, 85%, 90% or 95% when administered to a mammal in need thereof, relative to an effector moiety in a "diabody" immunoconjugate molecule. In another embodiment, the immunoconjugate prolongs the survival of mammals with malignant tumors by at least 30%, 32%, or 35% when administered to a mammal in need thereof, relative to an effector moiety in a "diabody" immunoconjugate molecule. In another embodiment, the immunoconjugate prolongs the survival of mammals with malignant tumors by about 30% when administered to a mammal in need thereof, relative to an effector moiety in a "diabody" immunoconjugate molecule. In another embodiment, the immunoconjugate prolongs the survival of mammals with malignant tumors by at least 5%, 10% or 15%, relative to a control effector moiety or an effector moiety in a "diabody" immunoconjugate molecule.

Antigen Binding Moieties

The antigen binding moiety of the immunoconjugate of the invention is generally a polypeptide molecule that binds to a specific antigenic determinant and is able to direct the entity to which it is attached (e.g., an effector moiety or a second antigen binding moiety) to a target site, for example to a specific type of tumor cell or tumor stroma that bears the antigenic determinant. The immunoconjugate can bind to antigenic determinants found, for example, on the surfaces of tumor cells, on the surfaces of virus-infected cells, on the surfaces of other diseased cells, free in blood serum, and/or in the extracellular matrix (ECM).

Non-limiting examples of tumor antigens include MAGE, MART-1/Melan-A, gp100, Dipeptidyl peptidase IV (DPPIV), adenosine deaminase-binding protein (ADAbp), cyclophilin b, Colorectal associated antigen (CRC)-C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-05), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100 Pmel117, PRAME, NY-ESO-1, cdc27, adenomatous polyposis coli protein (APC), fodrin, Connexin 37, Ig-idiotype, p15, gp75, GM2 and GD2 gangliosides, viral products such as human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, and c-erbB-2.

Non-limiting examples of viral antigens include influenza virus hemagglutinin, Epstein-Barr virus LMP-1, hepatitis C virus E2 glycoprotein, HIV gp160, and HIV gp120.

Non-limiting examples of ECM antigens include syndecan, heparanase, integrins, osteopontin, link, cadherins, laminin, laminin type EGF, lectin, fibronectin, notch, tenascin, and matrixin.

The immunoconjugates of the invention can bind to the following specific non-limiting examples of cell surface antigens: FAP, Her2, EGFR, CD2 (T-cell surface antigen), CD3 (heteromultimer associated with the TCR), CD22 (B-cell receptor), CD23 (low affinity IgE receptor), CD25 (IL-2 receptor α chain), CD30 (cytokine receptor), CD33 (myeloid cell surface antigen), CD40 (tumor necrosis factor receptor), IL-6R (IL6 receptor), CD20, MCSP, and PDGFβR (β platelet-derived growth factor receptor).

In one embodiment, the immunoconjugate of the invention comprises two or more antigen binding moieties, wherein each of these antigen binding moieties specifically bind to the same antigenic determinant. In another embodiment, the immunoconjugate of the invention comprises two or more antigen binding moieties, wherein each of these antigen binding moieties specifically bind to different antigenic determinants.

The antigen binding moiety can be any type of antibody or fragment thereof that retains specific binding to an antigenic determinant. Antibody fragments include, but are not limited to, $V_H$ fragments, $V_L$ fragments, Fab fragments, $F(ab')_2$ fragments, scFv fragments, Fv fragments, minibodies, diabodies, triabodies, and tetrabodies (see, e.g., Hudson and Souriau, *Nature Med.* 9: 129-134 (2003)).

In one embodiment, the immunoconjugate comprises at least one, typically two or more antigen binding moieties that are specific for the Extra Domain B of fibronectin (EDB). In another embodiment, the immunoconjugate comprises at least one, typically two or more antigen binding moieties that can compete with monoclonal antibody L19 for binding to an epitope of EDB. See, e.g., PCT publication WO 2007/128563 A1 (incorporated herein by reference in its entirety). In yet another embodiment, the immunoconjugate comprises a polypeptide sequence wherein a first Fab heavy chain derived from the L19 monoclonal antibody shares a carboxy-terminal peptide bond with an IL-2 molecule which in turn shares a carboxy-terminal peptide bond with a second Fab heavy chain derived from the L19 monoclonal antibody. In yet another embodiment, the immunoconjugate comprises a polypeptide sequence wherein a first Fab heavy chain derived from the L19 monoclonal antibody shares a carboxy-terminal peptide bond with an IL-12 molecule which in turn shares a carboxy-terminal peptide bond with a second Fab heavy chain derived from the L19 monoclonal antibody. In yet another embodiment, the immunoconjugate comprises a polypeptide sequence wherein a first Fab heavy chain derived from the L19 monoclonal antibody shares a carboxy-terminal peptide bond with an IFN α molecule which in turn shares a carboxy-terminal peptide bond with a second Fab heavy chain derived from the L19 monoclonal antibody. In yet another embodiment, the immunoconjugate comprises a polypeptide sequence wherein a first Fab heavy chain derived from the L19 monoclonal antibody shares a carboxy-terminal peptide bond with a GM-CSF molecule which in turn shares a carboxy-terminal peptide bond with a second Fab heavy chain derived from the L19 monoclonal antibody. In a further embodiment, the immunoconjugate comprises a polypeptide sequence wherein a first scFv derived from the L19 monoclonal antibody shares a carboxy-terminal peptide bond with an IL-2 molecule which in turn shares a carboxy-terminal peptide bond with a second scFv derived from the L19 monoclonal antibody. In a more specific embodiment, the immunoconjugate comprises the polypeptide sequence of SEQ ID NO: 95 or a variant thereof that retains functionality. In another embodiment, the immunoconjugate comprises an Fab light chain derived from the L19 monoclonal antibody. In a more specific embodiment, the immunoconjugate comprises a polypeptide sequence that is at least about 80%, 85%, 90%, 95%, 96%, 97%, 98%, 99% or 100% identical to SEQ ID NO: 96 or a variant thereof that retains functionality. In yet another embodiment, the immunoconjugate comprises two polypeptide sequences that are at least about 80%, 85%, 90%, 95%, 96%, 97%, 98%, 99% or 100% identical to SEQ ID NO: 95 and SEQ ID NO: 96 or variants thereof that retain functionality. In a more specific embodiment, the immunoconjugate comprises a polypeptide sequence that is at least about 80%, 85%, 90%, 95%, 96%, 97%, 98%, 99% or 100% identical to SEQ ID. NO: 104 or a variant thereof that retains functionality. In yet another embodiment, the immunoconjugate comprises two polypeptide sequences that are at least about 80%, 85%, 90%, 95%, 96%, 97%, 98%, 99% or 100% identical to SEQ ID NO: 104 and SEQ ID NO: 96 or variants thereof that retain functionality. In a more specific embodiment, the immunoconjugate comprises a polypeptide sequence that is at least about 80%, 85%, 90%, 95%, 96%, 97%, 98%, 99% or 100% identical to SEQ ID NO: 105 or a variant thereof that retains functionality. In yet another embodiment, the immunoconjugate comprises two polypeptide sequences that are at least about 80%, 85%, 90%, 95%, 96%, 97%, 98%, 99% or 100% identical to SEQ ID NO: 105 and SEQ ID NO: 96 or variants thereof that retain functionality. In a more specific embodiment, the immunoconjugate comprises a polypeptide sequence that is at least about 80%, 85%, 90%, 95%, 96%, 97%, 98%, 99% or 100% identical to SEQ ID NO: 106 or a variant thereof that retains functionality. In yet another embodiment, the immunoconjugate comprises two polypeptide sequences that are at least about 80%, 85%, 90%, 95%, 96%, 97%, 98%, 99% or 100% identical to SEQ ID NO: 106 and SEQ ID NO: 96 or variants thereof that retain functionality. In a more specific embodiment, the immunoconjugate comprises a polypeptide sequence that is at least about 80%, 85%, 90%, 95%, 96%, 97%, 98%, 99% or 100% identical to SEQ ID NO: 107 or a variant thereof that retains functionality. In yet another embodiment, the immunoconjugate comprises a polypeptide sequences that is at least about 80%, 85%, 90%, 95%, 96%, 97%, 98%, 99% or 100% identical to SEQ ID NO: 107 and SEQ ID NO: 96 or variants thereof that retain functionality. In another specific embodiment, the polypeptides are covalently linked, e.g., by a disulfide bond.

In one embodiment, the immunoconjugate of the invention comprises at least one, typically two or more antigen binding moieties that are specific for the A1 domain of Tenascin (TNC-A1). In another embodiment, the immunoconjugate comprises at least one, typically two or more antigen binding moieties that can compete with monoclonal antibody F16 for binding to an epitope of TNC-A1. See, e.g., PCT Publication WO 2007/128563 A1 (incorporated herein by reference in its entirety). In one embodiment, the immunoconjugate comprises at least one, typically two or more antigen binding moieties that are specific for the A1 and/or the A4 domain of Tenascin (TNC-A1 or TNC-A4 or TNC-A1/A4). In another embodiment, the immunoconjugate comprises a polypeptide sequence wherein a first Fab heavy chain specific for the A1 domain of Tenascin shares a carboxy-terminal peptide bond with an IL-2 molecule, an IL-12 molecule, an IFN α molecule or a GM-CSF molecule, which in turn shares a carboxy-terminal peptide bond with a second Fab heavy chain specific for the A1 domain of Tenascin. In yet another embodiment, the immunoconjugate comprises a polypeptide sequence wherein a first Fab heavy chain specific for the A1 domain of Tenascin shares a carboxy-terminal peptide bond with an IL-2 molecule which in turn shares a carboxy-terminal peptide bond with a second Fab heavy chain specific for the A1 domain of Tenascin. In a further embodiment, the immunoconjugate comprises a polypeptide sequence wherein a first scFv specific for the A1 domain of Tenascin shares a carboxy-terminal peptide bond with an IL-2 molecule which in turn shares a carboxy-terminal peptide bond with a second scFv specific for the A1 domain of Tenascin. In a specific embodiment, the antigen binding moieties of the immunoconjugate comprise a heavy chain variable region sequence that is at least about 80%, 85%, 90%, 95%, 96%, 97%, 98%, 99% or 100% identical to either SEQ ID NO: 13 or SEQ ID NO: 15, or variants thereof that retain functionality. In another specific embodiment, the antigen binding moieties of the immunoconjugate comprise a light chain variable region sequence that is at least about 80%, 85%, 90%, 95%, 96%, 97%, 98%, 99% or 100% identical to either SEQ ID NO: 9 or SEQ ID NO: 11, or variants thereof that retain functionality. In a more specific embodiment, the antigen binding moieties of the immunoconjugate comprise a heavy chain variable region sequence that is at least about 80%, 85%, 90%, 95%, 96%, 97%, 98%, 99% or 100% identical to either SEQ ID NO: 13 or SEQ ID NO: 15 or variants thereof that retain functionality, and a light chain variable region sequence that is at least about 80%, 85%, 90%, 95%, 96%, 97%, 98%, 99% or 100% identical to either SEQ ID NO: 9 or SEQ ID NO: 11 or variants thereof that retain functionality. In another specific embodiment, the heavy chain variable region sequence of the antigen binding moieties of the immunoconjugate is encoded by a polynucleotide sequence that is at least about 80%, 85%, 90%, 95%, 96%, 97%, 98%, or 99% identical to either SEQ ID NO: 14 or SEQ ID NO: 16. In yet another specific embodiment, the heavy chain variable region sequence of the antigen binding moieties of the immunoconjugate is encoded by the polynucleotide sequence of either SEQ ID NO: 14 or SEQ ID NO: 16. In another specific embodiment, the light chain variable region sequence of the antigen binding moieties of the immunoconjugate is encoded by a polynucleotide sequence that is at least about 80%, 85%, 90%, 95%, 96%, 97%, 98%, or 99% identical to either SEQ ID NO: 10 or SEQ ID NO: 12. In yet another specific embodiment, the light chain variable region sequence of the antigen binding moieties of the immunoconjugate is encoded by the polynucleotide sequence of either SEQ ID NO: 10 or SEQ ID NO: 12. In a specific embodiment, the immunoconjugate comprises a polypeptide sequence that is at least about 80%, 85%, 90%, 95%, 96%, 97%, 98%, 99% or 100% identical to SEQ ID NO: 99 or variants thereof that retain functionality. In another specific embodiment, the immunoconjugate of the invention comprises a polypeptide sequence that is at least about 80%, 85%, 90%, 95%, 96%, 97%, 98%, 99% or 100% identical to either SEQ ID NO: 100 or SEQ ID NO: 215, or variants thereof that retain functionality. In yet another specific embodiment, the immunoconjugate of the invention comprises a polypeptide sequence that is at least about 80%, 85%, 90%, 95%, 96%, 97%, 98%, 99% or 100% identical to either SEQ ID NO: 101 or SEQ ID NO: 235 or variants thereof that retain functionality. In a more specific embodiment, the immunoconjugate of the present invention comprises two polypeptide sequences that are at least about 80%, 85%, 90%, 95%, 96%, 97%, 98%, 99% or 100% identical to SEQ ID NO: 100 and SEQ ID NO: 101 or variants thereof that retain functionality. In another specific embodiment, the immunoconjugate of the present invention comprises two polypeptide sequences that are at least about 80%, 85%, 90%, 95%, 96%, 97%, 98%, 99% or 100% identical to SEQ ID NO: 215 and SEQ ID NO: 235 or variants thereof that retain functionality. In a specific embodiment, the immunoconjugate comprises a polypeptide sequence encoded by a polynucleotide sequence that is at least about 80%, 85%, 90%, 95%, 96%, 97%, 98%, or 99% identical to SEQ ID NO: 112. In another specific embodiment, the immunoconjugate comprises a polypeptide sequence encoded by the polynucleotide sequence of SEQ ID NO: 112. In another specific embodiment, the immunoconjugate comprises a polypeptide sequence encoded by a polynucleotide sequence that is at least about 80%, 85%, 90%, 95%, 96%, 97%, 98%, or 99% identical to either SEQ ID NO: 113 or SEQ ID NO: 216. In yet another specific embodiment, the immunoconjugate comprises a polypeptide sequence encoded by the polynucleotide sequence of either SEQ ID NO: 113 or SEQ ID NO: 216. In another specific embodiment, the immunoconjugate comprises a polypeptide sequence encoded by a polynucleotide sequence that is at least about 80%, 85%, 90%, 95%, 96%, 97%, 98%, or 99% identical to either SEQ ID NO: 114 or SEQ ID NO: 236. In yet another embodiment, the immunoconjugate comprises a polypeptide sequence encoded by the polynucleotide sequence of either SEQ ID NO: 114 or SEQ ID NO: 236.

In one embodiment, the immunoconjugate comprises at least one, typically two or more antigen binding moieties that are specific for the A2 domain of Tenascin (TNC-A2). In another embodiment, the immunoconjugate comprises a polypeptide sequence wherein a first Fab heavy chain specific for the A2 domain of Tenascin shares a carboxy-terminal peptide bond with an IL-2 molecule, an IL-12 molecule, an IFN α molecule or a GM-CSF molecule, which in turn shares a carboxy-terminal peptide bond with a second Fab heavy chain specific for the A2 domain of Tenascin. In yet another embodiment, the immunoconjugate comprises a polypeptide sequence wherein a first Fab heavy chain specific for the A2 domain of Tenascin shares a carboxy-terminal peptide bond with an IL-2 molecule, which in turn shares a carboxy-terminal peptide bond with a second Fab heavy chain specific for the A2 domain of Tenascin. In a specific embodiment, the antigen binding moieties of the immunoconjugate comprise a heavy chain variable region sequence that is at least about 80%, 85%, 90%, 95%, 96%, 97%, 98%, 99% or 100% identical to a sequence selected from the group of SEQ ID NO: 7, SEQ ID NO: 179, SEQ ID NO: 183, SEQ ID NO: 187, SEQ ID NO: 191, SEQ ID NO:195, SEQ ID NO: 199, SEQ ID NO: 203 and SEQ ID NO: 207, or variants thereof that retain functionality. In another specific embodiment, the antigen binding moieties of the immunoconjugate comprise a light chain variable region sequence that is at least about 80%, 85%, 90%, 95%, 96%, 97%, 98%, 99% or 100% identical to a sequence selected from the group of SEQ ID NO: 3, SEQ ID NO: 5; SEQ ID NO: 177, SEQ ID NO: 181, SEQ ID NO:185, SEQ ID NO: 189, SEQ ID NO: 193, SEQ ID NO: 197, SEQ ID NO: 201 and SEQ ID NO: 205, or variants thereof that retain functionality. In a more specific embodiment, the antigen binding moieties of the immunoconjugate comprise a heavy chain variable region sequence that is at least about 80%, 85%, 90%, 95%, 96%, 97%, 98%, 99% or 100% identical to a sequence selected from the group of SEQ ID NO: 7, SEQ ID NO: 179, SEQ ID NO: 183, SEQ ID NO: 187, SEQ ID NO: 191, SEQ ID NO:195, SEQ ID NO: 199, SEQ ID NO: 203 and SEQ ID NO: 207, or variants thereof that retain functionality, and a light chain variable region sequence that is at least about 80%, 85%, 90%, 95%, 96%, 97%, 98%, 99% or 100% identical to a sequence selected from the group of SEQ ID NO: 3, SEQ ID NO: 5; SEQ ID NO: 177, SEQ ID NO: 181, SEQ ID NO:185, SEQ ID NO: 189, SEQ ID NO: 193, SEQ ID NO: 197, SEQ ID NO: 201 and SEQ ID NO: 205, or variants thereof that retain functionality. In another specific embodiment, the heavy chain variable region sequence of the antigen binding moieties of the immunoconjugate is encoded by a polynucleotide sequence that is at least about 80%, 85%, 90%, 95%, 96%, 97%, 98%, or 99% identical to a sequence selected from the group of SEQ ID NO: 8, SEQ ID NO: 180, SEQ ID NO: 184, SEQ ID NO: 188, SEQ ID NO: 192, SEQ ID NO: 196, SEQ ID NO: 200, SEQ ID NO: 204 and SEQ ID NO: 208. In yet another specific embodiment, the heavy chain variable region sequence of the antigen binding moieties of the immunoconjugate is encoded by a polynucleotide sequence selected from the group of SEQ ID NO: 8, SEQ ID NO: 180, SEQ ID NO: 184, SEQ ID NO: 188, SEQ ID NO: 192, SEQ ID NO: 196, SEQ ID NO: 200, SEQ ID NO: 204 and SEQ ID NO: 208. In another specific embodiment, the light chain variable region sequence of the antigen binding moieties of the immunoconjugate is encoded by a polynucleotide sequence that is at least about 80%, 85%, 90%, 95%, 96%, 97%, 98%, or 99% identical to a sequence selected from the group of SEQ ID NO: 4, SEQ ID NO: 6, SEQ ID NO: 178, SEQ ID NO: 182, SEQ ID NO: 186, SEQ ID NO: 190, SEQ ID NO: 194, SEQ ID NO: 198, SEQ ID NO: 202 and SEQ ID NO: 206. In yet another specific embodiment, the light chain variable region sequence of the antigen binding moieties of the immunoconjugate is encoded by a polynucleotide sequence selected from the group of of SEQ ID NO: 4, SEQ ID NO: 6, SEQ ID NO: 178, SEQ ID NO: 182, SEQ ID NO: 186, SEQ ID NO: 190, SEQ ID NO: 194, SEQ ID NO: 198, SEQ ID NO: 202 and SEQ ID NO: 206. In a specific embodiment, the immunoconjugate of the invention comprises a polypeptide sequence that is at least about 80%, 85%, 90%, 95%, 96%, 97%, 98%, 99% or 100% identical to a sequence selected from the group of SEQ ID NO: 239, SEQ ID NO: 241 and SEQ ID NO: 243, or variants thereof that retain functionality. In another specific embodiment, the immunoconjugate of the invention comprises a polypeptide sequence that is at least about 80%, 85%, 90%, 95%, 96%, 97%, 98%, 99% or 100% identical to a sequence selected from the group of SEQ ID NO: 245, SEQ ID NO: 247 and SEQ ID NO:249, or variants thereof that retain functionality. In a more specific embodiment, the immunoconjugate of the present invention comprises a polypeptide sequence that is at least about 80%, 85%, 90%, 95%, 96%, 97%, 98%, 99% or 100% identical to a sequence selected from the group of SEQ ID NO: 239, SEQ ID NO: 241, and SEQ ID NO: 243 or variants thereof that retain functionality, and a polypeptide sequence that is at least about 80%, 85%, 90%, 95%, 96%, 97%, 98%, 99% or 100% identical to a sequence selected from the group of SEQ ID NO: 245, SEQ ID NO: 247 and SEQ ID NO:249 or variants thereof that retain functionality. In another specific embodiment, the immunoconjugate of the present invention comprises two polypeptide sequences that are at least about 80%, 85%, 90%, 95%, 96%, 97%, 98%, 99% or 100% identical to SEQ ID NO: 239 and either SEQ ID NO: 247 or SEQ ID NO: 249, or variants thereof that retain functionality. In yet another specific embodiment, the immunoconjugate of the present invention comprises two polypeptide sequences that are at least about 80%, 85%, 90%, 95%, 96%, 97%, 98%, 99% or 100% identical to SEQ ID NO: 241 and either SEQ ID NO: 245 or SEQ ID NO: 247, or variants thereof that retain functionality. In another specific embodiment, the immunoconjugate of the present invention comprises two polypeptide sequences that are at least about 80%, 85%, 90%, 95%, 96%, 97%, 98%, 99% or 100% identical to SEQ ID NO: 243 and SEQ ID NO: 245, or variants thereof that retain functionality. In a specific embodiment, the immunoconjugate comprises a polypeptide sequence encoded by a polynucleotide sequence that is at least about 80%, 85%, 90%, 95%, 96%, 97%, 98%, or 99% identical to a sequence selected from the group of SEQ ID NO: 240, SEQ ID NO: 242 and SEQ ID NO: 244. In another specific embodiment, the immunoconjugate comprises a polypeptide sequence encoded by a polynucleotide sequence selected from the group of of SEQ ID NO: 240, SEQ ID NO: 242 and SEQ ID NO: 244. In another specific embodiment, the immunoconjugate comprises a polypeptide sequence encoded by a polynucleotide sequence that is at least about 80%, 85%, 90%, 95%, 96%, 97%, 98%, or 99% identical to a sequence selected from the group of SEQ ID NO: 246, SEQ ID NO: 248 and SEQ ID NO: 250. In yet another specific embodiment, the immunoconjugate comprises a polypeptide sequence encoded by a polynucleotide sequence selected from the group of of SEQ ID NO: 246, SEQ ID NO: 248 and SEQ ID NO: 250.

In one embodiment, the immunoconjugate comprises at least one, typically two or more antigen binding moieties that are specific for the Fibroblast Activated Protein (FAP). In another embodiment, the immunoconjugate comprises a polypeptide sequence wherein a first Fab heavy chain specific for FAP shares a carboxy-terminal peptide bond with an IL-2 molecule, an IL-12 molecule, an IFN a molecule or a GM-CSF molecule, which in turn shares a carboxy-terminal peptide bond with a second Fab heavy chain specific for FAP. In yet another embodiment, the immunoconjugate comprises a polypeptide sequence wherein a first Fab heavy chain specific for FAP shares a carboxy-terminal peptide bond with an IL-2 molecule, which in turn shares a carboxy-terminal peptide bond with a second Fab heavy chain specific for FAP. In another embodiment, the immunoconjugate comprises a polypeptide sequence wherein a first Fab heavy chain specific for FAP shares a carboxy-terminal peptide bond with an IL-12 molecule, which in turn shares a carboxy-terminal peptide bond with a second Fab heavy chain specific for FAP. In a specific embodiment, the antigen binding moieties of the immunoconjugate comprise a heavy chain variable region sequence that is at least about 80%, 85%, 90%, 95%, 96%, 97%, 98%, 99% or 100% identical to a sequence selected from the group consisting of SEQ ID NO: 21, SEQ ID NO: 25, SEQ ID NO: 27, SEQ ID NO: 31, SEQ ID NO: 35, SEQ ID NO: 39, SEQ ID NO: 43, SEQ ID NO: 47, SEQ ID NO: 51, SEQ ID NO: 69, SEQ ID NO: 73, SEQ ID NO: 77, SEQ ID NO: 81, SEQ ID NO: 85, SEQ ID NO: 89, SEQ ID NO: 93, SEQ ID NO: 123, SEQ ID NO: 127, SEQ ID NO: 131, SEQ ID NO: 135, SEQ ID NO: 139, SEQ ID NO: 143, SEQ ID NO: 147, SEQ ID NO: 151, SEQ ID NO: 155, SEQ ID NO: 159, SEQ ID NO: 163, SEQ ID NO: 167, SEQ ID NO: 171 and SEQ ID NO: 175, or variants thereof that retain functionality. In another specific embodiment, the antigen binding moieties of the immunoconjugate comprise a light chain variable region sequence that is at least about 80%, 85%, 90%, 95%, 96%, 97%, 98%, 99% or 100% identical to a sequence selected from the group consisting of: SEQ ID NO: 17, SEQ ID NO: 19, SEQ ID NO: 23, SEQ ID NO: 29, SEQ ID NO: 33, SEQ ID NO: 37, SEQ ID NO: 41, SEQ ID NO: 45, SEQ ID NO: 49, SEQ ID NO: 67, SEQ ID NO: 71, SEQ ID NO: 75, SEQ ID NO: 79, SEQ ID NO: 83, SEQ ID NO: 87, SEQ ID NO: 91, SEQ ID NO: 121, SEQ ID NO: 125, SEQ ID NO: 129, SEQ ID NO: 133, SEQ ID NO: 137, SEQ ID NO: 141, SEQ ID NO: 145, SEQ ID NO: 149, SEQ ID NO: 153, SEQ ID NO: 157, SEQ ID NO: 161, SEQ ID NO: 165, SEQ ID NO: 169 and SEQ ID NO: 173, or variants thereof that retain functionality. In a more specific embodiment, the antigen binding moieties of the immunoconjugate comprise a heavy chain variable region sequence that is at least about 80%, 85%, 90%, 95%, 96%, 97%, 98%, 99% or 100% identical to a sequence selected from the group consisting of SEQ ID NO: 21, SEQ ID NO: 25, SEQ ID NO: 27, SEQ ID NO: 31, SEQ ID NO: 35, SEQ ID NO: 39, SEQ ID NO: 43, SEQ ID NO: 47, SEQ ID NO: 51, SEQ ID NO: 69, SEQ ID NO: 73, SEQ ID NO: 77, SEQ ID NO: 81, SEQ ID NO: 85, SEQ ID NO: 89, SEQ ID NO: 93, SEQ ID NO: 123, SEQ ID NO: 127, SEQ ID NO: 131, SEQ ID NO: 135, SEQ ID NO: 139, SEQ ID NO: 143, SEQ ID NO: 147, SEQ ID NO: 151, SEQ ID NO: 155, SEQ ID NO: 159, SEQ ID NO: 163, SEQ ID NO: 167, SEQ ID NO: 171, and SEQ ID NO: 175, or variants thereof that retain functionality, and a light chain variable region sequence that is at least about 80%, 85%, 90%, 95%, 96%, 97%, 98%, 99% or 100% identical to a sequence selected from the group consisting of: SEQ ID NO: 17, SEQ ID NO: 19, SEQ ID NO: 23, SEQ ID NO: 29, SEQ ID NO: 33, SEQ ID NO: 37, SEQ ID NO: 41, SEQ ID NO: 45, SEQ ID NO: 49, SEQ ID NO: 67, SEQ ID NO: 71, SEQ ID NO: 75, SEQ ID NO: 79, SEQ ID NO: 83, SEQ ID NO: 87, SEQ ID NO: 91, SEQ ID NO: 121, SEQ ID NO: 125, SEQ ID NO: 129, SEQ ID NO: 133, SEQ ID NO: 137, SEQ ID NO: 141, SEQ ID NO: 145, SEQ ID NO: 149, SEQ ID NO: 153, SEQ ID NO: 157, SEQ ID NO: 161, SEQ ID NO: 165, SEQ ID NO: 169, and SEQ ID NO: 173, or variants thereof that retain functionality. In another specific embodiment, the heavy chain variable region sequence of the antigen binding moieties of the immunoconjugate is encoded by a polynucleotide sequence that is at least about 80%, 85%, 90%, 95%, 96%, 97%, 98%, or 99% identical to a sequence selected from the group consisting of: SEQ ID NO: 22, SEQ ID NO: 26, SEQ ID NO: 28, SEQ ID NO: 32, SEQ ID NO: 36, SEQ ID NO: 40, SEQ ID NO: 44, SEQ ID NO: 48, SEQ ID NO: 52, SEQ ID NO: 70, SEQ ID NO: 74, SEQ ID NO: 78, SEQ ID NO: 82, SEQ ID NO: 86, SEQ ID NO: 90, SEQ ID NO: 94, SEQ ID NO: 124, SEQ ID NO: 128, SEQ ID NO: 132, SEQ ID NO: 136, SEQ ID NO: 140, SEQ ID NO: 144, SEQ ID NO: 148, SEQ ID NO: 152, SEQ ID NO: 156, SEQ ID NO: 160, SEQ ID NO: 164, SEQ ID NO: 168, SEQ ID NO: 172, and SEQ ID NO: 176. In yet another specific embodiment, the heavy chain variable region sequence of the antigen binding moieties of the immunoconjugate is encoded by a polynucleotide sequence selected from the group consisting of: SEQ ID NO: 22, SEQ ID NO: 26, SEQ ID NO: 28, SEQ ID NO: 32, SEQ ID NO: 36, SEQ ID NO: 40, SEQ ID NO: 44, SEQ ID NO: 48, SEQ ID NO: 52, SEQ ID NO: 70, SEQ ID NO: 74, SEQ ID NO: 78, SEQ ID NO: 82, SEQ ID NO: 86, SEQ ID NO: 90, SEQ ID NO: 94, SEQ ID NO: 124, SEQ ID NO: 128, SEQ ID NO: 132, SEQ ID NO: 136, SEQ ID NO: 140, SEQ ID NO: 144, SEQ ID NO: 148, SEQ ID NO: 152, SEQ ID NO: 156, SEQ ID NO: 160, SEQ ID NO: 164, SEQ ID NO: 168, SEQ ID NO: 172, and SEQ ID NO: 176. In another specific embodiment, the light chain variable region sequence of the antigen binding moieties of the immunoconjugate is encoded by a polynucleotide sequence that is at least about 80%, 85%, 90%, 95%, 96%, 97%, 98%, or 99% identical to sequence selected from the group consisting of: SEQ ID NO: 18, SEQ ID NO: 20, SEQ ID NO: 24, SEQ ID NO: 30, SEQ ID NO: 34, SEQ ID NO: 38, SEQ ID NO: 42, SEQ ID NO: 46, SEQ ID NO: 50, SEQ ID NO: 68, SEQ ID NO: 72, SEQ ID NO: 76, SEQ ID NO: 80, SEQ ID NO: 84, SEQ ID NO: 88, SEQ ID NO: 92, SEQ ID NO: 122, SEQ ID NO: 126, SEQ ID NO: 130, SEQ ID NO: 134, SEQ ID NO: 138, SEQ ID NO: 142, SEQ ID NO: 146, SEQ ID NO: 150, SEQ ID NO: 154, SEQ ID NO: 158, SEQ ID NO: 162, SEQ ID NO: 166, SEQ ID NO: 170, and SEQ ID NO: 174. In yet another specific embodiment, the light chain variable region sequence of the antigen binding moieties of the immunoconjugate is encoded by a polynucleotide sequence selected from the group consisting of: SEQ ID NO: 18, SEQ ID NO: 20, SEQ ID NO: 24, SEQ ID NO: 30, SEQ ID NO: 34, SEQ ID NO: 38, SEQ ID NO: 42, SEQ ID NO: 46, SEQ ID NO: 50, SEQ ID NO: 68, SEQ ID NO: 72, SEQ ID NO: 76, SEQ ID NO: 80, SEQ ID NO: 84, SEQ ID NO: 88, SEQ ID NO: 92, SEQ ID NO: 122, SEQ ID NO: 126, SEQ ID NO: 130, SEQ ID NO: 134, SEQ ID NO: 138, SEQ ID NO: 142, SEQ ID NO: 146, SEQ ID NO: 150, SEQ ID NO: 154, SEQ ID NO: 158, SEQ ID NO: 162, SEQ ID NO: 166, SEQ ID NO: 170, and SEQ ID NO: 174. In another specific embodiment, the immunoconjugate of the invention comprises a polypeptide sequence that is at least about 80%, 85%, 90%, 95%, 96%, 97%, 98%, 99% or 100% identical to a sequence selected from the group of SEQ ID NO: 209, SEQ ID NO: 211, SEQ ID NO: 213, SEQ ID NO: 217, SEQ ID NO: 219, SEQ ID NO: 221, SEQ ID NO: 223, SEQ ID NO: 225 and SEQ ID NO: 227, or variants thereof that retain functionality. In yet another specific embodiment, the immunoconjugate of the invention comprises a polypeptide sequence that is at least about 80%, 85%, 90%, 95%, 96%, 97%, 98%, 99% or 100% identical to a sequence selected from the group of SEQ ID NO: 229, SEQ ID NO: 231, SEQ ID NO: 233 and SEQ ID NO: 237 or variants thereof that retain functionality. In a more specific embodiment, the immunoconjugate of the present invention comprises a polypeptide sequence that is at least about 80%, 85%, 90%, 95%, 96%, 97%, 98%, 99% or 100% identical to a sequence selected from the group of SEQ ID NO: 211, SEQ ID NO: 219 and SEQ ID NO: 221 or variants thereof that retain functionality, and a polypeptide sequence that is at least about 80%, 85%, 90%, 95%, 96%, 97%, 98%, 99% or 100% identical to SEQ ID NO: 231 or variants thereof that retain functionality. In another specific embodiment, the immunoconjugate of the present invention comprises a polypeptide sequence that is at least about 80%, 85%, 90%, 95%, 96%, 97%, 98%, 99% or 100% identical to a sequence selected from the group of SEQ ID NO: 209, SEQ ID NO: 223, SEQ ID NO: 225 and SEQ ID NO: 227 or variants thereof that retain functionality, and a polypeptide sequence that is at least about 80%, 85%, 90%, 95%, 96%, 97%, 98%, 99% or 100% identical to SEQ ID NO: 229 or variants thereof that retain functionality. In a further specific embodiment, the immunoconjugate of the present invention comprises two polypeptide sequences that are at least about 80%, 85%, 90%, 95%, 96%, 97%, 98%, 99% or 100% identical to SEQ ID NO: 213 and SEQ ID NO: 233 or variants thereof that retain functionality. In yet another specific embodiment, the immunoconjugate of the present invention comprises two polypeptide sequences that are at least about 80%, 85%, 90%, 95%, 96%, 97%, 98%, 99% or 100% identical to SEQ ID NO: 217 and SEQ ID NO: 237 or variants thereof that retain functionality. In yet another specific embodiment, the immunoconjugate of the present invention comprises two polypeptide sequences that are at least about 80%, 85%, 90%, 95%, 96%, 97%, 98%, 99% or 100% identical to SEQ ID NO: 221 and SEQ ID NO: 231 or variants thereof that retain functionality. In yet another specific embodiment, the immunoconjugate of the present invention comprises two polypeptide sequences that are at least about 80%, 85%, 90%, 95%, 96%, 97%, 98%, 99% or 100% identical to SEQ ID NO: 223 and SEQ ID NO: 229 or variants thereof that retain functionality. In yet another specific embodiment, the immunoconjugate of the present invention comprises two polypeptide sequences that are at least about 80%, 85%, 90%, 95%, 96%, 97%, 98%, 99% or 100% identical to SEQ ID NO: 225 and SEQ ID NO: 229 or variants thereof that retain functionality. In yet another specific embodiment, the immunoconjugate of the present invention comprises two polypeptide sequences that are at least about 80%, 85%, 90%, 95%, 96%, 97%, 98%, 99% or 100% identical to SEQ ID NO: 227 and SEQ ID NO: 229 or variants thereof that retain functionality. In another specific embodiment, the immunoconjugate comprises a polypeptide sequence encoded by a polynucleotide sequence that is at least about 80%, 85%, 90%, 95%, 96%, 97%, 98%, or 99% identical to a sequence selected from the group of SEQ ID NO: 210, SEQ ID NO: 212, SEQ ID NO: 214, SEQ ID NO: 218, SEQ ID NO: 220, SEQ ID NO: 222, SEQ ID NO: 224, SEQ ID NO: 226, and SEQ ID NO: 228. In yet another specific embodiment, the immunoconjugate comprises a polypeptide sequence encoded by a polynucleotide sequence selected from the group of SEQ ID NO: 210, SEQ ID NO: 212, SEQ ID NO: 214, SEQ ID NO: 218, SEQ ID NO: 220, SEQ ID NO: 222, SEQ ID NO: 224, SEQ ID NO: 226, and SEQ ID NO: 228. In another specific embodiment, the immunoconjugate comprises a polypeptide sequence encoded by a polynucleotide sequence that is at least about 80%, 85%, 90%, 95%, 96%, 97%, 98%, or 99% identical to a sequence selected from the group of SEQ ID NO: 230, SEQ ID NO: 232, SEQ ID NO: 234, and SEQ ID NO: 238. In yet another specific embodiment, the immunoconjugate comprises a polypeptide sequence encoded by a polynucleotide sequence selected from the group of SEQ ID NO: 230, SEQ ID NO: 232, SEQ ID NO: 234, and SEQ ID NO: 238.

In one embodiment, the immunoconjugate comprises at least one, typically two or more antigen binding moieties that are specific for the Melanoma Chondroitin Sulfate Proteoglycan (MCSP). In another embodiment, the immunoconjugate comprises a polypeptide sequence wherein a first Fab heavy chain specific for MCSP shares a carboxy-terminal peptide bond with an IL-2 molecule, an IL-12 molecule, an IFN $\alpha$ molecule or a GM-CSF molecule, which in turn shares a carboxy-terminal peptide bond with a second Fab heavy chain specific for MCSP. In yet another embodiment, the immunoconjugate comprises a polypeptide sequence wherein a first Fab heavy chain specific for MCSP shares a carboxy-terminal peptide bond with an IL-2 molecule, which in turn shares a carboxy-terminal peptide bond with a second Fab heavy chain specific for MCSP. In a specific embodiment, the antigen binding moieties of the immunoconjugate comprise a heavy chain variable region sequence that is at least about 80%, 85%, 90%, 95%, 96%, 97%, 98%, 99% or 100% identical to the sequence of either SEQ ID NO: 257 or SEQ ID NO: 261 or variants thereof that retain functionality. In another specific embodiment, the antigen binding moieties of the immunoconjugate comprise a light chain variable region sequence that is at least about 80%, 85%, 90%, 95%, 96%, 97%, 98%, 99% or 100% identical to the sequence of either SEQ ID NO: 259 or SEQ ID NO: 271 or variants thereof that retain functionality. In a more specific embodiment, the antigen binding moieties of the immunoconjugate comprise a heavy chain variable region sequence that is at least about 80%, 85%, 90%, 95%, 96%, 97%, 98%, 99% or 100% identical to the sequence of either SEQ ID NO: 257 or SEQ ID NO: 261, or variants thereof that retain functionality, and a light chain variable region sequence that is at least about 80%, 85%, 90%, 95%, 96%, 97%, 98%, 99% or 100% identical to the sequence of either SEQ ID NO: 259 or SEQ ID NO: 271, or variants thereof that retain functionality. In a more specific embodiment, the antigen binding moieties of the immunoconjugate comprise a heavy chain variable region sequence that is at least about 80%, 85%, 90%, 95%, 96%, 97%, 98%, 99% or 100% identical to the sequence of SEQ ID NO: 257, and a light chain variable region sequence that is at least about 80%, 85%, 90%, 95%, 96%, 97%, 98%, 99% or 100% identical to the sequence of SEQ ID NO: 259. In another specific embodiment, the antigen binding moieties of the immunoconjugate comprise a heavy chain variable region sequence that is at least about 80%, 85%, 90%, 95%, 96%, 97%, 98%, 99% or 100% identical to the sequence of SEQ ID NO: 261, and a light chain variable region sequence that is at least about 80%, 85%, 90%, 95%, 96%, 97%, 98%, 99% or 100% identical to the sequence of SEQ ID NO: 259. In another specific embodiment, the heavy chain variable region sequence of the antigen binding moieties of the immunoconjugate is encoded by a polynucleotide sequence that is at least about 80%, 85%, 90%, 95%, 96%, 97%, 98%, or 99% identical to the sequence of either SEQ ID NO: 258 or SEQ ID NO: 262. In yet another specific embodiment, the heavy chain variable region sequence of the antigen binding moieties of the immunoconjugate is encoded by the polynucleotide sequence of either SEQ ID NO: 258 or SEQ ID NO: 262. In another specific embodiment, the light chain variable region sequence of the antigen binding moieties of the immunoconjugate is encoded by a polynucleotide sequence that is at least about 80%, 85%, 90%, 95%, 96%, 97%, 98%, or 99% identical to the sequence of either SEQ ID NO: 260 or SEQ ID NO: 272. In yet another specific embodiment, the light chain variable region sequence of the antigen binding moieties of the immunoconjugate is encoded by the polynucleotide sequence of either SEQ ID NO: 260 or SEQ. ID NO: 272. In a specific embodiment, the immunoconjugate of the invention comprises a polypeptide sequence that is at least about 80%, 85%, 90%, 95%, 96%, 97%, 98%, 99% or 100% identical to either SEQ ID NO: 251 or SEQ ID NO: 255, or variants thereof that retain functionality. In another specific embodiment, the immunoconjugate of the invention comprises a polypeptide sequence that is at least about 80%, 85%, 90%, 95%, 96%, 97%, 98%, 99% or 100% identical to either SEQ ID NO: 253 or SEQ ID NO: 265, or variants thereof that retain functionality. In a more specific embodiment, the immunoconjugate of the present invention comprises a polypeptide sequence that is at least about 80%, 85%, 90%, 95%, 96%, 97%, 98%, 99% or 100% identical to either SEQ ID NO: 251 or SEQ ID NO: 255 or variants thereof that retain functionality, and a polypeptide sequence that is at least about 80%, 85%, 90%, 95%, 96%, 97%, 98%, 99% or 100% identical to either SEQ ID NO: 253 or SEQ ID NO: 265, or variants thereof that retain functionality. In another specific embodiment, the immunoconjugate of the present invention comprises a polypeptide sequence that is at least about 80%, 85%, 90%, 95%, 96%, 97%, 98%, 99% or 100% identical to SEQ ID NO: 251 or variants thereof that retain functionality, and a polypeptide sequence that is at least about 80%, 85%, 90%, 95%, 96%, 97%, 98%, 99% or 100% identical to SEQ ID NO: 253 or variants thereof that retain functionality. In another specific embodiment, the immunoconjugate of the present invention comprises a polypeptide sequence that is at least about 80%, 85%, 90%, 95%, 96%, 97%, 98%, 99% or 100% identical to SEQ ID NO: 255 or variants thereof that retain functionality, and a polypeptide sequence that is at least about 80%, 85%, 90%, 95%, 96%, 97%, 98%, 99% or 100% identical to SEQ ID NO: 253 or variants thereof that retain functionality. In another specific embodiment, the immunoconjugate comprises a polypeptide sequence encoded by a polynucleotide sequence that is at least about 80%, 85%, 90%, 95%, 96%, 97%, 98%, or 99% identical to the sequence of either SEQ ID NO: 252 or SEQ ID NO: 256. In yet another specific embodiment, the immunoconjugate comprises a polypeptide sequence encoded by the polynucleotide sequence of either SEQ ID NO: 252 or SEQ ID NO: 256. In another specific embodiment, the immunoconjugate comprises a polypeptide sequence encoded by a polynucleotide sequence that is at least about 80%, 85%, 90%, 95%, 96%, 97%, 98%, or 99% identical to the sequence of either SEQ ID NO: 254 or SEQ ID NO: 266. In yet another specific embodiment, the immunoconjugate comprises a polypeptide sequence encoded by the polynucleotide sequence of either SEQ ID NO: 254 or SEQ ID NO: 266.

In one embodiment the antigen binding moieties comprise at least a variable region capable of binding an antigenic determinant. Non-limiting variable regions useful in the present invention can be of murine, primate, or human origin. Human variable regions can be derived from human monoclonal antibodies made by the hybridoma method. Human myeloma and mouse-human heteromyeloma cell lines for the production of human monoclonal antibodies have been described, for example, by Kozbor et al., *J Immunol.* 133: 3001-3005 (1984) and Brodeur et al., Monoclonal Antibody Production Techniques and Applications, pp. 51-63 (Marcel Dekker, Inc., New York, 1987). Human variable regions may also be produced by transgenic animals (e.g. mice) that are capable, upon immunization, of producing a repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigenic challenge. See, e.g., Jakobovits et al., *Nature* 362:255-258 (1993).

Alternatively, phage display can be used to produce human antibodies and human variable regions in vitro from immunoglobulin variable (V) domain gene repertoires e.g., from unimmunized donors. (McCafferty et al., *Nature* 348:552-554 (1990).) In one example of this technique, antibody V domain genes are cloned in-frame into either a major or minor coat protein gene of a filamentous bacteriophage, such as M13 or fd, and displayed as functional antibody fragments on the surface of the phage particle.

Because the filamentous particle contains a single-stranded DNA copy of the phage genome, selections based on the functional properties of the antibody/antibody fragments also result in selection of the gene encoding the antibody/antibody fragments exhibiting those properties. Thus, the phage mimics some of the properties of the B-cell. Phage display can be performed in a variety of formats. For a review of phage display formats, see Hoogenboom et al., *Nucleic Acids Res.* 19:4133-4137 (1991). Several sources of V-gene segments can be used for phage display. Clackson et al., isolated a diverse array of anti-oxazolone antibodies from a small random combinatorial library of V genes derived from the spleens of immunized mice. See Clackson et al., *Nature* 352: 624-628 (1991). A repertoire of V genes from unimmunized human donors can be constructed and antibodies to a diverse array of antigens (including self-antigens) can be isolated essentially following the techniques described by Marks et al., *J. Mol. Bio.* 222:581-597 (1991). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as “chain shuffling.” See Marks et al., *Biotech.* 10:779-783 (1992). In this method, the affinity of “primary” human antibodies or variable regions obtained by phage display can be improved by sequentially. replacing the heavy and light chain V region genes with repertoires of naturally occurring variants (repertoires) of V domain genes obtained from unimmunized donors. This technique allows the production of antibodies and variable regions with affinities in the nM range. A strategy for making very large phage antibody repertoires has been described by Waterhouse et al., *Nucl. Acids Res.* 21:2265-2266 (1993), and the isolation of a high affinity human antibody directly from such large phage library is reported by Griffith et al., *J. Cell. Bio.* 120:885-896 (1993). Gene shuffling can also be used to derive human antibodies and variable regions from rodent antibodies, where the human antibody or variable region has similar affinities and specificities to the starting rodent antibody or variable region. According to this method, which is also referred to as “epitope imprinting,” the heavy or light chain V domain gene of rodent antibodies obtained by phage display techniques is replaced with a repertoire of human V domain genes, creating rodent-human chimeras. Selection with antigen results in the isolation of human variable regions capable of restoring a functional antigen binding site, i.e., the epitope governs (imprints) the choice of partner. When the process is repeated to replace the remaining rodent V domain, a human antibody is obtained (see PCT publication WO 93/06213). Unlike traditional humanization of rodent antibodies, the epitope imprinting technique provides completely human antibodies or variable regions, which have no framework or CDR residues of rodent origin.

Variable regions that can be used also include murine variable region sequences that have either been primatized or humanized or primate variable region sequences that have been humanized. As used herein, the term “humanized” refers to an antigen-binding moiety variable region sequence derived from a non-human antibody, for example, a murine antibody, that retains or substantially retains the antigen-binding properties of the parent molecule but which is less immunogenic in humans. This may be achieved by various methods including (a) grafting only the non-human CDRs onto human framework regions with or without retention of critical framework residues (e.g., those that are important for retaining good antigen binding affinity or antibody functions) and (b) “cloaking” the non-human variable regions with a human-like section by replacement of surface residues. Such methods are disclosed by Jones et al., Morrison et al,. *Proc. Natl. Acad. Sci.,* 81:6851-6855 (1984); Morrison and Oi, *Adv.*

*Immunol.,* 44:65-92 (1988); Verhoeyen et al., *Science,* 239: 1534-1536 (1988); Padlan, *Molec. Immun.,* 28:489-498 (1991); Padlan, *Molec. Immun.,* 31(3):169-217 (1994), all of which are incorporated by reference in their entirety herein. There are generally 3 complementarity determining regions, or CDRs, (CDR1, CDR2, and CDR3) in each of the heavy and light chain variable regions of an antibody, which are flanked by four framework subregions (i.e., FR1, FR2, FR3, and FR4) in each of the heavy and light chain variable domains of an antibody: FR1-CDR1-FR2-CDR2-FR3-CDR3-FR4. A discussion of antibodies with humanized variable regions can be found, inter alia, in U.S. Pat. No. 6,632,927, and in published U.S. Application No. 2003/0175269, both of which are incorporated herein by reference in their entirety.

Similarly, as used herein, the term "primatized" is used to refer to an antigen-binding moiety variable region derived from a non-primate antibody, for example, a murine antibody, that retains or substantially retains the antigen-binding properties of the parent molecule but which is less immunogenic in primates.

The choice of human variable domains, both heavy and light, in making humanized antigen binding moieties is very important to reduce antigenicity. According to the so-called "best fit" method, the sequence of the variable region of a rodent antigen binding moiety is screened against the entire library of known human variable-region sequences. The human sequence which is closest to that of the rodent is then accepted as the human framework region (FR) for the humanized antigen binding moiety (Sims et al., *J. Immunol.,* 151: 2296 (1993); Chothia et al., *J. Mol. Biol.,* 196:901 (1987)). Another method of selecting the human framework sequence is to compare the sequence of each individual subregion of the full rodent framework (i.e., FR1, FR2, FR3, and FR4) or some combination of the individual subregions (e.g., FR1 and FR2) against a library of known human variable region sequences that correspond to that framework subregion (e.g., as determined by Kabat numbering), and choose the human sequence for each subregion or combination that is the closest to that of the rodent (U.S. Patent Application Publication No. 2003/0040606A1). Another method uses a particular framework region derived from the consensus sequence of all human antibodies of a particular subgroup of light or heavy chains. The same framework may be used for several different humanized antigen binding moieties (Carter et al., *Proc. Natl. Acad. Sci. USA,* 89:4285 (1992); Presta et al., *J. Immunol.,* 151:2623 (1993)).

Generally, the antigen binding moieties of the immunoconjugate of the invention retain high affinity for specific antigenic determinants and other favorable biological properties. Accordingly, humanized variable regions are prepared by analyzing the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformation structures of selected candidate immunoglobulin variable region sequences. Inspection of these displays permits analysis of the likely role of the residues in the functioning of the candidate immunoglobulin variable region sequence, i.e., the analysis of residues that influence the ability of the candidate variable region sequence to bind its antigen. In this way, FR residues can be selected and combined from the recipient and import sequences so that the desired antigen binding moiety characteristic, such as increased affinity for the target antigen(s), is achieved. In general, the hypervariable region residues are directly and most substantially involved in influencing antigen binding.

In another embodiment, the antigen binding molecules of the present invention are engineered to have enhanced binding affinity according to, for example, the methods disclosed in U.S. Pat. Appl. Publ. No. 2004/0132066, the entire contents of which are hereby incorporated by reference. The ability of the immunoconjugate of the invention to bind to either an effector moiety receptor or to a specific antigenic determinant can be measured either through an enzyme linked immunosorbent assay (ELISA) or other techniques familiar to one of skill in the art, e.g., surface plasmon resonance technique (analyzed on a BIACORE T100 system) (Liljeblad, et al., *Glyco. J.* 17:323-329 (2000)), and traditional binding assays (Heeley, R. P., *Endocr. Res.* 28:217-229 (2002)).

Effector Moieties

The effector moieties for use in the invention are generally polypeptides that influence cellular activity, for example, through signal transduction pathways. Accordingly, the effector moiety of the immunoconjugate of the invention can be associated with receptor-mediated signaling that transmits a signal from outside the cell membrane to modulate a response within the cell. For example, an effector moiety of the immunoconjugate can be a cytokine. In a particular embodiment, the effector moiety is a single-chain effector moiety as defined herein. In one embodiment, one or more effector moieties, typically single-chain effector moieties, of the immunoconjugates of the invention are cytokines selected from the group consisting of: IL-2, GM-CSF, IFN-α, and IL-12. In another embodiment, one or more single-chain effector moieties of the immunoconjugates are cytokines selected from the group consisting of: IL-8, MIP-1α, MIP-1β, and TGF-β.

In one embodiment, the effector moiety, preferably a single-chain effector moiety, of the immunoconjugate is IL-2. In a specific embodiment, the IL-2 effector moiety can elicit one or more of the cellular responses selected from the group consisting of: proliferation in an activated T lymphocyte cell, differentiation in an activated T lymphocyte cell, cytotoxic T cell (CTL) activity, proliferation in an activated B cell, differentiation in an activated B cell, proliferation in a natural killer (NK) cell, differentiation in a NK cell, and NK/lymphocyte activated killer (LAK) antitumor cytotoxicity. In one embodiment, the effector moiety, preferably a single-chain effector moiety, of the immunoconjugate is GM-CSF. In a specific embodiment, the GM-CSF effector moiety can elicit proliferation and/or differentiation in a granulocyte, a monocyte or a dendritic cell. In one embodiment, the effector moiety, preferably a single-chain effector moiety, of the immunoconjugate is IFN-α. In a specific embodiment, the IFN-α effector moiety can elicit one or more of the cellular responses selected from the group consisting of: inhibiting viral replication in a virus-infected cell, and upregulating the expression of major histocompatibility complex I (MHC I). In another specific embodiment, the IFN α effector moiety can inhibit proliferation in a tumor cell. In one embodiment, the effector moiety, preferably a single-chain effector moiety, of the immunoconjugate is IL-12. In a specific embodiment, the IL-12 effcctor moiety can elicit one or more of the cellular responses selected from the group consisting of: proliferation in a NK cell, differentiation in a NK cell, proliferation in a T cell, and differentiation in a T cell. In one embodiment, the effector moiety, preferably a single-chain effector moiety, of the immunoconjugate is IL-8. In a specific embodiment, the IL-8 effector moiety can elicit chemotaxis in neutrophils. In one embodiment, the effector moiety, preferably a single-chain effector moiety, of the immunoconjugate, is MIP-1α. In a specific embodiment, the MIP-1α effector moiety can elicit chemotaxis in monocytes and T lymphocyte cells. In one embodiment, the effector moiety, preferably a single-chain effector moiety, of the immunoconjugate is MIP-1β. In a specific embodiment, the MIP-1β effector moiety can elicit chemotaxis in monocytes and T lymphocyte cells. In one embodiment, the effector moiety, preferably a single-chain effector moiety, of the immunoconjugate is TGF-β. In a specific embodiment, the TGF-β effector moiety can elicit one or more of the cellular responses selected from the group consisting of: chemotaxis in monocytes, chemotaxis in macrophages, upregulating the expression of IL-1 in activated macrophages, and upregulating the expression of IgA in activated B cells.

Immunoconjugate Polypeptides and Polynucleotides

The immunoconjugates of the invention comprise polypeptides and fragments thereof. As used herein, term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

By an "isolated" polypeptide or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Also included as polypeptides of the present invention are derivatives, analogs, or variants of the foregoing polypeptides, and any combination thereof. The terms "variant," "derivative" and "analog" when referring to polypeptides of the present invention include any polypeptides that retain at least some of the biological, antigenic, or immunogenic properties of the corresponding native polypeptide. Variants of polypeptides of the present invention include polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions. Derivatives of polypeptides of the present invention, are polypeptides which have been altered so as to exhibit additional features not found on the native polypeptide. Examples include fusion proteins. Variant polypeptides may also be referred to herein as "polypeptide analogs." As used herein a "derivative" of a polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

Alternatively, recombinant variants encoding these same or similar polypeptides can be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence maybe reflected in the polypeptide or domains of other peptides added to the polypeptide to modify the properties of any part of the polypeptide, to change characteristics such as ligand-binding affinities, interchain affinities, or degradation/turnover rate.

Preferably, amino acid "substitutions" are the result of replacing one amino acid with another amino acid having similar structural and/or chemical properties, i.e., conservative amino acid replacements. "Conservative" amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino, acids include arginine, lysine, and histidine; and negatively charged (acidic) amino acids include aspartic acid and glutamic acid. "Insertions" or "deletions" are preferably in the range of about 1 to about 20 amino acids, more preferably 1 to 10 amino acids. The variation allowed may be experimentally determined by systematically making insertions, deletions, or substitutions of amino acids in a polypeptide molecule using recombinant DNA techniques and assaying the resulting recombinant variants for activity.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the references sequence.

As a practical matter, whether any particular polypeptide is at least 80%, 85%, 90%, 95%, 96,%, 97%, 98%, or 99% identical to a reference polypeptide can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., *Comp. Appl. Biosci.* 6:237-245 (1990). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty-0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini; relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case, the percent identity calculated by FASTDB is not manually corrected. Once again, only residue positions outside the N- and C-terminal ends of the subject sequence, as displayed in the FASTDB alignment, which are not matched/aligned with the query sequence are manually corrected for: No other manual corrections are to be made for the purposes of the present invention.

Polypeptides of the invention include those that are at least about 80%, 85%, 90%, 95%, 96%, 97%, 98%, 99%, or 100% identical to the sequences set forth in Tables 3 and 4, below, including functional fragments or variants thereof. The invention also encompasses polypeptides comprising sequences of Tables 3 or 4 with conservative amino acid substitutions.

The polypeptides of the invention may be encoded by a single polynucleotide. Alternatively, the may be encoded by multiple (e.g., two or more) polynucleotides, so that the polypeptides are co-expressed. Polypeptides that are co-expressed from multiple polynucleotides may associate through, e.g., disulfide bonds or other means to form a functional immunoconjugate. For example, the heavy chain portion of an antigen binding moiety may be encoded by a separate polynucleotide from the portion of the immunoconjugate comprising the light chain portion of the antigen binding moiety and the effector moiety. When co-expressed, the heavy chain polypeptides will associate with the light chain polypeptides to form the antigen binding moiety. Alternatively, in another example, the light chain portion of the antigen binding moiety could be encoded by a separate polynucleotide from the portion of the immunoconjugate comprising the heavy chain portion of the antigen binding moiety and the effector moiety.

Immunoconjugates of the present invention and fragments thereof are generally encoded by polynucleotides. The term "polynucleotide" is intended to encompass a singular nucleic acid as well as plural nucleic acids, and refers to an isolated nucleic acid molecule or construct, e.g., messenger RNA (mRNA), virally-derived RNA, or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a therapeutic polypeptide contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of the present invention, as well as positive and negative strand forms, and double-stranded forms, of pestivirus vectors disclosed herein.

Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' non-translated regions, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a vector of the present invention may encode one or more polyproteins, which are post- or co-translationally separated into the final proteins via proteolytic cleavage. In addition, a vector, polynucleotide, or nucleic acid of the invention may encode heterologous coding regions, either fused or unfused to a first or second nucleic acid encoding the immunoconjugate of the invention, or variant or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid, which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions, which function in vertebrate cells, such as, but not limited to, promoter and enhancer segments from cytomegaloviruses (e.g., the immediate early promoter, in conjunction with intron-A), simian virus 40 (e.g., the early promoter), and retroviruses (such as, e.g., Rous sarcoma virus). Other transcription control regions include those derived from vertebrate genes such as actin, heat shock protein, bovine growth hormone and rabbit B-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence).

In other embodiments, a polynucleotide of the present invention is RNA, for example, in the form of messenger RNA (mRNA). RNA of the present invention may be single stranded or double stranded.

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In one embodiment, the expression cassette of the invention comprises polynucleotide sequences that encode immunoconjugates of the invention or fragments thereof.

The term "expression vector" is synonymous with "expression contsruct" and refers to a DNA molecule that is used to introduce and direct the expression of a specific gene to which it is operably associated into a target cell. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette comprises polynucleotide sequences that encode immunoconjugates of the invention or fragments thereof.

The term "artificial" refers to a synthetic, or non-host cell derived composition, e.g., a chemically-synthesized oligonucleotide.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence.

As a practical matter, whether any particular nucleic acid molecule or polypeptide is at least 80%, 85%, 90%, 95%, 96%, 97%, 98%, or 99% identical to a nucleotide sequence or polypeptide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al., Comp. Appl. Biosci. 6:237-245 (1990). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty-30, Randomization Group Length=0, Cutoff Score=1, Gap Penalty=5, Gap Size Penalty=0.05, Window Size=500 or the length of the subject nucleotide sequences, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matached/aligned with the query. In this case the percent identity calculated by FASTDB is not manually corrected. Once again, only bases 5' and 3' of the subject sequence which are not matched/aligned with the query sequence are manually corrected for. No other manual corrections are to be made for the purposes of the present invention.

Polynucleotides of the invention include those that are at least about 80%, 85%, 90%, 95%, 96%, 97%, 98%, 99%, or 100% identical to the sequences set forth in Tables 6 and 8, below, including functional fragments or variants thereof. The polynucleotides may be expressed as a single polynucleotide that encodes the entire immunoconjugate or as multiple (e.g., two or more) polynucleotides that are coexpressed. Polypeptides encoded by polynucleotides that are co-expressed may associate through, e.g., disulfide bonds or other means to form a functional immunoconjugate. For example, the heavy chain portion of an antigen binding moiety may be encoded by a separate polynucleotide from the portion of the immunoconjugate comprising the light chain portion of the antigen binding moiety and the effector moiety. When coexpressed, the heavy chain polypeptides will associate with the light chain polypeptides to form the antigen binding moiety. Alternatively, in another example, the light chain portion of the antigen binding moiety could be encoded by a separate polynucleotide from the portion of the immunoconjugate comprising the heavy chain portion of the antigen binding moiety and the effector moiety.

In a specific embodiment, an isolated polynucleotide of the invention encodes a fragment of an immunoconjugate comprising at least one effector moiety, preferably a single-chain effector moiety, and at least one, preferably two or more antigen binding moieties, wherein a first effector moiety shares an amino- or carboxy-terminal peptide bond with a first antigen binding moiety and a second antigen binding moiety shares an amino- or carboxy-terminal peptide bond with either the first effector moiety or the first antigen binding moiety. In a preferred embodiment, the antigen binding moieties are independently selected from the group consisting of Fv and Fab. In another specific embodiment, the polynucleotide encodes the heavy chains of two of the antigen binding moieties and one of the effector moieties. In another specific embodiment, the polynucleotide encodes the light chains of two of the antigen binding moieties and one of the effector moieties. In another specific embodiment, the polynucleotide encodes one light chain from one of the antigen binding moieties, one heavy chain from a second antigen binding moiety and one of the effector moieties.

In another specific embodiment, an isolated polynucleotide of the invention encodes a fragment of an immunoconjugate, wherein the polynucleotide encodes the heavy chains of two Fab molecules and an effector moiety, preferably a single-chain effector moiety. In another specific embodiment, an isolated polynucleotide of the invention encodes a fragment of an immunoconjugate, wherein the polynucleotide encodes the light chains of two Fab molecules and an effector moiety, preferably a single-chain effector moiety. In another specific embodiment an isolated polynucleotide of the invention encodes a fragment of an immunoconjugate, wherein the polynucleotide encodes the heavy chain of one Fab molecule, the light chain of second Fab molecule and an effector moiety, preferably a single-chain effector moiety.

In one embodiment, an isolated polynucleotide of the invention encodes an immunoconjugate comprising at least one effector moiety, preferably a single-chain effector moiety, joined at its amino- and carboxy-terminal amino acids to one or more scFv molecules.

In one embodiment, an isolated polynucleotide of the invention encodes an immunoconjugate fragment comprising at least one effector moiety, preferably a single-chain effector moiety and at least first and second antigen binding moieties, wherein each of the antigen binding moieties comprises an scFv molecule joined at its carboxy-terminal amino acid to a constant region comprising an immunoglobulin constant domain independently selected from the group consisting of IgG1 CH1, IgG $C_{kappa}$, and IgE CH4, and wherein one of the antigen binding moieties is joined at its constant region carboxy-terminal amino acid to the amino-terminal amino acid of one of the effector moieties, and wherein the first and second antigen binding moieties are covalently linked through a disulfide bond. In a further embodiment, the polynucleotide of the invention encodes one of the antigen binding moieties and an effector moiety, preferably a single-chain effector moiety.

In one embodiment, an isolated polynucleotide of the invention encodes an immunoconjugate fragment comprising first and second effector moieties and two antigen binding moieties, wherein each of the antigen binding moieties comprises an scFv molecule joined at its carboxy-terminal amino acid to a constant region comprising an immunoglobulin constant domain, and wherein one of the antigen binding moieties is joined at its constant region carboxy-terminal amino acid to the amino-terminal amino acid of one of the effector moieties, and wherein the second antigen binding moiety is joined at its constant region carboxy-terminal amino acid to the amino-terminal amino acid of the second effector moiety, and wherein the first and second antigen binding moieties are covalently linked through a disulfide bond. In a preferred embodiment, the first and/or second effector moieties are single chain effector moieties. In a preferred embodiment, the constant domain is independently selected from the group consisting of IgG1 CH1, IgG $C_{kappa}$, and IgE CH4. In a further embodiment, the polynucleotide of the invention encodes one of the antigen binding moieties and one of the effector moieties.

In one embodiment, an isolated polynucleotide of the invention encodes an immunoconjugate fragment comprising at least one effector moiety, preferably a single-chain effector moiety, and at least first and second antigen binding moieties, wherein each of the antigen binding moieties comprises an scFv molecule joined at its carboxy-terminal amino acid to an IgG CH3 domain, and wherein one of the antigen binding moieties is joined at its carboxy-terminal amino acid to the amino-terminal amino acid of one of the effector moieties, and wherein the first and second antigen binding moieties are covalently linked through a disulfide bond. In a further embodiment, the polynucleotide of the invention encodes one of the antigen binding moieties and an effector moiety, preferably a single chain effector moiety.

In one embodiment, an isolated polynucleotide of the invention encodes an immunoconjugate fragment comprising two effector moieties and two antigen binding moieties, wherein each of the antigen binding moieties comprises an scFv molecule joined at its carboxy-terminal amino acid to an IgG CH3 domain, and wherein one of the antigen binding moieties is joined at its carboxy-terminal amino acid to the amino-terminal amino acid of one of the effector moieties, and wherein the second antigen binding moiety is joined at its carboxy-terminal amino acid to the amino-terminal amino acid of the second effector moiety, and wherein the first and second antigen binding moieties are covalently linked through a disulfide bond. In a preferred embodiment, the first and/or second effector moieties are single chain effector moieties. In a further embodiment, the polynucleotide of the invention encodes one of the antigen binding moieties and one of the effector moieties, preferably a single chain effector moiety.

In one embodiment, an isolated polynucleotide of the invention encodes an immunoconugate fragment comprising two effector moieties and two antigen binding moieties, wherein each of the antigen binding moieties comprises an Fab molecule joined at its heavy or light chain carboxy-terminal amino acid to an IgG1 CH3 domain, and wherein each of the IgG1 CH3 domains is joined at its carboxy-terminal amino acid to the amino-terminal amino acid of one of the effector moieties, and wherein the first and second antigen binding moieties are covalently linked through a disulfide bond. In a preferred embodiment, the first and/or second effector moieties are single chain effector moieties. In a further embodiment, the polynucleotide of the invention comprises a sequence encoding the heavy chain variable region of one of the antigen binding moieties and one of said effector moieties, preferably a single chain moiety. In yet another embodiment, the polynucleotide of the invention comprises a sequence encoding the light chain variable region of one of the antigen binding moieties and one of the effector moieties, preferably a single chain effector moiety.

In another embodiment, the present invention is directed to an isolated polynucleotide encoding an immunoconjugate or fragment thereof, wherein the polynucleotide comprises a sequence that encodes a variable region sequence as shown in Table 3 below. In another embodiment, the present invention is directed to an isolated polynucleotide encoding an immunoconjugate or fragment thereof, wherein the polynucleotide comprises a sequence that encodes a polypeptide sequence as shown in Table 4. In another embodiment, the invention is further directed to an isolated nucleic acid encoding an immunoconjugate or fragment thereof, wherein the nucleic acid comprises a sequence that is at least about 80%, 85%, 90%, 95%, 96%, 97%, 98%, or 99% identical to a nucleotide sequence shown in Tables 6 and 8 below. In another embodiment, the invention is directed to an isolated nucleic acid encoding an immunoconjugate or fragment thereof, wherein the nucleic acid comprises a nucleic acid sequence shown in Tables 6 and 8. In another embodiment, the invention is directed to an isolated nucleic acid encoding an immunoconjugate or fragment thereof, wherein the nucleic acid comprises a sequence that encodes a variable region sequence that is at least about 80%, 85%, 90%, 95%, 96%, 97%, 98%, or 99% identical to an amino acid sequence in Table 3. In another embodiment, the invention is directed to an isolated nucleic acid encoding an immunoconjugate or fragment thereof, wherein the nucleic acid comprises a sequence that encodes a polypeptide sequence that is at least 80%, 85%, 90%, 95%, 96%, 97%, 98%, or 99% identical to an amino acid sequence in Table 4. The invention encompasses an isolated nucleic acid encoding an immunoconjugate or fragment thereof, wherein the nucleic acid comprises a sequence that encodes the variable region sequences of Table 3 with conservative amino acid substitutions. The invention also encompasses an isolated nucleic acid encoding an immunoconjugate of the invention or fragment thereof, wherein the nucleic acid comprises a sequence that encodes the polypeptide sequences of Table 4 with conservative amino acid substitutions.

TABLE 2

| Construct | NUCLEOTIDE SEQUENCE | SEQ ID NO |
|---|---|---|
| Library Template for DP47-3 library; complete Fab coding region comprising PelB leader sequence + Vk3_20 kappa V-domain + CL constant domain for light chain and PelB + VH3_23 V-domain + CH1 constant domain for heavy chain; pMS25opt | ATGAAATACCTATTGCCTACGGCAGCC GCTGGATTGTTATTACTCGCGGCCCAG CCGGCCATGGCCGAAATCGTGTTAACG CAGTCTCCAGGCACCCTGTCTTTGTCT CCAGGGGAAAGAGCCACCCTCTCTTGC AGGGCCAGTCAGAGTGTTAGCAGCAGC TACTTAGCCTGGTACCAGCAGAAACCT GGCCAGGCTCCCAGGCTCCTCATCTAT GGAGCATCCAGCAGGGCCACTGGCATC CCAGACAGGTTCAGTGGCAGTGGATCC GGGACAGACTTCACTCTCACCATCAGC AGACTGGAGCCTGAAGATTTTGCAGTG TATTACTGTCAGCAGTATGGTAGCTCA CCGCTGACGTTCGGCCAGGGGACCAAA GTGGAAATCAAACGTACGGTGGCTGCA CCATCTGTCTTCATCTTCCCGCCATCT GATGAGCAGTTGAAATCTGGAACTGCC TCTGTTGTGTGCCTGCTGAATAACTTC TATCCCAGAGAGGCCAAAGTACAGTGG AAGGTGGATAACGCCCTCCAATCGGGT | 1 |

TABLE 2-continued

| Construct | NUCLEOTIDE SEQUENCE | SEQ ID NO |
|---|---|---|
| | AACTCCCAGGAGAGTGTCACAGAGCAG<br>GACAGCAAGGACAGCACCTACAGCCTC<br>AGCAGCACCCTGACGCTGAGCAAAGCA<br>GACTACGAGAAACACAAAGTCTACGCC<br>TGCGAAGTCACCCATCAGGGCCTGAGC<br>TCGCCCGTCACAAAGAGCTTCAACAGG<br>GGAGAGTGTGGAGCCGCAGAACAAAAA<br>CTCATCTCAGAAGAGGATCTGAATGGA<br>GCCGCAGACTACAAGGACGACGACGAC<br>AAGGGTGCCGCATAATAAGGCGCGCCA<br>ATTCTATTTCAAGGAGACAGTCATATG<br>AAATACCTGCTGCCGACCGCTGCTGCT<br>GGTCTGCTGCTCCTCGCTGCCCAGCCG<br>GCGATGGCCGAGGTGCAATTGCTGGAG<br>TCTGGGGGAGGCTTGGTACAGCCTGGG<br>GGGTCCCTGAGACTCTCCTGTGCAGCC<br>TCCGGATTCACCTTTAGCAGTTATGCC<br>ATGAGCTGGGTCCGCCAGGCTCCAGGG<br>AAGGGGCTGGAGTGGGTCTCAGCTATT<br>AGTGGTAGTGGTGGTAGCACATACTAC<br>GCAGACTCCGTGAAGGGCCGGTTCACC<br>ATCTCCAGAGACAATTCCAAGAACACG<br>CTGTATCTGCAGATGAACAGCCTGAGA<br>GCCGAGGACACGGCCGTATATTACTGT<br>GCGAAACCGTTTCCGTATTTTGACTAC<br>TGGGGCCAAGGAACCCTGGTCACCGTC<br>TCGAGTGCTAGCACCAAAGGCCCATCG<br>GTCTTCCCCCTGGCACCCTCCTCCAAG<br>AGCACCTCTGGGGGCACAGCGGCCCTG<br>GGCTGCCTGGTCAAGGACTACTTCCCC<br>GAACCGGTGACGGTGTCGTGGAACTCA<br>GGCGCCCTGACCAGCGGCGTGCACACC<br>TTCCCGGCTGTCCTACAGTCCTCAGGA<br>CTCTACTCCCTCAGCAGCGTGGTGACC<br>GTGCCCTCCAGCAGCTTGGGCACCCAG<br>ACCTACATCTGCAACGTGAATCACAAG<br>CCCAGCAACACCAAAGTGGACAAGAAA<br>GTTGAGCCCAAATCTTGTGACGCGGCC<br>GCAAGCACTAGTGCCCATCACCATCAC<br>CATCACGCCGCGGCATAG | |
| Library Template for DP88-3 library; complete Fab coding region comprising PelB leader sequence + Vk1_17 kappa V-domain + CL constant domain for light chain and PelB + VH1_69 V-domain + CH1 constant domain for heavy chain; pRJH32 | ATGAAATACCTATTGCCTACGGCAGCC<br>GCTGGATTGTTATTACTCGCGGCCCAG<br>CCGGCCATGGCCGATATCCAGATGACC<br>CAGTCTCCATCCTCCCTGTCTGCATCT<br>GTCGGAGACCGGGTCACCATCACCTGC<br>CGGGCAAGTCAGGGCATTAGAAATGAT<br>TTAGGCTGGTACCAGCAGAAGCCAGGG<br>AAAGCCCCTAAGCGCCTGATCTATGCT<br>GCATCCAGTTTGCAGAGTGGCGTCCCA<br>TCAAGGTTCAGCGGCAGTGGATCCGGG<br>ACAGAGTTCACTCTCACCATCAGCAGC<br>TTGCAGCCTGAAGATTTTGCCACCTAT<br>TACTGCTTGCAGCATAATAGTTACCCC<br>ACGTTTGGCCAGGGCACCAAAGTCGAG<br>ATCAAGCGTACGGTGGCTGCACCATCT<br>GTCTTCATCTTCCCGCCATCTGATGAG<br>CAGTTGAAATCTGGAACTGCCTCTGTT<br>GTGTGCCTGCTGAATAACTTCTATCCC<br>AGAGAGGCCAAAGTACAGTGGAAGGTG<br>GATAACGCCCTCCAATCGGGTAACTCC<br>CAGGAGAGTGTCACAGAGCAGGACAGC<br>AAGGACAGCACCTACAGCCTCAGCAGC<br>ACCCTGACGCTGAGCAAAGCAGACTAC<br>GAGAAACACAAAGTCTACGCCTGCGAA<br>GTCACCCATCAGGGCCTGAGCTCGCCC<br>GTCACAAAGAGCTTCAACAGGGGAGAG<br>TGTGGAGCCGCAGAACAAAAACTCATC<br>TCAGAAGAGGATCTGAATGGAGCCGCA<br>GACTACAAGGACGACGACGACAAGGGT<br>GCCGCATAATAAGGCGCGCCAATTCTA<br>TTTCAAGGAGACAGTCATATGAAATAC<br>CTGCTGCCGACCGCTGCTGCTGGTCTG<br>CTGCTCCTCGCTGCCCAGCCGGCGATG<br>GCCCAGGTGCAATTGGTGCAGTCTGGG<br>GCTGAGGTGAAGAAGCCTGGGTCCTCG | 2 |

TABLE 2-continued

| Construct | NUCLEOTIDE SEQUENCE | SEQ ID NO |
|---|---|---|
| | GTGAAGGTCTCCTGCAAGGCCTCCGGA<br>GGCACATTCAGCAGCTACGCTATAAGC<br>TGGGTGCGACAGGCCCCTGGACAAGGG<br>CTCGAGTGGATGGGAGGGATCATCCCT<br>ATCTTTGGTACAGCAAACTACGCACAG<br>AAGTTCCAGGGCAGGGTCACCATTACT<br>GCAGACAAATCCACGAGCACAGCCTAC<br>ATGGAGCTGAGCAGCCTGAGATCTGAG<br>GACACCGCCGTGTATTACTGTGCGAGA<br>CTATCCCCAGGCGGTTACTATGTTATG<br>GATGCCTGGGGCCAAGGGACCACCGTG<br>ACCGTCTCCTCAGCTAGCACCAAAGGC<br>CCATCGGTCTTCCCCCTGGCACCCTCC<br>TCCAAGAGCACCTCTGGGGGCACAGCG<br>GCCCTGGGCTGCCTGGTCAAGGACTAC<br>TTCCCCGAACCGGTGACGGTGTCGTGG<br>AACTCAGGCGCCCTGACCAGCGGCGTG<br>CACACCTTCCCGGCTGTCCTACAGTCC<br>TCAGGACTCTACTCCCTCAGCAGCGTG<br>GTGACCGTGCCCTCCAGCAGCTTGGGC<br>ACCCAGACCTACATCTGCAACGTGAAT<br>CACAAGCCCAGCAACACCAAAGTGGAC<br>AAGAAAGTTGAGCCCAAATCTTGTGAC<br>GCGGCCGCAAGCACTAGTGCCCATCAC<br>CATCACCATCACGCCGCGGCATAG | |

TABLE 3

| Construct | POLYPEPTIDE SEQUENCE | SEQ ID NO |
|---|---|---|
| 2B10; $V_L$ | DIQMTQSPSSLSASVGDRVTITCRASQGIRNDL<br>GWYQQKPGKAPKRLIYAASSLQSGVPSRFSGGG<br>SGTEFTLTISSLQPEDFATYYCLQNGLQPATFG<br>QGTKVEIK | 3 |
| 2B10(GS); $V_L$ | DIQMTQSPSSLSASVGDRVTITCRASQGIRNDL<br>GWYQQKPGKAPKRLIYAASSLQSGVPSRFSGSG<br>SGTEFTLTISSLQPEDFATYYCLQNGLQPATFG<br>QGTKVEIK | 5 |
| 2B10; $V_H$ | QVQLVQSGAEVKKPGSSVKVSCKASGGTFSSYA<br>ISWVRQAPGQGLEWMGGIIPIFGTANYAQKFQG<br>RVTITADKSTSTAYMELSSLRSEDTAVYYCARL<br>YGYAYYGAFDYWGQGTTVTVSS | 7 |
| 2F11; $V_L$ | EIVLTQSPGTLSLSPGERATLSCRASQSVSSSY<br>LAWYQQKPGQAPRLLIYGASSRATGVPDRFSGS<br>GSGTDFTLTISRLEPEDFAVYYCQQGQYTPPTF<br>GQGTKVEIK | 9 |
| 2F11(VI); $V_L$ | EIVLTQSPGTLSLSPGERATLSCRASQSVSSSY<br>LAWYQQKPGQAPRLLIYGASSRATGIPDRFSGS<br>GSGTDFTLTISRLEPEDFAVYYCQQGQYTPPTF<br>GQGTKVEIK | 11 |
| 2F11; $V_H$ | EVQLLESGGGLVQPGGSLRLSCAASGFTFSSYA<br>MSWVRQAPGKGLEWVSAISGSGGSTYYADSVKG<br>RFTISRDNSKNTLYLQMNSLRAEDMAVYYCAKW<br>RWMMFDYWGQGTLVTVSS | 13 |
| 2F11(MT); $V_H$ | EVQLLESGGGLVQPGGSLRLSCAASGFTFSSYA<br>MSWVRQAPGKGLEWVSAISGSGGSTYYADSVKG<br>RFTISRDNSKNTLYLQMNSLRAEDTAVYYCAKW<br>RWMMFDYWGQGTLVTVSS | 15 |
| 3F2; $V_L$ | EIVLTQSPGTLSLYPGERATLSCRASQSVTSSY<br>LAWYQQKPGQAPRLLINVGSRRATGIPDRFSGS<br>GSGTDFTLTISRLEPEDFAVYYCQQGIMLPPTF<br>GQGTKVEIK | 17 |

TABLE 3-continued

| Construct | POLYPEPTIDE SEQUENCE | SEQ ID NO |
|---|---|---|
| 3F2(YS); $V_L$ | EIVLTQSPGTLSLSPGERATLSCRASQSVTSSYLAWYQQKPGQAPRLLINVGSRRATGIPDRFSGSGSGTDFTLTISRLEPEDFAVYYCQQGIMLPPTFGQGTKVEIK | 19 |
| 3F2; $V_H$ | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKGWFGGFNYWGQGTLVTVSS | 21 |
| 3D9, $V_L$ | EIVLTQSPGTLSLSPGERATLSCRASQSVSSSYLAWYQQKPGQAPRLLIYGASSRATGIPDRFSGSGSGTDFTLTISRLEPEDFAVYYCQQGQLIPPTFGQGTKVEIK | 23 |
| 3D9, $V_H$ | EVQLLESGGGLVQPGGSLRLSCAASGFTFSSYAMSWVRQTPGKGLEWVSAIGVSTGSTYYADSVKGRFTISRDNSKNTLYLQMNSLRAEDTAVYYCAKGWLGPFDYWGQGTLVTVSS | 25 |
| 2D9(TA); $V_H$ | EVQLLESGGGLVQPGGSLRLSCAASGFTFSSYAMSWVRQAPGKGLEWVSAIGVSTGSTYYADSVKGRFTISRDNSKNTLYLQMNSLRAEDTAVYYCAKGWLGPFDYWGQGTLVTVSS | 27 |
| 4G8; $V_L$ | EIVLTQSPGTLSLSPGERATLSCRASQSVSRSYLAWYQQKPGQAPRLLIIGASTRATGIPDRFSGSGSGTDFTLTISRLEPEDFAVYYCQQGQVIPPTFGQGTKVEIK | 29 |
| 4G8; $V_H$ | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKGWLGNFDYWGQGTLVTVSS | 31 |
| 4B3; $V_L$ | EIVLTQSPGTLSLSPGERATLSCRASQSVSSNYLAWYQQKPGQAPRLLIYGAYIRATGIPDRFSGSGSGTDFTLTISRLEPEDFAVYYCQQGQVIPPTFGQGTKVEIK | 33 |
| 4B3; $V_H$ | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKGWLGNFDYWGQGTLVTVSS | 35 |
| 4D6; $V_L$ | EIVLTQSPGTLSLSPGERATLSCRASQSVSSNYLAWYQQKPGQAPRLLIQGASSRATGIPDRFSGSGSGTDFTLTISRLEPEDFAVYYCQQGQVIPPTFGQGTKVEIK | 37 |
| 4D6; $V_H$ | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKGWLGNFDYWGQGTLVTVSS | 39 |
| 2C6; $V_L$ | EIVLTQSPGTLSLSPGERATLSCRASQSVSSSYLAWYQQKPGQAPRLLIYGASSRATGIPDRFSGSGSGTDFTLTISRLEPEDFAVYYCQQGQQIPPTFGQGTKVEIK | 41 |
| 2C6; $V_H$ | EVQLLESGGGLVQPGGSLRLSCAASGSTFSSYAMSWVRQAPGKGLEWVSAISGSAGYTYYADSVKGRFTISRDNSKNTLYLQMNSLRAEDTAVYYCAKGWFGNFDYWGQGTLVTVSS | 43 |
| 5H5; $V_L$ | EIVLTQSPGTLSLSPGERATLSCRASQSVSSSYLAWYQQKPGQAPRLLIYGASSRATGIPDRFSGSGSGTDFTLTISRLEPEDFAVYYCQQGNQIPPTFGQGTKVEIK | 45 |
| 5H5; $V_H$ | EVQLLESGGGLVQPGGSLRLSCAASGFTFSSYTMSWVRRSPGKGLEWVSAISGGGRTYYADSVKGRFTISRDNSKNTLYLQMNSLRAEDTAVYYCAKGWFTPFDYWGQGTLVTVSS | 47 |

TABLE 3-continued

| Construct | POLYPEPTIDE SEQUENCE | SEQ ID NO |
|---|---|---|
| 2C4; $V_L$ | EIVLTQSPGTLSLSPGERATLSCRASQSVSSNYLAWYQQKPGQAPRLLIYGASIRATGIPDRFSGSGSGTDFTLTISRLEPEDFAVYYCQQGNQIPPTFGQGTKVEIK | 49 |
| 2C4; $V_H$ | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKGWFTPFDYWGQGTLVTVSS | 51 |
| 2D9; $V_L$ | EIVLTQSPGTLSLSPGERATLSCRASQSVSSSYLAWYQQKPGQAPRLLIYGASSRATGIPDRFSGSGSGTDFTLTISRLEPEDFAVYYCQQGNQIPPTFGQGTKVEIK | 67 |
| 2D9; $V_H$ | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKGWFTPFDYWGQGTLVTVSS | 69 |
| 4B8; $V_L$ | EIVLTQSPGTLSLSPGERATLSCRASQSVSSSYLAWYQQKPGQAPRLLIYGASSRATGIPDRFSGSGSGTDFTLTISRLEPEDFAVYYCQQGQVIPPTFGQGTKVEIK | 71 |
| 4B8; $V_H$ | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKGWLGNFDYWGQGTLVTVSS | 73 |
| 7A1; $V_L$ | EIVLTQSPGTLSLSPGERATLSCRASQSVSSSYLAWYQQKPGQAPRLLIYGASSRATGIPDRFSGSGSGTDFTLTISRLEPEDFAVYYCQQGQQIPPTFGQGTKVEIK | 75 |
| 7A1; $V_H$ | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKGWFGNFDWGQGTLVTVSS | 77 |
| 13C2; $V_L$ | EIVLTQSPGTLSLSPGERATLSCRASQSVSSSYLAWYQQKPGQAPRLLIYGASSRATGIPDRFSGSGSGTDFTLTISRLEPEDFAVYYCQQGQLIPPTFGQGTKVEIK | 79 |
| 13C2; $V_H$ | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKGWLGPFDYWGQGTLVTVSS | 81 |
| 13E8; $V_L$ | EIVLTQSPGTLSLSPGERATLSCRASQSVSSSYLAWYQQKPGQAPRLLIYGASSRATGIPDRFSGSGSGTDFTLTISRLEPEDFAVYYCQQGLNIPSTFGQGTKVEIK | 83 |
| 13E8; $V_H$ | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKGWLGPFDYWGQGTLVTVSS | 85 |
| 14C10; $V_L$ | EIVLTQSPGTLSLSPGERATLSCRASQSVSSSYLAWYQQKPGQAPRLLIYGASSRATGIPDRFSGSGSGTDFTLTISRLEPEDFAVYYCQQGHIIPPTFGQGTKVEIK | 87 |
| 14C10; $V_H$ | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKAWMGPFDYWGQGTLVTVSS | 89 |
| 17A11; $V_L$ | EIVLTQSPGTLSLSPGERATLSCRASQSVSSSYLAWYQQKPGQAPRLLIYGASSRATGIPDRFSGSGSGTDFTLTISRLEPEDFAVYYCQQGLNIPSTFGQGTKVEIK | 91 |

TABLE 3-continued

| Construct | POLYPEPTIDE SEQUENCE | SEQ ID NO |
|---|---|---|
| 17A11; $V_H$ | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKGWLGPFDYWGQGTLVTVSS | 93 |
| 19G1; $V_L$ | EIVLTQSPGTLSLSPGERATLSCRASQSVTSSYLAWYQQKPGQAPRLLINVGSRRATGIPDRFSGSGSGTDFTLTISRLEPEDFAVYYCQQGIMLPPTFGQGTKVEIK | 121 |
| 19G1; $V_H$ | EVQLLESGGGLVQPGGSLRLSCAASGFTFSSYAMSWVRQAPGKGLEWVSAIISSGGLTYYADSVKGRFTISRDNSKNTLYLQMNSLRAEDTAVYYCAKGWFGGFNYWGQGTLVTVSS | 123 |
| 20G8; $V_L$ | EIVLTQSPGTLSLSPGERATLSCRASQSVTSSYLAWYQQKPGQAPRLLINVGSRRATGIPDRFSGSGSGTDFTLTISRLEPEDFAVYYCQQGIMLPPTFGQGTKVEIK | 125 |
| 20G8; $V_H$ | EVQLLESGGGLVQPGGSLRLSCAASGFTFSSYAMSWVRQAPGKGLEWVSAIIGSGSRTYYADSVKGRFTISRDNSKNTLYLQMNSLRAEDTAVYYCAKGWFGGF**N**YWGQGTLVTVSS | 127 |
| 4B9; $V_L$ | EIVLTQSPGTLSLSPGERATLSCRASQSVTSSYLAWYQQKPGQAPRLLINVGSRRATGIPDRFSGSGSGTDFTLTISRLEPEDFAVYYCQQGIMLPPTFGQGTKVEIK | 129 |
| 4B9; $V_H$ | EVQLLESGGGLVQPGGSLRLSCAASGFTFSSYAMSWVRQAPGKGLEWVSAIIGSGASTYYADSVKGRFTISRDNSKNTLYLQMNSLRAEDTAVYYCAKGWFGGFNYWGQGTLVTVSS | 131 |
| 5B8; $V_L$ | EIVLTQSPGTLSLSPGERATLSCRASQSVTSSYLAWYQQKPGQAPRLLINVGSRRATGIPDRFSGSGSGTDFTLTISRLEPEDFAVYYCQQGIMLPPTFGQGTKVEIK | 133 |
| 5B8; $V_H$ | EVQLLESGGGLVQPGGSLRLSCAASGFTFSSYAMSWVRQAPGKGLEWVSAIWGGGRSTYYADSVKGRFTISRDNSKNTLYLQMNSLRAEDTAVYYCAKGWFGGFNYWGQGTLVTVSS | 135 |
| 5F1; $V_L$ | EIVLTQSPGTLSLSPGERATLSCRASQSVTSSYLAWYQQKPGQAPRLLINVGSRRATGIPDRFSGSGSGTDFTLTISRLEPEDFAVYYCQQGIMLPPTFGQGTKVEIK | 137 |
| 5F1; $V_H$ | EVQLLESGGGLVQPGGSLRLSCAASGFTFSSYAMSWVRQAPGKGLEWVSAIISSGASTYYADSVKGRFTISRDNSKNTLYLQMNSLRAEDTAVYYCAKGWFGGFNYWGQGTLVTVSS | 139 |
| 14B3; $V_L$ | EIVLTQSPGTLSLSPGERATLSCRASQSVTSSYLAWYQQKPGQAPRLLINVGSRRATGIPDRFSGSGSGTDFTLTISRLEPEDFAVYYCQQGIMLPPTFGQGTKVEIK | 141 |
| 14B3; $V_H$ | EVQLLESGGGLVQPGGSLRLSCAASGFTFSSYAMSWVRQAPGKGLEWVSAILASGAITYYADSVKGRFTISRDNSKNTLYLQMNSLRAEDTAVYYCAKGWFGGFNYWGQGTLVTVSS | 143 |
| 16F1; $V_L$ | EIVLTQSPGTLSLSPGERATLSCRASQSVTSSYLAWYQQKPGQAPRLLINVGSRRATGIPDRFSGSGSGTDFTLTISRLEPEDFAVYYCQQGIMLPPTFGQGTKVEIK | 145 |
| 16F1; $V_H$ | EVQLLESGGGLVQPGGSLRLSCAASGFTFSSYAMSWVRQAPGKGLEWVSGIIGSGGITYYADSVKGRFTISRDNSKNTLYLQMNSLRAEDTAVYYCAKGWFGGFNYWGQGTLVTVSS | 147 |

TABLE 3-continued

| Construct | POLYPEPTIDE SEQUENCE | SEQ ID NO |
|---|---|---|
| 16F8; $V_L$ | EIVLTQSPGTLSLSPGERATLSCRASQSVTSSYLAWYQQKPGQAPRLLINVGSRRATGIPDRFSGSGSGTDFTLTISRLEPEDFAVYYCQQGIMLPPTFGQGTKVEIK | 149 |
| 16F8; $V_H$ | EVQLLESGGGLVQPGGSLRLSCAASGFTFSSYAMSWVRQAPGKGLEWVSAILGSGGSTYYADSVKGRFTISRDNSKNTLYLQMNSLRAEDTAVYYCAKGWFGGFNYWGQGTLVTVSS | 151 |
| 03C9; $V_L$ | EIVLTQSPGTLSLSPGERATLSCRASQSVTSSYLAWYQQKPGQAPRLLINVGSRRATGIPDRFSGSGSGTDFTLTISRLEPEDFAVYYCQQGIMLPPTFGQGTKVEIK | 153 |
| 03C9; $V_H$ | EVQLLESGGGLVQPGGSLRLSCAASGFTFSSFAMSWVRQSPGKGLEWVSAIIGSGSNTYYADSVKGRFTISRDNSKNTLYLQMNSLRAEDTAVYYCAKGWFGGFNYWGQGTLVTVSS | 155 |
| 02D7; $V_L$ | EIVLTQSPGTLSLSPGERATLSCRASQSVTSSYLAWYQQKPGQAPRLLINVGSRRATGTPDRFSGSGSGTDFTLTISRLEPEDFAVYYCQQAIMLPPTFGQGTKVEIK | 157 |
| 02D7; $V_H$ | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAKGWFGGFNYWGQGTLVTVSS | 159 |
| 28H1; $V_L$ | EIVLTQSPGTLSLSPGERATLSCRASQSVSRSYLAWYQQKPGQAPRLLIIGASTRATGIPDRFSGSGSGTDFTLTISRLEPEDFAVYYCQQGQVIPPTFGQGTKVEIK | 161 |
| 28H1; $V_H$ | EVQLLESGGGLVQPGGSLRLSCAASGFTFSSHAMSWVRQAPGKGLEWVSAIWASGEQYYADSVKGRFTISRDNSKNTLYLQMNSLRAEDTAVYYCAKGWLGNFDYWGQGTLVTVSS | 163 |
| 22A3; $V_L$ | EIVLTQSPGTLSLSPGERATLSCRASQSVTSSYLAWYQQKPGQAPRLLINVGSRRATGIPDRFSGSGSGTDFTLTISRLEPEDFAVYYCQQGIMLPPTFGQGTKVEIK | 165 |
| 22A3; $V_H$ | EVQLLESGGGLVQPGGSLRLSCAASGFTFSSYAMSWVRQAPGKGLEWVSAIIGSGSITYYADSVKGRFTISRDNSKNTLYLQMNSLRAEDTAVYYCAKGWFGGFNYWGQGTLVTVSS | 167 |
| 29B11; $V_L$ | EIVLTQSPGTLSLSPGERATLSCRASQSVTSSYLAWYQQKPGQAPRLLINVGSRRATGIPDRFSGSGSGTDFTLTISRLEPEDFAVYYCQQGIMLPPTFGQGTKVELK | 169 |
| 29B11; $V_H$ | EVQLLESGGGLVQPGGSLRLSCAASGFTFSSYAMSWVRQAPGKGLEWVSAIIGSGGITYYADSVKGRFTISRDNSKNTLYLQMNSLRAEDTAVYYCAKGWFGGFNYWGQGTLVTVSS | 171 |
| 23C10; $V_L$ | EIVLTQSPGTLSLSPGERATLSCRASQSVSRSYLAWYQQKPGQAPRLLIIGASTRATGIPDRFSGSGSGTDFTLTISRLEPEDFAVYYCQQGQVIPPTFGQGTKVEIK | 173 |
| 23C10; $V_H$ | EVQLLESGGGLVQPGGSLRLSCAASGFTFSSSAMSWVRQAPGKGLEWVSAISTNGNYTYYADSVKGRFTISRDNSKNTLYLQMNSLRAEDTAVYYCAKGWLGNFDYWGQGTLVTVSS | 175 |
| 2B10_C3B6; $V_L$ | DIQMTQSPSSLSASVGDRVTITCRASQGIRNDLGWYQQKPGKAPKRLIYAASSLQSGVPSRFSGSGSGTEFTLTISSLQPEDFATYYCLQNGLQPATFGQGTKVEIK | 177 |

TABLE 3-continued

| Construct | POLYPEPTIDE SEQUENCE | SEQ ID NO |
|---|---|---|
| 2B10_C3B6; $V_H$ | QVQLVQSGAEVKKPGSSVKVSCKASGGTFSSYA ISWVRQAPGQGLEWMGAIIPILGIANYAQKFQG RVTITADKSTSTAYMELSSLRSEDTAVYYCARL YGYAYYGAFDYWGQGTTVTVSS | 179 |
| 2B10_6A12; $V_L$ | DIQMTQSPSSLSASVGDRVTITCRASQGIRNDL GWYQQKPGKAPKRLIYAASSLQSGVPSRFSGSG SGTEFTLTISSLQPEDFATYYCLQNGLQPATFG QGTKVEIK | 181 |
| 2B10_6A12; $V_H$ | QVQLVQSGAEVKKPGSSVKVSCKASGGTFSSYA ISWVRQAPGQGLEWMGVIIPILGTANYAQKFQG RVTITADKSTSTAYMELSSLRSEDTAVYYCARL YGYAYYGAFDYWGQGTTVTVSS | 183 |
| 2B10_C3A6; $V_L$ | DIQMTQSPSSLSASVGDRVTITCRASQGIRNVL GWYQQKPGKAPKRLIYDSSSLQSGVPSRFSGGG SGTEFTLTISSLQPEDFATYYCLQNGLQPATFG QGTKVEIK | 185 |
| 2B10_C3A6; $V_H$ | QVQLVQSGAEVKKPGSSVKVSCKASGGTFSSYA ISWVRQAPGQGLEWMGGIIPIFGTANYAQKFQG RVTITADKSTSTAYMELSSLRSEDTAVYYCARL YGYAYYGAFDYWGQGTTVTVSS | 187 |
| 2B10_D1A2_wt; $V_L$ | DIQMTQSPSSLSASVGDRVTITCRASQGIRNVL GWYQQKPGKAPKRLIYDAYSLQSGVPSRFSGGG SGTEFTLTISSLQPEDFATYYCLQNGLQPATFG QGTKVEIK | 189 |
| 2B10_D1A2_wt; $V_H$ | QVQLVQSGAEVKKPGSSVKVSCKASGGTFSSYA ISWVRQAPGQGLEWMGGIIPIFGTANYAQKFQG RVTITADKSTSTAYMELSSLRSEDTAVYYCARL YGYAYYGAFDYWGQGTTVTVSS | 191 |
| 2B10_D1A2_VD; $V_L$ | DIQMTQSPSSLSASVGDRVTITCRASQGIRNDL GWYQQKPGKAPKRLIYDAYSLQSGVPSRFSGGG SGTEFTLTISSLQPEDFATYYCLQNGLQPATFG QGTKVEIK | 193 |
| 2B10_D1A2_VD; $V_H$ | QVQLVQSGAEVKKPGSSVKVSCKASGGTFSSYA ISWVRQAPGQGLEWMGGIIPIFGTANYAQKFQG RVTITADKSTSTAYMELSSLRSEDTAVYYCARL YGYAYYGAFDYWGQGTTVTVSS | 195 |
| 2B10_O7D8; $V_L$ | DIQMTQSPSSLSASVGDRVTITCRASQSIRNVL GWYQQKPGKAPKRLIYDVSSLQSGVPSRFSGGG SGTEFTLTISSLQPEDFATYYCLQNGLQPATFG QGTKVEIK | 197 |
| 2B10_O7D8; $V_H$ | QVQLVQSGAEVKKPGSSVKVSCKASGGTFSSYA ISWVRQAPGQGLEWMGGIIPIFGTANYAQKFQG RVTITADKSTSTAYMELSSLRSEDTAVYYCARL YGYAYYGAFDYWGQGTTVTVSS | 199 |
| 2B10_O1F7; $V_L$ | DIQMTQSPSSLSASVGDRVTITCRASQGIRNVL GWYQQKPGKAPKRLIYDASSLQSGVPSRFSGGG SGTEFTLTISSLQPEDFATYYCLQNGLQPATFG QGTKVEIK | 201 |
| 2B10_O1F7; $V_H$ | QVQLVQSGAEVKKPGSSVKVSCKASGGTFSSYA ISWVRQAPGQGLEWMGGIIPIFGTANYAQKFQG RVTITADKSTSTAYMELSSLRSEDTAVYYCARL YGYAYYGAFDYWGQGTTVTVSS | 203 |
| 2B10_6H10; $V_L$ | DIQMTQSPSSLSASVGDRVTITCRASQGIRNVL GWYQQKPGKAPKRLIQAATSLQSGVPSRFSGGG SGTEFTLTISSLQPEDFATYYCLQNGLQPATFG QGTKVEIK | 205 |
| 2B10_6H10; $V_H$ | QVQLVQSGAEVKKPGSSVKVSCKASGGTFSSYA ISWVRQAPGQGLEWMGGIIPIFGTANYAQKFQG RVTITADKSTSTAYMELSSLRSEDTAVYYCARL YGYAYYGAFDYWGQGTTVTVSS | 207 |
| MHLG1; $V_H$ | EVQLVESGGGLVKPGGSLRLSCAASGFTFSNYW MNWVRQAPGKGLEWVAEIRLKSNNFGRYYAASV KGRFTISRDDSKNTLYLQMNSLKTEDTAVYYCT TYGNYVGHYFDHWGQGTTVTVSS | 257 |
| KV9; $V_L$ | DIQLTQSPSFLSASVGDRVTITCKASQNVDTNV AWYQQKPGQAPRPLIYSASYRYTGVPSRFSGSG SGTEFTLTISSLQPEDFATYYCQQYNSYPLTFG GGTKVEIKRT | 259 |
| MHLG; $V_H$ | EVQLVESGGGLVQPGGSLRLSCAASGFTFSNYW MNWVRQAPGKGLEWVAEIRLKSNNFGRYYAASV KGRFTISRDDSKNTLYLQMNSLKTEDTAVYYCT TYGNYVGHYFDHWGQGTTVTVSS | 261 |
| KV1; $V_L$ | DIQLTQSPSFLSASVGDRVTITCRASQNVDTNL AWYQQKPGKAPKLLIYSASYRYTGVPSRFSGSG SGTEFTLTISSLQPEDFATYYCQQYNSYPLTFG GGTKVEIKRT | 269 |
| KV7; $V_L$ | DIQLTQSPSFLSASVGDRVTITCKASQNVDTNV AWYQQKPGKAPKPLIYSASYRYTGVPSRFSGSG SGTEFTLTISSLQPEDFATYYCQQYNSYPLTFG GGTKVEIKRT | 271 |

TABLE 4

| Construct | POLYPEPTIDE SEQUENCE | SEQ ID NO |
|---|---|---|
| Fab heavy chain derived from L19 monoclonal antibody-C125A variant of IL2-Fab heavy chain derived from L19 monoclonal antibody | EVQLLESGGGLVQPGGSLRLSCAASGFTFSSFSMSWVRQAP GKGLEWVSSISGSSGTTYYADSVKGRFTISRDNSKNTLYLQ MNSLRAEDTAVYYCAKPFPYFDYWGQGTLVTVSSASTKGP SVFPLAPSSKSTSGGTAALGCLVKDYFPEPVTVSWNSGALTS GVHTFPAVLQSSGLYSLSSVVTVPSSSLGTQTYICNVNHKPS NTKVDKKVEPKSCDSGGGGSGGGGSGGGGAPTSSSTKKTQ LQLEHLLLDLQMILNGINNYKNPKLTRMLTFKFYMPKKATE LKHLQCLEEELKPLEEVLNLAQSKNFHLRPRDLISNINVIVLE LKGSETTFMCEYADETATIVEFLNRWITFAQSIISTLTSGGGG SGGGGSGGGGEVQLLESGGGLVQPGGSLRLSCAASGFTFSSF SMSWVRQAPGKGLEWVSSISGSSGTTYYADSVKGRFTISRD NSKNTLYLQMNSLRAEDTAVYYCAKPFPYFDYWGQGTLVT VSSASTKGPSVFPLAPSSKSTSGGTAALGCLVKDYFPEPVTV SWNSGALTSGVHTFPAVLQSSGLYSLSSVVTVPSSSLGTQTY ICNVNHKPSNTKVDKKVEPKSCD | 95 |

TABLE 4-continued

| Construct | POLYPEPTIDE SEQUENCE | SEQ ID NO |
|---|---|---|
| Fab light chain derived from L19 monoclonal antibody | EIVLTQSPGTLSLSPGERATLSCRASQSVSSSYLAWYQQKPG QAPRLLIYYASSRATGIPDRFSGSGSGTDFTLTISRLEPEDFAV YYCQQTGRIPPTFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC | 96 |
| scFv derived from L19 monoclonal antibody-8 amino acid linker-C125A variant of IL2 | EVQLLESGGGLVQPGGSLRLSCAASGFTFSSFSMSWVRQAP GKGLEWVSSISGSSGTTYYADSVKGRFTISRDNSKNTLYLQ MNSLRAEDTAVYYCAKPFPYFDYWGQGTLVTVSSSGGSGG ASEIVLTQSPGTLSLSPGERATLSCRASQSVSSSYLAWYQQK PGQAPRLLIYYASSRATGIPDRFSGSGSGTDFTLTISRLEPEDF AVYYCQQTGRIPPTFGQGTKVEISVLSSSSGSSSSGSSSSGAP TSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFAQSIIS TLT | 97 |
| F16-diabody-IL2 protein | EVQLLESGGGLVQPGGSLRLSCAASGFTFSRYGMSWVRQAP GKGLEWVSAISGSGGSTYYADSVKGRFTISRDNSKNTLYLQ MNSLRAEDTAVYYCAKAHNAFDYWGQGTLVTVSSASGGSS ELTQDPAVSVALGQTVRITCQGDSLRSYYASWYQQKPGQAP VLVIYGKNNRPSGIPDRFSGSSSGNTASLTITGAQAEDEADY YCNSSVYTMPPVVFGGGTKLTVLGSSSSGSSSSGSSSSGAPTS SSTKKTQLQLEHLLLDLQMILNGINNYKNPKLTRMLTFKFY MPKKATELKHLQCLEEELKPLEEVLNLAQSKNFHLRPRDLIS NINVIVLELKGSETTFMCEYADETATIVEFLNRWITFAQSIIST LT | 98 |
| scFv-IL2-scFv (F16, protein) | EVQLLESGGGLVQPGGSLRLSCAASGFTFSRYGMSWVRQAP GKGLEWVSAISGSGGSTYYADSVKGRFTISRDNSKNTLYLQ MNSLRAEDTAVYYCAKAHNAFDYWGQGTLVTVSRGGGGS GGGGSGGGGSSELTQDPAVSVALGQTVRITCQGDSLRSYYA SWYQQKPGQAPVLVIYGKNNRPSGIPDRFSGSSSGNTASLTI TGAQAEDEADYYCNSSVYTMPPVVFGGGTKLTVLGSSSSGS SSSGSSSSGAPTSSSTKKTQLQLEHLLLDLQMILNGINNYKNP KLTRMLTFKFYMPKKATELKHLQCLEEELKPLEEVLNLAQS KNFHLRPRDLISNINVIVLELKGSETTFMCEYADETATIVEFL NRWITFAQSIISTLTSGGGGSGGGGSGGGGSSELTQDPAVSV ALGQTVRITCQGDSLRSYYASWYQQKPGQAPVLVIYGKNN RPSGIPDRFSGSSSGNTASLTITGAQAEDEADYYCNSSVYTM PPVVFGGGTKLTVLGSGGGSGGGSGGGSGSEVQLLESGGGL VQPGGSLRLSCAASGFTFSRYGMSWVRQAPGKGLEWVSAIS GSGGSTYYADSVKGRFTISRDNSKNTLYLQMNSLRAEDTAV YYCAKAHNAFDYWGQGTLVTVS | 99 |
| Fab-IL2-Fab (F16, heavy chain cytokine fusion construct, protein) | EVQLLESGGGLVQPGGSLRLSCAASGFTFSRYGMSWVRQAP GKGLEWVSAISGSGGSTYYADSVKGRFTISRDNSKNTLYLQ MNSLRAEDTAVYYCAKAHNAFDYWGQGTLVTVSSASTKG PSVFPLAPSSKSTSGGTAALGCLVKDYFPEPVTVSWNSGALT SGVHTFPAVLQSSGLYSLSSVVTVPSSSLGTQTYICNVNHKP SNTKVDKKVEPKSCDSSSSGSSSSGSSSSGAPTSSSTKKTQLQ LEHLLLDLQMILNGINNYKNPKLTRMLTFKFYMPKKATELK HLQCLEEELKPLEEVLNLAQSKNFHLRPRDLISNINVIVLELK GSETTFMCEYADETATIVEFLNRWITFAQSIISTLTSGGGGSG GGGSGGGGEVQLLESGGGLVQPGGSLRLSCAASGFTFSRYG MSWVRQAPGKGLEWVSAISGSGGSTYYADSVKGRFTISRDN SKNTLYLQMNSLRAEDTAVYYCAKAHNAFDYWGQGTLVT VSSASTKGPSVFPLAPSSKSTSGGTAALGCLVKDYFPEPVTV SWNSGALTSGVHTFPAVLQSSGLYSLSSVVTVPSSSLGTQTY ICNVNHKPSNTKVDKKVEPKSCD | 100 |
| F16, light chain, protein | SSELTQDPAVSVALGQTVRITCQGDSLRSYYASWYQQKPGQ APVLVIYGKNNRPSGIPDRFSGSSSGNTASLTITGAQAEDEAD YYCNSSVYTMPPVVFGGGTKLTVLGQPKAAPSVTLFPPSSEE LQANKATLVCLISDFYPGAVTVAWKADSSPVKAGVETTTPS KQSNNKYAASSYLSLTPEQWKSHRSYSCQVTHEGSTVEKTV APTECS | 101 |
| IL2R-beta-Fc(hole) fusion protein, protein | MDMRVPAQLLGLLLLWFPGARCAVNGTSQFTCFYNSRANIS CVWSQDGALQDTSCQVHAWPDRRRWNQTCELLPVSQASW ACNLILGAPDSQKLTTVDIVTLRVLCREGVRWRVMAIQDFK PFENLRLMAPISLQVVHVETHRCNISWEISQASHYFERHLEFE ARTLSPGHTWEEAPLLTLKQKQEWICLETLTPDTQYEFQVR VKPLQGEFTTWSPWSQPLAFRTKPAALGKDTGAQDKTHTCP PCPAPELLGGPSVFLFPPKPKDTLMISRTPEVTCVVVDVSHE | 102 |

TABLE 4-continued

| Construct | POLYPEPTIDE SEQUENCE | SEQ ID NO |
|---|---|---|
| | DPEVKFNWYVDGVEVHNAKTKPREEQYNSTYRVVSVLTVL HQDWLNGKEYKCKVSNKALPAPIEKTISKAKGQPREPQVCT LPPSRDELTKNQVSLSCAVKGFYPSDIAVEWESNGQPENNY KTTPPVLDSDGSFFLVSKLTVDKSRWQQGNVFSCSVMHEAL HNHYTQKSLSLSPGK | |
| IL2R-gamma-Fc(knob), protein | MLKPSLPFTSLLFLQLPLLGVGLNTTILTPNGNEDTTADFFLT TMPTDSLSVSTLPLPEVQCFVFNVEYMNCTWNSSSEPQPTNL TLHYWYKNSDNDKVQKCSHYLFSEEITSGCQLQKKEIHLYQ TFVVQLQDPREPRRQATQMLKLQNLVIPWAPENLTLHKLSE SQLELNWNNRFLNHCLEHLVQYRTDWDHSWTEQSVDYRH KFSLPSVDGQKRYTFRVRSRFNPLCGSAQHWSEWSHPIHWG SNTSKENPFLFALEAGAQDKTHTCPPCPAPELLGGPSVFLFPP KPKDTLMISRTPEVTCVVVDVSHEDPEVKFNWYVDGVEVH NAKTKPREEQYNSTYRVVSVLTVLHQDWLNGKEYKCKVSN KALPAPIEKTISKAKGQPREPQVYTLPPCRDELTKNQVSLWC LVKGFYPSDIAVEWESNGQPENNYKTTPPVLDSDGSFFLYSK LTVDKSRWQQGNVFSCSVMHEALHNHYTQKSLSLSPGK | 103 |
| Fab-IL12-Fab L19 antibody, murine scIL 12, protein | EVQLLESGGGLVQPGGSLRLSCAASGFTFSSFSMSWVRQAP GKGLEWVSSISGSSGTTYYADSVKGRFTISRDNSKNTLYLQ MNSLRAEDTAVYYCAKPFPYFDYVVGQGTLVTVSSASTKGP SVFPLAPSSKSTSGGTAALGCLVKDYFPEPVTVSWNSGALTS GVHTFPAVLQSSGLYSLSSVVTVPSSSLGTQTYICNVNHKPS NTKVDKKVEPKSCDSGGGGSGGGGSGGGGAMWELEKDVY VVEVDWTPDAPGETVNLTCDTPEEDDITWTSDQRHGVIGSG KTLTITVKEFLDAGQYTCHKGGETLSHSHLLLHKKENGIWS TEILKNFKNKTFLKCEAPNYSGRFTCSWLVQRNMDLKFNIK SSSSPPDSRAVTCGMASLSAEKVTLDQRDYEKYSVSCQEDV TCPTAEETLPIELALEARQQNKYENYSTSFFIRDIIKPDPPKNL QMKPLKNSQVEVSWEYPDSWSTPRSYFSLKFFVRIQRKKEK MKETEEGCNQKGAFFVEKTSTEVQCKGGNVCVQAQDRYY NSSCSKWACVPCRVRSGGDGSGGGGSGGGGSRVIPVSGPAR CLSQSRNLLKTTDDMVKTAREKLKHYSCTAEDIDHEDITRD QTSTLKTCLPLELHKNESCLATRETSSTTRGSCLPPQKTSLM MTLCLGSIYEDLKMYQTEFQAINAALQNHNHQQIILDKGML VAIDELMQSLNHNGETLRQKPPVGEADPYRVKMKLCILLHA FSTRVVTINRVMGYLSSAGGGGSGGGGSGGGGEVQLLESGG GLVQPGGSLRLSCAASGFTFSSFSMSWVRQAPGKGLEWVSS ISGSSGTTYYADSVKGRFTISRDNSKNTLYLQMNSLRAEDTA VYYCAKPFPYFDYWGQGTLVTVSSASTKGPSVFPLAPSSKST SGGTAALGCLVKDYFPEPVTVSWNSGALTSGVHTFPAVLQS SGLYSLSSVVTVPSSSLGTQTYICNVNHKPSNTKVDKKVEPK SCD | 104 |
| Fab-IL12-Fab L19 antibody, human scIL12, protein | EVQLLESGGGLVQPGGSLRLSCAASGFTFSSFSMSWVRQAP GKGLEWVSSIRGSSGTTYYADSVKGRFTISRDNSKNTLYLQ MNSLRAEDTAVYYCAKPFPYFDWGQGTLVTVSSASTKGP SVFPLAPSSKSTSGGTAALGCLVKDYFPEPVTVSWNSGALTS GVHTFPAVLQSSGLYSLSSVVTVPSSSLGTQTYICNVNHKPS NTKVDKKVEPKSCDSGGGGSGGGGSGGGGIWELKKDVYV VELDWYPDAPGEMVVLTCDTPEEDGITWTLDQSSEVLGSGK TLTIQVKEFGDAGQYTCHKGGEVLSHSLLLLHKKEDGIWST DILKDQKEPKNKTFLRCEAKNYSGRFTCWWLITISTDLTFSV KSSRGSSDPQGVTCGAATLSAERVRGDNKEYEYSVECQEDS ACPAAEESLPIEVMVDAVHKLKYENYTSSFFIRDIIKPDPPKN LQLKPLKNSRQVEVSWEYPDTWSTPHSYFSLTFCVQVQGKS KREKKDRVFTDKTSATVICRKNASISVRAQDRYYSSSWSEW ASVPCSGGGGSGGGGSGGGGSRNLPVATPDPGMFPCLHHSQ NLLRAVSNMLQKARQTLEFYPCTSEEIDHEDITKDKTSTVEA CLPLELTKNESCLNSRETSFITNGSCLASRKTSFMMALCLSSI YEDLKMYQVEFKTMNAKLLMDPKRQIFLDQNMLAVIDELM QALNFNSETVPQKSSLEEPDFYKTKIKLCILLHAFRIRAVTID RVMSYLNASGGGGSGGGGSGGGGEVQLLESGGGLVQPGGS LRLSCAASGFTFSSFSMSWVRQAPGKGLEWVSSIRGSSGTTY YADSVKGRFTISRDNSKNTLYLQMNSLRAEDTAVYYCAKPF PYFDYWGQGTLVTVSSASTKGPSVFPLAPSSKSTSGGTAALG CLVKDYFPEPVTVSWNSGALTSGVHTFPAVLQSSGLYSLSSV VTVPSSSLGTQTYICNVNHKPSNTKVDKKVEPKSCD | 105 |
| Fab-GMCSF-Fab L19 antibody, human GM-CSF, protein | EVQLLESGGGLVQPGGSLRLSCAASGFTFSSFSMSWVRQAP GKGLEWVSSIRGSSGTTYYADSVKGRFTISRDNSKNTLYLQ MNSLRAEDTAVYYCAKPFPYFDYWGQGTLVTVSSASTKGP SVFPLAPSSKSTSGGTAALGCLVKDYFPEPVTVSWNSGALTS GVHTFPAVLQSSGLYSLSSVVTVPSSSLGTQTYICNVNHKPS NTKVDKKVEPKSCDSGGGGSGGGGSGGGGAPARSPSPSTQP | 106 |

TABLE 4-continued

| Construct | POLYPEPTIDE SEQUENCE | SEQ ID NO |
|---|---|---|
| | WEHVNAIQEARRLLNLSRDTAAEMNETVEVISEMFDLQEPT<br>CLQTRLELYKQGLRGSLTKLKGPLTMMASHYKQHCPPTPET<br>SCATQIITFESFKENLKDFLLVIPFDCWEPVQESGGGGSGGGG<br>SGGGGEVQLLESGGGLVQPGGSLRLSCAASGFTFSSFSMSW<br>VRQAPGKGLEWVSSIRGSSGTTYYADSVKGRFTISRDNSKN<br>TLYLQMNSLRAEDTAVYYCAKPFPYFDYWGQGTLVTVSSA<br>STKGPSVFPLAPSSKSTSGGTAALGCLVKDYFPEPVTVSWNS<br>GALTSGVHTFPAVLQSSGLYSLSSVVTVPSSSLGTQTYICNV<br>NHKPSNTKVDKKVEPKSCD | |
| Fab-IFNα2-Fab, L19 antibody, protein | EVQLLESGGGLVQPGGSLRLSCAASGFTFSSFSMSWVRQAP<br>GKGLEWVSSIRGSSGTTYYADSVKGRFTISRDNSKNTLYLQ<br>MNSLRAEDTAVYYCAKPFPYFDYWGQGTLVTVSSASTKGP<br>SVFPLAPSSKSTSGGTAALGCLVKDYFPEPVTVSWNSGALTS<br>GVHTFPAVLQSSGLYSLSSVVTVPSSSLGTQTYICNVNHKPS<br>NTKVDKKVEPKSCDSGGGGSGGGGSGGGGCDLPQTHSLGN<br>RRALILLAQMRRISPFSCLKDRHDFGFPQEEFDGNQFQKAQA<br>ISVLHEMIQQTFNLFSTKDSSAAWDESLLEKFYTELYQQLND<br>LEACVIQEVGVEETPLMNVDSILAVKKYFQRITLYLTEKKYS<br>PCAWEVVRAEIMRSFSLSTNLQERLRRKESGGGGSGGGGSG<br>GGGEVQLLESGGGLVQPGGSLRLSCAASGFTFSSFSMSWVR<br>QAPGKGLEWVSSIRGSSGTTYYADSVKGRFTISRDNSKNTLY<br>LQMNSLRAEDTAVYYCAKPFPYFDYWGQGTLVTVSSASTK<br>GPSVFPLAPSSKSTSGGTAALGCLVKDYFPEPVTVSWNSGAL<br>TSGVHTFPAVLQSSGLYSLSSVVTVPSSSLGTQTYICNVNHK<br>PSNTKVDKKVEPKSCD | 107 |
| 3F2 Fab-IL2-Fab (heavy chain cytokine fusion construct) | EVQLLESGGGLVQPGGSLRLSCAASGFTFSSYAMSWVRQAP<br>GKGLEWVSAISGSGGSTYYADSVKGRFTISRDNSKNTLYLQ<br>MNSLRAEDTAVYYCAKGWFGGFNYWGQGTLVTVSSASTK<br>GPSVFPLAPSSKSTSGGTAALGCLVKDYFPEPVTVSWNSGAL<br>TSGVHTFPAVLQSSGLYSLSSVVTVPSSSLGTQTYICNVNHK<br>PSNTKVDKKVEPKSCDSGGGGSGGGGSGGGGAPTSSSTKKT<br>QLQLEHLLLDLQMILNGINNYKNPKLTRMLTFKFYMPKKAT<br>ELKHLQCLEEELKPLEEVLNLAQSKNFHLRPRDLISNINVIVL<br>ELKGSETTFMCEYADETATIVEFLNRWITFAQSIISTLTSGGG<br>GSGGGGSGGGGEVQLLESGGGLVQPGGSLRLSCAASGFTFS<br>SYAMSWVRQAPGKGLEWVSAISGSGGSTYYADSVKGRFTIS<br>RDNSKNTLYLQMNSLRAEDTAVYYCAKGWFGGFNYWGQG<br>TLVTVSSASTKGPSVFPLAPSSKSTSGGTAALGCLVKDYFPE<br>PVTVSWNSGALTSGVHTFPAVLQSSGLYSLSSVVTVPSSSLG<br>TQTYICNVNHKPSNTKVDKKVEPKSCD | 209 |
| 4G8 Fab-IL2-Fab (heavy chain cytokine fusion construct) | EVQLLESGGGLVQPGGSLRLSCAASGFTFSSYAMSWVRQAP<br>GKGLEWVSAISGSGGSTYYADSVKGRFTISRDNSKNTLYLQ<br>MNSLRAEDTAVYYCAKGWLGNFDYWGQGTLVTVSSASTK<br>GPSVFPLAPSSKSTSGGTAALGCLVKDYFPEPVTVSWNSGAL<br>TSGVHTFPAVLQSSGLYSLSSVVTVPSSSLGTQTYICNVNHK<br>PSNTKVDKKVEPKSCDSGGGGSGGGGSGGGGAPTSSSTKKT<br>QLQLEHLLLDLQMILNGINNYKNPKLTRMLTFKFYMPKKAT<br>ELKHLQCLEEELKPLEEVLNLAQSKNFHLRPRDLISNINVIVL<br>ELKGSETTFMCEYADETATIVEFLNRWITFAQSIISTLTSGGG<br>GSGGGGSGGGGEVQLLESGGGLVQPGGSLRLSCAASGFTFS<br>SYAMSWVRQAPGKGLEWVSAISGSGGSTYYADSVKGRFTIS<br>RDNSKNTLYLQMNSLRAEDTAVYYCAKGWLGNFDYWGQG<br>TLVTVSSASTKGPSVFPLAPSSKSTSGGTAALGCLVKDYFPE<br>PVTVSWNSGALTSGVHTFPAVLQSSGLYSLSSVVTVPSSSLG<br>TQTYICNVNHKPSNTKVDKKVEPKSCD | 211 |
| 3D9 Fab-IL2-Fab (heavy chain cytokine fusion construct) | EVQLLESGGGLVQPGGSLRLSCAASGFTFSSYAMSWVRQTP<br>GKGLEWVSAIGVSTGSTYYADSVKGRFTISRDNSKNTLYLQ<br>MNSLRAEDTAVYYCAKGWLGPFDYWGQGTLVTVSSASTK<br>GPSVFPLAPSSKSTSGGTAALGCLVKDYFPEPVTVSWNSGAL<br>TSGVHTFPAVLQSSGLYSLSSVVTVPSSSLGTQTYICNVNHK<br>PSNTKVDKKVEPKSCDSGGGGSGGGGSGGGGAPTSSSTKKT<br>QLQLEHLLLDLQMILNGINNYKNPKLTRMLTFKFYMPKKAT<br>ELKHLQCLEEELKPLEEVLNLAQSKNFHLRPRDLISNINVIVL<br>ELKGSETTFMCEYADETATIVEFLNRWITFAQSIISTLTSGGG<br>GSGGGGSGGGGEVQLLESGGGLVQPGGSLRLSCAASGFTFS<br>SYAMSWVRQTPGKGLEWVSAIGVSTGSTYYADSVKGRFTIS<br>RDNSKNTLYLQMNSLRAEDTAVYYCAKGWLGPFDYWGQG<br>TLVTVSSASTKGPSVFPLAPSSKSTSGGTAALGCLVKDYFPE<br>PVTVSWNSGALTSGVHTFPAVLQSSGLYSLSSVVTVPSSSLG<br>TQTYICNVNHKPSNTKVDKKVEPKSCD | 213 |

TABLE 4-continued

| Construct | POLYPEPTIDE SEQUENCE | SEQ ID NO |
|---|---|---|
| 2F11 Fab-IL2-Fab (heavy chain cytokine fusion construct) | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKWRWMMFDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKKVEPKSCDSGGGGSGGGGSGGGGAPTSSSTK KTQLQLEHLLLDLQMILNGINNYKNPKLTRMLTFKFYMPKK ATELKHLQCLEEELKPLEEVLNLAQSKNFHLRPRDLISNINVI VLELKGSETTFMCEYADETATIVEFLNRWITFAQSIISTLTSG GGGSGGGGSGGGGEVQLLESGGGLVQPGGSLRLSCAASGFT FSSYAMSWVRQAPGKGLEWVSAISGSGGSTYYADSVKGRF TISRDNSKNTLYLQMNSLRAEDTAVYYCAKWRWMMFDYW GQGTLVTVSSASTKGPSVFPLAPSSKSTSGGTAALGCLVKDY FPEPVTVSWNSGALTSGVHTFPAVLQSSGLYSLSSVVTVPSS SLGTQTYICNVNHKPSNTKVDKKVEPKSCD | 215 |
| 4B3 Fab-IL2-Fab (heavy chain cytokine fusion construct) | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGWLGNFDYWGQGTLVTVSSASTK GPSVFPLAPSSKSTSGGTAALGCLVKDYFPEPVTVSWNSGAL TSGVHTFPAVLQSSGLYSLSSVVTVPSSSLGTQTYICNVNHK PSNTKVDKKVEPKSCDSGGGGSGGGGSGGGGAPTSSSTKKT QLQLEHLLLDLQMILNGINNYKNPKLTRMLTFKFYMPKKAT ELKHLQCLEEELKPLEEVLNLAQSKNFHLRPRDLISNINVIVL ELKGSETTFMCEYADETATIVEFLNRWITFAQSIISTLTSGGG GSGGGGSGGGGEVQLLESGGGLVQPGGSLRLSCAASGFTFS SYAMSWVRQAPGKGLEWVSAISGSGGSTYYADSVKGRFTIS RDNSKNTLYLQMNSLRAEDTAVYYCAKGWLGNFDYWGQG TLVTVSSASTKGPSVFPLAPSSKSTSGGTAALGCLVKDYFPE PVTVSWNSGALTSGVHTFPAVLQSSGLYSLSSVVTVPSSSLG TQTYICNVNHKPSNTKVDKKVEPKSCD | 217 |
| 4G8 Fab-IL12-Fab (murine IL-12; heavy chain cytokine fusion construct) | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGWLGNFDYWGQGTLVTVSSASTK GPSVFPLAPSSKSTSGGTAALGCLVKDYFPEPVTVSWNSGAL TSGVHTFPAVLQSSGLYSLSSVVTVPSSSLGTQTYICNVNHK PSNTKVDKKVEPKSCDSGGGGSGGGGSGGGGAMWELEKD VYVVEVDWTPDAPGETVNLTCDTPEEDDITWTSDQRHGVIG SGKTLTITVKEFLDAGQYTCHKGGETLSHSHLLLHKKENGI WSTEILKNFKNKTFLKCEAPNYSGRFTCSWLVQRNMDLKFN IKSSSSPPDSRAVTCGMASLSAEKVTLDQRDYEKYSVSCQED VTCPTAEETLPIELALEARQQNKYENYSTSFFIRDIIKPDPPKN LQMKPLKNSQVEVSWEYPDSWSTPRSYFSLKFFVRIQRKKE KMKETEEGCNQKGAFFVEKTSTEVQCKGGNVCVQAQDRY YNSSCSKWACVPCRVRSGGDGSGGGGSGGGGSRVIPVSGPA RCLSQSRNLLKTTDDMVKTAREKLKHYSCTAEDIDHEDITR DQTSTLKTCLPLELHKNESCLATRETSSTTRGSCLPPQKTSL MMTLCLGSIYEDLKMYQTEFQAINAALQNHNHQQIILDKGM LVAIDELMQSLNHNGETLRQKPPVGEADPYRVKMKLCILLH AFSTRVVTINRVMGYLSSAGGGGSGGGGSGGGGEVQLLESG GGLVQPGGSLRLSCAASGFTFSSYAMSWVRQAPGKGLEWV SAISGSGGSTYYADSVKGRFTISRDNSKNTLYLQMNSLRAED TAVYYCAKGWLGNFDYWGQGTLVTVSSASTKGPSVFPLAP SSKSTSGGTAALGCLVKDYFPEPVTVSWNSGALTSGVHTFP AVLQSSGLYSLSSVVTVPSSSLGTQTYICNVNHKPSNTKVDK KVEPKSCD | 219 |
| 28H1 Fab-IL2-Fab (heavy chain cytokine fusion construct) | EVQLLESGGGLVQPGGSLRLSCAASGFTFSSHAMSWVRQAP GKGLEWVSAIWASGEQYYADSVKGRFTISRDNSKNTLYLQ MNSLRAEDTAVYYCAKGWLGNFDYWGQGTLVTVSSASTK GPSVFPLAPSSKSTSGGTAALGCLVKDYFPEPVTVSWNSGAL TSGVHTFPAVLQSSGLYSLSSVVTVPSSSLGTQTYICNVNHK PSNTKVDKKVEPKSCDSGGGGSGGGGSGGGGAPTSSSTKKT QLQLEHLLLDLQMILNGINNYKNPKLTRMLTFKFYMPKKAT ELKHLQCLEEELKPLEEVLNLAQSKNFHLRPRDLISNINVIVL ELKGSETTFMCEYADETATIVEFLNRWITFAQSIISTLTSGGG GSGGGGSGGGGEVQLLESGGGLVQPGGSLRLSCAASGFTFS SHAMSWVRQAPGKGLEWVSAIWASGEQYYADSVKGRFTIS RDNSKNTLYLQMNSLRAEDTAVYYCAKGWLGNFDYWGQG TLVTVSSASTKGPSVFPLAPSSKSTSGGTAALGCLVKDYFPE PVTVSWNSGALTSGVHTFPAVLQSSGLYSLSSVVTVPSSSLG TQTYICNVNHKPSNTKVDKKVEPKSCD | 221 |

TABLE 4-continued

| Construct | POLYPEPTIDE SEQUENCE | SEQ ID NO |
|---|---|---|
| 29B11 Fab-IL2-Fab (heavy chain cytokine fusion construct) | EVQLLESGGGLVQPGGSLRLSCAASGFTFSSYAMSWVRQAP GKGLEWVSAIIGSGGITYYADSVKGRFTISRDNSKNTLYLQM NSLRAEDTAVYYCAKGWFGGFNYWGQGTLVTVSSASTKGP SVFPLAPSSKSTSGGTAALGCLVKDYFPEPVTVSWNSGALTS GVHTFPAVLQSSGLYSLSSVVTVPSSSLGTQTYICNVNHKPS NTKVDKKVEPKSCDSGGGGSGGGGSGGGGAPTSSSTKKTQ LQLEHLLLDLQMILNGINNYKNPKLTRMLTFKFYMPKKATE LKHLQCLEEELKPLEEVLNLAQSKNFHLRPRDLISNINVIVLE LKGSETTFMCEYADETATIVEFLNRWITFAQSIISTLTSGGGG SGGGGSGGGGEVQLLESGGGLVQPGGSLRLSCAASGFTFSS YAMSWVRQAPGKGLEWVSAIIGSGGITYYADSVKGRFTISR DNSKNTLYLQMNSLRAEDTAVYYCAKGWFGGFNYWGQGT LVTVSSASTKGPSVFPLAPSSKSTSGGTAALGCLVKDYFPEP VTVSWNSGALTSGVHTFPAVLQSSGLYSLSSVVTVPSSSLGT QTYICNVNHKPSNTKVDKKVEPKSCD | 223 |
| 19G1 Fab-IL2-Fab (heavy chain cytokine fusion construct) | EVQLLESGGGLVQPGGSLRLSCAASGFTFSSYAMSWVRQAP GKGLEWVSAIISSGGLTYYADSVKGRFTISRDNSKNTLYLQ MNSLRAEDTAVYYCAKGWFGGFNYWGQGTLVTVSSASTK GPSVFPLAPSSKSTSGGTAALGCLVKDYFPEPVTVSWNSGAL TSGVHTFPAVLQSSGLYSLSSVVTVPSSSLGTQTYICNVNHK PSNTKVDKKVEPKSCDSGGGGSGGGGSGGGGAPTSSSTKKT QLQLEHLLLDLQMILNGINNYKNPKLTRMLTFKFYMPKKAT ELKHLQCLEEELKPLEEVLNLAQSKNFHLRPRDLISNINVIVL ELKGSETTFMCEYADETATIVEFLNRWITFAQSIISTLTSGGG GSGGGGSGGGGEVQLLESGGGLVQPGGSLRLSCAASGFTFS SYAMSWVRQAPGKGLEWVSAIISSGGLTYYADSVKGRFTIS RDNSKNTLYLQMNSLRAEDTAVYYCAKGWFGGFNYWGQG TLVTVSSASTKGPSVFPLAPSSKSTSGGTAALGCLVKDYFPE PVTVSWNSGALTSGVHTFPAVLQSSGLYSLSSVVTVPSSSLG TQTYICNVNHKPSNTKVDKKVEPKSCD | 225 |
| 20G8 Fab-IL2-Fab (heavy chain cytokine fusion construct) | EVQLLESGGGLVQPGGSLRLSCAASGFTFSSYAMSWVRQAP GKGLEWVSAIIGSGSRTYYADSVKGRFTISRDNSKNTLYLQ MNSLRAEDTAVYYCAKGWFGGFNYWGQGTLVTVSSASTK GPSVFPLAPSSKSTSGGTAALGCLVKDYFPEPVTVSWNSGAL TSGVHTFPAVLQSSGLYSLSSVVTVPSSSLGTQTYICNVNHK PSNTKVDKKVEPKSCDSGGGGSGGGGSGGGGAPTSSSTKKT QLQLEHLLLDLQMILNGINNYKNPKLTRMLTFKFYMPKKAT ELKHLQCLEEELKPLEEVLNLAQSKNFHLRPRDLISNINVIVL ELKGSETTFMCEYADETATIVEFLNRWITFAQSIISTLTSGGG GSGGGGSGGGGEVQLLESGGGLVQPGGSLRLSCAASGFTFS SYAMSWVRQAPGKGLEWVSAIIGSGSRTYYADSVKGRFTIS RDNSKNTLYLQMNSLRAEDTAVYYCAKGWFGGFNYWGQG TLVTVSSASTKGPSVFPLAPSSKSTSGGTAALGCLVKDYFPE PVTVSWNSGALTSGVHTFPAVLQSSGLYSLSSVVTVPSSSLG TQTYICNVNHKPSNTKVDKKVEPKSCD | 227 |
| 3F2 light chain | EIVLTQSPGTLSLSPGERATLSCRASQSVTSSYLAWYQQKPG QAPRLLINVGSRRATGIPDRFSGSGSGTDFTLTISRLEPEDFA VYYCQQGIMLPPTFGQGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC | 229 |
| 4G8 light chain | EIVLTQSPGTLSLSPGERATLSCRASQSVSRSYLAWYQQKPG QAPRLLIIGASTRATGIPDRFSGSGSGTDFTLTISRLEPEDFAV YYCQQGQVIPPTFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC | 231 |
| 3D9 light chain | EIVLTQSPGTLSLSPGERATLSCRASQSVSSSYLAWYQQKPG QAPRLLIYGASSRATGIPDRFSGSGSGTDFTLTISRLEPEDFAV YYCQQGQLIPPTFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC | 233 |
| 2F11 light chain | EIVLTQSPGTLSLSPGERATLSCRASQSVSSSYLAWYQQKPG QAPRLLIYGASSRATGIP**D**RFSGSGSGTDFTLTISRLEPEDFAV YYCQQGQYTPPTFGQGTKVEIKRTVAAPSVF**IF**PPSDEQLKS GTASVVCLLNNFYPREAKVQWKVDNALQSGNSQESVTEQD SKDSTYSLSSTLTLSKADYEKHKVYACEVTHQGLSSPVTKSF NRGEC | 235 |

TABLE 4-continued

| Construct | POLYPEPTIDE SEQUENCE | SEQ ID NO |
|---|---|---|
| 4B3 light chain | EIVLTQSPGTLSLSPGERATLSCRASQSVSSNYLAWYQQKPG QAPRLLIYGAYIRATGIPDRFSGSGSGTDFTLTISRLEPEDFAV YYCQQGQVIPPTFGQGTKVEIKRTVAAPSVFIFPPSDEQLKSG TASVVCLLNNFYPREAKVQWKVDNALQSGNSQESVTEQDS KDSTYSLSSTLTLSKADYEKHKVYACEVTHQGLSSPVTKSF NRGEC | 237 |
| 2B10 Fab-IL2-Fab (heavy chain cytokine fusion construct) | QVQLVQSGAEVKKPGSSVKVSCKASGGTFSSYAISWVRQAP GQGLEWMGGIIPIFGTANYAQKFQGRVTITADKSTSTAYME LSSLRSEDTAVYYCARLYGYAYYGAFDYWGQGTTVTVSSA STKGPSVFPLAPSSKSTSGGTAALGCLVKDYFPEPVTVSWNS GALTSGVHTFPAVLQSSGLYSLSSVVTVPSSSLGTQTYICNV NHKPSNTKVDKKVEPKSCDSGGGGSGGGGSGGGGAPTSSST KKTQLQLEHLLLDLQMILNGINNYKNPKLTRMLTFKFYMPK KATELKHLQCLEEELKPLEEVLNLAQSKNFHLRPRDLISNIN VIVLELKGSETTFMCEYADETATIVEFLNRWITFAQSIISTLTS GGGGSGGGGSGGGGQVQLVQSGAEVKKPGSSVKVSCKASG GTFSSYAISWVRQAPGQGLEWMGGIIPIFGTANYAQKFQGR VTITADKSTSTAYMELSSLRSEDTAVYYCARLYGYAYYGAF DYWGQGTTVTVSSASTKGPSVFPLAPSSKSTSGGTAALGCL VKDYFPEPVTVSWNSGALTSGVHTFPAVLQSSGLYSLSSVV TVPSSSLGTQTYICNVNHKPSNTKVDKKVEPKSCD | 239 |
| C3B6 Fab-IL2-Fab (heavy chain cytokine fusion construct) | QVQLVQSGAEVKKPGSSVKVSCKASGGTFSSYAISWVRQAP GQGLEWMGAIIPILGIANYAQKFQGRVTITADKSTSTAYMEL SSLRSEDTAVYYCARLYGYAYYGAFDYWGQGTTVTVSSAS TKGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKKVEPKSCDSGGGGSGGGGSGGGGAPTSSSTK KTQLQLEHLLLDLQMILNGINNYKNPKLTRMLTFKFYMPKK ATELKHLQCLEEELKPLEEVLNLAQSKNFHLRPRDLISNINVI VLELKGSETTFMCEYADETATIVEFLNRWITFAQSIISTLTSG GGGSGGGGSGGGGQVQLVQSGAEVKKPGSSVKVSCKASGG TFSSYAISWVRQAPGQGLEWMGAIIPILGIANYAQKFQGRVT ITADKSTSTAYMELSSLRSEDTAVYYCARLYGYAYYGAFDY WGQGTTVTVSSASTKGPSVFPLAPSSKSTSGGTAALGCLVK DYFPEPVTVSWNSGALTSGVHTFPAVLQSSGLYSLSSVVTVP SSSLGTQTYICNVNHKPSNTKVDKKVEPKSCD | 241 |
| 6A12 Fab-IL2-Fab (heavy chain cytokine fusion construct) | QVQLVQSGAEVKKPGSSVKVSCKASGGTFSSYAISWVRQAP GQGLEWMGVIIPILGTANYAQKFQGRVTITADKSTSTAYME LSSLRSEDTAVYYCARLYGYAYYGAFDYWGQGTTVTVSSA STKGPSVFPLAPSSKSTSGGTAALGCLVKDYFPEPVTVSWNS GALTSGVHTFPAVLQSSGLYSLSSVVTVPSSSLGTQTYICNV NHKPSNTKVDKKVEPKSCDSGGGGSGGGGSGGGGAPTSSST KKTQLQLEHLLLDLQMILNGINNYKNPKLTRMLTFKFYMPK KATELKHLQCLEEELKPLEEVLNLAQSKNFHLRPRDLISNIN VIVLELKGSETTFMCEYADETATIVEFLNRWITFAQSIISTLTS GGGGSGGGGSGGGGQVQLVQSGAEVKKPGSSVKVSCKASG GTFSSYAISWVRQAPGQGLEWMGVIIPILGTANYAQKFQGR VTITADKSTSTAYMELSSLRSEDTAVYYCARLYGYAYYGAF DYWGQGTTVTVSSASTKGPSVFPLAPSSKSTSGGTAALGCL VKDYFPEPVTVSWNSGALTSGVHTFPAVLQSSGLYSLSSVV TVPSSSLGTQTYICNVNHKPSNTKVDKKVEPKSCD | 243 |
| 2B10 light chain | DIQMTQSPSSLSASVGDRVTITCRASQGIRNDLGWYQQKPG KAPKRLIYAASSLQSGVPSRFSGSGSGTEFTLTISSLQPEDFAT YYCLQNGLQPATFGQGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC | 245 |
| D1A2 light chain | DIQMTQSPSSLSASVGDRVTITCRASQGIRNDLGWYQQKPG KAPKRLIYDAYSLQSGVPSRFSGGGSGTEFTLTISSLQPEDFA TYYCLQNGLQPATFGQGTKVEIKRTVAAPSVFIFPPSDEQLK SGTASVVCLLNNFYPREAKVQWKVDNALQSGNSQESVTEQ DSKDSTYSLSSTLTLSKADYEKHKVYACEVTHQGLSSPVTK SFNRGEC | 247 |
| O7D8 light chain | DIQMTQSPSSLSASVGDRVTITCRASQSIRNVLGWYQQKPGK APKRLIYDVSSLQSGVPSRFSGGGSGTEFTLTISSLQPEDFAT YYCLQNGLQPATFGQGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC | 249 |

TABLE 4-continued

| Construct | POLYPEPTIDE SEQUENCE | SEQ ID NO |
|---|---|---|
| MHLG1 Fab-IL2-Fab (heavy chain cytokine fusion construct) | EVQLVESGGGLVKPGGSLRLSCAASGFTFSNYWMNWVRQA PGKGLEWVAEIRLKSNNFGRYYAASVKGRFTISRDDSKNTL YLQMNSLKTEDTAVYYCTTYGNYVGHYFDHWGQGTTVTV SSASTKGPSVFPLAPSSKSTSGGTAALGCLVKDYFPEPVTVS WNSGALTSGVHTFPAVLQSSGLYSLSSVVTVPSSSLGTQTYI CNVNHKPSNTKVDKKVEPKSCDSGGGGSGGGGSGGGGAPT SSSTKKTQLQLEHLLLDLQMILNGINNYKNPKLTRMLTFKFY MPKKATELKHLQCLEEELKPLEEVLNLAQSKNFHLRPRDLIS NINVIVLELKGSETTFMCEYADETATIVEFLNRWITFAQSIIST LTSGGGGSGGGGSGGGGEVQLVESGGGLVKPGGSLRLSCA ASGFTFSNYWMNWVRQAPGKGLEWVAEIRLKSNNFGRYY AASVKGRFTISRDDSKNTLYLQMNSLKTEDTAVYYCTTYGN YVGHYFDHWGQGTTVTVSSASTKGPSVFPLAPSSKSTSGGT AALGCLVKDYFPEPVTVSWNSGALTSGVHTFPAVLQSSGLY SLSSVVTVPSSSLGTQTYICNVNHKPSNTKVDKKVEPKSCD | 251 |
| KV9 light chain | DIQLTQSPSFLSASVGDRVTITCKASQNVDTNVAWYQQKPG QAPRPLIYSASYRYTGVPSRFSGSGSGTEFTLTISSLQPEDFAT YYCQQYNSYPLTFGGGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGEC | 253 |
| MHLG Fab-IL2-Fab (heavy chain cytokine fusion construct) | EVQLVESGGGLVQPGGSLRLSCAASGFTFSNYWMNWVRQA PGKGLEWVAEIRLKSNNFGRYYAASVKGRFTISRDDSKNTL YLQMNSLKTEDTAVYYCTTYGNYVGHYFDHWGQGTTVTV SSASTKGPSVFPLAPSSKSTSGGTAALGCLVKDYFPEPVTVS WNSGALTSGVHTFPAVLQSSGLYSLSSVVTVPSSSLGTQTYI CNVNHKPSNTKVDKKVEPKSCDSGGGGSGGGGSGGGGAPT SSSTKKTQLQLEHLLLDLQMILNGINNYKNPKLTRMLTFKFY MPKKATELKHLQCLEEELKPLEEVLNLAQSKNFHLRPRDLIS NINVIVLELKGSETTFMCEYADETATIVEFLNRWITFAQSIIST LTSGGGGSGGGGSGGGGEVQLVESGGGLVQPGGSLRLSCA ASGFTFSNYWMNWVRQAPGKGLEWVAEIRLKSNNFGRYY AASVKGRFTISRDDSKNTLYLQMNSLKTEDTAVYYCTTYGN YVGHYFDHWGQGTTVTVSSASTKGPSVFPLAPSSKSTSGGT AALGCLVKDYFPEPVTVSWNSGALTSGVHTFPAVLQSSGLY SLSSVVTVPSSSLGTQTYICNVNHKPSNTKVDKKVEPKSCD | 255 |
| KV1 light chain | DIQLTQSPSFLSASVGDRVTITCRASQNVDTNLAWYQQKPGKA PKLLIYSASYRYTGVPSRFSGSGSGTEFTLTISSLQPEDFATYYC QQYNSYPLTFGGGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC | 263 |
| KV7 light chain | DIQLTQSPSFLSASVGDRVTITCKASQNVDTNVAWYQQKPGKA PKPLIYSASYRYTGVPSRFSGSGSGTEFTLTISSLQPEDFATYYC QQYNSYPLTFGGGTKVEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC | 265 |

TABLE 5

| Construct | POLYPEPTIDE SEQUENCE | SEQ ID NO |
|---|---|---|
| Human FAP ectodomain + poly-lys-tag + $his_6$-tag | RPSRVHNSEENTMRALTLKDILNGTFSYKTFFPNWISGQEYL HQSADNNIVLYNIETGQSYTILSNRTMKSVNASNYGLSPDRQ FVYLESDYSKLWRYSYTATYYIYDLSNGEFVRGNELPRPIQY LCWSPVGSKLAYVYQNNIYLKQRPGDPPFQITFNGRENKIFN GIPDWVYEEEMLATKYALWWSPNGKFLAYAEFNDTDIPVIA YSYYGDEQYPRTINIPYPKAGAKNPVVRIFIIDTTYPAYVGPQ EVPVPAMIASSDYYFSWLTWVTDERVCLQWLKRVQNVSVL SICDFREDWQTWDCPKTQEHIEESRTGWAGGFFVSTPVFSY DAISYYKIFSDKDGYKHIHYIKDTVENAIQITSGKWEAINIFR VTQDSLFYSSNEFEEYPGRRNIYRISIGSYPPSKKCVTCHLRK ERCQYYTASFSDYAKYYALVCYGPGIPISTLHDGRTDQEIKI LEENKELENALKNIQLPKEEIKKLEVDEITLWYKMILPPQFD RSKKYPLLIQVYGGPCSQSVRSVFAVNWISYLASKEGMVIAL VDGRGTAFQGDKLLYAVYRKLGVYEVEDQITAVRKFIEMG | 53 |

TABLE 5-continued

| Construct | POLYPEPTIDE SEQUENCE | SEQ ID NO |
|---|---|---|
| | FIDEKRIAIWGWSYGGYVSSLALASGTGLFKCGIAVAPVSSW EYYASVYTERFMGLPTKDDNLEHYKNSTVMARAEYFRNVD YLLIHGTADDNVHFQNSAQIAKALVNAQVDFQAMWYSDQ NHGLSGLSTNHLYTHMTHFLKQCFSLSDGKKKKKKGHHHH HH | |
| Murine FAP ectodomain + poly-lys-tag + $his_6$-tag | RPSRVYKPEGNTKRALTLKDILNGTFSYKTYFPNWISEQEYL HQSEDDNIVFYNIETRESYIILSNSTMKSVNATDYGLSPDRQF VYLESDYSKLWRYSYTATYYIYDLQNGEFVRGYELPRPIQY LCWSPVGSKLAYVYQNNIYLKQRPGDPPFQITYTGRENRIFN GIPDWVYEEEMLATKYALWWSPDGKFLAYVEFNDSDIPIIA YSYYGDGQYPRTINIPYPKAGAKNPVVRVFIVDTTYPHHVG PMEVPVPEMIASSDYYFSWLTWVSSERVCLQWLKRVQNVS VLSICDFREDWHAWECPKNQEHVEESRTGWAGGFFVSTPAF SQDATSYYKIFSDKDGYKHIHYIKDTVENAIQITSGKWEAIYI FRVTQDSLFYSSNEFEGYPGRRNIYRISIGNSPPSKKCVTCHL RKERCQYYTASFSYKAKYYALVCYGPGLPISTLHDGRTDQE IQVLEENKELENSLRNIQLPKVEIKKLKDGGLTFWYKMILPP QFDRSKKYPLLIQVYGGPCSQSVKSVFAVNWITYLASKEGIV IALVDGRGTAFQGDKFLHAVYRKLGVYEVEDQLTAVRKFIE MGFIDEERIAIWGWSYGGYVSSLALASGTGLFKCGIAVAPVS SWEYYASIYSERFMGLPTKDDNLEHYKNSTVMARAEYFRN VDYLLIHGTADDNVHFQNSAQIAKALVNAQVDFQAMWYS DQNHGILSGRSQNHLYTHMTHFLKQCFSLSDGKKKKKKGH HHHHH | 55 |
| Human TNC-A2 + avi-tag + $his_6$-tag | ASTGETPNLGEVVVAEVGWDALKLNWTAPEGAYEYFFIQV QEADTVEAAQNLTVPGGLRSTDLPGLKAATHYTITIRGVTQ DFSTTPLSVEVLTASGLNDIFEAQKIEWHEGTHHHHHH | 57 |
| Human TNC-A1 + avi-tag + $his_6$-tag | EQAPELENLTVTEVGWDGLRLNWTAADQAYEHFIIQVQEA NKVEAARNLTVPGSLRAVDIPGLKAATPYTVSIYGVIQGYRT PVLSAEASTASGLNDIFEAQKIEWHEGTHHHHHH | 59 |
| Murine TNC-A1 + avi-tag + $his_6$-tag | ISEFGSSTEEVPSLENLTVTEAGWDGLRLNWTADDLAYEYF VIQVQEANNVETAHNFTVPGNLRAADIPGLKVATSYRVSIY GVARGYRTPVLSAETSTASGLNDIFEAQKIEWHEGTHHHHHH | 61 |
| Human TNC-A4 + avi-tag + $his_6$-tag | EDLPQLGDLAVSEVGWDGLRLNWTAADNAYEHFVIQVQEV NKVEAAQNLTLPGSLRAVDIPGLEAATPYRVSIYGVIRGYRT PVLSAEASTASGLNDIFEAQKIEWHEGTHHHHHH | 63 |
| Murine TNC-A4 + avi-tag + $his_6$-tag | ISEFGSLTEDLPQLGGLSVTEVSWDGLTLNWTTDDLAYKHF VVQVQEANNVEAAQNLTVPGSLRAVDIPGLKADTPYRVSIY GVIQGYRTPMLSTDVSTASGLNDIFEAQKIEWHEGTHHHHHH | 65 |

TABLE 6

| Construct | POLYNUCLEOTIDE SEQUENCE | SEQ ID NO |
|---|---|---|
| 2B10; $V_L$ | GATATCCAGATGACCCAGTCTCCATCCTCCCTGTCTGCAT CTGTCGGAGACCGGGTCACCATCACCTGCCGGGCAAGTC AGGGCATTAGAAATGATTTAGGCTGGTACCAGCAGAAGC CAGGGAAAGCCCCTAAGCGCCTGATCTATGCTGCATCCA GTTTGCAGAGTGGCGTCCCATCAAGGTTCAGCGGCGGTG GATCCGGGACAGAGTTCACTCTCACCATCAGCAGCTTGCA GCCTGAAGATTTTGCCACCTATTACTGCTTGCAGAATGGT CTGCAGCCCGCGACGTTTGGCCAGGGCACCAAAGTCGAG ATCAAG | 4 |
| 2B10(GS); $V_L$ | GATATCCAGATGACCCAGTCTCCATCCTCCCTGTCTGCAT CTGTCGGAGACCGGGTCACCATCACCTGCCGGGCAAGTC AGGGCATTAGAAATGATTTAGGCTGGTACCAGCAGAAGC CAGGGAAAGCCCCTAAGCGCCTGATCTATGCTGCATCCA GTTTGCAGAGTGGCGTCCCATCAAGGTTCAGCGGCAGTG GATCCGGGACAGAGTTCACTCTCACCATCAGCAGCTTGCA GCCTGAAGATTTTGCCACCTATTACTGCTTGCAGAATGGT CTGCAGCCCGCGACGTTTGGCCAGGGCACCAAAGTCGAG ATCAAG | 6 |
| 2B10; $V_H$ | CAGGTGCAATTGGTGCAGTCTGGGGCTGAGGTGAAGAAG CCTGGGTCCTCGGTGAAGGTCTCCTGCAAGGCCTCCGGAG GCACATTCAGCAGCTACGCTATAAGCTGGGTGCGACAGG CCCCTGGACAAGGGCTCGAGTGGATGGGAGGGATCATCC CTATCTTTGGTACAGCAAACTACGCACAGAAGTTCCAGGG | 8 |

TABLE 6-continued

| Construct | POLYNUCLEOTIDE SEQUENCE | SEQ ID NO |
|---|---|---|
| | CAGGGTCACCATTACTGCAGACAAATCCACGAGCACAGC CTACATGGAGCTGAGCAGCCTGAGATCTGAGGACACCGC CGTGTATTACTGTGCGAGACTGTACGGTTACGCTTACTAC GGTGCTTTTGACTACTGGGGCCAAGGGACCACCGTGACC GTCTCCTCA | |
| 2F11; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTAGCAGCAGCTACTTAGCCTGGTACCAGCAGA AACCTGGCCAGGCTCCCAGGCTCCTCATCTATGGAGCATC CAGCAGGGCCACTGGCGTCCCAGACAGGTTCAGTGGCAG TGGATCCGGGACAGACTTCACTCTCACCATCAGCAGACTG GAGCCTGAAGATTTTGCAGTGTATTACTGTCAGCAGGGTC AGTATACTCCCCCCACGTTCGGCCAGGGGACCAAAGTGG AAATCAAA | 10 |
| 2F11(VI); $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTAGCAGCAGCTACTTAGCCTGGTACCAGCAGA AACCTGGCCAGGCTCCCAGGCTCCTCATCTATGGAGCATC CAGCAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTC AGTATACTCCCCCCACGTTCGGCCAGGGGACCAAAGTGG AAATCAAA | 12 |
| 2F11; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTAGTGG TAGTGGTGGTAGCACATACTACGCAGACTCCGTGAAGGG CCGGTTCACCATCTCCAGAGACAATTCCAAGAACACGCTG TATCTGCAGATGAACAGCCTGAGAGCCGAGGACATGGCC GTATATTACTGTGCGAAATGGAGATGGATGATGTTTGACT ACTGGGGCCAAGGAACCCTGGTCACCGTCTCGAGT | 14 |
| 2F11(MT); $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTAGTGG TAGTGGTGGTAGCACATACTACGCAGACTCCGTGAAGGG CCGGTTCACCATCTCCAGAGACAATTCCAAGAACACGCTG TATCTGCAGATGAACAGCCTGAGAGCCGAGGACACCGCC GTATATTACTGTGCGAAATGGAGATGGATGATGTTTGACT ACTGGGGCCAAGGAACCCTGGTCACCGTCTCGAGT | 16 |
| 3F2; $V_L$ | GAAATCGTGTTAACGCAGTCTCCAGGCACCCTGTCTTTGT ATCCAGGGGAAAGAGCCACCCTCTCTTGCAGGGCCAGTC AGAGTGTTACCAGTAGCTACTTAGCCTGGTACCAGCAGA AACCTGGCCAGGCTCCCAGGCTCCTCATCAATGTGGGCTC CCGTAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTA TTATGCTTCCCCCGACGTTCGGCCAGGGGACCAAAGTGGA AATCAAA | 18 |
| 3F2(YS); $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTACCAGTAGCTACTTAGCCTGGTACCAGCAGA AACCTGGCCAGGCTCCCAGGCTCCTCATCAATGTGGGCTC CCGTAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTA TTATGCTTCCCCCGACGTTCGGCCAGGGGACCAAAGTGGA AATCAAA | 20 |
| 3F2; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTAGTGG TAGTGGTGGTAGCACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAAGGGTGGTTTGGTGGTTTTAACT ACTGGGGCCAAGGAACCCTGGTCACCGTCTCGAGT | 22 |

TABLE 6-continued

| Construct | POLYNUCLEOTIDE SEQUENCE | SEQ ID NO |
|---|---|---|
| 3D9, $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTAGCAGCAGCTACTTAGCCTGGTACCAGCAGA AACCTGGCCAGGCTCCCAGGCTCCTCATCTATGGAGCATC CAGCAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTC AGCTTATTCCCCCTACGTTCGGCCAGGGGACCAAAGTGGA AATCAAA | 24 |
| 3D9, $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCTATGAGCTGGGTCCGCCAGAC TCCAGGGAAGGGGCTGGAGTGGGTCTCAGCTATTGGTGTT AGTACTGGTAGCACATACTACGCAGACTCCGTGAAGGGC CGGTTCACCATCTCCAGAGACAATTCCAAGAACACGCTGT ATCTGCAGATGAACAGCCTGAGAGCCGAGGACACGGCCG TATATTACTGTGCGAAAGGTTGGCTGGGTCCTTTTGACTA CTGGGGCCAAGGAACCCTGGTCACCGTCTCGAGT | 26 |
| 2D9(TA); $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCTATGAGCTGGGTCCGCCAGGC TCCAGGGAAGGGGCTGGAGTGGGTCTCAGCTATTGGTGTT AGTACTGGTAGCACATACTACGCAGACTCCGTGAAGGGC CGGTTCACCATCTCCAGAGACAATTCCAAGAACACGCTGT ATCTGCAGATGAACAGCCTGAGAGCCGAGGACACGGCCG TATATTACTGTGCGAAAGGTTGGCTGGGTCCTTTTGACTA CTGGGGCCAAGGAACCCTGGTCACCGTCTCGAGT | 28 |
| 4G8; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTAGCCGCAGCTACTTAGCCTGGTACCAGCAGA AACCTGGCCAGGCTCCCAGGCTCCTCATCATTGGGGCCTC CACCAGGGCCACTGGCATCCCAGACAGGTTCAGTGGCAG TGGATCCGGGACGGACTTCACTCTCACCATCAGCAGACTG GAGCCTGAAGATTTTGCAGTGTATTACTGTCAGCAGGGTC AGGTTATTCCCCCTACGTTCGGCCAGGGGACCAAAGTGG AAATCAAA | 30 |
| 4G8; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTAGTGG TAGTGGTGGTAGCACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAAGGGTGGCTGGGTAATTTTGACT ACTGGGGCCAAGGAACCCTGGTCACCGTCTCGAGT | 32 |
| 4B3; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTAGCAGCAATTACTTAGCCTGGTACCAGCAGA AACCTGGCCAGGCTCCCAGGCTCCTCATCTATGGCGCCTA CATCAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTC AGGTTATTCCCCCTACGTTCGGCCAGGGGACCAAAGTGG AAATCAAA | 34 |
| 4B3; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTAGTGG TAGTGGTGGTAGCACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAAGGGTGGCTGGGTAATTTTGACT ACTGGGGCCAAGGAACCCTGGTCACCGTCTCGAGT | 36 |

TABLE 6-continued

| Construct | POLYNUCLEOTIDE SEQUENCE | SEQ ID NO |
|---|---|---|
| 4D6; $V_L$ | GAAATCGTGTTAACGCAGTCTCCAGGCACCCTGTCTTTGT<br>CTCCAGGGGAAAGAGCCACCCTCTCTTGCAGGGCCAGTC<br>AGAGTGTTAGCAGCAACTACTTAGCCTGGTACCAGCAGA<br>AACCTGGCCAGGCTCCCAGGCTCCTCATCCAGGGCGCCTC<br>CAGCAGGGCCACTGGCATCCCAGACAGGTTCAGTGGCAG<br>TGGATCCGGGACAGACTTCACTCTCACCATCAGCAGACTG<br>GAGCCTGAAGATTTTGCAGTGTATTACTGTCAGCAGGGTC<br>AGGTTATTCCCCCTACGTTCGGCCAGGGGACCAAAGTGG<br>AAATCAAA | 38 |
| 4D6; $V_H$ | GAGGTGCAATTGTTGGAGTCTGGGGGAGGCTTGGTACAG<br>CCTGGGGGGTCCCTGAGACTCTCCTGTGCAGCCTCCGGAT<br>TCACCTTTAGCAGTTATGCCATGAGCTGGGTCCGCCAGGC<br>TCCAGGGAAGGGGCTGGAGTGGGTCTCAGCTATTAGTGG<br>TAGTGGTGGTAGCACATACTACGCAGACTCCGTGAAGGG<br>CCGGTTCACCATCTCCAGAGACAATTCCAAGAACACGCTG<br>TATCTGCAGATGAACAGCCTGAGAGCCGAGGACACGGCC<br>GTATATTACTGTGCGAAAGGGTGGCTGGGTAATTTTGACT<br>ACTGGGGCCAAGGAACCCTGGTCACCGTCTCGAGT | 40 |
| 2C6; $V_L$ | GAAATCGTGTTAACGCAGTCTCCAGGCACCCTGTCTTTGT<br>CTCCAGGGGAAAGAGCCACCCTCTCTTGCAGGGCCAGTC<br>AGAGTGTTAGCAGCAGCTACTTAGCCTGGTACCAGCAGA<br>AACCTGGCCAGGCTCCCAGGCTCCTCATCTATGGAGCATC<br>CAGCAGGGCCACTGGCATCCCAGACAGGTTCAGTGGCAG<br>TGGATCCGGGACAGACTTCACTCTCACCATCAGCAGGCTG<br>GAGCCTGAAGATTTTGCAGTGTATTACTGTCAGCAGGGTC<br>AGCAGATTCCCCCTACGTTCGGCCAGGGGACCAAAGTGG<br>AAATCAAA | 42 |
| 2C6; $V_H$ | GAGGTGCAATTGTTGGAGTCTGGGGGAGGCTTGGTACAG<br>CCTGGGGGGTCCCTGAGACTCTCCTGTGCAGCCTCCGGAT<br>CCACCTTTAGCAGTTATGCCATGAGCTGGGTCCGCCAGGC<br>TCCAGGGAAGGGGCTGGAGTGGGTCTCAGCTATTAGTGG<br>GAGTGCTGGTTATACATACTACGCAGACTCCGTGAAGGG<br>CCGGTTCACCATCTCCAGAGACAATTCCAAGAACACGCTG<br>TATCTGCAGATGAACAGCCTGAGAGCCGAGGACACGGCC<br>GTATATTACTGTGCGAAAGGTTGGTTTGGGAATTTTGACT<br>ACTGGGGCCAAGGAACCCTGGTCACCGTCTCGAGT | 44 |
| 5H5; $V_L$ | GAAATCGTGTTAACGCAGTCTCCAGGCACCCTGTCTTTGT<br>CTCCAGGGGAAAGAGCCACCCTCTCTTGCAGGGCCAGTC<br>AGAGTGTTAGCAGCAGCTACTTAGCCTGGTACCAGCAGA<br>AACCTGGCCAGGCTCCCAGGCTCCTCATCTATGGAGCATC<br>CAGCAGGGCCACTGGCATCCCAGACAGGTTCAGTGGCAG<br>TGGATCCGGGACAGACTTCACTCTCACCATCAGCAGACTG<br>GAGCCTGAAGATTTTGCAGTGTATTACTGTCAGCAGGGTA<br>ATCAGATTCCCCCTACGTTCGGTCAGGGGACCAAAGTGG<br>AAATCAAA | 46 |
| 5H5; $V_H$ | GAGGTGCAATTGTTGGAGTCTGGGGGAGGCTTGGTACAG<br>CCTGGGGGGTCCCTGAGACTCTCCTGTGCAGCCTCCGGAT<br>TCACCTTTAGCAGTTATACCATGAGCTGGGTCCGCCGGTC<br>TCCAGGGAAGGGGCTGGAGTGGGTCTCAGCTATTAGTGG<br>TGGTGGTAGGACATACTACGCAGACTCCGTGAAGGGCCG<br>GTTCACCATCTCCAGAGACAATTCCAAGAACACGCTGTAT<br>CTGCAGATGAACAGCCTGAGAGCCGAGGACACGGCCGTA<br>TATTACTGTGCGAAAGGTTGGTTTACGCCTTTTGACTACT<br>GGGGCCAAGGAACCCTGGTCACCGTCTCGAGT | 48 |
| 2C4; $V_L$ | GAAATCGTGTTAACGCAGTCTCCAGGCACCCTGTCTTTGT<br>CTCCAGGGGAAAGAGCCACCCTCTCTTGCAGGGCCAGTC<br>AGAGTGTTAGCAGTAACTACTTAGCCTGGTACCAGCAGA<br>AACCTGGCCAGGCTCCCAGGCTCCTCATCTATGGTGCCTC<br>CATTAGGGCCACTGGCATCCCAGACAGGTTCAGTGGCAG<br>TGGATCCGGGACAGACTTCACTCTCACCATCAGCAGACTG<br>GAGCCTGAAGATTTTGCAGTGTATTACTGTCAGCAGGGTA<br>ATCAGATTCCCCCTACGTTCGGTCAGGGGACCAAAGTGG<br>AAATCAAA | 50 |

TABLE 6-continued

| Construct | POLYNUCLEOTIDE SEQUENCE | SEQ ID NO |
|---|---|---|
| 2C4; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTAGCGG TAGTGGTGGTAGCACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAAGGTTGGTTTACGCCTTTTGACT ACTGGGGCCAAGGAACCCTGGTCACCGTCTCGAGT | 52 |
| 2D9; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTAGCAGCAGCTACTTAGCCTGGTACCAGCAGA AACCTGGCCAGGCTCCCAGGCTCCTCATCTATGGAGCATC CAGCAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTA ATCAGATTCCCCCTACGTTCGGTCAGGGGACCAAAGTGG AAATCAAA | 68 |
| 2D9; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTAGCGG TAGTGGTGGTAGCACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAAGGTTGGTTTACGCCTTTTGACT ACTGGGGCCAAGGAACCCTGGTCACCGTCTCGAGT | 70 |
| 4B8; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTAGCAGCAGCTACTTAGCCTGGTACCAGCAGA AACCTGGCCAGGCTCCCAGGCTCCTCATCTATGGAGCATC CAGCAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTC AGGTTATTCCCCCTACGTTCGGCCAGGGGACCAAAGTGG AAATCAAA | 72 |
| 4B8; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTAGTGG TAGTGGTGGTAGCACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAAGGGTGGCTGGGTAATTTTGACT ACTGGGGCCAAGGAACCCTGGTCACCGTCTCGAGT | 74 |
| 7A1; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTAGCAGCAGCTACTTAGCCTGGTACCAGCAGA AACCTGGCCAGGCTCCCAGGCTCCTCATCTATGGAGCATC CAGCAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTC AGCAGATTCCCCCTACGTTCGGCCAGGGGACCAAAGTGG AAATCAAA | 76 |
| 7A1; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTAGTGG TAGTGGTGGTAGCACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAAGGTTGGTTTGGGAATTTTGACT ACTGGGGCCAAGGAACCCTGGTCACCGTCTCGAGT | 78 |

TABLE 6-continued

| Construct | POLYNUCLEOTIDE SEQUENCE | SEQ ID NO |
|---|---|---|
| 13C2; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTAGCAGCAGCTACTTAGCCTGGTACCAGCAGA AACCTGGCCAGGCTCCCAGGCTCCTCATCTATGGAGCATC CAGCAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTC AGCTTATTCCCCCTACGTTCGGCCAGGGGACCAAAGTGGA AATCAAA | 80 |
| 13C2; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTAGTGG TAGTGGTGGTAGCACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAAGGTTGGCTGGGTCCTTTTGACT ACTGGGGCCAAGGAACCCTGGTCACCGTCTCGAGT | 82 |
| 13E8; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTAGCAGCAGCTACTTAGCCTGGTACCAGCAGA AACCTGGCCAGGCTCCCAGGCTCCTCATCTATGGAGCATC CAGCAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTC TGAATATTCCCTCGACGTTCGGCCAGGGGACCAAAGTGG AAATCAAA | 84 |
| 13E8; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTAGTGG TAGTGGTGGTAGCACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAAGGTTGGTTGGGTCCGTTTGACT ACTGGGGCCAAGGAACCCTGGTCACCGTCTCGAGT | 86 |
| 14C10; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTAGCAGCAGCTACTTAGCCTGGTACCAGCAGA AACCTGGCCAGGCTCCCAGGCTCCTCATCTATGGAGCATC CAGCAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTC ATATTATTCCCCCGACGTTCGGCCAGGGGACCAAAGTGG AAATCAAA | 88 |
| 14C10; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTAGTGG TAGTGGTGGTAGCACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAAGCTTGGATGGGGCCTTTTGACT ACTGGGGCCAAGGAACCCTGGTCACCGTCTCGAGT | 90 |
| 17A11; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTAGCAGCAGCTACTTAGCCTGGTACCAGCAGA AACCTGGCCAGGCTCCCAGGCTCCTCATCTATGGAGCATC CAGCAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTC TGAATATTCCCTCGACGTTCGGCCAGGGGACCAAAGTGG AAATCAAA | 92 |

TABLE 6-continued

| Construct | POLYNUCLEOTIDE SEQUENCE | SEQ ID NO |
|---|---|---|
| 17A11; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTAGTGG TAGTGGTGGTAGCACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAAGGTTGGTTGGGTCCGTTTGACT ACTGGGGCCAAGGAACCCTGGTCACCGTCTCGAGT | 94 |
| 19G1; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTACCAGTAGCTACTTAGCCTGGTACCAGCAGA AACCTGGCCAGGCTCCCAGGCTCCTCATCAATGTGGGCTC CCGTAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTA TTATGCTTCCCCCGACGTTCGGCCAGGGGACCAAAGTGGA AATCAAA | 122 |
| 19G1; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCGATGAGCTGGGTCCGCCAGGC TCCAGGGAAGGGGCTGGAGTGGGTCTCAGCGATTATTAG TAGTGGTGGTCTCACATACTACGCAGACTCCGTGAAGGGC CGGTTCACCATCTCCAGAGACAATTCCAAGAACACGCTGT ATCTGCAGATGAACAGCCTGAGAGCCGAGGACACGGCCG TATATTACTGTGCGAAAGGGTGGTTTGGTGGTTTTAACTA CTGGGGCCAAGGAACCCTGGTCACCGTCTCGTCC | 124 |
| 20G8; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTACCAGTAGCTACTTAGCCTGGTACCAGCAGA AACCTGGCCAGGCTCCCAGGCTCCTCATCAATGTGGGCTC CCGTAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTA TTATGCTTCCCCCGACGTTCGGCCAGGGGACCAAAGTGGA AATCAAA | 126 |
| 20G8; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCAATGAGCTGGGTCCGCCAGGC TCCAGGGAAGGGGCTGGAGTGGGTCTCAGCTATTATTGG GAGTGGTAGTCGTACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAAGGGTGGTTTGGTGGTTTTAACT ACTGGGGCCAAGGAACCCTGGTCACCGTCTCGTCC | 128 |
| 4B9; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTACCAGTAGCTACTTAGCCTGGTACCAGCAGA AACCTGGCCAGGCTCCCAGGCTCCTCATCAATGTGGGCTC CCGTAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTA TTATGCTTCCCCCGACGTTCGGCCAGGGGACCAAAGTGGA AATCAAA | 130 |
| 4B9; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCTATGAGCTGGGTCCGCCAGGC TCCAGGGAAGGGGCTGGAGTGGGTCTCAGCTATTATTGGT AGTGGTGCTAGCACATACTACGCAGACTCCGTGAAGGGC CGGTTCACCATCTCCAGAGACAATTCCAAGAACACGCTGT ATCTGCAGATGAACAGCCTGAGAGCCGAGGACACGGCCG TATATTACTGTGCGAAAGGGTGGTTTGGTGGTTTTAACTA CTGGGGCCAAGGAACCCTGGTCACCGTCTCGTCC | 132 |

TABLE 6-continued

| Construct | POLYNUCLEOTIDE SEQUENCE | SEQ ID NO |
|---|---|---|
| 5B8; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTACCAGTAGCTACTTAGCCTGGTACCAGCAGA AACCTGGCCAGGCTCCCAGGCTCCTCATCAATGTGGGCTC CCGTAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTA TTATGCTTCCCCCGACGTTCGGCCAGGGGACCAAAGTGGA AATCAAA | 134 |
| 5B8; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCTATGAGCTGGGTCCGCCAGGC TCCAGGGAAGGGGCTGGAGTGGGTCTCAGCTATTTGGGG TGGTGGTCGTAGCACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAAGGGTGGTTTGGTGGTTTTAACT ACTGGGGCCAAGGAACCCTGGTCACCGTCTCGTCC | 136 |
| 5F1; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTACCAGTAGCTACTTAGCCTGGTACCAGCAGA AACCTGGCCAGGCTCCCAGGCTCCTCATCAATGTGGGCTC CCGTAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTA TTATGCTTCCCCCGACGTTCGGCCAGGGGACCAAAGTGGA AATCAAA | 138 |
| 5F1; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCTATGAGCTGGGTCCGCCAGGC TCCAGGGAAGGGGCTGGAGTGGGTCTCAGCTATTATTAGT AGTGGGGCTAGCACATACTACGCAGACTCCGTGAAGGGC CGGTTCACCATCTCCAGAGACAATTCCAAGAACACGCTGT ATCTGCAGATGAACAGCCTGAGAGCCGAGGACACGGCCG TATATTACTGTGCGAAAGGGTGGTTTGGTGGTTTTAACTA CTGGGGCCAAGGAACCCTGGTCACCGTCTCGTCC | 140 |
| 14B3; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTACCAGTAGCTACTTAGCCTGGTACCAGCAGA AACCTGGCCAGGCTCCCAGGCTCCTCATCAATGTGGGCTC CCGTAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTA TTATGCTTCCCCCGACGTTCGGCCAGGGGACCAAAGTGGA AATCAAA | 142 |
| 14B3; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCTATGAGCTGGGTCCGCCAGGC TCCAGGGAAGGGGCTGGAGTGGGTCTCAGCTATTTTGGCT AGTGGTGCGATCACATACTACGCAGACTCCGTGAAGGGC CGGTTCACCATCTCCAGAGACAATTCCAAGAACACGCTGT ATCTGCAGATGAACAGCCTGAGAGCCGAGGACACGGCCG TATATTACTGTGCGAAAGGGTGGTTTGGTGGTTTTAACTA CTGGGGCCAAGGAACCCTGGTCACCGTCTCGTCC | 144 |
| 16F1; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTACCAGTAGCTACTTAGCCTGGTACCAGCAGA AACCTGGCCAGGCTCCCAGGCTCCTCATCAATGTGGGCTC CCGTAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTA TTATGCTTCCCCCGACGTTCGGCCAGGGGACCAAAGTGGA AATCAAA | 146 |

TABLE 6-continued

| Construct | POLYNUCLEOTIDE SEQUENCE | SEQ ID NO |
|---|---|---|
| 16F1; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCTATGAGCTGGGTCCGCCAGGC TCCAGGGAAGGGGCTGGAGTGGGTCTCAGGTATTATTGG TAGTGGTGGTATCACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAAGGGTGGTTTGGTGGTTTTAACT ACTGGGGCCAAGGAACCCTGGTCACCGTCTCGTCC | 148 |
| 16F8; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTACCAGTAGCTACTTAGCCTGGTACCAGCAGA AACCTGGCCAGGCTCCCAGGCTCCTCATCAATGTGGGCTC CCGTAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTA TTATGCTTCCCCCGACGTTCGGCCAGGGGACCAAAGTGGA AATCAAA | 150 |
| 16F8; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTCTTGGT AGTGGTGGTAGCACATACTACGCAGACTCCGTGAAGGGC CGGTTCACCATCTCCAGAGACAATTCCAAGAACACGCTGT ATCTGCAGATGAACAGCCTGAGAGCCGAGGACACGGCCG TATATTACTGTGCGAAAGGGTGGTTTGGTGGTTTTAACTA CTGGGGCCAAGGAACCCTGGTCACCGTCTCGTCC | 152 |
| O3C9; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTACCAGTAGCTACTTAGCCTGGTACCAGCAGA AACCTGGCCAGGCTCCCAGGCTCCTCATCAATGTGGGCTC CCGTAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTA TTATGCTTCCCCCGACGTTCGGCCAGGGGACCAAAGTGGA AATCAAA | 154 |
| O3C9; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTTTGCCATGAGCTGGGTCCGTCAGTC TCCAGGGAAGGGGCTGGAGTGGGTCTCAGCTATTATTGGT AGTGGTAGTAACACATACTACGCAGACTCCGTGAAGGGC CGGTTCACCATCTCCAGAGACAATTCCAAGAACACGCTGT ATCTGCAGATGAACAGCCTGAGAGCCGAGGACACGGCCG TATATTACTGTGCGAAAGGGTGGTTTGGTGGTTTTAACTA CTGGGGCCAAGGAACCCTGGTCACCGTCTCGTCC | 156 |
| O2D7; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTACCAGTAGCTACTTAGCCTGGTACCAGCAGA AACCTGGCCAGGCTCCCAGGCTCCTCATCAATGTGGGCTC CCGTAGGGCCACTGGCACCCCAGACAGGTTCAGTGGCAG TGGATCCGGGACAGACTTCACTCTCACCATCAGCAGACTG GAGCCTGAAGATTTTGCAGTGTATTACTGTCAGCAGGCTA TTATGCTTCCTCCGACGTTCGGCCAGGGGACCAAAGTGGA AATCAAA | 158 |
| O2D7; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTAGTGG TAGTGGTGGTAGCACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAAGGGTGGTTTGGTGGTTTTAACT ACTGGGGCCAAGGAACCCTGGTCACCGTCTCGTCC | 160 |

TABLE 6-continued

| Construct | POLYNUCLEOTIDE SEQUENCE | SEQ ID NO |
|---|---|---|
| 28H1; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTAGCCGCAGCTACTTAGCCTGGTACCAGCAGA AACCTGGCCAGGCTCCCAGGCTCCTCATCATTGGGGCCTC CACCAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTC AGGTTATTCCCCCTACGTTCGGCCAGGGGACCAAAGTGG AAATCAAA | 162 |
| 28H1; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTCATGCTATGAGCTGGGTCCGCCAGGC TCCAGGGAAGGGGCTGGAGTGGGTCTCAGCTATTTGGGC TAGTGGGGAGCAATACTACGCAGACTCCGTGAAGGGCCG GTTCACCATCTCCAGAGACAATTCCAAGAACACGCTGTAT CTGCAGATGAACAGCCTGAGAGCCGAGGACACGGCCGTA TATTACTGTGCGAAAGGGTGGCTGGGTAATTTTGACTACT GGGGCCAAGGAACCCTGGTCACCGTCTCGAGT | 164 |
| 22A3; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTACCAGTAGCTACTTAGCCTGGTACCAGCAGA AACCTGGCCAGGCTCCCAGGCTCCTCATCAATGTGGGCTC CCGTAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTA TTATGCTTCCCCCGACGTTCGGCCAGGGGACCAAAGTGGA AATCAAA | 166 |
| 22A3; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTATTGGT AGTGGTAGTATCACATACTACGCAGACTCCGTGAAGGGC CGGTTCACCATCTCCAGAGACAATTCCAAGAACACGCTGT ATCTGCAGATGAACAGCCTGAGAGCCGAGGACACGGCCG TATATTACTGTGCGAAAGGGTGGTTTGGTGGTTTTAACTA CTGGGGCCAAGGAACCCTGGTCACCGTCTCGAGT | 168 |
| 29B11; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTACCAGTAGCTACTTAGCCTGGTACCAGCAGA AACCTGGCCAGGCTCCCAGGCTCCTCATCAATGTGGGCTC CCGTAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTA TTATGCTTCCCCCGACGTTCGGCCAGGGGACCAAAGTGGA AATCAAA | 170 |
| 29B11; $V_H$ | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCTATGAGCTGGGTCCGCCAGGC TCCAGGGAAGGGGCTGGAGTGGGTCTCAGCTATTATTGGT AGTGGTGGTATCACATACTACGCAGACTCCGTGAAGGGC CGGTTCACCATCTCCAGAGACAATTCCAAGAACACGCTGT ATCTGCAGATGAACAGCCTGAGAGCCGAGGACACGGCCG TATATTACTGTGCGAAAGGGTGGTTTGGTGGTTTTAACTA CTGGGGCCAAGGAACCCTGGTCACCGTCTCGAGT | 172 |
| 23C10; $V_L$ | GAAATCGTGTTAACGCAGTCTCCAGGCACCCTGTCTTTGT CTCCAGGGGAAAGAGCCACCCTCTCTTGCAGGGCCAGTC AGAGTGTTAGCCGCAGCTACTTAGCCTGGTACCAGCAGA AACCTGGCCAGGCTCCCAGGCTCCTCATCATTGGGGCCTC CACCAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTC AGGTTATTCCCCCTACGTTCGGCCAGGGGACCAAAGTGG AAATCAAA | 174 |

TABLE 6-continued

| Construct | POLYNUCLEOTIDE SEQUENCE | SEQ ID NO |
|---|---|---|
| 23C10; $V_H$ | GAGGTGCAATTGTTGGAGTCTGGGGGAGGCTTGGTACAG<br>CCTGGGGGGTCCCTGAGACTCTCCTGTGCAGCCTCCGGAT<br>TCACCTTTAGCAGTTCTGCCATGAGCTGGGTCCGCCAGGC<br>TCCAGGGAAGGGGCTGGAGTGGGTCTCAGCTATTAGTAC<br>TAATGGTAATTATACATACTACGCAGACTCCGTGAAGGGC<br>CGGTTCACCATCTCCAGAGACAATTCCAAGAACACGCTGT<br>ATCTGCAGATGAACAGCCTGAGAGCCGAGGACACGGCCG<br>TATATTACTGTGCGAAAGGGTGGCTGGGTAATTTTGACTA<br>CTGGGGCCAAGGAACCCTGGTCACCGTCTCGAGT | 176 |
| 2B10_C3B6; $V_L$ | GATATCCAGATGACCCAGTCTCCATCCTCCCTGTCTGCAT<br>CTGTCGGAGACCGGGTCACCATCACCTGCCGGGCAAGTC<br>AGGGCATTAGAAATGATTTAGGCTGGTACCAGCAGAAGC<br>CAGGGAAAGCCCCTAAGCGCCTGATCTATGCTGCATCCA<br>GTTTGCAGAGTGGCGTCCCATCAAGGTTCAGCGGCAGTG<br>GATCCGGGACAGAGTTCACTCTCACCATCAGCAGCTTGCA<br>GCCTGAAGATTTTGCCACCTATTACTGCTTGCAGAATGGT<br>CTGCAGCCCGCGACGTTTGGCCAGGGCACCAAAGTCGAG<br>ATCAAG | 178 |
| 2B10_C3B6; $V_H$ | CAGGTGCAATTGGTGCAGTCTGGGGCTGAGGTGAAGAAG<br>CCTGGGTCCTCGGTGAAGGTCTCCTGCAAGGCCTCCGGAG<br>GCACATTCAGCAGCTACGCTATAAGCTGGGTGCGACAGG<br>CCCCTGGACAAGGGCTCGAGTGGATGGGAGCTATCATCC<br>CGATCCTTGGTATCGCAAACTACGCACAGAAGTTCCAGG<br>GCAGGGTCACCATTACTGCAGACAAATCCACGAGCACAG<br>CCTACATGGAGCTGAGCAGCCTGAGATCTGAGGACACCG<br>CCGTGTATTACTGTGCGAGACTGTACGGTTACGCTTACTA<br>CGGTGCTTTTGACTACTGGGGCCAAGGGACCACCGTGACC<br>GTCTCCTCA | 180 |
| 2B10_6A12; $V_L$ | GATATCCAGATGACCCAGTCTCCATCCTCCCTGTCTGCAT<br>CTGTCGGAGACCGGGTCACCATCACCTGCCGGGCAAGTC<br>AGGGCATTAGAAATGATTTAGGCTGGTACCAGCAGAAGC<br>CAGGGAAAGCCCCTAAGCGCCTGATCTATGCTGCATCCA<br>GTTTGCAGAGTGGCGTCCCATCAAGGTTCAGCGGCAGTG<br>GATCCGGGACAGAGTTCACTCTCACCATCAGCAGCTTGCA<br>GCCTGAAGATTTTGCCACCTATTACTGCTTGCAGAATGGT<br>CTGCAGCCCGCGACGTTTGGCCAGGGCACCAAAGTCGAG<br>ATCAAG | 182 |
| 2B10_6A12; $V_H$ | CAGGTGCAATTGGTGCAGTCTGGGGCTGAGGTGAAGAAG<br>CCTGGGTCCTCGGTGAAGGTCTCCTGCAAGGCCTCCGGAG<br>GCACATTCAGCAGCTATGCTATAAGCTGGGTGCGACAGG<br>CCCCTGGACAAGGGCTCGAGTGGATGGGAGTGATCATCC<br>CTATCCTTGGTACCGCAAACTACGCACAGAAGTTCCAGGG<br>CAGGGTCACCATTACTGCAGACAAATCCACGAGCACAGC<br>CTACATGGAGCTGAGCAGCCTGAGATCTGAGGACACCGC<br>CGTGTATTACTGTGCGAGACTGTACGGTTACGCTTACTAC<br>GGTGCTTTTGACTACTGGGGCCAAGGGACCACCGTGACC<br>GTCTCCTCA | 184 |
| 2B10_C3A6; $V_L$ | GACATCCAGATGACCCAGTCTCCTTCCTCCCTGTCTGCAT<br>CTGTCGGAGACCGGGTCACCATCACCTGCCGGGCAAGTC<br>AGGGCATTCGTAATGTTTTAGGCTGGTACCAGCAGAAGCC<br>AGGGAAAGCCCCTAAGCGCCTGATCTATGATTCGTCCAGT<br>TTGCAGAGTGGCGTCCCATCAAGGTTCAGCGGCGGTGGA<br>TCCGGGACAGAGTTCACTCTCACCATCAGCAGCTTGCAGC<br>CTGAAGATTTTGCCACCTATTACTGCTTGCAGAATGGTCT<br>GCAGCCCGCGACGTTTGGCCAGGGCACCAAAGTCGAGAT<br>CAAG | 186 |
| 2B10_C3A6; $V_H$ | CAGGTGCAATTGGTGCAGTCTGGGGCTGAGGTGAAGAAG<br>CCTGGGTCCTCGGTGAAGGTCTCCTGCAAGGCCTCCGGAG<br>GCACATTCAGCAGCTACGCTATAAGCTGGGTGCGACAGG<br>CCCCTGGACAAGGGCTCGAGTGGATGGGAGGGATCATCC<br>CTATCTTTGGTACAGCAAACTACGCACAGAAGTTCCAGGG<br>CAGGGTCACCATTACTGCAGACAAATCCACGAGCACAGC<br>CTACATGGAGCTGAGCAGCCTGAGATCTGAGGACACCGC<br>CGTGTATTACTGTGCGAGACTGTACGGTTACGCTTACTAC<br>GGTGCTTTTGACTACTGGGGCCAAGGGACCACCGTGACC<br>GTCTCCTCA | 188 |
| 2B10_D1A2_wt; $V_L$ | GATATCCAGATGACCCAGTCTCCATCCTCCCTGTCTGCAT<br>CTGTCGGAGACCGGGTCACCATCACCTGCCGGGCAAGTC<br>AGGGGATTCGTAATGTTTTAGGCTGGTACCAGCAGAAGC<br>CAGGGAAAGCCCCTAAGCGCCTGATCTATGATGCTTACA<br>GCTTGCAGAGTGGCGTCCCATCAAGGTTCAGCGGCGGTG | 190 |

TABLE 6-continued

| Construct | POLYNUCLEOTIDE SEQUENCE | SEQ ID NO |
|---|---|---|
| | GATCCGGGACAGAGTTCACTCTCACCATCAGCAGCTTGCA GCCTGAAGATTTTGCCACCTATTACTGCTTGCAGAATGGT CTGCAGCCCGCGACGTTTGGCCAGGGCACCAAAGTCGAG ATCAAG | |
| 2B10_D1A2_wt; $V_H$ | CAGGTGCAATTGGTGCAGTCTGGGGCTGAGGTGAAGAAG CCTGGGTCCTCGGTGAAGGTCTCCTGCAAGGCCTCCGGAG GCACATTCAGCAGCTACGCTATAAGCTGGGTGCGACAGG CCCCTGGACAAGGGCTCGAGTGGATGGGAGGGATCATCC CTATCTTTGGTACAGCAAACTACGCACAGAAGTTCCAGGG CAGGGTCACCATTACTGCAGACAAATCCACGAGCACAGC CTACATGGAGCTGAGCAGCCTGAGATCTGAGGACACCGC CGTGTATTACTGTGCGAGACTGTACGGTTACGCTTACTAC GGTGCTTTTGACTACTGGGGCCAAGGGACCACCGTGACC GTCTCCTCA | 192 |
| 2B10_D1A2_VD; $V_L$ | GACATCCAGATGACCCAGTCTCCATCCTCCCTGTCTGCAT CTGTCGGAGACCGGGTCACCATCACCTGCCGGGCAAGTC AGGGGATTCGTAATGATTTAGGCTGGTACCAGCAGAAGC CAGGGAAAGCCCCTAAGCGCCTGATCTATGATGCTTACA GCTTGCAGAGTGGCGTCCCATCAAGGTTCAGCGGCGGTG GATCCGGGACAGAGTTCACTCTCACCATCAGCAGCTTGCA GCCTGAAGATTTTGCCACCTATTACTGCTTGCAGAATGGT CTGCAGCCCGCGACGTTTGGCCAGGGCACCAAAGTCGAG ATCAAG | 194 |
| 2B10_D1A2_VD; $V_H$ | CAGGTGCAATTGGTGCAGTCTGGGGCTGAGGTGAAGAAG CCTGGGTCCTCGGTGAAGGTCTCCTGCAAGGCCTCCGGAG GCACATTCAGCAGCTACGCTATAAGCTGGGTGCGACAGG CCCCTGGACAAGGGCTCGAGTGGATGGGAGGGATCATCC CTATCTTTGGTACAGCAAACTACGCACAGAAGTTCCAGGG CAGGGTCACCATTACTGCAGACAAATCCACGAGCACAGC CTACATGGAGCTGAGCAGCCTGAGATCTGAGGACACCGC CGTGTATTACTGTGCGAGACTGTACGGTTACGCTTACTAC GGTGCTTTTGACTACTGGGGCCAAGGGACCACCGTGACC GTCTCCTCA | 196 |
| 2B10_O7D8; $V_L$ | GATATCCAGATGACCCAGTCTCCATCCTCCCTGTCTGCAT CTGTCGGAGACCGGGTCACCATCACCTGCCGGGCAAGTC AGAGCATTCGTAATGTTTTAGGCTGGTACCAGCAGAAGCC AGGGAAAGCCCCTAAGCGCCTGATCTATGATGTGTCCAGT TTGCAGAGTGGCGTCCCATCAAGGTTCAGCGGCGGTGGA TCCGGGACAGAGTTCACTCTCACCATCAGCAGCTTGCAGC CTGAAGATTTTGCCACCTATTACTGCTTGCAGAATGGTCT GCAGCCCGCGACGTTTGGCCAGGGCACCAAAGTCGAGAT CAAG | 198 |
| 2B10_O7D8; $V_H$ | CAGGTGCAATTGGTGCAGTCTGGGGCTGAGGTGAAGAAG CCTGGGTCCTCGGTGAAGGTCTCCTGCAAGGCCTCCGGAG GCACATTCAGCAGCTACGCTATAAGCTGGGTGCGACAGG CCCCTGGACAAGGGCTCGAGTGGATGGGAGGGATCATCC CTATCTTTGGTACAGCAAACTACGCACAGAAGTTCCAGGG CAGGGTCACCATTACTGCAGACAAATCCACGAGCACAGC CTACATGGAGCTGAGCAGCCTGAGATCTGAGGACACCGC CGTGTATTACTGTGCGAGACTGTACGGTTACGCTTACTAC GGTGCTTTTGACTACTGGGGCCAAGGGACCACCGTGACC GTCTCCTCA | 200 |
| 2B10_O1F7; $V_L$ | GATATCCAGATGACCCAGTCTCCATCCTCCCTGTCTGCAT CTGTCGGAGACCGGGTCACCATCACCTGCCGGGCAAGTC AGGGCATTCGTAATGTTTTAGGCTGGTACCAGCAGAAGCC AGGGAAAGCCCCTAAGCGCCTGATCGTATGATGCGTCCAG TTTGCAGAGTGGCGTCCCATCAAGGTTCAGCGGCGGTGG ATCCGGGACAGAGTTCACTCTCACCATCAGCAGCTTGCAG CCTGAAGATTTTGCCACCTATTACTGCCTGCAGAATGGTC TGCAGCCCGCGACGTTTGGCCAGGGCACCAAAGTCGAGA TCAAG | 202 |
| 2B10_O1F7; $V_H$ | CAGGTGCAATTGGTGCAGTCTGGGGCTGAGGTGAAGAAG CCTGGGTCCTCGGTGAAGGTCTCCTGCAAGGCCTCCGGAG GCACATTCAGCAGCTACGCTATAAGCTGGGTGCGACAGG CCCCTGGACAAGGGCTCGAGTGGATGGGAGGGATCATCC CTATCTTTGGTACAGCAAACTACGCACAGAAGTTCCAGGG CAGGGTCACCATTACTGCAGACAAATCCACGAGCACAGC CTACATGGAGCTGAGCAGCCTGAGATCTGAGGACACCGC CGTGTATTACTGTGCGAGACTGTACGGTTACGCTTACTAC GGTGCTTTTGACTACTGGGGCCAAGGGACCACCGTGACC GTCTCCTCA | 204 |

TABLE 6-continued

| Construct | POLYNUCLEOTIDE SEQUENCE | SEQ ID NO |
| --- | --- | --- |
| 2B10_6H10; $V_L$ | GACATCCAGATGACCCAGTCTCCATCCTCCCTGTCTGCAT<br>CTGTCGGAGACCGGGTCACCATCACCTGCCGGGCAAGTC<br>AGGGCATTCGTAATGTTTTAGGCTGGTACCAGCAGAAGCC<br>AGGGAAAGCCCCTAAGCGCCTGATCCAGGCTGCTACCAG<br>TTTGCAGAGTGGCGTCCCATCAAGGTTCAGCGGCGGTGG<br>ATCCGGGACAGAGTTCACTCTCACCATCAGCAGCTTGCAG<br>CCTGAAGATTTTGCCACCTATTACTGCTTGCAGAATGGTC<br>TGCAGCCCGCGACGTTTGGCCAGGGCACCAAAGTCGAGA<br>TCAAG | 206 |
| 2B10_6H10; $V_H$ | CAGGTGCAATTGGTGCAGTCTGGGGCTGAGGTGAAGAAG<br>CCTGGGTCCTCGGTGAAGGTCTCCTGCAAGGCCTCCGGAG<br>GCACATTCAGCAGCTACGCTATAAGCTGGGTGCGACAGG<br>CCCCTGGACAAGGGCTCGAGTGGATGGGAGGGATCATCC<br>CTATCTTTGGTACAGCAAACTACGCACAGAAGTTCCAGGG<br>CAGGGTCACCATTACTGCAGACAAATCCACGAGCACAGC<br>CTACATGGAGCTGAGCAGCCTGAGATCTGAGGACACCGC<br>CGTGTATTACTGTGCGAGACTGTACGGTTACGCTTACTAC<br>GGTGCTTTTGACTACTGGGGCCAAGGGACCACCGTGACC<br>GTCTCCTCA | 208 |
| MHLG1; $V_H$ | GAAGTGCAGCTGGTGGAGTCTGGAGGAGGCTTGGTCAAG<br>CCTGGCGGGTCCCTGCGGCTCTCCTGTGCAGCCTCCGGAT<br>TCACATTTAGCAACTATTGGATGAACTGGGTGCGGCAGGC<br>TCCTGGAAAGGGCCTCGAGTGGGTGGCCGAGATCAGATT<br>GAAATCCAATAACTTCGGAAGATATTACGCTGCAAGCGT<br>GAAGGGCCGGTTCACCATCAGCAGAGATGATTCCAAGAA<br>CACGCTGTACCTGCAGATGAACAGCCTGAAGACCGAGGA<br>TACGGCCGTGTATTACTGTACCACATACGGCAACTACGTT<br>GGGCACTACTTCGACCACTGGGGCCAAGGGACCACCGTC<br>ACCGTCTCCAGT | 258 |
| KV9; $V_L$ | GATATCCAGTTGACCCAGTCTCCATCCTTCCTGTCTGCATC<br>TGTGGGCGACCGGGTCACCATCACCTGCAAGGCCAGTCA<br>GAATGTGGATACTAACGTGGCTTGGTACCAGCAGAAGCC<br>AGGGCAGGCACCTAGGCCTCTGATCTATTCGGCATCCTAC<br>CGGTACACTGGCGTCCCATCAAGGTTCAGCGGCAGTGGA<br>TCCGGGACAGAGTTCACTCTCACAATCTCAAGCCTGCAAC<br>CTGAAGATTTCGCAACTTACTACTGTCAACAGTACAATAG<br>TTACCCTCTGACGTTCGGCGGAGGTACCAAGGTGGAGATC<br>AAGCGTACG | 260 |
| MHLG; $V_H$ | GAAGTGCAGCTGGTGGAGTCTGGAGGAGGCTTGGTCCAG<br>CCTGGCGGGTCCCTGCGGCTCTCCTGTGCAGCCTCCGGAT<br>TCACATTTAGCAACTATTGGATGAACTGGGTGCGGCAGGC<br>TCCTGGAAAGGGCCTCGAGTGGGTGGCCGAGATCAGATT<br>GAAATCCAATAACTTCGGAAGATATTACGCTGCAAGCGT<br>GAAGGGCCGGTTCACCATCAGCAGAGATGATTCCAAGAA<br>CACGCTGTACCTGCAGATGAACAGCCTGAAGACCGAGGA<br>TACGGCCGTGTATTACTGTACCACATACGGCAACTACGTT<br>GGGCACTACTTCGACCACTGGGGCCAAGGGACCACCGTC<br>ACCGTCTCCAGT | 262 |
| KV1; $V_L$ | GATATCCAGTTGACCCAGTCTCCATCCTTCCTGTCTGCATCT<br>GTGGGCGACCGGGTCACCATCACCTGCAGGGCCAGTCAGAA<br>TGTGGATACTAACTTAGCTTGGTACCAGCAGAAGCCAGGGA<br>AAGCACCTAAGCTCCTGATCTATTCGGCATCCTACCGTTACA<br>CTGGCGTCCCATCAAGGTTCAGCGGCAGTGGATCCGGGACA<br>GAGTTCACTCTCACAATCTCAAGCCTGCAACCTGAAGATTTC<br>GCAACTTACTACTGTCAACAGTACAATAGTTACCCTCTGACG<br>TTCGGCGGAGGTACCAAGGTGGAGATCAAGCGTACGGTG | 270 |
| KV7; $V_L$ | GATATCCAGTTGACCCAGTCTCCATCCTTCCTGTCTGCATC<br>TGTGGGCGACCGGGTCACCATCACCTGCAAGGCCAGTCA<br>GAATGTGGATACTAACGTGGCTTGGTACCAGCAGAAGCC<br>AGGGAAAGCACCTAAGCCTCTGATCTATTCGGCATCCTAC<br>CGGTACACTGGCGTCCCATCAAGGTTCAGCGGCAGTGGA<br>TCCGGGACAGAGTTCACTCTCACAATCTCAAGCCTGCAAC<br>CTGAAGATTTCGCAACTTACTACTGTCAACAGTACAATAG<br>TTACCCTCTGACGTTCGGCGGAGGTACCAAGGTGGAGATC<br>AAGCGTACGGTG | 272 |

TABLE 7

| Construct | POLYNUCLEOTIDE SEQUENCE | SEQ ID NO |
| --- | --- | --- |
| Human FAP ectodomain + poly-lys-tag + $his_6$-tag | CGCCCTTCAAGAGTTCATAACTCTGAAGAAAATACAATG<br>AGAGCACTCACACTGAAGGATATTTTAAATGGAACATTTT<br>CTTATAAAACATTTTTTCCAAACTGGATTTCAGGACAAGA<br>ATATCTTCATCAATCTGCAGATAACAATATAGTACTTTAT<br>AATATTGAAACAGGACAATCATATACCATTTTGAGTAATA<br>GAACCATGAAAAGTGTGAATGCTTCAAATTACGGCTTATC<br>ACCTGATCGGCAATTTGTATATCTAGAAAGTGATTATTCA<br>AAGCTTTGGAGATACTCTTACACAGCAACATATTACATCT<br>ATGACCTTAGCAATGGAGAATTTGTAAGAGGAAATGAGC<br>TTCCTCGTCCAATTCAGTATTTATGCTGGTCGCCTGTTGGG<br>AGTAAATTAGCATATGTCTATCAAAACAATATCTATTTGA<br>AACAAAGACCAGGAGATCCACCTTTTCAAATAACATTTA<br>ATGGAAGAGAAAATAAAATATTTAATGGAATCCCAGACT<br>GGGTTTATGAAGAGGAAATGCTTGCTACAAAATATGCTCT<br>CTGGTGGTCTCCTAATGGAAAATTTTTGGCATATGCGGAA<br>TTTAATGATACGGATATACCAGTTATTGCCTATTCCTATTA<br>TGGCGATGAACAATATCCTAGAACAATAAATATTCCATAC<br>CCAAAGGCTGGAGCTAAGAATCCCGTTGTTCGGATATTTA<br>TTATCGATACCACTTACCCTGCGTATGTAGGTCCCCAGGA<br>AGTGCCTGTTCCAGCAATGATAGCCTCAAGTGATTATTAT<br>TTCAGTTGGCTCACGTGGGTTACTGATGAACGAGTATGTT<br>TGCAGTGGCTAAAAAGAGTCCAGAATGTTTCGGTCCTGTC<br>TATATGTGACTTCAGGGAAGACTGGCAGACATGGGATTG<br>TCCAAAGACCCAGGAGCATATAGAAGAAAGCAGAACTGG<br>ATGGGCTGGTGGATTCTTTGTTTCAACACCAGTTTTCAGC<br>TATGATGCCATTTCGTACTACAAAATATTTAGTGACAAGG<br>ATGGCTACAAACATATTCACTATATCAAAGACACTGTGGA<br>AAATGCTATTCAAATTACAAGTGGCAAGTGGGAGGCCAT<br>AAATATATTCAGAGTAACACAGGATTCACTGTTTTATTCT<br>AGCAATGAATTTGAAGAATACCCTGGAAGAAGAAACATC<br>TACAGAATTAGCATTGGAAGCTATCCTCCAAGCAAGAAG<br>TGTGTTACTTGCCATCTAAGGAAAGAAAGGTGCCAATATT<br>ACACAGCAAGTTTCAGCGACTACGCCAAGTACTATGCACT<br>TGTCTGCTACGGCCCAGGCATCCCCATTTCCACCCTTCAT<br>GATGGACGCACTGATCAAGAAATTAAAATCCTGGAAGAA<br>AACAAGGAATTGGAAAATGCTTTGAAAAATATCCAGCTG<br>CCTAAAGAGGAAATTAAGAAACTTGAAGTAGATGAAATT<br>ACTTTATGGTACAAGATGATTCTTCCTCCTCAATTTGACA<br>GATCAAAGAAGTATCCCTTGCTAATTCAAGTGTATGGTGG<br>TCCCTGCAGTCAGAGTGTAAGGTCTGTATTTGCTGTTAAT<br>TGGATATCTTATCTTGCAAGTAAGGAAGGGATGGTCATTG<br>CCTTGGTGGATGGTCGAGGAACAGCTTTCCAAGGTGACA<br>AACTCCTCTATGCAGTGTATCGAAAGCTGGGTGTTTATGA<br>AGTTGAAGACCAGATTACAGCTGTCAGAAAATTCATAGA<br>AATGGGTTTCATTGATGAAAAAAGAATAGCCATATGGGG<br>CTGGTCCTATGGAGGATACGTTTCATCACTGCCCTTGCA<br>TCTGGAACTGGTCTTTTCAAATGTGGTATAGCAGTGGCTC<br>CAGTCTCCAGCTGGGAATATTACGCGTCTGTCTACACAGA<br>GAGATTCATGGGTCTCCCAACAAAGGATGATAATCTTGA<br>GCACTATAAGAATTCAACTGTGATGGCAAGAGCAGAATA<br>TTTCAGAAATGTAGACTATCTTCTCATCCACGGAACAGCA<br>GATGATAATGTGCACTTTCAAAACTCAGCACAGATTGCTA<br>AAGCTCTGGTTAATGCACAAGTGGATTTCCAGGCAATGTG<br>GTACTCTGACCAGAACCACGGCTTATCCGGCCTGTCCACG<br>AACCACTTATACACCCACATGACCCACTTCCTAAAGCAGT<br>GTTTCTCTTTGTCAGACGGCAAAAAGAAAAAGAAAAAGG<br>GCCACCACCATCACCATCAC | 54 |
| Murine FAP ectodomain + poly-lys-tag + $his_6$-tag | CGTCCCTCAAGAGTTTACAAACCTGAAGGAAACACAAAG<br>AGAGCTCTTACCTTGAAGGATATTTTAAATGGAACATTCT<br>CATATAAAACATATTTTCCCAACTGGATTTCAGAACAAGA<br>ATATCTTCATCAATCTGAGGATGATAACATAGTATTTTAT<br>AATATTGAAACAAGAGAATCATATATCATTTTGAGTAATA<br>GCACCATGAAAAGTGTGAATGCTACAGATTATGGTTTGTC<br>ACCTGATCGGCAATTTGTGTATCTAGAAAGTGATTATTCA<br>AAGCTCTGGCGATATTCATACACAGCGACATACTACATCT<br>ACGACCTTCAGAATGGGGAATTTGTAAGAGGATACGAGC<br>TCCCTCGTCCAATTCAGTATCTATGCTGGTCGCCTGTTGG<br>GAGTAAATTAGCATATGTATATCAAAACAATATTTATTTG<br>AAACAAAGACCAGGAGATCCACCTTTTCAAATAACTTAT<br>ACTGGAAGAGAAAATAGAATATTTAATGGAATACCAGAC<br>TGGGTTTATGAAGAGGAAATGCTTGCCACAAAATATGCTC<br>TTTGGTGGTCTCCAGATGGAAAATTTTTGGCATATGTAGA<br>ATTTAATGATTCAGATATACCAATTATTGCCTATTCTTATT<br>ATGGTGATGGACAGTATCCTAGAACTATAAATATTCCATA<br>TCCAAAGGCTGGGGCTAAGAATCCGGTTGTTCGTGTTTTT<br>ATTGTTGACACCACCTACCCTCACCACGTGGGCCCAATGG<br>AAGTGCCAGTTCCAGAAATGATAGCCTCAAGTGACTATTA | 56 |

TABLE 7-continued

| Construct | POLYNUCLEOTIDE SEQUENCE | SEQ ID NO |
|---|---|---|
| | TTTCAGCTGGCTCACATGGGTGTCCAGTGAACGAGTATGC TTGCAGTGGCTAAAAAGAGTGCAGAATGTCTCAGTCCTGT CTATATGTGATTTCAGGGAAGACTGGCATGCATGGGAAT GTCCAAAGAACCAGGAGCATGTAGAAGAAAGCAGAACA GGATGGGCTGGTGGATTCTTTGTTTCGACACCAGCTTTTA GCCAGGATGCCACTTCTTACTACAAAATATTTAGCGACAA GGATGGTTACAAACATATTCACTACATCAAAGACACTGTG GAAAATGCTATTCAAATTACAAGTGGCAAGTGGGAGGCC ATATATATATTCCGCGTAACACAGGATTCACTGTTTTATT CTAGCAATGAATTTGAAGGTTACCCTGGAAGAAGAAACA TCTACAGAATTAGCATTGGAAACTCTCCTCCGAGCAAGAA GTGTGTTACTTGCCATCTAAGGAAAGAAAGGTGCCAATAT TACACAGCAAGTTTCAGCTACAAAGCCAAGTACTATGCA CTCGTCTGCTATGGCCCTGGCCTCCCCATTTCCACCCTCCA TGATGGCCGCACAGACCAAGAAATACAAGTATTAGAAGA AAACAAAGAACTGGAAAATTCTCTGAGAAATATCCAGCT GCCTAAAGTGGAGATTAAGAAGCTCAAAGACGGGGACT GACTTTCTGGTACAAGATGATTCTGCCTCCTCAGTTTGAC AGATCAAAGAAGTACCCTTTGCTAATTCAAGTGTATGGTG GTCCTTGTAGCCAGAGTGTTAAGTCTGTGTTTGCTGTTAA TTGGATAACTTATCTCGCAAGTAAGGAGGGGATAGTCATT GCCCTGGTAGATGGTCGGGGCACTGCTTTCCAAGGTGACA AATTCCTGCATGCCGTGTATCGAAAACTGGGTGTATATGA AGTTGAGGACCAGCTCACAGCTGTCAGAAAATTCATAGA AATGGGTTTCATTGATGAAGAAAGAATAGCCATATGGGG CTGGTCCTACGGAGGTTATGTTTCATCCCTGGCCCTTGCA TCTGGAACTGGTCTTTTCAAATGTGGCATAGCAGTGGCTC CAGTCTCCAGCTGGGAATATTACGCATCTATCTACTCAGA GAGATTCATGGGCCTCCCAACAAAGGACGACAATCTCGA ACACTATAAAAATTCAACTGTGATGGCAAGAGCAGAATA TTTCAGAAATGTAGACTATCTTCTCATCCACGGAACAGCA GATGATAATGTGCACTTTCAGAACTCAGCACAGATTGCTA AAGCTTTGGTTAATGCACAAGTGGATTTCCAGGCGATGTG GTACTCTGACCAGAACCATGGTATATTATCTGGGCGCTCC CAGAATCATTTATATACCCACATGACGCACTTCCTCAAGC AATGCTTTTCTTTATCAGACGGCAAAAAGAAAAAGAAAA AGGGCCACCACCATCACCATCAC | |
| Human TNC-A2 + avi-tag + $his_6$-tag | GCGTCCACCGGGGAAACCCCGAACCTGGGCGAAGTGGTG GTGGCGGAAGTGGGTTGGGATGCGCTGAAACTGAACTGG ACCGCGCCGGAAGGCGCGTATGAATATTTTTTCATCCAGG TGCAGGAAGCGGATACCGTTGAAGCGGCGCAGAACCTGA CCGTTCCGGGCGGTCTGCGTAGCACCGATCTGCCGGGCCT GAAAGCGGCGACCCATTATACCATTACCATCCGTGGGGT GACCCAGGATTTTAGCACCACCCCGCTGTCTGTGGAAGTG CTGACCGCTAGCGGCCTGAACGACATCTTCGAGGCTCAG AAAATCGAATGGCACGAAGGTACCCATCACCATCACCAC CAC | 58 |
| Human TNC-A1 + avi-tag + $his_6$-tag | GAACAAGCCCCTGAGCTGGAAAACCTCACCGTGACTGAG GTTGGCTGGGATGGCCTCAGACTCAACTGGACCGCGGCT GACCAGGCCTATGAGCACTTTATCATTCAGGTGCAGGAG GCCAACAAGGTGGAGGCAGCTCGGAACCTCACCGTGCCT GGCAGCCTTCGGGCTGTGGACATACCGGGCCTCAAGGCT GCTACGCCTTATACAGTCTCCATCTATGGGGTGATCCAGG GCTATAGAACACCAGTGCTCTCTGCTGAGGCCTCCACAGC TAGCGGCCTGAACGACATCTTCGAGGCTCAGAAAATCGA ATGGCACGAAGGTACCCATCACCATCACCACCAC | 60 |
| Murine TNC-A1 + avi-tag + $his_6$-tag | ATTTCAGAATTCGGATCCAGCACCGAAGAAGTGCCGAGC CTGGAAAACCTGACCGTGACCGAAGCGGGCTGGGATGGC CTGCGTCTGAACTGGACCGCGGATGATCTGGCCTATGAAT ATTTTGTGATCCAGGTGCAGGAAGCGAACAACGTTGAAA CCGCGCATAACTTTACCGTGCCGGGCAATCTGCGTGCGGC GGATATTCCGGGCCTGAAAGTGGCGACCAGCTATCGTGT GAGCATTTATGGCGTGGCGCGTGGCTATCGTACCCCGGTT CTGAGCGCGGAAACCAGCACCGCTAGCGGCCTGAACGAC ATCTTCGAGGCTCAGAAAATCGAATGGCACGAAGGTACC CATCACCATCACCACCAC | 62 |

TABLE 7-continued

| Construct | POLYNUCLEOTIDE SEQUENCE | SEQ ID NO |
|---|---|---|
| Human TNC-A4 +<br>avi-tag + his$_6$-tag | GAAGATCTGCCGCAGCTGGGCGATCTGGCCGTGAGCGAA<br>GTGGGCTGGGATGGCCTGCGTCTGAACTGGACCGCGGCG<br>GATAACGCGTATGAACATTTTGTGATTCAGGTGCAGGAA<br>GTGAACAAAGTTGAAGCGGCGCAGAACCTGACCCTGCCG<br>GGCAGCCTGCGTGCGGTGGATATTCCGGGCCTGGAAGCG<br>GCGACCCCGTATCGTGTGAGCATCTATGGCGTGATTCGTG<br>GCTATCGTACCCCGGTTCTGAGCGCGGAAGCGAGCACCG<br>CTAGCGGCCTGAACGACATCTTCGAGGCTCAGAAAATCG<br>AATGGCACGAAGGTACCCATCACCATCACCACCAC | 64 |
| Murine TNC-A4 +<br>avi-tag + his$_6$-tag | ATTTCAGAATTCGGATCCCTGACCGAAGATCTGCCGCAGC<br>TGGGCGGTCTGAGCGTGACCGAAGTGAGCTGGGATGGCC<br>TGACCCTGAACTGGACCACCGATGATCTGGCCTATAAACA<br>TTTTGTGGTGCAGGTGCAGGAAGCGAACAACGTTGAAGC<br>GGCGCAGAACCTGACCGTTCCGGGTAGCCTGCGTGCGGT<br>GGATATTCCGGGCCTGAAAGCGGATACCCCGTATCGTGTG<br>AGCATTTATGGCGTGATTCAGGGCTATCGTACCCCGATGC<br>TGTCTACCGATGTGAGCACCGCTAGCGGCCTGAACGACAT<br>CTTCGAGGCTCAGAAAATCGAATGGCACGAAGGTACCCA<br>TCACCATCACCACCAC | 66 |

TABLE 8

| Construct | POLYNUCLEOTIDE SEQUENCE | SEQ ID NO |
|---|---|---|
| Fab heavy chain<br>derived from L19<br>monoclonal<br>antibody-C125A<br>variant of IL2-Fab<br>heavy chain<br>derived from L19<br>monoclonal<br>antibody | GAGGTGCAGCTGTTGGAGTCTGGGGGAGGCTTGGTACAG<br>CCTGGGGGGTCCCTGAGACTCTCCTGTGCAGCCTCTGGAT<br>TCACCTTTAGCAGTTTTTCGATGAGCTGGGTCCGCCAGGC<br>TCCAGGGAAGGGGCTGGAGTGGGTCTCATCTATTTCCGGT<br>AGTTCGGGTACCACATACTACGCAGACTCCGTGAAGGGC<br>CGGTTCACCATCTCCAGAGACAATTCCAAGAACACGCTGT<br>ATCTGCAAATGAACAGCCTGAGAGCCGAGGACACGGCCG<br>TATATTACTGTGCGAAACCGTTTCCGTATTTTGACTACTG<br>GGGCCAGGGAACCCTGGTCACCGTCTCGAGTGCTAGCAC<br>CAAGGGCCCATCGGTCTTCCCCCTGGCACCCTCCTCCAAG<br>AGCACCTCTGGGGGCACAGCGGCCCTGGGCTGCCTGGTC<br>AAGGACTACTTCCCCGAACCGGTGACGGTGTCGTGGAAC<br>TCAGGCGCCCTGACCAGCGGCGTGCACACCTTCCCGGCTG<br>TCCTACAGTCCTCAGGACTCTACTCCCTCAGCAGCGTGGT<br>GACCGTGCCCTCCAGCAGCTTGGGCACCCAGACCTACATC<br>TGCAACGTGAATCACAAGCCCAGCAACACCAAGGTGGAT<br>AAGAAAGTTGAGCCCAAATCTTGTGACTCCGGCGGAGGA<br>GGGAGCGGCGGAGGTGGCTCCGGAGGTGGCGGAGCACCT<br>ACTTCAAGTTCTACAAAGAAAACACAGCTACAACTGGAG<br>CATTTACTGCTGGATTTACAGATGATTTTGAATGGAATTA<br>ATAATTACAAGAATCCCAAACTCACCAGGATGCTCACATT<br>TAAGTTTTACATGCCCAAGAAGGCCACAGAACTGAAACA<br>TCTTCAGTGTCTAGAAGAAGAACTCAAACCTCTGGAGGA<br>AGTGCTAAATTTAGCTCAAAGCAAAAACTTTCACTTAAGA<br>CCCAGGGACTTAATCAGCAATATCAACGTAATAGTTCTGG<br>AACTAAAGGGATCTGAAACAACATTCATGTGTGAATATG<br>CTGATGAGACAGCAACCATTGTAGAATTTCTGAACAGAT<br>GGATTACCTTTGCCCAAAGCATCATCTCAACACTGACTTC<br>CGGCGGAGGAGGATCCGGCGGAGGTGGCTCTGGCGGTGG<br>CGGAGAGGTGCAGCTGTTGGAGTCTGGGGGAGGCTTGGT<br>ACAGCCTGGGGGGTCCCTGAGACTCTCCTGTGCAGCCTCT<br>GGATTCACCTTTAGCAGTTTTTCGATGAGCTGGGTCCGCC<br>AGGCTCCAGGGAAGGGGCTGGAGTGGGTCTCATCTATTTC<br>CGGTAGTTCGGGTACCACATACTACGCAGACTCCGTGAA<br>GGGCCGGTTCACCATCTCCAGAGACAATTCCAAGAACAC<br>GCTGTATCTGCAAATGAACAGCCTGAGAGCCGAGGACAC<br>GGCCGTATATTACTGTGCGAAACCGTTTCCGTATTTTGAC<br>TACTGGGGCCAGGGAACCCTGGTCACCGTCTCGAGTGCTA<br>GCACCAAGGGCCCATCGGTCTTCCCCCTGGCACCCTCCTC<br>CAAGAGCACCTCTGGGGGCACAGCGGCCCTGGGCTGCCT<br>GGTCAAGGACTACTTCCCCGAACCGGTGACGGTGTCGTG<br>GAACTCAGGCGCCCTGACCAGCGGCGTGCACACCTTCCC<br>GGCTGTCCTACAGTCCTCAGGACTCTACTCCCTCAGCAGC<br>GTGGTGACCGTGCCCTCCAGCAGCTTGGGCACCCAGACCT<br>ACATCTGCAACGTGAATCACAAGCCCAGCAACACCAAGG<br>TGGATAAGAAAGTTGAGCCCAAATCTTGTGACTGA | 108 |

TABLE 8-continued

| Construct | POLYNUCLEOTIDE SEQUENCE | SEQ ID NO |
|---|---|---|
| Fab light chain derived from L19 monoclonal antibody | GAAATTGTGTTGACGCAGTCTCCAGGCACCCTGTCTTTGT<br>CTCCAGGGGAAAGAGCCACCCTCTCCTGCAGGGCCAGTC<br>AGAGTGTTAGCAGCAGCTACTTAGCCTGGTACCAGCAGA<br>AACCTGGCCAGGCTCCCAGGCTCCTCATCTATTATGCATC<br>CAGCAGGGCCACTGGCATCCCAGACAGGTTCAGTGGCAG<br>TGGGTCTGGGACAGACTTCACTCTCACCATCAGCAGACTG<br>GAGCCTGAAGATTTTGCAGTGTATTACTGTCAGCAGACGG<br>GTCGTATTCCTCCGACGTTCGGCCAAGGGACCAAGGTGG<br>AAATCAAACGTACGGTGGCTGCACCATCTGTCTTCATCTT<br>CCCGCCATCTGATGAGCAGTTGAAATCTGGAACTGCCTCT<br>GTTGTGTGCCTGCTGAATAACTTCTATCCCAGAGAGGCCA<br>AAGTACAGTGGAAGGTGGATAACGCCCTCCAATCGGGTA<br>ACTCCCAGGAGAGTGTCACAGAGCAGGACAGCAAGGACA<br>GCACCTACAGCCTCAGCAGCACCCTGACGCTGAGCAAAG<br>CAGACTACGAGAAACACAAAGTCTACGCCTGCGAAGTCA<br>CCCATCAGGGCCTGAGCTCGCCCGTCACAAAGAGCTTCA<br>ACAGGGGAGAGTGTTAG | 109 |
| scFv derived from L19 monoclonal antibody-8 amino acid linker-C125A variant of IL2 | GAGGTGCAGCTGTTGGAGTCTGGGGGAGGCTTGGTACAG<br>CCTGGGGGGTCCCTGAGACTCTCCTGTGCAGCCTCTGGAT<br>TCACCTTTAGCAGTTTTTCGATGAGCTGGGTCCGCCAGGC<br>TCCAGGGAAGGGGCTGGAGTGGGTCTCATCTATTTCCGGT<br>AGTTCGGGTACCACATACTACGCAGACTCCGTGAAGGGC<br>CGGTTCACCATCTCCAGAGACAATTCCAAGAACACGCTGT<br>ATCTGCAAATGAACAGCCTGAGAGCCGAGGACACGGCCG<br>TATATTACTGTGCGAAACCGTTTCCGTATTTTGACTACTG<br>GGGCCAGGGAACCCTGGTCACCGTCTCGAGTAGCGGCGG<br>GAGCGGCGGGGCTAGCGAAATTGTGTTGACGCAGTCTCC<br>AGGCACCCTGTCTTTGTCTCCAGGGGAAAGAGCCACCCTC<br>TCCTGCAGGGCCAGTCAGAGTGTTAGCAGCAGCTACTTAG<br>CCTGGTACCAGCAGAAACCTGGCCAGGCTCCCAGGCTCCT<br>CATCTATTATGCATCCAGCAGGGCCACTGGCATCCCAGAC<br>AGGTTCAGTGGCAGTGGGTCTGGGACAGACTTCACTCTCA<br>CCATCAGCAGACTGGAGCCTGAAGATTTTGCAGTGTATTA<br>CTGTCAGCAGACGGGTCGTATTCCTCCGACGTTCGGCCAA<br>GGGACCAAGGTGGAAATCTCCGTGCTGTCTTCCTCATCGG<br>GTAGTAGCTCTTCCGGCTCATCGTCCTCCGGAGCACCTAC<br>TTCAAGTTCTACAAAGAAAACACAGCTACAACTGGAGCA<br>TTTACTGCTGGATTTACAGATGATTTTGAATGGAATTAAT<br>AATTACAAGAATCCCAAACTCACCAGGATGCTCACATTTA<br>AGTTTTACATGCCCAAGAAGGCCACAGAACTGAAACATC<br>TTCAGTGTCTAGAAGAAGAACTCAAACCTCTGGAGGAAG<br>TGCTAAATTTAGCTCAAAGCAAAAACTTTCACTTAAGACC<br>CAGGGACTTAATCAGCAATATCAACGTAATAGTTCTGGA<br>ACTAAAGGGATCTGAAACAACATTCATGTGTGAATATGCT<br>GATGAGACAGCAACCATTGTAGAATTTCTGAACAGATGG<br>ATTACCTTTGCCCAAAGCATCATCTCAACACTGACTTGA | 110 |
| F16-diabody-IL2 DNA | GAGGTGCAGCTGTTGGAGTCTGGGGGAGGCTTGGTACAG<br>CCTGGGGGGTCCCTGAGACTCTCCTGTGCAGCCTCTGGAT<br>TCACCTTTAGCCGGTATGGTATGAGCTGGGTCCGCCAGGC<br>TCCAGGGAAGGGGCTGGAGTGGGTCTCAGCTATTAGTGG<br>TAGTGGTGGTAGCACATACTACGCAGACTCCGTGAAGGG<br>CCGGTTCACCATCTCCAGAGACAATTCCAAGAACACGCTG<br>TATCTGCAAATGAACAGCCTGAGAGCCGAGGACACGGCC<br>GTATATTACTGTGCGAAAGCGCATAATGCTTTTGACTACT<br>GGGGCCAGGGAACCCTGGTCACCGTGTCGAGTGCTAGCG<br>GCGGATCGTCTGAGCTGACTCAGGACCCTGCTGTGTCTGT<br>GGCCTTGGGACAGACAGTCAGGATCACATGCCAAGGAGA<br>CAGCCTCAGAAGCTATTATGCAAGCTGGTACCAGCAGAA<br>GCCAGGACAGGCCCCTGTACTTGTCATCTATGGTAAAAAC<br>AACCGGCCCTCAGGGATCCCAGACCGATTCTCTGGCTCCA<br>GCTCAGGAAACACAGCTTCCTTGACCATCACTGGGGCTCA<br>GGCGGAAGATGAGGCTGACTATTACTGTAACTCCTCTGTT<br>TATACTATGCCGCCCGTGGTATTCGGCGGAGGGACCAAG<br>CTGACCGTCCTAGGCTCTTCCTCATCGGGTAGTAGCTCTT<br>CCGGCTCATCGTCCTCCGGAGCACCTACTTCAAGTTCTAC<br>AAAGAAAACACAGCTACAACTGGAGCATTTACTGCTGGA<br>TTTACAGATGATTTTGAATGGAATTAATAATTACAAGAAT<br>CCCAAACTCACCAGGATGCTCACATTTAAGTTTTACATGC<br>CCAAGAAGGCCACAGAACTGAAACATCTTCAGTGTCTAG<br>AAGAAGAACTCAAACCTCTGGAGGAAGTGCTAAATTTAG<br>CTCAAAGCAAAAACTTTCACTTAAGACCCAGGGACTTAAT<br>CAGCAATATCAACGTAATAGTTCTGGAACTAAAGGGATC<br>TGAAACAACATTCATGTGTGAATATGCTGATGAGACAGC<br>AACCATTGTAGAATTTCTGAACAGATGGATTACCTTTGCC<br>CAAAGCATCATCTCAACACTGACTTGA | 111 |

TABLE 8-continued

| Construct | POLYNUCLEOTIDE SEQUENCE | SEQ ID NO |
|---|---|---|
| scFv-IL2-scFv<br>(F16, DNA) | GAGGTGCAGCTGTTGGAGTCTGGGGGAGGCTTGGTACAG<br>CCTGGGGGGTCCCTGAGACTCTCCTGTGCAGCCTCTGGAT<br>TCACCTTTAGCCGGTATGGTATGAGCTGGGTCCGCCAGGC<br>TCCAGGGAAGGGGCTGGAGTGGGTCTCAGCTATTAGTGG<br>TAGTGGTGGTAGCACATACTACGCAGACTCCGTGAAGGG<br>CCGGTTCACCATCTCCAGAGACAATTCCAAGAACACGCTG<br>TATCTGCAAATGAACAGCCTGAGAGCCGAGGACACGGCC<br>GTATATTACTGTGCGAAAGCGCATAATGCTTTTGACTACT<br>GGGGCCAGGGAACCCTGGTCACCGTGTCGAGAGGTGGAG<br>GCGGTTCAGGCGGAGGTGGCTCTGGCGGTGGCGGATCGT<br>CTGAGCTGACTCAGGACCCTGCTGTGTCTGTGGCCTTGGG<br>ACAGACAGTCAGGATCACATGCCAAGGAGACAGCCTCAG<br>AAGCTATTATGCAAGCTGGTACCAGCAGAAGCCAGGACA<br>GGCCCCTGTACTTGTCATCTATGGTAAAAACAACCGGCCC<br>TCAGGGATCCCAGACCGATTCTCTGGCTCCAGCTCAGGAA<br>ACACAGCTTCCTTGACCATCACTGGGGCTCAGGCGGAAG<br>ATGAGGCTGACTATTACTGTAACTCCTCTGTTTATACTAT<br>GCCGCCCGTGGTATTCGGCGGAGGGACCAAGCTGACCGT<br>CCTAGGCTCTTCCTCATCGGGTAGTAGCTCTTCCGGCTCA<br>TCGTCCTCCGGAGCACCTACTTCAAGTTCTACAAAGAAAA<br>CACAGCTACAACTGGAGCATTTACTGCTGGATTTACAGAT<br>GATTTTGAATGGAATTAATAATTACAAGAATCCCAAACTC<br>ACCAGGATGCTCACATTTAAGTTTTACATGCCCAAGAAGG<br>CCACAGAACTGAAACATCTTCAGTGTCTAGAAGAAGAAC<br>TCAAACCTCTGGAGGAAGTGCTAAATTTAGCTCAAAGCA<br>AAAACTTTCACTTAAGACCCAGGGACTTAATCAGCAATAT<br>CAACGTAATAGTTCTGGAACTAAAGGGATCTGAAACAAC<br>ATTCATGTGTGAATATGCTGATGAGACAGCAACCATTGTA<br>GAATTTCTGAACAGATGGATTACCTTTGCCCAAAGCATCA<br>TCTCAACACTGACTTCCGGCGGAGGAGGGAGCGGCGGAG<br>GTGGCTCTGGCGGTGGCGGATCGTCTGAGCTCACTCAGGA<br>CCCTGCTGTGTCTGTGGCCTTGGGACAGACAGTCAGGATC<br>ACATGCCAAGGAGACAGCCTCAGAAGCTATTATGCAAGC<br>TGGTACCAGCAGAAGCCAGGACAGGCCCCTGTACTTGTC<br>ATCTATGGTAAAAACAACCGGCCCTCAGGGATCCCAGAC<br>CGATTCTCTGGCTCCAGCTCAGGAAACACAGCTTCCTTGA<br>CCATCACTGGGGCTCAGGCGGAAGATGAGGCTGACTATT<br>ACTGTAACTCCTCTGTTTATACTATGCCGCCCGTGGTATTC<br>GGCGGAGGGACCAAGCTTACCGTACTAGGCTCAGGAGGC<br>GGTTCAGGCGGAGGTTCTGGCGGCGGTAGCGGATCGGAG<br>GTGCAGCTGTTGGAGTCTGGGGGAGGCTTGGTACAGCCT<br>GGGGGGTCCCTGAGACTCTCCTGTGCAGCCTCTGGATTCA<br>CCTTTAGCCGGTATGGTATGAGCTGGGTCCGCCAGGCTCC<br>AGGGAAGGGGCTGGAGTGGGTCTCAGCTATTAGTGGTAG<br>TGGTGGTAGCACATACTACGCAGACTCCGTGAAGGGCCG<br>GTTCACCATCTCCAGAGACAATTCCAAGAACACGCTGTAT<br>CTGCAAATGAACAGCCTGAGAGCCGAGGACACGGCCGTA<br>TATTACTGTGCGAAAGCGCATAATGCTTTTGACTACTGGG<br>GCCAGGGAACCCTGGTCACCGTGTCGTGA | 112 |
| Fab-IL2-Fab<br>(F16, heavy chain<br>cytokine fusion<br>construct, DNA) | GAGGTGCAGCTGTTGGAGTCTGGGGGAGGCTTGGTACAG<br>CCTGGGGGGTCCCTGAGACTCTCCTGTGCAGCCTCTGGAT<br>TCACCTTTAGCCGGTATGGTATGAGCTGGGTCCGCCAGGC<br>TCCAGGGAAGGGGCTGGAGTGGGTCTCAGCTATTAGTGG<br>TAGTGGTGGTAGCACATACTACGCAGACTCCGTGAAGGG<br>CCGGTTCACCATCTCCAGAGACAATTCCAAGAACACGCTG<br>TATCTGCAAATGAACAGCCTGAGAGCCGAGGACACGGCC<br>GTATATTACTGTGCGAAAGCGCATAATGCTTTTGACTACT<br>GGGGCCAGGGAACCCTGGTCACCGTGTCGAGTGCTAGCA<br>CCAAGGGCCCATCGGTCTTCCCCCTGGCACCCTCCTCCAA<br>GAGCACCTCTGGGGGCACAGCGGCCCTGGGCTGCCTGGT<br>CAAGGACTACTTCCCCGAACCGGTGACGGTGTCGTGGAA<br>CTCAGGCGCCCTGACCAGCGGCGTGCACACCTTCCCGGCT<br>GTCCTACAGTCCTCAGGACTCTACTCCCTCAGCAGCGTGG<br>TGACCGTGCCCTCCAGCAGCTTGGGCACCCAGACCTACAT<br>CTGCAACGTGAATCACAAGCCCAGCAACACCAAGGTGGA<br>TAAGAAAGTTGAGCCCAAATCTTGTGACTCTTCCTCATCG<br>GGTAGTAGCTCTTCCGGCTCATCGTCCTCCGGAGCACCTA<br>CTTCAAGTTCTACAAAGAAAACACAGCTACAACTGGAGC<br>ATTTACTGCTGGATTTACAGATGATTTTGAATGGAATTAA<br>TAATTACAAGAATCCCAAACTCACCAGGATGCTCACATTT<br>AAGTTTTACATGCCCAAGAAGGCCACAGAACTGAAACAT<br>CTTCAGTGTCTAGAAGAAGAACTCAAACCTCTGGAGGAA<br>GTGCTAAATTTAGCTCAAAGCAAAAACTTTCACTTAAGAC<br>CCAGGGACTTAATCAGCAATATCAACGTAATAGTTCTGGA<br>ACTAAAGGGATCTGAAACAACATTCATGTGTGAATATGCT<br>GATGAGACAGCAACCATTGTAGAATTTCTGAACAGATGG<br>ATTACCTTTGCCCAAAGCATCATCTCAACACTGACTTCCG | 113 |

TABLE 8-continued

| Construct | POLYNUCLEOTIDE SEQUENCE | SEQ ID NO |
|---|---|---|
| | GCGGAGGAGGGAGCGGCGGAGGTGGCTCTGGCGGTGGCG GAGAGGTGCAATTGTTGGAGTCTGGGGGAGGCTTGGTAC AGCCTGGGGGGTCCCTGAGACTCTCCTGTGCAGCCTCTGG ATTCACCTTTAGCCGGTATGGTATGAGCTGGGTCCGCCAG GCTCCAGGGAAGGGGCTGGAGTGGGTCTCAGCTATTAGT GGTAGTGGTGGTAGCACATACTACGCAGACTCCGTGAAG GGCCGGTTCACCATCTCCAGAGACAATTCCAAGAACACG CTGTATCTGCAAATGAACAGCCTGAGAGCCGAGGACACG GCCGTATATTACTGTGCGAAAGCGCATAATGCTTTTGACT ACTGGGGCCAGGGAACCCTGGTCACCGTGTCGAGTGCTA GCACCAAGGGCCCATCGGTCTTCCCCCTGGCACCCTCCTC CAAGAGCACCTCTGGGGGCACAGCGGCCCTGGGCTGCCT GGTCAAGGACTACTTCCCCGAACCGGTGACGGTGTCGTG GAACTCAGGCGCCCTGACCAGCGGCGTGCACACCTTCCC GGCTGTCCTACAGTCCTCAGGACTCTACTCCCTCAGCAGC GTGGTGACCGTGCCCTCCAGCAGCTTGGGCACCCAGACCT ACATCTGCAACGTGAATCACAAGCCCAGCAACACCAAGG TGGACAAGAAAGTTGAGCCCAAATCTTGTGACTGA | |
| F16, light chain, DNA | TCTTCTGAGCTGACTCAGGACCCTGCTGTGTCTGTGGCCT TGGGACAGACAGTCAGGATCACATGCCAAGGAGACAGCC TCAGAAGCTATTATGCAAGCTGGTACCAGCAGAAGCCAG GACAGGCCCCTGTACTTGTCATCTATGGTAAAAACAACCG GCCCTCAGGGATCCCAGACCGATTCTCTGGCTCCAGCTCA GGAAACACAGCTTCCTTGACCATCACTGGGGCTCAGGCG GAAGATGAGGCTGACTATTACTGTAACTCCTCTGTTTATA CTATGCCGCCCGTGGTATTCGGCGGAGGGACCAAGCTGA CCGTCCTAGGTCAACCCAAGGCTGCCCCCAGCGTGACCCT GTTCCCCCCCAGCAGCGAGGAACTGCAGGCCAACAAGGC CACCCTGGTCTGCCTGATCAGCGACTTCTACCCAGGCGCC GTGACCGTGGCCTGGAAGGCCGACAGCAGCCCCGTGAAG GCCGGCGTGGAGACCACCACCCCCAGCAAGCAGAGCAAC AACAAGTACGCCGCCAGCAGCTACCTGAGCCTGACCCCC GAGCAGTGGAAGAGCCACAGGTCCTACAGCTGCCAGGTG ACCCACGAGGGCAGCACCGTGGAGAAAACCGTGGCCCCC ACCGAGTGCAGCTGA | 114 |
| IL2R-beta-Fc(hole) fusion protein, DNA | ATGGACATGAGGGTCCCCGCTCAGCTCCTGGGCCTCCTGC TGCTCTGGTTCCCAGGTGCCAGGTGTGCGGTGAATGGCAC TTCCCAGTTCACATGCTTCTACAACTCGAGAGCCAACATC TCCTGTGTCTGGAGCCAAGATGGGGCTCTGCAGGACACTT CCTGCCAAGTCCATGCCTGGCCGGACAGACGGCGGTGGA ACCAAACCTGTGAGCTGCTCCCCGTGAGTCAAGCATCCTG GGCCTGCAACCTGATCCTCGGAGCCCCAGATTCTCAGAAA CTGACCACAGTTGACATCGTCACCCTGAGGGTGCTGTGCC GTGAGGGGGTGCGATGGAGGGTGATGGCCATCCAGGACT TCAAGCCCTTTGAGAACCTTCGCCTGATGGCCCCCATCTC CCTCCAAGTTGTCCACGTGGAGACCCACAGATGCAACAT AAGCTGGGAAATCTCCCAAGCCTCCCACTACTTTGAAAGA CACCTGGAGTTCGAGGCCCGGACGCTGTCCCCAGGCCAC ACCTGGGAGGAGGCCCCCCTGCTGACTCTCAAGCAGAAG CAGGAATGGATCTGCCTGGAGACGCTCACCCCAGACACC CAGTATGAGTTTCAGGTGCGGGTCAAGCCTCTGCAAGGC GAGTTCACGACCTGGAGCCCCTGGAGCCAGCCCCTGGCCT TCAGAACAAAGCCTGCAGCCCTTGGGAAGGACACCGGAG CTCAGGACAAAACTCACACATGCCCACCGTGCCCAGCAC CTGAACTCCTGGGGGGACCGTCAGTCTTCCTCTTCCCCCC AAAACCCAAGGACACCCTCATGATCTCCCGGACCCCTGA GGTCACATGCGTGGTGGTGGACGTGAGCCACGAAGACCC TGAGGTCAAGTTCAACTGGTACGTGGACGGCGTGGAGGT GCATAATGCCAAGACAAAGCCGCGGGAGGAGCAGTACAA CAGCACGTACCGTGTGGTCAGCGTCCTCACCGTCCTGCAC CAGGACTGGCTGAATGGCAAGGAGTACAAGTGCAAGGTC TCCAACAAAGCCCTCCCAGCCCCCATCGAGAAAACCATCT CCAAAGCCAAAGGGCAGCCCCGAGAACCACAGGTGTGCA CCCTGCCCCCATCCCGGGATGAGCTGACCAAGAACCAGG TCAGCCTCTCGTGCGCAGTCAAAGGCTTCTATCCCAGCGA CATCGCCGTGGAGTGGGAGAGCAATGGGCAGCCGGAGAA CAACTACAAGACCACGCCTCCCGTGCTGGACTCCGACGG CTCCTTCTTCCTCGTGAGCAAGCTCACCGTGGACAAGAGC AGGTGGCAGCAGGGGAACGTCTTCTCATGCTCCGTGATGC ATGAGGCTCTGCACAACCACTACACGCAGAAGAGCCTCT CCCTGTCTCCGGGTAAATGA | 115 |

TABLE 8-continued

| Construct | POLYNUCLEOTIDE SEQUENCE | SEQ ID NO |
|---|---|---|
| IL2R-gamma-Fc(knob), DNA | ATGTTGAAGCCATCATTACCATTCACATCCCTCTTATTCCT GCAGCTGCCCCTGCTGGGAGTGGGGCTGAACACGACAAT TCTGACGCCCAATGGAATGAAGACACCACAGCTGATTT CTTCCTGACCACTATGCCCACTGACTCCCTCAGTGTTTCCA CTCTGCCCCTCCCAGAGGTTCAGTGTTTTGTGTTCAATGTC GAGTACATGAATTGCACTTGGAACAGCAGCTCTGAGCCC CAGCCTACCAACCTCACTCTGCATTATTGGTACAAGAACT CGGATAATGATAAAGTCCAGAAGTGCAGCCACTATCTATT CTCTGAAGAAATCACTTCTGGCTGTCAGTTGCAAAAAAAG GAGATCCACCTCTACCAAACATTTGTTGTTCAGCTCCAGG ACCCACGGGAACCCAGGAGACAGGCCACACAGATGCTAA AACTGCAGAATCTGGTGATCCCCTGGGCTCCAGAGAACCT AACACTTCACAAACTGAGTGAATCCCAGCTAGAACTGAA CTGGAACAACAGATTCTTGAACCACTGTTTGGAGCACTTG GTGCAGTACCGGACTGACTGGGACCACAGCTGGACTGAA CAATCAGTGGATTATAGACATAAGTTCTCCTTGCCTAGTG TGGATGGGCAGAAACGCTACACGTTTCGTGTTCGGAGCC GCTTTAACCCACTCTGTGGAAGTGCTCAGCATTGGAGTGA ATGGAGCCACCCAATCCACTGGGGGAGCAATACTTCAAA AGAGAATCCTTTCCTGTTTGCATTGGAAGCCGGAGCTCAG GACAAAACTCACACATGCCCACCGTGCCCAGCACCTGAA CTCCTGGGGGGACCGTCAGTCTTCCTCTTCCCCCCAAAAC CCAAGGACACCCTCATGATCTCCCGGACCCCTGAGGTCAC ATGCGTGGTGGTGGACGTGAGCCACGAAGACCCTGAGGT CAAGTTCAACTGGTACGTGGACGGCGTGGAGGTGCATAA TGCCAAGACAAAGCCGCGGGAGGAGCAGTACAACAGCAC GTACCGTGTGGTCAGCGTCCTCACCGTCCTGCACCAGGAC TGGCTGAATGGCAAGGAGTACAAGTGCAAGGTCTCCAAC AAAGCCCTCCCAGCCCCCATCGAGAAAACCATCTCCAAA GCCAAAGGGCAGCCCCGAGAACCACAGGTGTACACCCTG CCCCCATGCCGGGATGAGCTGACCAAGAACCAGGTCAGC CTGTGGTGCCTGGTCAAAGGCTTCTATCCCAGCGACATCG CCGTGGAGTGGGAGAGCAATGGGCAGCCGGAGAACAACT ACAAGACCACGCCTCCCGTGCTGGACTCCGACGGCTCCTT CTTCCTCTACAGCAAGCTCACCGTGGACAAGAGCAGGTG GCAGCAGGGGAACGTCTTCTCATGCTCCGTGATGCATGAG GCTCTGCACAACCACTACACGCAGAAGAGCCTCTCCCTGT CTCCGGGTAAATGA | 116 |
| Fab-IL12-Fab L19 antibody, murine scIL12, DNA | GAGGTGCAGCTGTTGGAGTCTGGGGGAGGCTTGGTACAG CCTGGGGGGTCCCTGAGACTCTCCTGTGCAGCCTCTGGAT TCACCTTTAGCAGTTTTTCGATGAGCTGGGTCCGCCAGGC TCCAGGGAAGGGGCTGGAGTGGGTCTCATCTATTTCCGGT AGTTCGGGTACCACATACTACGCAGACTCCGTGAAGGGC CGGTTCACCATCTCCAGAGACAATTCCAAGAACACGCTGT ATCTGCAAATGAACAGCCTGAGAGCCGAGGACACGGCCG TATATTACTGTGCGAAACCGTTTCCGTATTTTGACTACTG GGGCCAGGGAACCCTGGTCACCGTCTCGAGTGCTAGCAC CAAGGGCCCATCGGTCTTCCCCCTGGCACCCTCCTCCAAG AGCACCTCTGGGGGCACAGCGGCCCTGGGCTGCCTGGTC AAGGACTACTTCCCCGAACCGGTGACGGTGTCGTGGAAC TCAGGCGCCCTGACCAGCGGCGTGCACACCTTCCCGGCTG TCCTACAGTCCTCAGGACTCTACTCCCTCAGCAGCGTGGT GACCGTGCCCTCCAGCAGCTTGGGCACCCAGACCTACATC TGCAACGTGAATCACAAGCCCAGCAACACCAAGGTGGAT AAGAAAGTTGAGCCCAAATCTTGTGACTCCGGCGGAGGA GGGAGCGGCGGAGGTGGCTCCGGAGGGGGCGGAGCCAT GTGGGAGCTGGAAAAGGACGTGTACGTGGTGGAGGTGGA CTGGACCCCCGACGCCCCTGGCGAGACAGTGAACCTGAC CTGCGACACCCCCGAAGAGGACGACATCACCTGGACCAG CGACCAGCGGCACGGCGTGATCGGCAGCGGCAAGACCCT GACCATCACCGTGAAAGAGTTTCTGGACGCCGGCCAGTA CACCTGCCACAAGGGCGGCGAGACACTGAGCCACAGCCA CCTGCTGCTGCACAAGAAAGAGAACGGCATCTGGTCCAC CGAGATCCTGAAGAACTTCAAGAACAAGACCTTCCTGAA GTGCGAGGCCCCCAACTACAGCGGCCGGTTCACCTGCAG CTGGCTGGTGCAGCGGAACATGGACCTGAAGTTCAACAT CAAGAGCAGCAGCAGCCCCCCTGACAGCAGGGCCGTGAC CTGCGGCATGGCCAGCCTGAGCGCCGAGAAGGTGACCCT GGACCAGAGGGACTACGAGAAGTACAGCGTGAGCTGCCA GGAAGATGTCACCTGCCCCACCGCCGAGGAAACCCTGCC CATCGAGCTGGCCCTGGAAGCCCGGCAGCAGAACAAGTA CGAGAACTACTCTACCAGCTTCTTCATCCGGGACATCATC AAGCCCGACCCCCCCAAGAACCTGCAGATGAAGCCCCTG AAGAACAGCCAGGTGGAGGTGTCCTGGGAGTACCCTGAC AGCTGGTCCACCCCCCAGAAGCTACTTCAGCCTGAAGTTCT TCGTGAGAATCCAGCGGAAGAAAGAAAAGATGAAAGAG ACAGAGGAAGGCTGCAACCAGAAGGGCGCCTTCTTCGTC | 117 |

TABLE 8-continued

| Construct | POLYNUCLEOTIDE SEQUENCE | SEQ ID NO |
|---|---|---|
| | GAGAAAACCAGCACCGAGGTGCAGTGCAAGGGCGGCAA<br>CGTGTGCGTGCAGGCCCAGGACCGGTACTACAACAGCAG<br>CTGCAGCAAGTGGGCCTGCGTGCCCTGCAGAGTGCGGTCT<br>GGCGGCGACGGCTCTGGCGGCGGAGGAAGCGGCGGAGG<br>GGGCAGCAGAGTGATCCCCGTGAGCGGCCCTGCCCGGTG<br>CCTGAGCCAGAGCCGGAACCTGCTGAAAACCACCGACGA<br>CATGGTGAAAACCGCCAGAGAGAAGCTGAAGCACTACAG<br>CTGCACAGCCGAGGACATCGACCACGAGGACATCACCCG<br>GGACCAGACCAGCACCCTGAAAACCTGCCTGCCCCTGGA<br>ACTGCACAAAAACGAGAGCTGCCTGGCCACCCGGGAGAC<br>AAGCAGCACCACCCGGGGCAGCTGCCTGCCTCCCCAGAA<br>AACCTCCCTGATGATGACCCTGTGCCTGGGCAGCATCTAC<br>GAGGACCTGAAGATGTACCAGACCGAGTTCCAGGCCATC<br>AACGCCGCCCTGCAGAACCACAATCACCAGCAGATCATC<br>CTGGACAAGGGCATGCTGGTCGCCATCGACGAGCTGATG<br>CAGAGCCTGAACCACAACGGCGAAACCCTGCGGCAGAAA<br>CCCCCCGTGGGCGAGGCCGACCCCTACCGGGTGAAGATG<br>AAGCTGTGCATCCTGCTGCACGCCTTCAGCACCCGGGTGG<br>TGACCATCAACCGGGTGATGGGCTACCTGTCCTCTGCCGG<br>GGGAGGGGGATCCGGCGGAGGTGGCTCTGGCGGTGGCGG<br>AGAGGTGCAGCTGTTGGAGTCTGGGGGAGGCTTGGTACA<br>GCCTGGGGGGTCCCTGAGACTCTCCTGTGCAGCCTCTGGA<br>TTCACCTTTAGCAGTTTTTCGATGAGCTGGGTCCGCCAGG<br>CTCCAGGGAAGGGGCTGGAGTGGGTCTCATCTATTTCCGG<br>TAGTTCGGGTACCACATACTACGCAGACTCCGTGAAGGG<br>CCGGTTCACCATCTCCAGAGACAATTCCAAGAACACGCTG<br>TATCTGCAAATGAACAGCCTGAGAGCCGAGGACACGGCC<br>GTATATTACTGTGCGAAACCGTTTCCGTATTTTGACTACT<br>GGGGCCAGGGAACCCTGGTCACCGTCTCGAGTGCTAGCA<br>CCAAGGGCCCATCGGTCTTCCCCCTGGCACCCTCCTCCAA<br>GAGCACCTCTGGGGGCACAGCGGCCCTGGGCTGCCTGGT<br>CAAGGACTACTTCCCCGAACCGGTGACGGTGTCGTGGAA<br>CTCAGGCGCCCTGACCAGCGGCGTGCACACCTTCCCGGCT<br>GTCCTACAGTCCTCAGGACTCTACTCCCTCAGCAGCGTGG<br>TGACCGTGCCCTCCAGCAGCTTGGGCACCCAGACCTACAT<br>CTGCAACGTGAATCACAAGCCCAGCAACACCAAGGTGGA<br>TAAGAAAGTTGAGCCCAAATCTTGTGACTGA | |
| Fab-IL12-FabL19 antibody, human scIL12, DNA | GAGGTGCAGCTGTTGGAGTCTGGGGGAGGCTTGGTACAG<br>CCTGGGGGGTCCCTGAGACTCTCCTGTGCAGCCTCTGGAT<br>TCACCTTTAGCAGTTTTTCGATGAGCTGGGTCCGCCAGGC<br>TCCAGGGAAGGGGCTGGAGTGGGTCTCATCTATTAGAGG<br>TAGTTCGGGTACCACATACTACGCAGACTCCGTGAAGGG<br>CCGGTTCACCATCTCCAGAGACAATTCCAAGAACACGCTG<br>TATCTGCAAATGAACAGCCTGAGAGCCGAGGACACGGCC<br>GTATATTACTGTGCGAAACCGTTTCCGTATTTTGACTACT<br>GGGGCCAGGGAACCCTGGTCACCGTCTCGAGTGCTAGCA<br>CCAAGGGCCCATCGGTCTTCCCCCTGGCACCCTCCTCCAA<br>GAGCACCTCTGGGGGCACAGCGGCCCTGGGCTGCCTGGT<br>CAAGGACTACTTCCCCGAACCGGTGACGGTGTCGTGGAA<br>CTCAGGCGCCCTGACCAGCGGCGTGCACACCTTCCCGGCT<br>GTCCTACAGTCCTCAGGACTCTACTCCCTCAGCAGCGTGG<br>TGACCGTGCCCTCCAGCAGCTTGGGCACCCAGACCTACAT<br>CTGCAACGTGAATCACAAGCCCAGCAACACCAAGGTGGA<br>TAAGAAAGTTGAGCCCAAATCTTGTGACTCCGGCGGAGG<br>AGGGAGCGGCGGAGGTGGCTCCGGAGGGGGCGGAATCTG<br>GGAGCTGAAGAAAGACGTGTACGTGGTGGAGCTGGACTG<br>GTATCCCGACGCCCCTGGCGAGATGGTGGTGCTGACCTGC<br>GACACCCCCGAAGAGGACGGCATCACCTGGACCCTGGAC<br>CAGAGCAGCGAGGTGCTGGGCAGCGGCAAGACCCTGACC<br>ATCCAGGTGAAAGAGTTCGGCGACGCCGGCCAGTACACC<br>TGCCACAAGGGCGGCGAAGTGCTGTCCCACAGCCTGCTG<br>CTGCTGCACAAGAAAGAGGATGGCATCTGGTCCACCGAC<br>ATCCTGAAGGACCAGAAAGAGCCCAAGAACAAGACCTTC<br>CTGCGGTGCGAGGCCAAGAACTACAGCGGCCGGTTCACC<br>TGTTGGTGGCTGACCACCATCAGCACCGACCTGACCTTCA<br>GCGTGAAGAGCAGCCGGGGCAGCAGCGACCCTCAGGGCG<br>TGACCTGCGGAGCCGCCACCCTGAGCGCCGAGAGAGTGC<br>GGGGCGACAACAAAGAGTACGAGTACAGCGTCGAGTGCC<br>AGGAAGATAGCGCCTGCCCTGCCGCCGAGGAAAGCCTGC<br>CCATCGAGGTGATGGTGGACGCCGTGCACAAGCTGAAGT<br>ACGAGAACTACACCAGCAGCTTTTTCATCCGGGACATCAT<br>CAAGCCCGACCCCCCCAAGAACCTGCAGCTGAAGCCCCT<br>GAAGAACAGCCGGCAGGTGGAGGTGTCCTGGGAGTACCC<br>TGACACCTGGTCCACCCCCCACAGCTACTTCAGCCTGACA<br>TTCTGTGTGCAGGTGCAGGGCAAGAGCAAGCGGGAGAAG<br>AAAGACCGGGTGTTCACCGACAAGACCAGCGCCACCGTG<br>ATCTGCCGGAAGAACGCCAGCATCAGCGTGCGGGCCCAG | 118 |

TABLE 8-continued

| Construct | POLYNUCLEOTIDE SEQUENCE | SEQ ID NO |
|---|---|---|
| | GACCGGTACTACAGCAGCTCCTGGTCCGAGTGGGCCAGC GTGCCTTGCAGCGGCGGAGGGGGCTCTGGCGGCGGAGGA TCTGGGGGAGGGGGCAGCCGGAACCTGCCCGTGGCCACC CCCGACCCCGGCATGTTCCCCTGCCTGCACCACAGCCAGA ACCTGCTGCGGGCCGTGAGCAACATGCTGCAGAAGGCCC GGCAGACCCTGGAATTCTACCCCTGCACCAGCGAGGAAA TCGACCACGAGGACATCACCAAGGATAAGACCAGCACCG TGGAGGCCTGCCTGCCCCTGGAACTGACCAAGAACGAGA GCTGCCTGAACAGCCGGGAGACAAGCTTCATCACCAACG GCAGCTGCCTGGCCAGCAGAAAGACCAGCTTCATGATGG CCCTGTGCCTGAGCAGCATCTACGAGGACCTGAAGATGT ACCAGGTGGAGTTCAAGACCATGAACGCCAAGCTGCTGA TGGACCCCAAGCGGCAGATCTTCCTGGATCAGAACATGCT GGCCGTGATCGACGAGCTGATGCAGGCCCTGAACTTCAA CAGCGAGACAGTGCCCCAGAAGTCCAGCCTGGAAGAGCC CGACTTCTACAAGACCAAGATCAAGCTGTGCATCCTGCTG CACGCCTTCAGAATCCGGGCCGTGACCATCGACCGGGTG ATGAGCTACCTGAACGCCAGCGGAGGGGGGGGATCCGGC GGAGGTGGCTCTGGCGGTGGCGGAGAGGTGCAGCTGTTG GAGTCTGGGGGAGGCTTGGTACAGCCTGGGGGGTCCCTG AGACTCTCCTGTGCAGCCTCTGGATTCACCTTTAGCAGTT TTTCGATGAGCTGGGTCCGCCAGGCTCCAGGGAAGGGGC TGGAGTGGGTCTCATCTATTAGAGGTAGTTCGGGTACCAC ATACTACGCAGACTCCGTGAAGGGCCGGTTCACCATCTCC AGAGACAATTCCAAGAACACGCTGTATCTGCAAATGAAC AGCCTGAGAGCCGAGGACACGGCCGTATATTACTGTGCG AAACCGTTTCCGTATTTTGACTACTGGGGCCAGGGAACCC TGGTCACCGTCTCGAGTGCTAGCACCAAGGGCCCATCGGT CTTCCCCCTGGCACCCTCCTCCAAGAGCACCTCTGGGGGC ACAGCGGCCCTGGGCTGCCTGGTCAAGGACTACTTCCCCG AACCGGTGACGGTGTCGTGGAACTCAGGCGCCCTGACCA GCGGCGTGCACACCTTCCCGGCTGTCCTACAGTCCTCAGG ACTCTACTCCCTCAGCAGCGTGGTGACCGTGCCCTCCAGC AGCTTGGGCACCCAGACCTACATCTGCAACGTGAATCAC AAGCCCAGCAACACCAAGGTGGATAAGAAAGTTGAGCCC AAATCTTGTGACTGA | |
| Fab-GMCSF-Fab L19 antibody, human GM-CSF, DNA | GAGGTGCAGCTGTTGGAGTCTGGGGGAGGCTTGGTACAG CCTGGGGGGTCCCTGAGACTCTCCTGTGCAGCCTCTGGAT TCACCTTTAGCAGTTTTTCGATGAGCTGGGTCCGCCAGGC TCCAGGGAAGGGGCTGGAGTGGGTCTCATCTATTAGAGG TAGTTCGGGTACCACATACTACGCAGACTCCGTGAAGGG CCGGTTCACCATCTCCAGAGACAATTCCAAGAACACGCTG TATCTGCAAATGAACAGCCTGAGAGCCGAGGACACGGCC GTATATTACTGTGCGAAACCGTTTCCGTATTTTGACTACT GGGGCCAGGGAACCCTGGTCACCGTCTCGAGTGCTAGCA CCAAGGGCCCATCGGTCTTCCCCCTGGCACCCTCCTCCAA GAGCACCTCTGGGGGCACAGCGGCCCTGGGCTGCCTGGT CAAGGACTACTTCCCCGAACCGGTGACGGTGTCGTGGAA CTCAGGCGCCCTGACCAGCGGCGTGCACACCTTCCCGGCT GTCCTACAGTCCTCAGGACTCTACTCCCTCAGCAGCGTGG TGACCGTGCCCTCCAGCAGCTTGGGCACCCAGACCTACAT CTGCAACGTGAATCACAAGCCCAGCAACACCAAGGTGGA TAAGAAAGTTGAGCCCAAATCTTGTGACTCCGGCGGAGG AGGGAGCGGCGGAGGTGGCTCCGGAGGTGGCGGAGCACC CGCCCGCTCGCCCAGCCCCAGCACGCAGCCCTGGGAGCA TGTGAATGCCATCCAGGAGGCCCGGCGTCTCCTGAACCTG AGTAGAGACACTGCTGCTGAGATGAATGAAACAGTAGAA GTCATCTCAGAAATGTTTGACCTCCAGGAGCCGACCTGCC TACAGACCCGCCTGGAGCTGTACAAGCAGGGCCTGCGGG GCAGCCTCACCAAGCTCAAGGGCCCCTTGACCATGATGG CCAGCCACTACAAGCAGCACTGCCCTCCAACCCCGGAAA CTTCCTGTGCAACCCAGATTATCACCTTTGAAAGTTTCAA AGAGAACCTGAAGGACTTTCTGCTTGTCATCCCCTTTGAC TGCTGGGAGCCAGTCCAGGAGTCCGGCGGAGGAGGATCC GGCGGAGGTGGCTCTGGCGGTGGCGGAGAGGTGCAGCTG TTGGAGTCTGGGGGAGGCTTGGTACAGCCTGGGGGGTCC CTGAGACTCTCCTGTGCAGCCTCTGGATTCACCTTTAGCA GTTTTTCGATGAGCTGGGTCCGCCAGGCTCCAGGGAAGG GGCTGGAGTGGGTCTCATCTATTAGAGGTAGTTCGGGTAC CACATACTACGCAGACTCCGTGAAGGGCCGGTTCACCATC TCCAGAGACAATTCCAAGAACACGCTGTATCTGCAAATG AACAGCCTGAGAGCCGAGGACACGGCCGTATATTACTGT GCGAAACCGTTTCCGTATTTTGACTACTGGGGCCAGGGAA CCCTGGTCACCGTCTCGAGTGCTAGCACCAAGGGCCCATC GGTCTTCCCCCTGGCACCCTCCTCCAAGAGCACCTCTGGG GGCACAGCGGCCCTGGGCTGCCTGGTCAAGGACTACTTCC CCGAACCGGTGACGGTGTCGTGGAACTCAGGCGCCCTGA | 119 |

TABLE 8-continued

| Construct | POLYNUCLEOTIDE SEQUENCE | SEQ ID NO |
|---|---|---|
| | CCAGCGGCGTGCACACCTTCCCGGCTGTCCTACAGTCCTC AGGACTCTACTCCCTCAGCAGCGTGGTGACCGTGCCCTCC AGCAGCTTGGGCACCCAGACCTACATCTGCAACGTGAAT CACAAGCCCAGCAACACCAAGGTGGATAAGAAAGTTGAG CCCAAATCTTGTGACTGA | |
| Fab-IFNα2-Fab, L19 antibody, DNA | GAGGTGCAGCTGTTGGAGTCTGGGGGAGGCTTGGTACAG CCTGGGGGGTCCCTGAGACTCTCCTGTGCAGCCTCTGGAT TCACCTTTAGCAGTTTTTCGATGAGCTGGGTCCGCCAGGC TCCAGGGAAGGGGCTGGAGTGGGTCTCATCTATTAGAGG TAGTTCGGGTACCACATACTACGCAGACTCCGTGAAGGG CCGGTTCACCATCTCCAGAGACAATTCCAAGAACACGCTG TATCTGCAAATGAACAGCCTGAGAGCCGAGGACACGGCC GTATATTACTGTGCGAAACCGTTTCCGTATTTTGACTACT GGGGCCAGGGAACCCTGGTCACCGTCTCGAGTGCTAGCA CCAAGGGCCCATCGGTCTTCCCCCTGGCACCCTCCTCCAA GAGCACCTCTGGGGGCACAGCGGCCCTGGGCTGCCTGGT CAAGGACTACTTCCCCGAACCGGTGACGGTGTCGTGGAA CTCAGGCGCCCTGACCAGCGGCGTGCACACCTTCCCGGCT GTCCTACAGTCCTCAGGACTCTACTCCCTCAGCAGCGTGG TGACCGTGCCCTCCAGCAGCTTGGGCACCCAGACCTACAT CTGCAACGTGAATCACAAGCCCAGCAACACCAAGGTGGA TAAGAAAGTTGAGCCCAAATCTTGTGACTCCGGCGGAGG AGGGAGCGGCGGAGGTGGCTCCGGAGGGGGCGGATGCG ACCTGCCCCAGACCCACAGCCTGGGCAACAGACGGGCCC TGATCCTGCTGGCCCAGATGCGGCGGATCAGCCCCTTCAG CTGCCTGAAGGACCGGCACGACTTCGGCTTCCCCCAGGA AGAGTTCGACGGCAACCAGTTCCAGAAGGCCCAGGCCAT CAGCGTGCTGCACGAGATGATCCAGCAGACCTTCAACCT GTTCAGCACCAAGGACAGCAGCGCCGCCTGGGACGAGAG CCTGCTGGAAAAGTTCTACACCGAGCTGTACCAGCAGCTG AACGACCTGGAAGCCTGCGTGATCCAGGAAGTGGGCGTC GAGGAAACCCCCCTGATGAACGTGGACAGCATCCTGGCC GTGAAGAAGTACTTCCAGCGGATCACCCTGTACCTGACCG AGAAGAAGTATAGCCCCTGCGCCTGGGAGGTGGTGCGGG CCGAGATCATGCGGAGCTTCAGCCTGAGCACCAACCTGC AGGAACGGCTGCGGCGGAAAGAGAGCGGCGGAGGGGGA TCCGGCGGAGGTGGCTCTGGCGGTGGCGGAGAGGTGCAG CTGTTGGAGTCTGGGGGAGGCTTGGTACAGCCTGGGGGG TCCCTGAGACTCTCCTGTGCAGCCTCTGGATTCACCTTTA GCAGTTTTTCGATGAGCTGGGTCCGCCAGGCTCCAGGGAA GGGGCTGGAGTGGGTCTCATCTATTAGAGGTAGTTCGGGT ACCACATACTACGCAGACTCCGTGAAGGGCCGGTTCACC ATCTCCAGAGACAATTCCAAGAACACGCTGTATCTGCAA ATGAACAGCCTGAGAGCCGAGGACACGGCCGTATATTAC TGTGCGAAACCGTTTCCGTATTTTGACTACTGGGGCCAGG GAACCCTGGTCACCGTCTCGAGTGCTAGCACCAAGGGCC CATCGGTCTTCCCCCTGGCACCCTCCTCCAAGAGCACCTC TGGGGGCACAGCGGCCCTGGGCTGCCTGGTCAAGGACTA CTTCCCCGAACCGGTGACGGTGTCGTGGAACTCAGGCGCC CTGACCAGCGGCGTGCACACCTTCCCGGCTGTCCTACAGT CCTCAGGACTCTACTCCCTCAGCAGCGTGGTGACCGTGCC CTCCAGCAGCTTGGGCACCCAGACCTACATCTGCAACGTG AATCACAAGCCCAGCAACACCAAGGTGGATAAGAAAGTT GAGCCCAAATCTTGTGACTGA | 120 |
| 3F2 Fab-IL2-Fab (heavy chain cytokine fusion construct) | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTAGTGG TAGTGGTGGTAGCACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAAGGGTGGTTTGGTGGTTTTAACT ACTGGGGCCAAGGAACCCTGGTCACCGTCTCGAGTGCTA GCACCAAGGGCCCATCGGTCTTCCCCCTGGCACCCTCCTC CAAGAGCACCTCTGGGGGCACAGCGGCCCTGGGCTGCCT GGTCAAGGACTACTTCCCCGAACCGGTGACGGTGTCGTG GAACTCAGGCGCCCTGACCAGCGGCGTGCACACCTTCCC GGCTGTCCTACAGTCCTCAGGACTCTACTCCCTCAGCAGC GTGGTGACCGTGCCCTCCAGCAGCTTGGGCACCCAGACCT ACATCTGCAACGTGAATCACAAGCCCAGCAACACCAAGG TGGATAAGAAAGTTGAGCCCAAATCTTGTGACTCCGGCG GAGGAGGGAGCGGCGGAGGTGGCTCCGGAGGTGGCGGA GCACCTACTTCAAGTTCTACAAAGAAAACACAGCTACAA CTGGAGCATTTACTGCTGGATTTACAGATGATTTTGAATG GAATTAATAATTACAAGAATCCCAAACTCACCAGGATGC TCACATTTAAGTTTTACATGCCCAAGAAGGCCACAGAACT | 210 |

TABLE 8-continued

| Construct | POLYNUCLEOTIDE SEQUENCE | SEQ ID NO |
|---|---|---|
| | GAAACATCTTCAGTGTCTAGAAGAAGAACTCAAACCTCT GGAGGAAGTGCTAAATTTAGCTCAAAGCAAAAACTTTCA CTTAAGACCCAGGGACTTAATCAGCAATATCAACGTAAT AGTTCTGGAACTAAAGGGATCTGAAACAACATTCATGTGT GAATATGCTGATGAGACAGCAACCATTGTAGAATTTCTGA ACAGATGGATTACCTTTGCCCAAAGCATCATCTCAACACT GACTTCCGGCGGAGGAGGATCCGGCGGAGGTGGCTCTGG CGGTGGCGGAGAGGTGCAATTGTTGGAGTCTGGGGGAGG CTTGGTACAGCCTGGGGGGTCCCTGAGACTCTCCTGTGCA GCCTCCGGATTCACCTTTAGCAGTTATGCCATGAGCTGGG TCCGCCAGGCTCCAGGGAAGGGGCTGGAGTGGGTCTCAG CTATTAGTGGTAGTGGTGGTAGCACATACTACGCAGACTC CGTGAAGGGCCGGTTCACCATCTCCAGAGACAATTCCAA GAACACGCTGTATCTGCAGATGAACAGCCTGAGAGCCGA GGACACGGCCGTATATTACTGTGCGAAAGGGTGGTTTGGT GGTTTTAACTACTGGGGCCAAGGAACCCTGGTCACCGTCT CGAGTGCTAGCACCAAGGGCCCATCGGTCTTCCCCCTGGC ACCCTCCTCCAAGAGCACCTCTGGGGGCACAGCGGCCCT GGGCTGCCTGGTCAAGGACTACTTCCCCGAACCGGTGAC GGTGTCGTGGAACTCAGGCGCCCTGACCAGCGGCGTGCA CACCTTCCCGGCTGTCCTACAGTCCTCAGGACTCTACTCC CTCAGCAGCGTGGTGACCGTGCCCTCCAGCAGCTTGGGCA CCCAGACCTACATCTGCAACGTGAATCACAAGCCCAGCA ACACCAAGGTGGATAAGAAAGTTGAGCCCAAATCTTGTG ACTGA | |
| 4G8 Fab-IL2-Fab (heavy chain cytokine fusion construct) | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTAGTGG TAGTGGTGGTAGCACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAAGGGTGGCTGGGTAATTTTGACT ACTGGGGCCAAGGAACCCTGGTCACCGTCTCGAGTGCTA GCACCAAGGGCCCATCGGTCTTCCCCCTGGCACCCTCCTC CAAGAGCACCTCTGGGGGCACAGCGGCCCTGGGCTGCCT GGTCAAGGACTACTTCCCCGAACCGGTGACGGTGTCGTG GAACTCAGGCGCCCTGACCAGCGGCGTGCACACCTTCCC GGCTGTCCTACAGTCCTCAGGACTCTACTCCCTCAGCAGC GTGGTGACCGTGCCCTCCAGCAGCTTGGGCACCCAGACCT ACATCTGCAACGTGAATCACAAGCCCAGCAACACCAAGG TGGATAAGAAAGTTGAGCCCAAATCTTGTGACTCCGGCG GAGGAGGGAGCGGCGGAGGTGGCTCCGGAGGTGGCGGA GCACCTACTTCAAGTTCTACAAAGAAAACACAGCTACAA CTGGAGCATTTACTGCTGGATTTACAGATGATTTTGAATG GAATTAATAATTACAAGAATCCCAAACTCACCAGGATGC TCACATTTAAGTTTTACATGCCCAAGAAGGCCACAGAACT GAAACATCTTCAGTGTCTAGAAGAAGAACTCAAACCTCT GGAGGAAGTGCTAAATTTAGCTCAAAGCAAAAACTTTCA CTTAAGACCCAGGGACTTAATCAGCAATATCAACGTAAT AGTTCTGGAACTAAAGGGATCTGAAACAACATTCATGTGT GAATATGCTGATGAGACAGCAACCATTGTAGAATTTCTGA ACAGATGGATTACCTTTGCCCAAAGCATCATCTCAACACT GACTTCCGGCGGAGGAGGATCCGGCGGAGGTGGCTCTGG CGGTGGCGGAGAGGTGCAATTGTTGGAGTCTGGGGGAGG CTTGGTACAGCCTGGGGGGTCCCTGAGACTCTCCTGTGCA GCCTCCGGATTCACCTTTAGCAGTTATGCCATGAGCTGGG TCCGCCAGGCTCCAGGGAAGGGGCTGGAGTGGGTCTCAG CTATTAGTGGTAGTGGTGGTAGCACATACTACGCAGACTC CGTGAAGGGCCGGTTCACCATCTCCAGAGACAATTCCAA GAACACGCTGTATCTGCAGATGAACAGCCTGAGAGCCGA GGACACGGCCGTATATTACTGTGCGAAAGGGTGGCTGGG TAATTTTGACTACTGGGGCCAAGGAACCCTGGTCACCGTC TCGAGTGCTAGCACCAAGGGCCCATCGGTCTTCCCCCTGG CACCCTCCTCCAAGAGCACCTCTGGGGGCACAGCGGCCCT GGGCTGCCTGGTCAAGGACTACTTCCCCGAACCGGTGAC GGTGTCGTGGAACTCAGGCGCCCTGACCAGCGGCGTGCA CACCTTCCCGGCTGTCCTACAGTCCTCAGGACTCTACTCC CTCAGCAGCGTGGTGACCGTGCCCTCCAGCAGCTTGGGCA CCCAGACCTACATCTGCAACGTGAATCACAAGCCCAGCA ACACCAAGGTGGATAAGAAAGTTGAGCCCAAATCTTGTG ACTGA | 212 |

TABLE 8-continued

| Construct | POLYNUCLEOTIDE SEQUENCE | SEQ ID NO |
|---|---|---|
| 3D9 Fab-IL2-Fab (heavy chain cytokine fusion construct) | GAGGTGCAATTGTTGGAGTCTGGGGGAGGCTTGGTACAG<br>CCTGGGGGGTCCCTGAGACTCTCCTGTGCAGCCTCCGGAT<br>TCACCTTTAGCAGTTATGCTATGAGCTGGGTCCGCCAGAC<br>TCCAGGGAAGGGGCTGGAGTGGGTCTCAGCTATTGGTGTT<br>AGTACTGGTAGCACATACTACGCAGACTCCGTGAAGGGC<br>CGGTTCACCATCTCCAGAGACAATTCCAAGAACACGCTGT<br>ATCTGCAGATGAACAGCCTGAGAGCCGAGGACACGGCCG<br>TATATTACTGTGCGAAAGGTTGGCTGGGTCCTTTTGACTA<br>CTGGGGCCAAGGAACCCTGGTCACCGTCTCGAGTGCTAG<br>CACCAAGGGCCCATCGGTCTTCCCCCTGGCACCCTCCTCC<br>AAGAGCACCTCTGGGGGCACAGCGGCCCTGGGCTGCCTG<br>GTCAAGGACTACTTCCCCGAACCGGTGACGGTGTCGTGG<br>AACTCAGGCGCCCTGACCAGCGGCGTGCACACCTTCCCG<br>GCTGTCCTACAGTCCTCAGGACTCTACTCCCTCAGCAGCG<br>TGGTGACCGTGCCCTCCAGCAGCTTGGGCACCCAGACCTA<br>CATCTGCAACGTGAATCACAAGCCCAGCAACACCAAGGT<br>GGATAAGAAAGTTGAGCCCAAATCTTGTGACTCCGGCGG<br>AGGAGGGAGCGGCGGAGGTGGCTCCGGAGGTGGCGGAG<br>CACCTACTTCAAGTTCTACAAAGAAAACACAGCTACAACT<br>GGAGCATTTACTGCTGGATTTACAGATGATTTTGAATGGA<br>ATTAATAATTACAAGAATCCCAAACTCACCAGGATGCTCA<br>CATTTAAGTTTTACATGCCCAAGAAGGCCACAGAACTGA<br>AACATCTTCAGTGTCTAGAAGAAGAACTCAAACCTCTGG<br>AGGAAGTGCTAAATTTAGCTCAAAGCAAAAACTTTCACTT<br>AAGACCCAGGGACTTAATCAGCAATATCAACGTAATAGT<br>TCTGGAACTAAAGGGATCTGAAACAACATTCATGTGTGA<br>ATATGCTGATGAGACAGCAACCATTGTAGAATTTCTGAAC<br>AGATGGATTACCTTTGCCCAAAGCATCATCTCAACACTGA<br>CTTCCGGCGGAGGAGGATCCGGCGGAGGTGGCTCTGGCG<br>GTGGCGGAGAGGTGCAATTGTTGGAGTCTGGGGGAGGCT<br>TGGTACAGCCTGGGGGGTCCCTGAGACTCTCCTGTGCAGC<br>CTCCGGATTCACCTTTAGCAGTTATGCTATGAGCTGGGTC<br>CGCCAGACTCCAGGGAAGGGGCTGGAGTGGGTCTCAGCT<br>ATTGGTGTTAGTACTGGTAGCACATACTACGCAGACTCCG<br>TGAAGGGCCGGTTCACCATCTCCAGAGACAATTCCAAGA<br>ACACGCTGTATCTGCAGATGAACAGCCTGAGAGCCGAGG<br>ACACGGCCGTATATTACTGTGCGAAAGGTTGGCTGGGTCC<br>TTTTGACTACTGGGGCCAAGGAACCCTGGTCACCGTCTCG<br>AGTGCTAGCACCAAGGGCCCATCGGTCTTCCCCCTGGCAC<br>CCTCCTCCAAGAGCACCTCTGGGGGCACAGCGGCCCTGG<br>GCTGCCTGGTCAAGGACTACTTCCCCGAACCGGTGACGGT<br>GTCGTGGAACTCAGGCGCCCTGACCAGCGGCGTGCACAC<br>CTTCCCGGCTGTCCTACAGTCCTCAGGACTCTACTCCCTC<br>AGCAGCGTGGTGACCGTGCCCTCCAGCAGCTTGGGCACC<br>CAGACCTACATCTGCAACGTGAATCACAAGCCCAGCAAC<br>ACCAAGGTGGATAAGAAAGTTGAGCCCAAATCTTGTGAC<br>TGA | 214 |
| 2F11 Fab-IL2-Fab (heavy chain cytokine fusion construct) | GAGGTGCAATTGTTGGAGTCTGGGGGAGGCTTGGTACAG<br>CCTGGGGGGTCCCTGAGACTCTCCTGTGCAGCCTCCGGAT<br>TCACCTTTAGCAGTTATGCCATGAGCTGGGTCCGCCAGGC<br>TCCAGGGAAGGGGCTGGAGTGGGTCTCAGCTATTAGTGG<br>TAGTGGTGGTAGCACATACTACGCAGACTCCGTGAAGGG<br>CCGGTTCACCATCTCCAGAGACAATTCCAAGAACACGCTG<br>TATCTGCAGATGAACAGCCTGAGAGCCGAGGACACCGCC<br>GTATATTACTGTGCGAAATGGAGATGGATGATGTTTGACT<br>ACTGGGGCCAAGGAACCCTGGTCACCGTCTCGAGTGCTA<br>GCACCAAGGGCCCATCGGTCTTCCCCCTGGCACCCTCCTC<br>CAAGAGCACCTCTGGGGGCACAGCGGCCCTGGGCTGCCT<br>GGTCAAGGACTACTTCCCCGAACCGGTGACGGTGTCGTG<br>GAACTCAGGCGCCCTGACCAGCGGCGTGCACACCTTCCC<br>GGCTGTCCTACAGTCCTCAGGACTCTACTCCCTCAGCAGC<br>GTGGTGACCGTGCCCTCCAGCAGCTTGGGCACCCAGACCT<br>ACATCTGCAACGTGAATCACAAGCCCAGCAACACCAAGG<br>TGGATAAGAAAGTTGAGCCCAAATCTTGTGACTCCGGCG<br>GAGGAGGGAGCGGCGGAGGTGGCTCCGGAGGTGGCGGA<br>GCACCTACTTCAAGTTCTACAAAGAAAACACAGCTACAA<br>CTGGAGCATTTACTGCTGGATTTACAGATGATTTTGAATG<br>GAATTAATAATTACAAGAATCCCAAACTCACCAGGATGC<br>TCACATTTAAGTTTTACATGCCCAAGAAGGCCACAGAACT<br>GAAACATCTTCAGTGTCTAGAAGAAGAACTCAAACCTCT<br>GGAGGAAGTGCTAAATTTAGCTCAAAGCAAAAACTTTCA<br>CTTAAGACCCAGGGACTTAATCAGCAATATCAACGTAAT<br>AGTTCTGGAACTAAAGGGATCTGAAACAACATTCATGTGT<br>GAATATGCTGATGAGACAGCAACCATTGTAGAATTTCTGA<br>ACAGATGGATTACCTTTGCCCAAAGCATCATCTCAACACT<br>GACTTCCGGCGGAGGAGGATCCGGCGGAGGTGGCTCTGG<br>CGGTGGCGGAGAGGTGCAATTGTTGGAGTCTGGGGGAGG | 216 |

TABLE 8-continued

| Construct | POLYNUCLEOTIDE SEQUENCE | SEQ ID NO |
|---|---|---|
| | CTTGGTACAGCCTGGGGGGTCCCTGAGACTCTCCTGTGCA GCCTCCGGATTCACCTTTAGCAGTTATGCCATGAGCTGGG TCCGCCAGGCTCCAGGGAAGGGGCTGGAGTGGGTCTCAG CTATTAGTGGTAGTGGTGGTAGCACATACTACGCAGACTC CGTGAAGGGCCGGTTCACCATCTCCAGAGACAATTCCAA GAACACGCTGTATCTGCAGATGAACAGCCTGAGAGCCGA GGACACCGCCGTATATTACTGTGCGAAATGGAGATGGAT GATGTTTGACTACTGGGGCCAAGGAACCCTGGTCACCGTC TCGAGTGCTAGCACCAAGGGCCCATCGGTCTTCCCCCTGG CACCCTCCTCCAAGAGCACCTCTGGGGGCACAGCGGCCCT GGGCTGCCTGGTCAAGGACTACTTCCCCGAACCGGTGAC GGTGTCGTGGAACTCAGGCGCCCTGACCAGCGGCGTGCA CACCTTCCCGGCTGTCCTACAGTCCTCAGGACTCTACTCC CTCAGCAGCGTGGTGACCGTGCCCTCCAGCAGCTTGGGCA CCCAGACCTACATCTGCAACGTGAATCACAAGCCCAGCA ACACCAAGGTGGATAAGAAAGTTGAGCCCAAATCTTGTG ACTGA | |
| 4B3 Fab-IL2-Fab (heavy chain cytokine fusion construct) | GAGGTGCAATTGTTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTAGTGG TAGTGGTGGTAGCACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAAGGGTGGCTGGGTAATTTTGACT ACTGGGGCCAAGGAACCCTGGTCACCGTCTCGAGTGCTA GCACCAAGGGCCCATCGGTCTTCCCCCTGGCACCCTCCTC CAAGAGCACCTCTGGGGGCACAGCGGCCCTGGGCTGCCT GGTCAAGGACTACTTCCCCGAACCGGTGACGGTGTCGTG GAACTCAGGCGCCCTGACCAGCGGCGTGCACACCTTCCC GGCTGTCCTACAGTCCTCAGGACTCTACTCCCTCAGCAGC GTGGTGACCGTGCCCTCCAGCAGCTTGGGCACCCAGACCT ACATCTGCAACGTGAATCACAAGCCCAGCAACACCAAGG TGGATAAGAAAGTTGAGCCCAAATCTTGTGACTCCGGCG GAGGAGGGAGCGGCGGAGGTGGCTCCGGAGGTGGCGGA GCACCTACTTCAAGTTCTACAAAGAAAACACAGCTACAA CTGGAGCATTTACTGCTGGATTTACAGATGATTTTGAATG GAATTAATAATTACAAGAATCCCAAACTCACCAGGATGC TCACATTTAAGTTTTACATGCCCAAGAAGGCCACAGAACT GAAACATCTTCAGTGTCTAGAAGAAGAACTCAAACCTCT GGAGGAAGTGCTAAATTTAGCTCAAAGCAAAAACTTTCA CTTAAGACCCAGGGACTTAATCAGCAATATCAACGTAAT AGTTCTGGAACTAAAGGGATCTGAAACAACATTCATGTGT GAATATGCTGATGAGACAGCAACCATTGTAGAATTTCTGA ACAGATGGATTACCTTTGCCCAAAGCATCATCTCAACACT GACTTCCGGCGGAGGAGGATCCGGCGGAGGTGGCTCTGG CGGTGGCGGAGAGGTGCAATTGTTGGAGTCTGGGGGAGG CTTGGTACAGCCTGGGGGGTCCCTGAGACTCTCCTGTGCA GCCTCCGGATTCACCTTTAGCAGTTATGCCATGAGCTGGG TCCGCCAGGCTCCAGGGAAGGGGCTGGAGTGGGTCTCAG CTATTAGTGGTAGTGGTGGTAGCACATACTACGCAGACTC CGTGAAGGGCCGGTTCACCATCTCCAGAGACAATTCCAA GAACACGCTGTATCTGCAGATGAACAGCCTGAGAGCCGA GGACACGGCCGTATATTACTGTGCGAAAGGGTGGCTGGG TAATTTTGACTACTGGGGCCAAGGAACCCTGGTCACCGTC TCGAGTGCTAGCACCAAGGGCCCATCGGTCTTCCCCCTGG CACCCTCCTCCAAGAGCACCTCTGGGGGCACAGCGGCCCT GGGCTGCCTGGTCAAGGACTACTTCCCCGAACCGGTGAC GGTGTCGTGGAACTCAGGCGCCCTGACCAGCGGCGTGCA CACCTTCCCGGCTGTCCTACAGTCCTCAGGACTCTACTCC CTCAGCAGCGTGGTGACCGTGCCCTCCAGCAGCTTGGGCA CCCAGACCTACATCTGCAACGTGAATCACAAGCCCAGCA ACACCAAGGTGGATAAGAAAGTTGAGCCCAAATCTTGTG ACTGA | 218 |
| 4G8 Fab-IL12-Fab (murine IL-12; heavy chain cytokine fusion construct) | GAGGTGCAATTGCTGGAAAGCGGCGGAGGACTGGTGCAG CCTGGCGGCAGCCTGAGACTGAGCTGCGCCGCCAGCGGC TTCACCTTCAGCAGCTACGCCATGTCTTGGGTCCGCCAGG CCCCTGGAAAGGGCCTGGAATGGGTGTCCGCCATCAGCG GCAGCGGCGGCAGCACCTACTACGCCGACAGCGTGAAGG GCCGGTTCACCATCAGCCGGGACAACAGCAAGAACACCC TGTACCTGCAGATGAACAGCCTGAGAGCCGAGGACACCG CCGTGTACTACTGCGCCAAGGGCTGGCTGGGCAACTTCGA CTACTGGGGCCAGGGCACTCTGGTCACAGTGTCTAGCGCT AGCACCAAGGGCCCATCGGTCTTCCCCCTGGCACCCTCCT CCAAGAGCACCTCTGGGGGCACAGCGGCCCTGGGCTGCC TGGTCAAGGACTACTTCCCCGAACCGGTGACGGTGTCGTG | 220 |

TABLE 8-continued

| Construct | POLYNUCLEOTIDE SEQUENCE | SEQ ID NO |
|---|---|---|
| | GAACTCAGGCGCCCTGACCAGCGGCGTGCACACCTTCCC<br>GGCTGTCCTACAGTCCTCAGGACTCTACTCCCTCAGCAGC<br>GTGGTGACCGTGCCCTCCAGCAGCTTGGGCACCCAGACCT<br>ACATCTGCAACGTGAATCACAAGCCCAGCAACACCAAGG<br>TGGATAAGAAAGTTGAGCCCAAATCTTGTGACTCCGGCG<br>GAGGAGGGAGCGGCGGAGGTGGCTCCGGAGGGGGCGGA<br>GCCATGTGGGAGCTGGAAAAGGACGTGTACGTGGTGGAG<br>GTGGACTGGACCCCCGACGCCCCTGGCGAGACAGTGAAC<br>CTGACCTGCGACACCCCCGAAGAGGACGACATCACCTGG<br>ACCAGCGACCAGCGGCACGGCGTGATCGGCAGCGGCAAG<br>ACCCTGACCATCACCGTGAAAGAGTTTCTGGACGCCGGCC<br>AGTACACCTGCCACAAGGGCGGCGAGACACTGAGCCACA<br>GCCACCTGCTGCTGCACAAGAAAGAGAACGGCATCTGGT<br>CCACCGAGATCCTGAAGAACTTCAAGAACAAGACCTTCC<br>TGAAGTGCGAGGCCCCCAACTACAGCGGCCGGTTCACCT<br>GCAGCTGGCTGGTGCAGCGGAACATGGACCTGAAGTTCA<br>ACATCAAGAGCAGCAGCAGCCCCCCTGACAGCAGGGCCG<br>TGACCTGCGGCATGGCCAGCCTGAGCGCCGAGAAGGTGA<br>CCCTGGACCAGAGGGACTACGAGAAGTACAGCGTGAGCT<br>GCCAGGAAGATGTCACCTGCCCCACCGCCGAGGAAACCC<br>TGCCCATCGAGCTGGCCCTGGAAGCCCGGCAGCAGAACA<br>AGTACGAGAACTACTCTACCAGCTTCTTCATCCGGGACAT<br>CATCAAGCCCGACCCCCCCAAGAACCTGCAGATGAAGCC<br>CCTGAAGAACAGCCAGGTGGAGGTGTCCTGGGAGTACCC<br>TGACAGCTGGTCCACCCCCAGAAGCTACTTCAGCCTGAAG<br>TTCTTCGTGAGAATCCAGCGGAAGAAAGAAAAGATGAAA<br>GAGACAGAGGAAGGCTGCAACCAGAAGGGCGCCTTCTTC<br>GTCGAGAAAACCAGCACCGAGGTGCAGTGCAAGGGCGGC<br>AACGTGTGCGTGCAGGCCCAGGACCGGTACTACAACAGC<br>AGCTGCAGCAAGTGGGCCTGCGTGCCCTGCAGAGTGCGG<br>TCTGGCGGCGACGGCTCTGGCGGCGGAGGAAGCGGCGGA<br>GGGGGCAGCAGAGTGATCCCCGTGAGCGGCCCTGCCCGG<br>TGCCTGAGCCAGAGCCGGAACCTGCTGAAAACCACCGAC<br>GACATGGTGAAAACCGCCAGAGAGAAGCTGAAGCACTAC<br>AGCTGCACAGCCGAGGACATCGACCACGAGGACATCACC<br>CGGGACCAGACCAGCACCCTGAAAACCTGCCTGCCCCTG<br>GAACTGCACAAAAACGAGAGCTGCCTGGCCACCCGGGAG<br>ACAAGCAGCACCACCCGGGGCAGCTGCCTGCCTCCCCAG<br>AAAACCTCCCTGATGATGACCCTGTGCCTGGGCAGCATCT<br>ACGAGGACCTGAAGATGTACCAGACCGAGTTCCAGGCCA<br>TCAACGCCGCCCTGCAGAACCACAATCACCAGCAGATCA<br>TCCTGGACAAGGGCATGCTGGTCGCCATCGACGAGCTGA<br>TGCAGAGCCTGAACCACAACGGCGAAACCCTGCGGCAGA<br>AACCCCCCGTGGGCGAGGCCGACCCCTACCGGGTGAAGA<br>TGAAGCTGTGCATCCTGCTGCACGCCTTCAGCACCCGGGT<br>GGTGACCATCAACCGGGTGATGGGCTACCTGTCCTCTGCC<br>GGGGGAGGGGGATCCGGCGGAGGTGGCTCTGGCGGTGGC<br>GGAGAGGTGCAATTGCTGGAAAGCGGCGGAGGACTGGTG<br>CAGCCTGGCGGCAGCCTGAGACTGAGCTGCGCCGCCAGC<br>GGCTTCACCTTCAGCAGCTACGCCATGTCTTGGGTCCGCC<br>AGGCCCCTGGAAAGGGCCTGGAATGGGTGTCCGCCATCA<br>GCGGCAGCGGCGGCAGCACCTACTACGCCGACAGCGTGA<br>AGGGCCGGTTCACCATCAGCCGGGACAACAGCAAGAACA<br>CCCTGTACCTGCAGATGAACAGCCTGAGAGCCGAGGACA<br>CCGCCGTGTACTACTGCGCCAAGGGCTGGCTGGGCAACTT<br>CGACTACTGGGGCCAGGGCACTCTGGTCACAGTGTCTAGC<br>GCTAGCACCAAGGGCCCATCGGTCTTCCCCCTGGCACCCT<br>CCTCCAAGAGCACCTCTGGGGGCACAGCGGCCCTGGGCT<br>GCCTGGTCAAGGACTACTTCCCCGAACCGGTGACGGTGTC<br>GTGGAACTCAGGCGCCCTGACCAGCGGCGTGCACACCTT<br>CCCGGCTGTCCTACAGTCCTCAGGACTCTACTCCCTCAGC<br>AGCGTGGTGACCGTGCCCTCCAGCAGCTTGGGCACCCAG<br>ACCTACATCTGCAACGTGAATCACAAGCCCAGCAACACC<br>AAGGTGGATAAGAAAGTTGAGCCCAAATCTTGTGACTGA | |
| 28H1 Fab-IL2-Fab (heavy chain cytokine fusion construct) | GAAGTGCAGCTGCTGGAATCCGGCGGAGGCCTGGTGCAG<br>CCTGGCGGATCTCTGAGACTGTCCTGCGCCGCCTCCGGCT<br>TCACCTTCTCCTCCCACGCCATGTCCTGGGTCCGACAGGC<br>TCCTGGCAAAGGCCTGGAATGGGTGTCCGCCATCTGGGCC<br>TCCGGCGAGCAGTACTACGCCGACTCTGTGAAGGGCCGG<br>TTCACCATCTCCCGGGACAACTCCAAGAACACCCTGTACC<br>TGCAGATGAACTCCCTGCGGGCCGAGGACACCGCCGTGT<br>ACTACTGTGCCAAGGGCTGGCTGGGCAACTTCGACTACTG<br>GGGACAGGGCACCCTGGTCACCGTGTCCAGCGCTAGCAC<br>CAAGGGACCCTCCGTGTTCCCCCTGGCCCCCTCCAGCAAG<br>TCTACCTCTGGCGGCACCGCCGCTCTGGGCTGCCTGGTCA<br>AGGACTACTTCCCCGAGCCCGTGACCGTGTCCTGGAACTC<br>TGGCGCCCTGACCAGCGGCGTCCACACCTTTCCAGCCGTG | 222 |

TABLE 8-continued

| Construct | POLYNUCLEOTIDE SEQUENCE | SEQ ID NO |
|---|---|---|
| | CTGCAGTCCTCCGGCCTGTACTCCCTGTCCTCCGTCGTGA CCGTGCCCTCCAGCTCTCTGGGCACCCAGACCTACATCTG CAACGTGAACCACAAGCCCTCCAACACCAAGGTGGACAA GAAGGTGGAACCCAAGTCCTGCGACAGTGGTGGGGGAGG ATCTGGTGGCGGAGGTTCTGGCGGAGGTGGCGCTCCTAC ATCCTCCAGCACCAAGAAAACCCAGCTCCAGCTGGAACA TCTCCTGCTGGATCTGCAGATGATCCTGAACGGCATCAAC AACTACAAGAACCCCAAGCTGACCCGGATGCTGACCTTC AAGTTCTACATGCCCAAGAAGGCCACCGAGCTGAAACAT CTGCAGTGCCTGGAAGAGGAACTGAAGCCTCTGGAAGAG GTGCTGAACCTGGCCCAGTCCAAGAACTTCCACCTGAGGC CTCGGGACCTGATCTCCAACATCAACGTGATCGTGCTGGA ACTGAAGGGCTCCGAGACAACCTTCATGTGCGAGTACGC CGACGAGACAGCTACCATCGTGGAATTTCTGAACCGGTG GATCACCTTCGCCCAGTCCATCATCTCCACCCTGACCTCC GGTGGTGGCGGATCCGGGGGAGGGGGTTCTGGCGGAGGC GGAGAAGTGCAGCTGCTGGAATCCGGCGGAGGCCTGGTG CAGCCTGGCGGATCTCTGAGACTGTCCTGCGCCGCCTCCG GCTTCACCTTCTCCTCCCACGCCATGTCCTGGGTCCGACA GGCTCCAGGCAAGGGCCTGGAATGGGTGTCCGCCATCTG GGCCTCCGGCGAGCAGTACTACGCCGACTCTGTGAAGGG CCGGTTCACCATCTCCCGGGACAACTCCAAGAACACCCTG TACCTGCAGATGAACTCCCTGCGGGCCGAGGACACCGCC GTGTACTACTGTGCCAAGGGCTGGCTGGGCAACTTCGACT ACTGGGGCCAGGGCACCCTGGTCACCGTGTCCTCCGCCTC TACCAAGGGCCCCTCCGTGTTCCCTCTGGCCCCCTCCAGC AAGTCTACCTCTGGCGGCACCGCCGCTCTGGGCTGCCTGG TCAAGGACTACTTCCCCGAGCCCGTGACCGTGTCCTGGAA CTCTGGCGCCCTGACCAGCGGCGTGCACACCTTTCCAGCC GTGCTGCAGTCCTCCGGCCTGTACTCCCTGTCCTCCGTCGT GACCGTGCCCTCCAGCTCTCTGGGCACCCAGACCTACATC TGCAACGTGAACCACAAGCCCTCCAACACCAAGGTGGAC AAGAAGGTGGAACCCAAGTCCTGCGACTGA | |
| 29B11 Fab-IL2-Fab (heavy chain cytokine fusion construct) | GAAGTGCAGCTGCTGGAATCCGGCGGAGGCCTGGTGCAG CCTGGCGGATCTCTGAGACTGTCCTGCGCCGCCTCCGGCT TCACCTTCTCCTCCTACGCCATGTCCTGGGTCCGACAGGC TCCTGGCAAAGGCCTGGAATGGGTGTCCGCCATCATCGGC TCCGGCGGCATCACCTACTACGCCGACTCTGTGAAGGGCC GGTTCACCATCTCCCGGGACAACTCCAAGAACACCCTGTA CCTGCAGATGAACTCCCTGCGGGCCGAGGACACCGCCGT GTACTACTGTGCCAAGGGCTGGTTCGGAGGCTTCAACTAC TGGGGACAGGGCACCCTGGTCACCGTGTCCAGCGCTAGC ACCAAGGGACCCTCCGTGTTCCCCCTGGCCCCCTCCAGCA AGTCTACCTCTGGCGGCACCGCCGCTCTGGGCTGCCTGGT CAAGGACTACTTCCCCGAGCCCGTGACCGTGTCCTGGAAC TCTGGCGCCCTGACCAGCGGCGTCCACACCTTTCCAGCCG TGCTGCAGTCCTCCGGCCTGTACTCCCTGTCCTCCGTCGTG ACCGTGCCCTCCAGCTCTCTGGGCACCCAGACCTACATCT GCAACGTGAACCACAAGCCCTCCAACACCAAGGTGGACA AGAAGGTGGAACCCAAGTCCTGCGACAGTGGTGGGGGAG GATCTGGTGGCGGAGGTTCTGGCGGAGGTGGCGCTCCTA CATCCTCCAGCACCAAGAAAACCCAGCTCCAGCTGGAAC ATCTCCTGCTGGATCTGCAGATGATCCTGAACGGCATCAA CAACTACAAGAACCCCAAGCTGACCCGGATGCTGACCTT CAAGTTCTACATGCCCAAGAAGGCCACCGAGCTGAAACA TCTGCAGTGCCTGGAAGAGGAACTGAAGCCTCTGGAAGA GGTGCTGAACCTGGCCCAGTCCAAGAACTTCCACCTGAG GCCTCGGGACCTGATCTCCAACATCAACGTGATCGTGCTG GAACTGAAGGGCTCCGAGACAACCTTCATGTGCGAGTAC GCCGACGAGACAGCTACCATCGTGGAATTTCTGAACCGG TGGATCACCTTCGCCCAGTCCATCATCTCCACCCTGACCT CCGGTGGTGGCGGATCCGGGGGAGGGGGTTCTGGCGGAG GCGGAGAAGTGCAGCTGCTGGAATCCGGCGGAGGCCTGG TGCAGCCTGGCGGATCTCTGAGACTGTCCTGCGCCGCCTC CGGCTTCACCTTCTCCTCCTATGCCATGTCCTGGGTCCGAC AGGCTCCAGGCAAGGGCCTGGAATGGGTGTCCGCCATCA TCGGCTCCGGCGGCATCACCTACTACGCCGACTCTGTGAA GGGCCGGTTCACCATCTCCCGGGACAACTCCAAGAACAC CCTGTACCTGCAGATGAACTCCCTGCGGGCCGAGGACAC CGCCGTGTACTACTGTGCCAAGGGCTGGTTCGGAGGCTTC AACTACTGGGGCCAGGGCACCCTGGTCACCGTGTCCTCCG CCTCTACCAAGGGCCCCTCCGTGTTCCCTCTGGCCCCCTC CAGCAAGTCTACCTCTGGCGGCACCGCCGCTCTGGGCTGC CTGGTCAAGGACTACTTCCCCGAGCCCGTGACCGTGTCCT | 224 |

TABLE 8-continued

| Construct | POLYNUCLEOTIDE SEQUENCE | SEQ ID NO |
|---|---|---|
| | GGAACTCTGGCGCCCTGACCAGCGGCGTGCACACCTTTCC AGCCGTGCTGCAGTCCTCCGGCCTGTACTCCCTGTCCTCC GTCGTGACCGTGCCCTCCAGCTCTCTGGGCACCCAGACCT ACATCTGCAACGTGAACCACAAGCCCTCCAACACCAAGG TGGACAAGAAGGTGGAACCCAAGTCCTGCGACTGA | |
| 19G1 Fab-IL2-Fab (heavy chain cytokine fusion construct) | GAGGTGCAGCTGCTCGAAAGCGGCGGAGGACTGGTGCAG CCTGGCGGCAGCCTGAGACTGTCTTGCGCCGCCAGCGGCT TCACCTTCAGCAGCTACGCCATGAGCTGGGTCCGCCAGGC CCCTGGCAAGGGACTGGAATGGGTGTCCGCCATCATCAG CTCTGGCGGCCTGACCTACTACGCCGACAGCGTGAAGGG CCGGTTCACCATCAGCCGGGACAACAGCAAGAACACCCT GTACCTGCAGATGAACAGCCTGCGGGCCGAGGACACCGC CGTGTACTACTGCGCCAAGGGATGGTTCGGCGGCTTCAAC TACTGGGGACAGGGCACCCTGGTCACAGTGTCCAGCGCT AGCACCAAGGGACCCAGCGTGTTCCCCCTGGCCCCCAGC AGCAAGAGCACATCTGGCGGAACAGCCGCCCTGGGCTGC CTGGTCAAAGACTACTTCCCCGAGCCCGTGACCGTGTCCT GGAACAGCGGAGCCCTGACCAGCGGCGTGCACACCTTTC CAGCCGTGCTGCAGAGCAGCGGCCTGTACAGCCTGAGCA GCGTGGTCACCGTGCCTAGCTCTAGCCTGGGCACCCAGAC CTACATCTGCAACGTGAACCACAAGCCCAGCAACACCAA GGTGGACAAGAAGGTGGAACCCAAGAGCTGCGACTCCGG CGGAGGCGGATCTGGCGGTGGAGGCTCCGGAGGCGGAGG CGCTCCTACTAGCAGCTCCACCAAGAAAACCCAGCTCCA GCTGGAACATCTGCTGCTGGATCTGCAGATGATCCTGAAC GGCATCAACAACTACAAGAACCCCAAGCTGACCCGGATG CTGACCTTCAAGTTCTACATGCCCAAGAAGGCCACCGAAC TGAAACATCTGCAGTGCCTGGAAGAGGAACTGAAGCCTC TGGAAGAGGTGCTGAACCTGGCCCAGAGCAAGAACTTCC ACCTGAGGCCCAGGGACCTGATCAGCAACATCAACGTGA TCGTGCTGGAACTGAAGGGCAGCGAGACAACCTTCATGT GCGAGTACGCCGACGAGACAGCCACCATCGTGGAATTTC TGAACCGGTGGATCACCTTCGCCCAGAGCATCATCAGCAC CCTGACAAGCGGAGGCGGCGGATCCGGCGGAGGCGGATC TGGCGGAGGAGGCGAGGTCCAGCTGCTCGAAAGCGGCGG AGGACTGGTGCAGCCTGGCGGCAGCCTGAGACTGTCTTG CGCCGCCAGCGGCTTCACCTTCAGCAGCTACGCCATGAGC TGGGTCCGCCAGGCCCCTGGCAAGGGACTGGAATGGGTG TCCGCCATCATCAGCTCTGGCGGCCTGACCTACTACGCCG ACAGCGTGAAGGGCCGGTTCACCATCAGCCGGGACAACA GCAAGAACACCCTGTACCTGCAGATGAACAGCCTGCGGG CCGAGGACACCGCCGTGTACTACTGCGCCAAGGGATGGT TCGGCGGCTTCAACTACTGGGGACAGGGCACCCTGGTCA CAGTGTCCAGCGCCAGCACCAAGGGCCCCAGCGTGTTCC CCCTGGCCCCCAGCAGCAAGAGCACATCTGGCGGAACAG CCGCCCTGGGCTGCCTGGTCAAAGACTACTTCCCCGAGCC CGTGACCGTGTCCTGGAACAGCGGAGCCCTGACCAGCGG CGTGCACACCTTTCCAGCCGTGCTGCAGAGCAGCGGCCTG TACAGCCTGAGCAGCGTGGTCACCGTGCCTAGCTCTAGCC TGGGCACCCAGACCTACATCTGCAACGTGAACCACAAGC CCAGCAACACCAAGGTGGACAAGAAGGTGGAACCCAAG AGCTGCGACTGA | 226 |
| 20G8 Fab-IL2-Fab (heavy chain cytokine fusion construct) | GAGGTGCAGCTGCTCGAAAGCGGCGGAGGACTGGTGCAG CCTGGCGGCAGCCTGAGACTGTCTTGCGCCGCCAGCGGCT TCACCTTCAGCAGCTACGCCATGAGCTGGGTCCGCCAGGC CCCTGGCAAGGGACTGGAATGGGTGTCCGCCATCATCGG CTCTGGCAGCCGGACCTACTACGCCGACAGCGTGAAGGG CCGGTTCACCATCAGCCGGGACAACAGCAAGAACACCCT GTACCTGCAGATGAACAGCCTGCGGGCCGAGGACACCGC CGTGTACTACTGCGCCAAGGGATGGTTCGGCGGCTTCAAC TACTGGGGACAGGGCACCCTGGTCACAGTGTCCAGCGCT AGCACCAAGGGACCCAGCGTGTTCCCCCTGGCCCCCAGC AGCAAGAGCACATCTGGCGGAACAGCCGCCCTGGGCTGC CTGGTCAAAGACTACTTCCCCGAGCCCGTGACCGTGTCCT GGAACAGCGGAGCCCTGACCAGCGGCGTGCACACCTTTC CAGCCGTGCTGCAGAGCAGCGGCCTGTACAGCCTGAGCA GCGTGGTCACCGTGCCTAGCTCTAGCCTGGGCACCCAGAC CTACATCTGCAACGTGAACCACAAGCCCAGCAACACCAA GGTGGACAAGAAGGTGGAACCCAAGAGCTGCGACTCCGG CGGAGGCGGATCTGGCGGTGGAGGCTCCGGAGGCGGAGG CGCTCCTACTAGCAGCTCCACCAAGAAAACCCAGCTCCA GCTGGAACATCTGCTGCTGGATCTGCAGATGATCCTGAAC GGCATCAACAACTACAAGAACCCCAAGCTGACCCGGATG CTGACCTTCAAGTTCTACATGCCCAAGAAGGCCACCGAAC TGAAACATCTGCAGTGCCTGGAAGAGGAACTGAAGCCTC TGGAAGAGGTGCTGAACCTGGCCCAGAGCAAGAACTTCC | 228 |

TABLE 8-continued

| Construct | POLYNUCLEOTIDE SEQUENCE | SEQ ID NO |
|---|---|---|
| | ACCTGAGGCCCAGGGACCTGATCAGCAACATCAACGTGA TCGTGCTGGAACTGAAGGGCAGCGAGACAACCTTCATGT GCGAGTACGCCGACGAGACAGCCACCATCGTGGAATTTC TGAACCGGTGGATCACCTTCGCCCAGAGCATCATCAGCAC CCTGACAAGCGGAGGCGGCGGATCCGGCGGAGGCGGATC TGGCGGAGGAGGCGAGGTCCAGCTGCTCGAAAGCGGCGG AGGACTGGTGCAGCCTGGCGGCAGCCTGAGACTGTCTTG CGCCGCCAGCGGCTTCACCTTCAGCAGCTACGCCATGAGC TGGGTCCGCCAGGCCCCTGGCAAGGGACTGGAATGGGTG TCCGCCATCATCGGCTCTGGCAGCCGGACCTACTACGCCG ACAGCGTGAAGGGCCGGTTCACCATCAGCCGGGACAACA GCAAGAACACCCTGTACCTGCAGATGAACAGCCTGCGGG CCGAGGACACCGCCGTGTACTACTGCGCCAAGGGATGGT TCGGCGGCTTCAACTACTGGGGACAGGGCACCCTGGTCA CAGTGTCCAGCGCCAGCACCAAGGGCCCCAGCGTGTTCC CCCTGGCCCCCAGCAGCAAGAGCACATCTGGCGGAACAG CCGCCCTGGGCTGCCTGGTCAAAGACTACTTCCCCGAGCC CGTGACCGTGTCCTGGAACAGCGGAGCCCTGACCAGCGG CGTGCACACCTTTCCAGCCGTGCTGCAGAGCAGCGGCCTG TACAGCCTGAGCAGCGTGGTCACCGTGCCTAGCTCTAGCC TGGGCACCCAGACCTACATCTGCAACGTGAACCACAAGC CCAGCAACACCAAGGTGGACAAGAAGGTGGAACCCAAG AGCTGCGACTGA | |
| 3F2 light chain | GAGATCGTGCTGACCCAGTCCCCCGGCACCCTGTCTCTGA GCCCTGGCGAGAGAGCCACCCTGTCCTGCAGAGCCTCCC AGTCCGTGACCTCCTCCTACCTCGCCTGGTATCAGCAGAA GCCCGGCCAGGCCCCTCGGCTGCTGATCAACGTGGGCAG TCGGAGAGCCACCGGCATCCCTGACCGGTTCTCCGGCTCT GGCTCCGGCACCGACTTCACCCTGACCATCTCCCGGCTGG AACCCGAGGACTTCGCCGTGTACTACTGCCAGCAGGGCA TCATGCTGCCCCCCACCTTTGGCCAGGGCACCAAGGTGGA AATCAAGCGTACGGTGGCCGCTCCCTCCGTGTTCATCTTC CCACCCTCCGACGAGCAGCTGAAGTCCGGCACCGCCTCC GTCGTGTGCCTGCTGAACAACTTCTACCCCCGCGAGGCCA AGGTGCAGTGGAAGGTGGACAACGCCCTGCAGTCCGGCA ACTCCCAGGAATCCGTCACCGAGCAGGACTCCAAGGACA GCACCTACTCCCTGTCCTCCACCCTGACCCTGTCCAAGGC CGACTACGAGAAGCACAAGGTGTACGCCTGCGAAGTGAC CCACCAGGGCCTGTCCAGCCCCGTGACCAAGTCCTTCAAC CGGGGCGAGTGCTGATGA | 230 |
| 4G8 light chain | GAGATCGTGCTGACCCAGTCCCCCGGCACCCTGTCTCTGA GCCCTGGCGAGAGAGCCACCCTGTCCTGCAGAGCCTCCC AGTCCGTGTCCCGGTCCTACCTCGCCTGGTATCAGCAGAA GCCCGGCCAGGCCCCTCGGCTGCTGATCATCGGCGCCTCT ACCAGAGCCACCGGCATCCCTGACCGGTTCTCCGGCTCTG GCTCCGGCACCGACTTCACCCTGACCATCTCCCGGCTGGA ACCCGAGGACTTCGCCGTGTACTACTGCCAGCAGGGCCA GGTCATCCCTCCCACCTTTGGCCAGGGCACCAAGGTGGAA ATCAAGCGTACGGTGGCCGCTCCCTCCGTGTTCATCTTCC CACCCTCCGACGAGCAGCTGAAGTCCGGCACCGCCTCCGT CGTGTGCCTGCTGAACAACTTCTACCCCCGCGAGGCCAAG GTGCAGTGGAAGGTGGACAACGCCCTGCAGTCCGGCAAC TCCCAGGAATCCGTCACCGAGCAGGACTCCAAGGACAGC ACCTACTCCCTGTCCTCCACCCTGACCCTGTCCAAGGCCG ACTACGAGAAGCACAAGGTGTACGCCTGCGAAGTGACCC ACCAGGGCCTGTCCAGCCCCGTGACCAAGTCCTTCAACCG GGGCGAGTGCTGATGA | 232 |
| 3D9 light chain | GAAATCGTGTTAACGCAGTCTCCAGGCACCCTGTCTTTGT CTCCAGGGGAAAGAGCCACCCTCTCTTGCAGGGCCAGTC AGAGTGTTAGCAGCAGCTACTTAGCCTGGTACCAGCAGA AACCTGGCCAGGCTCCCAGGCTCCTCATCTATGGAGCATC CAGCAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTC AGCTTATTCCCCCTACGTTCGGCCAGGGGACCAAAGTGGA AATCAAACGTACGGTGGCTGCACCATCTGTCTTCATCTTC CCGCCATCTGATGAGCAGTTGAAATCTGGAACTGCCTCTG TTGTGTGCCTGCTGAATAACTTCTATCCCAGAGAGGCCAA AGTACAGTGGAAGGTGGATAACGCCCTCCAATCGGGTAA CTCCCAGGAGAGTGTCACAGAGCAGGACAGCAAGGACAG CACCTACAGCCTCAGCAGCACCCTGACGCTGAGCAAAGC AGACTACGAGAAACACAAAGTCTACGCCTGCGAAGTCAC CCATCAGGGCCTGAGCTCGCCCGTCACAAAGAGCTTCAA CAGGGGAGAGTGTTAG | 234 |

TABLE 8-continued

| Construct | POLYNUCLEOTIDE SEQUENCE | SEQ ID NO |
|---|---|---|
| 2F11 light chain | GAAATCGTGTTAACGCAGTCTCCAGGCACCCTGTCTTTGT CTCCAGGGGAAAGAGCCACCCTCTCTTGCAGGGCCAGTC AGAGTGTTAGCAGCAGCTACTTAGCCTGGTACCAGCAGA AACCTGGCCAGGCTCCCAGGCTCCTCATCTATGGAGCATC CAGCAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTC AGTATACTCCCCCCACGTTCGGCCAGGGGACCAAAGTGG AAATCAAACGTACGGTGGCTGCACCATCTGTCTTCATCTT CCCGCCATCTGATGAGCAGTTGAAATCTGGAACTGCCTCT GTTGTGTGCCTGCTGAATAACTTCTATCCCAGAGAGGCCA AAGTACAGTGGAAGGTGGATAACGCCCTCCAATCGGGTA ACTCCCAGGAGAGTGTCACAGAGCAGGACAGCAAGGACA GCACCTACAGCCTCAGCAGCACCCTGACGCTGAGCAAAG CAGACTACGAGAAACACAAAGTCTACGCCTGCGAAGTCA CCCATCAGGGCCTGAGCTCGCCCGTCACAAAGAGCTTCA ACAGGGGAGAGTGTTAG | 236 |
| 4B3 light chain | GAAATCGTGTTAACGCAGTCTCCAGGCACCCTGTCTTTGT CTCCAGGGGAAAGAGCCACCCTCTCTTGCAGGGCCAGTC AGAGTGTTAGCAGCAATTACTTAGCCTGGTACCAGCAGA AACCTGGCCAGGCTCCCAGGCTCCTCATCTATGGCGCCTA CATCAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGGGTC AGGTTATTCCCCCTACGTTCGGCCAGGGGACCAAAGTGG AAATCAAACGTACGGTGGCTGCACCATCTGTCTTCATCTT CCCGCCATCTGATGAGCAGTTGAAATCTGGAACTGCCTCT GTTGTGTGCCTGCTGAATAACTTCTATCCCAGAGAGGCCA AAGTACAGTGGAAGGTGGATAACGCCCTCCAATCGGGTA ACTCCCAGGAGAGTGTCACAGAGCAGGACAGCAAGGACA GCACCTACAGCCTCAGCAGCACCCTGACGCTGAGCAAAG CAGACTACGAGAAACACAAAGTCTACGCCTGCGAAGTCA CCCATCAGGGCCTGAGCTCGCCCGTCACAAAGAGCTTCA ACAGGGGAGAGTGTTAG | 238 |
| 2B10 Fab-IL2-Fab (heavy chain cytokine fusion construct) | CAGGTGCAATTGGTGCAGTCTGGGGCTGAGGTGAAGAAG CCTGGGTCCTCGGTGAAGGTCTCCTGCAAGGCCTCCGGAG GCACATTCAGCAGCTACGCTATAAGCTGGGTGCGACAGG CCCCTGGACAAGGGCTCGAGTGGATGGGAGGGATCATCC CTATCTTTGGTACAGCAAACTACGCACAGAAGTTCCAGGG CAGGGTCACCATTACTGCAGACAAATCCACGAGCACAGC CTACATGGAGCTGAGCAGCCTGAGATCTGAGGACACCGC CGTGTATTACTGTGCGAGACTGTACGGTTACGCTTACTAC GGTGCTTTTGACTACTGGGGCCAAGGGACCACCGTGACC GTCTCCTCAGCTAGCACCAAGGGCCCATCGGTCTTCCCCC TGGCACCCTCCTCCAAGAGCACCTCTGGGGGCACAGCGG CCCTGGGCTGCCTGGTCAAGGACTACTTCCCCGAACCGGT GACGGTGTCGTGGAACTCAGGCGCCCTGACCAGCGGCGT GCACACCTTCCCGGCTGTCCTACAGTCCTCAGGACTCTAC TCCCTCAGCAGCGTGGTGACCGTGCCCTCCAGCAGCTTGG GCACCCAGACCTACATCTGCAACGTGAATCACAAGCCCA GCAACACCAAGGTGGATAAGAAAGTTGAGCCCAAATCTT GTGACTCCGGCGGAGGAGGGAGCGGCGGAGGTGGCTCCG GAGGTGGCGGAGCACCTACTTCAAGTTCTACAAAGAAAA CACAGCTACAACTGGAGCATTTACTGCTGGATTTACAGAT GATTTTGAATGGAATTAATAATTACAAGAATCCCAAACTC ACCAGGATGCTCACATTTAAGTTTTACATGCCCAAGAAGG CCACAGAACTGAAACATCTTCAGTGTCTAGAAGAAGAAC TCAAACCTCTGGAGGAAGTGCTAAATTTAGCTCAAAGCA AAAACTTTCACTTAAGACCCAGGGACTTAATCAGCAATAT CAACGTAATAGTTCTGGAACTAAAGGGATCTGAAACAAC ATTCATGTGTGAATATGCTGATGAGACAGCAACCATTGTA GAATTTCTGAACAGATGGATTACCTTTGCCCAAAGCATCA TCTCAACACTGACTTCCGGCGGAGGAGGATCCGGCGGAG GTGGCTCTGGCGGTGGCGGACAGGTGCAATTGGTGCAGT CTGGGGCTGAGGTGAAGAAGCCTGGGTCCTCGGTGAAGG TCTCCTGCAAGGCCTCCGGAGGCACATTCAGCAGCTACGC TATAAGCTGGGTGCGACAGGCCCCTGGACAAGGGCTCGA GTGGATGGGAGGGATCATCCCTATCTTTGGTACAGCAAAC TACGCACAGAAGTTCCAGGGCAGGGTCACCATTACTGCA GACAAATCCACGAGCACAGCCTACATGGAGCTGAGCAGC CTGAGATCTGAGGACACCGCCGTGTATTACTGTGCGAGAC TGTACGGTTACGCTTACTACGGTGCTTTTGACTACTGGGG CCAAGGGACCACCGTGACCGTCTCCTCAGCTAGCACCAA GGGCCCATCGGTCTTCCCCCTGGCACCCTCCTCCAAGAGC ACCTCTGGGGGCACAGCGGCCCTGGGCTGCCTGGTCAAG GACTACTTCCCCGAACCGGTGACGGTGTCGTGGAACTCAG | 240 |

TABLE 8-continued

| Construct | POLYNUCLEOTIDE SEQUENCE | SEQ ID NO |
|---|---|---|
| | GCGCCCTGACCAGCGGCGTGCACACCTTCCCGGCTGTCCT ACAGTCCTCAGGACTCTACTCCCTCAGCAGCGTGGTGACC GTGCCCTCCAGCAGCTTGGGCACCCAGACCTACATCTGCA ACGTGAATCACAAGCCCAGCAACACCAAGGTGGATAAGA AAGTTGAGCCCAAATCTTGTGACTGA | |
| C3B6 Fab-IL2-Fab (heavy chain cytokine fusion construct) | CAGGTGCAATTGGTGCAGTCTGGGGCTGAGGTGAAGAAG CCTGGGTCCTCGGTGAAGGTCTCCTGCAAGGCCTCCGGAG GCACATTCAGCAGCTACGCTATAAGCTGGGTGCGACAGG CCCCTGGACAAGGGCTCGAGTGGATGGGAGCTATCATCC CGATCCTTGGTATCGCAAACTACGCACAGAAGTTCCAGG GCAGGGTCACCATTACTGCAGACAAATCCACGAGCACAG CCTACATGGAGCTGAGCAGCCTGAGATCTGAGGACACCG CCGTGTATTACTGTGCGAGACTGTACGGTTACGCTTACTA CGGTGCTTTTGACTACTGGGGCCAAGGGACCACCGTGACC GTCTCCTCAGCTAGCACCAAGGGCCCATCGGTCTTCCCCC TGGCACCCTCCTCCAAGAGCACCTCTGGGGGCACAGCGG CCCTGGGCTGCCTGGTCAAGGACTACTTCCCCGAACCGGT GACGGTGTCGTGGAACTCAGGCGCCCTGACCAGCGGCGT GCACACCTTCCCGGCTGTCCTACAGTCCTCAGGACTCTAC TCCCTCAGCAGCGTGGTGACCGTGCCCTCCAGCAGCTTGG GCACCCAGACCTACATCTGCAACGTGAATCACAAGCCCA GCAACACCAAGGTGGATAAGAAAGTTGAGCCCAAATCTT GTGACTCCGGCGGAGGAGGGAGCGGCGGAGGTGGCTCCG GAGGTGGCGGAGCACCTACTTCAAGTTCTACAAAGAAAA CACAGCTACAACTGGAGCATTTACTGCTGGATTTACAGAT GATTTTGAATGGAATTAATAATTACAAGAATCCCAAACTC ACCAGGATGCTCACATTTAAGTTTTACATGCCCAAGAAGG CCACAGAACTGAAACATCTTCAGTGTCTAGAAGAAGAAC TCAAACCTCTGGAGGAAGTGCTAAATTTAGCTCAAAGCA AAAACTTTCACTTAAGACCCAGGGACTTAATCAGCAATAT CAACGTAATAGTTCTGGAACTAAAGGGATCTGAAACAAC ATTCATGTGTGAATATGCTGATGAGACAGCAACCATTGTA GAATTTCTGAACAGATGGATTACCTTTGCCCAAAGCATCA TCTCAACACTGACTTCCGGCGGAGGAGGATCCGGCGGAG GTGGCTCTGGCGGTGGCGGACAGGTGCAATTGGTGCAGT CTGGGGCTGAGGTGAAGAAGCCTGGGTCCTCGGTGAAGG TCTCCTGCAAGGCCTCCGGAGGCACATTCAGCAGCTACGC TATAAGCTGGGTGCGACAGGCCCCTGGACAAGGGCTCGA GTGGATGGGAGCTATCATCCCGATCCTTGGTATCGCAAAC TACGCACAGAAGTTCCAGGGCAGGGTCACCATTACTGCA GACAAATCCACGAGCACAGCCTACATGGAGCTGAGCAGC CTGAGATCTGAGGACACCGCCGTGTATTACTGTGCGAGAC TGTACGGTTACGCTTACTACGGTGCTTTTGACTACTGGGG CCAAGGGACCACCGTGACCGTCTCCTCAGCTAGCACCAA GGGCCCATCGGTCTTCCCCCTGGCACCCTCCTCCAAGAGC ACCTCTGGGGGCACAGCGGCCCTGGGCTGCCTGGTCAAG GACTACTTCCCCGAACCGGTGACGGTGTCGTGGAACTCAG GCGCCCTGACCAGCGGCGTGCACACCTTCCCGGCTGTCCT ACAGTCCTCAGGACTCTACTCCCTCAGCAGCGTGGTGACC GTGCCCTCCAGCAGCTTGGGCACCCAGACCTACATCTGCA ACGTGAATCACAAGCCCAGCAACACCAAGGTGGATAAGA AAGTTGAGCCCAAATCTTGTGACTGA | 242 |
| 6A12 Fab-IL2-Fab (heavy chain cytokine fusion construct) | CAGGTGCAATTGGTGCAGTCTGGGGCTGAGGTGAAGAAG CCTGGGTCCTCGGTGAAGGTCTCCTGCAAGGCCTCCGGAG GCACATTCAGCAGCTATGCTATAAGCTGGGTGCGACAGG CCCCTGGACAAGGGCTCGAGTGGATGGGAGTGATCATCC CTATCCTTGGTACCGCAAACTACGCACAGAAGTTCCAGGG CAGGGTCACCATTACTGCAGACAAATCCACGAGCACAGC CTACATGGAGCTGAGCAGCCTGAGATCTGAGGACACCGC CGTGTATTACTGTGCGAGACTGTACGGTTACGCTTACTAC GGTGCTTTTGACTACTGGGGCCAAGGGACCACCGTGACC GTCTCCTCAGCTAGCACCAAGGGCCCATCGGTCTTCCCCC TGGCACCCTCCTCCAAGAGCACCTCTGGGGGCACAGCGG CCCTGGGCTGCCTGGTCAAGGACTACTTCCCCGAACCGGT GACGGTGTCGTGGAACTCAGGCGCCCTGACCAGCGGCGT GCACACCTTCCCGGCTGTCCTACAGTCCTCAGGACTCTAC TCCCTCAGCAGCGTGGTGACCGTGCCCTCCAGCAGCTTGG GCACCCAGACCTACATCTGCAACGTGAATCACAAGCCCA GCAACACCAAGGTGGATAAGAAAGTTGAGCCCAAATCTT GTGACTCCGGCGGAGGAGGGAGCGGCGGAGGTGGCTCCG GAGGTGGCGGAGCACCTACTTCAAGTTCTACAAAGAAAA CACAGCTACAACTGGAGCATTTACTGCTGGATTTACAGAT GATTTTGAATGGAATTAATAATTACAAGAATCCCAAACTC ACCAGGATGCTCACATTTAAGTTTTACATGCCCAAGAAGG CCACAGAACTGAAACATCTTCAGTGTCTAGAAGAAGAAC TCAAACCTCTGGAGGAAGTGCTAAATTTAGCTCAAAGCA | 244 |

TABLE 8-continued

| Construct | POLYNUCLEOTIDE SEQUENCE | SEQ ID NO |
|---|---|---|
| | AAAACTTTCACTTAAGACCCAGGGACTTAATCAGCAATAT CAACGTAATAGTTCTGGAACTAAAGGGATCTGAAACAAC ATTCATGTGTGAATATGCTGATGAGACAGCAACCATTGTA GAATTTCTGAACAGATGGATTACCTTTGCCCAAAGCATCA TCTCAACACTGACTTCCGGCGGAGGAGGATCCGGCGGAG GTGGCTCTGGCGGTGGCGGACAGGTGCAATTGGTGCAGT CTGGGGCTGAGGTGAAGAAGCCTGGGTCCTCGGTGAAGG TCTCCTGCAAGGCCTCCGGAGGCACATTCAGCAGCTATGC TATAAGCTGGGTGCGACAGGCCCCTGGACAAGGGCTCGA GTGGATGGGAGTGATCATCCCTATCCTTGGTACCGCAAAC TACGCACAGAAGTTCCAGGGCAGGGTCACCATTACTGCA GACAAATCCACGAGCACAGCCTACATGGAGCTGAGCAGC CTGAGATCTGAGGACACCGCCGTGTATTACTGTGCGAGAC TGTACGGTTACGCTTACTACGGTGCTTTTGACTACTGGGG CCAAGGGACCACCGTGACCGTCTCCTCAGCTAGCACCAA GGGCCCATCGGTCTTCCCCCTGGCACCCTCCTCCAAGAGC ACCTCTGGGGGCACAGCGGCCCTGGGCTGCCTGGTCAAG GACTACTTCCCCGAACCGGTGACGGTGTCGTGGAACTCAG GCGCCCTGACCAGCGGCGTGCACACCTTCCCGGCTGTCCT ACAGTCCTCAGGACTCTACTCCCTCAGCAGCGTGGTGACC GTGCCCTCCAGCAGCTTGGGCACCCAGACCTACATCTGCA ACGTGAATCACAAGCCCAGCAACACCAAGGTGGATAAGA AAGTTGAGCCCAAATCTTGTGACTGA | |
| 2B10 light chain | GATATCCAGATGACCCAGTCTCCATCCTCCCTGTCTGCAT CTGTCGGAGACCGGGTCACCATCACCTGCCGGGCAAGTC AGGGCATTAGAAATGATTTAGGCTGGTACCAGCAGAAGC CAGGGAAAGCCCCTAAGCGCCTGATCTATGCTGCATCCA GTTTGCAGAGTGGCGTCCCATCAAGGTTCAGCGGCAGTG GATCCGGGACAGAGTTCACTCTCACCATCAGCAGCTTGCA GCCTGAAGATTTTGCCACCTATTACTGCTTGCAGAATGGT CTGCAGCCCGCGACGTTTGGCCAGGGCACCAAAGTCGAG ATCAAGCGTACGGTGGCTGCACCATCTGTCTTCATCTTCC CGCCATCTGATGAGCAGTTGAAATCTGGAACTGCCTCTGT TGTGTGCCTGCTGAATAACTTCTATCCCAGAGAGGCCAAA GTACAGTGGAAGGTGGATAACGCCCTCCAATCGGGTAAC TCCCAGGAGAGTGTCACAGAGCAGGACAGCAAGGACAGC ACCTACAGCCTCAGCAGCACCCTGACGCTGAGCAAAGCA GACTACGAGAAACACAAAGTCTACGCCTGCGAAGTCACC CATCAGGGCCTGAGCTCGCCCGTCACAAAGAGCTTCAAC AGGGGAGAGTGTTAG | 246 |
| D1A2 light chain | GACATCCAGATGACCCAGTCTCCATCCTCCCTGTCTGCAT CTGTCGGAGACCGGGTCACCATCACCTGCCGGGCAAGTC AGGGGATTCGTAATGATTTAGGCTGGTACCAGCAGAAGC CAGGGAAAGCCCCTAAGCGCCTGATCTATGATGCTTACA GCTTGCAGAGTGGCGTCCCATCAAGGTTCAGCGGCGGTG GATCCGGGACAGAGTTCACTCTCACCATCAGCAGCTTGCA GCCTGAAGATTTTGCCACCTATTACTGCTGCAGAATGGT CTGCAGCCCGCGACGTTTGGCCAGGGCACCAAAGTCGAG ATCAAGCGTACGGTGGCTGCACCATCTGTCTTCATCTTCC CGCCATCTGATGAGCAGTTGAAATCTGGAACTGCCTCTGT TGTGTGCCTGCTGAATAACTTCTATCCCAGAGAGGCCAAA GTACAGTGGAAGGTGGATAACGCCCTCCAATCGGGTAAC TCCCAGGAGAGTGTCACAGAGCAGGACAGCAAGGACAGC ACCTACAGCCTCAGCAGCACCCTGACGCTGAGCAAAGCA GACTACGAGAAACACAAAGTCTACGCCTGCGAAGTCACC CATCAGGGCCTGAGCTCGCCCGTCACAAAGAGCTTCAAC AGGGGAGAGTGTTAG | 248 |
| O7D8 light chain | GATATCCAGATGACCCAGTCTCCATCCTCCCTGTCTGCAT CTGTCGGAGACCGGGTCACCATCACCTGCCGGGCAAGTC AGAGCATTCGTAATGTTTTAGGCTGGTACCAGCAGAAGCC AGGGAAAGCCCCTAAGCGCCTGATCTATGATGTGTCCAGT TTGCAGAGTGGCGTCCCATCAAGGTTCAGCGGCGGTGGA TCCGGGACAGAGTTCACTCTCACCATCAGCAGCTTGCAGC CTGAAGATTTTGCCACCTATTACTGCTTGCAGAATGGTCT GCAGCCCGCGACGTTTGGCCAGGGCACCAAAGTCGAGAT CAAGCGTACGGTGGCTGCACCATCTGTCTTCATCTTCCCG CCATCTGATGAGCAGTTGAAATCTGGAACTGCCTCTGTTG TGTGCCTGCTGAATAACTTCTATCCCAGAGAGGCCAAAGT ACAGTGGAAGGTGGATAACGCCCTCCAATCGGGTAACTC CCAGGAGAGTGTCACAGAGCAGGACAGCAAGGACAGCA CCTACAGCCTCAGCAGCACCCTGACGCTGAGCAAAGCAG ACTACGAGAAACACAAAGTCTACGCCTGCGAAGTCACCC ATCAGGGCCTGAGCTCGCCCGTCACAAAGAGCTTCAACA GGGGAGAGTGTTAG | 250 |

TABLE 8-continued

| Construct | POLYNUCLEOTIDE SEQUENCE | SEQ ID NO |
|---|---|---|
| MHLG1 Fab-IL2-Fab (heavy chain cytokine fusion construct) | GAAGTGCAGCTGGTGGAGTCTGGAGGAGGCTTGGTCAAG<br>CCTGGCGGGTCCCTGCGGCTCTCCTGTGCAGCCTCCGGAT<br>TCACATTTAGCAACTATTGGATGAACTGGGTGCGGCAGGC<br>TCCTGGAAAGGGCCTCGAGTGGGTGGCCGAGATCAGATT<br>GAAATCCAATAACTTCGGAAGATATTACGCTGCAAGCGT<br>GAAGGGCCGGTTCACCATCAGCAGAGATGATTCCAAGAA<br>CACGCTGTACCTGCAGATGAACAGCCTGAAGACCGAGGA<br>TACGGCCGTGTATTACTGTACCACATACGGCAACTACGTT<br>GGGCACTACTTCGACCACTGGGGCCAAGGGACCACCGTC<br>ACCGTCTCCAGTGCTAGCACCAAGGGCCCATCGGTCTTCC<br>CCCTGGCACCCTCCTCCAAGAGCACCTCTGGGGGCACAGC<br>GGCCCTGGGCTGCCTGGTCAAGGACTACTTCCCCGAACCG<br>GTGACGGTGTCGTGGAACTCAGGCGCCCTGACCAGCGGC<br>GTGCACACCTTCCCGGCTGTCCTACAGTCCTCAGGACTCT<br>ACTCCCTCAGCAGCGTGGTGACCGTGCCCTCCAGCAGCTT<br>GGGCACCCAGACCTACATCTGCAACGTGAATCACAAGCC<br>CAGCAACACCAAGGTGGATAAGAAAGTTGAGCCCAAATC<br>TTGTGACTCCGGCGGAGGAGGGAGCGGCGGAGGTGGCTC<br>CGGAGGTGGCGGAGCACCTACTTCAAGTTCTACAAAGAA<br>AACACAGCTACAACTGGAGCATTTACTGCTGGATTTACAG<br>ATGATTTTGAATGGAATTAATAATTACAAGAATCCCAAAC<br>TCACCAGGATGCTCACATTTAAGTTTTACATGCCCAAGAA<br>GGCCACAGAACTGAAACATCTTCAGTGTCTAGAAGAAGA<br>ACTCAAACCTCTGGAGGAAGTGCTAAATTTAGCTCAAAG<br>CAAAAACTTTCACTTAAGACCCAGGGACTTAATCAGCAAT<br>ATCAACGTAATAGTTCTGGAACTAAAGGGATCTGAAACA<br>ACATTCATGTGTGAATATGCTGATGAGACAGCAACCATTG<br>TAGAATTTCTGAACAGATGGATTACCTTTGCCCAAAGCAT<br>CATCTCAACACTGACTTCCGGCGGAGGAGGATCCGGCGG<br>AGGTGGCTCTGGCGGTGGCGGAGAAGTGCAGCTGGTGGA<br>GTCTGGAGGAGGCTTGGTCAAGCCTGGCGGGTCCCTGCG<br>GCTCTCCTGTGCAGCCTCCGGATTCACATTTAGCAACTAT<br>TGGATGAACTGGGTGCGGCAGGCTCCTGGAAAGGGCCTC<br>GAGTGGGTGGCCGAGATCAGATTGAAATCCAATAACTTC<br>GGAAGATATTACGCTGCAAGCGTGAAGGGCCGGTTCACC<br>ATCAGCAGAGATGATTCCAAGAACACGCTGTACCTGCAG<br>ATGAACAGCCTGAAGACCGAGGATACGGCCGTGTATTAC<br>TGTACCACATACGGCAACTACGTTGGGCACTACTTCGACC<br>ACTGGGGCCAAGGGACCACCGTCACCGTCTCCAGTGCTA<br>GCACCAAGGGCCCATCGGTCTTCCCCCTGGCACCCTCCTC<br>CAAGAGCACCTCTGGGGGCACAGCGGCCCTGGGCTGCCT<br>GGTCAAGGACTACTTCCCCGAACCGGTGACGGTGTCGTG<br>GAACTCAGGCGCCCTGACCAGCGGCGTGCACACCTTCCC<br>GGCTGTCCTACAGTCCTCAGGACTCTACTCCCTCAGCAGC<br>GTGGTGACCGTGCCCTCCAGCAGCTTGGGCACCCAGACCT<br>ACATCTGCAACGTGAATCACAAGCCCAGCAACACCAAGG<br>TGGATAAGAAAGTTGAGCCCAAATCTTGTGACTGA | 252 |
| KV9 light chain | GATATCCAGTTGACCCAGTCTCCATCCTTCCTGTCTGCATC<br>TGTGGGCGACCGGGTCACCATCACCTGCAAGGCCAGTCA<br>GAATGTGGATACTAACGTGGCTTGGTACCAGCAGAAGCC<br>AGGGCAGGCACCTAGGCCTCTGATCTATTCGGCATCCTAC<br>CGGTACACTGGCGTCCCATCAAGGTTCAGCGGCAGTGGA<br>TCCGGGACAGAGTTCACTCTCACAATCTCAAGCCTGCAAC<br>CTGAAGATTTCGCAACTTACTACTGTCAACAGTACAATAG<br>TTACCCTCTGACGTTCGGCGGAGGTACCAAGGTGGAGATC<br>AAGCGTACGGTGGCTGCACCATCTGTCTTCATCTTCCCGC<br>CATCTGATGAGCAGTTGAAATCTGGAACTGCCTCTGTTGT<br>GTGCCTGCTGAATAACTTCTATCCCAGAGAGGCCAAAGTA<br>CAGTGGAAGGTGGATAACGCCCTCCAATCGGGTAACTCC<br>CAGGAGAGTGTCACAGAGCAGGACAGCAAGGACAGCAC<br>CTACAGCCTCAGCAGCACCCTGACGCTGAGCAAAGCAGA<br>CTACGAGAAACACAAAGTCTACGCCTGCGAAGTCACCCA<br>TCAGGGCCTGAGCTCGCCCGTCACAAAGAGCTTCAACAG<br>GGGAGAGTGTTAG | 254 |
| MHLG Fab-IL2-Fab (heavy chain cytokine fusion construct) | GAAGTGCAGCTGGTGGAGTCTGGAGGAGGCTTGGTCCAG<br>CCTGGCGGGTCCCTGCGGCTCTCCTGTGCAGCCTCCGGAT<br>TCACATTTAGCAACTATTGGATGAACTGGGTGCGGCAGGC<br>TCCTGGAAAGGGCCTCGAGTGGGTGGCCGAGATCAGATT<br>GAAATCCAATAACTTCGGAAGATATTACGCTGCAAGCGT<br>GAAGGGCCGGTTCACCATCAGCAGAGATGATTCCAAGAA<br>CACGCTGTACCTGCAGATGAACAGCCTGAAGACCGAGGA<br>TACGGCCGTGTATTACTGTACCACATACGGCAACTACGTT<br>GGGCACTACTTCGACCACTGGGGCCAAGGGACCACCGTC<br>ACCGTCTCCAGTGCTAGCACCAAGGGCCCATCGGTCTTCC<br>CCCTGGCACCCTCCTCCAAGAGCACCTCTGGGGGCACAGC<br>GGCCCTGGGCTGCCTGGTCAAGGACTACTTCCCCGAACCG | 256 |

TABLE 8-continued

| Construct | POLYNUCLEOTIDE SEQUENCE | SEQ ID NO |
|---|---|---|
| | GTGACGGTGTCGTGGAACTCAGGCGCCCTGACCAGCGGC GTGCACACCTTCCCGGCTGTCCTACAGTCCTCAGGACTCT ACTCCCTCAGCAGCGTGGTGACCGTGCCCTCCAGCAGCTT GGGCACCCAGACCTACATCTGCAACGTGAATCACAAGCC CAGCAACACCAAGGTGGATAAGAAAGTTGAGCCCAAATC TTGTGACTCCGGCGGAGGAGGGAGCGGCGGAGGTGGCTC CGGAGGTGGCGGAGCACCTACTTCAAGTTCTACAAAGAA AACACAGCTACAACTGGAGCATTTACTGCTGGATTTACAG ATGATTTTGAATGGAATTAATAATTACAAGAATCCCAAAC TCACCAGGATGCTCACATTTAAGTTTTACATGCCCAAGAA GGCCACAGAACTGAAACATCTTCAGTGTCTAGAAGAAGA ACTCAAACCTCTGGAGGAAGTGCTAAATTTAGCTCAAAG CAAAAACTTTCACTTAAGACCCAGGGACTTAATCAGCAAT ATCAACGTAATAGTTCTGGAACTAAAGGGATCTGAAACA ACATTCATGTGTGAATATGCTGATGAGACAGCAACCATTG TAGAATTTCTGAACAGATGGATTACCTTTGCCCAAAGCAT CATCTCAACACTGACTTCCGGCGGAGGAGGATCCGGCGG AGGTGGCTCTGGCGGTGGCGGAGAAGTGCAGCTGGTGGA GTCTGGAGGAGGCTTGGTCCAGCCTGGCGGGTCCCTGCG GCTCTCCTGTGCAGCCTCCGGATTCACATTTAGCAACTAT TGGATGAACTGGGTGCGGCAGGCTCCTGGAAAGGGCCTC GAGTGGGTGGCCGAGATCAGATTGAAATCCAATAACTTC GGAAGATATTACGCTGCAAGCGTGAAGGGCCGGTTCACC ATCAGCAGAGATGATTCCAAGAACACGCTGTACCTGCAG ATGAACAGCCTGAAGACCGAGGATACGGCCGTGTATTAC TGTACCACATACGGCAACTACGTTGGGCACTACTTCGACC ACTGGGGCCAAGGGACCACCGTCACCGTCTCCAGTGCTA GCACCAAGGGCCCATCGGTCTTCCCCCTGGCACCCTCCTC CAAGAGCACCTCTGGGGGCACAGCGGCCCTGGGCTGCCT GGTCAAGGACTACTTCCCCGAACCGGTGACGGTGTCGTG GAACTCAGGCGCCCTGACCAGCGGCGTGCACACCTTCCC GGCTGTCCTACAGTCCTCAGGACTCTACTCCCTCAGCAGC GTGGTGACCGTGCCCTCCAGCAGCTTGGGCACCCAGACCT ACATCTGCAACGTGAATCACAAGCCCAGCAACACCAAGG TGGATAAGAAAGTTGAGCCCAAATCTTGTGACTGA | |
| KV1 light chain | GATATCCAGTTGACCCAGTCTCCATCCTTCCTGTCTGCATCT GTGGGCGACCGGGTCACCATCACCTGCAGGGCCAGTCAGAA TGTGGATACTAACTTAGCTTGGTACCAGCAGAAGCCAGGGA AAGCACCTAAGCTCCTGATCTATTCGGCATCCTACCGTTACA CTGGCGTCCCATCAAGGTTCAGCGGCAGTGGATCCGGGACA GAGTTCACTCTCACAATCTCAAGCCTGCAACCTGAAGATTTC GCAACTTACTACTGTCAACAGTACAATAGTTACCCTCTGACG TTCGGCGGAGGTACCAAGGTGGAGATCAAGCGTACGGTGGC TGCACCATCTGTCTTCATCTTCCCGCCATCTGATGAGCAGTT GAAATCTGGAACTGCCTCTGTTGTGTGCCTGCTGAATAACTT CTATCCCAGAGAGGCCAAAGTACAGTGGAAGGTGGATAACG CCCTCCAATCGGGTAACTCCCAGGAGAGTGTCACAGAGCAG GACAGCAAGGACAGCACCTACAGCCTCAGCAGCACCCTGAC GCTGAGCAAAGCAGACTACGAGAAACACAAAGTCTACGCCT GCGAAGTCACCCATCAGGGCCTGAGCTCGCCCGTCACAAAG AGCTTCAACAGGGGAGAGTGTTAG | 264 |
| KV7 light chain | GATATCCAGTTGACCCAGTCTCCATCCTTCCTGTCTGCATCT GTGGGCGACCGGGTCACCATCACCTGCAAGGCCAGTCAGAA TGTGGATACTAACGTGGCTTGGTACCAGCAGAAGCCAGGGA AAGCACCTAAGCCTCTGATCTATTCGGCATCCTACCGGTACA CTGGCGTCCCATCAAGGTTCAGCGGCAGTGGATCCGGGACA GAGTTCACTCTCACAATCTCAAGCCTGCAACCTGAAGATTTC GCAACTTACTACTGTCAACAGTACAATAGTTACCCTCTGACG TTCGGCGGAGGTACCAAGGTGGAGATCAAGCGTACGGTGGC TGCACCATCTGTCTTCATCTTCCCGCCATCTGATGAGCAGTT GAAATCTGGAACTGCCTCTGTTGTGTGCCTGCTGAATAACTT CTATCCCAGAGAGGCCAAAGTACAGTGGAAGGTGGATAACG CCCTCCAATCGGGTAACTCCCAGGAGAGTGTCACAGAGCAG GACAGCAAGGACAGCACCTACAGCCTCAGCAGCACCCTGAC GCTGAGCAAAGCAGACTACGAGAAACACAAAGTCTACGCCT GCGAAGTCACCCATCAGGGCCTGAGCTCGCCCGTCACAAAG AGCTTCAACAGGGGAGAGTGTTAG | 266 |

Host Cells

As used herein, the term "host cell" refers to any kind of cellular system which can be engineered to generate the immunoconjugates of the invention or fragments thereof. In one embodiment, the host cell is engineered to allow the production of an immunoconjugate fragment. Host cells include cultured cells, e.g., mammalian cultured cells, such as CHO cells, HEK, BHK cells, NSO cells, Sp2/0 cells, YO myeloma cells, P3X63 mouse myeloma cells, PER cells, PER.C6 cells or hybridoma cells, yeast cells, insect cells, bacterial cells and plant cells, to name only a few, but also cells comprised within a transgenic animal, transgenic plant or cultured plant or animal tissue. In one embodiment, the host cell of the invention comprises an expression vector comprising polynucleotide sequences that encode immunoconjugates of the invention or fragments thereof. Host cells of the invention may be eukaryotic or prokaryotic.

Purification of Immunoconjugate Polypeptides and Fragments Thereof

The immunoconjugates of the invention or fragments thereof can be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity, etc., and will be apparent to those having skill in the art.

For affinity chromatography purification, a matrix with protein A or protein G may be used. Alternatively, for affinity chromatography purification, any antibody which specifically binds the single-chain effector moiety of the immunoconjugate may be used. For the production of antibodies, various host animals, including, but not limited to rabbits, mice, rats, etc., may be immunized by injection with a immunoconjugate of the invention or a fragment thereof. The immunoconjugate may be attached to a suitable carrier, such as bovine serum albumin (BSA), by means of a side chain functional group or linkers attached to a side chain functional group. Various adjuvants may be used to increase the immunological response, depending on the host species, including but not limited to, Freund's (complete and incomplete), mineral gels such as aluminum hydroxide, surface active substances such as lysolecithin, pluronic polyols, polyanions, peptides, oil emulsions, keyhold limpet hemocyanin, dinitrophenol, and potentially useful human adjuvants such as BCG (bacilli Calmette-Guerin) and *Cornyebacterium parvum*. Accordingly, one embodiment includes a method for producing the immunoconjugates of the invention by culturing a host cell comprising an expression vector comprising polynucleotide sequences that encode immunoconjugates of the invention or fragments thereof under conditions suitable for the expression of the same.

Methods of Using Immunoconjugates

The immunoconjugates of the invention are useful for targeting specific antigenic determinants and eliciting various cellular responses in target and recruited cells. The immunoconjugate of the invention is also useful as a diagnostic reagent. The binding of an immunoconjugate to an antigenic determinant can be readily detected by using a secondary antibody specific for the effector moiety. In one embodiment, the secondary antibody and the immunoconjugate facilitate the detection of binding of the immunoconjugate to an antigenic determinant located on a cell or tissue surface.

In some embodiments, an effective amount of the immunoconjugates of the invention are administered to a cell. In other embodiments, a therapeutically effective amount of the immunoconjugate of the invention is administered to an individual for the treatment of disease. The term "effective amount" as used herein is defined as the amount of the immunoconjugate of the invention that is necessary to result in a physiological change in the cell or tissue to which it is. administered. The term "therapeutically effective amount" as used herein is defined as the amount of the immunoconjugate of the invention that eliminates, decreases, delays, minimizes or prevents adverse effects of a disease.

The immunoconjugates of the invention may be administered to a subject per se or in the form of a pharmaceutical composition. In one embodiment, the disease is a proliferative disorder, such as cancer. Non-limiting examples of proliferative disorders such as cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using an immunoconjugate of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. Similarly, other cell proliferation disorders can also be treated by the immunoconjugates of the present invention. Examples of such cell proliferation disorders include, but are not limited to: hypergammaglobulinemia, lymphoproliferative disorders, paraproteinemias, purpura, sarcoidosis, Sezary Syndrome, Waldenstron's Macroglobulinemia, Gaucher's Disease, histiocytosis, and any other cell proliferation disease, besides neoplasia, located in an organ system listed above. In another embodiment, the disease is related to autoimmunity, transplantation rejection, post-traumatic immune responses and infectious diseases (e.g. HIV). More specifically, the immunoconjugates may be used in eliminating cells involved in immune cell-mediated disorders, including lymphoma; autoimmunity, transplantation rejection, graft-versus-host disease, ischemia and stroke. A skilled artisan readily recognizes that in many cases the immunoconjugates may not provide a cure but may only provide partial benefit. In some embodiments, a physiological change having some benefit is also considered therapeutically beneficial. Thus, in some embodiments, an amount of immunoconjugate that provides a physiological change is considered an "effective amount" or a "therapeutically effective amount."

The subject, patient, or individual in need of treatment is typically a mammal, more specifically a human.

Compositions, Formulations, Dosages, and Routes of Administration

Pharmaceutical compositions of the present invention comprise an effective amount of one or more immunoconjugates dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one immunoconjugate and optionally an additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards or corresponding authorities in other countires.

As used herein, "pharmaceutically acceptable carrier" includes any and all solvents, buffers, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The immunoconjugates may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostatically, intrasplenically, intrarenally, intrapleurally, intratracheally, intranasally, intravitreally, intravaginally, intrarectally, topically, intratumorally, intramuscularly, intraperitoneally, subcutaneously, subconjunctivally, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference). Parenteral administration, in particular intravenous injection, is most commonly used for administering polypeptide molecules such as the immunoconjugates of the invention.

The actual dosage amount of a composition of the present invention administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of the immunoconjugate of the invention. In other embodiments, the immunoconjugates may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The immunoconjugates may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof, and/or buffering agents to maintain physiologically acceptable pH values.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in some embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments, the immunoconjugate is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the immunoconjugates of the invention in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

Pharmaceutical compositions comprising the immunoconjugates of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

For topical administration the immunoconjugates of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, inhalation, oral or pulmonary administration.

For injection, the immunoconjugates of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents.

Alternatively, the immunoconjugates may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the immunoconjugates can be readily formulated by combining the immunoconjugates with pharmaceutically acceptable carriers well known in the art. Such carriers enable the immunoconjugates of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the immunoconjugates may take the form of tablets, lozenges, etc. formulated in conventional manner.

For administration by inhalation, the immunoconjugates for use according to the invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the immunoconjugate and a suitable powder base such as lactose or starch.

The immunoconjugates may also be formulated in rectal or vaginal compositions such as suppositories or retention enemas, e.g., containing conventional suppository bases such as cocoa butter or other glycerides.

In addition to the formulations described previously, the immunoconjugates may also be formulated as a depot preparation. Such long acting formulations may be administered by implantation (for example subcutaneously or intramuscularly) or by intramuscular injection. Thus, for example, the immunoconjugates may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver immunoconjugates of the invention. Certain organic solvents such as dimethylsulfoxide also may be employed, although usually at the cost of greater toxicity. Additionally, the immunoconjugates may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the immunoconjugates for a few weeks up to over 100 days. Depending on the chemical nature and the biological stability of the immunoconjugates, additional strategies for immunoconjugates stabilization may be employed.

As the immunoconjugates of the invention may contain charged side chains or termini, they may be included in any of the above-described formulations as the free acids or bases or as pharmaceutically acceptable salts. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms.

The immunoconjugates of the invention will generally be used in an amount effective to achieve the intended purpose. For use to treat or prevent a disease condition, the immunoconjugates of the invention, or pharmaceutical compositions thereof, are administered or applied in a therapeutically effective amount. A therapeutically effective amount is an amount effective to ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the immunoconjugates which are sufficient to maintain therapeutic effect. Usual patient dosages for administration by injection range from about 0.1 to 50 mg/kg/day, typically from about 0.5 to 1 mg/kg/day. Therapeutically effective serum levels may be achieved by administering multiple doses each day.

In cases of local administration or selective uptake, the effective local concentration of the immunoconjugates may not be related to plasma concentration. One having skill in the art will be able to optimize therapeutically effective local dosages without undue experimentation.

The amount of immunoconjugate administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs. In the case of autoimmune disorders, the drugs that may be used in combination with immunoconjugates of the invention include, but are not limited to, steroid and non-steroid anti-inflammatory agents.

Toxicity

A therapeutically effective dose of the immunoconjugates described herein will generally provide therapeutic benefit without causing substantial toxicity. Toxicity of the immunoconjugates can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In one embodiment, the immunoconjugate exhibits a high therapeutic index. The data obtained from these cell culture assays and animal studies can be used in formulating a dosage range that is not toxic, for example, for use in human. The dosage of the immunoconjugates described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1, p. 1) (incorporated herein by reference in its entirety.

Other Agents and Treatments

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1β, MCP-1, RANTES, and other chemokines. It is further contemplated that the upregulation of cell surface receptors or their ligands such as Fas/Fas ligand, DR4 or DR5/TRAIL would potentiate the apoptotic inducing abililties of the present invention by establishment of an autocrine or paracrine effect on hyperproliferative cells. Increases in intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody C225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

The immunonconjugates of the invention may also be administred in conjunction with chemotherapy, radiation therapy or other immunotherapies. Anti-cancer agents for such combination therapy may, e.g., be selected from the groups of microtubule disruptors (e.g. vinca alkaloids such as vinblastine or vincristine, taxanes such as docetaxel or paclitaxel, epothilones such as ixabepilone), antimetabolites (e.g. anti-folates such as methotrexate or aminopterin, anti-purines such as fludarabine, 6-mercaptopurine or 6-thioguanine, anti-pyrimidines such as 5-fluorouracil, capecitabine or gemcitabine, hydroxyurea), topoisomerase inhibitors (e.g. camptothecin, irinotecan, topotecan, or podophyllotoxins such as etoposide), DNA intercalators (e.g. doxorubicin, daunorubicin, actinomycin, bleomycin), alkylating agents (e.g. cyclophosphamide, chlorambucil, nitrosureas such as carmustine or nimustine, streptozocin, busulfan, cisplatin, oxaliplatin, triethylenemelamine, dacarbazine), hormonal therapies (e.g. glucocorticoids, aromatase inhibitors such as tamoxifene, antiandrogens such as flutamide, gonadotropin-releasing hormone (GnRH) analogs such as leuprolide), antibiotics, kinase inhibitors (e.g. erlotinib, gefitinib, imatinib), receptor antagonists (e.g. antibodies targeting cell surface receptors known to promote carcinogenesis and tumor growth), enzyme inhibitors (e.g. cyclin-dependent kinase (CDK) inhibitors), amino acid-depleting enzymes (e.g. asparaginase), leucovorin, retinoids, activators of tumor cell apoptosis, and antiangiogenic agents.

Examples

Example 1

Figure 12:
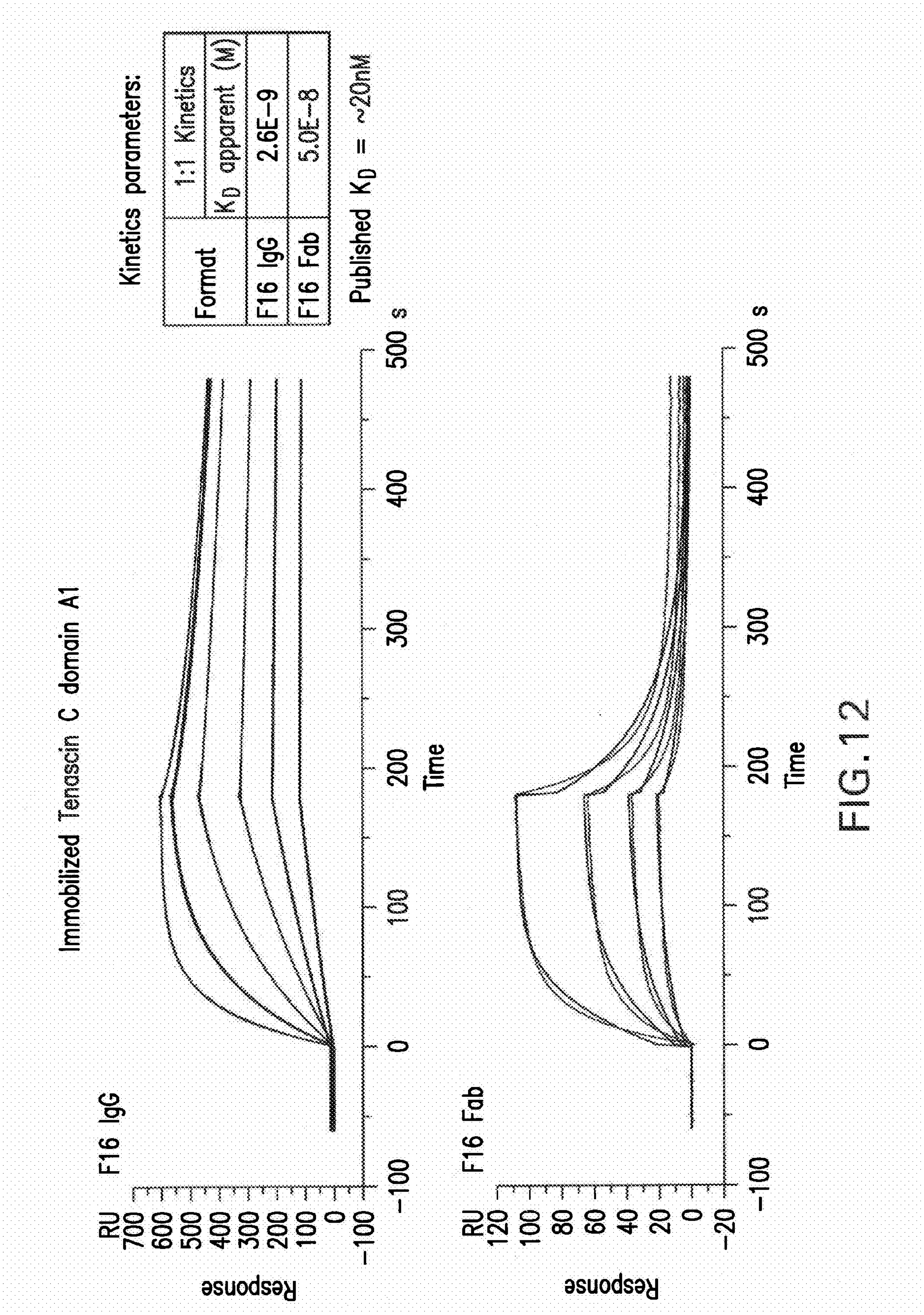

When antibody-mediated delivery of cytokines was first performed by Harvill E. T., and Morrison S. L. *Immunotech.* 1(2):95-105 (1995), the constructs had two antigen binding moieties for tumor antigen targeting and two cytokine moieties for inducing lymphocyte activation (an IL-2 molecule is fused to each of the heavy chain C-termini of IgG3). The affinity of the cytokine is generally high towards its receptor. A molecule carrying two cytokine units could have an even higher affinity towards cytokine receptors because of avidity (or multivalency) effects. Such a molecule could therefore easily activate lymphocytes in the blood stream, even before the targeting to the tumor takes place. This effect would not be desired for the patient. In contrast, an immunoconjugate molecule carrying only one cytokine moiety and two or more targeting domains would be less likely to activate lymphocytes in the circulation and could direct the entire immunoconjugate molecule to the tumor, where lymphocyte activation can take place at a lower speed. Therefore, molecules as depicted in FIGS. 1 and 2, were constructed with interleukin-2 (IL-2) as a model cytokine. All of the generated molecules are bivalent for the tumor antigen, and are either bivalent or monovalent for the IL-2 cytokine as indicated in the drawings. Affinities towards the antigen were compared for two different immunoconjugate formats using the L19 antibody as an example. As a reference, this antibody was cloned into the human IgG1 format, the diabody format (FIG. 1A), and the Fab-IL2-Fab fusion (FIG. 1B). One variable was tested within the diabody format such that the linker peptide between the $V_H$ and the $V_L$ was either eight or twelve amino acids in length. The purified antigen Extra Domain B of fibronectin (EDB) was immobilized on a BIACORE chip, and the antibody fusion construct was used as the soluble analyte for affinity determination. FIGS. 8 to 11 show the results of this experiment. The IgG was considered to be the ideal case of a bivalent binding event. Here, an affinity constant of 260 pM was observed. The Fab-IL2-Fab fusion construct gave an affinity of 310 μM, which is essentially identical to the IgG. The two variants of the diabody (shown in FIGS. 10 and 11) had measured affinities of 270 pM and 360 pM, respectively. Therefore, all of these constructs have similar affinities towards the antigen. The affinity towards the antigen and the IL-2 receptor was addressed using similar constructs based on the F16 antibody sequence (Brack, S. S. et al., *Clin. Canc. Res.* 12(10):3200-3208 (2006)). FIG. 12 shows the BIACORE sensograms of the F16 IgG and its corresponding monovalent Fab fragment, when the TNC-A1 domain was immobilized on the BIACORE chip. Under these particular experimental conditions, the IgG molecule showed an affinity constant of 2.6 nM, and the Fab molecules showed an affinity constant of 50 nM. Here, the increase of affinity attributed to bivalency is a factor of 20. The diabody, the Fab-IL2-Fab and the scFv-IL2-scFv immunoconjugates showed affinities toward the antigen of 5 nM, 4.8 nM, and 12 nM, respectively. All of these constructs therefore have affinities toward the antigen that more closely resemble the bivalent character of an IgG molecule than the monovalent behavior of the Fab fragment.

Figure 13:
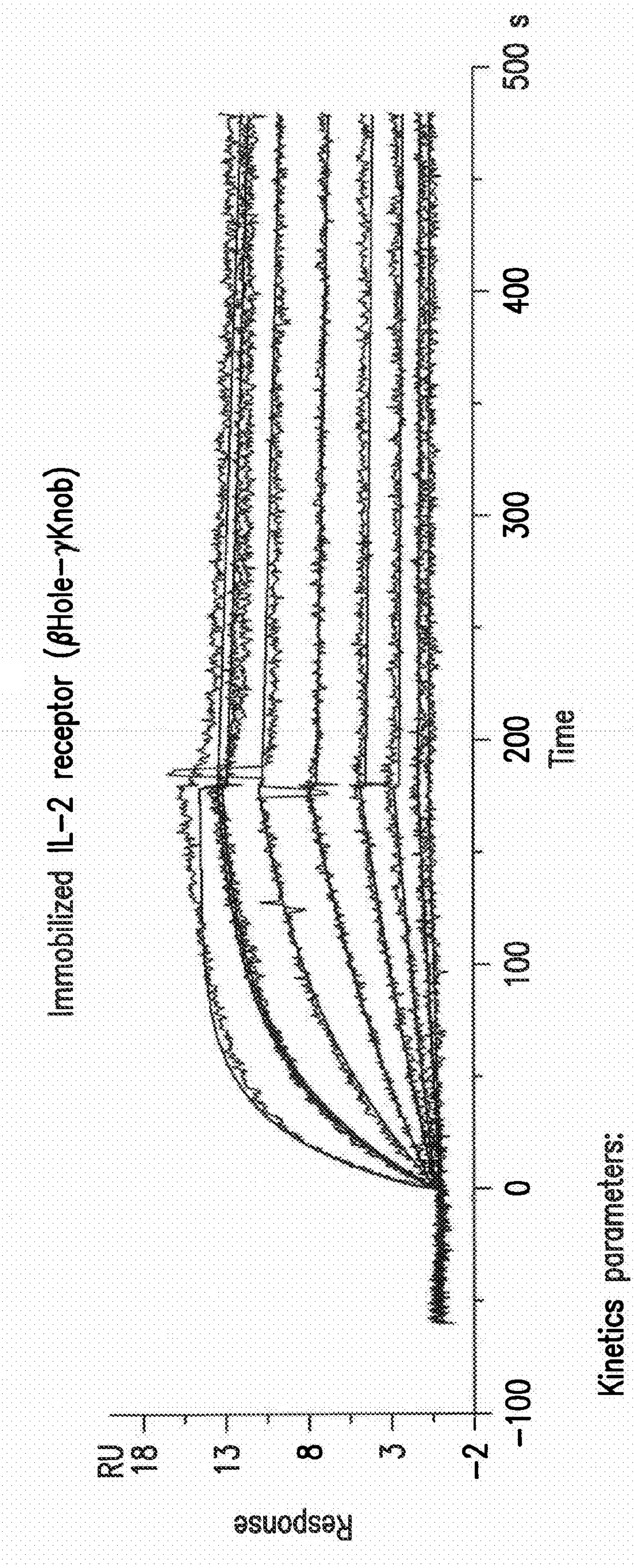
Figure 14:
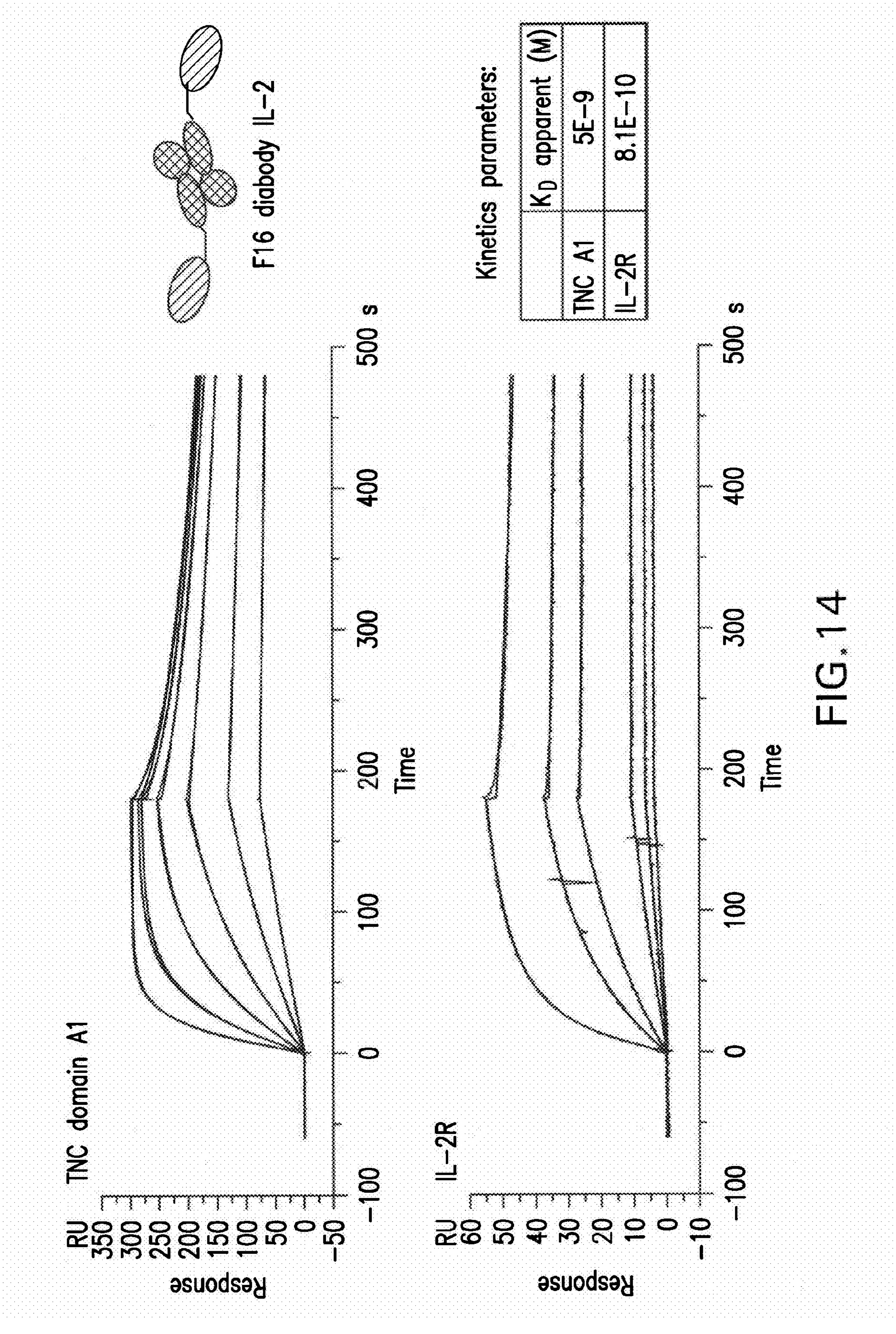
Figure 15:
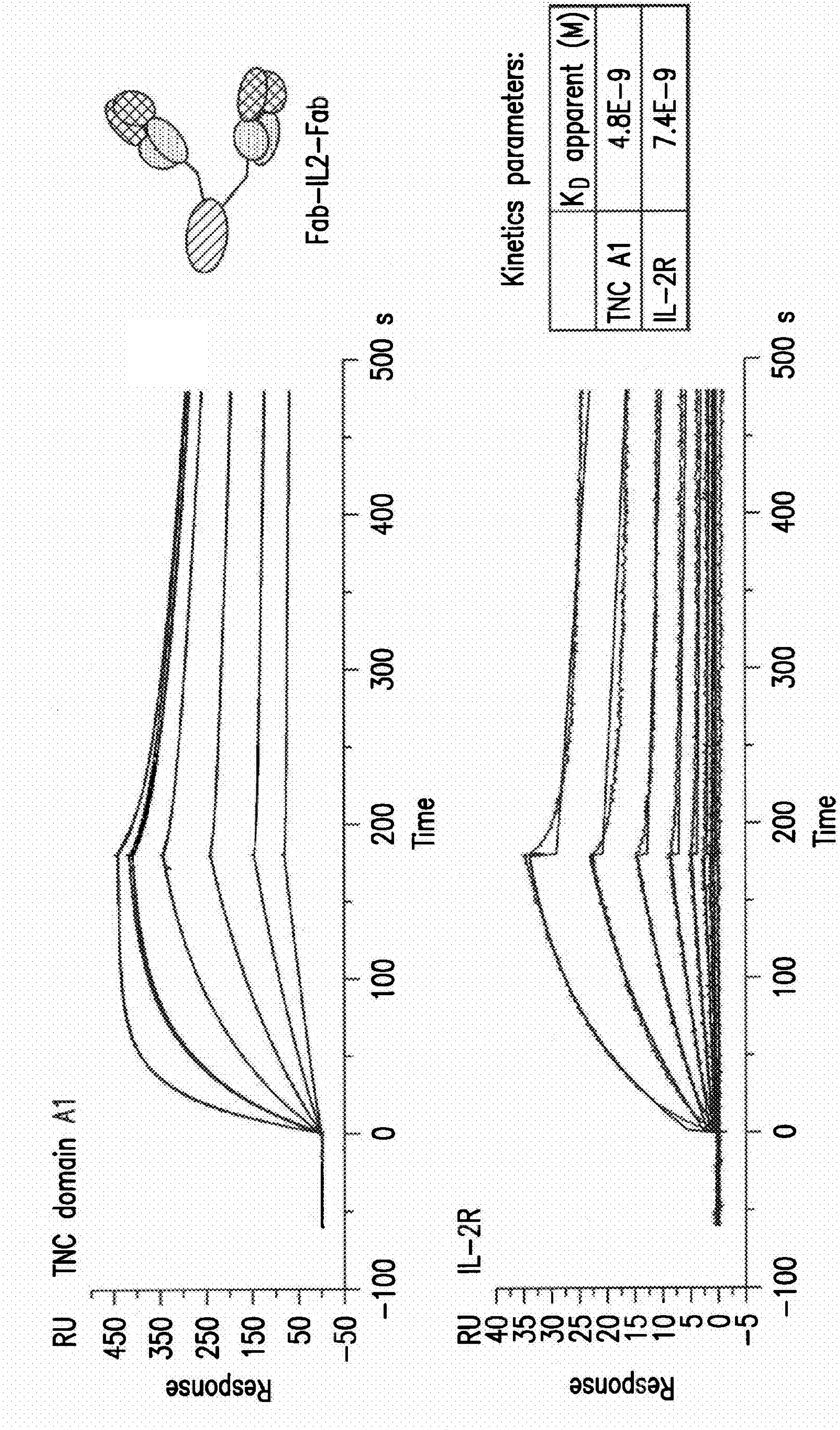
Figure 16:
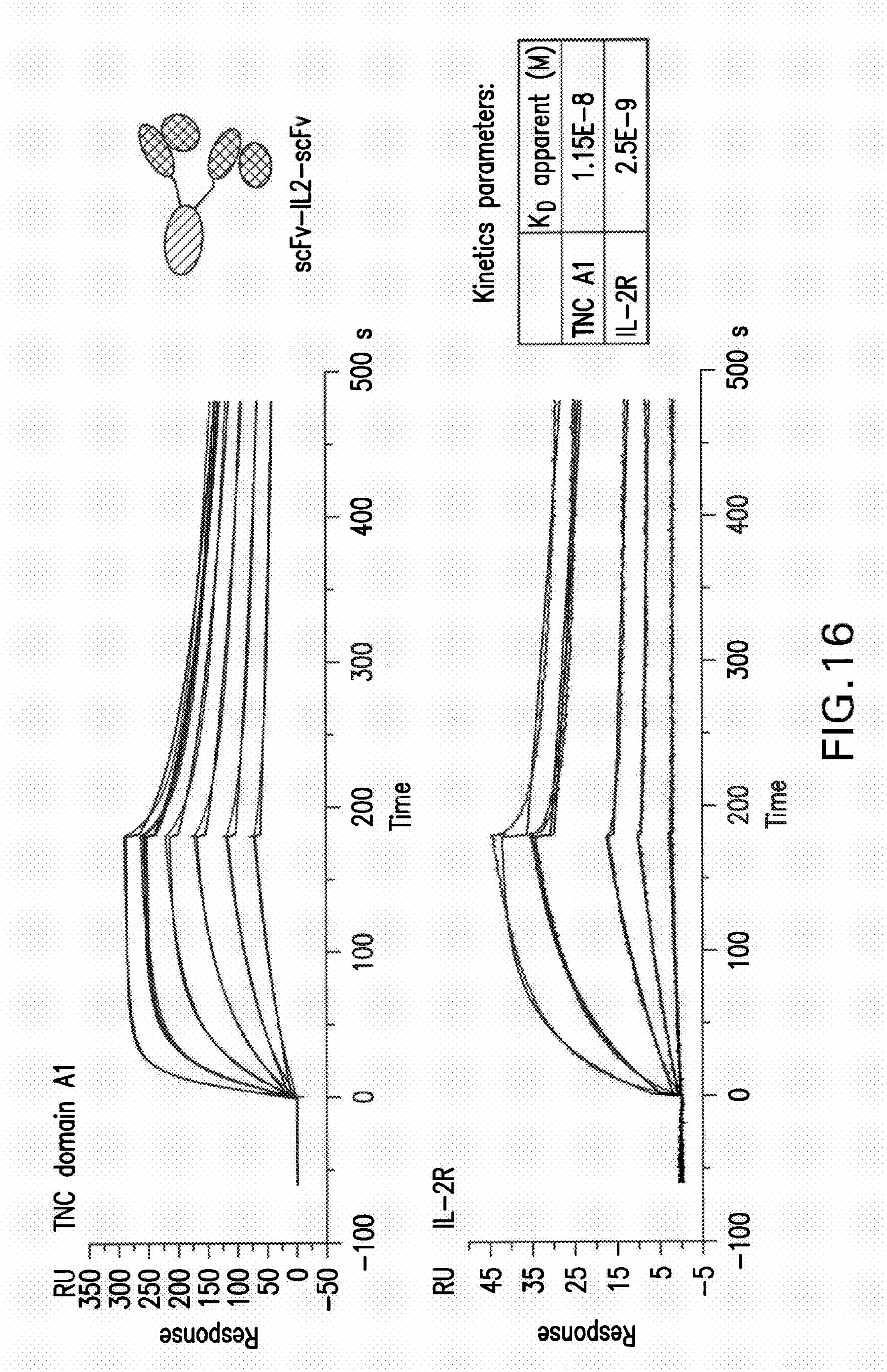
Figure 18:
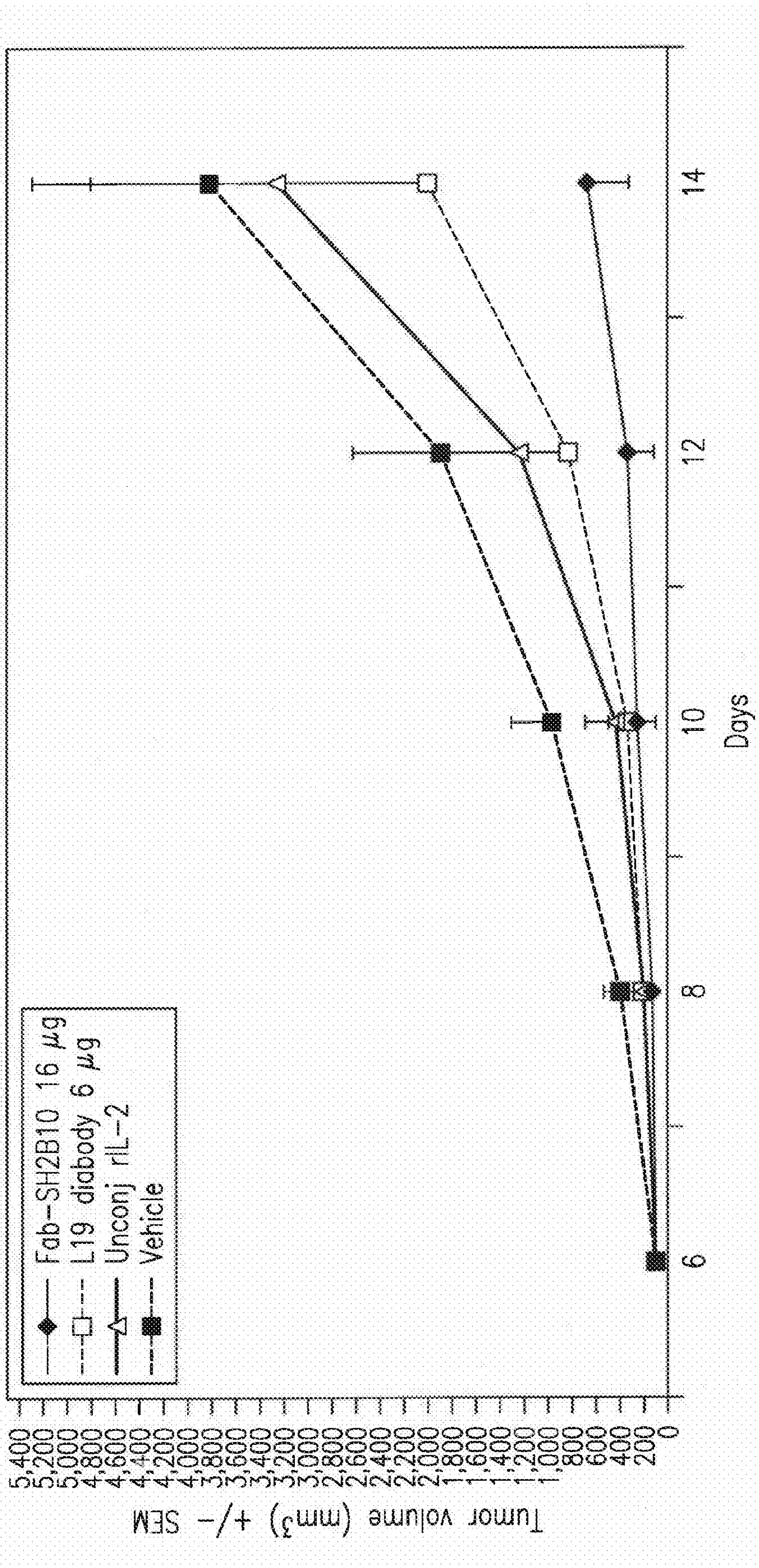
Figure 19:
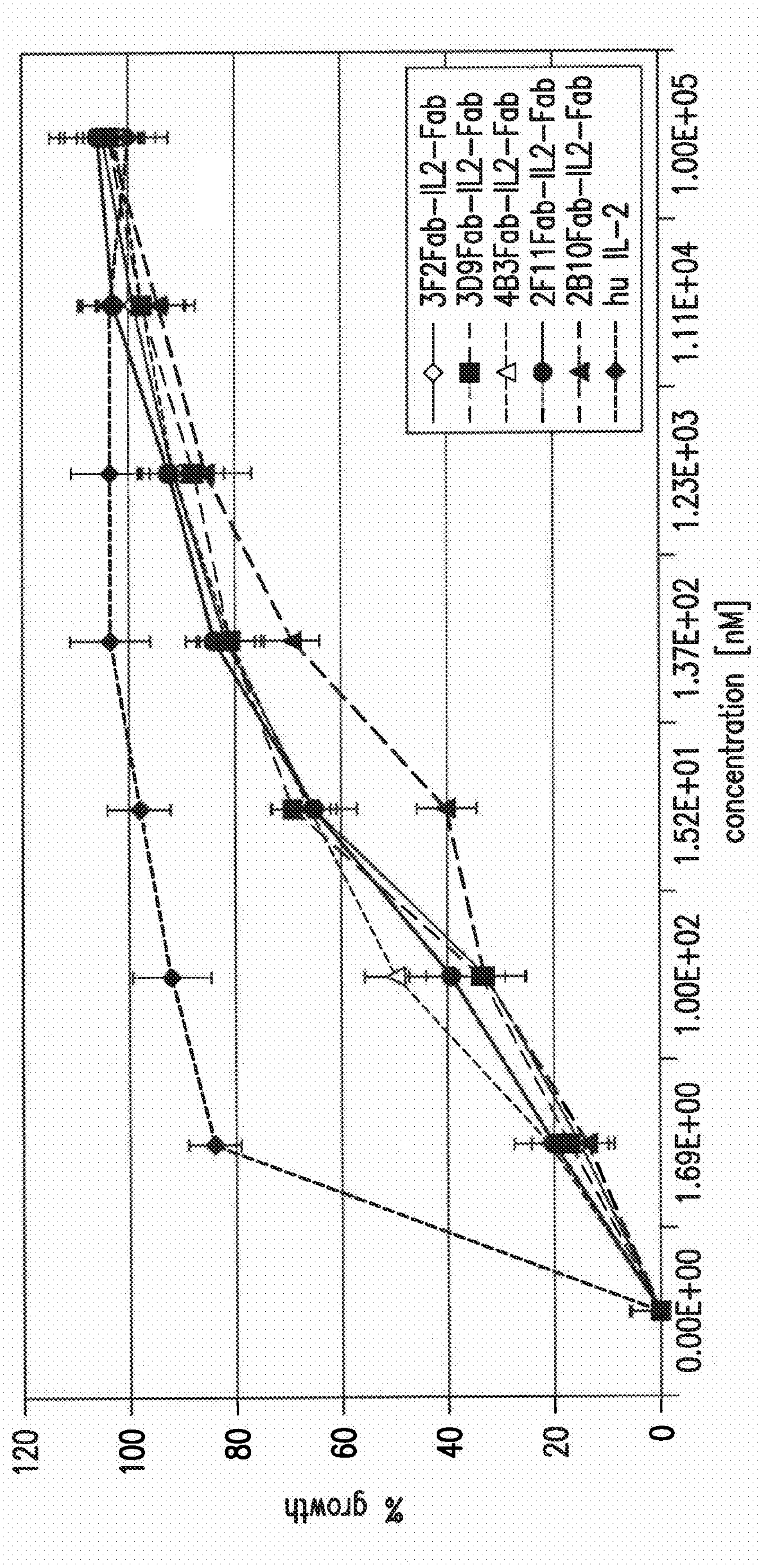
Figure 20A:
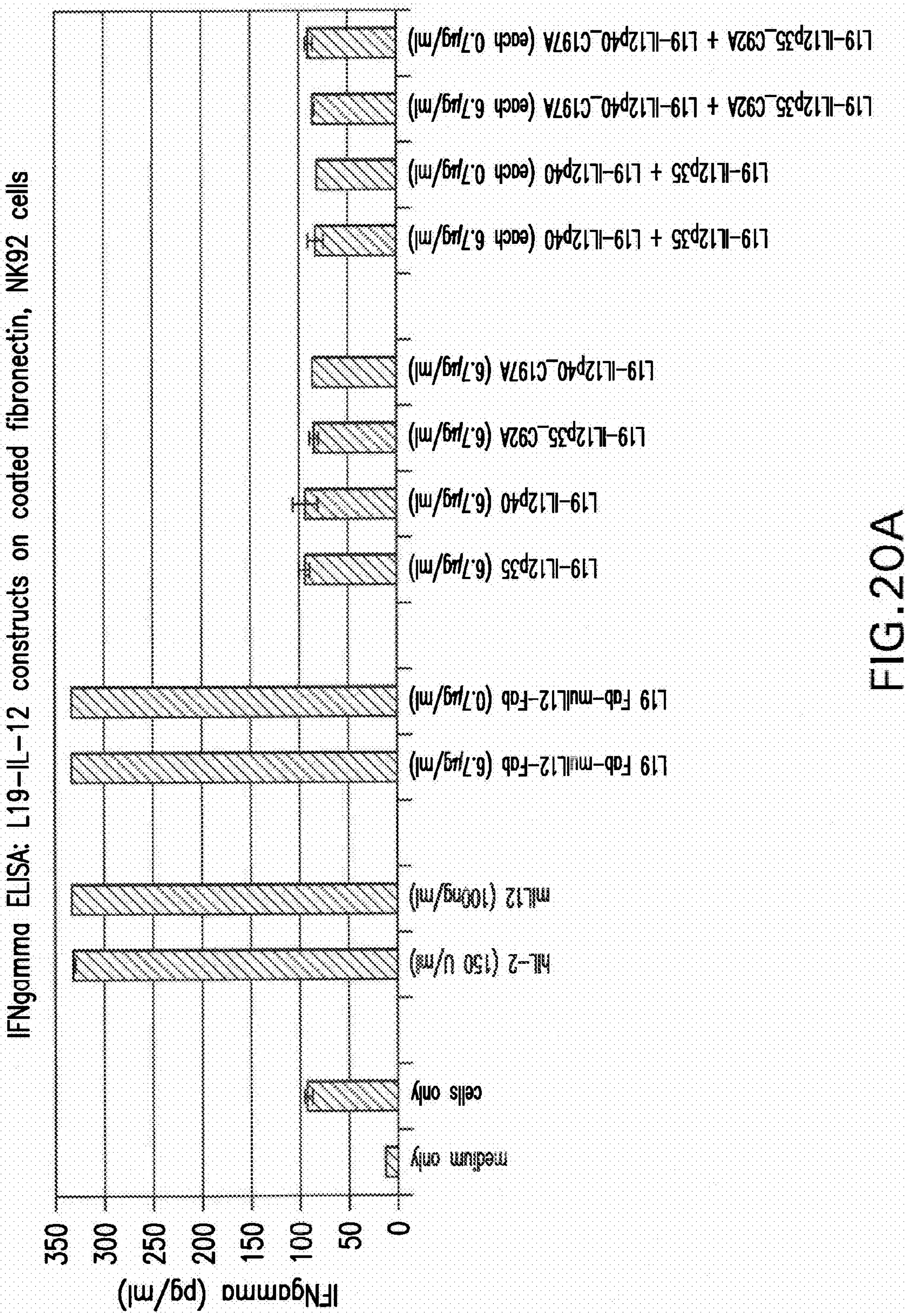
Figure 20B:
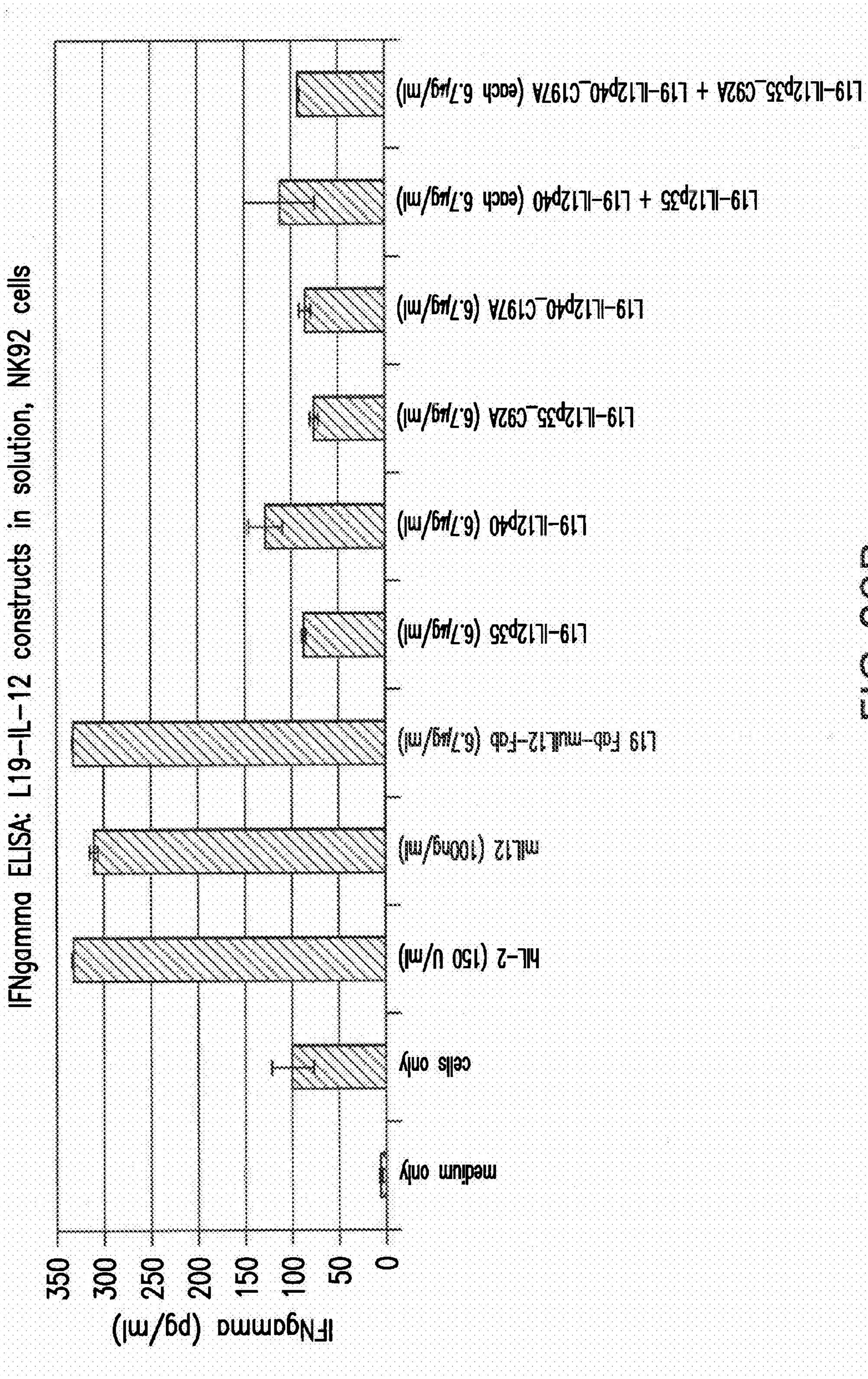
Figure 21A:
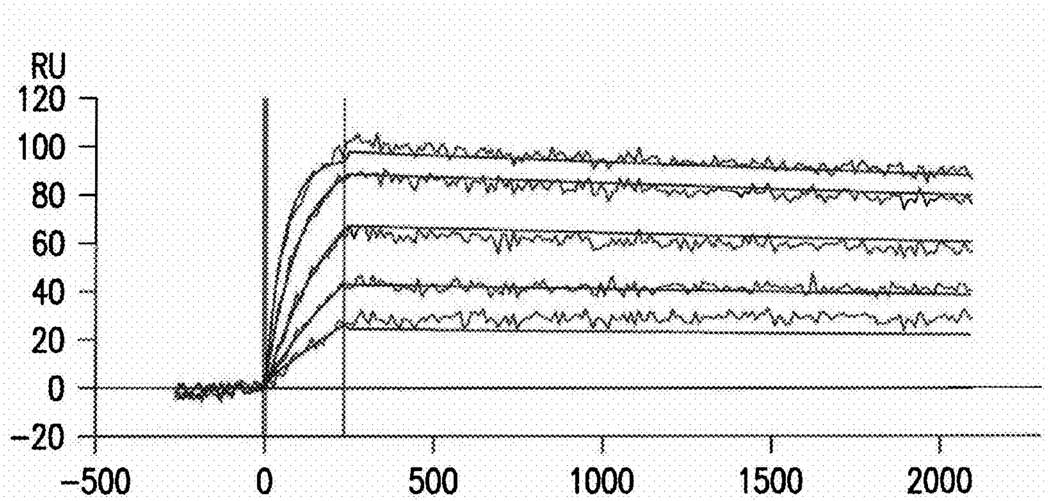
Figure 21B:
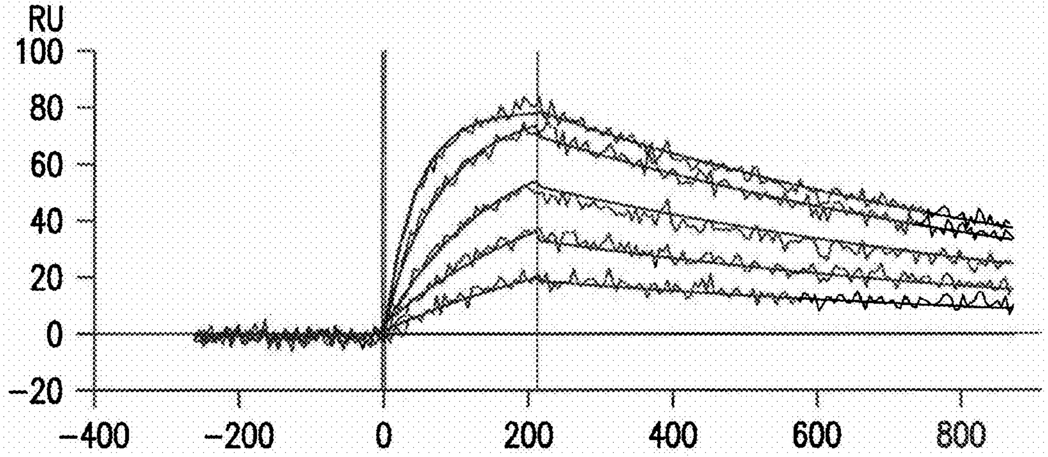
Figure 21C:
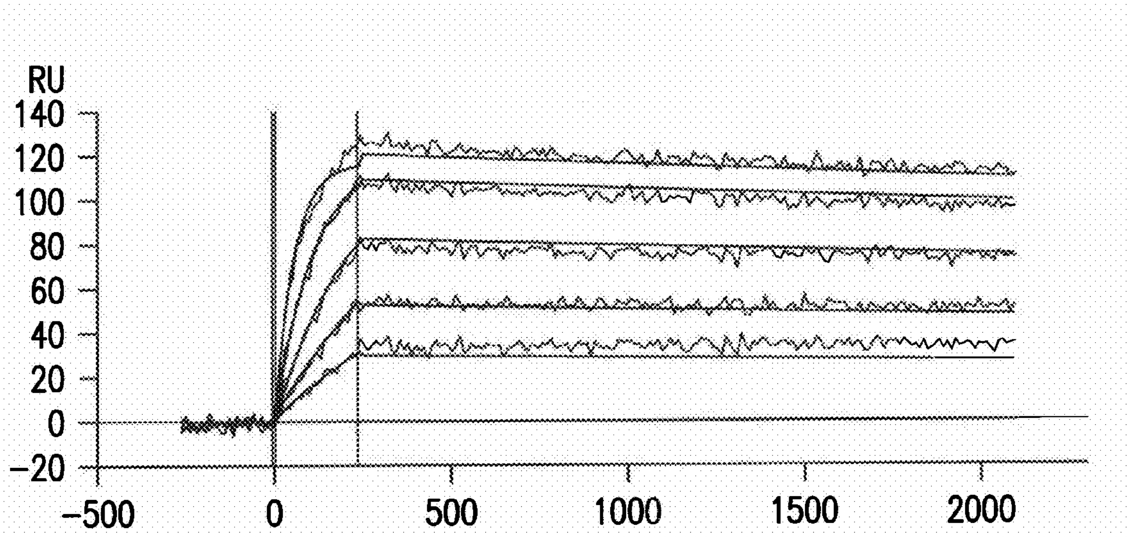
Figure 21D:
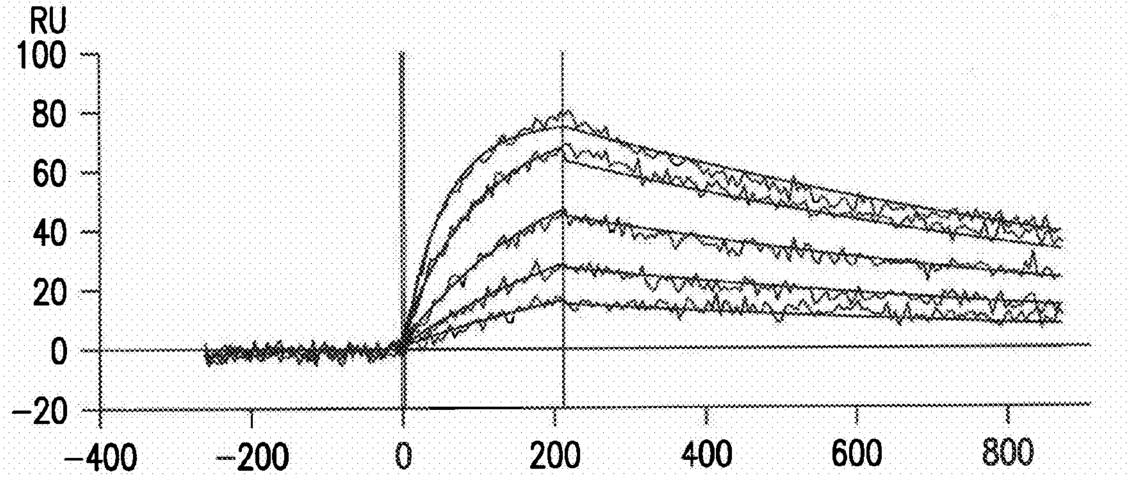
Figure 21E:
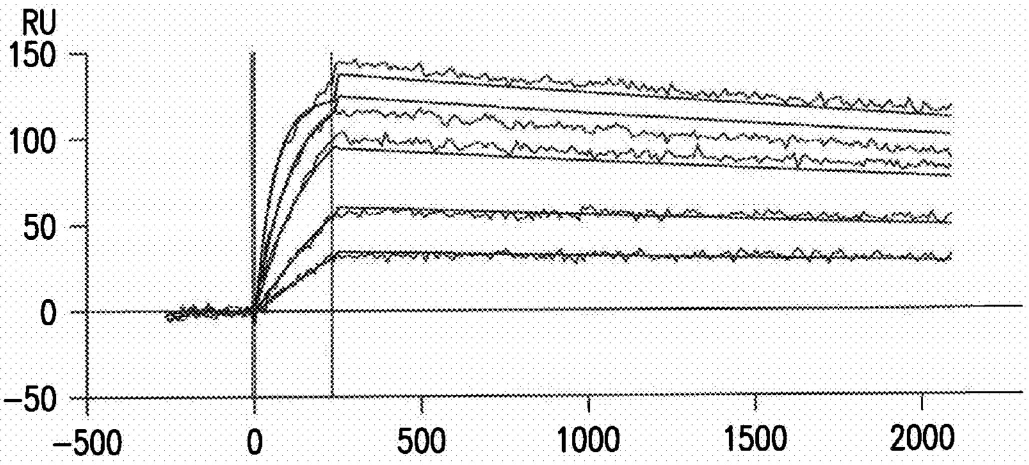
Figure 21F:
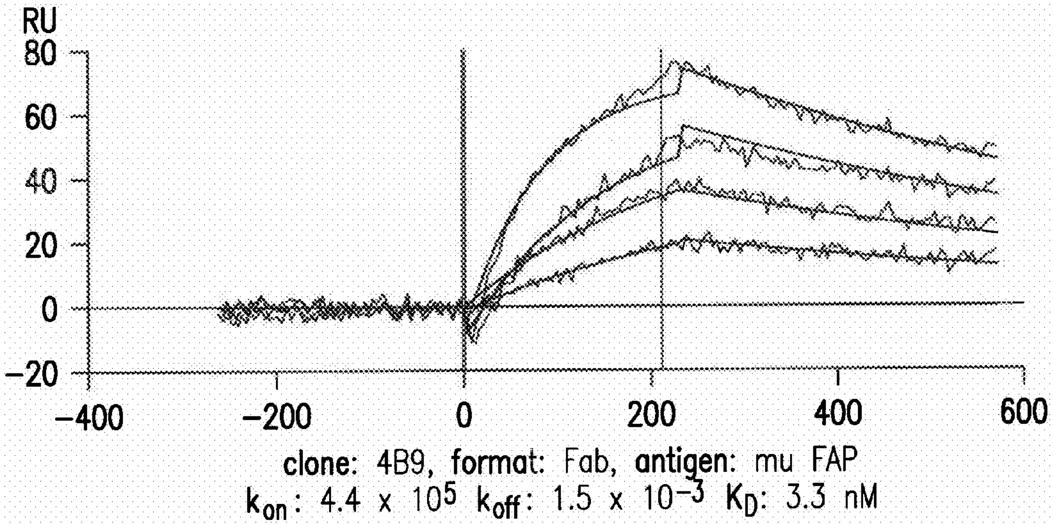
Figure 22A:
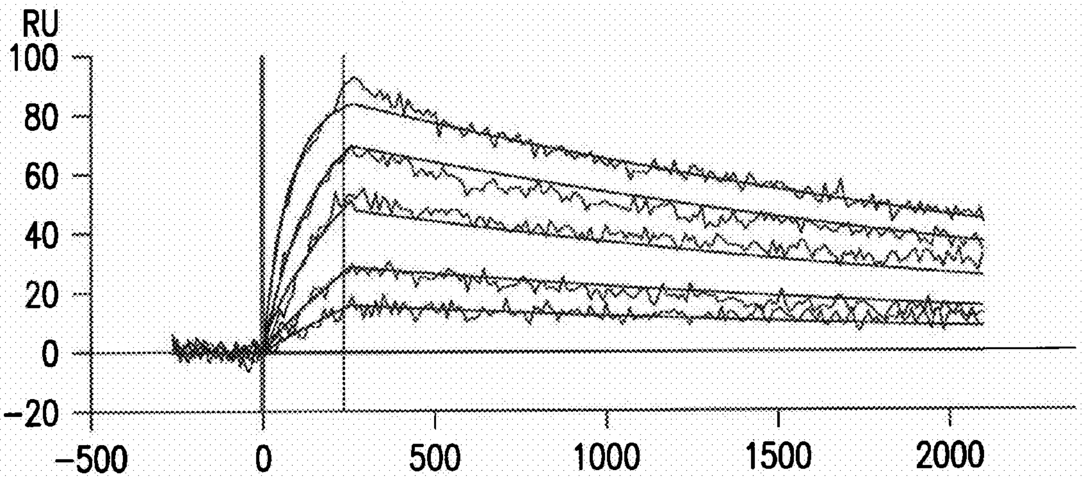
Figure 22B:
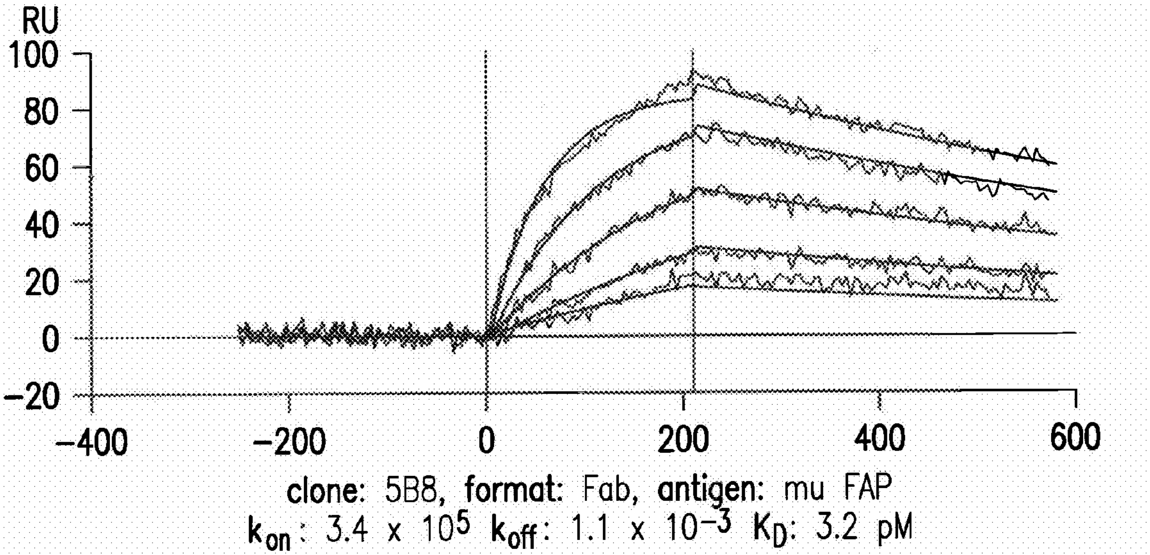
Figure 22C:
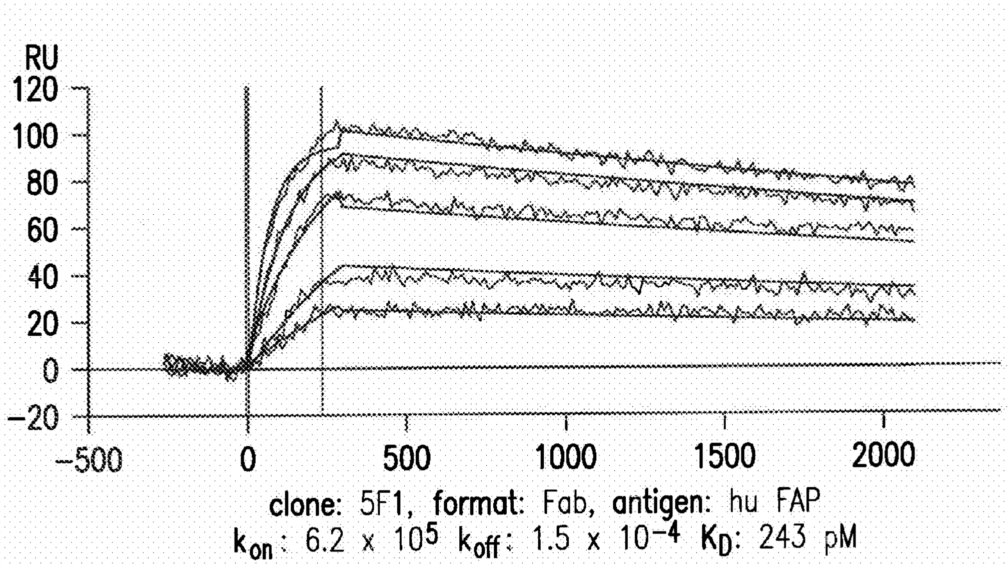
Figure 22D:
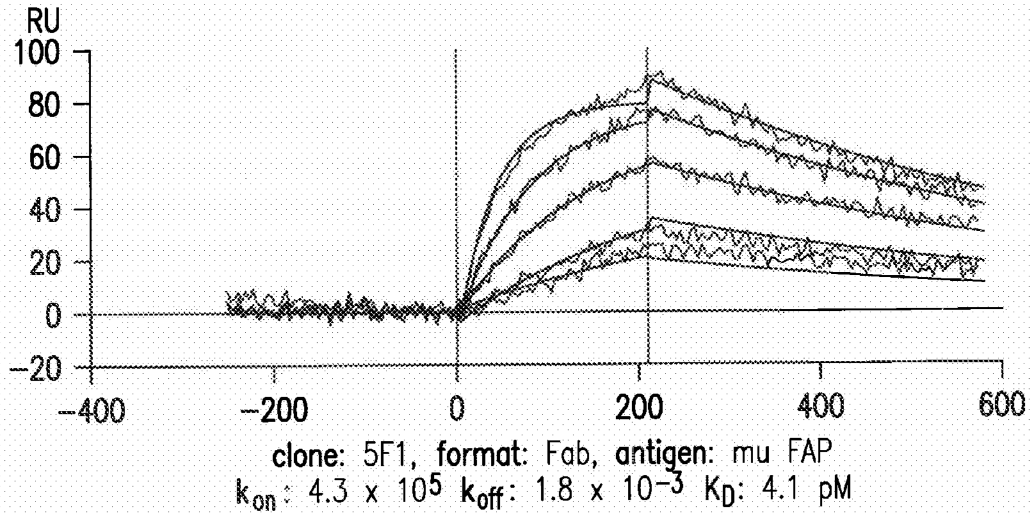
Figure 22E:
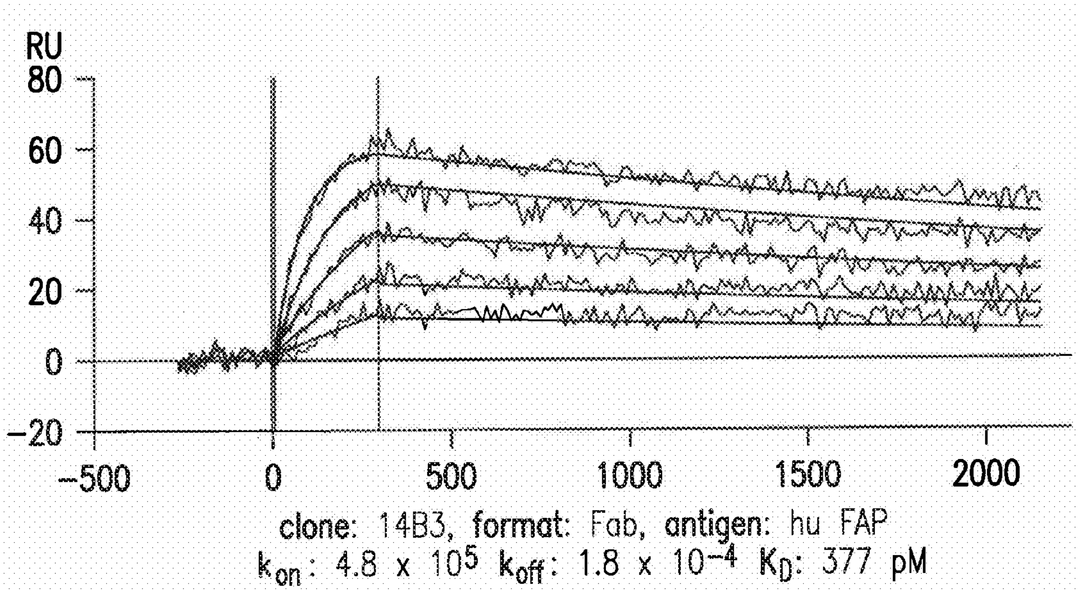
Figure 22F:
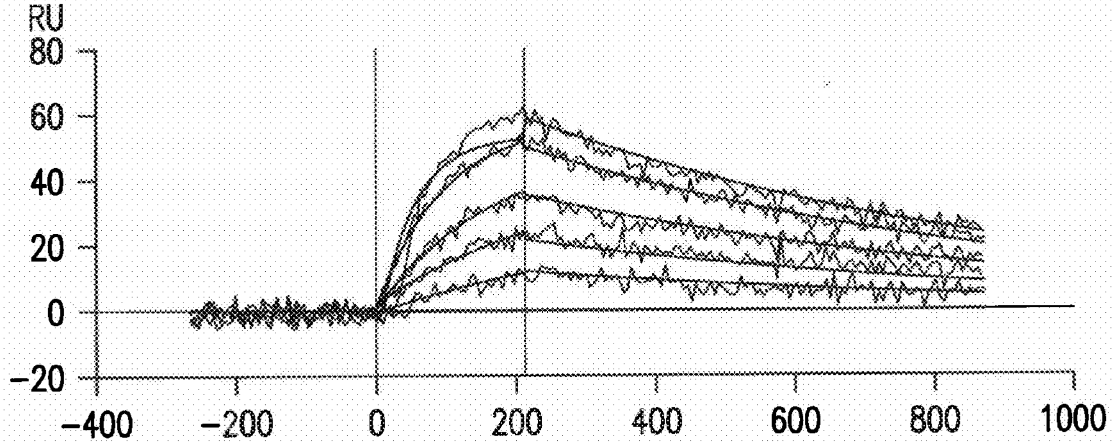
Figure 23A:
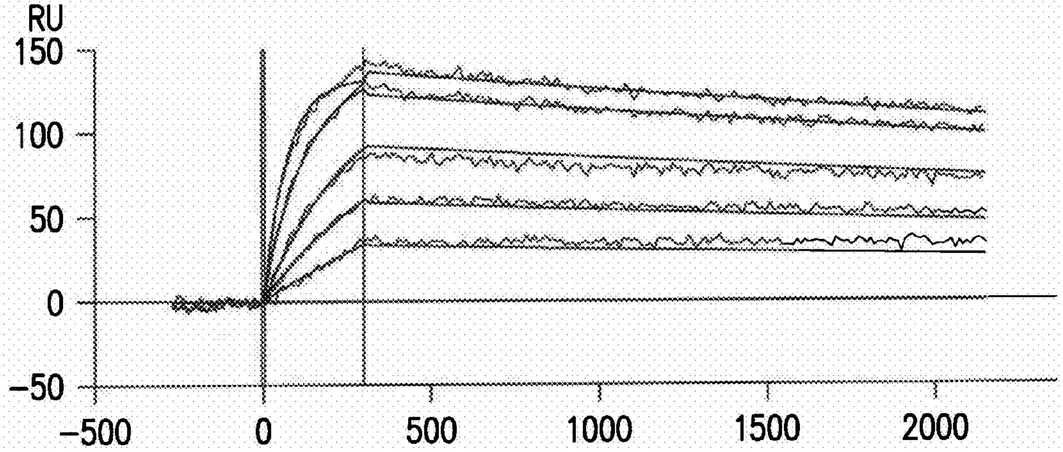
Figure 23B:
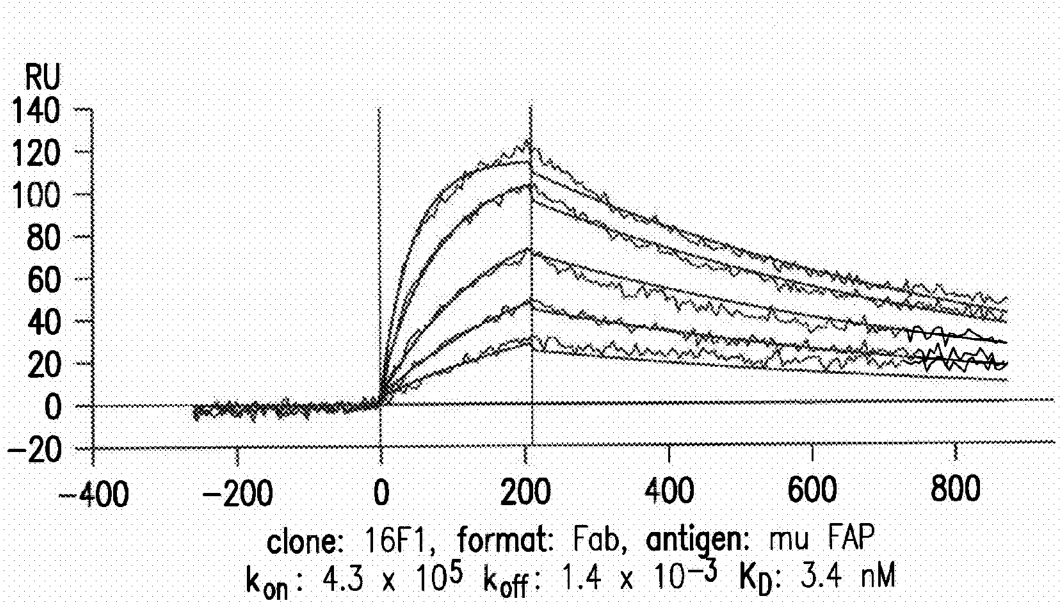
Figure 23C:
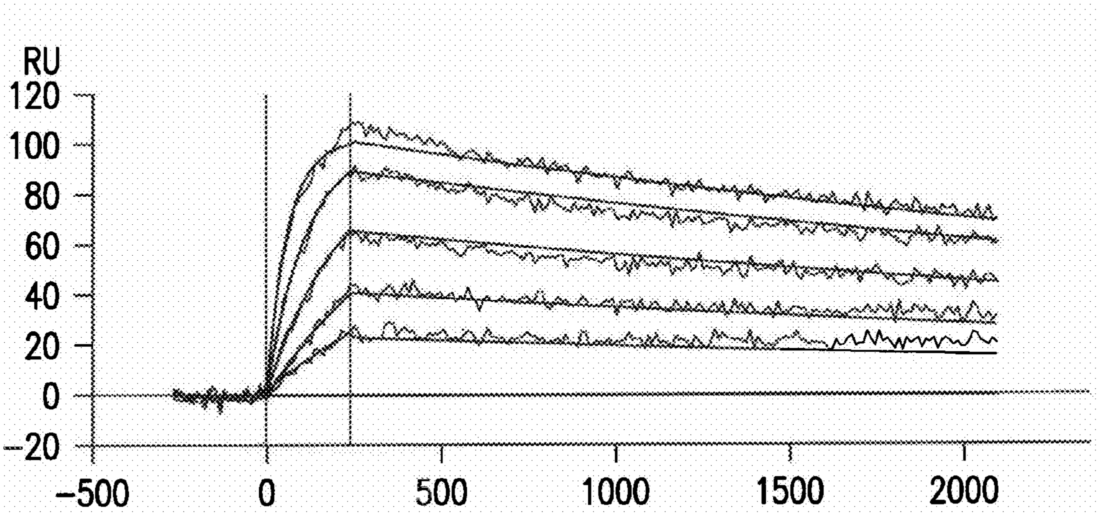
Figure 23D:
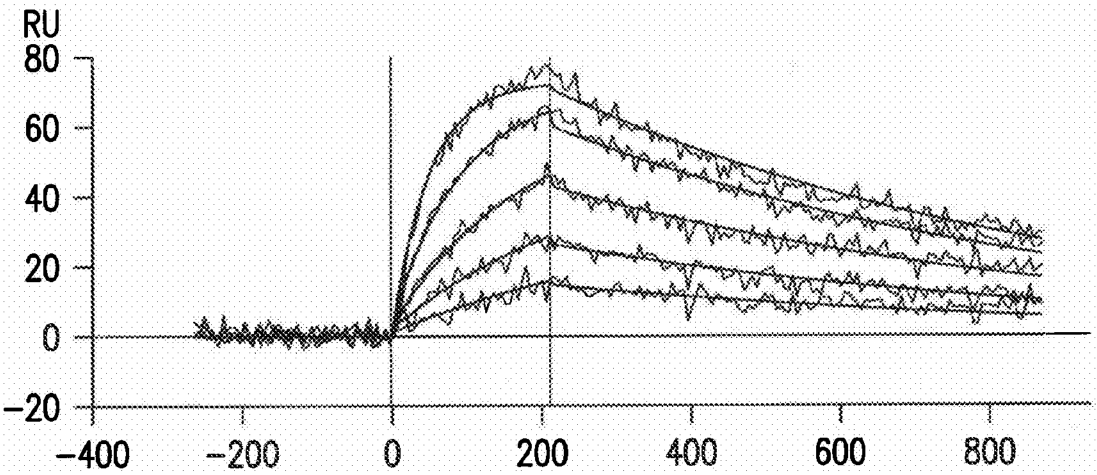
Figure 23E:
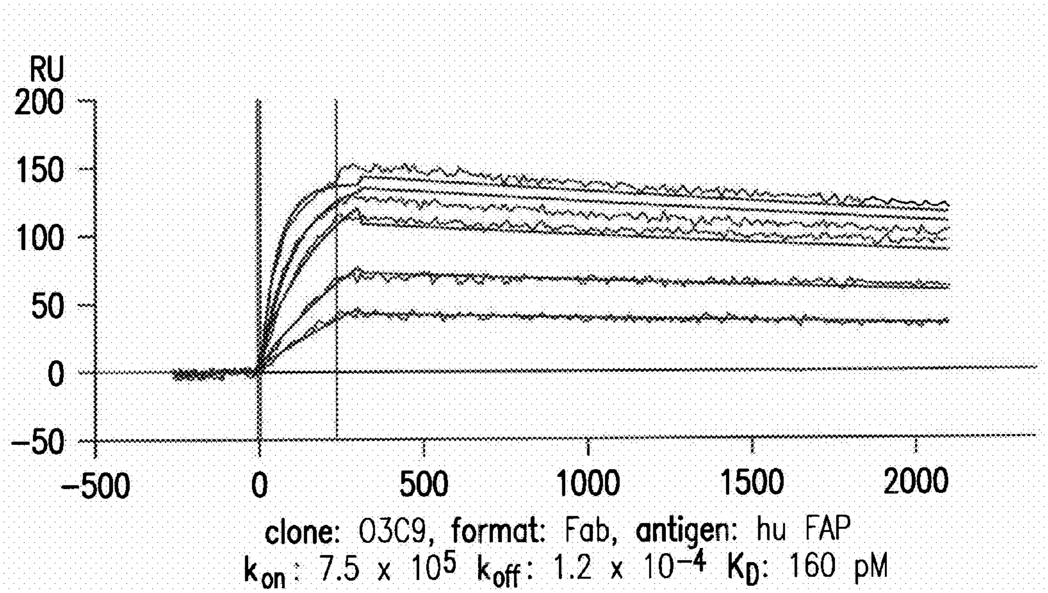
Figure 23F:
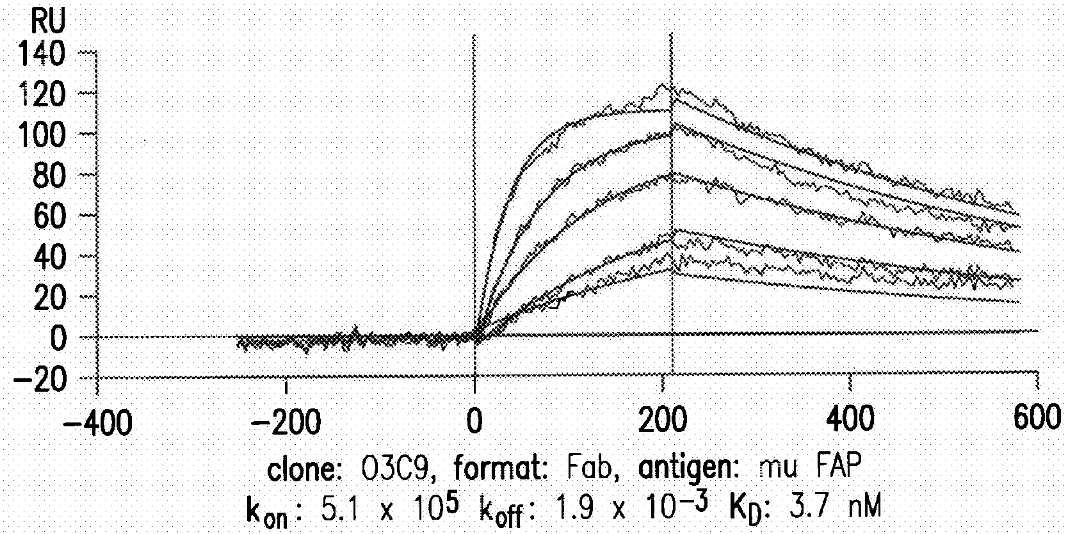
Figure 24A:
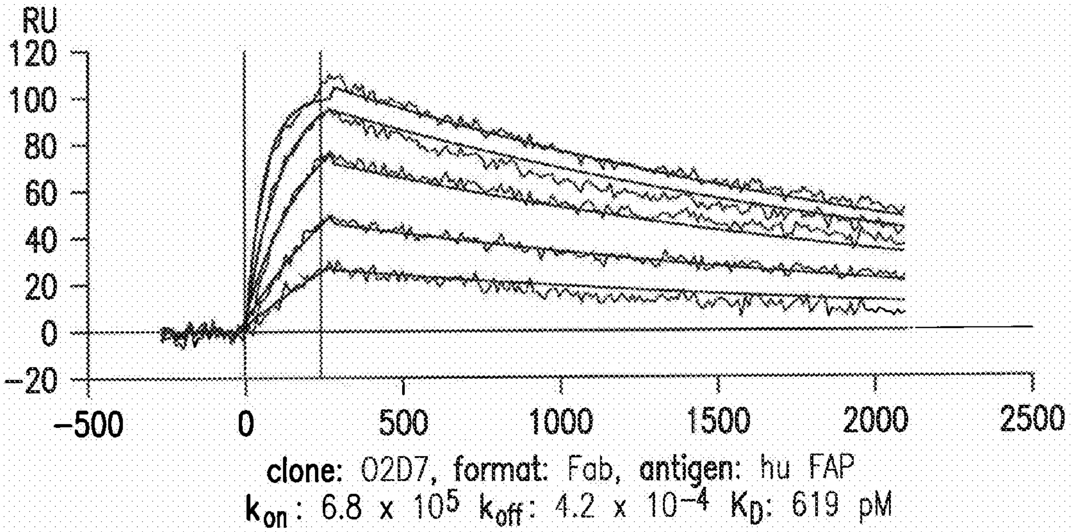
Figure 24B:
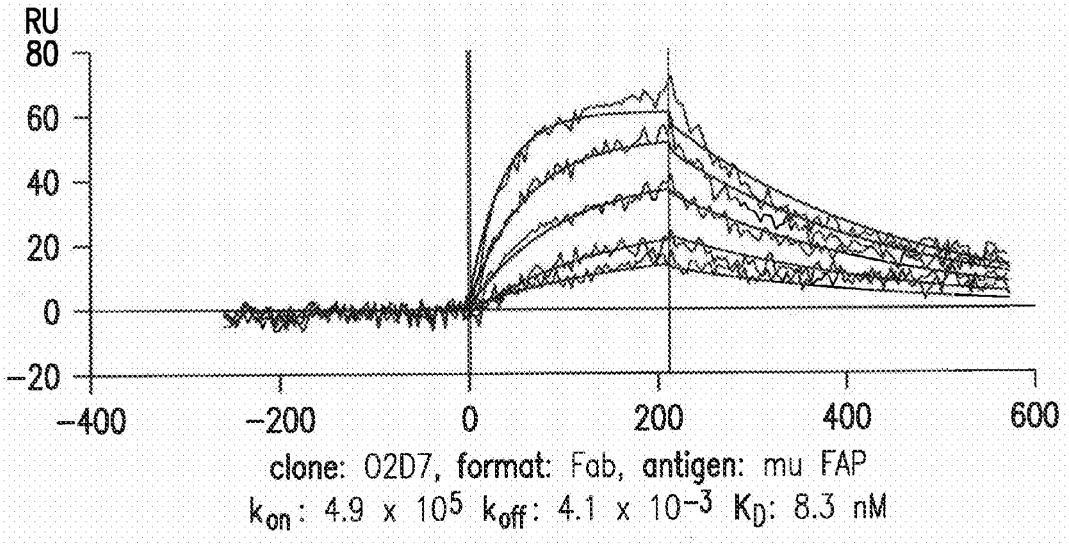
Figure 24C:
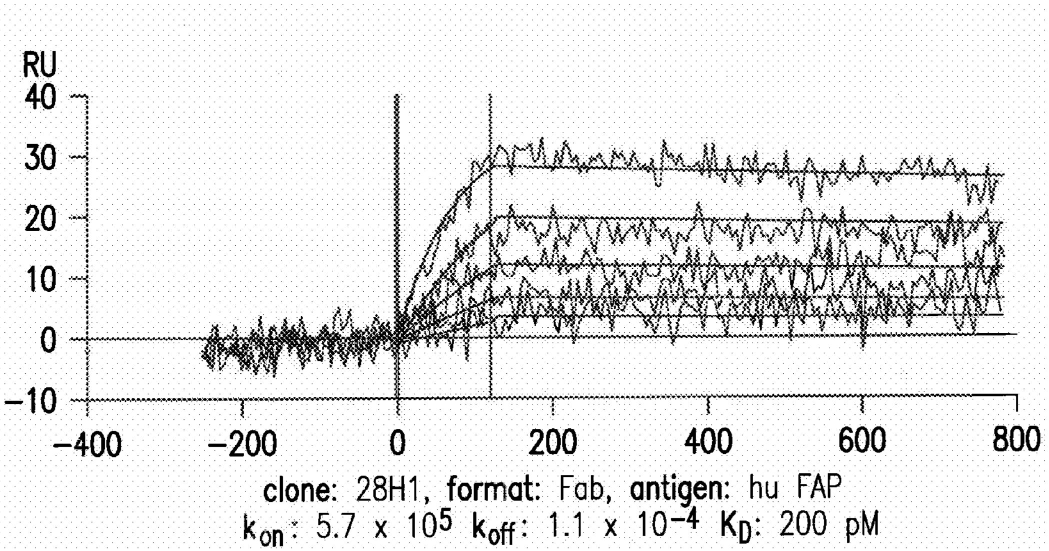
Figure 24D:
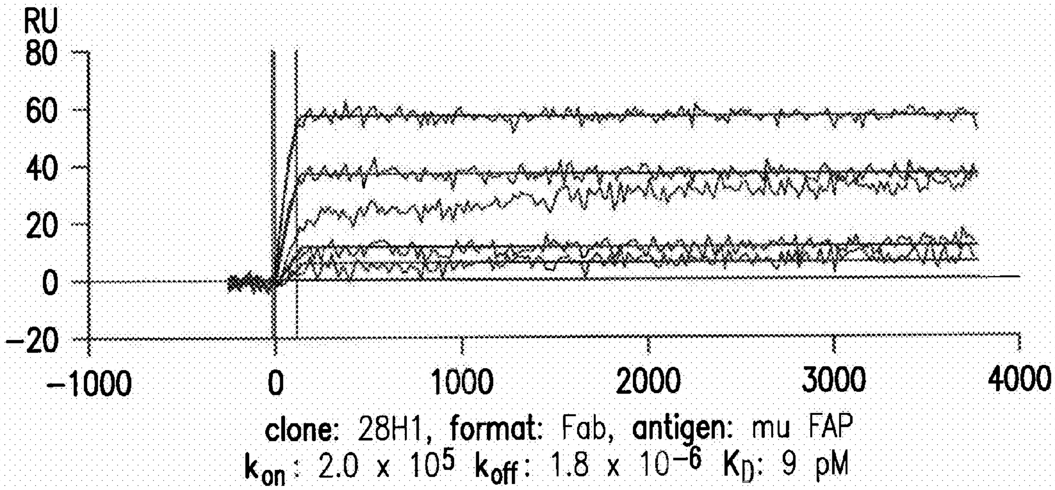
Figure 24E:
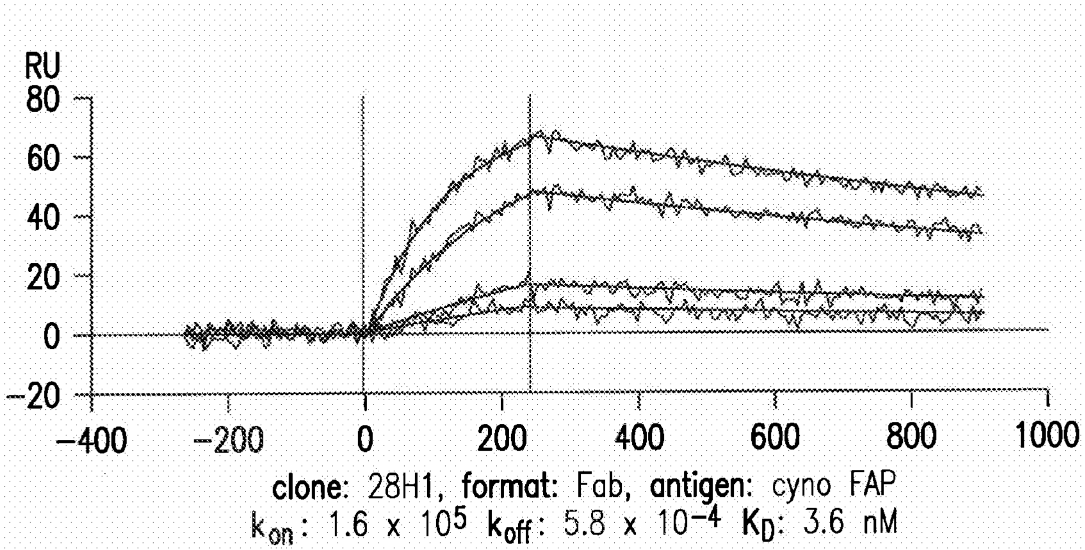
Figure 24F:
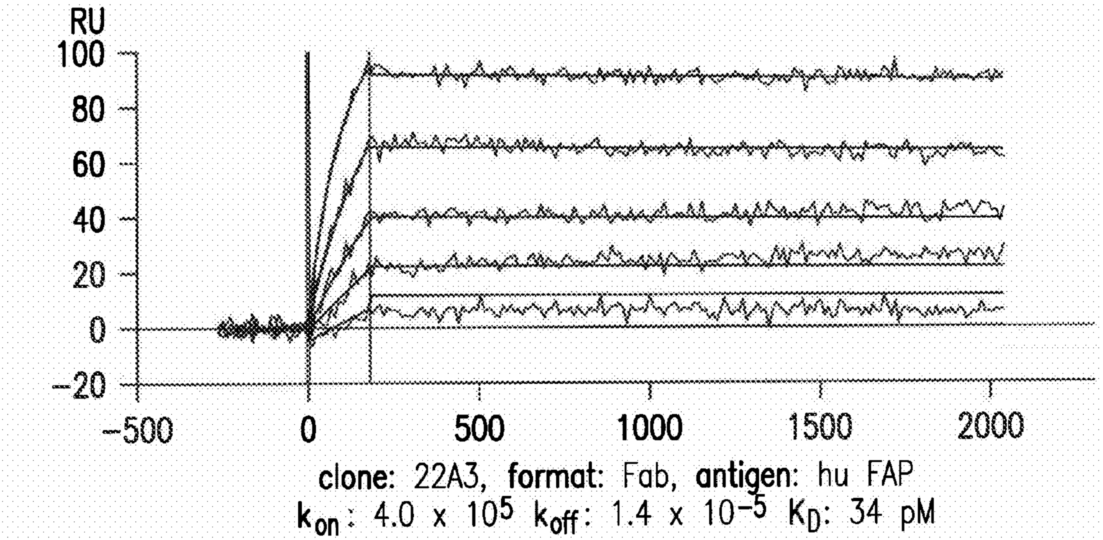
Figure 24G:
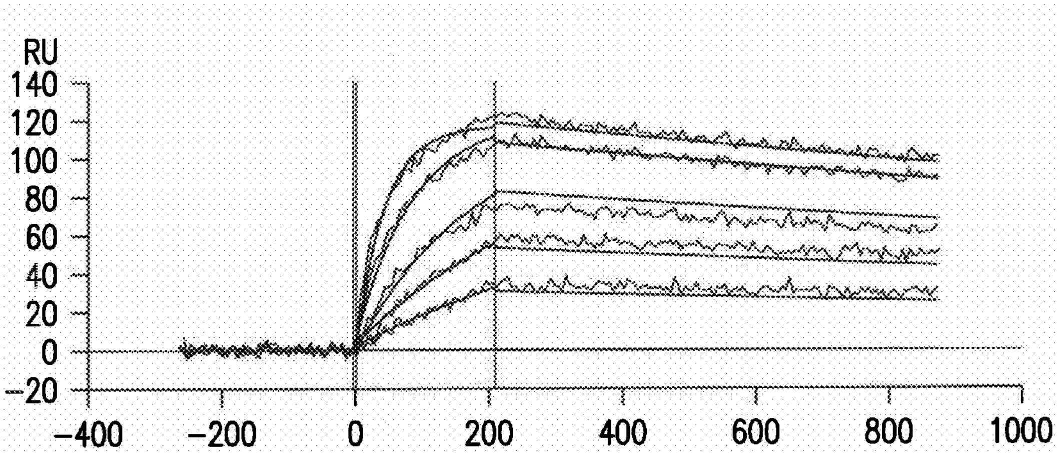
Figure 24H:
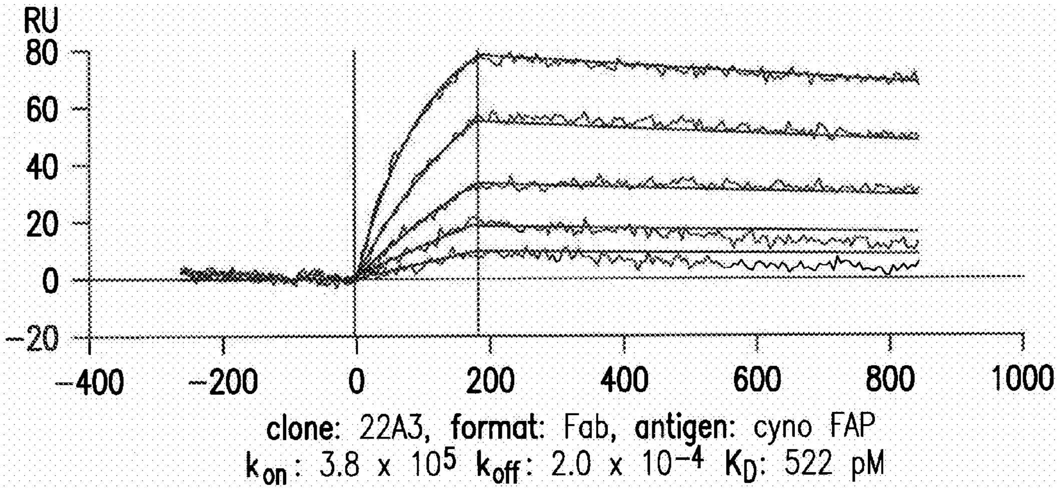
Figure 25A:
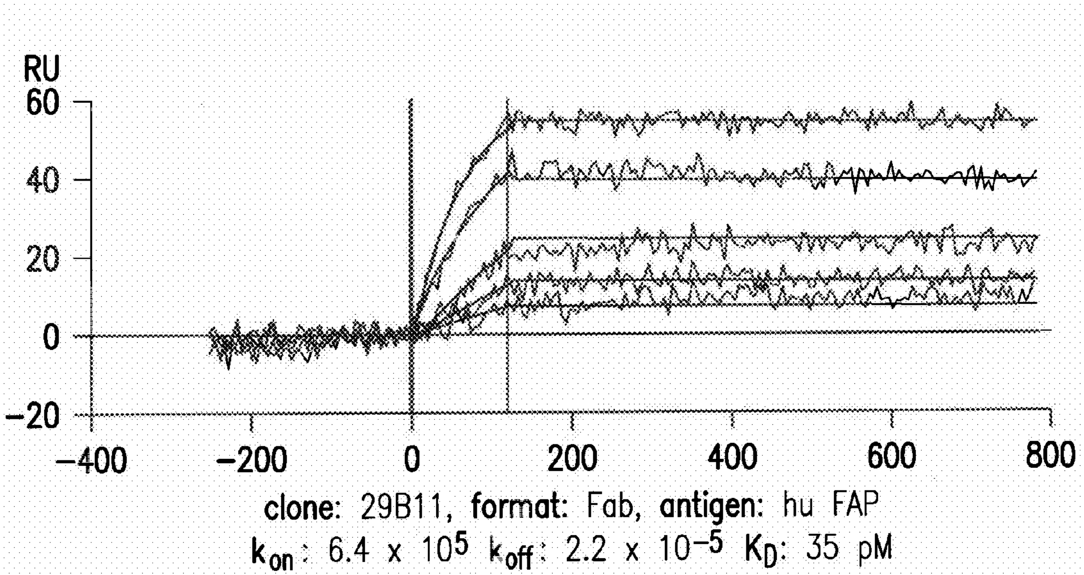
Figure 25B:
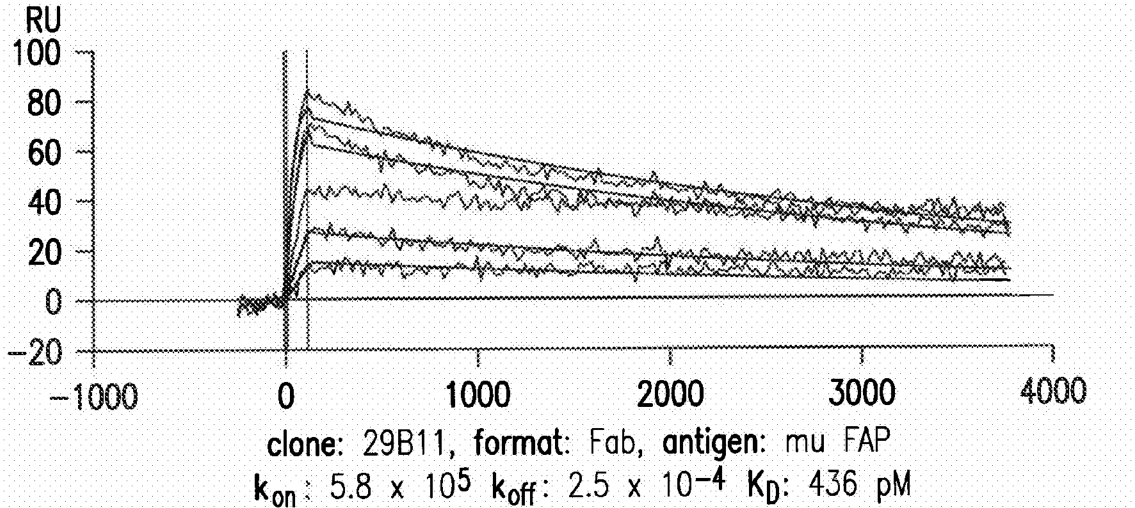
Figure 25C:
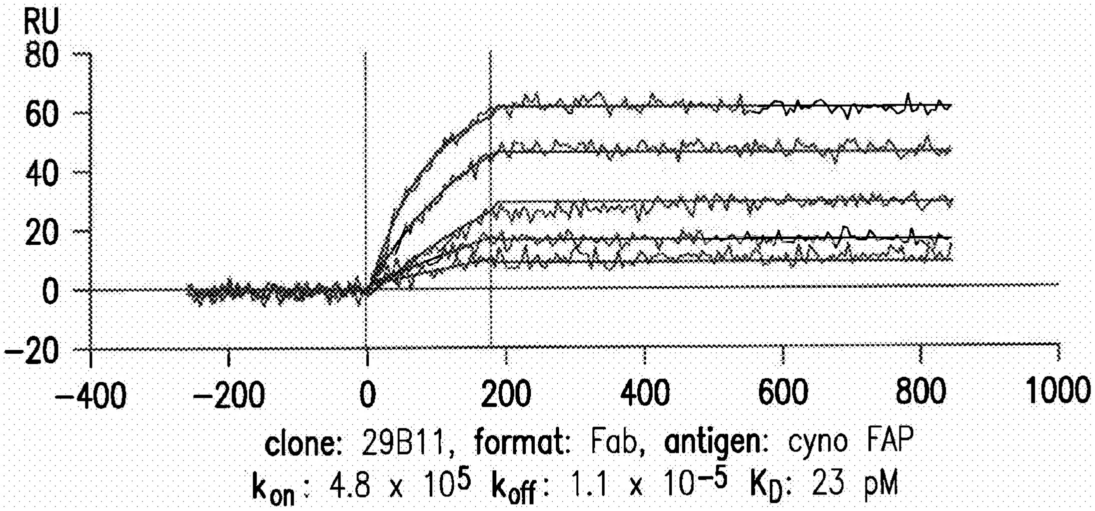
Figure 25D:
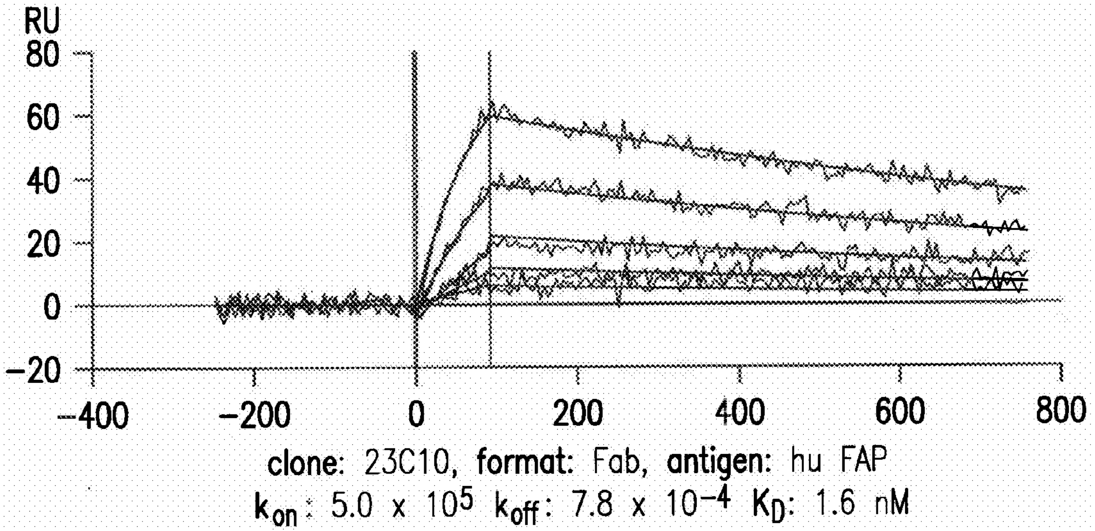
Figure 25E:
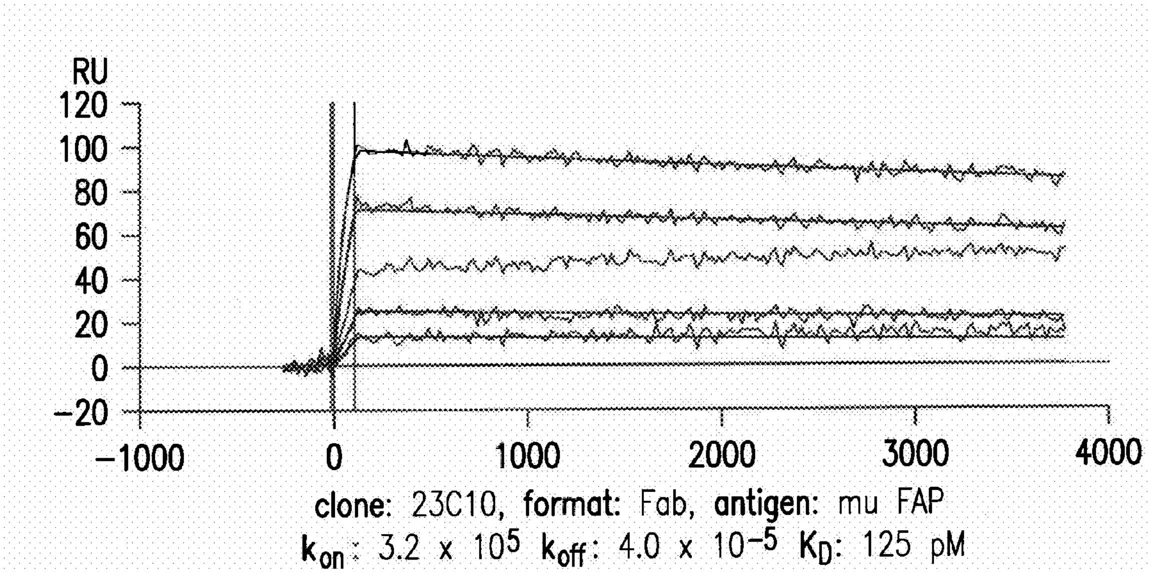
Figure 25F:
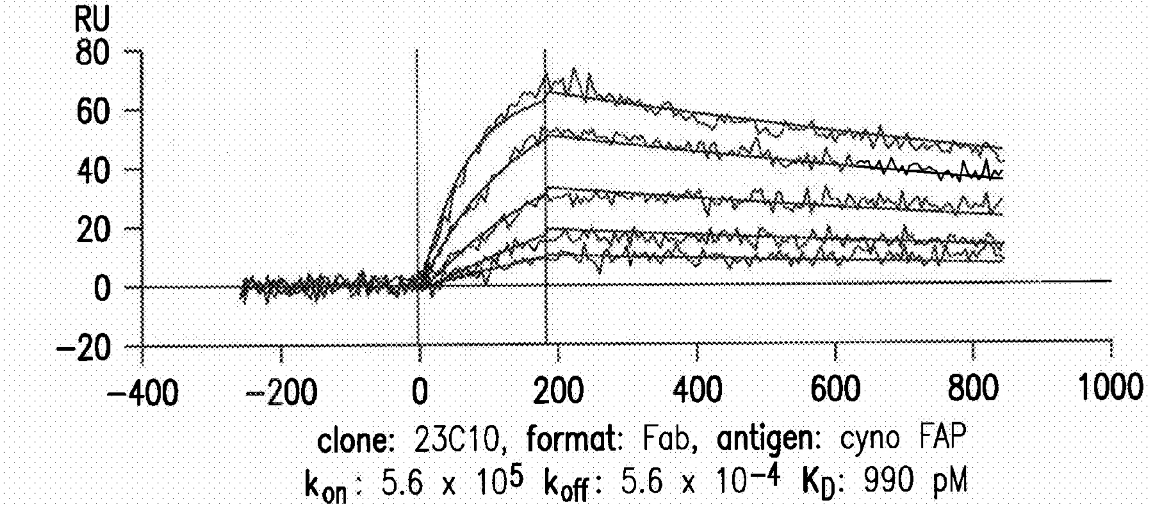
Figure 26A:
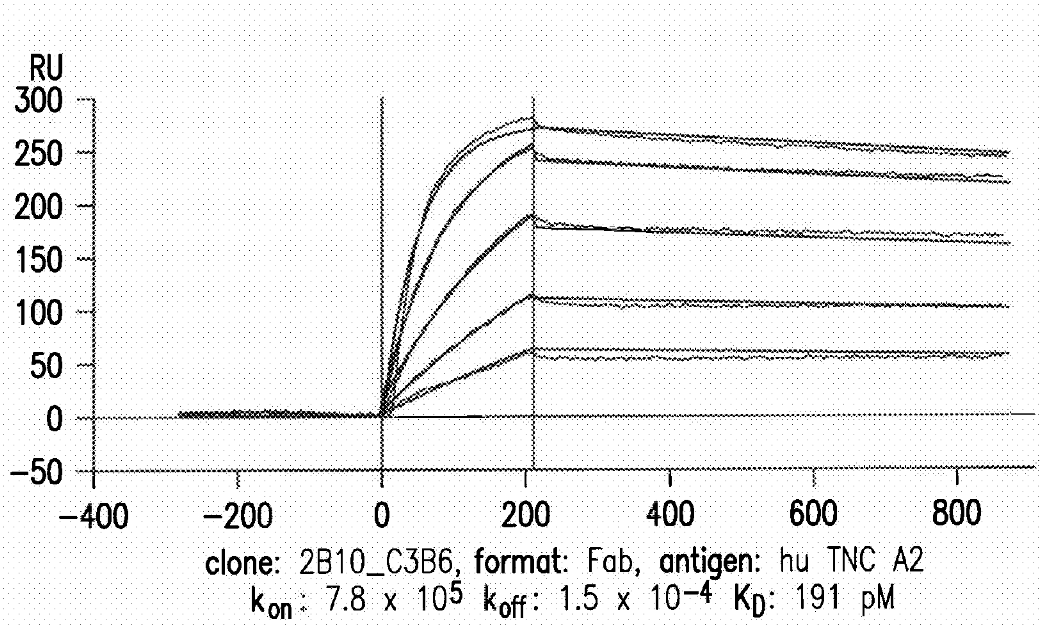
Figure 26B:
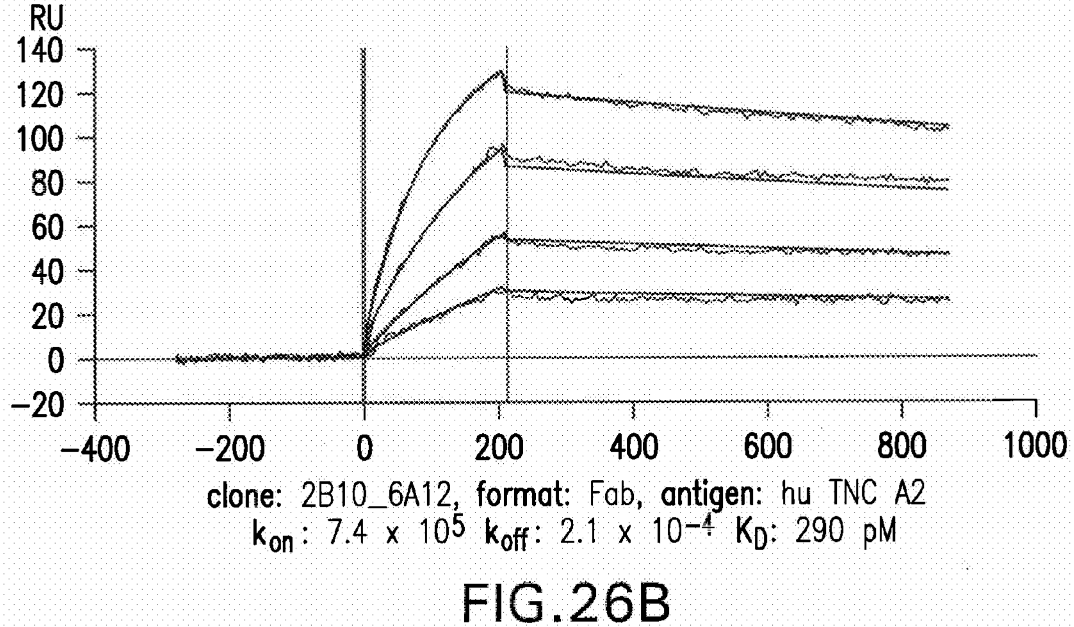
Figure 26C:
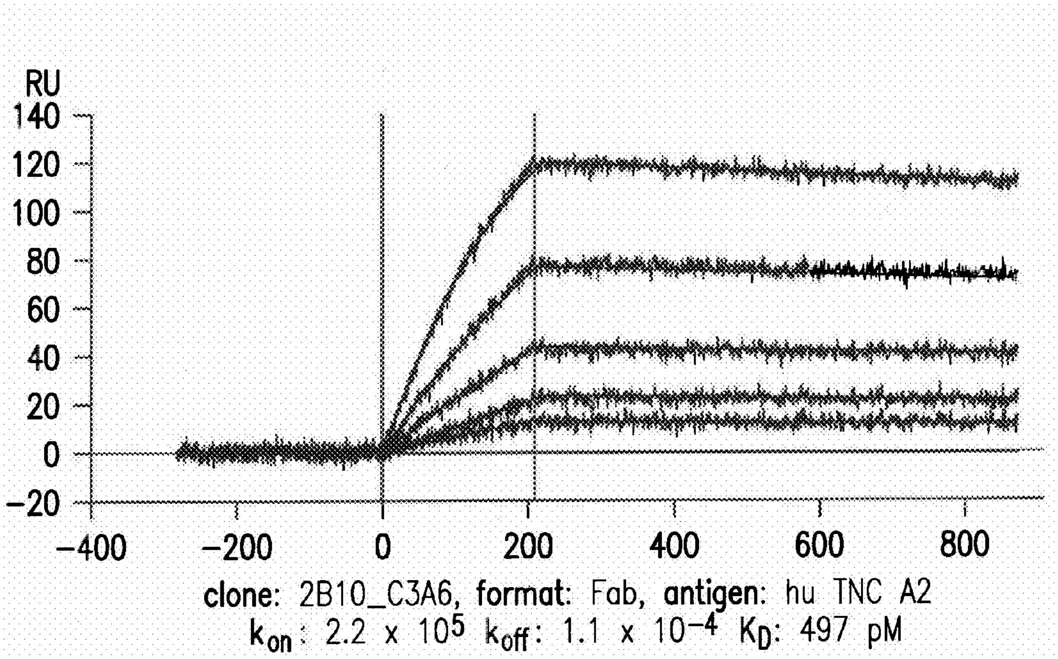
Figure 26D:
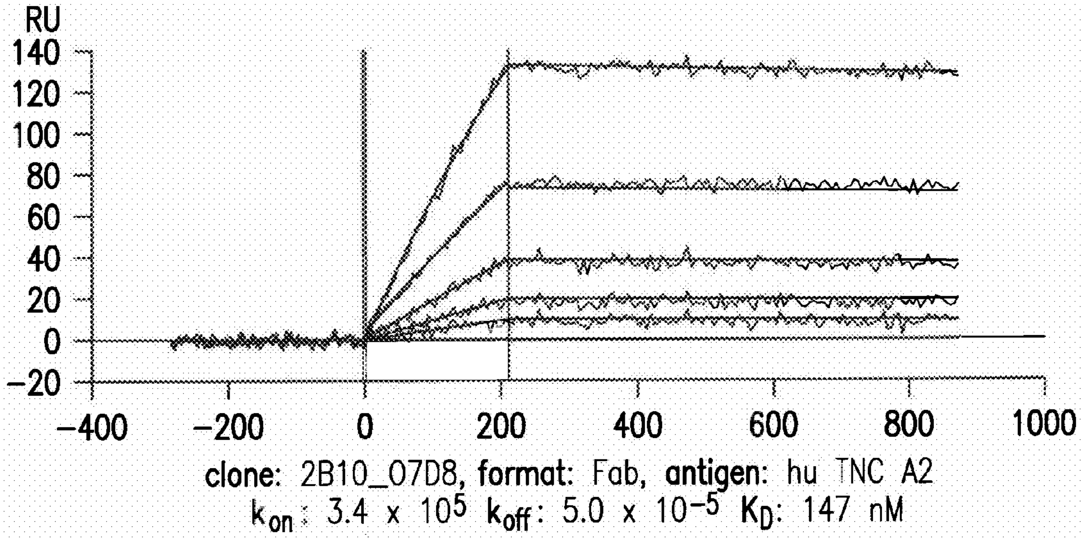
Figure 26E:
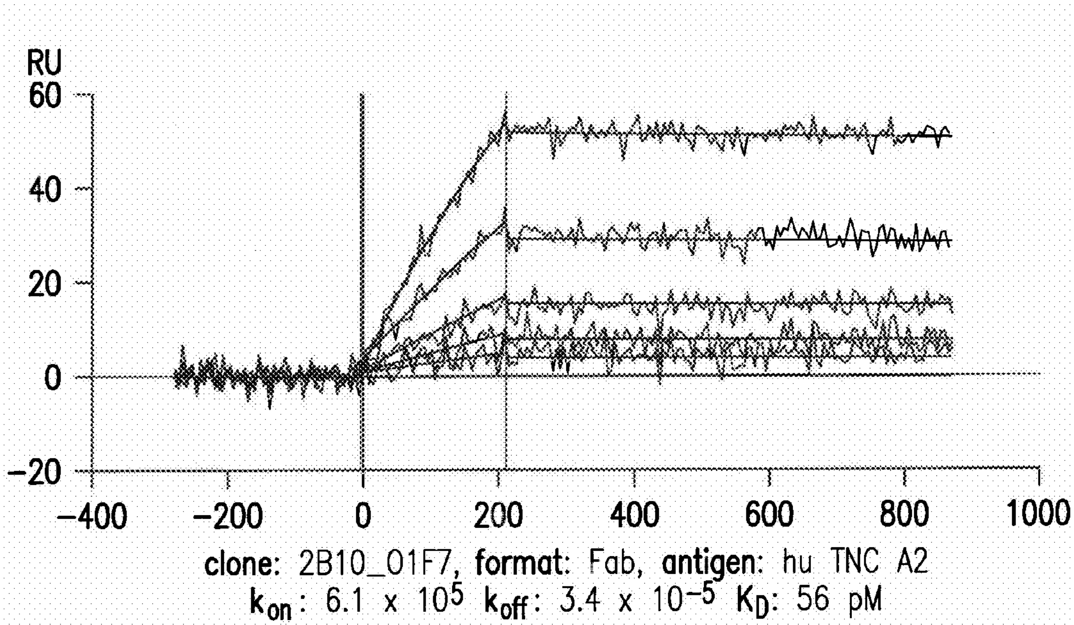
Figure 26F:
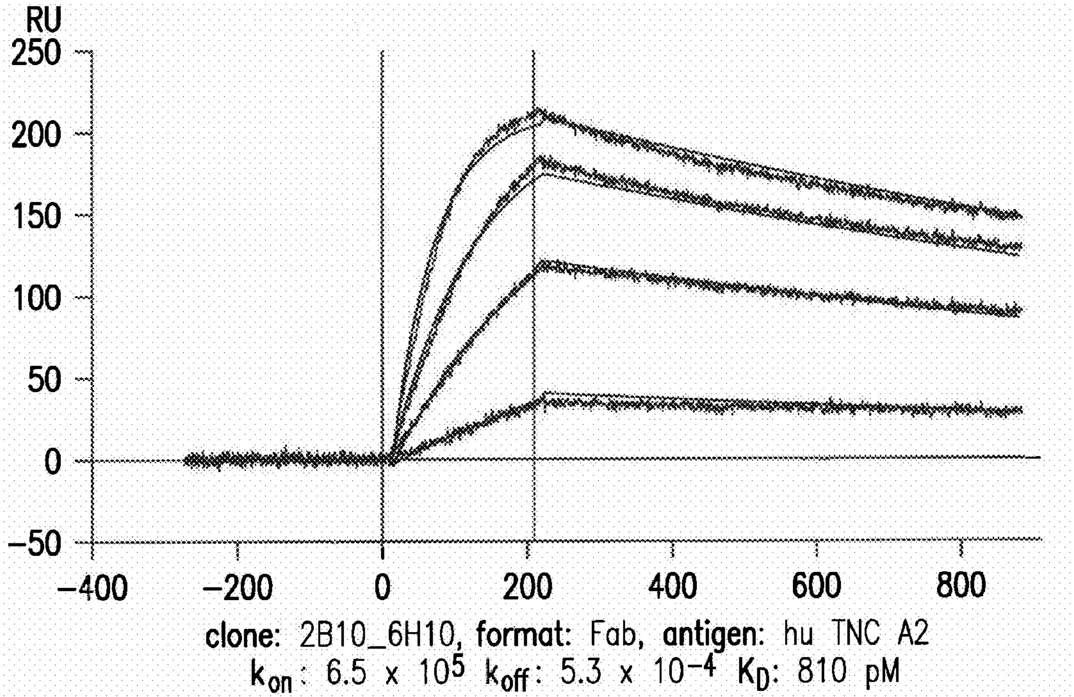

The differences were more pronounced when looking at affinities toward the IL-2 receptor. To study IL-2 receptor binding affinity, a tool was generated that allowed for the expression of a heterodimeric IL-2 receptor; the β chain of the IL-2 receptor was fused to an Fc molecule that was engineered to heterodimerize (Fc(knob)) using the "knobs-into-holes" technology (Merchant, A. M. et al., *Nat. Biotech.* 16:677-681 (1998)). The gamma chain of the IL-2 receptor was then fused to the Fc(hole) variant, which heterodimerized with Fc(knob). This heterodimeric Fc-fusion protein was then used as a substrate for analyzing the IL-2/IL-2 receptor interaction. FIG. 13 shows the BIACORE sensogram of commercially available IL-2 (Proleukin), as the analyte, with the immobilized IL-2 receptor. The measured affinity of ~0.5 nM is in accordance with previously published values. The affinities of the various constructs towards the IL-2 receptor are summarized in FIG. 17. An important result that was observed was the difference between the diabody (F16 dia IL2), which is bivalent with respect to the cytokine, and the Fab-IL2-Fab molecule which carries only one IL-2 moiety. The IL-2 receptor binding affinity of the diabody (0.8 nM) was similar to that of unconjugated IL-2 (Proleukin) (0.5 nM), despite the diabody being bivalent and the IL-2 being monovalent. The Fab-IL2-Fab fusion had an IL-2 receptor binding affinity almost reduced by a factor of 10 compared to the diabody, which was reflected in a reduced capacity to induce proliferation of NK92 cells as shown in FIG. 19.

Example 2

Construction of Generic Fab-Libraries

Generic antibody libraries in the Fab-format were constructed on the basis of human germline genes using the following V-domain pairings: Vk3_20 kappa light chain with VH3_23 heavy chain for the DP47-3 library and Vk1_17 kappa light chain with VH1_69 heavy chain for the DP88-3 library. See Table 2. Both libraries were randomized in CDR3 of the light chain (L3) and CDR3 of the heavy chain (H3) and were assembled from 3 fragments per library by splicing by overlapping extension (SOE) PCR. Fragment 1 comprises the 5' end of the antibody gene including randomized L3, fragment 2 is a central constant fragment spanning from L3 to H3, whereas fragment 3 comprises randomized H3 and the 3' portion of the antibody gene.

The following primer combinations were used to generate library fragments for DP47-3 library: fragment 1 (LMB3-LibL1b_new), fragment 2 (MS63-MS64), fragment 3 (Lib2H-fdseqlong). See Table 9. The following primer combinations were used to generate library fragments for the DP88-3 library: fragment 1 (LMB3-RJH_LIB3), fragment 2 (RJH31-RJH32) and fragment 3 (LIB88_2-fdseqlong). See Table 10.

TABLE 9

| Primers Used In the DP47-3 Library | |
|---|---|
| LMB3 | CAGGAAACAGCTATGACCATGATTAC |
| LibL1b_new | CACTTTGGTCCCCTGGCCGAACGTMNNGGGMNNMNNMNN ACCCTGCTGACAGTAATACACTGC |
| MS63 | TTTCGCACAGTAATATACGGCCGTGTCC |
| MS64 | ACGTTCGGCCAGGGGACCAAAGTGG |
| Lib2H | GGCCGTATATTACTGTGCGAAANNKNNKNNKNNKNNKTT TGACTACTGGGGCCAAGGAAC |
| fdseqlong | GACGTTAGTAAATGAATTTTCTGTATGAGG |

TABLE 10

| Primers Used in DP88-3 Library | |
|---|---|
| LMB3 | CAGGAAACAGCTATGACCATGATTAC |
| RJH_LIB3 | GACTTTGGTGCCCTGGCCAAACGT MNN GGG MNN MNN ACC MNN CTGCAAGCAGTAATAGGTGGCAAAATC |
| RJH31 | ACGTTTGGCCAGGGCACCAAAGTCGAG |
| RJH32 | TCTCGCACAGTAATACACGGCGGTGTCC |
| LIB88_2 | GGACACCGCCGTGTATTACTGTGCGAGA-[(33% GAC Asp; 26% GGT Gly; 10% GAA Glu; 9% CGT Arg; 7% Lys; 6% GTT Val; 5% TCT Ser; 4% CTG Leu)1-(23% GGT Gly; 17% TAC Tyr; 16% TCT Ser; 11% GCT Ala; 9% CGT Arg; 7% AAC Asn; 6% ACT Thr; 6% GTT Val; 5% CCG Pro)8]-TTTGACTACTGGGGCCAAGGGACCACCGTGACCGTCTCC |
| fdseqlong | GACGTTAGTAAATGAATTTTCTGTATGAGG |

The PCR protocol for the production of library fragments included: 5 minutes of initial denaturation at 94° C.; 25 cycles of 1 minute at 94° C., 1 minute at 58° C., and 1 minute at 72° C.; and terminal elongation for 10 minutes at 72° C. For assembly PCR, equimolar ratios of the 3 fragments were used as template. The assembly PCR protocol included: 3 minutes of initial denaturation at 94° C.; and 5 cycles of 30 seconds at 94° C., 1 minute at 58° C., and 2 minutes at 72° C. At this stage, primers complementary to sequence outside fragments 1-3 were added and an additional 20 cycles were performed prior to a terminal elongation for 10 min at 72° C.

After assembly of sufficient amounts of full length randomized Fab constructs, the Fab constructs were digested with NcoI/NotI for the DP47-3 library and with NcoI/NheI for the DP88-3 library alongside with similarly treated acceptor phagemid vector. For the DP47-3 library, 22.8 μg of Fab library was ligated with 16.2 μg of phagemid vector. For the DP88-3 library, 30.6 μg of Fab library was ligated with 30.6 μg of phagemid vector.

Purified ligations were used for 68 transformations for the DP47-3 library and 64 transformations for the DP88-3 library, respectively, to obtain final library sizes of $4.2\times10^{10}$ for DP47-3 and $3.3\times10^{9}$ for DP88-3.

Phagemid particles displaying the Fab libraries were rescued and purified by PEG/NaCl purification to be used for selections.

Example 3

Selection of Anti-TNC A2 Clone 2810

Selections were carried out against *E. coli*-expressed human TNC-A2 which was subcloned 5' of an avi-tag and 6×his-tag. See SEQ ID NO: 57 in Table 5. The antigen was biotinylated in vivo upon expression. Selections have been carried out in solution according to the following protocol: (i) binding of ~$10^{12}$ phagemid particles of library DP88-3 and 100 nM biotinylated human TNC A2 for 0.5 hours in a total volume of 1 ml; (ii) capture of biotinylated human TNC-A2 and attached phage by the addition of $5.4\times10^{7}$ streptavidin-coated magnetic beads for 10 minutes; (iii) washing of beads using 5×1 ml PBS/Tween20 and 5×1 ml PBS; (iv) elution of phage particles by the addition of 1 mL 100 mM TEA (triethylamine) for 10 minutes and neutralization by the addition of 500 μL 1M Tris/HCl pH 7.4; and (v) re-infection of log-phase *E. coli* TG1 cells, infection with helperphage VCSM13 and subsequent PEG/NaCl precipitation of phagemid particles to be used in subsequent selection rounds.

Selections were carried out over 3 rounds using constant antigen concentrations at 100 nM. In round 2, capture of antigen:phage complexes was performed on neutravidin plates instead of streptavidin beads. Specific binders were identified by ELISA as follows using: 100 μl of 100 riM biotinylated human TNC-A2 was coated in each well of neutravidin plates.

Fab-containing bacterial supernatants were added and binding Fabs were detected via their Flag-tags by using an anti-Flag/HRP secondary antibody. Once identified, clone 2B10 was bacterially expressed in a 0.5 liter culture volume, affinity purified and further characterized by SPR-analysis using BIACORE T100. See SEQ ID NOs: 3 and 7 of Table 3.

Example 4

Selection of Anti-TNC A1/A4 Clone 2F11

Selections were carried out against *E. coli* expressed human TNC A1 which was subcloned 5' of an avi-tag and 6×his-tag. See SEQ ID NO: 59 of Table 5. The antigen was biotinylated in vivo upon expression. Selections were carried out in solution according to the following protocol: (i) binding of ~$10^{12}$ phagemid particles of library DP47-3 and 100 nM biotinylated human TNC-A1 for 0.5 hours in a total volume of 1 mL; (ii) capture of biotinylated human TNC-A1 and attached phage by the addition of $5.4\times10^{7}$ streptavidin-coated magnetic beads for 10 minutes; (iii) washing of beads using 5×1 mL PBS/Tween20 and 5×1 ml PBS; (iv) elution of phage particles by the addition of 1 mL 100 mM TEA (triethylamine) for 10 minutes and neutralization by the addition of 500 μl 1M Tris/HCl pH 7.4; and (v) re-infection of log-phase *E. coli* TG1 cells, infection with helperphage VCSM13 and subsequent PEG/NaCl precipitation of phagemid particles to be used in subsequent selection round.

Selections were carried out over 3 rounds using constant antigen concentrations at 100 nM. In round 2, capture of antigen:phage complexes was performed on neutravidin plates instead of streptavidin beads.

All binding reactions were supplemented with 100 nM non-biotinylated human IgG CH3 constant domain comprising a carboxy-terminal avi-tag and 6×his-tag in order to compete for unwanted clones recognizing the tags of the antigen.

In a first screening step, specific binders were identified by ELISA as follows: 100 μl of 100 nM biotinylated human TNC-A1 was coated in each of neutravidin plates. Fab-containing bacterial supernatants were added and Fabs that specifically bound to human TNC-A1 were detected via their Flag-tags by using an anti-Flag/HRP secondary antibody.

In a second screening step, the above ELISA was repeated using also murine TNC-A1, human INC A4 and mu TNC A4 as antigens in order to determine cross-reactivity. All antigens comprised the same avi-tag and 6×his-tag at their C-terminus and were in vivo biotinylated. See SEQ ID NOs: 50 and 61 of Table 5.

Once identified, clone 2F11 was bacterially expressed in a 0.5 liter culture volume, affinity purified and further characterized by SPR-analysis using BIACORE T100. See SEQ ID NOs: 9 and 13 of Table 3.

Example 5

Selection of Anti-FAP Clones (Primary Selections)

Selections were carried out against the ectodomain of human or murine fibroblast activating protein (FAP) which were cloned upstream a poly-lysine and a 6×his-tag. See SEQ ID NOs: 53 and 55 of Table 5. Prior to selections, the antigens were coated into immunotubes at a concentration of either 10 μg/ml or 5 μg/ml, depending on round of selection. Selections were carried out according to the following protocol: (i) binding of ~$10^{12}$ phagemid particles of library DP47-3 to immobilized human or murine FAP for 2 hours; (ii) washing of immunotubes using 5×5 mL PBS/Tween20 and 5×5 ml PBS; (iii) elution of phage particles by addition of 1 mL 100 mM TEA (triethylamine) for 10 minutes and neutralization by the addition of 500 μL 1M Tris/HCl pH 7.4; and (iv) re-infection of log-phase *E. coli* TG1 cells, infection with helperphage VCSM13 and subsequent PEG/NaCl precipitation of phagemid particles to be used in subsequent selection rounds.

Selections have been carried out over three or four rounds using decreasing antigen concentrations of human FAP and in some cases using murine FAP at 5 ug/ml in the final selection round. Specific binders were defined as signals 5× higher than background and were identified by ELISA. NUNC maxisorp plates were coated with 10 ug/ml of human or murine FAP followed by addition of Fab-containing bacterial supernatants and detection of specifically binding Fabs via their Flag-tags by using an anti-Flag/HRP secondary antibody.

ELISA-positive clones were bacterially expressed as 1 mL cultures in 96-well format and supernatants were subjected to a kinetic screening experiment using BIACORE T100.

Example 6

Construction of Anti-FAP Affinity Maturation Libraries

Three affinity maturation libraries were constructed on basis of pre-selected antibodies from the primary anti-FAP selections. More precisely, they were based on (i) anti-human FAP clone 2D9 (library a.m.FAP2D9) (see SEQ ID NOs: 67 and 69 of Table 3), (ii) anti-murine FAP clone 4B8 (library a.m.FAP4B8) (see SEQ ID NOs: 71 and 73. of Table 3) and (iii) cross-reactive clones 7A1, 13B2, 13C2, 13E8, 14C10 and 17A11 (library a.m.FAPpool) (see SEQ ID NOs: 75 and 77 of Table 3 corresponding to the variable region sequences of 7A1; SEQ ID NOs: 79 and 81 of Table 3 corresponding to the variable region sequences of 13C2; SEQ ID NOs: 83 and 85 corresponding to the variable region sequences of 13E8; SEQ ID NOs: 87 and 89 corresponding to the variable region sequences of 14C10; and SEQ ID NOs: 91 and 93 corresponding to the variable region sequences of 17A11).

Each of these libraries consists of two sublibraries, randomized in either CDR1 and CDR2 of the light chain (L1/L2) or CDR1 and CDR2 of the heavy chain (H1/H2), respectively. These sublibraries were pooled upon transformation. Each of these sublibraries was constructed by four subsequent steps of amplification and assembly.

For L1/L2 libraries, the amplification and assembly protocol included: (i) amplification of fragment 1 (LMB3—DPK22_CDR1_rand_ba_opt) and fragment 2 (DPK22_CDR1_fo—DPK22_Ck_BsiWI_ba); (ii) assembly of fragments 1 and 2 using outer primers LMB3 and DPK22_Ck_BsiWI_ba to create the template for fragment 3; (iii) amplification of fragment 3 (LMB3—DPK22_CDR2_rand_ba) and fragment 4 (DPK22_CDR2_fo—DPK22_Ck_BsiWI_ba); and (iv) final assembly of fragments 3 and 4 using the same outer primers as above. See Table 11 for primer sequences.

TABLE 11

Primers Used in L1/L2 Affinity Maturation Libraries for anti-FAP Affinity Maturation

| | |
|---|---|
| LMB3 | CAGGAAACAGCTATGACCATGATTAC |
| DPK22_CDR1_rand_ba_opt | CAGGTTTCTGCTGGTACCAGGCTAAGTAGCTGCTGCTAACCTCTGACTGGCCCTGCAAG |
| DPK22_CDR1_fo | TTAGCCTGGTACCAGCAGAAACCTG |
| DPK22_Ck_BsiWI_ba | GGTGCAGCCACCGTACGTTTGATTTCC |
| DPK22_CDR2_rand_ba | CTGTCTGGGATGCCAGTGGCCCTGCTGGAGGCGCCATAGATGAGGAGCCTGGGAGCCTG |
| DPK22_CDR2_fo | AGGGCCACTGGCATCCCAGACAG |

Bold: 60% original base and 40% randomization as M
Underline: 60% original base and 40% randomization as N For H1/H2 libraries, the amplification and assembly protocol included: (i) amplification of fragment 1 (RJH53—DP47_CDR1_rand_ba_opt) and fragment 2 (DP47_CDR1_fo—MS52); (ii) assembly of fragments 1 and 2 using outer primers RJH53 and MS52 to create the template for fragment 3; (iii) amplification of fragment 3 (RJH53—DP47_CDR2_rand_ba) and fragment 4 (DP47_CDR2_fo—MS52); and (iv) final assembly of fragments 3 and 4 using the same outer primers as above. See Table 12 for primer sequences.

TABLE 12

Primers Used in H1/H2 Affinity Maturation Libraries for anti-FAP Affinity Maturation

| | |
|---|---|
| RJH53 | CATCAGGGCCTGAGCTCGCCCGTCAC |
| DP47_CDR1_rand_ba_opt | GAGCCTGGCGGACCCAGCTCATGGCATAACTGCTAAAGGTGAATCCGGAGGC |

TABLE 12-continued

| Primers Used in H1/H2 Affinity Maturation Libraries for anti-FAP Affinity Maturation | |
|---|---|
| DP47_CDR1_fo | ATGAGCTGGGTCCGCCAGGCTC |
| MS52 | GAAGACCGATGGGCCTTTGGTGCTAG |
| DP47_CDR2_rand_ba | CCTTCACGGAGTCTGCGTAGTATGT**G**CT**A**CC**A**CC**A**CT**A**CC**A**CTAAT**A**GCTGAGACCCACTCCAGCCCCTTCCC |
| DP47_CDR2_fo | ACATACTACGCAGACTCCGTGAAGG |

Bold: 60% original base and 40% randomization as M
Underline: 60% original base and 40% randomization as N Final assembly products have been digested with NcoI/BsiWI for L1/L2 sublibraries of a.m.FAP2D9 and a.m.FAP4B8, with MunI and NheI for H1/H2 sublibraries of a.m.FAP2D9 and a.m.FAP4B8 as well as with NcoI/BamHI for L1/L2 library of a.m.FAPpool and with BspEI/PstI for H1/H2 libraries of a.m.FAPpool, respectively, alongside with similarly treated acceptor vectors based on plasmid preparations of clones 2D9, 4B8 or an equimolar mixture of clones 7A1, 13B2, 13C2, 13E8, 14C10 and 17A11, respectively. The following amounts of digested randomized (partial) V-domains and digested acceptor vector(s) were ligated for the respective libraries (μg V-domain/μg vector): a.m.FAP2D9 L1/L2 sublibrary (5.7/21.5), a.m.FAP2D9 H1/H2 sublibrary (4.1/15.5), a.m.FAP4B8 L1/L2 sublibrary (6.5/24.5), a.m.FAP4B8 H1/H2 sublibrary (5.7/21.5), a.m.FAPpool L1/L2 sublibrary (4.4/20), a.m.FAPpool H1/H2 sublibrary (3.4/15.5).

Purified ligations of L1/L2 and H1/H2 sublibraries were pooled and used for 60 transformations for each of the 3 affinity maturation libraries, to obtain final library sizes of $6.2\times10^9$ for a.m.FAP2D9, $9.9\times10^9$ for a.m.FAP4B8 and $2.2\times10^9$ for a.m.FAPpool.

Phagemid particles displaying these Fab libraries were rescued and purified by PEG/NaCl purification to be used for secondary selections.

Example 7

Selection of Affinity-Matured Anti-FAP Clones

Selections were carried out against the ectodomain of human or murine fibroblast activating protein (FAP) which were cloned 5' of a poly-lysine and a 6×his-tag. See SEQ ID NOs: 53 and 55 of Table 5. Prior to selections, the antigens were coated into immunotubes at a concentration of either 10 μg/mL, 5 μg/mL or 0.2 μg/mL, depending on the library and round of selection. Selections were carried out according to the following protocol: (i) binding of $\sim10^{12}$ phagemid particles of library a.m.FAP2D9, a.m.FAP4B8 or a.m.FAPpool to immobilized human or murine FAP for 2 hours; (ii) washing of immuno tubes using 10-20×5 mL PBS/Tween20 and 10-20×5 mL PBS (depending on library and selection round); (iii) elution of phage particles by addition of 1 mL 100 m M TEA (triethylamine) for 10 minutes and neutralization by addition of 500 μL 1M Tris/HCl pH 7.4; and (iv) re-infection of log-phase *E. coli* TG1 cells, infection with helperphage VCSM13 and subsequent PEG/NaCl precipitation of phagemid particles to be used in subsequent selection rounds.

Selections were carried out over 2 rounds and conditions were adjusted for each of the 3 libraries individually. In detail, selection parameters were: a.m.FAP2D9 (5 μg/mL human FAP and 20 washes in total for round 1, 1 μg/mL human FAP and 30 washes in total for round 2), a.m.FAP4B8 (1 μg/mL murine FAP and 30 washes in total for round 1, 0.2 μg/mL human FAP and 40 washes in total for round 2) and a.m.FAPpool (5 μg/mL human FAP and 30 washes in total for round 1, 5 μg/mL murine FAP and 30 washes in total for round 2). Specific binders were defined as signals 5×higher than background and were identified by ELISA. NUNC maxisorp plates were coated with 1 μg/mL or 0.2 μg/mL of human or murine FAP followed by addition of Fab-containing bacterial supernatants and detection of specifically binding Fabs via their Flag-tags by using an anti-Flag/HRP secondary antibody.

ELISA-positive clones were bacterially expressed as lml cultures in 96-well format and supematants were subjected to a kinetic screening experiment using BIACORE T100.

Example 8

Efficacy Studies of Different Formats of Targeted IL-2

Figure 3:
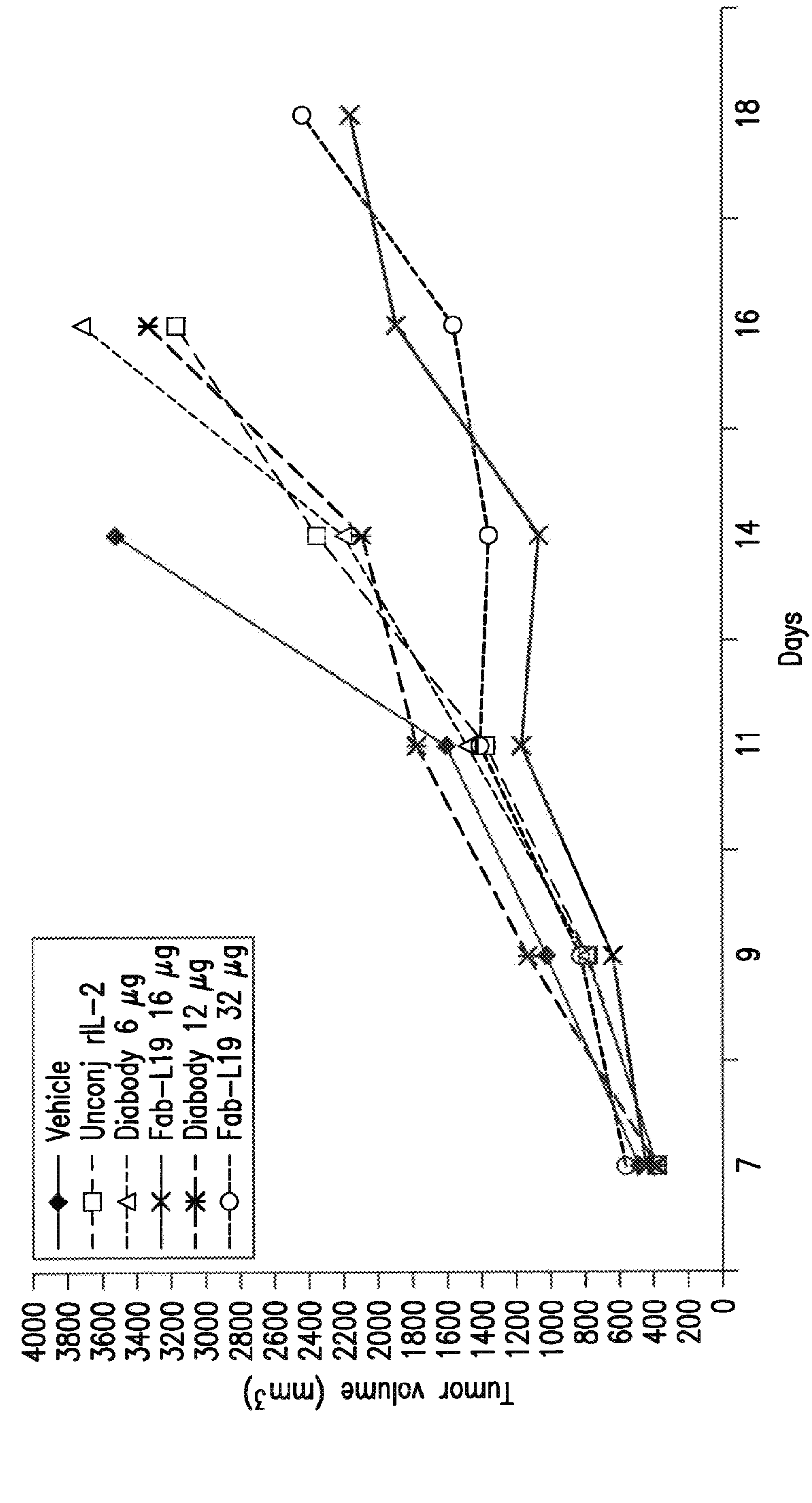

An efficacy experiment was performed using two different Interleukin-2 immunoconjugate molecular formats specific for tumor stroma. The F9 teratocarcinoma was subcutaneously injected into 129SvEv mice, and tumor size was measured using a caliper. The "diabody"-IL-2 molecule was compared at two different concentrations to the Fab-interleukin-2-Fab (Fab-IL2-Fab) immunoconjugate, wherein the concentrations reflected similar numbers of immunoconjugate molecules. Results are shown in FIG. 3. The Fab-IL2-Fab immunoconjugate shows a significant tumor growth inhibition and is better than the diabody format at two different concentrations and better than controls.

Figure 4:
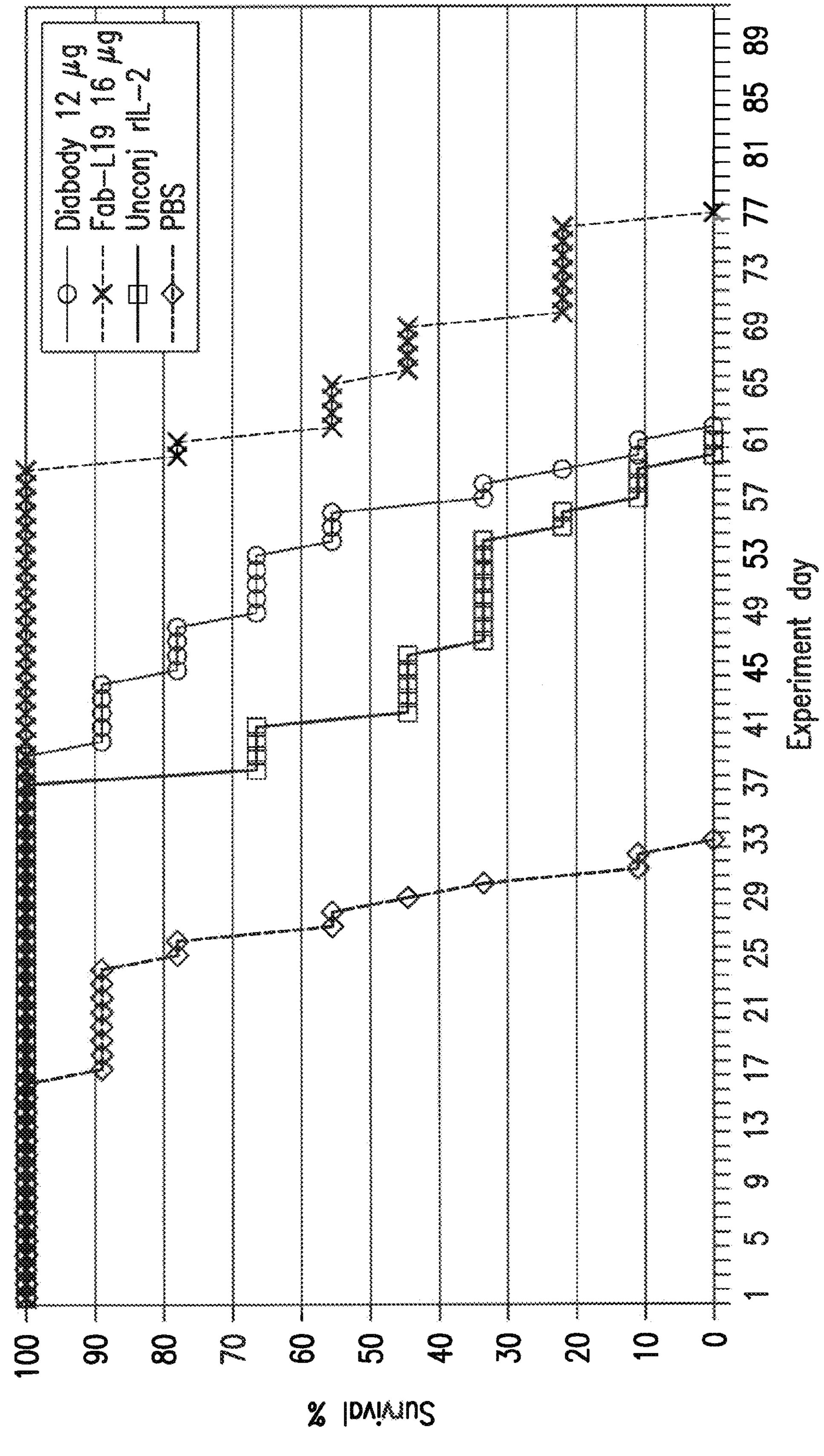
Figure 5:
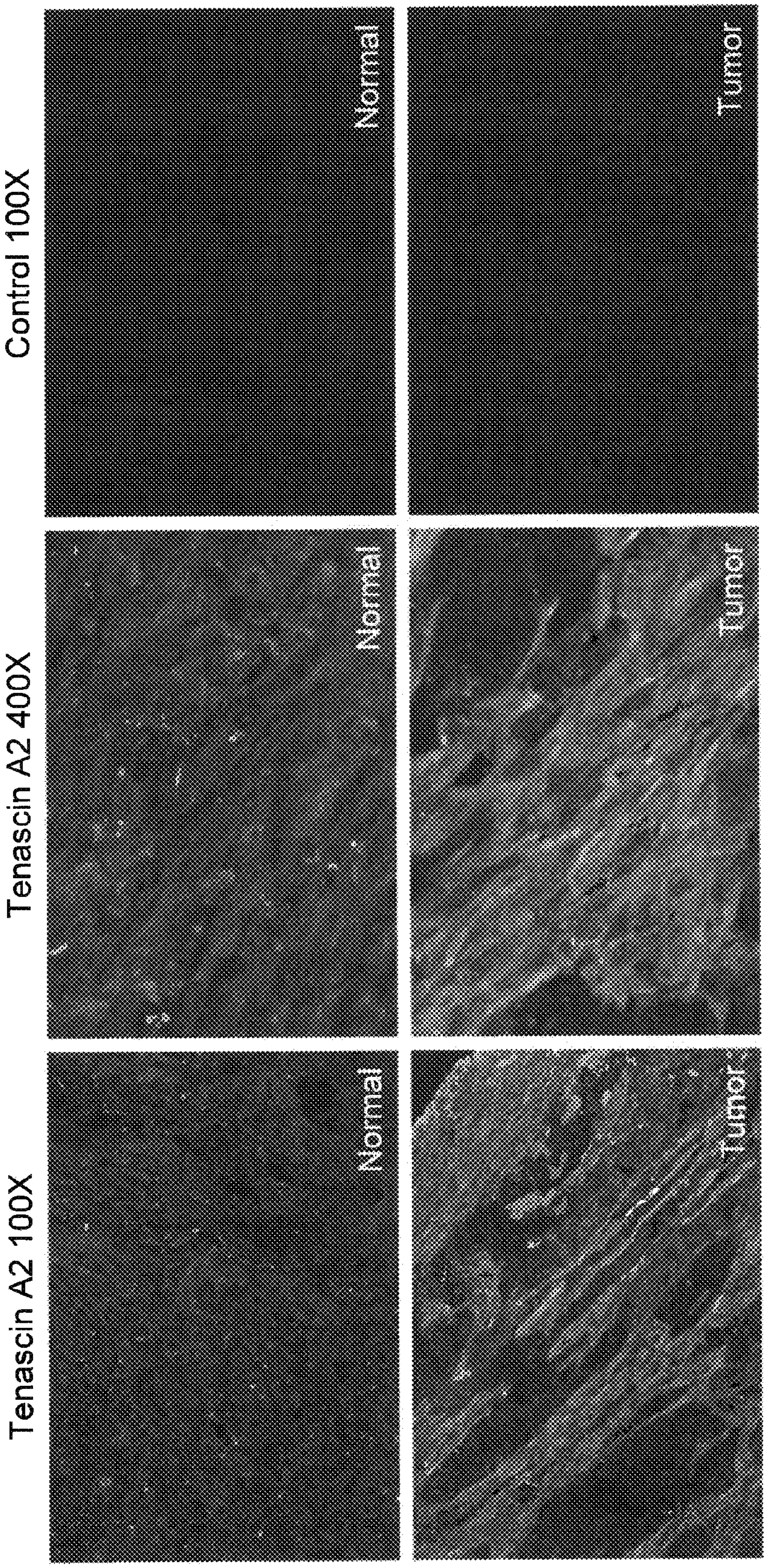
Figure 6:
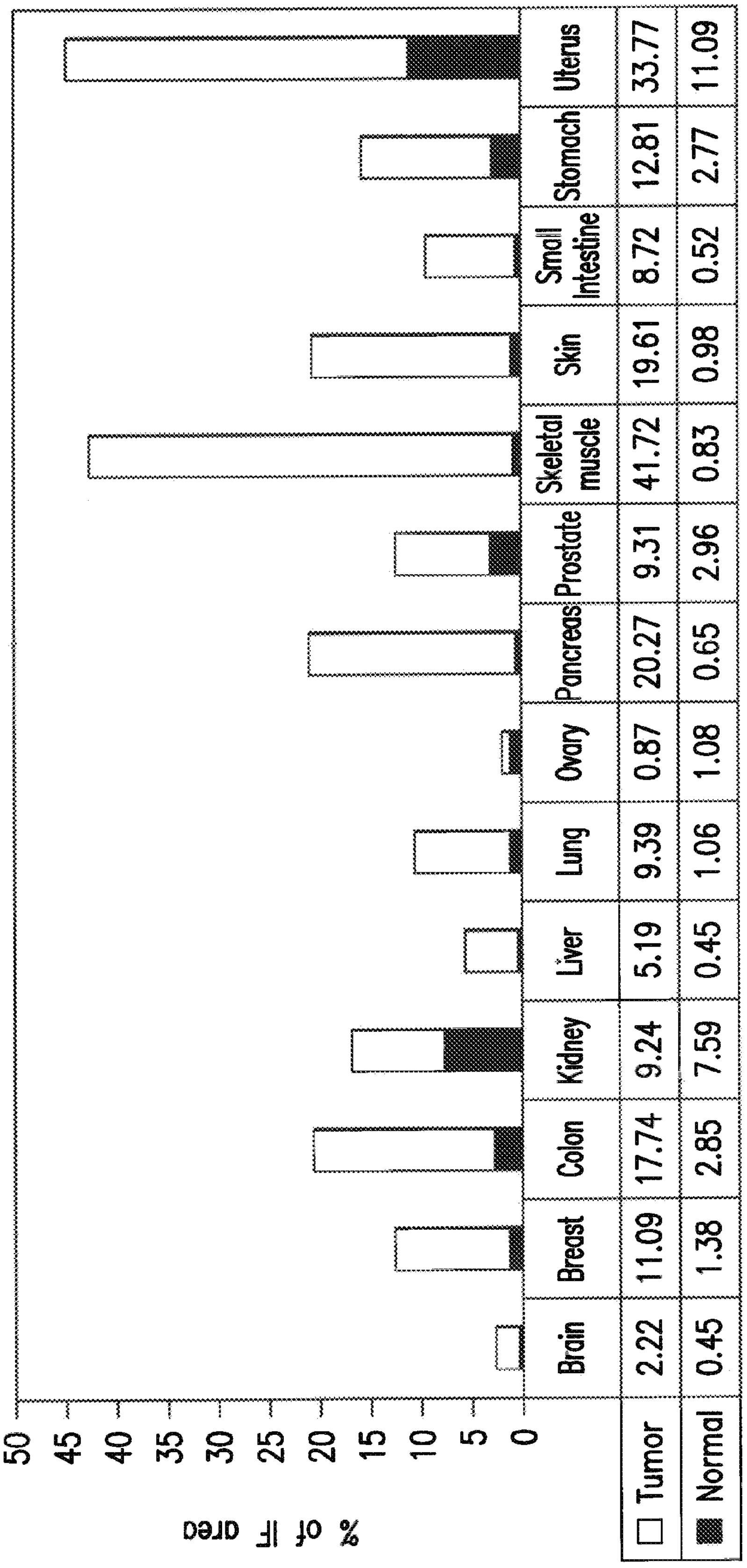
Figure 7:
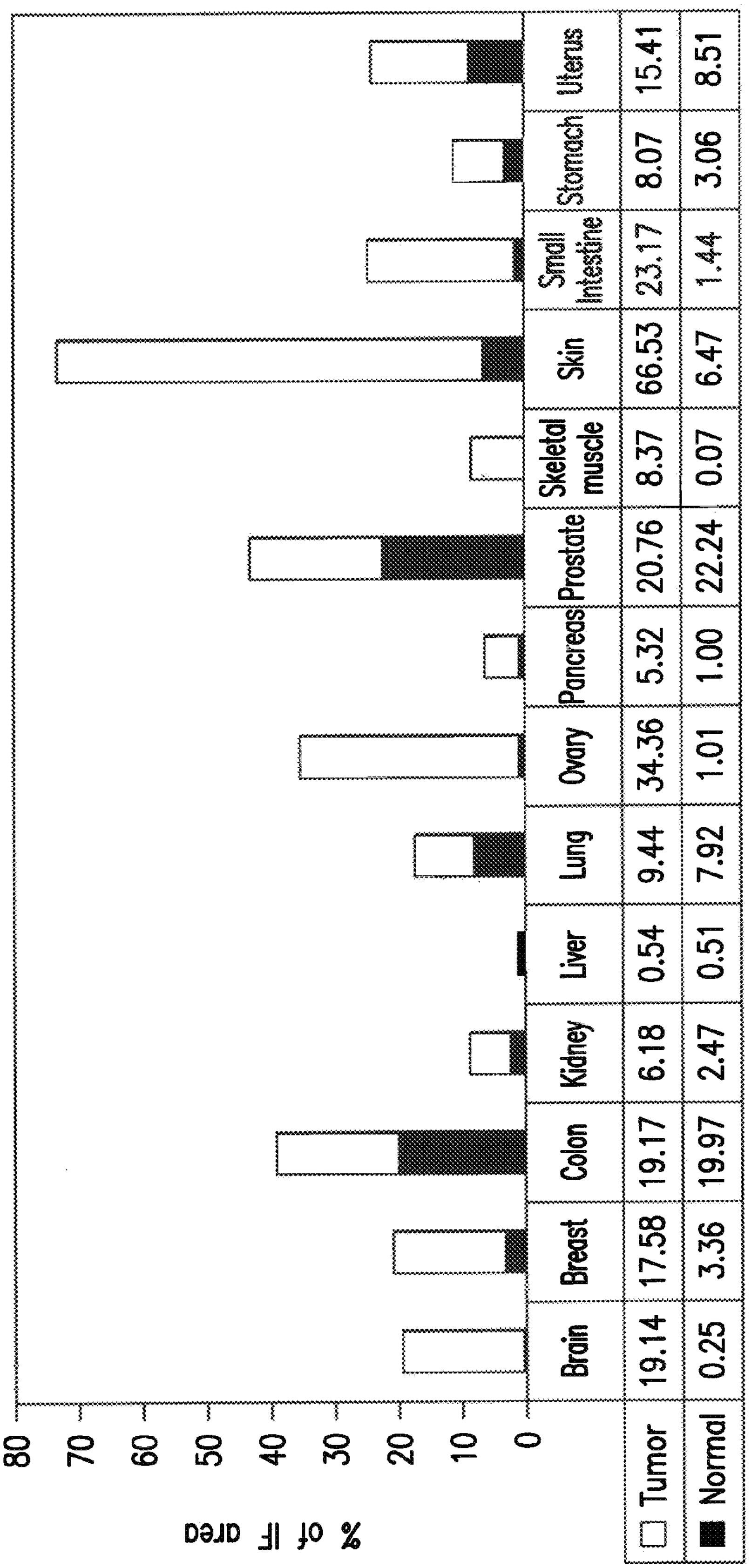
Figure 8:
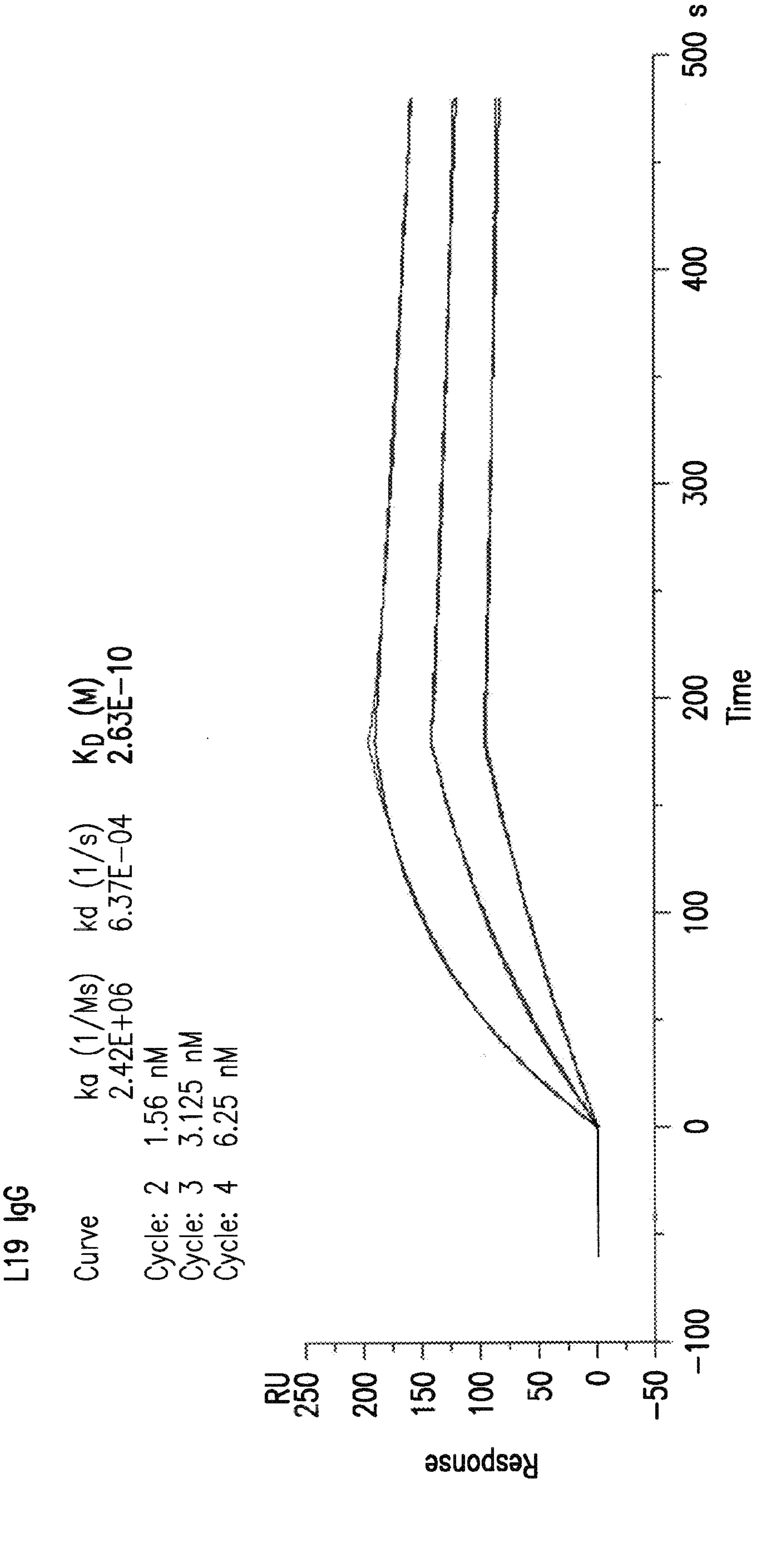
Figure 9:
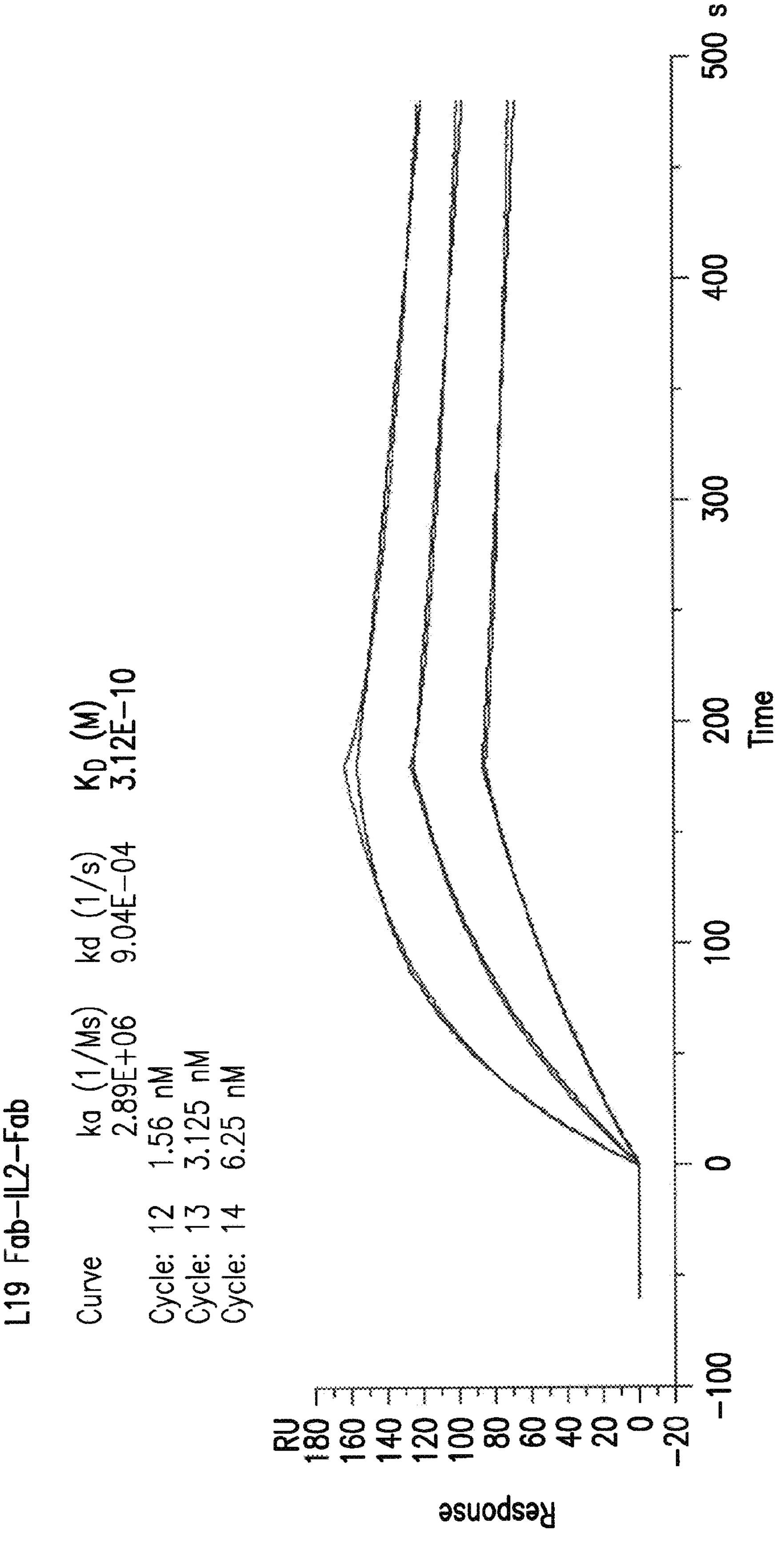
Figure 10:
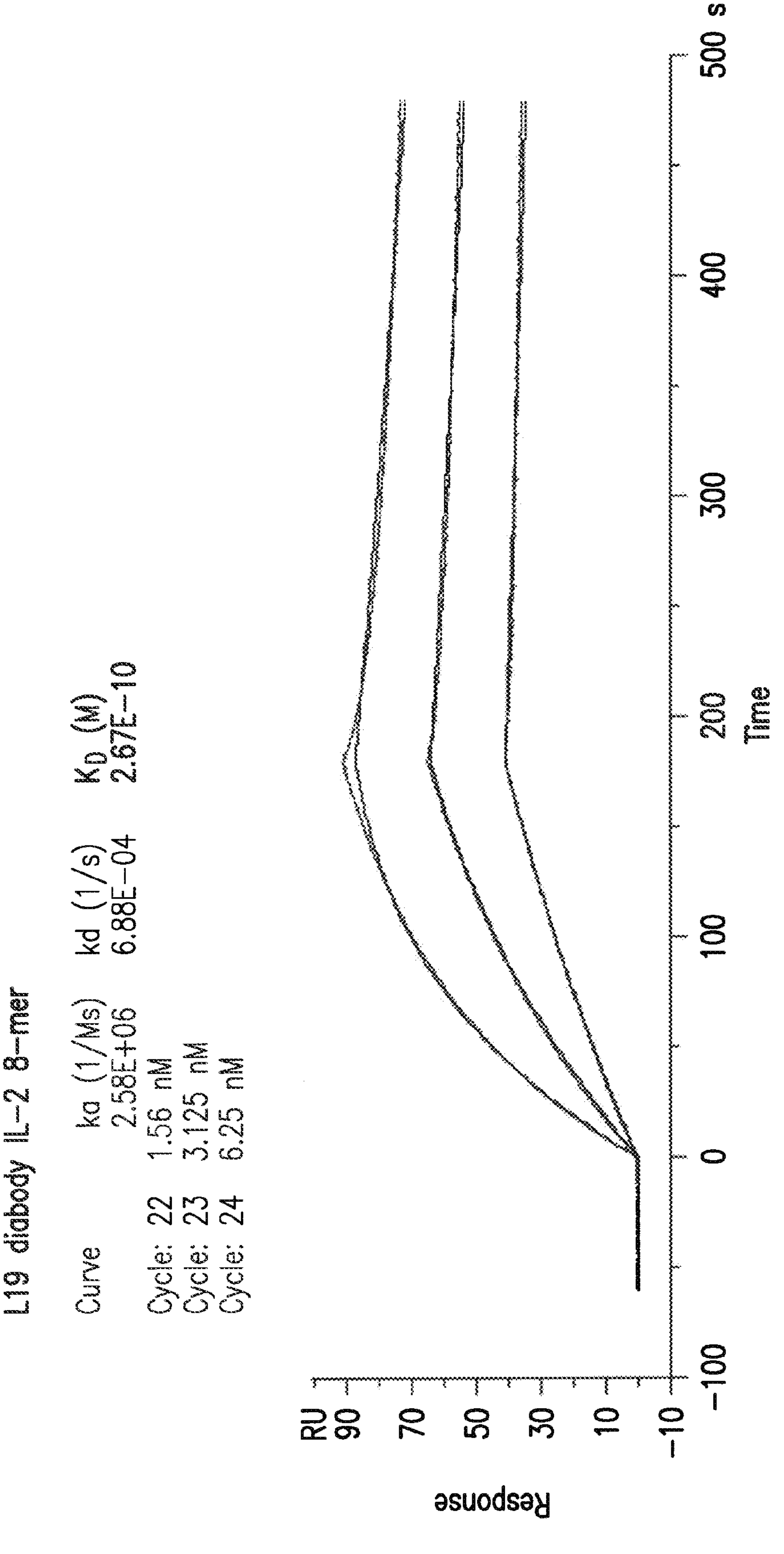
Figure 11:
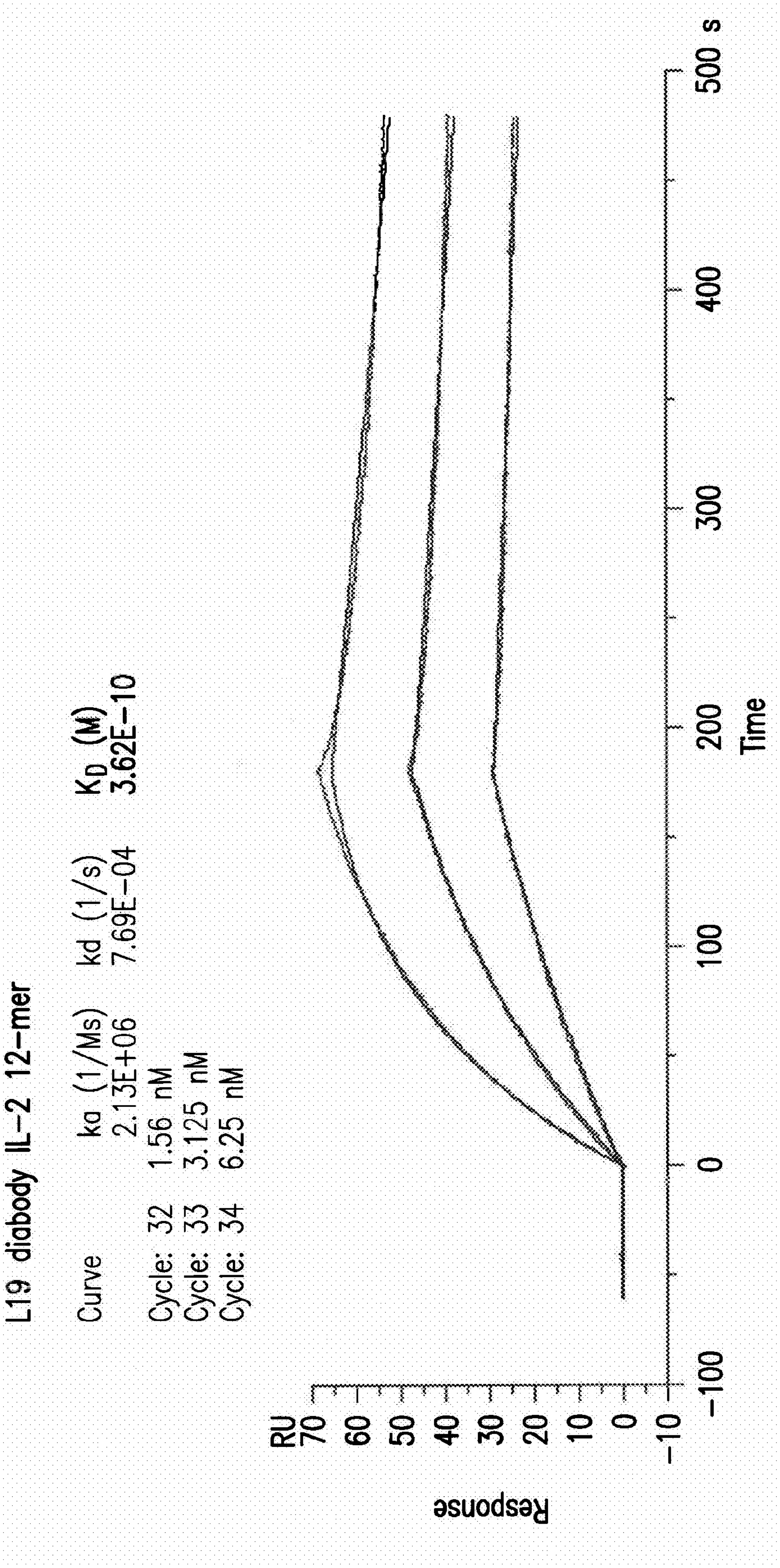

Survival of mice treated with two different Interleukin-2 immunoconjugate molecular formats specific for tumor stroma was also examined. Human gastric tumor cell-line LS174T was intrasplenically injected into SCID-beige mice. The "diabody"-IL-2 molecule was compared at two different concentrations to the Fab-IL-2-Fab immunoconjugate, wherein the concentrations reflected similar numbers of immunoconjugate molecules. Results are shown in FIG. 4. The Fab-IL-2-ab format resulted in a higher percent survival compared to the diabody format and controls.

Example 9

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

General information regarding the nucleotide sequences of human immunoglobulins light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments were prepared by Geneart AG (Regensburg, Germany) from synthetic oligonucleotides and PCR products by automated gene synthesis. The gene segments which are flanked by singular restriction endonuclease cleavage sites were cloned into pGA18 (ampR) plasmids. The plasmid DNA was purified from transformed bacteria and concentration determined by UV spectroscopy. The DNA sequence of the subcloned gene fragments was confirmed by DNA sequencing. Gene Segments were designed with suitable restriction sites to allow sub-cloning into the respective expression vectors. All constructs were designed with a 5'-end DNA sequence coding for a leader peptide which targets proteins for secretion in eukaryotic cells. Table 13 and 14 give exemplary leader peptides and polynucleotide sequences encoding them, respectively.

TABLE 13

Leader Sequences for Secretion: Polypeptide Sequences.

| Polypeptide Sequence | SEQ ID NO |
|---|---|
| MDWTWRILFLVAAATGAHS | 273 |
| MDMRVPAQLLGLLLLWFPGARC | 276 |
| MGWSCIILFLVATATGVHS | 278 |

TABLE 14

Leader Sequences for Secretion: Polynucleotide Sequences.

| Polynucleotide Sequence | SEQ ID NO |
|---|---|
| ATGGACTGGACCTGGAGAATCCTCTTCTTGGTGGCAGCAGCC ACAGGAGCCCACTCC | 274 |
| ATGGACTGGACCTGGAGGATCCTCTTCTTGGTGGCAGCAGCC ACAGGAGCCCACTCC | 275 |
| ATGGACATGAGGGTCCCCGCTCAGCTCCTGGGCCTCCTGCTGC TCTGGTTCCCAGGTGCCAGGTGT | 277 |
| ATGGGATGGAGCTGTATCATCCTCTTCTTGGTAGCAACAGCTA CCGGTGTGCATTCC | 279 |
| ATGGGCTGGTCCTGCATCATCCTGTTTCTGGTGGCTACCGCCA CTGGAGTGCATTCC | 280 |
| ATGGGCTGGTCCTGCATCATCCTGTTTCTGGTCGCCACAGCCA CCGGCGTGCACTCT | 281 |

Preparation of Immunoconjugates

The resulting DNA sequences were subcloned into mammalian expression vectors (one for the light chain and one for the heavy chain/fusion protein) under the control of the MPSV promoter and upstream of a synthetic polyA site, each vector carrying an EBV OriP sequence.

Immunoconjugates as applied in the examples below were produced by co-transfecting exponentially growing HEK293-EBNA cells with the mammalian expression vectors using a calcium phosphate-transfection. Alternatively, HEK293 cells growing in suspension were transfected by polyethylenimine (PEI) with the expression vectors, or stably transfected CHO cell pools were used. While 3F2 and 4G8 based FAP-targeted Fab-IL2-Fab constructs can be purified by affinity chromatography using a protein A matrix, 2B10 based TNC A2-targeted Fab-IL2-Fab constructs have to be purified by affinity chromatography on a protein G matrix.

Briefly, TNC A2-targeted 2B10 Fab-IL2-Fab was purified from supernatants by one affinity step (protein G) followed by size exclusion chromatography (Superdex 200, GE Healthcare). The protein G column was equilibrated in 20 mM sodium phosphate, 20 mM sodium citrate pH 7.5, supernatant was loaded, and the column was washed with 20 mM sodium phosphate, 20 mM sodium citrate, pH 7.5. Fab-IL2-Fab was eluted with 8.8 mM formic acid pH 3. The eluted fractions were pooled and polished by size exclusion chromatography in the final formulation buffer: 25 mM potassium phosphate, 125 mM sodium chloride, 100 mM glycine pH 6.7. FIG. 53 shows the exemplary results from purification and analytics.

FAP-targeted 3F2 Fab-IL2-Fab or 4G8 Fab-IL2-Fab were purified by a similar method composed of one affinity step (protein A) followed by size exclusion chromatography (Superdex 200, GE Healthcare). The protein A column was equilibrated in 20 mM sodium phosphate, 20 mM sodium citrate pH 7.5, supernatant was loaded, and the column was washed with 20 mM sodium phosphate, 20 mM sodium citrate, 500 mM sodium chloride, pH 7.5, followed by a wash with 13.3 mM sodium phosphate, 20 mM sodium citrate, 500 mM sodium chloride, pH 5.45. A third wash with 10 mM MES, 50 mM sodium chloride pH 5 was optionally performed. Fab-IL2-Fab was eluted with 20 mM sodium citrate, 100 mM sodium chloride, 100 mM glycine, pH 3. The eluted fractions were pooled and polished by size exclusion chromatography in the final formulation buffer: 25 mM potassium phosphate, 125 mM sodium chloride, 100 mM glycine pH 6.7.

Example 10

Construction of Additional Anti-FAP Affinity Maturation Libraries (Based on Clones 3F2, 3D9, 4G8, 4B3 and 2C6)

Four additional affinity maturation libraries were constructed on the basis of pre-selected cross-reactive antibodies from the first affinity-maturation campaign of anti-FAP antibodies, namely clones 3F2, 3D9, 4G8, 4B3 and 2C6 (see SEQ ID NOs: 17 and 21 of Table 3 corresponding to the variable region sequences of 3F2; SEQ ID NOs: 23 and 25 of Table 3 corresponding to the variable region sequences of 3D9; SEQ ID NOs: 33 and 35 of Table 3 corresponding to the variable region sequences of 4B3; SEQ ID NOs: 41 and 43 of Table 3 corresponding to the variable region sequences of 2C6). More precisely, the four libraries were based on 1) anti-FAP clones 3F2, 4G8 and 4B3 ($V_H$ library, randomized in CDRs 1 and 2 of variable heavy chain, i.e. H1/H2 library), 2) anti-FAP clones 3D9 and 2C6 ($V_L$ library, randomized in CDRs 1 and 2 of variable light chain, i.e. L1/L2 library), 3) anti-FAP clone 3F2 (L3 library with soft randomization in CDR3 of light chain, i.e. L3 library) and 4) anti-FAP clone 3F2 (H3 library with soft randomization in CDR3 of heavy chain, i.e. H3 library). The first two libraries were constructed exactly the same way as outlined for the first affinity-maturation campaign of anti-FAP antibodies, for the L1/L2 and H1/H2 libraries, respectively. In contrast, for the L3 and H3 affinity-maturation libraries based on clone 3F2, two new primers were used to introduce soft randomization in L3 (AM_3F2_DPK22_L3_ba: CACTTTGGTCCCCTGGCCGAACGT CGGGGGAAGCATAATACCCCT-GCTGACAGTAATACACTGC with underlined bases being 60% given base and 40% mixture N (mixture of the four nucleotides A, C, G, and T)) and H3 (AM_3F2_DP47_H3_fo: GGCCGTATATTACTGTGCG AAA GGGTGG TTT GGTGGT TTT AAC TACTGGGGCCAAG-GAAC with underlined bases being 60% given base and 40% mixture N, bases in italics being 60% given base and 40% G, as well as underlined bases in italics being 60% given base and 40% mixture K (mixture of the two nucleotides G and T)) of the parental clone. Library sizes were as follows:

H1/H2 library ($1.13\times10^{10}$), L1/L2 library ($5.6\times10^{9}$), L3 library ($2.3\times10^{10}$) and H3 library ($2.64\times10^{10}$).

Example 11

Selection of Affinity-Matured Anti-FAP Clones

Selections were carried out against the ectodomain of human and murine fibroblast activating protein (FAP) which were cloned upstream a 6×-lysine and a 6×-his tag (see SEQ ID NOs: 53 and 55 of Table 5). Prior to selections, the antigens were coated into immunotubes at a concentration of either 1 μg/ml, 0.2 μg/ml or 0.02 μg/ml, depending on the library and round of selection. Selections and ELISA-based screenings were carried out as described for the first affinity-maturation campaign of anti-FAP antibodies. Secondary screenings were carried out using a ProteOn XPR36 biosensor (Biorad), and kinetic rate constants and affinities were determined analyzing affinity-purified Fab preparations on the same instrument. The following affinity-matured clones were identified: 19G1 (see SEQ ID NOs: 121 and 123 of Table 3), 20G8 (see SEQ ID NOs: 125 and 127 of Table 3), 4B9 (see SEQ ID NOs: 129 and 131 of Table 3), 5B8 (see SEQ ID NOs: 133 and 135 of Table 3), 5F1 (see SEQ ID NOs: 137 and 139 of Table 3), 14B3 (see SEQ ID NOs: 141 and 143 of Table 3), 16F1 (see SEQ ID NOs: 145 and 147 of Table 3), 16F8 (see SEQ ID NOs: 149 and 151 of Table 3), O3C9 (see SEQ ID NOs: 153 and 155 of Table 3), 22A3 (see SEQ ID NOs: 165 and 167 of Table 3) and 29B11 (see SEQ ID NOs: 169 and 171 of Table 3) (all these clones were selected from the H1/H2 library and are derived from parental clone 3F2), O2D7 (see SEQ ID NOs: 157 and 159 of Table 3) (selected from the L3 library based on parental clone 3F2), and 28H1 (see SEQ ID NOs: 161 and 163 of Table 3) and 23C10 (see SEQ ID NOs: 173 and 175 of Table 3) (these two clones were selected from the H1/H2 library and are derived from parental clone 4G8).

FIGS. 21-25 show the Surface Plasmon Resonance sensorgrams of the selected affinity matured Fabs against FAP and Table 15 gives the respective affinities. The selected Fabs span a high affinity range in the pM to nM range and are cross-reactive for human (hu) and murine (mu) FAP, as well as Cynomolgus (cyno) FAP as determined for selected clones. The affinity matured anti-FAP Fabs were converted into the Fab-IL2-Fab format. Specificity of binding was shown by lack of binding to DPPIV as close homologue of FAP, expressed on HEK293 or CHO cells.

TABLE 15

Summary of kinetic equilibrium constants ($K_D$) of affinity-matured anti-FAP antibodies as Fab fragments (monovalent binding).

| antibody | affinity ($K_D$) to hu FAP [pM] | affinity ($K_D$) to mu FAP [pM] | affinity ($K_D$) to cyno FAP [pM] |
|---|---|---|---|
| 19G1 | 76 | 2600 | n.d. |
| 20G8 | 69 | 2800 | n.d. |
| 4B9 | 157 | 3300 | n.d. |
| 5B8 | 690 | 3200 | n.d. |
| 5F1 | 243 | 4100 | n.d. |
| 14B3 | 377 | 3800 | n.d. |
| 16F1 | 193 | 3400 | n.d. |
| 16F8 | 301 | 3800 | n.d. |
| O3C9 | 160 | 3700 | n.d. |
| O2D7 | 619 | 8300 | n.d. |
| 28H1 | 200 | 9 | 3600 |
| 22A3 | 34 | 655 | 522 |
| 29B11 | 35 | 436 | 23 |
| 23C10 | 1600 | 125 | 990 |

Example 12

Construction of Anti-TNC A2 Affinity Maturation Libraries (Based on Clone 2B10)

An affinity maturation library was constructed on the basis of a pre-selected antibody from the primary TNC A2 selections. More precisely, it was based on parental clone 2B10 and consisted of two sub-libraries: 1) $V_L$ sub-library, randomized in CDR1 and CDR2 of the light chain (L1/L2) and 2) $V_H$ sub-library, randomized in CDR1 and CDR2 of the heavy chain (H1/H2). These sub-libraries were pooled upon transformation. Each of these sub-libraries was constructed by four subsequent steps of amplification and assembly. For L1/L2 libraries: 1) amplification of fragment 1 (LMB3—AM_Vk1A30_L1_ba) and fragment 2 (RJH50 (Vk1A30_L1/L2fo)—RJH51 (Vk1A30_BsiWI_ba)), 2) assembly of fragments 1 and 2 using outer primers LMB3 and RJH51 (Vk1A30_BsiWI_ba) to create the template for 3) amplification of fragment 3 (LMB3—AM_Vk1A30_L2_ba) and fragment 4 (RJH52 (Vk1A30_L2/L3)—RJH51 (Vk1A30_BsiWI_ba)) and 4) final assembly of fragments 3 and 4 using the same outer primers as above. For H1/H2 libraries: 1) amplification of fragment 1 (RJH53—AM_DP88_H1_ba_opt) and fragment 2 (RJH54(DP88_H1/H2_Jo)—MS52), 2) assembly of fragments 1 and 2 using outer primers RJH53 and MS52 to create the template for 3) amplification of fragment 3 (RJH53—AM_DP88_H2_ba) and fragment 4 (RJH55 (DP88_H2H3_fo)—MS52) and 4) final assembly of fragments 3 and 4 using the same outer primers as above. Final assembly products have been digested NcoI/BsiWI for $V_L$ sub-libraries and MunI and NheI for $V_H$ sub-libraries and were cloned in similarly digested acceptor vectors. Library size resulted in $1.16\times10^{10}$ independent clones.

TABLE 16

Primers used in L1/L2 Affinity Maturation Libraries for Anti-TNC A2 binder 2B10

| | |
|---|---|
| LMB3 | CAGGAAACAGCTATGACCATGATTAC |
| AM_Vk1A30_L1_ba | CCTGGCTTCTGCTGGTACCAGCCTAAA**TCATT**A**CG**AATG**CC**CTGACTTGCCCGGCAGGTGATG |
| RJH50(Vk1A30_L1/L2_fo) | GCTGGTACCAGCAGAAGCCAGGGAAAG |
| RJH51(Vk1A30_BsiWI_ba) | GGTGCAGCCACCGTACGCTTGATCTC |
| AM_Vk1A30_L2_ba | CTTGATGGGACGCCACTCTGCAAA**CT**G**GA**C**GC**A**GC**A**TA**GATCAGGCGCTTAGGGGCTTTCC |
| RJH52(Vk1A30_L2/L3) | TTGCAGAGTGGCGTCCCATCAAGGTTC |

Underline: 60% original base and 40% randomization as V
Bold: 60% original base and 40% randomization as N

TABLE 17

| Primers used in H1/H2 Affinity Maturation Libraries for Anti-TNC A2 binder 2B10 | |
|---|---|
| RJH53 | CATCAGGGCCTGAGCTCGCCCGTCAC |
| AM_DP88_H1_ba_opt | GTCCAGGGGCCTGTCGCACCCAGCTTATAGCGTAGCTGCTGAATGTGCCTCCGGAGGCCTTG |
| RJH54(DP88_H1/H2_fo) | ATAAGCTGGGTGCGACAGGCCCCTGGAC |
| MS52 | GAAGACCGATGGGCCTTTGGTGCTAG |
| AM_DP88_H2_ba | GACCCTGCCCTGGAACTTCTGTGCGTAGTTTGCGGTACCAAAGATAGGGATGATCCCTCCCATCCACTCGAGCCCTTGTCCAG |
| RJH55 (DP88_H2H3_fo) | TACGCACAGAAGTTCCAGGGCAGGGTCAC |

Underligned: 60% original base and 40% randomization as V
Bold: 60% original base and 40% randomization as N

Example 13

Selection of Affinity-Matured Anti-TNC A2 Clones

Selections were carried out against *E. coli* expressed human TNC A2 which was cloned upstream an avi-tag and 6×his-tag (see SEQ ID NO: 57 of Table 5). The antigen was biotinylated in vivo upon expression. Selections have been carried out in solution as described for the primary TNC A2 selections using decreasing concentrations of human TNC A2 ranging from 100 to 2 nM. After identification of affinity-matured clones by ELISA, secondary screenings were carried out using a ProteOn XPR36 biosensor (Biorad) and kinetic rate constants and affinities were determined analyzing affinity-purified Fab preparations on the same instrument. The following affinity-matured clones were identified: 2B10_O1F7 (see SEQ ID NOs: 201 and 203 of Table 3), 2B10__6H10 (see SEQ ID NOs: 205 and 207 of Table 3), 2B10_C3A6 (see SEQ ID NOs: 185 and 187 of Table 3), 2B10_D1A2 (see SEQ ID NOs: 189 and 191 of Table 3), and 2B10_O7D8 (see SEQ ID NOs: 197 and 199 of Table 3) (all of these are derived from the $V_L$ sub-library), as well as 2B10_C3B6 (see SEQ ID NOs: 177 and 179 of Table 3) and 2B10__6A12 (see SEQ ID NOs: 181 and 183 of Table 3) (these two clones are derived from the $V_H$ sub-library). Moreover, for clone 2B10_D1A2, a V32D mutant was generated (see SEQ ID NOs: 193 and 195 of Table 3) (numbering according to Kabat).

FIG. 26 shows the Surface Plasmon Resonance sensorgrams of the selected affinity matured Fabs against TNC A2 and Table 18 gives the respective affinities. The selected Fabs span a high affinity range in the pM range.

TABLE 18

Summary of kinetic equilibrium constants ($K_D$) of affinity-matured anti-TNC A2 antibodies as Fab fragments (monovalent binding).

| antibody | affinity (KD) to hu TNC A2 [pM] |
|---|---|
| 2B10__C3B6 | 191 |
| 2B10__6A12 | 290 |
| 2B10__C3A6 | 497 |
| 2B10__O7D8 | 147 |
| 2B10__O1F7 | 56 |
| 2B10__6H10 | 810 |

Example 14

Purification of 2B10, 3F2 and 4G8-Based Fab-IL2-Fab Constructs

Another purification method (in addition to the one described in Example 9) was developed for 2B10, 3F2 and 4G8 based Fab-IL2-Fab constructs. While 3F2 and 4G8 based Fab-IL2-Fab constructs can be purified by affinity chromatography using a protein A matrix (e.g. MabSelect Sure), 2B10 based Fab-IL2-Fab constructs have to be purified by affinity chromatography on a protein G matrix. The purification procedure is based on the following four steps:

1. Affinity chromatography with MabSelect Sure or protein G
2. Low pH hold for retroviral inactivation
3. Anion exchange chromatography—CaptoQ chromatography, to remove DNA
4. Cation exchange chromatography—SP Sepharose FF chromatography, to remove aggregates For removal of aggregates in small scale, size exclusion chromatography on a Superdex 200 column (GE Healthcare) can be alternatively used.

Figure 27:
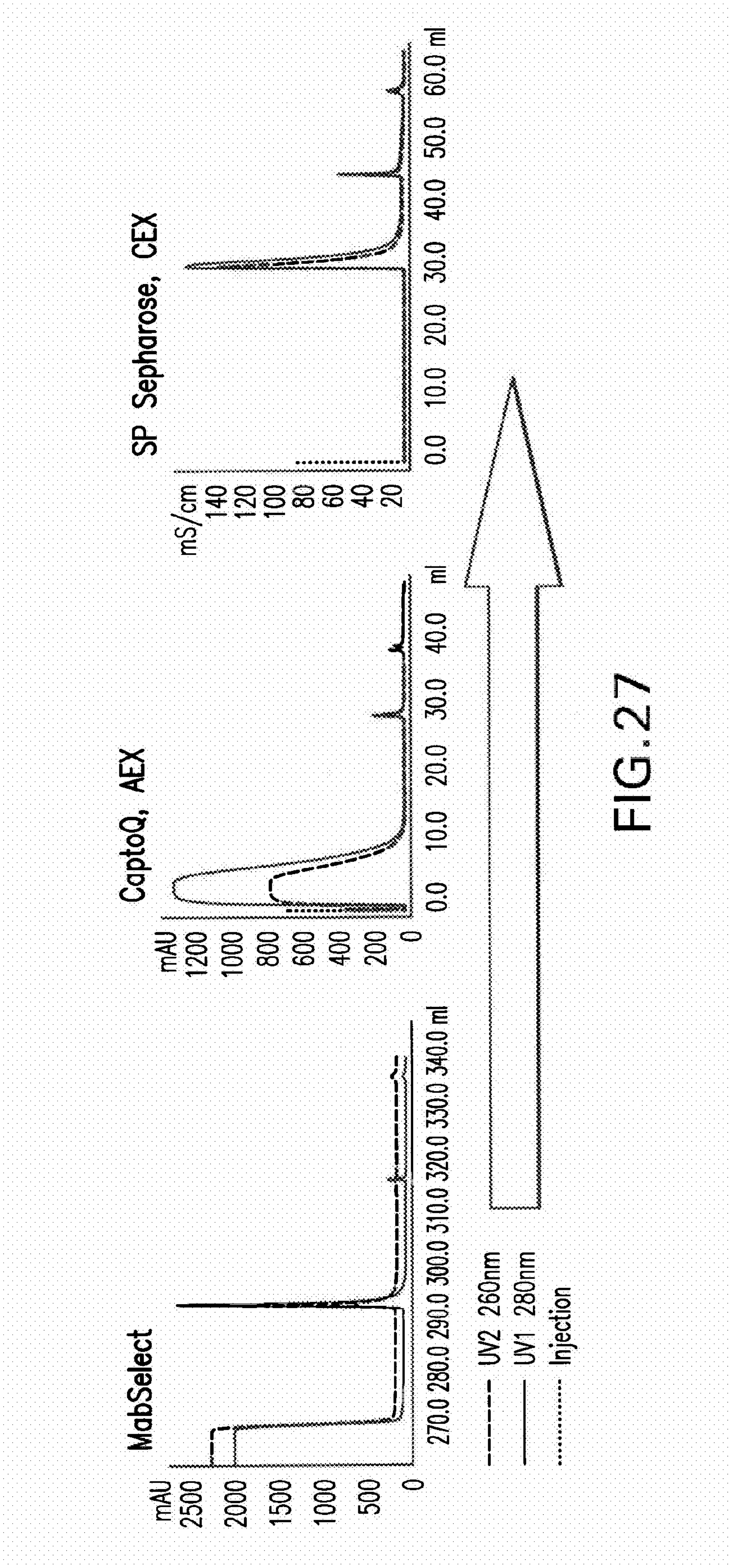

An example of the purification procedure is given subsequently for 3F2-based Fab-IL2-Fab. In a first step supernatant from transiently PEI-transfected HEK293 cells in Freestyle medium (Invitrogen) was adjusted to pH 7 and applied to a MabSelect protein A column (GE Healthcare), washed with 100 mM $NaPO_4$, 250 mM NaCl pH 7 and eluted with 8.8 mM sodium formiate pH 3. Selected fractions were exchanged in wash buffer and applied to a CaptoQ column (GE Healthcare), washed with 10 mM $NaPO_4$, 40 mM NaCl pH 6.5 and eluted with 2 M NaCl. The flowthrough was adjusted to pH 5 and applied to a SP Sepharose FF column (GE Healthcare), washed with 25 mM sodium acetate, 25 mM NaCl, pH 5 and eluted with 25 mM sodium acetate, 300 mM NaCl pH 5. Fractions were exchanged into final formulation buffer. FIG. 27 shows an overview of the purification procedure.

Figure 28A:
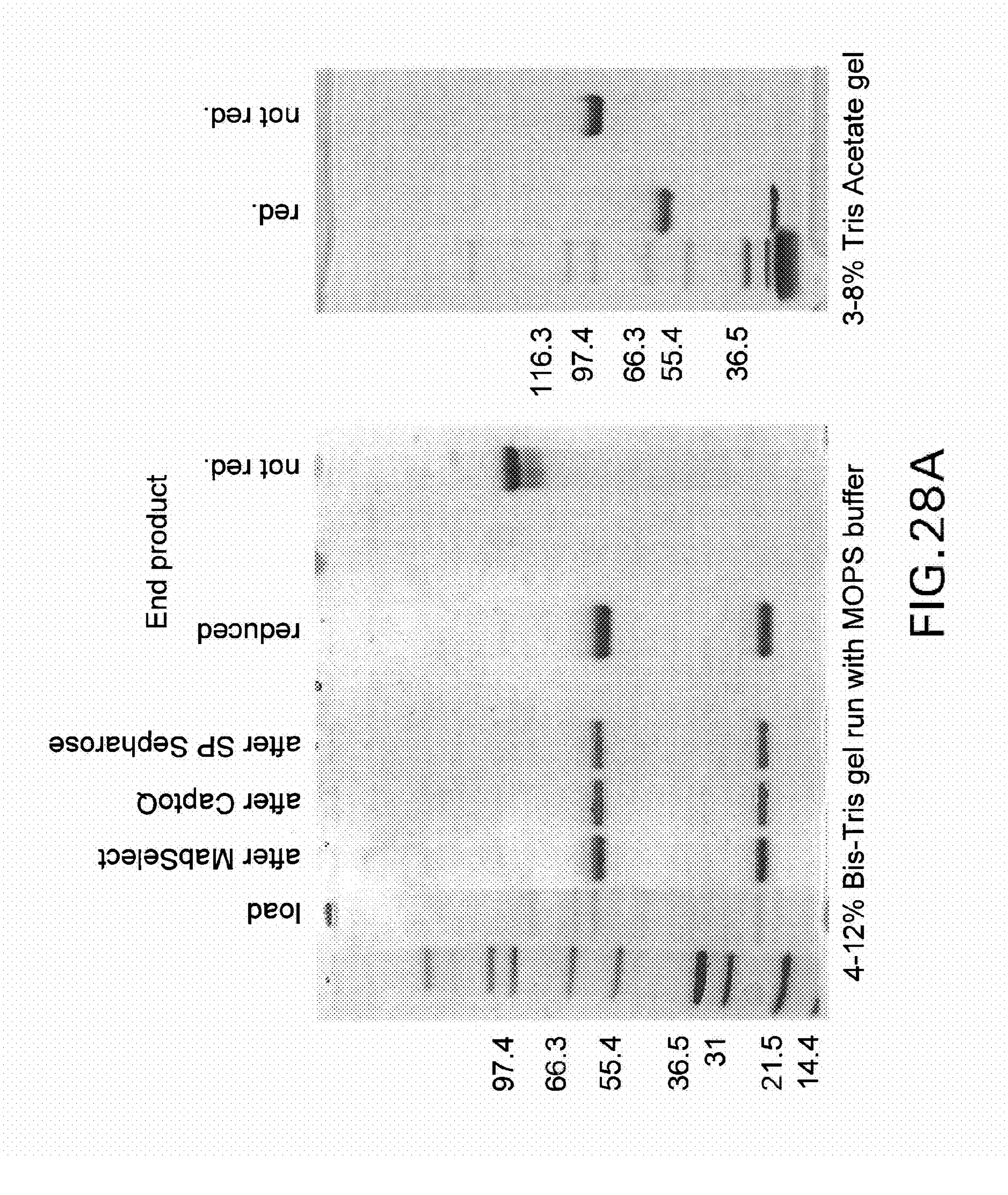
Figure 28B:
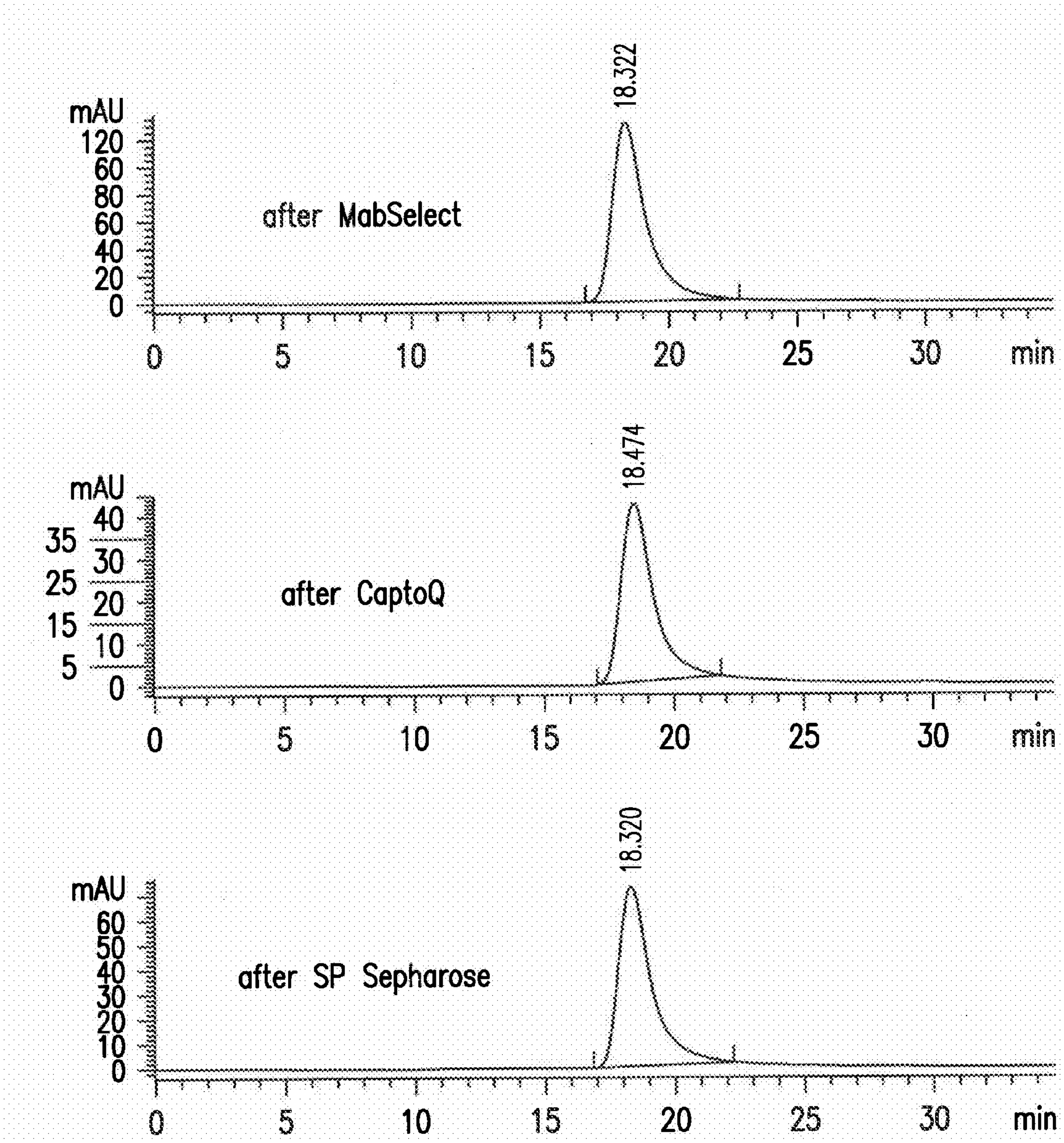
Figure 28C:
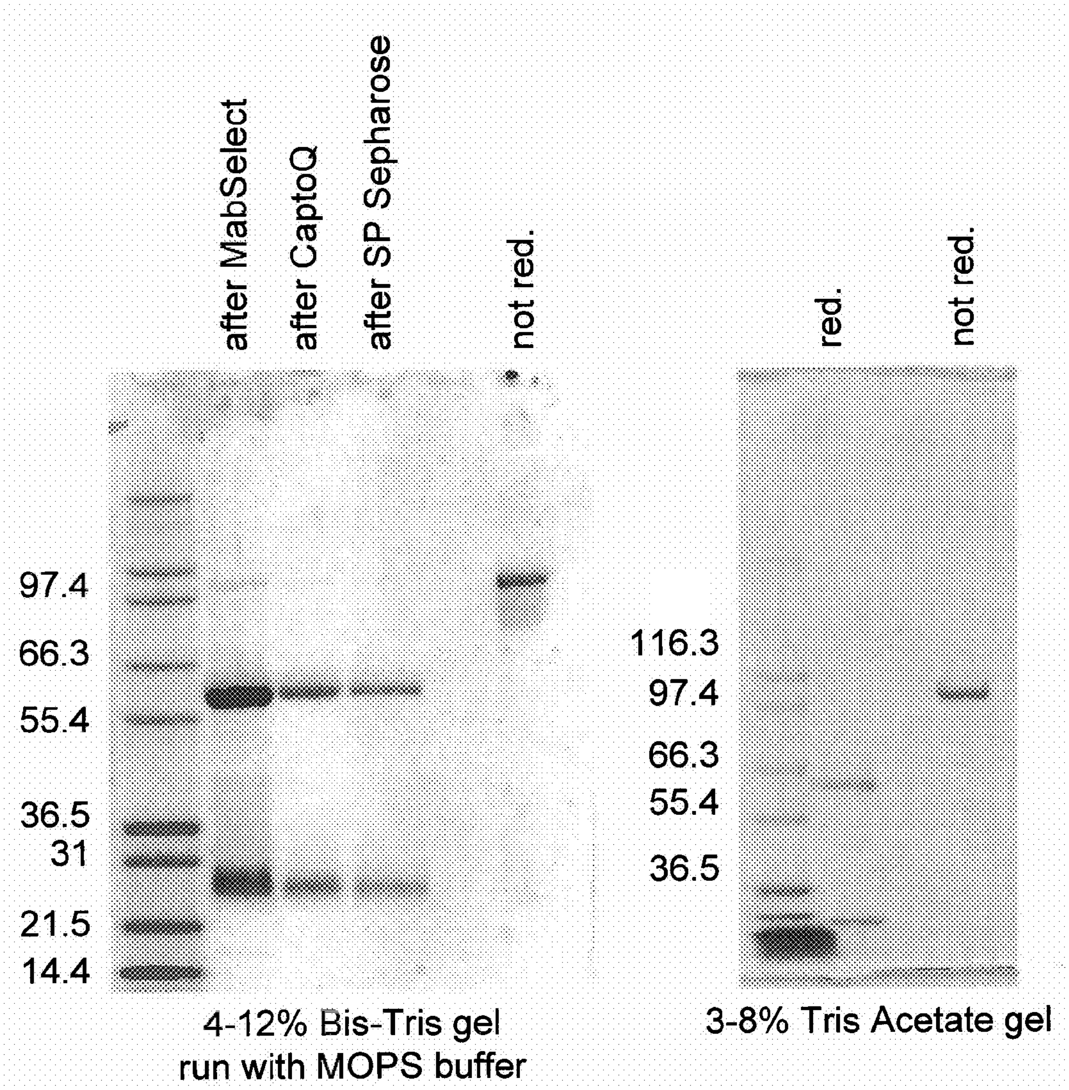
Figure 28D:
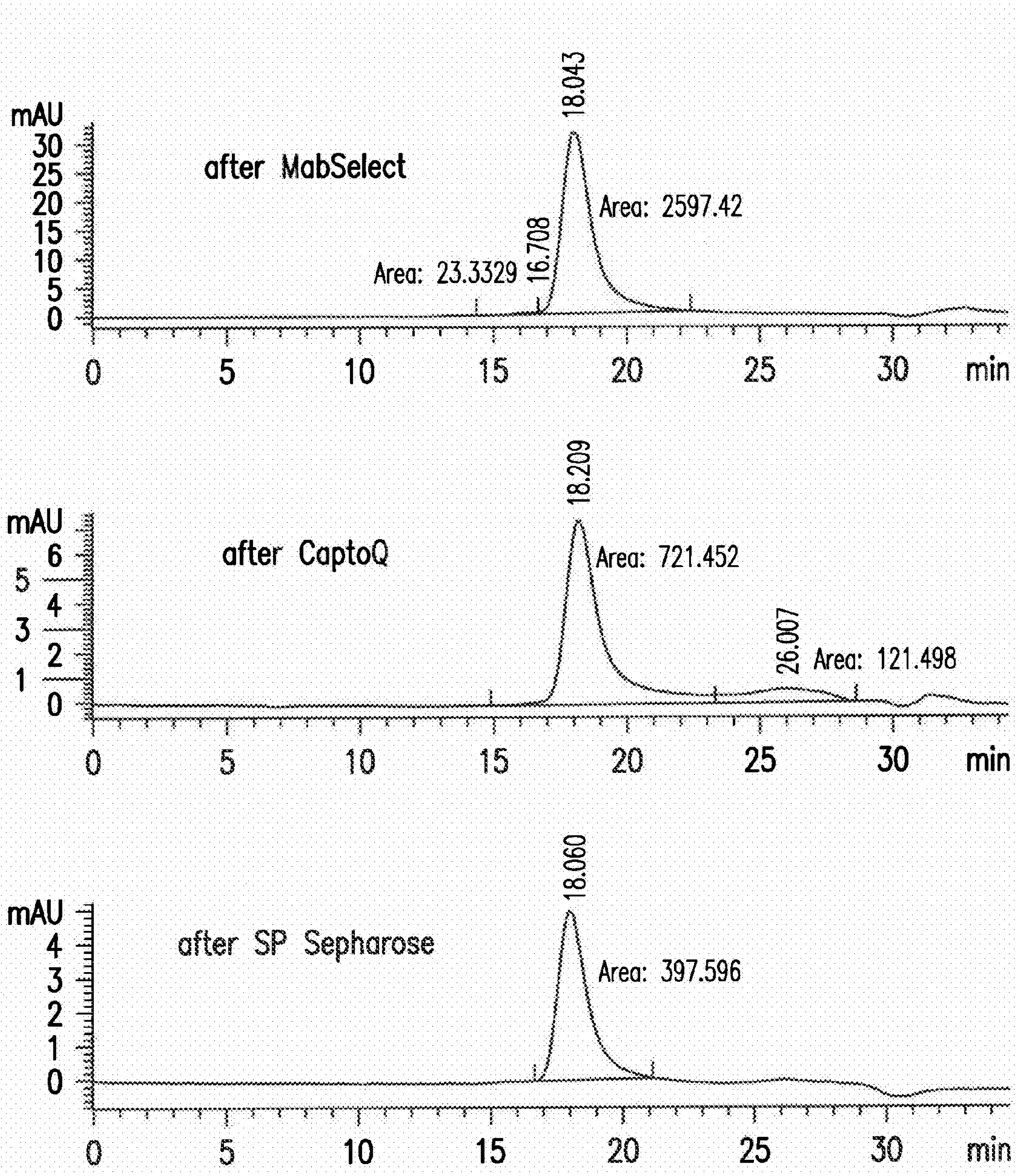

The purified 3F2-based Fab-IL2-Fab was pure after purification (FIG. 28A) and contained no aggregates (FIG. 28B). The described purification procedure was applied to 4G8-based Fab-IL2-Fab. 4G8-based Fab-IL2-Fab behaved similarly to the 3F2-based Fab-IL2-Fab. The purified material was pure after purification and contained no aggregates (FIG. 28, C-D).

Purification was performed for the Fab-IL2-Fab format with 2B10 (TNC A2 binder) as Fab fragment. In a first step supernatant from transiently PEI-transfected HEK293 cells in Freestyle medium (Invitrogen) was adjusted to pH 7 and applied to a protein G column (GE Healthcare), washed with 100 mM $NaPO_4$, 250 mM NaCl pH 7, and eluted with 8.8 mM Na formiate pH 3. Selected fractions were exchanged in wash buffer and applied to a CaptoQ column (GE Healthcare), washed with 10 mM $NaPO_4$, 40 mM NaCl pH 6.5 and eluted with 2 M NaCl. The flowthrough was adjusted to pH 5 and applied to a SP Sepharose FF column (GE Healthcare), washed with 25 mM sodium acetate, 25 mM NaCl, pH 5 and eluted with 25 mM sodium acetate, 300 mM NaCl pH 5. Fractions were exchanged into final formulation buffer.

Figure 29A:
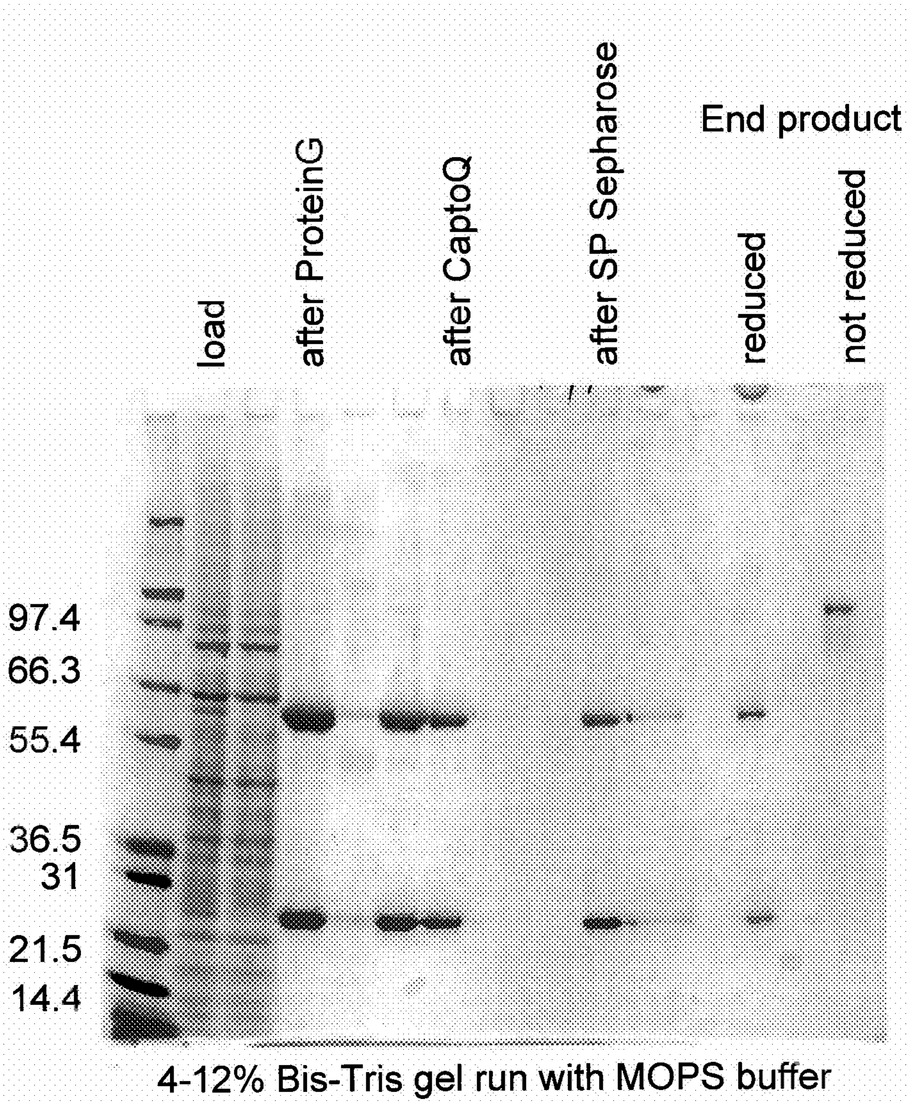
Figure 29B:
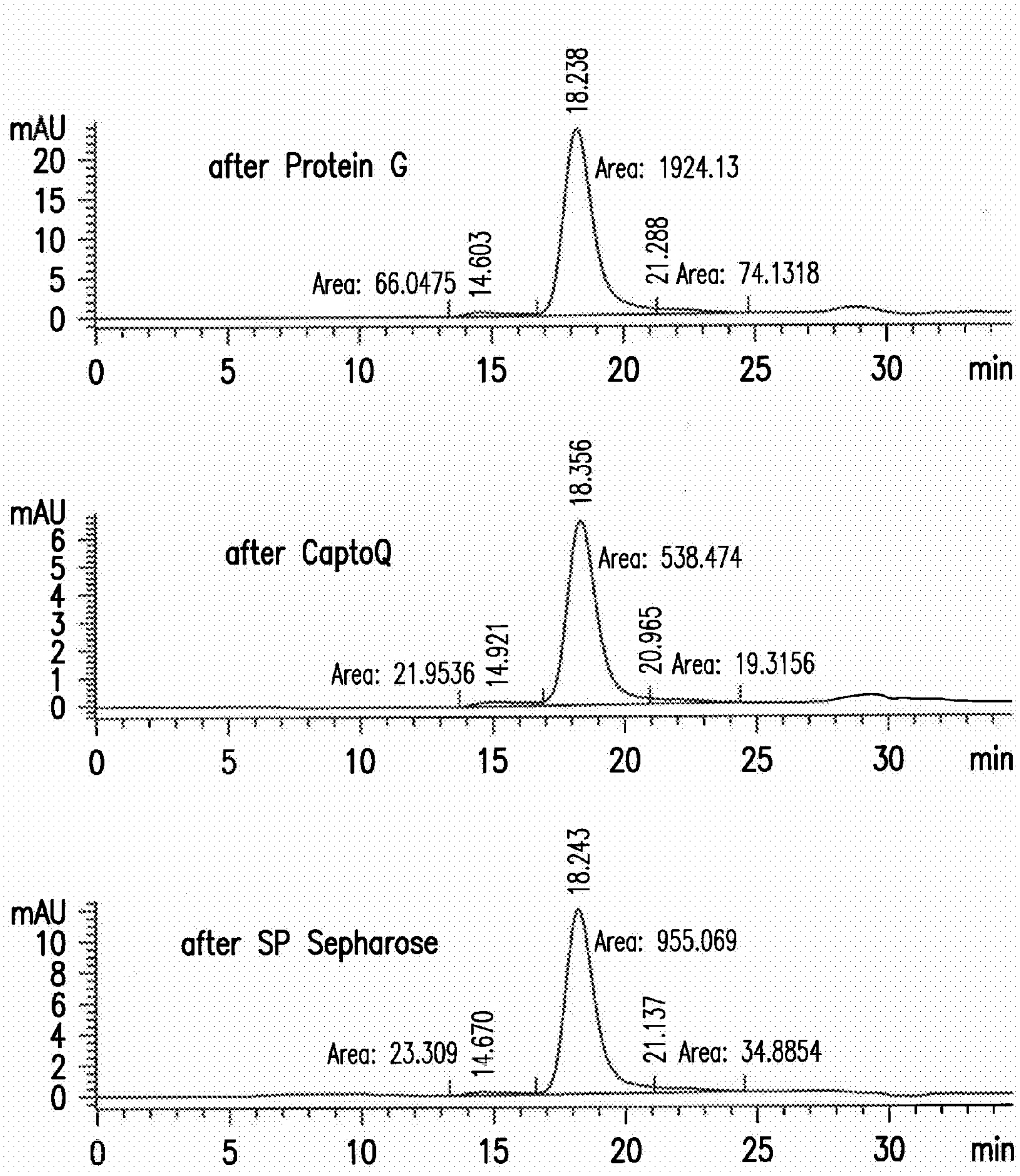

FIG. 29 shows the results from (A) the analytical characterization of the product by SDS-PAGE (NuPAGE Novex Bis-Tris Mini Gel, Invitrogen, MOPS running buffer, reduced and non-reduced) and (B) analytical size exclusion chromatography of the product after each of the three purification steps. 2.3% aggregates were detected in the final product.

Example 15

Stability Testing

Figure 30A:
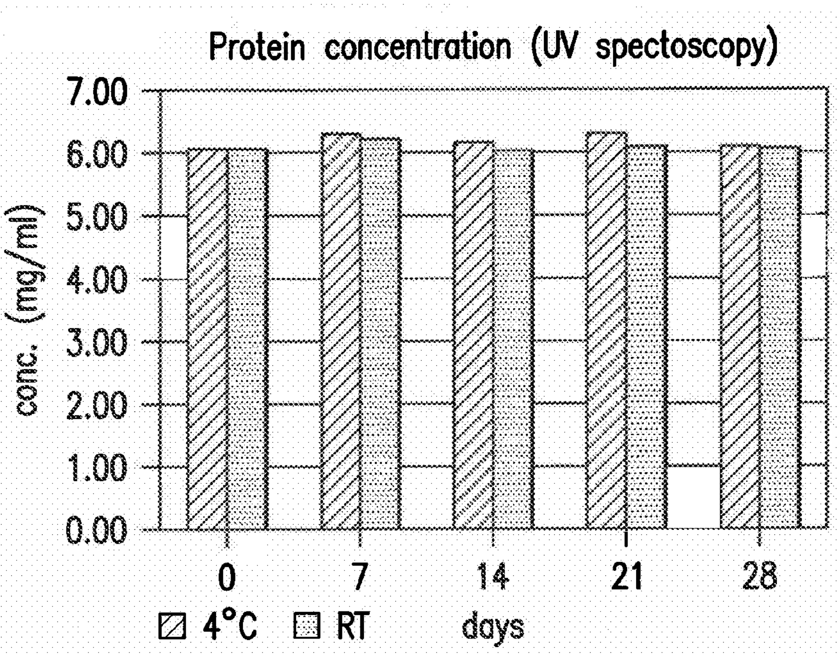
Figure 30B:
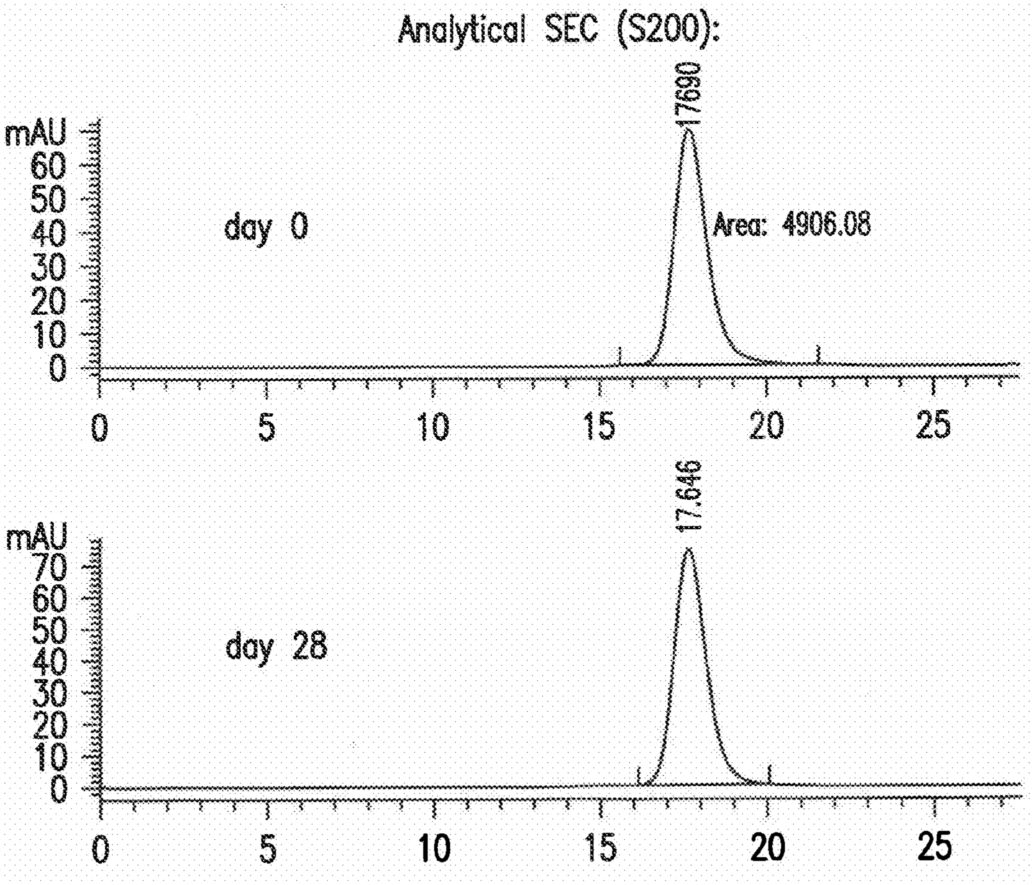
Figure 31A:
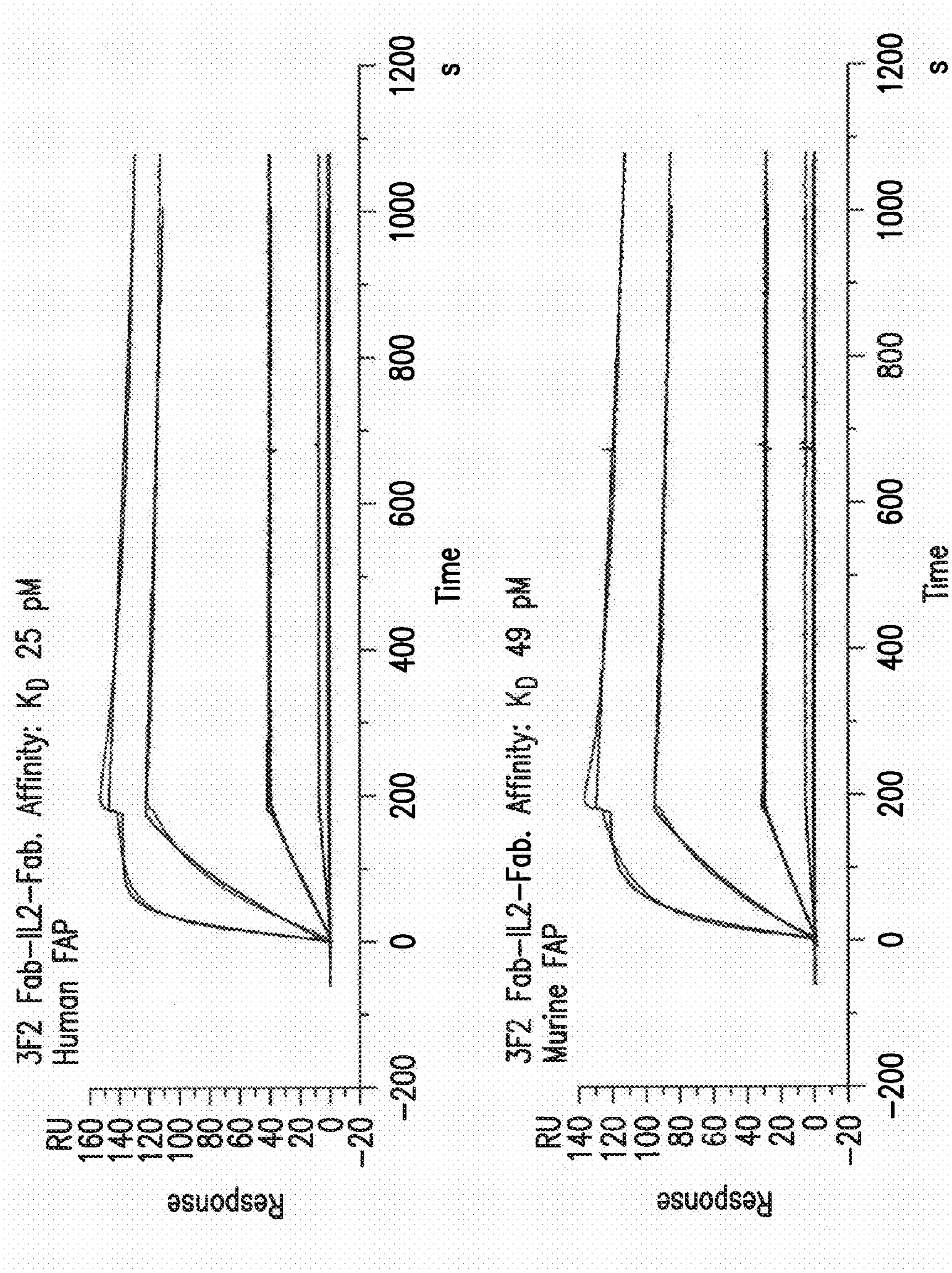
FIGS. 31A and 31B show SPR-based kinetic analyses of FAP-targeted 3F2 Fab-IL2-Fab immunoconjugates for human FAP (31A), murine FAP (31A) and Cynomolgus (cyno) FAP (31B) and human IL-2 receptor-β/γ (IL2R bg) (31B) as determined by Surface Plasmon Resonance. Smooth lines represent a global fit of the data to a 1:1 interaction model.
Figure 31B:
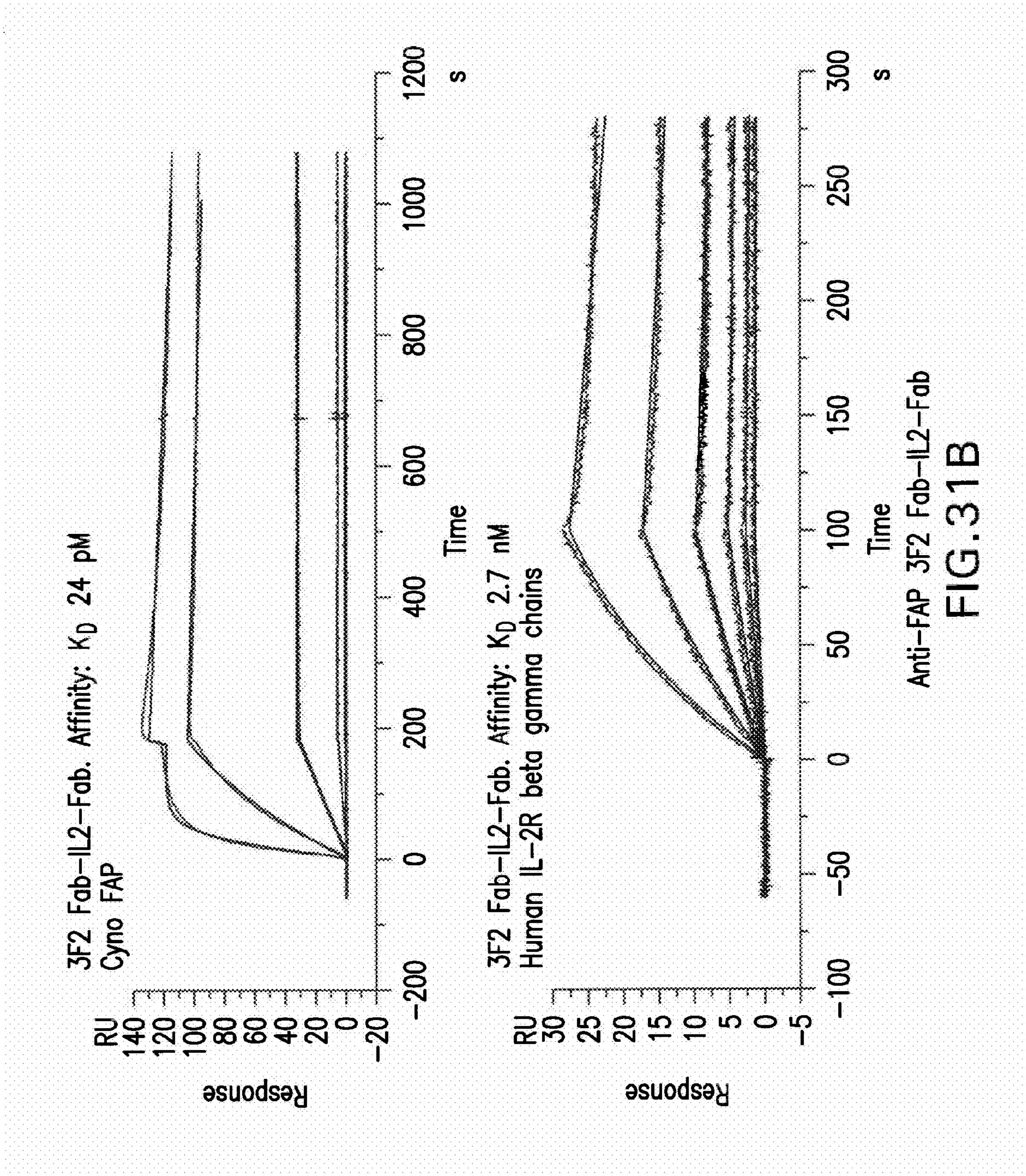
Figure 32:
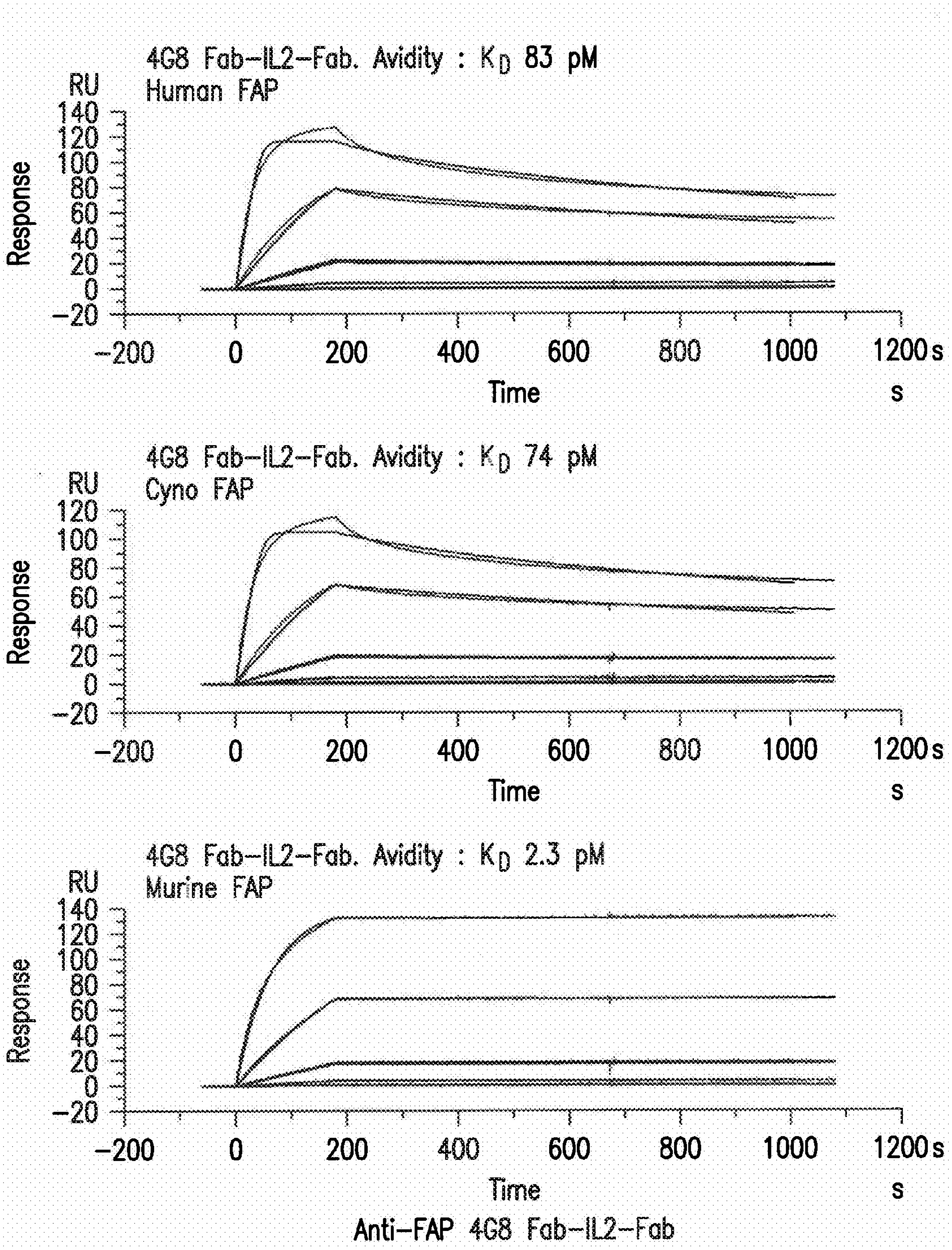
FIG. 32 shows SPR-based kinetic analyses of FAP-targeted 4G8 Fab-IL2-Fab immunoconjugates for human, murine and Cynomolgus (cyno) FAP as determined by Surface Plasmon Resonance. Smooth lines represent a global fit of the data to a 1:1 interaction model.
Figure 33A:
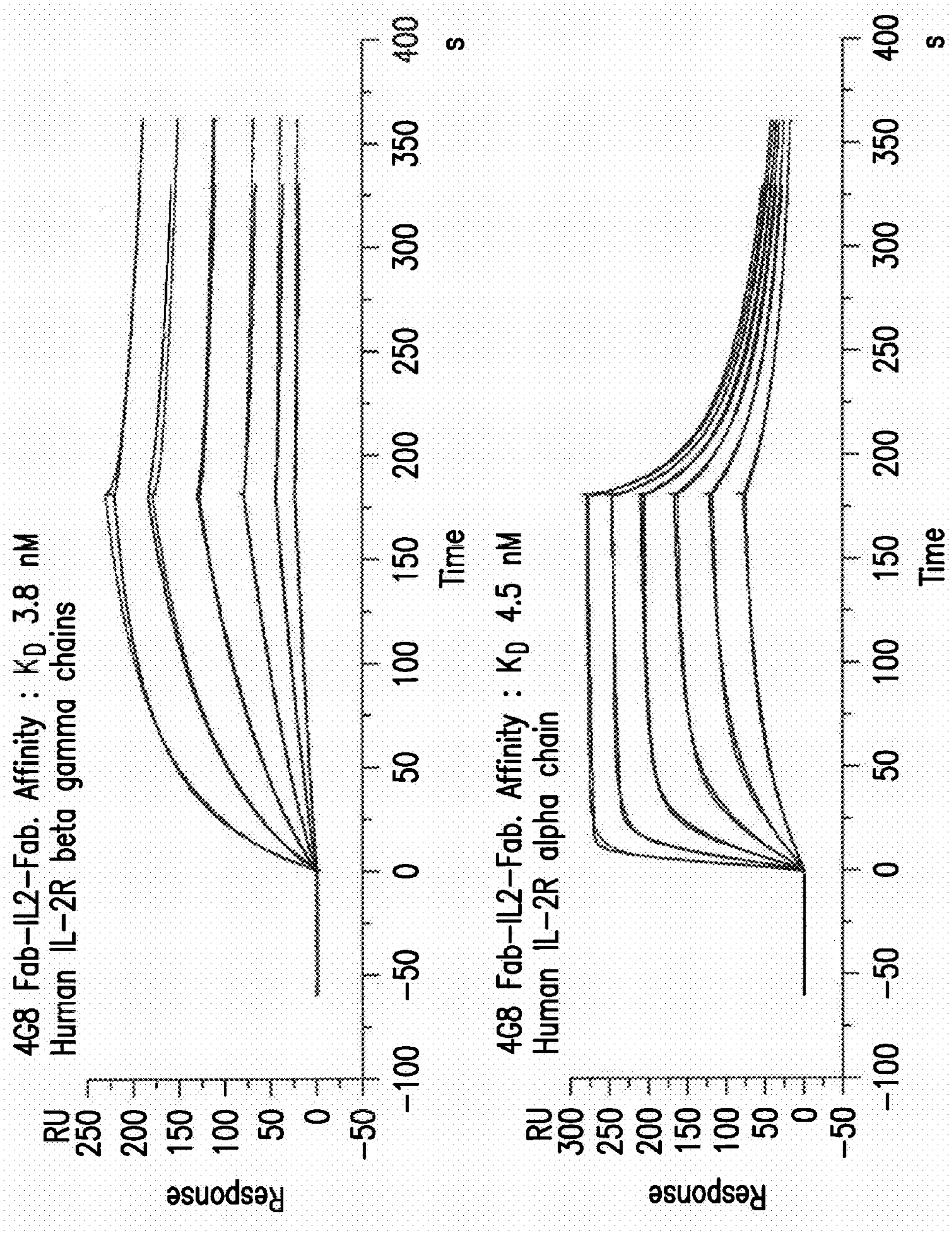
FIGS. 33A and 33B show SPR-based kinetic analyses of FAP-targeted 4G8 Fab-IL2-Fab constructs for human IL-2 receptor β/β and α chains (33A) and murine IL-2 receptor β/β and α chains (33B), as determined by Surface Plasmon Resonance. Smooth lines represent a global fit of the data to a two-state-reaction model.
Figure 33B:
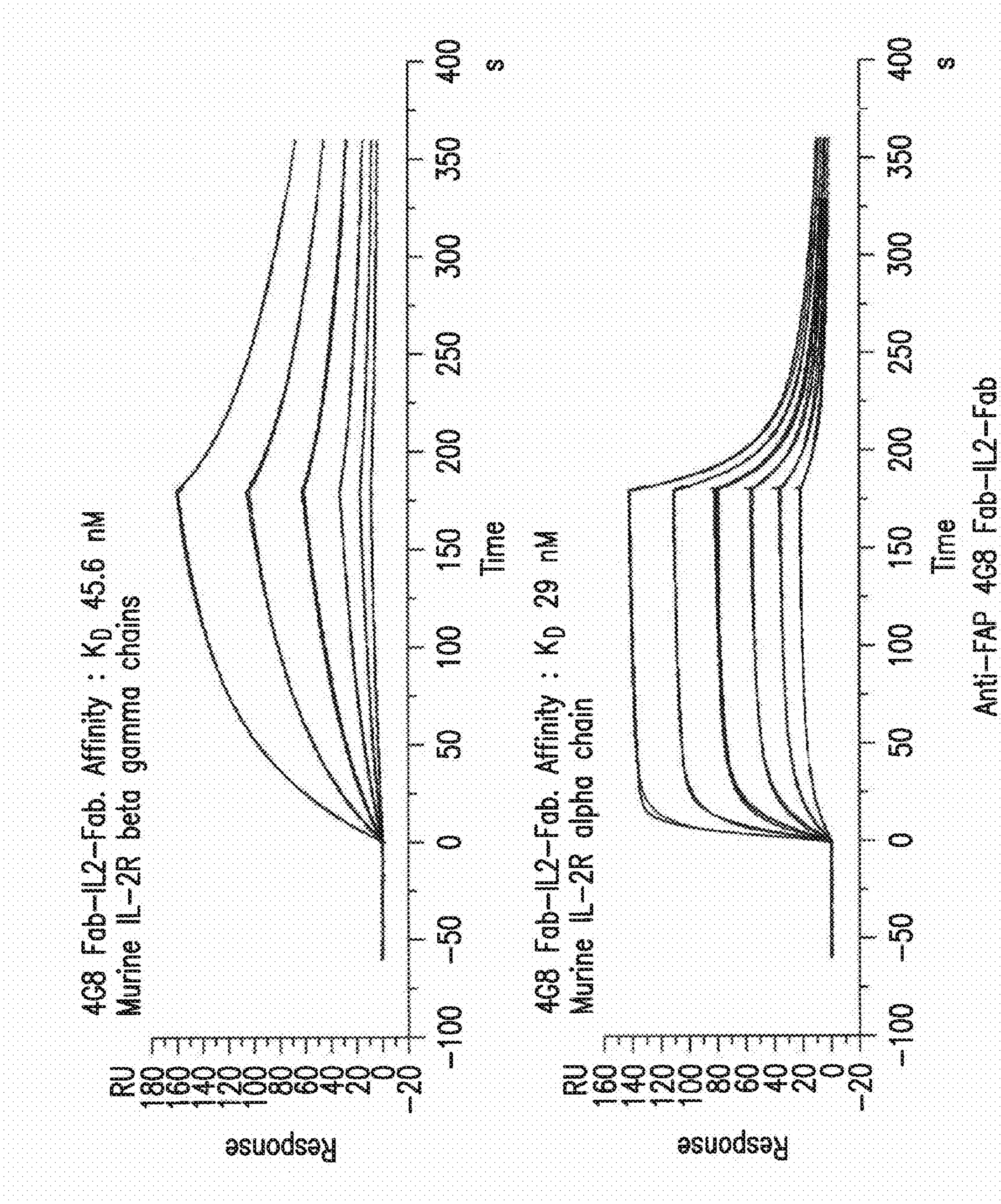
Figure 34A:
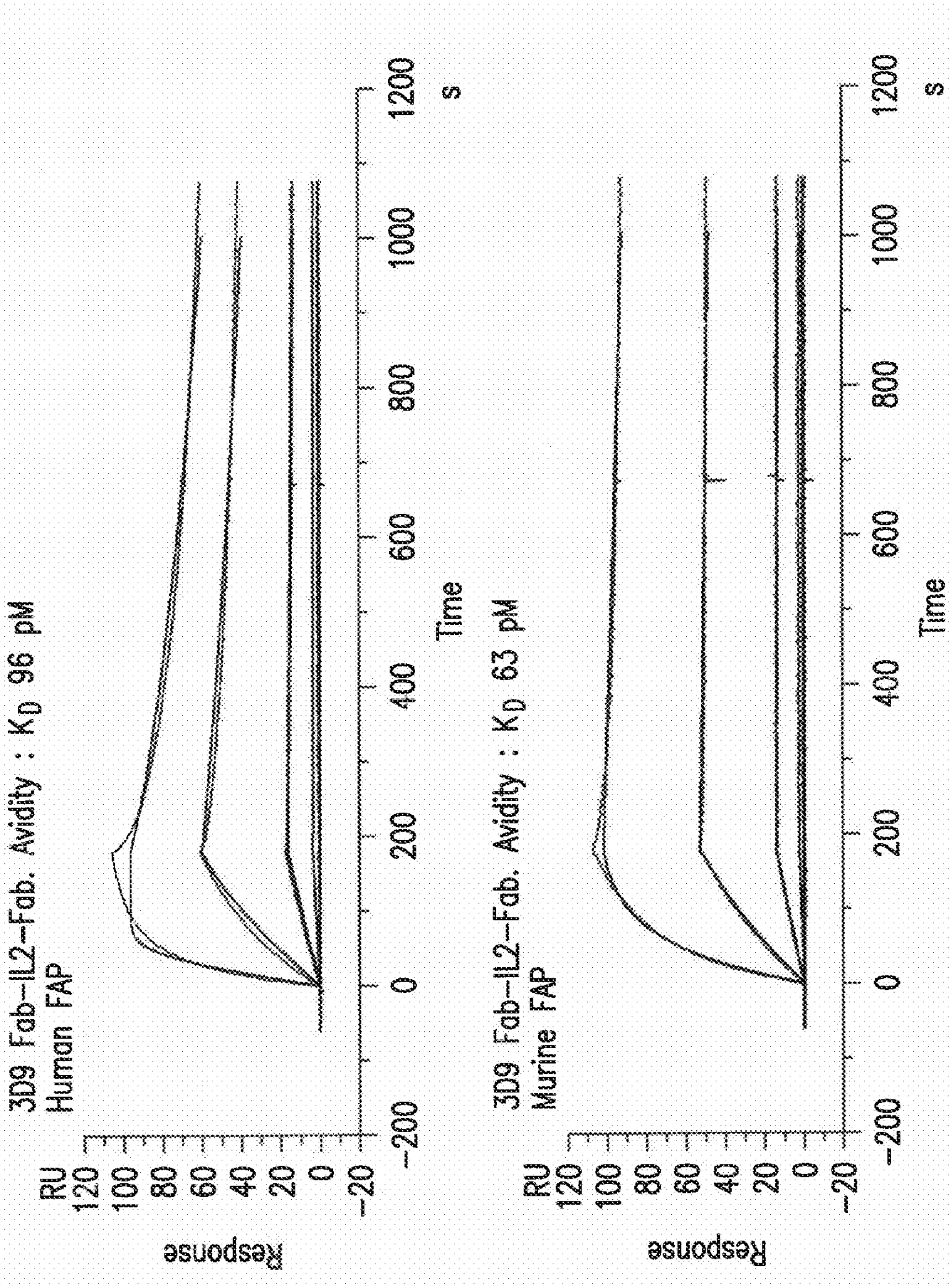
FIGS. 34A and 34B show SPR-based kinetic analyses of FAP-targeted 3D9 Fab-IL2-Fab constructs for human FAP (34A), murine FAP (34A) and Cynomolgus (cyno) FAP (34B) and human IL-2 receptor-β/γ (IL2R bg) (34B) as determined by Surface Plasmon Resonance. Smooth lines represent a global fit of the data to a 1:1 interaction model.
Figure 34B:
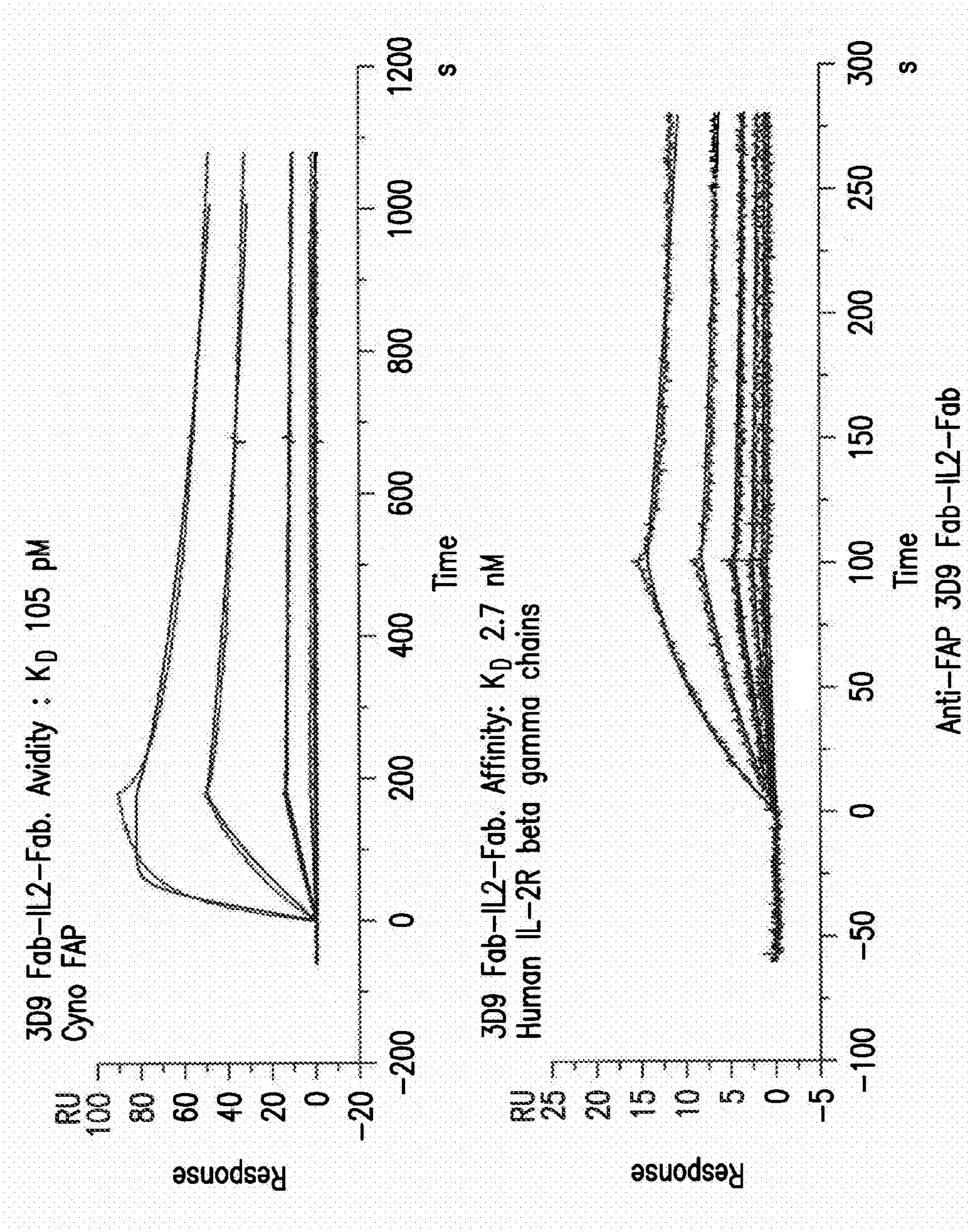

Stability testing was performed for the Fab-IL2-Fab format with the fibronectin Ectodomain-B binder L19 as Fab fragment. For stability tests the Fab-IL2-Fab construct was purified by protein A affinity chromatography with an elution step at pH 3, followed by size exclusion chromatography on a Superdex 200 column (GE Healthcare) as described. Three different buffers were tested and 20 mM histidine HCl, 140 mM NaCl, pH 6.0 was identified as a suitable buffer. Subsequently, L19 Fab-IL2-Fab was formulated in 20 mM Histidine HCl, 140 mM NaCl, pH 6.0 at a concentration of 6.3 mg/ml and stored for four weeks at room temperature and at 4° C. FIG. 30 shows exemplary stability data: Probes were analyzed every week for concentration by UV spectroscopy (FIG. 30A) (after centrifugation to pellet potential precipitated material) and for aggregate content by analytical size exclusion chromatography on a Superdex 200 column (FIG. 30B). The results show that no aggregation and no degradation occured, when the construct was stored at 4° C. or at room temperature for 28 days as well as after a freeze/thaw cycle at 6 mg/ml concentration. These data show that the Fab-IL2-Fab format is highly stable and behaves comparably to IgG antibodies.

Example 16

FAP-Ttargeted Fab-IL2-Fab Binding Affinities by Surface Plasmon Resonance (Biacore)

Binding affinities of the three FAP-targeted Fab-IL2-Fab constructs, 3F2 Fab-IL2-Fab, 4G8 Fab-IL2-Fab and 3D9 Fab-IL2-Fab, were determined by Surface Plasmon Resonance.

For determination of FAP binding, FAP was captured by an immobilized anti-His antibody (Penta His, Qiagen #34660) and the constructs were used as analytes. Temperature of analysis was 25° C. and Fab-IL2-Fab constructs were diluted 1:5 from 10 nM to 3.2 pM. The following measurement parameters were applied: Association time 180 s, dissociation 900 s, flow 90 μl/min. The chip was regenerated with 10 mM glycine pH 2 for 60 s. The curves were fitted with the 1:1 model to get the $K_D$ values (Rmax local, RI=0).

To determine the affinity for IL-2 receptor (IL-2R) chains, the β and γ chains (b/g; knob-into-hole construct) or the α chain (a) of IL-2R were immoblized on the chip and the Fab-IL2-Fab constructs were used as analytes. Temperature of analysis was 25° C. Fab-IL2-Fab constructs 3F2 and 3D9 were diluted 1:2 from 25 nM to 0.78 nM and the following measurement parameters were applied: Association time 100 s, dissociation 180 s, flow 90 μl/min. Regeneration was done with 10 mM glycine pH 1.5 for 20 s. Fab-IL2-Fab constructs 4G8 were diluted from 100 nM to 3.125 nM and the following measurement parameters were applied: Association time 180 s, dissociation 180 s, flow 40 μl/min. Regeneration with 3 M $MgCl_2$ for 30 s.

Table 19 gives a summary of binding affinities of the 3F2 Fab-IL2-Fab, 4G8 Fab-IL2-Fab and 3D9 Fab-IL2-Fab immunoconjugates. Picomolar values of affinity reach the limit of detection of the Biacore. FIGS. 31-34 show the respective Biacore sensorgrams and affinities.

TABLE 19

Summary of kinetic equilibrium constants ($K_D$) of FAP-targeted Fab-IL2-Fab constructs for FAP from different species and IL-2 receptor as determined by Surface Plasmon Resonance

| Construct | Human FAP | Murine FAP | Cynomolgus FAP | Affinity to IL-2 receptor (b/g) Receptor immobilized | Affinity to IL-2 receptor (a) Receptor immobilized |
|---|---|---|---|---|---|
| Fab-IL2-Fab 3F2 | Avidity: 25 pM | Avidity: 49 pM | Avidity: 24 pM | 2.7 nM hu IL-2R bg | ND |
| Fab-IL2-Fab 4G8 | Avidity: 83 pM | Avidity: 2.3 pM | Avidity: 74 pM | 3.8 nM hu IL-2R bg 45.6 nM mu IL-2R bg | 4.5 nM hu IL-2R a 29 nM mu IL-2R a |
| Fab-IL2-Fab 3D9 | Avidity: 96 pM | Avidity: 63 pM | Avidity: 105 pM | 2.7 nM hu IL-2R bg | ND |

Example 17

TNC A2-Targeted Fab-IL2-Fab Binding Affinities by Surface Plasmon Resonance (Biacore)

For determination of TNC A2 binding the biotinylated antigens (TNC fn5-A1-A2-A3 domains, fused together, expressed in *E. coli*. While the fn5 and the A3 domains are always of human origin, A1 and A2 domains are human, murine or cynomolgus) were immobilized on a streptavidin chip and the immunoconjugate constructs were used as analytes. Temperature of analysis was 25° C. Fab-IL2-Fab were diluted 1:2 from 25 nM to 0.39 nM and the following measurement parameters were applied: Association time 180 s, dissociation 180 s, flow 50 μl/min. Regeneration with 10 mM glycine pH 1.5 for 60 s. The curves were fitted with the 1:1 model to get the $K_D$ values. As a negative control, TNC domains 1 to 8 produced in HEK cells were applied (TNC 1-8 HEK).

To determine the affinity for IL-2 receptor (IL-2R) β and γ chains (b/g; knob-into-hole construct) the IL-2R construct was immoblized on the chip and the Fab-IL2-Fab immunoconjugates were used as analytes. Temperature of analysis was 25° C. Fab-IL2-Fab immunoconjugates were diluted 1:2 from 25 nM to 0.78 nM and the following measurement parameters were applied: Association time 100 s, dissociation 180 s, flow 90 μl/min. Regeneration was done with 10 mM glycine pH 1.5 for 20 s. Fab-IL2-Fab constructs were diluted from 100 nM to 3.125 nM and the following measurement parameters were applied: Association time 180 s, dissociation 180 s, flow 40 μl/min. Regeneration with 3 M $MgCl_2$ for 30 s. Table 20 gives a summary of binding affinities for the 2B10

Fab-IL2-Fab immunoconjugate, FIG. 35 shows the respective Biacore sensorgrams and affinities.

TABLE 20

Summary of kinetic equilibrium constants ($K_D$) of TNC A2-targeted Fab-IL2-Fab constructs for TNC A2 from different species and IL-2 receptor-β/γ as determined by Surface Plasmon Resonance

| Construct | Human TNC | Murine TNC | Cynomolgus TNC | Affinity to hu IL-2 receptor (β/γ) Receptor immobilized |
|---|---|---|---|---|
| Fab-IL2-Fab 2B10 Immob. *E. coli* Antigen | Avidity: 0.12 nM | Avidity: 0.77 nM | Avidity: 0.12 nM | 2.7 nM |
| TNC 1-8 HEK (neg. cont) | no binding | | | |

Example 18

Biological Activity Assays with Targeted IL-2 Fab-IL2-Fab Immunoconjugates

The biological activity of targeted IL-2 Fab-IL2-Fab immunoconjugates was investigated in several cellular assays in comparison to IL-2 (Proleukin).

Induction of Proliferation of NK92 Cells

Targeted IL-2 Fab-IL2-Fab molecules recognizing TNC A2 (2B10) or FAP (3F2 and 4G8) were investigated for their potential to induce proliferation of NK92 cells in comparison to IL-2 (Proleukin) and the IL-2 L19 diabody recognizing Fibronectin-EDB.

2 μg/ml of human Tenascin, FAP or Fibronectin were coated over night. at 4° C. in a 96-well flat bottom ELISA plate. After blocking the plate, the Fab-IL2-Fab constructs or the diabody were titrated into the plate and incubated for 90 min at room temperature (RT) for binding. After intensive washing to remove the unbound constructs, IL-2 starved NK92 cells (10000 cells/well) were added. As positive control, Proleukin was added in solution to some of the wells. The cells were incubated for 2 days at 37° C. in a humidified incubator (with 5% $CO_2$) before lysing the cells to determine proliferation by ATP measurement using the CellTiter Glo Kit (Promega).

The results in FIG. 36 show that all Fab-IL2-Fab constructs were able to activate IL-2R signaling on NK92 cells and stimulate their proliferation. Due to the reduced binding affinity for the IL-2R β/γ heterodimer required for signaling, the potency of induction of cell growth was reduced by a factor of approximately 10 or more compared to IL-2 (Proleukin). However, the overall efficacy at higher doses was retained and comparable to IL-2 (Proleukin).

Induction of STAT5 Phosphorylation

In another experiment we tested the induction of STAT5 phosphorylation as a consequence of IL-2 mediated IL-2R signaling following incubation with an IL-2 Fab-IL2-Fab molecule recognizing FAP (based on 4G8) on different effector cell populations, including A) $CD56^+$ NK cells, B) $CD4^+$ $CD25^-CD127^+$ helper T cells, C) $CD3^+$, $CD8^+$ cytotoxic T cells and D) $CD4^+CD25^+FOXP3^+$ regulatory T cells (Tregs) from human PBMCs in solution.

PBMCs isolated from blood of healthy donors were treated for 20 min with different concentrations of Proleukin or Fab-IL2-Fab before fixing/permeabilizing them and staining them with anti-PhosphoSTAT5 antibody (Becton Dickinson) according to the instructions of the supplier. After intracellular staining of phosphorylated STAT5 as well as FOXP3, surface markers (CD3, CD4, CD8, CD56 and CD127) were stained for determination of the different subpopulations by flow cytometry (FACS Canto II).

The results in FIG. 37 confirm the findings from FIG. 36 and show that the 4G8 Fab-IL2-Fab construct was able to activate IL-2R signaling on various IL-2R positive effector cells and induce IL-2R downstream signaling and STAT5 phosphorylation. Due to the reduced binding affinity for the IL-2R β/γ heterodimer required for signaling, the potency of induction of STAT5 phosphorylation was reduced by a factor of approximately 10 or more compared to IL-2 (Proleukin). However, the overall efficacy at higher doses was retained and comparable to IL-2 (Proleukin).

IFN-γ Release and Proliferation Induction in Solution and Upon Immobilization

In another experiment we aimed to mimic the situation as it will occur in a tumor where the targeted IL-2 immunoconjugate is bound and immobilized on the tumor cells or tumor stroma and can activate effector cells. In order to do this, we performed the IFN-γ release assay with NK92 cells as well as a proliferation assay with the immunoconjugates in solution or we coated microtiter plates with TNC or FAP antigen so that the targeted IL-2 immunoconjugates are immobilized upon binding to TNC or FAP.

2 μg/ml of human Tenascin or FAP were coated over night at 4° C. in a 96-well flat bottom ELISA plate. After blocking the plate, the Fab-IL2-Fab constructs were titrated into the plate and incubated for 90 min at RT for binding. After intensive washing to remove the unbound constructs, IL-2 starved NK92 cells (10000 cells/well) were added. As positive control, Proleukin was added in solution to some of the wells. For determination of proliferation the cells were incubated for 2 days at 37° C. in a humidified incubator (with 5% $CO_2$) before lysing the cells to determine proliferation by ATP measurement using the CellTiter Glo Kit (Promega). The release of IFN-γ was measured in a separate approach after 24 h of incubation with Fab-IL-2-Fab in the supernatant of the cells with the human IFN-γ ELISA Kit from Becton Dickinson.

Figure 38A:
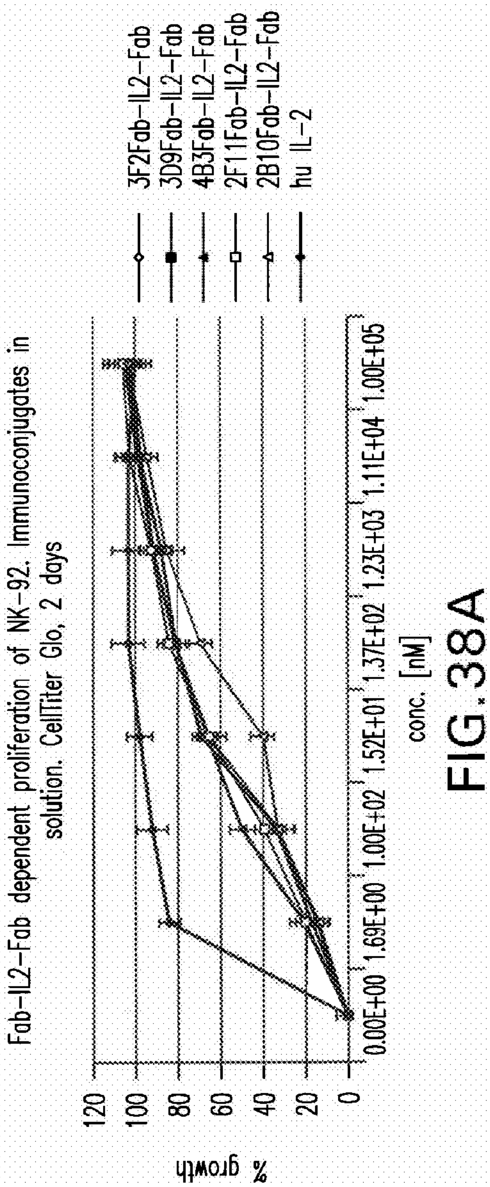
Figure 38B:
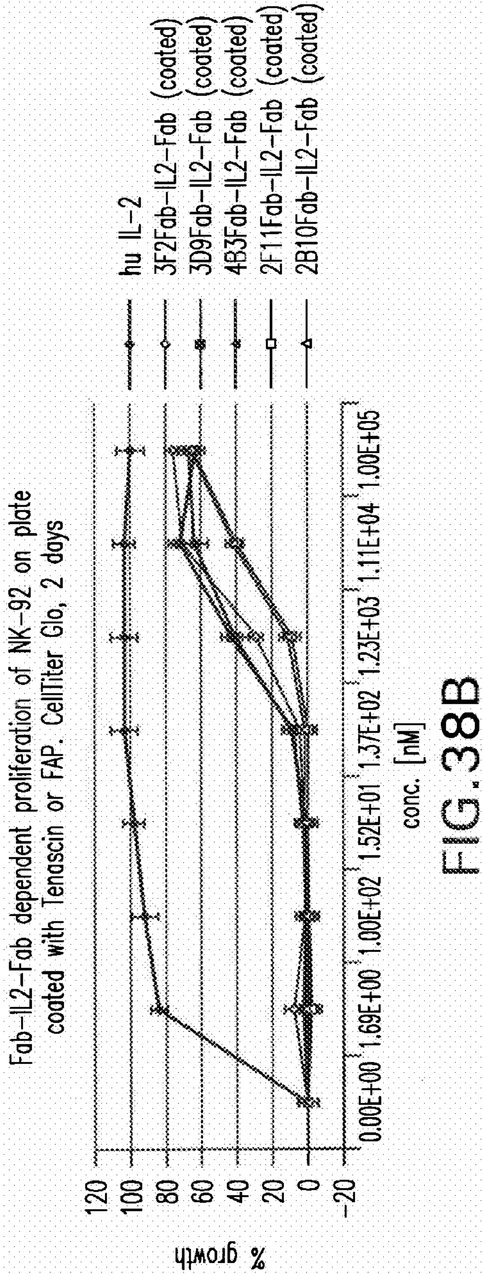
Figure 38C:
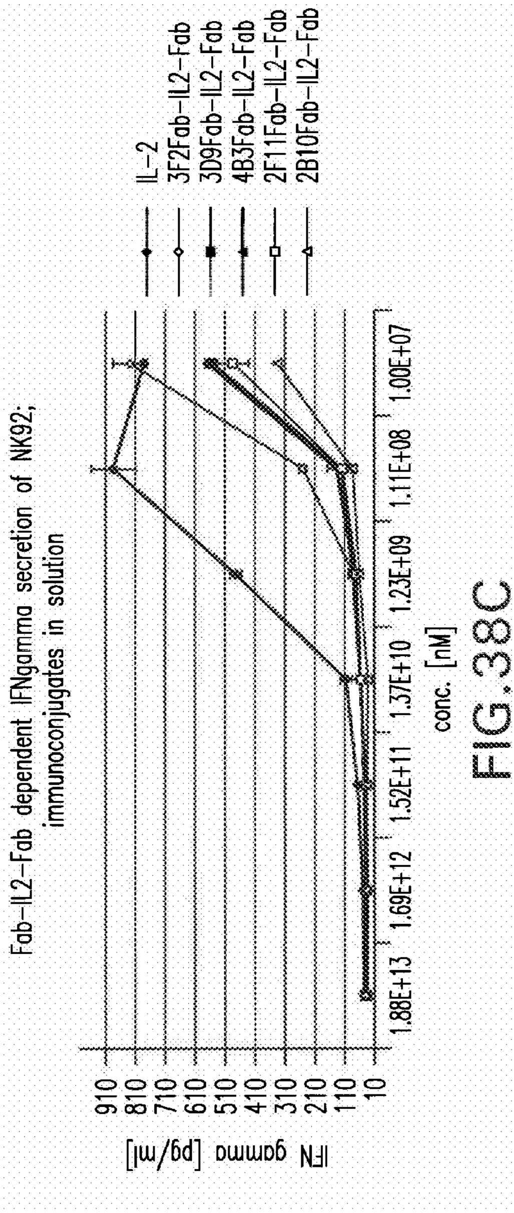
Figure 38D:
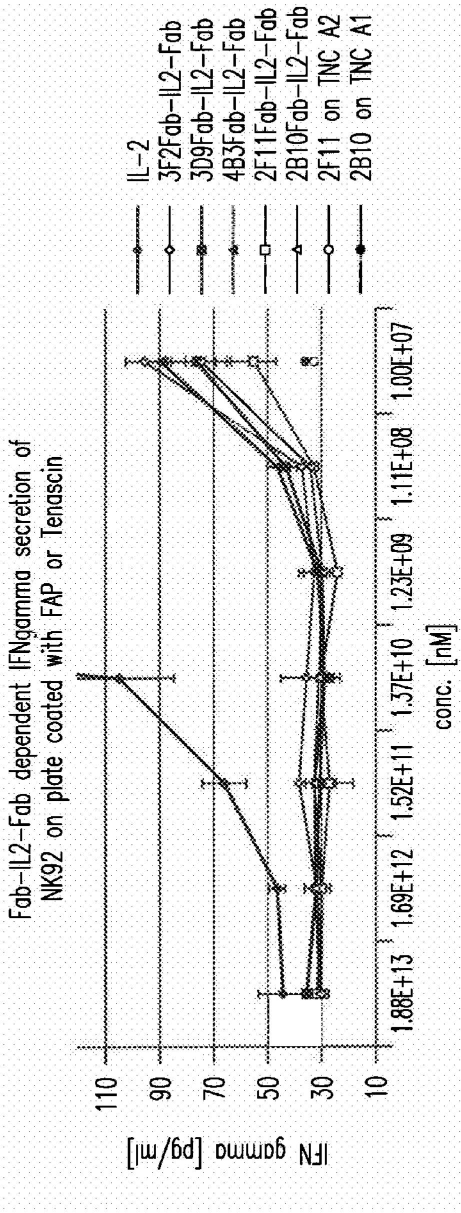

The results confirmed that all Fab-IL2-Fab constructs targeting FAP, TNC A1 or TNC A2 were able to activate IL-2R signaling on NK92 cells and induce proliferation (FIG. 38A) of the cells as well as IFN-γ secretion (FIG. 38C) when present in solution. Due to the reduced binding affinity for the IL-2R β/γ heterodimer required for signaling the potency of induction of IFN-γ release was reduced by a factor of approximately 10 or more compared to IL-2 (Proleukin). However, the overall efficacy at higher doses was retained and comparable to IL-2 (Proleukin). If the microtiter plates were coated with FAP or TNC and the constructs immobilized on the plate, all Fab-IL2-Fab constructs targeting FAP, TNC A1 or TNC A2 were still able to activate IL-2R signaling on NK92 cells and induce cell growth (FIG. 38B) and IFN-γ release (FIG. 38D). In comparison to the assay performed in solution the difference of efficacy between un-coated IL-2 (Proleukin) and the immobilized Fab-IL2-Fab constructs was an order of magnitude higher, however, the overall efficacy at higher doses was retained and comparable to IL-2 (Proleukin).

These data strongly support the concept of generating targeted immunoconjugates with low systemic exposure, but accumulation at the site of disease where they mediate their function.

In the following example we investigated whether these in vitro properties translate into superior efficacy in vivo in xenograft models.

Example 19

In vivo Efficacy of Targeted Fab-IL2-Fab Immunoconjugates Against FAP and TNC A2 in Xenografts of Human Tumor Cell Lines Targeted Fab-IL2-Fab immunoconjugates against FAP and TNC A2 were tested for their anti-tumoral efficacy in several xenograft models.

LS174T Xenograft Model

The TNC A2-targeted 2B10 Fab-IL2-Fab immunoconjugate was tested in the human colorectal LS174T cell line, intrasplenically injected into SCID mice.

LS174T cells (human colon carcinoma cells) were originally obtained from ECACC (European Collection of Cell Culture) and after expansion deposited in the Glycart internal cell bank. LS174T were cultured in MEM Eagle's medium containing 10% FCS (PAA Laboratories, Austria), 1% Glutamax and 1% MEM Non-Essential Amino Acids (Sigma). The cells were cultured at 37° C. in a water-saturated atmosphere at 5% $CO_2$. In vitro passage 15 was used for intrasplenic injection, at a viability of 92.8%. A small incision was made at the left abdominal site of anesthetized SCID/beige mice. Fifty microliters ($3\times10^6$ LS174T cells in AimV medium) cell suspension was injected through the abdominal wall just under the capsule of the spleen. Skin wounds were closed using clamps.

Female SCID mice; aged 8-9 weeks at the start of the experiment (purchased from Taconics, Denmark) were maintained under specific-pathogen-free conditions with daily cycles of 12 h light/12 h darkness according to committed guidelines (GV-Solas; Felasa; TierschG). The experimental study protocol was reviewed and approved by local government (P 2008016). After arrival, animals were maintained for one week to get accustomed to the new environment and for observation. Continuous health monitoring was carried out on a regular basis.

Mice were injected intrasplenically on study day 0 with $3\times10^6$ LS174T cells, randomized and weighed. One week after the tumor cell injection mice were injected i.v. TNC A2-targeted 2B10 Fab-IL2-Fab (Fab-IL2-Fab-SH2B10), Fibronectin-EDB targeted L19 IL-2-diabody, or Proleukin twice weekly for three weeks.

All mice were injected i.v. with 200 μl of the appropriate solution. The mice in the vehicle group were injected with PBS and the treatment groups with the Fab-IL2-Fab construct, the diabody, or Proleukin. To obtain the proper amount of immunoconjugate per 200 μl, the stock solutions were diluted with PBS when necessary.

FIG. 39 shows that the TNC A2 targeted 2B10 Fab-IL2-Fab immunoconjugate mediated superior efficacy in terms of enhanced median survival compared to naked IL-2 (Proleukin) and the IL-2 diabody molecule targeting fibronectin-EDB.

TABLE 21

| Compound | Dose | Formulation buffer | Concentration (mg/mL) |
|---|---|---|---|
| L19 IL-2 diabody | 12 μg | 20 mM sodium citrate, 190 mM sucrose, 20 mM arginine, pH 6.5 | 2.00 (=stock solution) |
| Proleukin (IL-2) | 4 μg | mannitol sodium laurylsulphate sodium phosphate | 1.0 (=stock solution) |

TABLE 21-continued

| Compound | Dose | Formulation buffer | Concentration (mg/mL) |
|---|---|---|---|
| huTNC A2 2B10 (G65S) Fab-IL2-Fab = SH2B10 | 16 μg | 25 mM potassium phosphate, 125 mM NaCl, 100 mM glycine, pH 6.7 | 1.86 (=stock solution) |

ACHN Xenograft Model

The FAP-targeted 3F2 or 4G8 Fab-IL2-Fab immunoconjugates were tested in the human renal cell line ACHN, intrarenally injected into SCID mice.

ACHN cells (human renal adenocarcinoma cells) were originally obtained from ATCC (American Type Culture Collection) and after expansion deposited in the Glycart internal cell bank. ACHN were cultured in DMEM containing 10% FCS. The cells were cultured at 37° C. in a water-saturated atmosphere at 5% $CO_2$. In vitro passage 9 was used for intrarenal injection, at a viability of 97.7%. A small incision (2 cm) was made at the right flank and peritoneal wall of anesthetized SCID mice. Fifty μl ($1\times10^6$ ACHN cells in AimV medium) cell suspension was injected 2 mm subcapsularly in the kidney. Skin wounds and peritoneal wall were closed using clamps.

Female SCID mice; aged 8-9 weeks at the start of the experiment (purchased from Charles River, Sulzfeld, Germany) were maintained under specific-pathogen-free conditions with daily cycles of 12 h light/12 h darkness according to committed guidelines (GV-Solas; Felasa; TierschG). The experimental study protocol was reviewed and approved by local government (P 2008016). After arrival, animals were maintained for one week to get accustomed to new environment and for observation. Continuous health monitoring was carried out on a regular basis.

Mice were injected intrarenally on study day 0 with $1\times10^6$ ACHN cells, randomized and weighed. One week after the tumor cell injection, mice were injected i.v. with Proleukin, L19 IL-2 diabody or FAP-targeted 4G8 or 3F2 Fab-IL2-Fab immunoconjugates twice weekly for three weeks.

All mice were injected i.v. with 200 μl of the appropriate solution. The mice in the vehicle group were injected with PBS and the treatment groups with Proleukin, L19 IL-2 diabody or FAP-targeted 4G8 or 3F2 Fab-IL2-Fab immunoconjugates. To obtain the proper amount of immunoconjugate per 200 μl the stock solutions were diluted with PBS when necessary.

FIG. 40 shows that the FAP targeted 3F2 and 4G8 Fab-IL2-Fab immunoconjugates mediated superior efficacy in terms of enhanced median survival compared to naked IL-2 (Proleukin) and the IL-2 diabody molecule targeting fibronectin-EDB. The 4G8-based Fab-IL2-Fab, which has a higher affinity for murine FAP, mediated superior efficacy than 3F2-based Fab-IL2-Fab.

TABLE 22

| Compound | Dose | Formulation buffer | Concentration (mg/mL) |
|---|---|---|---|
| L19 IL-2 diabody | 12 μg | 20 mM sodium citrate, 190 mM sucrose, 20 mM arginine, pH 6.5 | 2.00 (=stock solution) |
| Proleukin (IL2) | 4 μg | mannitol sodium laurylsulphate sodium phosphate | 1.0 (=stock solution) |

TABLE 22-continued

| Compound | Dose | Formulation buffer | Concentration (mg/mL) |
|---|---|---|---|
| FAP 3F2 Fab-IL2-Fab = FAP 3F2 | 16 μg | 25 mM potassium phosphate, 125 mM NaCl, 100 mM glycine, pH 6.7 | 2.46 (=stock solution) |
| FAP 4G8 Fab-IL2-Fab = FAP 4G8 | 16 μg | 25 mM potassium phosphate, 125 mM NaCl, 100 mM glycine, pH 6.7 | 11.8 (=stock solution) |

A549 Xenograft Model

The TNC A2-targeted 2B10 Fab-IL2-Fab immunoconjugate was tested in the human NSCLC cell line A549, injected i.v. into SCID-human FcγRIII transgenic mice.

The A549 non-small cell lung carcinoma cells were originally obtained from ATCC (CCL-185) and after expansion deposited in the Glycart internal cell bank. The tumor cell line was routinely cultured in DMEM containing 10% FCS (Gibco) at 37° C. in a water-saturated atmosphere at 5% CO2. Passage 2 was used for transplantation, at a viability of 98%. $2\times10^6$ cells per animal were injected i.v. into the tail vein in 200 μl of Aim V cell culture medium (Gibco).

Female SCID-FcγRIII mice (GLYCART-RCC), aged 8-9 weeks at the start of the experiment (bred at RCC, Switzerland) were maintained under specific-pathogen-free condition with daily cycles of 12 h light/12 h darkness according to committed guidelines (GV-Solas; Felasa; TierschG). The experimental study protocol was reviewed and approved by local government (P 2008016). After arrival, animals were maintained for one week to get accustomed to the new environment and for observation. Continuous health monitoring was carried out on a regular basis.

Mice were injected i.v. on study day 0 with $5\times10^6$ of A549 cells, randomized and weighed. One week after the tumor cell injection, mice were injected i.v. with 2B10 Fab-IL2-Fab or L19 IL-2 diabody twice weekly for three weeks.

All mice were injected i.v. with 200 μl of the appropriate solution. The mice in the vehicle group were injected with PBS and the treatment group with the 2B10 Fab-IL2-Fab construct or the L19 IL-2 diabody. To obtain the proper amount of immunoconjugate per 200 μl, the stock solutions were diluted with PBS when necessary.

FIG. 41 shows that the TNC A2 targeted 2B10 Fab-IL2-Fab immunoconjugate mediated superior efficacy in terms of enhanced median survival compared to the IL-2 diabody molecule targeting fibronectin-EDB.

TABLE 23

| Compound | Dose | Formulation buffer | Concentration (mg/mL) |
|---|---|---|---|
| L19 IL-2 diabody | 12 μg | 20 mM sodium citrate, 190 mM sucrose, 20 mM arginine, pH 6.5 | 2.00 (=stock solution) |
| huTNC A2 2B10 (G65S) Fab-IL2-Fab = 2B10 | 16 μg | 25 mM potassium phosphate, 125 mM NaCl, 100 mM glycine, pH 6.7 | 1.86 (=stock solution) |

Example 20

Purification of Targeted GM-CSF Fab-GM-CSF-Fab Immunoconjugate

Initial purification of the Fab-GM-CSF-Fab immunoconjugate with L19 (Fibronectin Ectodomain-B binder) as Fab fragment was performed from supernatants of transiently transfected HEK 293 EBNA cells. Briefly, Fab-GM-CSF-Fab was purified by protein A followed by size exclusion chromatography. The Protein A column was equilibrated in 20 mM sodium phosphate, 20 mM sodium citrate pH 7.5. The supernatant was loaded and the column washed first with 20 mM sodium phosphate, 20 mM sodium citrate pH 7.5, followed by 20 mM sodium phosphate, 20 mM sodium citrate, 100 mM sodium chloride, pH 7.5. Targeted GM-CSF was eluted with 20 mM sodium citrate, 100 mM sodium chloride, 100 mM glycine pH 3 and subsequently neutralized. For formulation the following buffer was applied: 25 mM potassium phosphate, 125 mM sodium chloride, 100 mM glycine pH 6.7.

FIG. 42 shows the elution profiles from the purification and the results from the analytical characterization of the product by SDS-PAGE (NuPAGE Novex Bis-Tris Mini Gel, Invitrogen, MOPS running buffer, reduced and non-reduced). The yield was 4.8 mg/L.

Example 21

Biological Activity Assay with Targeted GM-CSF Fab-GM-CSF-Fab Immunoconjugate The purified Fab-GM-CSF-Fab immunoconjugate with L19 (Fibronectin Ectodomain-B binder) as Fab was subsequently analyzed in a GM-CSF-dependent proliferation assay. Briefly, TF-1 cells, which grow GM-CSF-dependent, were seeded after over night starvation at 10000 cells/well into a 96-well flat bottom plate. Human recombinant GM-CSF (Miltenyi #130-093-862) or Fab-GM-CSF-Fab immunoconjugate were titrated onto the cells in solution. After 2 days of proliferation at 37° C. in a humidified incubator with 5% $CO_2$, the cells were lysed and ATP content was measured with the CellTiter Glo assay from Promega. GM-CSF-untreated cells were set as 0% growth for calculation. Results in FIG. 43 show that the Fab-GM-CSF-Fab immunoconjugate induced strong proliferation of TF-1 cells.

Example 22

Purification of Targeted-IL-12 Fab-IL12-Fab Immunoconjugate

Initial purification of the Fab-IL12-Fab immunoconjugate with 4G8 (FAP binder) as Fab fragment was performed from supernatants of transiently transfected HEK 293 EBNA cells. Briefly, Fab-IL12-Fab was purified by protein A followed by size exclusion chromatography. The protein A column was equilibrated with 20 mM sodium phosphate, 20 mM sodium citrate pH 7.5. Supernatant was loaded and the column washed with 20 mM sodium phosphate, 20 mM sodium citrate, 500 mM sodium chloride pH 7.5. A second wash was performed with 13.3 mM sodium phosphate, 20 mM sodium citrate, 500 mM sodium chloride, pH 5.45. After a third wash with 10 mM MES, 50 mM sodium chloride pH 5, targeted IL-12 was eluted with 20 mM sodium citrate, 100 mM sodium chloride, 100 mM glycine, pH 3 and subsequently neutralized. For formulation the following buffer was applied: 25 mM potassium phosphate, 125 mM sodium chloride, 100 mM glycine pH 6.7.

FIG. 44 shows the elution profiles from the purification and the results from the analytical characterization of the product by SDS-PAGE (NuPAGE Novex Bis-Tris Mini Gel, Invitrogen, MOPS running buffer, reduced and non-reduced). The yield was 43 mg/L.

Example 23

Biological Activity Assay with Targeted-IL-12 Fab-IL12-Fab Immunoconjugate

The purified Fab-IL12-Fab immunoconjugate with 4G8 (FAP binder) as Fab was subsequently analyzed for IL-12 induced IFN-γ release, comparing the effect of IL-12 and the purified 4G8 Fab-IL12-Fab immunoconjugate, using PBMCs isolated from fresh human blood of a healthy donor.

Briefly, PBMCs were isolated from fresh human blood of a healthy donor and seeded in a 96-well U-bottom plate ($1.5\times10^5$ cells/well) in AIM V medium. A constant concentration of 10 ng/ml hu IL-2 (Peprotech) was added to all wells. The Fab-IL12-Fab construct was diluted in medium and titrated onto the PBMCs. Supernatants were collected after approximately 20 hours to determine the IFN-γ concentrations using the hu IFN-γ ELISA Kit II from Becton Dickinson (#550612).

Results in FIG. 45 show that A) the chosen amount of human (hu) IL-2 alone as well as IL-12 alone were not able to induce significant IFN-γ release by human PBMCs whereas the combination of both cytokines led to significant IFN-γ release by PBMCs. B) The Fab-IL-12-Fab construct induced IFN-γ release by human PBMCs in a concentration-dependent manner in the presence of 10 ng/ml human IL-2.

Example 24

Purification of Targeted IFN-α Fab-IFNα2-Fab Immunoconjugate

Initial purification of the Fab-IFNα2-Fab immunoconjugate with L19 (Fibronectin Ectodomain-B binder) as Fab fragment was performed from supernatants of transiently transfected HEK 293 EBNA cells. Briefly, Fab-IFNα2-Fab was purified by protein A followed by size exclusion chromatography. The protein A column was equilibrated in 20 mM sodium phosphate, 20 mM sodium citrate pH 7.5. The supematant was loaded and the column washed first with 20 mM sodium phosphate, 20 mM sodium citrate pH 7.5, followed by 20 mM sodium phosphate, 20 mM sodium citrate, 100 mM sodium chloride, pH 7.5. Fab-IFNα2-Fab was eluted with 20 mM sodium citrate, 100 mM sodium chloride, 100 mM glycine pH 3 and subsequently neutralized. For formulation the following buffer was applied: 25 mM potassium phosphate, 125 mM sodium chloride, 100 mM glycine pH 6.7.

FIG. 46 shows the elution profiles from the purification and the results from the analytical characterization of the product by SDS-PAGE (NuPAGE Novex Bis-Tris Mini Gel, Invitrogen, MOPS running buffer, reduced and non-reduced). The yield was 8.4 mg/L.

Example 25

Biological Activity Assay with IFN-α Fab-IFNα2-Fab Immunoconjugate

The purified Fab-IFNα2-Fab immunoconjugate with L19 (Fibronectin Ectodomain-B binder) as Fab was subsequently analyzed for IFN-α-induced proliferation inhibition of Jurkat T cells and A549 tumor cells, comparing the effect of IFN-α (Roferon A, Roche) and the purified L19 Fab-IFNα2-Fab immunoconjugate. Briefly, A549 and Jurkat T cells which are susceptible for IFN-α-induced proliferation inhibition were seeded at 5000 cells/well (A549) or 10000 cells/well (Jurkat) into 96-well flat bottom plates. Dilutions of Roferon A (Roche) or Fab-IFNα2-Fab in the appropriate cell culture medium were titrated onto the cells in solution. After two days of proliferation at 37° C. in a humidified incubator with 5% $CO_2$, the cells were lysed and ATP content was measured with the CellTiter Glo assay from Promega. IFN-α-untreated cells were set as 0% growth for calculation.

Results in FIG. 47 show that Fab-IFNα2-Fab constructs inhibited proliferation of A) Jurkat T cells and B) A549 cells in a concentration-dependent manner comparable to IFN-α (Roferon A).

Example 26

Preparation of MCSP targeted Fab-IL2-Fab Immunoconjugates

The humanized anti-MCSP MHLG antibody was generated as described in WO 2006/100582 (see in particular Example 1 therein), the entire contents of which are incorporated herein by reference, and converted into the Fab-IL2-Fab format (see SEQ ID NOs: 255, 256, 261, 262).

The humanized anti-MCSP MHLG1 antibody was generated as follows: The murine amino acid sequence of anti-MCSP antibody 225.28 (light chain, and heavy chain, see below) was aligned to a collection of human germ-line antibody V-genes, and sorted according to sequence identity and homology.

225.28 light chain; GenBank Acc. No. CAA65007 (SEQ ID 267):

```
DIELTQSPKFMSTSVGDRVSVTCKASQNVDTNVAWYQQKPGQSPEPLLFS
ASYRYTGVPDRFTGSGSGTDFTLTISNVQSEDLAEYFCQQYNSYPLTFGG
GTKLEIK
```

225.28 heavy chain; no GenBank Acc. No. available (SEQ ID 268):

```
QVKLQQSGGGLVQPGGSMKLSCVVSGFTFSNYWMNWVRQSPEKGLEWIAE
IRLKSNNFGRYYAESVKGRFTISRDDSKSSAYLQMINLRAEDTGIYYCTS
YGNYVGHYFDHWGQGTTVTVSS
```

The potential acceptor sequence was selected based on high overall homology, and the presence of the right canonical residues already in the acceptor sequence. The human germ-line sequence IGHV3-15 (IMGT Acc. No. X92216) was chosen as the acceptor for the heavy chain and sequence IGKV1-9 (IMGT Acc. No. Z00013) was chosen for the light chain. The humanized constructs were denoted M-KV1 (see SEQ ID NOs: 263, 264, 269, 270), 7 (SEQ ID NOs: 265, 266, 271, 272), and 9 (SEQ ID NOs: 253, 254, 259, 260) for the light chain, and MHLG1 (see SEQ ID NOs: 251, 252, 257, 258), for the heavy chain.

The genes for those designed antibody sequences were generated by conventional PCR techniques and fused to human IgG1 and kappa constant domains for the construction of the expression plasmids.

Antibodies were expressed either as IgG or as Fab-IL2-Fab fusion proteins in mammalian cell culture systems like HEK or CHO, and purified via protein A and size exclusion chromatography. Comparison of the binding data of light chain variants M-KV1, and M-KV7 revealed that a proline residue at Kabat position 46 is essential for functional binding to the antigen. Two different approaches were taken to ensure the presence of this amino acid: A) A so-called back-mutation was introduced into the human framework of IGKV1-9. And B) To avoid the presence of back-mutations, the entire framework 2 region (Kabat positions 35 to 49) was exchanged by the corresponding region of the human antibody with GenBank entry AAA17574. This antibody has naturally a proline residue at position 46.

MCSP-targeted MHLG or MHLG1 KV9 Fab-IL2-Fab was purified by the method described above (Example 9) composed of one affinity step (protein A) followed by size exclusion chromatography (Superdex 200, GE Healthcare). The protein A column was equilibrated in 20 mM sodium phosphate, 20 mM sodium citrate pH 7.5, supernatant was loaded and the column was washed with 20 mM sodium phosphate, 20 mM sodium citrate, 500 mM sodium chloride, pH 7.5, followed by a wash with 13.3 mM sodium phosphate, 20 mM sodium citrate, 500 mM sodium chloride, pH 5.45. A third wash with 10 mM MES, 50 mM sodium chloride, pH 5 was optionally included. Fab-IL2-Fab was eluted with 20 mM sodium citrate, 100 mM sodium chloride, 100 mM glycine, pH 3. The eluted fractions were pooled and polished by size exclusion chromatography in the final formulation buffer: 25 mM potassium phosphate, 125 mM sodium chloride, 100 mM glycine pH 6.7.

FIG. 48 (for MHLG Fab-IL2-Fab) and FIG. 49 (for MHLG1 Fab-IL2-Fab) shows (A) the elution profiles from the purification and (B) the results from the analytical characterization of the MCSP-targeted MHLG or MHLG1 Fab-IL2-Fab by SDS-PAGE (NuPAGE Novex Bis-Tris Mini Gel, Invitrogen, MOPS running buffer, reduced and non-reduced). The yield was 30 mg/L.

Example 27

Biological Activity Assay with MCSP Targeted Fab-IL2-Fab Immunoconjugates

The purified Fab-IL2-Fab immunoconjugates with MHLG KV9 or MHLG1 KV9 (MCSP binders) as Fab were subsequently analyzed for IL-2 induced IFN-γ release, comparing the effect of purified 4G8 Fab-IL2-Fab (FAP binder) and MHLG or MHLG1 Fab-IL2-Fab on NK92 cells.

IL-2 starved NK92 cells (preincubated for 2 hours without IL-2) were seeded in a 96-well U bottom plates ($10^5$ cells/well) in NK cell medium (MEMa+10% FCS+10% horse serum+0.1 mM 2-mercaptoethanol+0.2 mM inositol+0.02 mM folic acid). The MCSP-targeted MHLG-based Fab-IL-2-Fab immunoconjugates were diluted in NK cell medium and titrated onto the NK92 cells in direct comparison to the FAP-targeted 4G8-based Fab-IL2-Fab immunoconjugate. Supernatants were collected after approximately 22 to 24 hours to determine the IFN-γ concentrations using the human IFN-γ ELISA Kit II from Becton Dickinson (#550612).

The results in FIG. 50 (for MHLG KV9 Fab-IL2-Fab) and FIG. 51 (for MHLG1 KV9 Fab-IL2-Fab) show that all Fab-IL2-Fab immunoconjugates, targeted against MCSP or FAP, induced comparable IFN-γ secretion in NK92 cells in a concentration dependent manner, independent of the antigen binding moiety used.

Example 28

Cellular Binding Assay with the MCSP-Targeted MHLG1 KV9 Fab-IL2-Fab Immunoconjugate The purified MCSP-targeted MHLG1-KV9 Fab-IL2-Fab immunoconjugate was tested by flow cytometry for binding to human MCSP-expressing Colo38 melanoma cells. Briefly, cells were harvested, counted and checked for viability. Cells were adjusted to $1.112\times10^6$ (viable) cells/ml in PBS/0.1% BSA and aliquoted 180 μl/well (200,000 cells/well) in a round-bottom 96-well plate. 20 μl MHLG1 KV9 Fab-IL2-Fab immunocytokine (in different dilutions) was added to the cell containing wells and incubated for 30 min at 4° C. Cells were subsequently collected by centrifugation (4 min, 400×g), washed with 150 μl/well PBS/0.1% BSA, resuspended and incubated for 30 min at 4° C. with 12 μl/well secondary antibody (FITC-conjugated AffiniPure F(ab')2 Fragment goat anti-human F(ab')2 (Jackson Immuno Research Lab #109-096-097), dissolved in 1.5 ml of a 1:1 mixture of water and glycerol=stock solution), diluted 1:20 in PBS/0.1% BSA. Cells were subsequently washed in 150 μl/well PBS/0.1% BSA, followed by a washing step in PBS, collected by centrifugation (4 min, 400×g), and resuspended with 200 μl/well PBS/0.1% BSA containing propidium iodide (PI). Measurements were performed using a FACSCantoII machine (Software FACS Diva). Results are presented in FIG. 52, which shows that the MCSP-targeted MHLG1 KV9 Fab-IL2-Fab immunoconjugate bound very well, in a dose-dependent manner, to Colo38 cells.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An immunoconjugate comprising:

(a) at least a first single-chain effector moiety; and (b) a first and a second antigen binding moiety;

wherein each of said first and second antigen binding moieties is a Fab molecule;

wherein said first effector moiety shares an amino- or carboxy-terminal peptide bond with said first antigen binding moiety;

wherein said second antigen binding moiety shares an amino- or carboxy-terminal peptide bond with either i) the first effector moiety, or ii) said first antigen binding moiety, and wherein said first effector moiety is not an Fc chain.

2. The immunoconjugate of claim 1, wherein said immunoconjugate consists essentially of a first effector moiety and first and second antigen binding moieties joined by one or more linker sequences.

3. The immunoconjugate of claim 1, wherein said first Fab molecule is joined at its heavy or light chain carboxy-terminal amino acid to the amino-terminal amino acid of the heavy or light chain of the second Fab molecule, and wherein (i) said second Fab molecule is joined at its heavy or light chain carboxy-terminal amino acid to the amino-terminal amino acid of said effector moiety, or (ii) said effector moiety is joined at its carboxy-terminal amino acid to the amino-terminal amino acid of the heavy or light chain of said first Fab molecule.

4. The immunoconjugate of claim 1, wherein said first Fab molecule is joined at its heavy or light chain carboxy-terminus to the amino-terminal amino acid of said effector moiety, and said effector moiety is joined at its carboxy-terminal amino acid to the terminal amino acid of the heavy or light chain of the second Fab molecule.

5. The immunoconjugate of claim 1, wherein proteolytic cleavage sites are located between said antigen binding moieties and said effector moieties.

6. The immunoconjugate of claim 1, wherein the variable regions of said first and second antigen binding moieties are specific for the same antigen.

7. The immunoconjugate of claim 1, wherein the variable region of said first and second antigen binding moieties are specific for different antigens.

8. The immunoconjugate of claim 1, wherein said first or second antigen binding moiety or said first and second antigen binding moieties is/are specific for an antigen selected from the group consisting of the Extra Domain B of fibronectin (EDB), the A1 domain of tenascin-C (TNC-A1), the A2 domain of tenascin-C (TNC-A2), the Fibroblast Activation Protein (FAP), and the Melanoma Chondroitin Sulfate Proteoglycan (MCSP).

9. The inunuoconjugate of claim 8, wherein said first or second antigen binding moiety or said first and second antigen binding moieties is/are specific for the A2 domain of Tenascin-C (TNC-A2).

10. The immunoconjugate of claim 8, wherein said first or second antigen binding moiety or said first and second antigen binding moieties is/are specific for Fibroblast Activated Protein (FAP).

11. The immunoconjugate of claim 8, wherein said first or second antigen binding moiety or said first and second antigen binding moieties is/are specific for Melanoma Chondroitin Sulfate Proteoglycan (MCSP).

12. The immunoconjugate of claim 1, wherein the variable regions of said first and second antigen binding moieties are specific for a cell surface antigen of a cancer cell or a virus-infected cell or for an extracellular matrix (ECM) molecule expressed in a tumor.

13. The immunoconjugate of claim 1, wherein said immunoconjugate has only one effector moiety; and wherein said effector moiety is a cytokine.

14. The immunoconjugate of claim 13, wherein said cytokine is selected from the group consisting of; interleukin-2

(IL-2), granulocyte macrophage-colony stimulating factor (GM-CSF), interferon-α (INF-α), and interleukin-12 (IL-12).

15. An immunoconjugate comprising a first single-chain effector moiety joined at its amino-terminal amino acid to one or more scFv molecules;

and wherein said first single-chain effector moiety is joined at its carboxy-terminal amino acid to one or more scFv molecules, and is not an Fc chain.

16. An isolated polynucleotide encoding a fragment of the immunoconjugate of claim 1, wherein said polynucleotide encodes (i) the heavy chains of said first and second antigen binding moieties and said first effector moiety; or (ii) the light chains of said first and second antigen binding moieties and said first effector moiety; or (iii) one light chain from said first antigen binding moiety, one heavy chain from said second antigen binding moiety and said first effector moiety.

17. An isolated polynucleotide encoding the immunoconjugate of claim 15.

18. An expression cassette comprising the polynucleotide sequence of claim 16 or 17.

19. An expression vector which comprises the expression cassette of claim 18.

20. An isolated host cell comprising the expression vector of claim 19.

21. A method of producing an immunoconjugate, wherein the method comprises culturing the host cell of claim 20 under conditions suitable for the expression of the immunoconjugate.

22. A method of treating a disease in an individual, comprising the steps of administering to said individual a therapeutically effective amount of a composition comprising the immunoconjugate of claim 1 or 15.

23. The method of claim 22, wherein said disease is cancer.

24. A composition comprising the immunoconjugate of claim 1 or 15 and a pharmaceutical carrier.

* * * * *

SEQUENCE LISTING

<160> NUMBER OF SEQ ID NOS: 281

<210> SEQ ID NO 1
<211> LENGTH: 1611
<212> TYPE: DNA
<213> ORGANISM: Artificial Sequence
<220> FEATURE:
<223> OTHER INFORMATION: Library Template for DP47-3 library

<400> SEQUENCE: 1
atgaaatacc tattgcctac ggcagccgct ggattgttat tactcgcggc ccagccggcc 60
atggccgaaa tcgtgttaac gcagtctcca ggcaccctgt ctttgtctcc aggggaaaga 120
gccaccctct cttgcagggc cagtcagagt gttagcagca gctacttagc ctggtaccag 180
cagaaacctg gccaggctcc caggctcctc atctatggag catccagcag ggccactggc 240
atcccagaca ggttcagtgg cagtggatcc gggacagact tcactctcac catcagcaga 300
ctggagcctg aagattttgc agtgtattac tgtcagcagt atggtagctc accgctgacg 360
ttcggccagg ggaccaaagt ggaaatcaaa cgtacggtgg ctgcaccatc tgtcttcatc 420
ttcccgccat ctgatgagca gttgaaatct ggaactgcct ctgttgtgtg cctgctgaat 480
aacttctatc ccagagaggc caaagtacag tggaaggtgg ataacgccct ccaatcgggt 540
aactcccagg agagtgtcac agagcaggac agcaaggaca gcacctacag cctcagcagc 600
accctgacgc tgagcaaagc agactacgag aaacacaaag tctacgcctg cgaagtcacc 660
catcagggcc tgagctcgcc cgtcacaaag agcttcaaca ggggagagtg tggagccgca 720
gaacaaaaac tcatctcaga agaggatctg aatggagccg cagactacaa ggacgacgac 780
gacaagggtg ccgcataata aggcgcgcca attctatttc aaggagacag tcatatgaaa 840
tacctgctgc cgaccgctgc tgctggtctg ctgctcctcg ctgcccagcc ggcgatggcc 900
gaggtgcaat tgctggagtc tgggggaggc ttggtacagc ctggggggtc cctgagactc 960
tcctgtgcag cctccggatt cacctttagc agttatgcca tgagctgggt ccgccaggct 1020
ccagggaagg ggctggagtg ggtctcagct attagtggta gtggtggtag cacatactac 1080
gcagactccg tgaagggccg gttcaccatc tccagagaca attccaagaa cacgctgtat 1140
ctgcagatga acagcctgag agccgaggac acggccgtat attactgtgc gaaaccgttt 1200
ccgtattttg actactgggg ccaaggaacc ctggtcaccg tctcgagtgc tagcaccaaa 1260
ggcccatcgg tcttccccct ggcaccctcc tccaagagca cctctggggg cacagcggcc 1320
ctgggctgcc tggtcaagga ctacttcccc gaaccggtga cggtgtcgtg gaactcaggc 1380
gccctgacca gcggcgtgca caccttcccg gctgtcctac agtcctcagg actctactcc 1440
ctcagcagcg tggtgaccgt gccctccagc agcttgggca cccagaccta catctgcaac 1500
gtgaatcaca agcccagcaa caccaaagtg gacaagaaag ttgagcccaa atcttgtgac 1560
gcggccgcaa gcactagtgc ccatcaccat caccatcacg ccgcggcata g 1611

<210> SEQ ID NO 2
<211> LENGTH: 1617
<212> TYPE: DNA
<213> ORGANISM: Artificial Sequence
<220> FEATURE:
<223> OTHER INFORMATION: Library Template for DP88-3 library

<400> SEQUENCE: 2
atgaaatacc tattgcctac ggcagccgct ggattgttat tactcgcggc ccagccggcc 60
atggccgata tccagatgac ccagtctcca tcctccctgt ctgcatctgt cggagaccgg 120

```
gtcaccatca cctgccgggc aagtcagggc attagaaatg atttaggctg gtaccagcag    180

aagccaggga aagcccctaa gcgcctgatc tatgctgcat ccagtttgca gagtggcgtc    240

ccatcaaggt tcagcggcag tggatccggg acagagttca ctctcaccat cagcagcttg    300

cagcctgaag attttgccac ctattactgc ttgcagcata atagttaccc cacgtttggc    360

cagggcacca aagtcgagat caagcgtacg gtggctgcac catctgtctt catcttcccg    420

ccatctgatg agcagttgaa atctggaact gcctctgttg tgtgcctgct gaataacttc    480

tatcccagag aggccaaagt acagtggaag gtggataacg ccctccaatc gggtaactcc    540

caggagagtg tcacagagca ggacagcaag gacagcacct acagcctcag cagcaccctg    600

acgctgagca aagcagacta cgagaaacac aaagtctacg cctgcgaagt cacccatcag    660

ggcctgagct cgcccgtcac aaagagcttc aacaggggag agtgtggagc cgcagaacaa    720

aaactcatct cagaagagga tctgaatgga gccgcagact acaaggacga cgacgacaag    780

ggtgccgcat aataaggcgc gccaattcta tttcaaggag acagtcatat gaaatacctg    840

ctgccgaccg ctgctgctgg tctgctgctc ctcgctgccc agccggcgat ggcccaggtg    900

caattggtgc agtctggggc tgaggtgaag aagcctgggt cctcggtgaa ggtctcctgc    960

aaggcctccg gaggcacatt cagcagctac gctataagct gggtgcgaca ggcccctgga   1020

caagggctcg agtggatggg agggatcatc cctatctttg gtacagcaaa ctacgcacag   1080

aagttccagg gcagggtcac cattactgca gacaaatcca cgagcacagc ctacatggag   1140

ctgagcagcc tgagatctga ggacaccgcc gtgtattact gtgcgagact atccccaggc   1200

ggttactatg ttatggatgc ctggggccaa gggaccaccg tgaccgtctc ctcagctagc   1260

accaaaggcc catcggtctt ccccctggca ccctcctcca agagcacctc tgggggcaca   1320

gcggccctgg gctgcctggt caaggactac ttccccgaac cggtgacggt gtcgtggaac   1380

tcaggcgccc tgaccagcgg cgtgcacacc ttcccggctg tcctacagtc ctcaggactc   1440

tactccctca gcagcgtggt gaccgtgccc tccagcagct tgggcaccca gacctacatc   1500

tgcaacgtga atcacaagcc cagcaacacc aaagtggaca agaaagttga gcccaaatct   1560

tgtgacgcgg ccgcaagcac tagtgcccat caccatcacc atcacgccgc ggcatag      1617
```

```
<210> SEQ ID NO 3
<211> LENGTH: 107
<212> TYPE: PRT
<213> ORGANISM: Artificial Sequence
<220> FEATURE:
<223> OTHER INFORMATION: 2B10; VL

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95
```

```
Thr Phe Gly Gln Gly Thr Lys Val Glu Ile Lys
            100                 105


<210> SEQ ID NO 4
<211> LENGTH: 321
<212> TYPE: DNA
<213> ORGANISM: Artificial Sequence
<220> FEATURE:
<223> OTHER INFORMATION: 2B10; VL

<400> SEQUENCE: 4

gatatccaga tgacccagtc tccatcctcc ctgtctgcat ctgtcggaga ccgggtcacc     60

atcacctgcc gggcaagtca gggcattaga aatgatttag gctggtacca gcagaagcca    120

gggaaagccc ctaagcgcct gatctatgct gcatccagtt tgcagagtgg cgtcccatca    180

aggttcagcg gcggtggatc cgggacagag ttcactctca ccatcagcag cttgcagcct    240

gaagattttg ccacctatta ctgcttgcag aatggtctgc agcccgcgac gtttggccag    300

ggcaccaaag tcgagatcaa g                                              321


<210> SEQ ID NO 5
<211> LENGTH: 107
<212> TYPE: PRT
<213> ORGANISM: Artificial Sequence
<220> FEATURE:
<223> OTHER INFORMATION: 2B10(GS); VL

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105


<210> SEQ ID NO 6
<211> LENGTH: 321
<212> TYPE: DNA
<213> ORGANISM: Artificial Sequence
<220> FEATURE:
<223> OTHER INFORMATION: 2B10(GS); VL

<400> SEQUENCE: 6

gatatccaga tgacccagtc tccatcctcc ctgtctgcat ctgtcggaga ccgggtcacc     60

atcacctgcc gggcaagtca gggcattaga aatgatttag gctggtacca gcagaagcca    120

gggaaagccc ctaagcgcct gatctatgct gcatccagtt tgcagagtgg cgtcccatca    180

aggttcagcg gcagtggatc cgggacagag ttcactctca ccatcagcag cttgcagcct    240

gaagattttg ccacctatta ctgcttgcag aatggtctgc agcccgcgac gtttggccag    300

ggcaccaaag tcgagatcaa g                                              321
```

<210> SEQ ID NO 7
<211> LENGTH: 121
<212> TYPE: PRT
<213> ORGANISM: Artificial Sequence
<220> FEATURE:
<223> OTHER INFORMATION: 2B10; VH

<400> SEQUENCE: 7

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120
```

<210> SEQ ID NO 8
<211> LENGTH: 363
<212> TYPE: DNA
<213> ORGANISM: Artificial Sequence
<220> FEATURE:
<223> OTHER INFORMATION: 2B10; VH

<400> SEQUENCE: 8

```
caggtgcaat tggtgcagtc tggggctgag gtgaagaagc ctgggtcctc ggtgaaggtc     60

tcctgcaagg cctccggagg cacattcagc agctacgcta taagctgggt gcgacaggcc    120

cctggacaag ggctcgagtg gatgggaggg atcatcccta tctttggtac agcaaactac    180

gcacagaagt tccagggcag ggtcaccatt actgcagaca aatccacgag cacagcctac    240

atggagctga gcagcctgag atctgaggac accgccgtgt attactgtgc gagactgtac    300

ggttacgctt actacggtgc ttttgactac tggggccaag ggaccaccgt gaccgtctcc    360

tca                                                                  363
```

<210> SEQ ID NO 9
<211> LENGTH: 108
<212> TYPE: PRT
<213> ORGANISM: Artificial Sequence
<220> FEATURE:
<223> OTHER INFORMATION: 2F11; VL

<400> SEQUENCE: 9

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Asp Arg Phe Ser
    50                  55                  60
```

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Gln Tyr Thr Pro
85 90 95

Pro Thr Phe Gly Gln Gly Thr Lys Val Glu Ile Lys
100 105

<210> SEQ ID NO 10
<211> LENGTH: 324
<212> TYPE: DNA
<213> ORGANISM: Artificial Sequence
<220> FEATURE:
<223> OTHER INFORMATION: 2F11; VL

<400> SEQUENCE: 10
gaaatcgtgt taacgcagtc tccaggcacc ctgtctttgt ctccagggga aagagccacc 60
ctctcttgca gggccagtca gagtgttagc agcagctact tagcctggta ccagcagaaa 120
cctggccagg ctcccaggct cctcatctat ggagcatcca gcagggccac tggcgtccca 180
gacaggttca gtggcagtgg atccgggaca gacttcactc tcaccatcag cagactggag 240
cctgaagatt ttgcagtgta ttactgtcag cagggtcagt atactccccc cacgttcggc 300
caggggacca aagtggaaat caaa 324

<210> SEQ ID NO 11
<211> LENGTH: 108
<212> TYPE: PRT
<213> ORGANISM: Artificial Sequence
<220> FEATURE:
<223> OTHER INFORMATION: 2F11(VI); VL

<400> SEQUENCE: 11

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Gln Tyr Thr Pro
85 90 95

Pro Thr Phe Gly Gln Gly Thr Lys Val Glu Ile Lys
100 105

<210> SEQ ID NO 12
<211> LENGTH: 324
<212> TYPE: DNA
<213> ORGANISM: Artificial Sequence
<220> FEATURE:
<223> OTHER INFORMATION: 2F11(VI); VL

<400> SEQUENCE: 12
gaaatcgtgt taacgcagtc tccaggcacc ctgtctttgt ctccagggga aagagccacc 60
ctctcttgca gggccagtca gagtgttagc agcagctact tagcctggta ccagcagaaa 120
cctggccagg ctcccaggct cctcatctat ggagcatcca gcagggccac tggcatccca 180
gacaggttca gtggcagtgg atccgggaca gacttcactc tcaccatcag cagactggag 240
cctgaagatt ttgcagtgta ttactgtcag cagggtcagt atactccccc cacgttcggc 300
caggggacca aagtggaaat caaa 324

<210> SEQ ID NO 13
<211> LENGTH: 117
<212> TYPE: PRT
<213> ORGANISM: Artificial Sequence
<220> FEATURE:
<223> OTHER INFORMATION: 2F11; VH

<400> SEQUENCE: 13

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Met Ala Val Tyr Tyr Cys
                85                  90                  95

Ala Lys Trp Arg Trp Met Met Phe Asp Tyr Trp Gly Gln Gly Thr Leu
            100                 105                 110

Val Thr Val Ser Ser
        115
```

<210> SEQ ID NO 14
<211> LENGTH: 351
<212> TYPE: DNA
<213> ORGANISM: Artificial Sequence
<220> FEATURE:
<223> OTHER INFORMATION: 2F11; VH

<400> SEQUENCE: 14
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac atggccgtat attactgtgc gaaatggaga 300
tggatgatgt ttgactactg gggccaagga accctggtca ccgtctcgag t 351

<210> SEQ ID NO 15
<211> LENGTH: 117
<212> TYPE: PRT
<213> ORGANISM: Artificial Sequence
<220> FEATURE:
<223> OTHER INFORMATION: 2F11(MT); VH

<400> SEQUENCE: 15

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Arg Trp Met Met Phe Asp Tyr Trp Gly Gln Gly Thr Leu
            100                 105                 110

Val Thr Val Ser Ser
        115
```

<210> SEQ ID NO 16
<211> LENGTH: 351
<212> TYPE: DNA
<213> ORGANISM: Artificial Sequence
<220> FEATURE:
<223> OTHER INFORMATION: 2F11(MT); VH

<400> SEQUENCE: 16

```
gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac accgccgtat attactgtgc gaaatggaga    300

tggatgatgt ttgactactg gggccaagga accctggtca ccgtctcgag t             351
```

<210> SEQ ID NO 17
<211> LENGTH: 108
<212> TYPE: PRT
<213> ORGANISM: Artificial Sequence
<220> FEATURE:
<223> OTHER INFORMATION: 3F2; VL

<400> SEQUENCE: 17

```
Glu Ile Val Leu Thr Gln Ser Pro Gly Thr Leu Ser Leu Tyr Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105
```

<210> SEQ ID NO 18
<211> LENGTH: 324
<212> TYPE: DNA
<213> ORGANISM: Artificial Sequence
<220> FEATURE:
<223> OTHER INFORMATION: 3F2; VL

<400> SEQUENCE: 18

-continued

```
gaaatcgtgt taacgcagtc tccaggcacc ctgtctttgt atccagggga aagagccacc     60

ctctcttgca gggccagtca gagtgttacc agtagctact tagcctggta ccagcagaaa    120

cctggccagg ctcccaggct cctcatcaat gtgggctccc gtagggccac tggcatccca    180

gacaggttca gtggcagtgg atccgggaca gacttcactc tcaccatcag cagactggag    240

cctgaagatt ttgcagtgta ttactgtcag cagggtatta tgcttccccc gacgttcggc    300

caggggacca aagtggaaat caaa                                           324
```

```
<210> SEQ ID NO 19
<211> LENGTH: 108
<212> TYPE: PRT
<213> ORGANISM: Artificial Sequence
<220> FEATURE:
<223> OTHER INFORMATION: 3F2(YS); VL

<400> SEQUENCE: 19

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105
```

```
<210> SEQ ID NO 20
<211> LENGTH: 324
<212> TYPE: DNA
<213> ORGANISM: Artificial Sequence
<220> FEATURE:
<223> OTHER INFORMATION: 3F2(YS); VL

<400> SEQUENCE: 20

gaaatcgtgt taacgcagtc tccaggcacc ctgtctttgt ctccagggga aagagccacc     60

ctctcttgca gggccagtca gagtgttacc agtagctact tagcctggta ccagcagaaa    120

cctggccagg ctcccaggct cctcatcaat gtgggctccc gtagggccac tggcatccca    180

gacaggttca gtggcagtgg atccgggaca gacttcactc tcaccatcag cagactggag    240

cctgaagatt ttgcagtgta ttactgtcag cagggtatta tgcttccccc gacgttcggc    300

caggggacca aagtggaaat caaa                                           324
```

```
<210> SEQ ID NO 21
<211> LENGTH: 117
<212> TYPE: PRT
<213> ORGANISM: Artificial Sequence
<220> FEATURE:
<223> OTHER INFORMATION: 3F2; VH

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

-continued

```
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115


<210> SEQ ID NO 22
<211> LENGTH: 351
<212> TYPE: DNA
<213> ORGANISM: Artificial Sequence
<220> FEATURE:
<223> OTHER INFORMATION: 3F2; VH

<400> SEQUENCE: 22

gaggtgcaat tgttggagtc tgggggaggc ttggtacagc ctggggggtc cctgagactc      60

tcctgtgcag cctccggatt cacctttagc agttatgcca tgagctgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcagatga acagcctgag agccgaggac acggccgtat attactgtgc gaaagggtgg     300

tttggtggtt ttaactactg gggccaagga accctggtca ccgtctcgag t              351


<210> SEQ ID NO 23
<211> LENGTH: 108
<212> TYPE: PRT
<213> ORGANISM: Artificial Sequence
<220> FEATURE:
<223> OTHER INFORMATION: 3D9, VL

<400> SEQUENCE: 23

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Leu Ile Pro
                85                  90                  95

Pro Thr Phe Gly Gln Gly Thr Lys Val Glu Ile Lys
            100                 105


<210> SEQ ID NO 24
<211> LENGTH: 324
<212> TYPE: DNA
<213> ORGANISM: Artificial Sequence
<220> FEATURE:
```

<223> OTHER INFORMATION: 3D9, VL

<400> SEQUENCE: 24
gaaatcgtgt taacgcagtc tccaggcacc ctgtctttgt ctccagggga aagagccacc 60
ctctcttgca gggccagtca gagtgttagc agcagctact tagcctggta ccagcagaaa 120
cctggccagg ctcccaggct cctcatctat ggagcatcca gcagggccac tggcatccca 180
gacaggttca gtggcagtgg atccgggaca gacttcactc tcaccatcag cagactggag 240
cctgaagatt ttgcagtgta ttactgtcag cagggtcagc ttattccccc tacgttcggc 300
caggggacca aagtggaaat caaa 324

<210> SEQ ID NO 25
<211> LENGTH: 117
<212> TYPE: PRT
<213> ORGANISM: Artificial Sequence
<220> FEATURE:
<223> OTHER INFORMATION: 3D9, VH

<400> SEQUENCE: 25

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Thr Pro Gly Lys Gly Leu Glu Trp Val
35 40 45

Ser Ala Ile Gly Val Ser Thr Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Trp Leu Gly Pro Phe Asp Tyr Trp Gly Gln Gly Thr Leu
100 105 110

Val Thr Val Ser Ser
115

<210> SEQ ID NO 26
<211> LENGTH: 351
<212> TYPE: DNA
<213> ORGANISM: Artificial Sequence
<220> FEATURE:
<223> OTHER INFORMATION: 3D9, VH

<400> SEQUENCE: 26
gaggtgcaat tgttggagtc tgggggaggc ttggtacagc ctggggggtc cctgagactc 60
tcctgtgcag cctccggatt cacctttagc agttatgcta tgagctgggt ccgccagact 120
ccagggaagg ggctggagtg ggtctcagct attggtgtta gtactggtag cacatactac 180
gcagactccg tgaagggccg gttcaccatc tccagagaca attccaagaa cacgctgtat 240
ctgcagatga acagcctgag agccgaggac acggccgtat attactgtgc gaaaggttgg 300
ctgggtcctt ttgactactg gggccaagga accctggtca ccgtctcgag t 351

<210> SEQ ID NO 27
<211> LENGTH: 117
<212> TYPE: PRT
<213> ORGANISM: Artificial Sequence
<220> FEATURE:
<223> OTHER INFORMATION: 2D9(TA); VH

<400> SEQUENCE: 27

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Gly Val Ser Thr Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Trp Leu Gly Pro Phe Asp Tyr Trp Gly Gln Gly Thr Leu
100 105 110

Val Thr Val Ser Ser
115

<210> SEQ ID NO 28
<211> LENGTH: 351
<212> TYPE: DNA
<213> ORGANISM: Artificial Sequence
<220> FEATURE:
<223> OTHER INFORMATION: 2D9(TA); VH

<400> SEQUENCE: 28
gaggtgcaat tgttggagtc tgggggaggc ttggtacagc ctggggggtc cctgagactc 60
tcctgtgcag cctccggatt cacctttagc agttatgcta tgagctgggt ccgccaggct 120
ccagggaagg ggctggagtg ggtctcagct attggtgtta gtactggtag cacatactac 180
gcagactccg tgaagggccg gttcaccatc tccagagaca attccaagaa cacgctgtat 240
ctgcagatga acagcctgag agccgaggac acggccgtat attactgtgc gaaaggttgg 300
ctgggtcctt ttgactactg gggccaagga accctggtca ccgtctcgag t 351

<210> SEQ ID NO 29
<211> LENGTH: 108
<212> TYPE: PRT
<213> ORGANISM: Artificial Sequence
<220> FEATURE:
<223> OTHER INFORMATION: 4G8; VL

<400> SEQUENCE: 29

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Arg Ser
20 25 30

Tyr Leu Ala Trp Tyr Gln Gln Lys Pro Gly Gln Ala Pro Arg Leu Leu
35 40 45

Ile Ile Gly Ala Ser Thr Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Gln Val Ile Pro
85 90 95

Pro Thr Phe Gly Gln Gly Thr Lys Val Glu Ile Lys
100 105

<210> SEQ ID NO 30
<211> LENGTH: 324
<212> TYPE: DNA
<213> ORGANISM: Artificial Sequence
<220> FEATURE:
<223> OTHER INFORMATION: 4G8; VL

<400> SEQUENCE: 30
gaaatcgtgt taacgcagtc tccaggcacc ctgtctttgt ctccagggga aagagccacc 60
ctctcttgca gggccagtca gagtgttagc cgcagctact tagcctggta ccagcagaaa 120
cctggccagg ctcccaggct cctcatcatt ggggcctcca ccagggccac tggcatccca 180
gacaggttca gtggcagtgg atccgggacg gacttcactc tcaccatcag cagactggag 240
cctgaagatt ttgcagtgta ttactgtcag cagggtcagg ttattccccc tacgttcggc 300
caggggacca aagtggaaat caaa 324

<210> SEQ ID NO 31
<211> LENGTH: 117
<212> TYPE: PRT
<213> ORGANISM: Artificial Sequence
<220> FEATURE:
<223> OTHER INFORMATION: 4G8; VH

<400> SEQUENCE: 31

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Trp Leu Gly Asn Phe Asp Tyr Trp Gly Gln Gly Thr Leu
100 105 110

Val Thr Val Ser Ser
115

<210> SEQ ID NO 32
<211> LENGTH: 351
<212> TYPE: DNA
<213> ORGANISM: Artificial Sequence
<220> FEATURE:
<223> OTHER INFORMATION: 4G8; VH

<400> SEQUENCE: 32
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaagggtgg 300
ctgggtaatt ttgactactg gggccaagga accctggtca ccgtctcgag t 351

-continued

<210> SEQ ID NO 33
<211> LENGTH: 108
<212> TYPE: PRT
<213> ORGANISM: Artificial Sequence
<220> FEATURE:
<223> OTHER INFORMATION: 4B3; VL

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Tyr Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105

<210> SEQ ID NO 34
<211> LENGTH: 324
<212> TYPE: DNA
<213> ORGANISM: Artificial Sequence
<220> FEATURE:
<223> OTHER INFORMATION: 4B3; VL

<400> SEQUENCE: 34
gaaatcgtgt taacgcagtc tccaggcacc ctgtctttgt ctccagggga aagagccacc 60
ctctcttgca gggccagtca gagtgttagc agcaattact tagcctggta ccagcagaaa 120
cctggccagg ctcccaggct cctcatctat ggcgcctaca tcagggccac tggcatccca 180
gacaggttca gtggcagtgg atccgggaca gacttcactc tcaccatcag cagactggag 240
cctgaagatt ttgcagtgta ttactgtcag cagggtcagg ttattccccc tacgttcggc 300
caggggacca aagtggaaat caaa 324

<210> SEQ ID NO 35
<211> LENGTH: 117
<212> TYPE: PRT
<213> ORGANISM: Artificial Sequence
<220> FEATURE:
<223> OTHER INFORMATION: 4B3; VH

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                85                  90                  95

Ala Lys Gly Trp Leu Gly Asn Phe Asp Tyr Trp Gly Gln Gly Thr Leu
            100                 105                 110

Val Thr Val Ser Ser
        115


<210> SEQ ID NO 36
<211> LENGTH: 351
<212> TYPE: DNA
<213> ORGANISM: Artificial Sequence
<220> FEATURE:
<223> OTHER INFORMATION: 4B3; VH

<400> SEQUENCE: 36

gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaagggtgg    300

ctgggtaatt ttgactactg gggccaagga accctggtca ccgtctcgag t             351


<210> SEQ ID NO 37
<211> LENGTH: 108
<212> TYPE: PRT
<213> ORGANISM: Artificial Sequence
<220> FEATURE:
<223> OTHER INFORMATION: 4D6; VL

<400> SEQUENCE: 37

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Gln Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105


<210> SEQ ID NO 38
<211> LENGTH: 324
<212> TYPE: DNA
<213> ORGANISM: Artificial Sequence
<220> FEATURE:
<223> OTHER INFORMATION: 4D6; VL

<400> SEQUENCE: 38

gaaatcgtgt taacgcagtc tccaggcacc ctgtctttgt ctccagggga aagagccacc     60

ctctcttgca gggccagtca gagtgttagc agcaactact tagcctggta ccagcagaaa    120

cctggccagg ctcccaggct cctcatccag ggcgcctcca gcagggccac tggcatccca    180

gacaggttca gtggcagtgg atccgggaca gacttcactc tcaccatcag cagactggag    240
```

```
cctgaagatt ttgcagtgta ttactgtcag cagggtcagg ttattccccc tacgttcggc    300

caggggacca aagtggaaat caaa                                           324


<210> SEQ ID NO 39
<211> LENGTH: 117
<212> TYPE: PRT
<213> ORGANISM: Artificial Sequence
<220> FEATURE:
<223> OTHER INFORMATION: 4D6; VH

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser
        115


<210> SEQ ID NO 40
<211> LENGTH: 351
<212> TYPE: DNA
<213> ORGANISM: Artificial Sequence
<220> FEATURE:
<223> OTHER INFORMATION: 4D6; VH

<400> SEQUENCE: 40

gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaagggtgg    300

ctgggtaatt ttgactactg gggccaagga accctggtca ccgtctcgag t             351


<210> SEQ ID NO 41
<211> LENGTH: 108
<212> TYPE: PRT
<213> ORGANISM: Artificial Sequence
<220> FEATURE:
<223> OTHER INFORMATION: 2C6; VL

<400> SEQUENCE: 41

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

```
Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Gln Ile Pro
                85                  90                  95

Pro Thr Phe Gly Gln Gly Thr Lys Val Glu Ile Lys
            100                 105


<210> SEQ ID NO 42
<211> LENGTH: 324
<212> TYPE: DNA
<213> ORGANISM: Artificial Sequence
<220> FEATURE:
<223> OTHER INFORMATION: 2C6; VL

<400> SEQUENCE: 42

gaaatcgtgt taacgcagtc tccaggcacc ctgtctttgt ctccagggga aagagccacc     60

ctctcttgca gggccagtca gagtgttagc agcagctact tagcctggta ccagcagaaa    120

cctggccagg ctcccaggct cctcatctat ggagcatcca gcagggccac tggcatccca    180

gacaggttca gtggcagtgg atccgggaca gacttcactc tcaccatcag caggctggag    240

cctgaagatt ttgcagtgta ttactgtcag cagggtcagc agattccccc tacgttcggc    300

caggggacca aagtggaaat caaa                                            324


<210> SEQ ID NO 43
<211> LENGTH: 117
<212> TYPE: PRT
<213> ORGANISM: Artificial Sequence
<220> FEATURE:
<223> OTHER INFORMATION: 2C6; VH

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Ala Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Asn Phe Asp Tyr Trp Gly Gln Gly Thr Leu
            100                 105                 110

Val Thr Val Ser Ser
        115


<210> SEQ ID NO 44
<211> LENGTH: 351
<212> TYPE: DNA
<213> ORGANISM: Artificial Sequence
<220> FEATURE:
<223> OTHER INFORMATION: 2C6; VH

<400> SEQUENCE: 44

gaggtgcaat tgttggagtc tgggggaggc ttggtacagc ctggggggtc cctgagactc     60
```

```
tcctgtgcag cctccggatc cacctttagc agttatgcca tgagctgggt ccgccaggct    120

ccagggaagg ggctggagtg ggtctcagct attagtggga gtgctggtta tacatactac    180

gcagactccg tgaagggccg gttcaccatc tccagagaca attccaagaa cacgctgtat    240

ctgcagatga acagcctgag agccgaggac acggccgtat attactgtgc gaaaggttgg    300

tttgggaatt ttgactactg ggccaagga accctggtca ccgtctcgag t             351


<210> SEQ ID NO 45
<211> LENGTH: 108
<212> TYPE: PRT
<213> ORGANISM: Artificial Sequence
<220> FEATURE:
<223> OTHER INFORMATION: 5H5; VL

<400> SEQUENCE: 45

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Asn Gln Ile Pro
                85                  90                  95

Pro Thr Phe Gly Gln Gly Thr Lys Val Glu Ile Lys
            100                 105


<210> SEQ ID NO 46
<211> LENGTH: 324
<212> TYPE: DNA
<213> ORGANISM: Artificial Sequence
<220> FEATURE:
<223> OTHER INFORMATION: 5H5; VL

<400> SEQUENCE: 46

gaaatcgtgt taacgcagtc tccaggcacc ctgtctttgt ctccagggga aagagccacc     60

ctctcttgca gggccagtca gagtgttagc agcagctact tagcctggta ccagcagaaa    120

cctggccagg ctcccaggct cctcatctat ggagcatcca gcagggccac tggcatccca    180

gacaggttca gtggcagtgg atccgggaca gacttcactc tcaccatcag cagactggag    240

cctgaagatt ttgcagtgta ttactgtcag cagggtaatc agattccccc tacgttcggt    300

caggggacca aagtggaaat caaa                                           324


<210> SEQ ID NO 47
<211> LENGTH: 116
<212> TYPE: PRT
<213> ORGANISM: Artificial Sequence
<220> FEATURE:
<223> OTHER INFORMATION: 5H5; VH

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Thr Met Ser Trp Val Arg Arg Ser Pro Gly Lys Gly Leu Glu Trp Val
        35                  40                  45

Ser Ala Ile Ser Gly Gly Gly Arg Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gly Trp Phe Thr Pro Phe Asp Tyr Trp Gly Gln Gly Thr Leu Val
            100                 105                 110

Thr Val Ser Ser
        115
```

<210> SEQ ID NO 48
<211> LENGTH: 348
<212> TYPE: DNA
<213> ORGANISM: Artificial Sequence
<220> FEATURE:
<223> OTHER INFORMATION: 5H5; VH

<400> SEQUENCE: 48

```
gaggtgcaat tgttggagtc tgggggaggc ttggtacagc ctggggggtc cctgagactc      60

tcctgtgcag cctccggatt cacctttagc agttatacca tgagctgggt ccgccggtct     120

ccagggaagg ggctggagtg ggtctcagct attagtggtg gtggtaggac atactacgca     180

gactccgtga agggccggtt caccatctcc agagacaatt ccaagaacac gctgtatctg     240

cagatgaaca gcctgagagc cgaggacacg gccgtatatt actgtgcgaa aggttggttt     300

acgccttttg actactgggg ccaaggaacc ctggtcaccg tctcgagt                  348
```

<210> SEQ ID NO 49
<211> LENGTH: 108
<212> TYPE: PRT
<213> ORGANISM: Artificial Sequence
<220> FEATURE:
<223> OTHER INFORMATION: 2C4; VL

<400> SEQUENCE: 49

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Asn Gln Ile Pro
                85                  90                  95

Pro Thr Phe Gly Gln Gly Thr Lys Val Glu Ile Lys
            100                 105
```

<210> SEQ ID NO 50
<211> LENGTH: 324
<212> TYPE: DNA
<213> ORGANISM: Artificial Sequence
<220> FEATURE:
<223> OTHER INFORMATION: 2C4; VL

<400> SEQUENCE: 50
gaaatcgtgt taacgcagtc tccaggcacc ctgtctttgt ctccagggga aagagccacc 60
ctctcttgca gggccagtca gagtgttagc agtaactact tagcctggta ccagcagaaa 120
cctggccagg ctcccaggct cctcatctat ggtgcctcca ttagggccac tggcatccca 180
gacaggttca gtggcagtgg atccgggaca gacttcactc tcaccatcag cagactggag 240
cctgaagatt ttgcagtgta ttactgtcag cagggtaatc agattccccc tacgttcggt 300
caggggacca aagtggaaat caaa 324

<210> SEQ ID NO 51
<211> LENGTH: 117
<212> TYPE: PRT
<213> ORGANISM: Artificial Sequence
<220> FEATURE:
<223> OTHER INFORMATION: 2C4; VH

<400> SEQUENCE: 51

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Trp Phe Thr Pro Phe Asp Tyr Trp Gly Gln Gly Thr Leu
100 105 110

Val Thr Val Ser Ser
115

<210> SEQ ID NO 52
<211> LENGTH: 351
<212> TYPE: DNA
<213> ORGANISM: Artificial Sequence
<220> FEATURE:
<223> OTHER INFORMATION: 2C4; VH

<400> SEQUENCE: 52
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagcggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaaggttgg 300
tttacgcctt ttgactactg gggccaagga accctggtca ccgtctcgag t 351

<210> SEQ ID NO 53
<211> LENGTH: 748
<212> TYPE: PRT
<213> ORGANISM: Artificial Sequence
<220> FEATURE:
<223> OTHER INFORMATION: Human FAP ectodomain+poly-lys-tag+his6-tag

<400> SEQUENCE: 53

```
Arg Pro Ser Arg Val His Asn Ser Glu Glu Asn Thr Met Arg Ala Leu
1               5                   10                  15

Thr Leu Lys Asp Ile Leu Asn Gly Thr Phe Ser Tyr Lys Thr Phe Phe
            20                  25                  30

Pro Asn Trp Ile Ser Gly Gln Glu Tyr Leu His Gln Ser Ala Asp Asn
        35                  40                  45

Asn Ile Val Leu Tyr Asn Ile Glu Thr Gly Gln Ser Tyr Thr Ile Leu
    50                  55                  60

Ser Asn Arg Thr Met Lys Ser Val Asn Ala Ser Asn Tyr Gly Leu Ser
65                  70                  75                  80

Pro Asp Arg Gln Phe Val Tyr Leu Glu Ser Asp Tyr Ser Lys Leu Trp
                85                  90                  95

Arg Tyr Ser Tyr Thr Ala Thr Tyr Tyr Ile Tyr Asp Leu Ser Asn Gly
            100                 105                 110

Glu Phe Val Arg Gly Asn Glu Leu Pro Arg Pro Ile Gln Tyr Leu Cys
        115                 120                 125

Trp Ser Pro Val Gly Ser Lys Leu Ala Tyr Val Tyr Gln Asn Asn Ile
    130                 135                 140

Tyr Leu Lys Gln Arg Pro Gly Asp Pro Pro Phe Gln Ile Thr Phe Asn
145                 150                 155                 160

Gly Arg Glu Asn Lys Ile Phe Asn Gly Ile Pro Asp Trp Val Tyr Glu
                165                 170                 175

Glu Glu Met Leu Ala Thr Lys Tyr Ala Leu Trp Trp Ser Pro Asn Gly
            180                 185                 190

Lys Phe Leu Ala Tyr Ala Glu Phe Asn Asp Thr Asp Ile Pro Val Ile
        195                 200                 205

Ala Tyr Ser Tyr Tyr Gly Asp Glu Gln Tyr Pro Arg Thr Ile Asn Ile
    210                 215                 220

Pro Tyr Pro Lys Ala Gly Ala Lys Asn Pro Val Val Arg Ile Phe Ile
225                 230                 235                 240

Ile Asp Thr Thr Tyr Pro Ala Tyr Val Gly Pro Gln Glu Val Pro Val
                245                 250                 255

Pro Ala Met Ile Ala Ser Ser Asp Tyr Tyr Phe Ser Trp Leu Thr Trp
            260                 265                 270

Val Thr Asp Glu Arg Val Cys Leu Gln Trp Leu Lys Arg Val Gln Asn
        275                 280                 285

Val Ser Val Leu Ser Ile Cys Asp Phe Arg Glu Asp Trp Gln Thr Trp
    290                 295                 300

Asp Cys Pro Lys Thr Gln Glu His Ile Glu Glu Ser Arg Thr Gly Trp
305                 310                 315                 320

Ala Gly Gly Phe Phe Val Ser Thr Pro Val Phe Ser Tyr Asp Ala Ile
                325                 330                 335

Ser Tyr Tyr Lys Ile Phe Ser Asp Lys Asp Gly Tyr Lys His Ile His
            340                 345                 350

Tyr Ile Lys Asp Thr Val Glu Asn Ala Ile Gln Ile Thr Ser Gly Lys
        355                 360                 365

Trp Glu Ala Ile Asn Ile Phe Arg Val Thr Gln Asp Ser Leu Phe Tyr
    370                 375                 380

Ser Ser Asn Glu Phe Glu Glu Tyr Pro Gly Arg Arg Asn Ile Tyr Arg
385                 390                 395                 400

Ile Ser Ile Gly Ser Tyr Pro Pro Ser Lys Lys Cys Val Thr Cys His
                405                 410                 415
```

```
Leu Arg Lys Glu Arg Cys Gln Tyr Tyr Thr Ala Ser Phe Ser Asp Tyr
            420                 425                 430

Ala Lys Tyr Tyr Ala Leu Val Cys Tyr Gly Pro Gly Ile Pro Ile Ser
        435                 440                 445

Thr Leu His Asp Gly Arg Thr Asp Gln Glu Ile Lys Ile Leu Glu Glu
    450                 455                 460

Asn Lys Glu Leu Glu Asn Ala Leu Lys Asn Ile Gln Leu Pro Lys Glu
465                 470                 475                 480

Glu Ile Lys Lys Leu Glu Val Asp Glu Ile Thr Leu Trp Tyr Lys Met
                485                 490                 495

Ile Leu Pro Pro Gln Phe Asp Arg Ser Lys Lys Tyr Pro Leu Leu Ile
            500                 505                 510

Gln Val Tyr Gly Gly Pro Cys Ser Gln Ser Val Arg Ser Val Phe Ala
        515                 520                 525

Val Asn Trp Ile Ser Tyr Leu Ala Ser Lys Glu Gly Met Val Ile Ala
    530                 535                 540

Leu Val Asp Gly Arg Gly Thr Ala Phe Gln Gly Asp Lys Leu Leu Tyr
545                 550                 555                 560

Ala Val Tyr Arg Lys Leu Gly Val Tyr Glu Val Glu Asp Gln Ile Thr
                565                 570                 575

Ala Val Arg Lys Phe Ile Glu Met Gly Phe Ile Asp Glu Lys Arg Ile
            580                 585                 590

Ala Ile Trp Gly Trp Ser Tyr Gly Gly Tyr Val Ser Ser Leu Ala Leu
        595                 600                 605

Ala Ser Gly Thr Gly Leu Phe Lys Cys Gly Ile Ala Val Ala Pro Val
    610                 615                 620

Ser Ser Trp Glu Tyr Tyr Ala Ser Val Tyr Thr Glu Arg Phe Met Gly
625                 630                 635                 640

Leu Pro Thr Lys Asp Asp Asn Leu Glu His Tyr Lys Asn Ser Thr Val
                645                 650                 655

Met Ala Arg Ala Glu Tyr Phe Arg Asn Val Asp Tyr Leu Leu Ile His
            660                 665                 670

Gly Thr Ala Asp Asp Asn Val His Phe Gln Asn Ser Ala Gln Ile Ala
        675                 680                 685

Lys Ala Leu Val Asn Ala Gln Val Asp Phe Gln Ala Met Trp Tyr Ser
    690                 695                 700

Asp Gln Asn His Gly Leu Ser Gly Leu Ser Thr Asn His Leu Tyr Thr
705                 710                 715                 720

His Met Thr His Phe Leu Lys Gln Cys Phe Ser Leu Ser Asp Gly Lys
                725                 730                 735

Lys Lys Lys Lys Lys Gly His His His His His His
            740                 745
```

<210> SEQ ID NO 54
<211> LENGTH: 2244
<212> TYPE: DNA
<213> ORGANISM: Artificial Sequence
<220> FEATURE:
<223> OTHER INFORMATION: Human FAP ectodomain+poly-lys-tag+his6-tag

<400> SEQUENCE: 54

```
cgcccttcaa gagttcataa ctctgaagaa aatacaatga gagcactcac actgaaggat      60

attttaaatg gaacattttc ttataaaaca tttttttccaa actggatttc aggacaagaa    120

tatcttcatc aatctgcaga taacaatata gtactttata atattgaaac aggacaatca    180
```

-continued

```
tataccattt tgagtaatag aaccatgaaa agtgtgaatg cttcaaatta cggcttatca    240
cctgatcggc aatttgtata tctagaaagt gattattcaa agctttggag atactcttac    300
acagcaacat attacatcta tgaccttagc aatggagaat ttgtaagagg aaatgagctt    360
cctcgtccaa ttcagtattt atgctggtcg cctgttggga gtaaattagc atatgtctat    420
caaaacaata tctatttgaa acaaagacca ggagatccac cttttcaaat aacatttaat    480
ggaagagaaa ataaaatatt taatggaatc ccagactggg tttatgaaga ggaaatgctt    540
gctacaaaat atgctctctg gtggtctcct aatggaaaat ttttggcata tgcggaattt    600
aatgatacgg atataccagt tattgcctat tcctattatg gcgatgaaca atatcctaga    660
acaataaata ttccataccc aaaggctgga gctaagaatc ccgttgttcg gatatttatt    720
atcgatacca cttaccctgc gtatgtaggt ccccaggaag tgcctgttcc agcaatgata    780
gcctcaagtg attattattt cagttggctc acgtgggtta ctgatgaacg agtatgtttg    840
cagtggctaa aaagagtcca gaatgtttcg gtcctgtcta tatgtgactt cagggaagac    900
tggcagacat gggattgtcc aaagacccag gagcatatag aagaaagcag aactggatgg    960
gctggtggat tctttgtttc aacaccagtt ttcagctatg atgccatttc gtactacaaa   1020
atatttagtg acaaggatgg ctacaaacat attcactata tcaaagacac tgtggaaaat   1080
gctattcaaa ttacaagtgg caagtgggag gccataaata tattcagagt aacacaggat   1140
tcactgtttt attctagcaa tgaatttgaa gaataccctg gaagaagaaa catctacaga   1200
attagcattg gaagctatcc tccaagcaag aagtgtgtta cttgccatct aaggaaagaa   1260
aggtgccaat attacacagc aagtttcagc gactacgcca agtactatgc acttgtctgc   1320
tacggcccag gcatccccat ttccaccctt catgatggac gcactgatca agaaattaaa   1380
atcctggaag aaaacaagga attggaaaat gctttgaaaa atatccagct gcctaaagag   1440
gaaattaaga aacttgaagt agatgaaatt actttatggt acaagatgat tcttcctcct   1500
caatttgaca gatcaaagaa gtatcccttg ctaattcaag tgtatggtgg tccctgcagt   1560
cagagtgtaa ggtctgtatt tgctgttaat tggatatctt atcttgcaag taaggaaggg   1620
atggtcattg ccttggtgga tggtcgagga acagctttcc aaggtgacaa actcctctat   1680
gcagtgtatc gaaagctggg tgtttatgaa gttgaagacc agattacagc tgtcagaaaa   1740
ttcatagaaa tgggtttcat tgatgaaaaa agaatagcca tatggggctg gtcctatgga   1800
ggatacgttt catcactggc ccttgcatct ggaactggtc ttttcaaatg tggtatagca   1860
gtggctccag tctccagctg ggaatattac gcgtctgtct acacagagag attcatgggt   1920
ctcccaacaa aggatgataa tcttgagcac tataagaatt caactgtgat ggcaagagca   1980
gaatatttca gaaatgtaga ctatcttctc atccacggaa cagcagatga taatgtgcac   2040
tttcaaaact cagcacagat tgctaaagct ctggttaatg cacaagtgga tttccaggca   2100
atgtggtact ctgaccagaa ccacggctta tccggcctgt ccacgaacca cttatacacc   2160
cacatgaccc acttcctaaa gcagtgtttc tctttgtcag acggcaaaaa gaaaaagaaa   2220
aagggccacc accatcacca tcac                                          2244
```

<210> SEQ ID NO 55
<211> LENGTH: 749
<212> TYPE: PRT
<213> ORGANISM: Artificial Sequence
<220> FEATURE:
<223> OTHER INFORMATION: Murine FAP ectodomain+poly-lys-tag+his6-tag

<400> SEQUENCE: 55

Arg Pro Ser Arg Val Tyr Lys Pro Glu Gly Asn Thr Lys Arg Ala Leu
1 5 10 15

Thr Leu Lys Asp Ile Leu Asn Gly Thr Phe Ser Tyr Lys Thr Tyr Phe
20 25 30

Pro Asn Trp Ile Ser Glu Gln Glu Tyr Leu His Gln Ser Glu Asp Asp
35 40 45

Asn Ile Val Phe Tyr Asn Ile Glu Thr Arg Glu Ser Tyr Ile Ile Leu
50 55 60

Ser Asn Ser Thr Met Lys Ser Val Asn Ala Thr Asp Tyr Gly Leu Ser
65 70 75 80

Pro Asp Arg Gln Phe Val Tyr Leu Glu Ser Asp Tyr Ser Lys Leu Trp
85 90 95

Arg Tyr Ser Tyr Thr Ala Thr Tyr Tyr Ile Tyr Asp Leu Gln Asn Gly
100 105 110

Glu Phe Val Arg Gly Tyr Glu Leu Pro Arg Pro Ile Gln Tyr Leu Cys
115 120 125

Trp Ser Pro Val Gly Ser Lys Leu Ala Tyr Val Tyr Gln Asn Asn Ile
130 135 140

Tyr Leu Lys Gln Arg Pro Gly Asp Pro Pro Phe Gln Ile Thr Tyr Thr
145 150 155 160

Gly Arg Glu Asn Arg Ile Phe Asn Gly Ile Pro Asp Trp Val Tyr Glu
165 170 175

Glu Glu Met Leu Ala Thr Lys Tyr Ala Leu Trp Trp Ser Pro Asp Gly
180 185 190

Lys Phe Leu Ala Tyr Val Glu Phe Asn Asp Ser Asp Ile Pro Ile Ile
195 200 205

Ala Tyr Ser Tyr Tyr Gly Asp Gly Gln Tyr Pro Arg Thr Ile Asn Ile
210 215 220

Pro Tyr Pro Lys Ala Gly Ala Lys Asn Pro Val Val Arg Val Phe Ile
225 230 235 240

Val Asp Thr Thr Tyr Pro His His Val Gly Pro Met Glu Val Pro Val
245 250 255

Pro Glu Met Ile Ala Ser Ser Asp Tyr Tyr Phe Ser Trp Leu Thr Trp
260 265 270

Val Ser Ser Glu Arg Val Cys Leu Gln Trp Leu Lys Arg Val Gln Asn
275 280 285

Val Ser Val Leu Ser Ile Cys Asp Phe Arg Glu Asp Trp His Ala Trp
290 295 300

Glu Cys Pro Lys Asn Gln Glu His Val Glu Glu Ser Arg Thr Gly Trp
305 310 315 320

Ala Gly Gly Phe Phe Val Ser Thr Pro Ala Phe Ser Gln Asp Ala Thr
325 330 335

Ser Tyr Tyr Lys Ile Phe Ser Asp Lys Asp Gly Tyr Lys His Ile His
340 345 350

Tyr Ile Lys Asp Thr Val Glu Asn Ala Ile Gln Ile Thr Ser Gly Lys
355 360 365

Trp Glu Ala Ile Tyr Ile Phe Arg Val Thr Gln Asp Ser Leu Phe Tyr
370 375 380

Ser Ser Asn Glu Phe Glu Gly Tyr Pro Gly Arg Arg Asn Ile Tyr Arg
385 390 395 400

Ile Ser Ile Gly Asn Ser Pro Pro Ser Lys Lys Cys Val Thr Cys His
405 410 415

```
Leu Arg Lys Glu Arg Cys Gln Tyr Tyr Thr Ala Ser Phe Ser Tyr Lys
            420                 425                 430

Ala Lys Tyr Tyr Ala Leu Val Cys Tyr Gly Pro Gly Leu Pro Ile Ser
        435                 440                 445

Thr Leu His Asp Gly Arg Thr Asp Gln Glu Ile Gln Val Leu Glu Glu
    450                 455                 460

Asn Lys Glu Leu Glu Asn Ser Leu Arg Asn Ile Gln Leu Pro Lys Val
465                 470                 475                 480

Glu Ile Lys Lys Leu Lys Asp Gly Gly Leu Thr Phe Trp Tyr Lys Met
                485                 490                 495

Ile Leu Pro Pro Gln Phe Asp Arg Ser Lys Lys Tyr Pro Leu Leu Ile
            500                 505                 510

Gln Val Tyr Gly Gly Pro Cys Ser Gln Ser Val Lys Ser Val Phe Ala
        515                 520                 525

Val Asn Trp Ile Thr Tyr Leu Ala Ser Lys Glu Gly Ile Val Ile Ala
    530                 535                 540

Leu Val Asp Gly Arg Gly Thr Ala Phe Gln Gly Asp Lys Phe Leu His
545                 550                 555                 560

Ala Val Tyr Arg Lys Leu Gly Val Tyr Glu Val Glu Asp Gln Leu Thr
                565                 570                 575

Ala Val Arg Lys Phe Ile Glu Met Gly Phe Ile Asp Glu Glu Arg Ile
            580                 585                 590

Ala Ile Trp Gly Trp Ser Tyr Gly Gly Tyr Val Ser Ser Leu Ala Leu
        595                 600                 605

Ala Ser Gly Thr Gly Leu Phe Lys Cys Gly Ile Ala Val Ala Pro Val
    610                 615                 620

Ser Ser Trp Glu Tyr Tyr Ala Ser Ile Tyr Ser Glu Arg Phe Met Gly
625                 630                 635                 640

Leu Pro Thr Lys Asp Asp Asn Leu Glu His Tyr Lys Asn Ser Thr Val
                645                 650                 655

Met Ala Arg Ala Glu Tyr Phe Arg Asn Val Asp Tyr Leu Leu Ile His
            660                 665                 670

Gly Thr Ala Asp Asp Asn Val His Phe Gln Asn Ser Ala Gln Ile Ala
        675                 680                 685

Lys Ala Leu Val Asn Ala Gln Val Asp Phe Gln Ala Met Trp Tyr Ser
    690                 695                 700

Asp Gln Asn His Gly Ile Leu Ser Gly Arg Ser Gln Asn His Leu Tyr
705                 710                 715                 720

Thr His Met Thr His Phe Leu Lys Gln Cys Phe Ser Leu Ser Asp Gly
                725                 730                 735

Lys Lys Lys Lys Lys Lys Gly His His His His His His
            740                 745
```

```
<210> SEQ ID NO 56
<211> LENGTH: 2247
<212> TYPE: DNA
<213> ORGANISM: Artificial Sequence
<220> FEATURE:
<223> OTHER INFORMATION: Murine FAP ectodomain+poly-lys-tag+his6-tag

<400> SEQUENCE: 56

cgtccctcaa gagtttacaa acctgaagga aacacaaaga gagctcttac cttgaaggat      60

attttaaatg gaacattctc atataaaaca tattttccca actggatttc agaacaagaa     120

tatcttcatc aatctgagga tgataacata gtattttata atattgaaac aagagaatca     180
```

```
tatatcattt tgagtaatag caccatgaaa agtgtgaatg ctacagatta tggtttgtca    240
cctgatcggc aatttgtgta tctagaaagt gattattcaa agctctggcg atattcatac    300
acagcgacat actacatcta cgaccttcag aatggggaat ttgtaagagg atacgagctc    360
cctcgtccaa ttcagtatct atgctggtcg cctgttggga gtaaattagc atatgtatat    420
caaaacaata tttatttgaa acaaagacca ggagatccac cttttcaaat aacttatact    480
ggaagagaaa atagaatatt taatggaata ccagactggg tttatgaaga ggaaatgctt    540
gccacaaaat atgctctttg gtggtctcca gatggaaaat ttttggcata tgtagaattt    600
aatgattcag atataccaat tattgcctat tcttattatg gtgatggaca gtatcctaga    660
actataaata ttccatatcc aaaggctggg gctaagaatc cggttgttcg tgtttttatt    720
gttgacacca cctaccctca ccacgtgggc ccaatggaag tgccagttcc agaaatgata    780
gcctcaagtg actattattt cagctggctc acatgggtgt ccagtgaacg agtatgcttg    840
cagtggctaa aaagagtgca gaatgtctca gtcctgtcta tatgtgattt cagggaagac    900
tggcatgcat gggaatgtcc aaagaaccag gagcatgtag aagaaagcag aacaggatgg    960
gctggtggat tctttgtttc gacaccagct tttagccagg atgccacttc ttactacaaa   1020
atatttagcg acaaggatgg ttacaaacat attcactaca tcaaagacac tgtggaaaat   1080
gctattcaaa ttacaagtgg caagtgggag gccatatata tattccgcgt aacacaggat   1140
tcactgtttt attctagcaa tgaatttgaa ggttaccctg gaagaagaaa catctacaga   1200
attagcattg gaaactctcc tccgagcaag aagtgtgtta cttgccatct aaggaaagaa   1260
aggtgccaat attacacagc aagtttcagc tacaaagcca agtactatgc actcgtctgc   1320
tatggccctg gcctccccat ttccaccctc catgatggcc gcacagacca agaaatacaa   1380
gtattagaag aaaacaaaga actggaaaat tctctgagaa atatccagct gcctaaagtg   1440
gagattaaga agctcaaaga cgggggactg actttctggt acaagatgat tctgcctcct   1500
cagtttgaca gatcaaagaa gtaccctttg ctaattcaag tgtatggtgg tccttgtagc   1560
cagagtgtta agtctgtgtt tgctgttaat tggataactt atctcgcaag taaggagggg   1620
atagtcattg ccctggtaga tggtcggggc actgctttcc aaggtgacaa attcctgcat   1680
gccgtgtatc gaaaactggg tgtatatgaa gttgaggacc agctcacagc tgtcagaaaa   1740
ttcatagaaa tgggtttcat tgatgaagaa agaatagcca tatggggctg gtcctacgga   1800
ggttatgttt catccctggc ccttgcatct ggaactggtc ttttcaaatg tggcatagca   1860
gtggctccag tctccagctg ggaatattac gcatctatct actcagagag attcatgggc   1920
ctcccaacaa aggacgacaa tctcgaacac tataaaaatt caactgtgat ggcaagagca   1980
gaatatttca gaaatgtaga ctatcttctc atccacggaa cagcagatga taatgtgcac   2040
tttcagaact cagcacagat tgctaaagct ttggttaatg cacaagtgga tttccaggcg   2100
atgtggtact ctgaccagaa ccatggtata ttatctgggc gctcccagaa tcatttatat   2160
acccacatga cgcacttcct caagcaatgc ttttctttat cagacggcaa aaagaaaaag   2220
aaaaagggcc accaccatca ccatcac                                       2247
```

<210> SEQ ID NO 57
<211> LENGTH: 119
<212> TYPE: PRT
<213> ORGANISM: Artificial Sequence
<220> FEATURE:
<223> OTHER INFORMATION: Human TNC-A2+avi-tag +his6-tag

<400> SEQUENCE: 57

Ala Ser Thr Gly Glu Thr Pro Asn Leu Gly Glu Val Val Val Ala Glu
1 5 10 15

Val Gly Trp Asp Ala Leu Lys Leu Asn Trp Thr Ala Pro Glu Gly Ala
20 25 30

Tyr Glu Tyr Phe Phe Ile Gln Val Gln Glu Ala Asp Thr Val Glu Ala
35 40 45

Ala Gln Asn Leu Thr Val Pro Gly Gly Leu Arg Ser Thr Asp Leu Pro
50 55 60

Gly Leu Lys Ala Ala Thr His Tyr Thr Ile Thr Ile Arg Gly Val Thr
65 70 75 80

Gln Asp Phe Ser Thr Thr Pro Leu Ser Val Glu Val Leu Thr Ala Ser
85 90 95

Gly Leu Asn Asp Ile Phe Glu Ala Gln Lys Ile Glu Trp His Glu Gly
100 105 110

Thr His His His His His His
115

<210> SEQ ID NO 58
<211> LENGTH: 357
<212> TYPE: DNA
<213> ORGANISM: Artificial Sequence
<220> FEATURE:
<223> OTHER INFORMATION: Human TNC-A2+avi-tag +his6-tag

<400> SEQUENCE: 58
gcgtccaccg gggaaacccc gaacctgggc gaagtggtgg tggcggaagt gggttgggat 60
gcgctgaaac tgaactggac cgcgccggaa ggcgcgtatg aatatttttt catccaggtg 120
caggaagcgg ataccgttga agcggcgcag aacctgaccg ttccgggcgg tctgcgtagc 180
accgatctgc cgggcctgaa agcggcgacc cattatacca ttaccatccg tggggtgacc 240
caggatttta gcaccacccc gctgtctgtg gaagtgctga ccgctagcgg cctgaacgac 300
atcttcgagg ctcagaaaat cgaatggcac gaaggtaccc atcaccatca ccaccac 357

<210> SEQ ID NO 59
<211> LENGTH: 116
<212> TYPE: PRT
<213> ORGANISM: Artificial Sequence
<220> FEATURE:
<223> OTHER INFORMATION: Human TNC-A1+avi-tag +his6-tag

<400> SEQUENCE: 59

Glu Gln Ala Pro Glu Leu Glu Asn Leu Thr Val Thr Glu Val Gly Trp
1 5 10 15

Asp Gly Leu Arg Leu Asn Trp Thr Ala Ala Asp Gln Ala Tyr Glu His
20 25 30

Phe Ile Ile Gln Val Gln Glu Ala Asn Lys Val Glu Ala Ala Arg Asn
35 40 45

Leu Thr Val Pro Gly Ser Leu Arg Ala Val Asp Ile Pro Gly Leu Lys
50 55 60

Ala Ala Thr Pro Tyr Thr Val Ser Ile Tyr Gly Val Ile Gln Gly Tyr
65 70 75 80

Arg Thr Pro Val Leu Ser Ala Glu Ala Ser Thr Ala Ser Gly Leu Asn
85 90 95

Asp Ile Phe Glu Ala Gln Lys Ile Glu Trp His Glu Gly Thr His His
100 105 110

His His His His
115

<210> SEQ ID NO 60
<211> LENGTH: 348
<212> TYPE: DNA
<213> ORGANISM: Artificial Sequence
<220> FEATURE:
<223> OTHER INFORMATION: Human TNC-A1+avi-tag +his6-tag

<400> SEQUENCE: 60
gaacaagccc ctgagctgga aaacctcacc gtgactgagg ttggctggga tggcctcaga 60
ctcaactgga ccgcggctga ccaggcctat gagcacttta tcattcaggt gcaggaggcc 120
aacaaggtgg aggcagctcg gaacctcacc gtgcctggca gccttcgggc tgtggacata 180
ccgggcctca aggctgctac gccttataca gtctccatct atggggtgat ccagggctat 240
agaacaccag tgctctctgc tgaggcctcc acagctagcg gcctgaacga catcttcgag 300
gctcagaaaa tcgaatggca cgaaggtacc catcaccatc accaccac 348

<210> SEQ ID NO 61
<211> LENGTH: 124
<212> TYPE: PRT
<213> ORGANISM: Artificial Sequence
<220> FEATURE:
<223> OTHER INFORMATION: Murine TNC-A1+avi-tag +his6-tag

<400> SEQUENCE: 61

Ile Ser Glu Phe Gly Ser Ser Thr Glu Glu Val Pro Ser Leu Glu Asn
1 5 10 15

Leu Thr Val Thr Glu Ala Gly Trp Asp Gly Leu Arg Leu Asn Trp Thr
20 25 30

Ala Asp Asp Leu Ala Tyr Glu Tyr Phe Val Ile Gln Val Gln Glu Ala
35 40 45

Asn Asn Val Glu Thr Ala His Asn Phe Thr Val Pro Gly Asn Leu Arg
50 55 60

Ala Ala Asp Ile Pro Gly Leu Lys Val Ala Thr Ser Tyr Arg Val Ser
65 70 75 80

Ile Tyr Gly Val Ala Arg Gly Tyr Arg Thr Pro Val Leu Ser Ala Glu
85 90 95

Thr Ser Thr Ala Ser Gly Leu Asn Asp Ile Phe Glu Ala Gln Lys Ile
100 105 110

Glu Trp His Glu Gly Thr His His His His His His
115 120

<210> SEQ ID NO 62
<211> LENGTH: 372
<212> TYPE: DNA
<213> ORGANISM: Artificial Sequence
<220> FEATURE:
<223> OTHER INFORMATION: Murine TNC-A1+avi-tag +his6-tag

<400> SEQUENCE: 62
atttcagaat tcggatccag caccgaagaa gtgccgagcc tggaaaacct gaccgtgacc 60
gaagcgggct gggatggcct gcgtctgaac tggaccgcgg atgatctggc ctatgaatat 120
tttgtgatcc aggtgcagga agcgaacaac gttgaaaccg cgcataactt taccgtgccg 180
ggcaatctgc gtgcggcgga tattccgggc ctgaaagtgg cgaccagcta tcgtgtgagc 240
atttatggcg tggcgcgtgg ctatcgtacc ccggttctga gcgcggaaac cagcaccgct 300

```
agcggcctga acgacatctt cgaggctcag aaaatcgaat ggcacgaagg tacccatcac    360

catcaccacc ac                                                        372


<210> SEQ ID NO 63
<211> LENGTH: 116
<212> TYPE: PRT
<213> ORGANISM: Artificial Sequence
<220> FEATURE:
<223> OTHER INFORMATION: Human TNC-A4+ avi-tag +his6-tag

<400> SEQUENCE: 63

Glu Asp Leu Pro Gln Leu Gly Asp Leu Ala Val Ser Glu Val Gly Trp
1               5                   10                  15

Asp Gly Leu Arg Leu Asn Trp Thr Ala Ala Asp Asn Ala Tyr Glu His
            20                  25                  30

Phe Val Ile Gln Val Gln Glu Val Asn Lys Val Glu Ala Ala Gln Asn
        35                  40                  45

Leu Thr Leu Pro Gly Ser Leu Arg Ala Val Asp Ile Pro Gly Leu Glu
    50                  55                  60

Ala Ala Thr Pro Tyr Arg Val Ser Ile Tyr Gly Val Ile Arg Gly Tyr
65                  70                  75                  80

Arg Thr Pro Val Leu Ser Ala Glu Ala Ser Thr Ala Ser Gly Leu Asn
                85                  90                  95

Asp Ile Phe Glu Ala Gln Lys Ile Glu Trp His Glu Gly Thr His His
            100                 105                 110

His His His His
        115


<210> SEQ ID NO 64
<211> LENGTH: 348
<212> TYPE: DNA
<213> ORGANISM: Artificial Sequence
<220> FEATURE:
<223> OTHER INFORMATION: Human TNC-A4+ avi-tag +his6-tag

<400> SEQUENCE: 64

gaagatctgc cgcagctggg cgatctggcc gtgagcgaag tgggctggga tggcctgcgt     60

ctgaactgga ccgcggcgga taacgcgtat gaacattttg tgattcaggt gcaggaagtg    120

aacaaagttg aagcggcgca gaacctgacc ctgccgggca gcctgcgtgc ggtggatatt    180

ccgggcctgg aagcggcgac cccgtatcgt gtgagcatct atggcgtgat tcgtggctat    240

cgtaccccgg ttctgagcgc ggaagcgagc accgctagcg gcctgaacga catcttcgag    300

gctcagaaaa tcgaatggca cgaaggtacc catcaccatc accaccac                 348


<210> SEQ ID NO 65
<211> LENGTH: 124
<212> TYPE: PRT
<213> ORGANISM: Artificial Sequence
<220> FEATURE:
<223> OTHER INFORMATION: Murine TNC-A4 +avi-tag +his6-tag

<400> SEQUENCE: 65

Ile Ser Glu Phe Gly Ser Leu Thr Glu Asp Leu Pro Gln Leu Gly Gly
1               5                   10                  15

Leu Ser Val Thr Glu Val Ser Trp Asp Gly Leu Thr Leu Asn Trp Thr
            20                  25                  30

Thr Asp Asp Leu Ala Tyr Lys His Phe Val Val Gln Val Gln Glu Ala
        35                  40                  45
```

-continued

```
Asn Asn Val Glu Ala Ala Gln Asn Leu Thr Val Pro Gly Ser Leu Arg
    50                  55                  60

Ala Val Asp Ile Pro Gly Leu Lys Ala Asp Thr Pro Tyr Arg Val Ser
65                  70                  75                  80

Ile Tyr Gly Val Ile Gln Gly Tyr Arg Thr Pro Met Leu Ser Thr Asp
                85                  90                  95

Val Ser Thr Ala Ser Gly Leu Asn Asp Ile Phe Glu Ala Gln Lys Ile
            100                 105                 110

Glu Trp His Glu Gly Thr His His His His His His
        115                 120


<210> SEQ ID NO 66
<211> LENGTH: 372
<212> TYPE: DNA
<213> ORGANISM: Artificial Sequence
<220> FEATURE:
<223> OTHER INFORMATION: Murine TNC-A4 +avi-tag +his6-tag

<400> SEQUENCE: 66

atttcagaat tcggatccct gaccgaagat ctgccgcagc tgggcggtct gagcgtgacc      60

gaagtgagct gggatggcct gaccctgaac tggaccaccg atgatctggc ctataaacat     120

tttgtggtgc aggtgcagga agcgaacaac gttgaagcgg cgcagaacct gaccgttccg     180

ggtagcctgc gtgcggtgga tattccgggc ctgaaagcgg ataccccgta tcgtgtgagc     240

atttatggcg tgattcaggg ctatcgtacc ccgatgctgt ctaccgatgt gagcaccgct     300

agcggcctga acgacatctt cgaggctcag aaaatcgaat ggcacgaagg tacccatcac     360

catcaccacc ac                                                         372


<210> SEQ ID NO 67
<211> LENGTH: 108
<212> TYPE: PRT
<213> ORGANISM: Artificial Sequence
<220> FEATURE:
<223> OTHER INFORMATION: 2D9; VL

<400> SEQUENCE: 67

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Asn Gln Ile Pro
                85                  90                  95

Pro Thr Phe Gly Gln Gly Thr Lys Val Glu Ile Lys
            100                 105


<210> SEQ ID NO 68
<211> LENGTH: 324
<212> TYPE: DNA
<213> ORGANISM: Artificial Sequence
<220> FEATURE:
<223> OTHER INFORMATION: 2D9; VL

<400> SEQUENCE: 68
```

```
gaaatcgtgt taacgcagtc tccaggcacc ctgtctttgt ctccagggga aagagccacc     60

ctctcttgca gggccagtca gagtgttagc agcagctact tagcctggta ccagcagaaa    120

cctggccagg ctcccaggct cctcatctat ggagcatcca gcagggccac tggcatccca    180

gacaggttca gtggcagtgg atccgggaca gacttcactc tcaccatcag cagactggag    240

cctgaagatt ttgcagtgta ttactgtcag cagggtaatc agattccccc tacgttcggt    300

caggggacca aagtggaaat caaa                                           324


<210> SEQ ID NO 69
<211> LENGTH: 117
<212> TYPE: PRT
<213> ORGANISM: Artificial Sequence
<220> FEATURE:
<223> OTHER INFORMATION: 2D9; VH

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Thr Pro Phe Asp Tyr Trp Gly Gln Gly Thr Leu
            100                 105                 110

Val Thr Val Ser Ser
        115


<210> SEQ ID NO 70
<211> LENGTH: 351
<212> TYPE: DNA
<213> ORGANISM: Artificial Sequence
<220> FEATURE:
<223> OTHER INFORMATION: 2D9; VH

<400> SEQUENCE: 70

gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagcggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaaggttgg    300

tttacgcctt ttgactactg gggccaagga accctggtca ccgtctcgag t             351


<210> SEQ ID NO 71
<211> LENGTH: 108
<212> TYPE: PRT
<213> ORGANISM: Artificial Sequence
<220> FEATURE:
<223> OTHER INFORMATION: 4B8; VL

<400> SEQUENCE: 71
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105
```

<210> SEQ ID NO 72
<211> LENGTH: 324
<212> TYPE: DNA
<213> ORGANISM: Artificial Sequence
<220> FEATURE:
<223> OTHER INFORMATION: 4B8; VL

<400> SEQUENCE: 72

```
gaaatcgtgt taacgcagtc tccaggcacc ctgtctttgt ctccagggga aagagccacc     60

ctctcttgca gggccagtca gagtgttagc agcagctact tagcctggta ccagcagaaa    120

cctggccagg ctcccaggct cctcatctat ggagcatcca gcagggccac tggcatccca    180

gacaggttca gtggcagtgg atccgggaca gacttcactc tcaccatcag cagactggag    240

cctgaagatt ttgcagtgta ttactgtcag cagggtcagg ttattccccc tacgttcggc    300

caggggacca aagtggaaat caaa                                            324
```

<210> SEQ ID NO 73
<211> LENGTH: 117
<212> TYPE: PRT
<213> ORGANISM: Artificial Sequence
<220> FEATURE:
<223> OTHER INFORMATION: 4B8; VH

<400> SEQUENCE: 73

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser
        115
```

<210> SEQ ID NO 74

<211> LENGTH: 351
<212> TYPE: DNA
<213> ORGANISM: Artificial Sequence
<220> FEATURE:
<223> OTHER INFORMATION: 4B8; VH

<400> SEQUENCE: 74
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaagggtgg 300
ctgggtaatt ttgactactg gggccaagga accctggtca ccgtctcgag t 351

<210> SEQ ID NO 75
<211> LENGTH: 108
<212> TYPE: PRT
<213> ORGANISM: Artificial Sequence
<220> FEATURE:
<223> OTHER INFORMATION: 7A1; VL

<400> SEQUENCE: 75

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Gln Gln Ile Pro
85 90 95

Pro Thr Phe Gly Gln Gly Thr Lys Val Glu Ile Lys
100 105

<210> SEQ ID NO 76
<211> LENGTH: 324
<212> TYPE: DNA
<213> ORGANISM: Artificial Sequence
<220> FEATURE:
<223> OTHER INFORMATION: 7A1; VL

<400> SEQUENCE: 76
gaaatcgtgt taacgcagtc tccaggcacc ctgtctttgt ctccagggga aagagccacc 60
ctctcttgca gggccagtca gagtgttagc agcagctact tagcctggta ccagcagaaa 120
cctggccagg ctcccaggct cctcatctat ggagcatcca gcagggccac tggcatccca 180
gacaggttca gtggcagtgg atccgggaca gacttcactc tcaccatcag cagactggag 240
cctgaagatt ttgcagtgta ttactgtcag cagggtcagc agattccccc tacgttcggc 300
caggggacca aagtggaaat caaa 324

<210> SEQ ID NO 77
<211> LENGTH: 117
<212> TYPE: PRT
<213> ORGANISM: Artificial Sequence
<220> FEATURE:

<223> OTHER INFORMATION: 7A1; VH

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Asn Phe Asp Tyr Trp Gly Gln Gly Thr Leu
            100                 105                 110

Val Thr Val Ser Ser
        115

<210> SEQ ID NO 78
<211> LENGTH: 351
<212> TYPE: DNA
<213> ORGANISM: Artificial Sequence
<220> FEATURE:
<223> OTHER INFORMATION: 7A1; VH

<400> SEQUENCE: 78
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaaggttgg 300
tttgggaatt ttgactactg gggccaagga accctggtca ccgtctcgag t 351

<210> SEQ ID NO 79
<211> LENGTH: 108
<212> TYPE: PRT
<213> ORGANISM: Artificial Sequence
<220> FEATURE:
<223> OTHER INFORMATION: 13C2; VL

<400> SEQUENCE: 79

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Leu Ile Pro
                85                  90                  95

Pro Thr Phe Gly Gln Gly Thr Lys Val Glu Ile Lys

```
            100                 105


<210> SEQ ID NO 80
<211> LENGTH: 324
<212> TYPE: DNA
<213> ORGANISM: Artificial Sequence
<220> FEATURE:
<223> OTHER INFORMATION: 13C2; VL

<400> SEQUENCE: 80

gaaatcgtgt taacgcagtc tccaggcacc ctgtctttgt ctccagggga aagagccacc      60

ctctcttgca gggccagtca gagtgttagc agcagctact tagcctggta ccagcagaaa     120

cctggccagg ctcccaggct cctcatctat ggagcatcca gcagggccac tggcatccca     180

gacaggttca gtggcagtgg atccgggaca gacttcactc tcaccatcag cagactggag     240

cctgaagatt ttgcagtgta ttactgtcag cagggtcagc ttattccccc tacgttcggc     300

caggggacca aagtggaaat caaa                                            324


<210> SEQ ID NO 81
<211> LENGTH: 117
<212> TYPE: PRT
<213> ORGANISM: Artificial Sequence
<220> FEATURE:
<223> OTHER INFORMATION: 13C2; VH

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Pro Phe Asp Tyr Trp Gly Gln Gly Thr Leu
            100                 105                 110

Val Thr Val Ser Ser
        115


<210> SEQ ID NO 82
<211> LENGTH: 351
<212> TYPE: DNA
<213> ORGANISM: Artificial Sequence
<220> FEATURE:
<223> OTHER INFORMATION: 13C2; VH

<400> SEQUENCE: 82

gaggtgcaat tgttggagtc tgggggaggc ttggtacagc ctggggggtc cctgagactc      60

tcctgtgcag cctccggatt cacctttagc agttatgcca tgagctgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcagatga acagcctgag agccgaggac acggccgtat attactgtgc gaaaggttgg     300

ctgggtcctt ttgactactg gggccaagga accctggtca ccgtctcgag t              351
```

<210> SEQ ID NO 83
<211> LENGTH: 108
<212> TYPE: PRT
<213> ORGANISM: Artificial Sequence
<220> FEATURE:
<223> OTHER INFORMATION: 13E8; VL

<400> SEQUENCE: 83

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Leu Asn Ile Pro
                85                  90                  95

Ser Thr Phe Gly Gln Gly Thr Lys Val Glu Ile Lys
            100                 105
```

<210> SEQ ID NO 84
<211> LENGTH: 324
<212> TYPE: DNA
<213> ORGANISM: Artificial Sequence
<220> FEATURE:
<223> OTHER INFORMATION: 13E8; VL

<400> SEQUENCE: 84

```
gaaatcgtgt taacgcagtc tccaggcacc ctgtctttgt ctccagggga aagagccacc      60

ctctcttgca gggccagtca gagtgttagc agcagctact tagcctggta ccagcagaaa     120

cctggccagg ctcccaggct cctcatctat ggagcatcca gcagggccac tggcatccca     180

gacaggttca gtggcagtgg atccgggaca gacttcactc tcaccatcag cagactggag     240

cctgaagatt ttgcagtgta ttactgtcag cagggtctga atattccctc gacgttcggc     300

caggggacca aagtggaaat caaa                                            324
```

<210> SEQ ID NO 85
<211> LENGTH: 117
<212> TYPE: PRT
<213> ORGANISM: Artificial Sequence
<220> FEATURE:
<223> OTHER INFORMATION: 13E8; VH

<400> SEQUENCE: 85

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Gly Trp Leu Gly Pro Phe Asp Tyr Trp Gly Gln Gly Thr Leu
            100                 105                 110

Val Thr Val Ser Ser
        115


<210> SEQ ID NO 86
<211> LENGTH: 351
<212> TYPE: DNA
<213> ORGANISM: Artificial Sequence
<220> FEATURE:
<223> OTHER INFORMATION: 13E8; VH

<400> SEQUENCE: 86

gaggtgcaat tgttggagtc tgggggaggc ttggtacagc ctggggggtc cctgagactc      60

tcctgtgcag cctccggatt cacctttagc agttatgcca tgagctgggt ccgccaggct     120

ccagggaagg ggctggagtg ggtctcagct attagtggta gtggtggtag cacatactac     180

gcagactccg tgaagggccg gttcaccatc tccagagaca attccaagaa cacgctgtat     240

ctgcagatga acagcctgag agccgaggac acggccgtat attactgtgc gaaaggttgg     300

ttgggtccgt ttgactactg gggccaagga accctggtca ccgtctcgag t              351


<210> SEQ ID NO 87
<211> LENGTH: 108
<212> TYPE: PRT
<213> ORGANISM: Artificial Sequence
<220> FEATURE:
<223> OTHER INFORMATION: 14C10; VL

<400> SEQUENCE: 87

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly His Ile Ile Pro
                85                  90                  95

Pro Thr Phe Gly Gln Gly Thr Lys Val Glu Ile Lys
            100                 105


<210> SEQ ID NO 88
<211> LENGTH: 324
<212> TYPE: DNA
<213> ORGANISM: Artificial Sequence
<220> FEATURE:
<223> OTHER INFORMATION: 14C10; VL

<400> SEQUENCE: 88

gaaatcgtgt taacgcagtc tccaggcacc ctgtctttgt ctccagggga aagagccacc      60

ctctcttgca gggccagtca gagtgttagc agcagctact tagcctggta ccagcagaaa     120

cctggccagg ctcccaggct cctcatctat ggagcatcca gcagggccac tggcatccca     180

gacaggttca gtggcagtgg atccgggaca gacttcactc tcaccatcag cagactggag     240
```

```
cctgaagatt ttgcagtgta ttactgtcag cagggtcata ttattccccc gacgttcggc    300

caggggacca aagtggaaat caaa                                           324


<210> SEQ ID NO 89
<211> LENGTH: 117
<212> TYPE: PRT
<213> ORGANISM: Artificial Sequence
<220> FEATURE:
<223> OTHER INFORMATION: 14C10; VH

<400> SEQUENCE: 89

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Trp Met Gly Pro Phe Asp Tyr Trp Gly Gln Gly Thr Leu
            100                 105                 110

Val Thr Val Ser Ser
        115


<210> SEQ ID NO 90
<211> LENGTH: 351
<212> TYPE: DNA
<213> ORGANISM: Artificial Sequence
<220> FEATURE:
<223> OTHER INFORMATION: 14C10; VH

<400> SEQUENCE: 90

gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaagcttgg    300

atggggcctt ttgactactg gggccaagga accctggtca ccgtctcgag t             351


<210> SEQ ID NO 91
<211> LENGTH: 108
<212> TYPE: PRT
<213> ORGANISM: Artificial Sequence
<220> FEATURE:
<223> OTHER INFORMATION: 17A11; VL

<400> SEQUENCE: 91

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

```
Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Leu Asn Ile Pro
                85                  90                  95

Ser Thr Phe Gly Gln Gly Thr Lys Val Glu Ile Lys
            100                 105


<210> SEQ ID NO 92
<211> LENGTH: 324
<212> TYPE: DNA
<213> ORGANISM: Artificial Sequence
<220> FEATURE:
<223> OTHER INFORMATION: 17A11; VL

<400> SEQUENCE: 92

gaaatcgtgt taacgcagtc tccaggcacc ctgtctttgt ctccagggga aagagccacc      60

ctctcttgca gggccagtca gagtgttagc agcagctact tagcctggta ccagcagaaa     120

cctggccagg ctcccaggct cctcatctat ggagcatcca gcagggccac tggcatccca     180

gacaggttca gtggcagtgg atccgggaca gacttcactc tcaccatcag cagactggag     240

cctgaagatt ttgcagtgta ttactgtcag cagggtctga atattccctc gacgttcggc     300

caggggacca aagtggaaat caaa                                            324


<210> SEQ ID NO 93
<211> LENGTH: 117
<212> TYPE: PRT
<213> ORGANISM: Artificial Sequence
<220> FEATURE:
<223> OTHER INFORMATION: 17A11; VH

<400> SEQUENCE: 93

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Pro Phe Asp Tyr Trp Gly Gln Gly Thr Leu
            100                 105                 110

Val Thr Val Ser Ser
        115


<210> SEQ ID NO 94
<211> LENGTH: 351
<212> TYPE: DNA
<213> ORGANISM: Artificial Sequence
<220> FEATURE:
<223> OTHER INFORMATION: 17A11; VH

<400> SEQUENCE: 94
```

-continued

```
gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaaggttgg    300

ttgggtccgt ttgactactg gggccaagga accctggtca ccgtctcgag t             351
```

<210> SEQ ID NO 95
<211> LENGTH: 603
<212> TYPE: PRT
<213> ORGANISM: Artificial Sequence
<220> FEATURE:
<223> OTHER INFORMATION: Fab heavy chain derived from L19 monoclonal antibody-C125A variant of IL2-Fab heavy chain derived from L19 monoclonal antibody

<400> SEQUENCE: 95

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Ser Gly Gly Gly
    210                 215                 220

Gly Ser Gly Gly Gly Gly Ser Gly Gly Gly Gly Ala Pro Thr Ser Ser
225                 230                 235                 240

Ser Thr Lys Lys Thr Gln Leu Gln Leu Glu His Leu Leu Leu Asp Leu
                245                 250                 255

Gln Met Ile Leu Asn Gly Ile Asn Asn Tyr Lys Asn Pro Lys Leu Thr
            260                 265                 270

Arg Met Leu Thr Phe Lys Phe Tyr Met Pro Lys Lys Ala Thr Glu Leu
        275                 280                 285

Lys His Leu Gln Cys Leu Glu Glu Glu Leu Lys Pro Leu Glu Glu Val
```

-continued

```
    290                 295                 300

Leu Asn Leu Ala Gln Ser Lys Asn Phe His Leu Arg Pro Arg Asp Leu
305                 310                 315                 320

Ile Ser Asn Ile Asn Val Ile Val Leu Glu Leu Lys Gly Ser Glu Thr
                325                 330                 335

Thr Phe Met Cys Glu Tyr Ala Asp Glu Thr Ala Thr Ile Val Glu Phe
            340                 345                 350

Leu Asn Arg Trp Ile Thr Phe Ala Gln Ser Ile Ile Ser Thr Leu Thr
        355                 360                 365

Ser Gly Gly Gly Gly Ser Gly Gly Gly Gly Ser Gly Gly Gly Gly Glu
    370                 375                 380

Val Gln Leu Leu Glu Ser Gly Gly Gly Leu Val Gln Pro Gly Gly Ser
385                 390                 395                 400

Leu Arg Leu Ser Cys Ala Ala Ser Gly Phe Thr Phe Ser Ser Phe Ser
                405                 410                 415

Met Ser Trp Val Arg Gln Ala Pro Gly Lys Gly Leu Glu Trp Val Ser
            420                 425                 430

Ser Ile Ser Gly Ser Ser Gly Thr Thr Tyr Tyr Ala Asp Ser Val Lys
        435                 440                 445

Gly Arg Phe Thr Ile Ser Arg Asp Asn Ser Lys Asn Thr Leu Tyr Leu
    450                 455                 460

Gln Met Asn Ser Leu Arg Ala Glu Asp Thr Ala Val Tyr Tyr Cys Ala
465                 470                 475                 480

Lys Pro Phe Pro Tyr Phe Asp Tyr Trp Gly Gln Gly Thr Leu Val Thr
                485                 490                 495

Val Ser Ser Ala Ser Thr Lys Gly Pro Ser Val Phe Pro Leu Ala Pro
            500                 505                 510

Ser Ser Lys Ser Thr Ser Gly Gly Thr Ala Ala Leu Gly Cys Leu Val
        515                 520                 525

Lys Asp Tyr Phe Pro Glu Pro Val Thr Val Ser Trp Asn Ser Gly Ala
    530                 535                 540

Leu Thr Ser Gly Val His Thr Phe Pro Ala Val Leu Gln Ser Ser Gly
545                 550                 555                 560

Leu Tyr Ser Leu Ser Ser Val Val Thr Val Pro Ser Ser Ser Leu Gly
                565                 570                 575

Thr Gln Thr Tyr Ile Cys Asn Val Asn His Lys Pro Ser Asn Thr Lys
            580                 585                 590

Val Asp Lys Lys Val Glu Pro Lys Ser Cys Asp
        595                 600


<210> SEQ ID NO 96
<211> LENGTH: 215
<212> TYPE: PRT
<213> ORGANISM: Artificial Sequence
<220> FEATURE:
<223> OTHER INFORMATION: Fab light chain derived from L19 monoclonal
      antibody

<400> SEQUENCE: 96

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45
```

```
Ile Tyr Tyr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 97
<211> LENGTH: 382
<212> TYPE: PRT
<213> ORGANISM: Artificial Sequence
<220> FEATURE:
<223> OTHER INFORMATION: scFv derived from L19 monoclonal antibody-8
      amino acid linker-C125A variant of IL2

<400> SEQUENCE: 97

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Ser Gly Gly Ser Gly Gly Ala Ser Glu Ile Val Leu
        115                 120                 125

Thr Gln Ser Pro Gly Thr Leu Ser Leu Ser Pro Gly Glu Arg Ala Thr
    130                 135                 140

Leu Ser Cys Arg Ala Ser Gln Ser Val Ser Ser Ser Tyr Leu Ala Trp
145                 150                 155                 160

Tyr Gln Gln Lys Pro Gly Gln Ala Pro Arg Leu Leu Ile Tyr Tyr Ala
                165                 170                 175

Ser Ser Arg Ala Thr Gly Ile Pro Asp Arg Phe Ser Gly Ser Gly Ser
            180                 185                 190
```

```
Gly Thr Asp Phe Thr Leu Thr Ile Ser Arg Leu Glu Pro Glu Asp Phe
        195                 200                 205

Ala Val Tyr Tyr Cys Gln Gln Thr Gly Arg Ile Pro Pro Thr Phe Gly
    210                 215                 220

Gln Gly Thr Lys Val Glu Ile Ser Val Leu Ser Ser Ser Ser Gly Ser
225                 230                 235                 240

Ser Ser Ser Gly Ser Ser Ser Ser Gly Ala Pro Thr Ser Ser Ser Thr
                245                 250                 255

Lys Lys Thr Gln Leu Gln Leu Glu His Leu Leu Leu Asp Leu Gln Met
            260                 265                 270

Ile Leu Asn Gly Ile Asn Asn Tyr Lys Asn Pro Lys Leu Thr Arg Met
        275                 280                 285

Leu Thr Phe Lys Phe Tyr Met Pro Lys Lys Ala Thr Glu Leu Lys His
    290                 295                 300

Leu Gln Cys Leu Glu Glu Glu Leu Lys Pro Leu Glu Glu Val Leu Asn
305                 310                 315                 320

Leu Ala Gln Ser Lys Asn Phe His Leu Arg Pro Arg Asp Leu Ile Ser
                325                 330                 335

Asn Ile Asn Val Ile Val Leu Glu Leu Lys Gly Ser Glu Thr Thr Phe
            340                 345                 350

Met Cys Glu Tyr Ala Asp Glu Thr Ala Thr Ile Val Glu Phe Leu Asn
        355                 360                 365

Arg Trp Ile Thr Phe Ala Gln Ser Ile Ile Ser Thr Leu Thr
    370                 375                 380


<210> SEQ ID NO 98
<211> LENGTH: 377
<212> TYPE: PRT
<213> ORGANISM: Artificial Sequence
<220> FEATURE:
<223> OTHER INFORMATION: F16-diabody-IL2protein

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Ser Ala Ser Gly Gly Ser Ser Glu Leu Thr Gln Asp Pro
        115                 120                 125

Ala Val Ser Val Ala Leu Gly Gln Thr Val Arg Ile Thr Cys Gln Gly
    130                 135                 140

Asp Ser Leu Arg Ser Tyr Tyr Ala Ser Trp Tyr Gln Gln Lys Pro Gly
145                 150                 155                 160

Gln Ala Pro Val Leu Val Ile Tyr Gly Lys Asn Asn Arg Pro Ser Gly
                165                 170                 175
```

```
Ile Pro Asp Arg Phe Ser Gly Ser Ser Ser Gly Asn Thr Ala Ser Leu
            180                 185                 190

Thr Ile Thr Gly Ala Gln Ala Glu Asp Glu Ala Asp Tyr Tyr Cys Asn
        195                 200                 205

Ser Ser Val Tyr Thr Met Pro Pro Val Val Phe Gly Gly Gly Thr Lys
    210                 215                 220

Leu Thr Val Leu Gly Ser Ser Ser Ser Gly Ser Ser Ser Ser Gly Ser
225                 230                 235                 240

Ser Ser Ser Gly Ala Pro Thr Ser Ser Ser Thr Lys Lys Thr Gln Leu
                245                 250                 255

Gln Leu Glu His Leu Leu Leu Asp Leu Gln Met Ile Leu Asn Gly Ile
            260                 265                 270

Asn Asn Tyr Lys Asn Pro Lys Leu Thr Arg Met Leu Thr Phe Lys Phe
        275                 280                 285

Tyr Met Pro Lys Lys Ala Thr Glu Leu Lys His Leu Gln Cys Leu Glu
    290                 295                 300

Glu Glu Leu Lys Pro Leu Glu Glu Val Leu Asn Leu Ala Gln Ser Lys
305                 310                 315                 320

Asn Phe His Leu Arg Pro Arg Asp Leu Ile Ser Asn Ile Asn Val Ile
                325                 330                 335

Val Leu Glu Leu Lys Gly Ser Glu Thr Thr Phe Met Cys Glu Tyr Ala
            340                 345                 350

Asp Glu Thr Ala Thr Ile Val Glu Phe Leu Asn Arg Trp Ile Thr Phe
        355                 360                 365

Ala Gln Ser Ile Ile Ser Thr Leu Thr
    370                 375


<210> SEQ ID NO 99
<211> LENGTH: 641
<212> TYPE: PRT
<213> ORGANISM: Artificial Sequence
<220> FEATURE:
<223> OTHER INFORMATION: scFv-IL2-scFv (F16, protein)

<400> SEQUENCE: 99

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg Gly Gly Gly Gly Ser Gly Gly Gly Gly Ser Gly Gly
        115                 120                 125

Gly Gly Ser Ser Glu Leu Thr Gln Asp Pro Ala Val Ser Val Ala Leu
    130                 135                 140

Gly Gln Thr Val Arg Ile Thr Cys Gln Gly Asp Ser Leu Arg Ser Tyr
145                 150                 155                 160
```

-continued

```
Tyr Ala Ser Trp Tyr Gln Gln Lys Pro Gly Gln Ala Pro Val Leu Val
                165                 170                 175

Ile Tyr Gly Lys Asn Asn Arg Pro Ser Gly Ile Pro Asp Arg Phe Ser
            180                 185                 190

Gly Ser Ser Ser Gly Asn Thr Ala Ser Leu Thr Ile Thr Gly Ala Gln
        195                 200                 205

Ala Glu Asp Glu Ala Asp Tyr Tyr Cys Asn Ser Ser Val Tyr Thr Met
    210                 215                 220

Pro Pro Val Val Phe Gly Gly Gly Thr Lys Leu Thr Val Leu Gly Ser
225                 230                 235                 240

Ser Ser Ser Gly Ser Ser Ser Ser Gly Ser Ser Ser Ser Gly Ala Pro
                245                 250                 255

Thr Ser Ser Ser Thr Lys Lys Thr Gln Leu Gln Leu Glu His Leu Leu
            260                 265                 270

Leu Asp Leu Gln Met Ile Leu Asn Gly Ile Asn Asn Tyr Lys Asn Pro
        275                 280                 285

Lys Leu Thr Arg Met Leu Thr Phe Lys Phe Tyr Met Pro Lys Lys Ala
    290                 295                 300

Thr Glu Leu Lys His Leu Gln Cys Leu Glu Glu Glu Leu Lys Pro Leu
305                 310                 315                 320

Glu Glu Val Leu Asn Leu Ala Gln Ser Lys Asn Phe His Leu Arg Pro
                325                 330                 335

Arg Asp Leu Ile Ser Asn Ile Asn Val Ile Val Leu Glu Leu Lys Gly
            340                 345                 350

Ser Glu Thr Thr Phe Met Cys Glu Tyr Ala Asp Glu Thr Ala Thr Ile
        355                 360                 365

Val Glu Phe Leu Asn Arg Trp Ile Thr Phe Ala Gln Ser Ile Ile Ser
    370                 375                 380

Thr Leu Thr Ser Gly Gly Gly Gly Ser Gly Gly Gly Gly Ser Gly Gly
385                 390                 395                 400

Gly Gly Ser Ser Glu Leu Thr Gln Asp Pro Ala Val Ser Val Ala Leu
                405                 410                 415

Gly Gln Thr Val Arg Ile Thr Cys Gln Gly Asp Ser Leu Arg Ser Tyr
            420                 425                 430

Tyr Ala Ser Trp Tyr Gln Gln Lys Pro Gly Gln Ala Pro Val Leu Val
        435                 440                 445

Ile Tyr Gly Lys Asn Asn Arg Pro Ser Gly Ile Pro Asp Arg Phe Ser
    450                 455                 460

Gly Ser Ser Ser Gly Asn Thr Ala Ser Leu Thr Ile Thr Gly Ala Gln
465                 470                 475                 480

Ala Glu Asp Glu Ala Asp Tyr Tyr Cys Asn Ser Ser Val Tyr Thr Met
                485                 490                 495

Pro Pro Val Val Phe Gly Gly Gly Thr Lys Leu Thr Val Leu Gly Ser
            500                 505                 510

Gly Gly Gly Ser Gly Gly Gly Ser Gly Gly Gly Ser Gly Ser Glu Val
        515                 520                 525

Gln Leu Leu Glu Ser Gly Gly Gly Leu Val Gln Pro Gly Gly Ser Leu
    530                 535                 540

Arg Leu Ser Cys Ala Ala Ser Gly Phe Thr Phe Ser Arg Tyr Gly Met
545                 550                 555                 560

Ser Trp Val Arg Gln Ala Pro Gly Lys Gly Leu Glu Trp Val Ser Ala
                565                 570                 575
```

-continued

```
Ile Ser Gly Ser Gly Gly Ser Thr Tyr Tyr Ala Asp Ser Val Lys Gly
            580                 585                 590

Arg Phe Thr Ile Ser Arg Asp Asn Ser Lys Asn Thr Leu Tyr Leu Gln
        595                 600                 605

Met Asn Ser Leu Arg Ala Glu Asp Thr Ala Val Tyr Tyr Cys Ala Lys
    610                 615                 620

Ala His Asn Ala Phe Asp Tyr Trp Gly Gln Gly Thr Leu Val Thr Val
625                 630                 635                 640

Ser


<210> SEQ ID NO 100
<211> LENGTH: 603
<212> TYPE: PRT
<213> ORGANISM: Artificial Sequence
<220> FEATURE:
<223> OTHER INFORMATION: Fab-IL2-Fab (F16, heavy chain cytokine fusion
      construct, protein)

<400> SEQUENCE: 100

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Ser Ser Ser Ser
    210                 215                 220

Gly Ser Ser Ser Ser Gly Ser Ser Ser Ser Gly Ala Pro Thr Ser Ser
225                 230                 235                 240

Ser Thr Lys Lys Thr Gln Leu Gln Leu Glu His Leu Leu Leu Asp Leu
                245                 250                 255

Gln Met Ile Leu Asn Gly Ile Asn Asn Tyr Lys Asn Pro Lys Leu Thr
            260                 265                 270

Arg Met Leu Thr Phe Lys Phe Tyr Met Pro Lys Lys Ala Thr Glu Leu
        275                 280                 285
```

-continued

```
Lys His Leu Gln Cys Leu Glu Glu Glu Leu Lys Pro Leu Glu Glu Val
    290                 295                 300

Leu Asn Leu Ala Gln Ser Lys Asn Phe His Leu Arg Pro Arg Asp Leu
305                 310                 315                 320

Ile Ser Asn Ile Asn Val Ile Val Leu Glu Leu Lys Gly Ser Glu Thr
                325                 330                 335

Thr Phe Met Cys Glu Tyr Ala Asp Glu Thr Ala Thr Ile Val Glu Phe
            340                 345                 350

Leu Asn Arg Trp Ile Thr Phe Ala Gln Ser Ile Ile Ser Thr Leu Thr
        355                 360                 365

Ser Gly Gly Gly Gly Ser Gly Gly Gly Gly Ser Gly Gly Gly Gly Glu
    370                 375                 380

Val Gln Leu Leu Glu Ser Gly Gly Gly Leu Val Gln Pro Gly Gly Ser
385                 390                 395                 400

Leu Arg Leu Ser Cys Ala Ala Ser Gly Phe Thr Phe Ser Arg Tyr Gly
                405                 410                 415

Met Ser Trp Val Arg Gln Ala Pro Gly Lys Gly Leu Glu Trp Val Ser
            420                 425                 430

Ala Ile Ser Gly Ser Gly Gly Ser Thr Tyr Tyr Ala Asp Ser Val Lys
        435                 440                 445

Gly Arg Phe Thr Ile Ser Arg Asp Asn Ser Lys Asn Thr Leu Tyr Leu
    450                 455                 460

Gln Met Asn Ser Leu Arg Ala Glu Asp Thr Ala Val Tyr Tyr Cys Ala
465                 470                 475                 480

Lys Ala His Asn Ala Phe Asp Tyr Trp Gly Gln Gly Thr Leu Val Thr
                485                 490                 495

Val Ser Ser Ala Ser Thr Lys Gly Pro Ser Val Phe Pro Leu Ala Pro
            500                 505                 510

Ser Ser Lys Ser Thr Ser Gly Gly Thr Ala Ala Leu Gly Cys Leu Val
        515                 520                 525

Lys Asp Tyr Phe Pro Glu Pro Val Thr Val Ser Trp Asn Ser Gly Ala
    530                 535                 540

Leu Thr Ser Gly Val His Thr Phe Pro Ala Val Leu Gln Ser Ser Gly
545                 550                 555                 560

Leu Tyr Ser Leu Ser Ser Val Val Thr Val Pro Ser Ser Ser Leu Gly
                565                 570                 575

Thr Gln Thr Tyr Ile Cys Asn Val Asn His Lys Pro Ser Asn Thr Lys
            580                 585                 590

Val Asp Lys Lys Val Glu Pro Lys Ser Cys Asp
        595                 600
```

<210> SEQ ID NO 101
<211> LENGTH: 214
<212> TYPE: PRT
<213> ORGANISM: Artificial Sequence
<220> FEATURE:
<223> OTHER INFORMATION: F16, light chain, protein

<400> SEQUENCE: 101

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45
```

-continued

```
Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Val Tyr Thr Met Pro Pro
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 102
<211> LENGTH: 466
<212> TYPE: PRT
<213> ORGANISM: Artificial Sequence
<220> FEATURE:
<223> OTHER INFORMATION: IL2R-beta-Fc(hole) fusion protein, protein

<400> SEQUENCE: 102

```
Met Asp Met Arg Val Pro Ala Gln Leu Leu Gly Leu Leu Leu Leu Trp
1               5                   10                  15

Phe Pro Gly Ala Arg Cys Ala Val Asn Gly Thr Ser Gln Phe Thr Cys
            20                  25                  30

Phe Tyr Asn Ser Arg Ala Asn Ile Ser Cys Val Trp Ser Gln Asp Gly
        35                  40                  45

Ala Leu Gln Asp Thr Ser Cys Gln Val His Ala Trp Pro Asp Arg Arg
    50                  55                  60

Arg Trp Asn Gln Thr Cys Glu Leu Leu Pro Val Ser Gln Ala Ser Trp
65                  70                  75                  80

Ala Cys Asn Leu Ile Leu Gly Ala Pro Asp Ser Gln Lys Leu Thr Thr
                85                  90                  95

Val Asp Ile Val Thr Leu Arg Val Leu Cys Arg Glu Gly Val Arg Trp
            100                 105                 110

Arg Val Met Ala Ile Gln Asp Phe Lys Pro Phe Glu Asn Leu Arg Leu
        115                 120                 125

Met Ala Pro Ile Ser Leu Gln Val Val His Val Glu Thr His Arg Cys
    130                 135                 140

Asn Ile Ser Trp Glu Ile Ser Gln Ala Ser His Tyr Phe Glu Arg His
145                 150                 155                 160

Leu Glu Phe Glu Ala Arg Thr Leu Ser Pro Gly His Thr Trp Glu Glu
                165                 170                 175

Ala Pro Leu Leu Thr Leu Lys Gln Lys Gln Glu Trp Ile Cys Leu Glu
            180                 185                 190
```

```
Thr Leu Thr Pro Asp Thr Gln Tyr Glu Phe Gln Val Arg Val Lys Pro
        195                 200                 205

Leu Gln Gly Glu Phe Thr Thr Trp Ser Pro Trp Ser Gln Pro Leu Ala
    210                 215                 220

Phe Arg Thr Lys Pro Ala Ala Leu Gly Lys Asp Thr Gly Ala Gln Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Cys
        355                 360                 365

Thr Leu Pro Pro Ser Arg Asp Glu Leu Thr Lys Asn Gln Val Ser Leu
    370                 375                 380

Ser Cys Ala Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Val Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465


<210> SEQ ID NO 103
<211> LENGTH: 492
<212> TYPE: PRT
<213> ORGANISM: Artificial Sequence
<220> FEATURE:
<223> OTHER INFORMATION: IL2R-gamma-Fc(knob), protein

<400> SEQUENCE: 103

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80
```

-continued

```
Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Gly Ala Gln Asp Lys Thr His Thr Cys Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Cys Arg
385                 390                 395                 400

Asp Glu Leu Thr Lys Asn Gln Val Ser Leu Trp Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490
```

<210> SEQ ID NO 104
<211> LENGTH: 991
<212> TYPE: PRT
<213> ORGANISM: Artificial Sequence
<220> FEATURE:
<223> OTHER INFORMATION: Fab-IL12-Fab, L19 antibody, murine scIL12, protein

<400> SEQUENCE: 104

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Ser Gly Gly Gly
    210                 215                 220

Gly Ser Gly Gly Gly Gly Ser Gly Gly Gly Gly Ala Met Trp Glu Leu
225                 230                 235                 240

Glu Lys Asp Val Tyr Val Val Glu Val Asp Trp Thr Pro Asp Ala Pro
                245                 250                 255

Gly Glu Thr Val Asn Leu Thr Cys Asp Thr Pro Glu Glu Asp Asp Ile
            260                 265                 270

Thr Trp Thr Ser Asp Gln Arg His Gly Val Ile Gly Ser Gly Lys Thr
        275                 280                 285

Leu Thr Ile Thr Val Lys Glu Phe Leu Asp Ala Gly Gln Tyr Thr Cys
    290                 295                 300

His Lys Gly Gly Glu Thr Leu Ser His Ser His Leu Leu Leu His Lys
305                 310                 315                 320

Lys Glu Asn Gly Ile Trp Ser Thr Glu Ile Leu Lys Asn Phe Lys Asn
                325                 330                 335

Lys Thr Phe Leu Lys Cys Glu Ala Pro Asn Tyr Ser Gly Arg Phe Thr
            340                 345                 350

Cys Ser Trp Leu Val Gln Arg Asn Met Asp Leu Lys Phe Asn Ile Lys
        355                 360                 365
```

-continued

```
Ser Ser Ser Ser Pro Pro Asp Ser Arg Ala Val Thr Cys Gly Met Ala
    370                 375                 380

Ser Leu Ser Ala Glu Lys Val Thr Leu Asp Gln Arg Asp Tyr Glu Lys
385                 390                 395                 400

Tyr Ser Val Ser Cys Gln Glu Asp Val Thr Cys Pro Thr Ala Glu Glu
                405                 410                 415

Thr Leu Pro Ile Glu Leu Ala Leu Glu Ala Arg Gln Gln Asn Lys Tyr
            420                 425                 430

Glu Asn Tyr Ser Thr Ser Phe Phe Ile Arg Asp Ile Ile Lys Pro Asp
        435                 440                 445

Pro Pro Lys Asn Leu Gln Met Lys Pro Leu Lys Asn Ser Gln Val Glu
    450                 455                 460

Val Ser Trp Glu Tyr Pro Asp Ser Trp Ser Thr Pro Arg Ser Tyr Phe
465                 470                 475                 480

Ser Leu Lys Phe Phe Val Arg Ile Gln Arg Lys Lys Glu Lys Met Lys
                485                 490                 495

Glu Thr Glu Glu Gly Cys Asn Gln Lys Gly Ala Phe Phe Val Glu Lys
            500                 505                 510

Thr Ser Thr Glu Val Gln Cys Lys Gly Gly Asn Val Cys Val Gln Ala
        515                 520                 525

Gln Asp Arg Tyr Tyr Asn Ser Ser Cys Ser Lys Trp Ala Cys Val Pro
    530                 535                 540

Cys Arg Val Arg Ser Gly Gly Asp Gly Ser Gly Gly Gly Gly Ser Gly
545                 550                 555                 560

Gly Gly Gly Ser Arg Val Ile Pro Val Ser Gly Pro Ala Arg Cys Leu
                565                 570                 575

Ser Gln Ser Arg Asn Leu Leu Lys Thr Thr Asp Asp Met Val Lys Thr
            580                 585                 590

Ala Arg Glu Lys Leu Lys His Tyr Ser Cys Thr Ala Glu Asp Ile Asp
        595                 600                 605

His Glu Asp Ile Thr Arg Asp Gln Thr Ser Thr Leu Lys Thr Cys Leu
    610                 615                 620

Pro Leu Glu Leu His Lys Asn Glu Ser Cys Leu Ala Thr Arg Glu Thr
625                 630                 635                 640

Ser Ser Thr Thr Arg Gly Ser Cys Leu Pro Pro Gln Lys Thr Ser Leu
                645                 650                 655

Met Met Thr Leu Cys Leu Gly Ser Ile Tyr Glu Asp Leu Lys Met Tyr
            660                 665                 670

Gln Thr Glu Phe Gln Ala Ile Asn Ala Ala Leu Gln Asn His Asn His
        675                 680                 685

Gln Gln Ile Ile Leu Asp Lys Gly Met Leu Val Ala Ile Asp Glu Leu
    690                 695                 700

Met Gln Ser Leu Asn His Asn Gly Glu Thr Leu Arg Gln Lys Pro Pro
705                 710                 715                 720

Val Gly Glu Ala Asp Pro Tyr Arg Val Lys Met Lys Leu Cys Ile Leu
                725                 730                 735

Leu His Ala Phe Ser Thr Arg Val Val Thr Ile Asn Arg Val Met Gly
            740                 745                 750

Tyr Leu Ser Ser Ala Gly Gly Gly Gly Ser Gly Gly Gly Gly Ser Gly
        755                 760                 765

Gly Gly Gly Glu Val Gln Leu Leu Glu Ser Gly Gly Gly Leu Val Gln
    770                 775                 780

Pro Gly Gly Ser Leu Arg Leu Ser Cys Ala Ala Ser Gly Phe Thr Phe
```

785 790 795 800

Ser Ser Phe Ser Met Ser Trp Val Arg Gln Ala Pro Gly Lys Gly Leu
805 810 815

Glu Trp Val Ser Ser Ile Ser Gly Ser Ser Gly Thr Thr Tyr Tyr Ala
820 825 830

Asp Ser Val Lys Gly Arg Phe Thr Ile Ser Arg Asp Asn Ser Lys Asn
835 840 845

Thr Leu Tyr Leu Gln Met Asn Ser Leu Arg Ala Glu Asp Thr Ala Val
850 855 860

Tyr Tyr Cys Ala Lys Pro Phe Pro Tyr Phe Asp Tyr Trp Gly Gln Gly
865 870 875 880

Thr Leu Val Thr Val Ser Ser Ala Ser Thr Lys Gly Pro Ser Val Phe
885 890 895

Pro Leu Ala Pro Ser Ser Lys Ser Thr Ser Gly Gly Thr Ala Ala Leu
900 905 910

Gly Cys Leu Val Lys Asp Tyr Phe Pro Glu Pro Val Thr Val Ser Trp
915 920 925

Asn Ser Gly Ala Leu Thr Ser Gly Val His Thr Phe Pro Ala Val Leu
930 935 940

Gln Ser Ser Gly Leu Tyr Ser Leu Ser Ser Val Val Thr Val Pro Ser
945 950 955 960

Ser Ser Leu Gly Thr Gln Thr Tyr Ile Cys Asn Val Asn His Lys Pro
965 970 975

Ser Asn Thr Lys Val Asp Lys Lys Val Glu Pro Lys Ser Cys Asp
980 985 990

<210> SEQ ID NO 105
<211> LENGTH: 987
<212> TYPE: PRT
<213> ORGANISM: Artificial Sequence
<220> FEATURE:
<223> OTHER INFORMATION: Fab-IL12-Fab L19 antibody, human scIL12, protein

<400> SEQUENCE: 105

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Phe
20 25 30

Ser Met Ser Trp Val Arg Gln Ala Pro Gly Lys Gly Leu Glu Trp Val
35 40 45

Ser Ser Ile Arg Gly Ser Ser Gly Thr Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Pro Phe Pro Tyr Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

-continued

```
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Ser Gly Gly Gly
    210                 215                 220

Gly Ser Gly Gly Gly Gly Ser Gly Gly Gly Gly Ile Trp Glu Leu Lys
225                 230                 235                 240

Lys Asp Val Tyr Val Val Glu Leu Asp Trp Tyr Pro Asp Ala Pro Gly
                245                 250                 255

Glu Met Val Val Leu Thr Cys Asp Thr Pro Glu Glu Asp Gly Ile Thr
            260                 265                 270

Trp Thr Leu Asp Gln Ser Ser Glu Val Leu Gly Ser Gly Lys Thr Leu
        275                 280                 285

Thr Ile Gln Val Lys Glu Phe Gly Asp Ala Gly Gln Tyr Thr Cys His
    290                 295                 300

Lys Gly Gly Glu Val Leu Ser His Ser Leu Leu Leu Leu His Lys Lys
305                 310                 315                 320

Glu Asp Gly Ile Trp Ser Thr Asp Ile Leu Lys Asp Gln Lys Glu Pro
                325                 330                 335

Lys Asn Lys Thr Phe Leu Arg Cys Glu Ala Lys Asn Tyr Ser Gly Arg
            340                 345                 350

Phe Thr Cys Trp Trp Leu Thr Thr Ile Ser Thr Asp Leu Thr Phe Ser
        355                 360                 365

Val Lys Ser Ser Arg Gly Ser Ser Asp Pro Gln Gly Val Thr Cys Gly
    370                 375                 380

Ala Ala Thr Leu Ser Ala Glu Arg Val Arg Gly Asp Asn Lys Glu Tyr
385                 390                 395                 400

Glu Tyr Ser Val Glu Cys Gln Glu Asp Ser Ala Cys Pro Ala Ala Glu
                405                 410                 415

Glu Ser Leu Pro Ile Glu Val Met Val Asp Ala Val His Lys Leu Lys
            420                 425                 430

Tyr Glu Asn Tyr Thr Ser Ser Phe Phe Ile Arg Asp Ile Ile Lys Pro
        435                 440                 445

Asp Pro Pro Lys Asn Leu Gln Leu Lys Pro Leu Lys Asn Ser Arg Gln
    450                 455                 460

Val Glu Val Ser Trp Glu Tyr Pro Asp Thr Trp Ser Thr Pro His Ser
465                 470                 475                 480

Tyr Phe Ser Leu Thr Phe Cys Val Gln Val Gln Gly Lys Ser Lys Arg
                485                 490                 495

Glu Lys Lys Asp Arg Val Phe Thr Asp Lys Thr Ser Ala Thr Val Ile
            500                 505                 510

Cys Arg Lys Asn Ala Ser Ile Ser Val Arg Ala Gln Asp Arg Tyr Tyr
        515                 520                 525

Ser Ser Ser Trp Ser Glu Trp Ala Ser Val Pro Cys Ser Gly Gly Gly
    530                 535                 540

Gly Ser Gly Gly Gly Gly Ser Gly Gly Gly Gly Ser Arg Asn Leu Pro
545                 550                 555                 560

Val Ala Thr Pro Asp Pro Gly Met Phe Pro Cys Leu His His Ser Gln
                565                 570                 575

Asn Leu Leu Arg Ala Val Ser Asn Met Leu Gln Lys Ala Arg Gln Thr
```

```
            580                 585                 590

Leu Glu Phe Tyr Pro Cys Thr Ser Glu Glu Ile Asp His Glu Asp Ile
        595                 600                 605

Thr Lys Asp Lys Thr Ser Thr Val Glu Ala Cys Leu Pro Leu Glu Leu
    610                 615                 620

Thr Lys Asn Glu Ser Cys Leu Asn Ser Arg Glu Thr Ser Phe Ile Thr
625                 630                 635                 640

Asn Gly Ser Cys Leu Ala Ser Arg Lys Thr Ser Phe Met Met Ala Leu
                645                 650                 655

Cys Leu Ser Ser Ile Tyr Glu Asp Leu Lys Met Tyr Gln Val Glu Phe
            660                 665                 670

Lys Thr Met Asn Ala Lys Leu Leu Met Asp Pro Lys Arg Gln Ile Phe
        675                 680                 685

Leu Asp Gln Asn Met Leu Ala Val Ile Asp Glu Leu Met Gln Ala Leu
    690                 695                 700

Asn Phe Asn Ser Glu Thr Val Pro Gln Lys Ser Ser Leu Glu Glu Pro
705                 710                 715                 720

Asp Phe Tyr Lys Thr Lys Ile Lys Leu Cys Ile Leu Leu His Ala Phe
                725                 730                 735

Arg Ile Arg Ala Val Thr Ile Asp Arg Val Met Ser Tyr Leu Asn Ala
            740                 745                 750

Ser Gly Gly Gly Gly Ser Gly Gly Gly Gly Ser Gly Gly Gly Gly Glu
        755                 760                 765

Val Gln Leu Leu Glu Ser Gly Gly Gly Leu Val Gln Pro Gly Gly Ser
    770                 775                 780

Leu Arg Leu Ser Cys Ala Ala Ser Gly Phe Thr Phe Ser Ser Phe Ser
785                 790                 795                 800

Met Ser Trp Val Arg Gln Ala Pro Gly Lys Gly Leu Glu Trp Val Ser
                805                 810                 815

Ser Ile Arg Gly Ser Ser Gly Thr Thr Tyr Tyr Ala Asp Ser Val Lys
            820                 825                 830

Gly Arg Phe Thr Ile Ser Arg Asp Asn Ser Lys Asn Thr Leu Tyr Leu
        835                 840                 845

Gln Met Asn Ser Leu Arg Ala Glu Asp Thr Ala Val Tyr Tyr Cys Ala
    850                 855                 860

Lys Pro Phe Pro Tyr Phe Asp Tyr Trp Gly Gln Gly Thr Leu Val Thr
865                 870                 875                 880

Val Ser Ser Ala Ser Thr Lys Gly Pro Ser Val Phe Pro Leu Ala Pro
                885                 890                 895

Ser Ser Lys Ser Thr Ser Gly Gly Thr Ala Ala Leu Gly Cys Leu Val
            900                 905                 910

Lys Asp Tyr Phe Pro Glu Pro Val Thr Val Ser Trp Asn Ser Gly Ala
        915                 920                 925

Leu Thr Ser Gly Val His Thr Phe Pro Ala Val Leu Gln Ser Ser Gly
    930                 935                 940

Leu Tyr Ser Leu Ser Ser Val Val Thr Val Pro Ser Ser Ser Leu Gly
945                 950                 955                 960

Thr Gln Thr Tyr Ile Cys Asn Val Asn His Lys Pro Ser Asn Thr Lys
                965                 970                 975

Val Asp Lys Lys Val Glu Pro Lys Ser Cys Asp
            980                 985
```

<210> SEQ ID NO 106

```
<211> LENGTH: 597
<212> TYPE: PRT
<213> ORGANISM: Artificial Sequence
<220> FEATURE:
<223> OTHER INFORMATION: Fab-GMCSF-Fab, L19 antibody, human GM-CSF,
      protein

<400> SEQUENCE: 106

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Arg Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Ser Gly Gly Gly
    210                 215                 220

Gly Ser Gly Gly Gly Gly Ser Gly Gly Gly Gly Ala Pro Ala Arg Ser
225                 230                 235                 240

Pro Ser Pro Ser Thr Gln Pro Trp Glu His Val Asn Ala Ile Gln Glu
                245                 250                 255

Ala Arg Arg Leu Leu Asn Leu Ser Arg Asp Thr Ala Ala Glu Met Asn
            260                 265                 270

Glu Thr Val Glu Val Ile Ser Glu Met Phe Asp Leu Gln Glu Pro Thr
        275                 280                 285

Cys Leu Gln Thr Arg Leu Glu Leu Tyr Lys Gln Gly Leu Arg Gly Ser
    290                 295                 300

Leu Thr Lys Leu Lys Gly Pro Leu Thr Met Met Ala Ser His Tyr Lys
305                 310                 315                 320

Gln His Cys Pro Pro Thr Pro Glu Thr Ser Cys Ala Thr Gln Ile Ile
                325                 330                 335

Thr Phe Glu Ser Phe Lys Glu Asn Leu Lys Asp Phe Leu Leu Val Ile
            340                 345                 350

Pro Phe Asp Cys Trp Glu Pro Val Gln Glu Ser Gly Gly Gly Gly Ser
        355                 360                 365

Gly Gly Gly Gly Ser Gly Gly Gly Gly Glu Val Gln Leu Leu Glu Ser
```

```
    370                 375                 380

Gly Gly Gly Leu Val Gln Pro Gly Gly Ser Leu Arg Leu Ser Cys Ala
385                 390                 395                 400

Ala Ser Gly Phe Thr Phe Ser Ser Phe Ser Met Ser Trp Val Arg Gln
                405                 410                 415

Ala Pro Gly Lys Gly Leu Glu Trp Val Ser Ser Ile Arg Gly Ser Ser
            420                 425                 430

Gly Thr Thr Tyr Tyr Ala Asp Ser Val Lys Gly Arg Phe Thr Ile Ser
        435                 440                 445

Arg Asp Asn Ser Lys Asn Thr Leu Tyr Leu Gln Met Asn Ser Leu Arg
    450                 455                 460

Ala Glu Asp Thr Ala Val Tyr Tyr Cys Ala Lys Pro Phe Pro Tyr Phe
465                 470                 475                 480

Asp Tyr Trp Gly Gln Gly Thr Leu Val Thr Val Ser Ser Ala Ser Thr
                485                 490                 495

Lys Gly Pro Ser Val Phe Pro Leu Ala Pro Ser Ser Lys Ser Thr Ser
            500                 505                 510

Gly Gly Thr Ala Ala Leu Gly Cys Leu Val Lys Asp Tyr Phe Pro Glu
        515                 520                 525

Pro Val Thr Val Ser Trp Asn Ser Gly Ala Leu Thr Ser Gly Val His
    530                 535                 540

Thr Phe Pro Ala Val Leu Gln Ser Ser Gly Leu Tyr Ser Leu Ser Ser
545                 550                 555                 560

Val Val Thr Val Pro Ser Ser Ser Leu Gly Thr Gln Thr Tyr Ile Cys
                565                 570                 575

Asn Val Asn His Lys Pro Ser Asn Thr Lys Val Asp Lys Lys Val Glu
            580                 585                 590

Pro Lys Ser Cys Asp
        595


<210> SEQ ID NO 107
<211> LENGTH: 636
<212> TYPE: PRT
<213> ORGANISM: Artificial Sequence
<220> FEATURE:
<223> OTHER INFORMATION: Fab-IFNa2-Fab, L19 antibody, protein

<400> SEQUENCE: 107

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Arg Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
```

```
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Ser Gly Gly Gly
    210                 215                 220

Gly Ser Gly Gly Gly Gly Ser Gly Gly Gly Gly Cys Asp Leu Pro Gln
225                 230                 235                 240

Thr His Ser Leu Gly Asn Arg Arg Ala Leu Ile Leu Leu Ala Gln Met
                245                 250                 255

Arg Arg Ile Ser Pro Phe Ser Cys Leu Lys Asp Arg His Asp Phe Gly
            260                 265                 270

Phe Pro Gln Glu Glu Phe Asp Gly Asn Gln Phe Gln Lys Ala Gln Ala
        275                 280                 285

Ile Ser Val Leu His Glu Met Ile Gln Gln Thr Phe Asn Leu Phe Ser
    290                 295                 300

Thr Lys Asp Ser Ser Ala Ala Trp Asp Glu Ser Leu Leu Glu Lys Phe
305                 310                 315                 320

Tyr Thr Glu Leu Tyr Gln Gln Leu Asn Asp Leu Glu Ala Cys Val Ile
                325                 330                 335

Gln Glu Val Gly Val Glu Glu Thr Pro Leu Met Asn Val Asp Ser Ile
            340                 345                 350

Leu Ala Val Lys Lys Tyr Phe Gln Arg Ile Thr Leu Tyr Leu Thr Glu
        355                 360                 365

Lys Lys Tyr Ser Pro Cys Ala Trp Glu Val Val Arg Ala Glu Ile Met
    370                 375                 380

Arg Ser Phe Ser Leu Ser Thr Asn Leu Gln Glu Arg Leu Arg Arg Lys
385                 390                 395                 400

Glu Ser Gly Gly Gly Gly Ser Gly Gly Gly Gly Ser Gly Gly Gly Gly
                405                 410                 415

Glu Val Gln Leu Leu Glu Ser Gly Gly Gly Leu Val Gln Pro Gly Gly
            420                 425                 430

Ser Leu Arg Leu Ser Cys Ala Ala Ser Gly Phe Thr Phe Ser Ser Phe
        435                 440                 445

Ser Met Ser Trp Val Arg Gln Ala Pro Gly Lys Gly Leu Glu Trp Val
    450                 455                 460

Ser Ser Ile Arg Gly Ser Ser Gly Thr Thr Tyr Tyr Ala Asp Ser Val
465                 470                 475                 480

Lys Gly Arg Phe Thr Ile Ser Arg Asp Asn Ser Lys Asn Thr Leu Tyr
                485                 490                 495

Leu Gln Met Asn Ser Leu Arg Ala Glu Asp Thr Ala Val Tyr Tyr Cys
            500                 505                 510

Ala Lys Pro Phe Pro Tyr Phe Asp Tyr Trp Gly Gln Gly Thr Leu Val
        515                 520                 525

Thr Val Ser Ser Ala Ser Thr Lys Gly Pro Ser Val Phe Pro Leu Ala
    530                 535                 540

Pro Ser Ser Lys Ser Thr Ser Gly Gly Thr Ala Ala Leu Gly Cys Leu
545                 550                 555                 560
```

```
Val Lys Asp Tyr Phe Pro Glu Pro Val Thr Val Ser Trp Asn Ser Gly
                565                 570                 575

Ala Leu Thr Ser Gly Val His Thr Phe Pro Ala Val Leu Gln Ser Ser
            580                 585                 590

Gly Leu Tyr Ser Leu Ser Ser Val Val Thr Val Pro Ser Ser Ser Leu
        595                 600                 605

Gly Thr Gln Thr Tyr Ile Cys Asn Val Asn His Lys Pro Ser Asn Thr
    610                 615                 620

Lys Val Asp Lys Lys Val Glu Pro Lys Ser Cys Asp
625                 630                 635


<210> SEQ ID NO 108
<211> LENGTH: 1812
<212> TYPE: DNA
<213> ORGANISM: Artificial Sequence
<220> FEATURE:
<223> OTHER INFORMATION: Fab heavy chain derived from L19 monoclonal
      antibody-C125A variant of IL2-Fab heavy chain derived from L19
      monoclonal antibody

<400> SEQUENCE: 108

gaggtgcagc tgttggagtc tgggggaggc ttggtacagc ctggggggtc cctgagactc     60

tcctgtgcag cctctggatt cacctttagc agtttttcga tgagctgggt ccgccaggct    120

ccagggaagg ggctggagtg ggtctcatct atttccggta gttcgggtac cacatactac    180

gcagactccg tgaagggccg gttcaccatc tccagagaca attccaagaa cacgctgtat    240

ctgcaaatga acagcctgag agccgaggac acggccgtat attactgtgc gaaaccgttt    300

ccgtattttg actactgggg ccagggaacc ctggtcaccg tctcgagtgc tagcaccaag    360

ggcccatcgg tcttccccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtg gataagaaag ttgagcccaa atcttgtgac    660

tccggcggag gagggagcgg cggaggtggc tccggaggtg gcggagcacc tacttcaagt    720

tctacaaaga aaacacagct acaactggag catttactgc tggatttaca gatgattttg    780

aatggaatta ataattacaa gaatcccaaa ctcaccagga tgctcacatt taagttttac    840

atgcccaaga aggccacaga actgaaacat cttcagtgtc tagaagaaga actcaaacct    900

ctggaggaag tgctaaattt agctcaaagc aaaaactttc acttaagacc cagggactta    960

atcagcaata tcaacgtaat agttctggaa ctaaagggat ctgaaacaac attcatgtgt   1020

gaatatgctg atgagacagc aaccattgta gaatttctga acagatggat tacctttgcc   1080

caaagcatca tctcaacact gacttccggc ggaggaggat ccggcggagg tggctctggc   1140

ggtggcggag aggtgcagct gttggagtct gggggaggct tggtacagcc tggggggtcc   1200

ctgagactct cctgtgcagc ctctggattc acctttagca gtttttcgat gagctgggtc   1260

cgccaggctc cagggaaggg gctggagtgg gtctcatcta tttccggtag ttcgggtacc   1320

acatactacg cagactccgt gaagggccgg ttcaccatct ccagagacaa ttccaagaac   1380

acgctgtatc tgcaaatgaa cagcctgaga gccgaggaca cggccgtata ttactgtgcg   1440

aaaccgtttc cgtattttga ctactggggc cagggaaccc tggtcaccgt ctcgagtgct   1500

agcaccaagg gcccatcggt cttccccctg gcaccctcct ccaagagcac ctctgggggc   1560
```

```
acagcggccc tgggctgcct ggtcaaggac tacttccccg aaccggtgac ggtgtcgtgg   1620

aactcaggcg ccctgaccag cggcgtgcac accttcccgg ctgtcctaca gtcctcagga   1680

ctctactccc tcagcagcgt ggtgaccgtg ccctccagca gcttgggcac ccagacctac   1740

atctgcaacg tgaatcacaa gcccagcaac accaaggtgg ataagaaagt tgagcccaaa   1800

tcttgtgact ga                                                       1812
```

```
<210> SEQ ID NO 109
<211> LENGTH: 648
<212> TYPE: DNA
<213> ORGANISM: Artificial Sequence
<220> FEATURE:
<223> OTHER INFORMATION: Fab light chain derived from L19 monoclonal
      antibody

<400> SEQUENCE: 109

gaaattgtgt tgacgcagtc tccaggcacc ctgtctttgt ctccagggga aagagccacc     60

ctctcctgca gggccagtca gagtgttagc agcagctact tagcctggta ccagcagaaa    120

cctggccagg ctcccaggct cctcatctat tatgcatcca gcagggccac tggcatccca    180

gacaggttca gtggcagtgg gtctgggaca gacttcactc tcaccatcag cagactggag    240

cctgaagatt ttgcagtgta ttactgtcag cagacgggtc gtattcctcc gacgttcggc    300

caagggacca aggtggaaat caaacgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgttag                 648
```

```
<210> SEQ ID NO 110
<211> LENGTH: 1149
<212> TYPE: DNA
<213> ORGANISM: Artificial Sequence
<220> FEATURE:
<223> OTHER INFORMATION: scFv derived from L19 monoclonal antibody-8
      amino acid linker-C125A variant of IL2

<400> SEQUENCE: 110

gaggtgcagc tgttggagtc tgggggaggc ttggtacagc ctggggggtc cctgagactc     60

tcctgtgcag cctctggatt cacctttagc agtttttcga tgagctgggt ccgccaggct    120

ccagggaagg ggctggagtg ggtctcatct atttccggta gttcgggtac cacatactac    180

gcagactccg tgaagggccg gttcaccatc tccagagaca attccaagaa cacgctgtat    240

ctgcaaatga acagcctgag agccgaggac acggccgtat attactgtgc gaaaccgttt    300

ccgtattttg actactgggg ccagggaacc ctggtcaccg tctcgagtag cggcgggagc    360

ggcggggcta gcgaaattgt gttgacgcag tctccaggca ccctgtcttt gtctccaggg    420

gaaagagcca ccctctcctg cagggccagt cagagtgtta gcagcagcta cttagcctgg    480

taccagcaga aacctggcca ggctcccagg ctcctcatct attatgcatc cagcagggcc    540

actggcatcc cagacaggtt cagtggcagt gggtctggga cagacttcac tctcaccatc    600

agcagactgg agcctgaaga ttttgcagtg tattactgtc agcagacggg tcgtattcct    660

ccgacgttcg gccaagggac caaggtggaa atctccgtgc tgtcttcctc atcgggtagt    720
```

-continued agctcttccg gctcatcgtc ctccggagca cctacttcaa gttctacaaa gaaaacacag 780
ctacaactgg agcatttact gctggattta cagatgattt tgaatggaat taataattac 840
aagaatccca aactcaccag gatgctcaca tttaagtttt acatgcccaa gaaggccaca 900
gaactgaaac atcttcagtg tctagaagaa gaactcaaac ctctggagga agtgctaaat 960
ttagctcaaa gcaaaaactt tcacttaaga cccagggact taatcagcaa tatcaacgta 1020
atagttctgg aactaaaggg atctgaaaca acattcatgt gtgaatatgc tgatgagaca 1080
gcaaccattg tagaatttct gaacagatgg attacctttg cccaaagcat catctcaaca 1140
ctgacttga 1149

<210> SEQ ID NO 111
<211> LENGTH: 1134
<212> TYPE: DNA
<213> ORGANISM: Artificial Sequence
<220> FEATURE:
<223> OTHER INFORMATION: F16-diabody-IL2

<400> SEQUENCE: 111
gaggtgcagc tgttggagtc tgggggaggc ttggtacagc ctggggggtc cctgagactc 60
tcctgtgcag cctctggatt cacctttagc cggtatggta tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcaaatga acagcctgag agccgaggac acggccgtat attactgtgc gaaagcgcat 300
aatgcttttg actactgggg ccagggaacc ctggtcaccg tgtcgagtgc tagcggcgga 360
tcgtctgagc tgactcagga ccctgctgtg tctgtggcct tgggacagac agtcaggatc 420
acatgccaag gagacagcct cagaagctat tatgcaagct ggtaccagca gaagccagga 480
caggcccctg tacttgtcat ctatggtaaa aacaaccggc cctcagggat cccagaccga 540
ttctctggct ccagctcagg aaacacagct tccttgacca tcactggggc tcaggcggaa 600
gatgaggctg actattactg taactcctct gtttatacta tgccgcccgt ggtattcggc 660
ggagggacca agctgaccgt cctaggctct tcctcatcgg gtagtagctc ttccggctca 720
tcgtcctccg gagcacctac ttcaagttct acaaagaaaa cacagctaca actggagcat 780
ttactgctgg atttacagat gattttgaat ggaattaata attacaagaa tcccaaactc 840
accaggatgc tcacatttaa gttttacatg cccaagaagg ccacagaact gaaacatctt 900
cagtgtctag aagaagaact caaacctctg gaggaagtgc taaatttagc tcaaagcaaa 960
aactttcact taagacccag ggacttaatc agcaatatca acgtaatagt tctggaacta 1020
aagggatctg aaacaacatt catgtgtgaa tatgctgatg agacagcaac cattgtagaa 1080
tttctgaaca gatggattac ctttgcccaa agcatcatct caacactgac ttga 1134

<210> SEQ ID NO 112
<211> LENGTH: 1926
<212> TYPE: DNA
<213> ORGANISM: Artificial Sequence
<220> FEATURE:
<223> OTHER INFORMATION: scFv-IL2-scFv (F16, DNA)

<400> SEQUENCE: 112
gaggtgcagc tgttggagtc tgggggaggc ttggtacagc ctggggggtc cctgagactc 60
tcctgtgcag cctctggatt cacctttagc cggtatggta tgagctgggt ccgccaggct 120
ccagggaagg ggctggagtg ggtctcagct attagtggta gtggtggtag cacatactac 180

```
gcagactccg tgaagggccg gttcaccatc tccagagaca attccaagaa cacgctgtat    240
ctgcaaatga acagcctgag agccgaggac acggccgtat attactgtgc gaaagcgcat    300
aatgcttttg actactgggg ccagggaacc ctggtcaccg tgtcgagagg tggaggcggt    360
tcaggcggag gtggctctgg cggtggcgga tcgtctgagc tgactcagga ccctgctgtg    420
tctgtggcct tgggacagac agtcaggatc acatgccaag gagacagcct cagaagctat    480
tatgcaagct ggtaccagca gaagccagga caggcccctg tacttgtcat ctatggtaaa    540
aacaaccggc cctcagggat cccagaccga ttctctggct ccagctcagg aaacacagct    600
tccttgacca tcactggggc tcaggcggaa gatgaggctg actattactg taactcctct    660
gtttatacta tgccgcccgt ggtattcggc ggagggacca agctgaccgt cctaggctct    720
tcctcatcgg gtagtagctc ttccggctca tcgtcctccg gagcacctac ttcaagttct    780
acaaagaaaa cacagctaca actggagcat ttactgctgg atttacagat gattttgaat    840
ggaattaata attacaagaa tcccaaactc accaggatgc tcacatttaa gttttacatg    900
cccaagaagg ccacagaact gaaacatctt cagtgtctag aagaagaact caaacctctg    960
gaggaagtgc taaatttagc tcaaagcaaa aactttcact taagacccag ggacttaatc   1020
agcaatatca acgtaatagt tctggaacta aagggatctg aaacaacatt catgtgtgaa   1080
tatgctgatg agacagcaac cattgtagaa tttctgaaca gatggattac ctttgcccaa   1140
agcatcatct caacactgac ttccggcgga ggagggagcg gcggaggtgg ctctggcggt   1200
ggcggatcgt ctgagctcac tcaggaccct gctgtgtctg tggccttggg acagacagtc   1260
aggatcacat gccaaggaga cagcctcaga agctattatg caagctggta ccagcagaag   1320
ccaggacagg cccctgtact tgtcatctat ggtaaaaaca accggccctc agggatccca   1380
gaccgattct ctggctccag ctcaggaaac acagcttcct tgaccatcac tggggctcag   1440
gcggaagatg aggctgacta ttactgtaac tcctctgttt atactatgcc gcccgtggta   1500
ttcggcggag ggaccaagct taccgtacta ggctcaggag gcggttcagg cggaggttct   1560
ggcggcggta gcggatcgga ggtgcagctg ttggagtctg ggggaggctt ggtacagcct   1620
ggggggtccc tgagactctc ctgtgcagcc tctggattca cctttagccg gtatggtatg   1680
agctgggtcc gccaggctcc agggaagggg ctggagtggg tctcagctat tagtggtagt   1740
ggtggtagca catactacgc agactccgtg aagggccggt tcaccatctc cagagacaat   1800
tccaagaaca cgctgtatct gcaaatgaac agcctgagag ccgaggacac ggccgtatat   1860
tactgtgcga aagcgcataa tgcttttgac tactggggcc agggaaccct ggtcaccgtg   1920
tcgtga                                                              1926
```

<210> SEQ ID NO 113
<211> LENGTH: 1812
<212> TYPE: DNA
<213> ORGANISM: Artificial Sequence
<220> FEATURE:
<223> OTHER INFORMATION: Fab-IL2-Fab (F16, heavy chain cytokine fusion construct, DNA)

<400> SEQUENCE: 113

```
gaggtgcagc tgttggagtc tgggggaggc ttggtacagc ctggggggtc cctgagactc     60
tcctgtgcag cctctggatt cacctttagc cggtatggta tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
```

ctgcaaatga acagcctgag agccgaggac acggccgtat attactgtgc gaaagcgcat 300
aatgcttttg actactgggg ccagggaacc ctggtcaccg tgtcgagtgc tagcaccaag 360
ggcccatcgg tcttcccct ggcaccctcc tccaagagca cctctggggg cacagcggcc 420
ctgggctgcc tggtcaagga ctacttcccc gaaccggtga cggtgtcgtg gaactcaggc 480
gccctgacca gcggcgtgca caccttcccg gctgtcctac agtcctcagg actctactcc 540
ctcagcagcg tggtgaccgt gccctccagc agcttgggca cccagaccta catctgcaac 600
gtgaatcaca agcccagcaa caccaaggtg gataagaaag ttgagcccaa atcttgtgac 660
tcttcctcat cgggtagtag ctcttccggc tcatcgtcct ccggagcacc tacttcaagt 720
tctacaaaga aaacacagct acaactggag catttactgc tggatttaca gatgattttg 780
aatggaatta ataattacaa gaatcccaaa ctcaccagga tgctcacatt taagttttac 840
atgcccaaga aggccacaga actgaaacat cttcagtgtc tagaagaaga actcaaacct 900
ctggaggaag tgctaaattt agctcaaagc aaaaactttc acttaagacc cagggactta 960
atcagcaata tcaacgtaat agttctggaa ctaaagggat ctgaaacaac attcatgtgt 1020
gaatatgctg atgagacagc aaccattgta gaatttctga acagatggat tacctttgcc 1080
caaagcatca tctcaacact gacttccggc ggaggaggga gcggcggagg tggctctggc 1140
ggtggcggag aggtgcaatt gttggagtct gggggaggct tggtacagcc tggggggtcc 1200
ctgagactct cctgtgcagc ctctggattc acctttagcc ggtatggtat gagctgggtc 1260
cgccaggctc cagggaaggg gctggagtgg gtctcagcta ttagtggtag tggtggtagc 1320
acatactacg cagactccgt gaagggccgg ttcaccatct ccagagacaa ttccaagaac 1380
acgctgtatc tgcaaatgaa cagcctgaga gccgaggaca cggccgtata ttactgtgcg 1440
aaagcgcata atgcttttga ctactggggc cagggaaccc tggtcaccgt gtcgagtgct 1500
agcaccaagg gcccatcggt cttcccctg gcaccctcct ccaagagcac ctctgggggc 1560
acagcggccc tgggctgcct ggtcaaggac tacttccccg aaccggtgac ggtgtcgtgg 1620
aactcaggcg ccctgaccag cggcgtgcac accttcccgg ctgtcctaca gtcctcagga 1680
ctctactccc tcagcagcgt ggtgaccgtg ccctccagca gcttgggcac ccagacctac 1740
atctgcaacg tgaatcacaa gcccagcaac accaaggtgg acaagaaagt tgagcccaaa 1800
tcttgtgact ga 1812

<210> SEQ ID NO 114
<211> LENGTH: 645
<212> TYPE: DNA
<213> ORGANISM: Artificial Sequence
<220> FEATURE:
<223> OTHER INFORMATION: F16, light chain, DNA

<400> SEQUENCE: 114
tcttctgagc tgactcagga ccctgctgtg tctgtggcct tgggacagac agtcaggatc 60
acatgccaag gagacagcct cagaagctat tatgcaagct ggtaccagca gaagccagga 120
caggcccctg tacttgtcat ctatggtaaa aacaaccggc cctcagggat cccagaccga 180
ttctctggct ccagctcagg aaacacagct tccttgacca tcactggggc tcaggcggaa 240
gatgaggctg actattactg taactcctct gtttatacta tgccgcccgt ggtattcggc 300
ggagggacca agctgaccgt cctaggtcaa cccaaggctg cccccagcgt gaccctgttc 360
ccccccagca gcgaggaact gcaggccaac aaggccaccc tggtctgcct gatcagcgac 420

```
ttctacccag gcgccgtgac cgtggcctgg aaggccgaca gcagccccgt gaaggccggc    480

gtggagacca ccacccccag caagcagagc aacaacaagt acgccgccag cagctacctg    540

agcctgaccc ccgagcagtg gaagagccac aggtcctaca gctgccaggt gacccacgag    600

ggcagcaccg tggagaaaac cgtggccccc accgagtgca gctga                    645
```

<210> SEQ ID NO 115
<211> LENGTH: 1401
<212> TYPE: DNA
<213> ORGANISM: Artificial Sequence
<220> FEATURE:
<223> OTHER INFORMATION: IL2R-beta-Fc(hole) fusion protein, DNA

<400> SEQUENCE: 115

```
atggacatga gggtccccgc tcagctcctg ggcctcctgc tgctctggtt cccaggtgcc     60

aggtgtgcgg tgaatggcac ttcccagttc acatgcttct acaactcgag agccaacatc    120

tcctgtgtct ggagccaaga tggggctctg caggacactt cctgccaagt ccatgcctgg    180

ccggacagac ggcggtggaa ccaaacctgt gagctgctcc ccgtgagtca agcatcctgg    240

gcctgcaacc tgatcctcgg agccccagat tctcagaaac tgaccacagt tgacatcgtc    300

accctgaggg tgctgtgccg tgagggggtg cgatggaggg tgatggccat ccaggacttc    360

aagccctttg agaaccttcg cctgatggcc cccatctccc tccaagttgt ccacgtggag    420

acccacagat gcaacataag ctgggaaatc tcccaagcct cccactactt tgaaagacac    480

ctggagttcg aggcccggac gctgtcccca ggccacacct gggaggaggc ccccctgctg    540

actctcaagc agaagcagga atggatctgc ctggagacgc tcaccccaga cacccagtat    600

gagtttcagg tgcgggtcaa gcctctgcaa ggcgagttca cgacctggag cccctggagc    660

cagcccctgg ccttcagaac aaagcctgca gcccttggga aggacaccgg agctcaggac    720

aaaactcaca catgcccacc gtgcccagca cctgaactcc tggggggacc gtcagtcttc    780

ctcttccccc caaaacccaa ggacaccctc atgatctccc ggacccctga ggtcacatgc    840

gtggtggtgg acgtgagcca cgaagaccct gaggtcaagt tcaactggta cgtggacggc    900

gtggaggtgc ataatgccaa gacaaagccg cgggaggagc agtacaacag cacgtaccgt    960

gtggtcagcg tcctcaccgt cctgcaccag gactggctga atggcaagga gtacaagtgc   1020

aaggtctcca acaaagccct cccagccccc atcgagaaaa ccatctccaa agccaaaggg   1080

cagccccgag aaccacaggt gtgcaccctg cccccatccc gggatgagct gaccaagaac   1140

caggtcagcc tctcgtgcgc agtcaaaggc ttctatccca gcgacatcgc cgtggagtgg   1200

gagagcaatg ggcagccgga gaacaactac aagaccacgc ctcccgtgct ggactccgac   1260

ggctccttct tcctcgtgag caagctcacc gtggacaaga gcaggtggca gcaggggaac   1320

gtcttctcat gctccgtgat gcatgaggct ctgcacaacc actacacgca gaagagcctc   1380

tccctgtctc cgggtaaatg a                                             1401
```

<210> SEQ ID NO 116
<211> LENGTH: 1479
<212> TYPE: DNA
<213> ORGANISM: Artificial Sequence
<220> FEATURE:
<223> OTHER INFORMATION: IL2R-gamma-Fc(knob), DNA

<400> SEQUENCE: 116

```
atgttgaagc catcattacc attcacatcc ctcttattcc tgcagctgcc cctgctggga     60

gtggggctga acacgacaat tctgacgccc aatgggaatg aagacaccac agctgatttc    120
```

```
ttcctgacca ctatgcccac tgactccctc agtgtttcca ctctgcccct cccagaggtt    180

cagtgttttg tgttcaatgt cgagtacatg aattgcactt ggaacagcag ctctgagccc    240

cagcctacca acctcactct gcattattgg tacaagaact cggataatga taaagtccag    300

aagtgcagcc actatctatt ctctgaagaa atcacttctg gctgtcagtt gcaaaaaaag    360

gagatccacc tctaccaaac atttgttgtt cagctccagg acccacggga acccaggaga    420

caggccacac agatgctaaa actgcagaat ctggtgatcc cctgggctcc agagaaccta    480

acacttcaca aactgagtga atcccagcta gaactgaact ggaacaacag attcttgaac    540

cactgtttgg agcacttggt gcagtaccgg actgactggg accacagctg gactgaacaa    600

tcagtggatt atagacataa gttctccttg cctagtgtgg atgggcagaa acgctacacg    660

tttcgtgttc ggagccgctt taacccactc tgtggaagtg ctcagcattg gagtgaatgg    720

agccacccaa tccactgggg gagcaatact tcaaaagaga atcctttcct gtttgcattg    780

gaagccggag ctcaggacaa aactcacaca tgcccaccgt gcccagcacc tgaactcctg    840

gggggaccgt cagtcttcct cttcccccca aaacccaagg acaccctcat gatctcccgg    900

acccctgagg tcacatgcgt ggtggtggac gtgagccacg aagaccctga ggtcaagttc    960

aactggtacg tggacggcgt ggaggtgcat aatgccaaga caaagccgcg ggaggagcag   1020

tacaacagca cgtaccgtgt ggtcagcgtc ctcaccgtcc tgcaccagga ctggctgaat   1080

ggcaaggagt acaagtgcaa ggtctccaac aaagccctcc cagcccccat cgagaaaacc   1140

atctccaaag ccaaagggca gccccgagaa ccacaggtgt acaccctgcc cccatgccgg   1200

gatgagctga ccaagaacca ggtcagcctg tggtgcctgg tcaaaggctt ctatcccagc   1260

gacatcgccg tggagtggga gagcaatggg cagccggaga acaactacaa gaccacgcct   1320

cccgtgctgg actccgacgg ctccttcttc ctctacagca agctcaccgt ggacaagagc   1380

aggtggcagc aggggaacgt cttctcatgc tccgtgatgc atgaggctct gcacaaccac   1440

tacacgcaga agagcctctc cctgtctccg ggtaaatga                          1479
```

<210> SEQ ID NO 117
<211> LENGTH: 2976
<212> TYPE: DNA
<213> ORGANISM: Artificial Sequence
<220> FEATURE:
<223> OTHER INFORMATION: Fab-IL12-Fab, L19 antibody, murine scIL12, DNA

<400> SEQUENCE: 117

```
gaggtgcagc tgttggagtc tgggggaggc ttggtacagc ctggggggtc cctgagactc     60

tcctgtgcag cctctggatt cacctttagc agtttttcga tgagctgggt ccgccaggct    120

ccagggaagg ggctggagtg ggtctcatct atttccggta gttcgggtac cacatactac    180

gcagactccg tgaagggccg gttcaccatc tccagagaca attccaagaa cacgctgtat    240

ctgcaaatga acagcctgag agccgaggac acggccgtat attactgtgc gaaaccgttt    300

ccgtattttg actactgggg ccagggaacc ctggtcaccg tctcgagtgc tagcaccaag    360

ggcccatcgg tcttccccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtg gataagaaag ttgagcccaa atcttgtgac    660
```

-continued

```
tccggcggag gagggagcgg cggaggtggc tccggagggg gcggagccat gtgggagctg    720
gaaaaggacg tgtacgtggt ggaggtggac tggacccccg acgcccctgg cgagacagtg    780
aacctgacct gcgacacccc cgaagaggac gacatcacct ggaccagcga ccagcggcac    840
ggcgtgatcg gcagcggcaa gaccctgacc atcaccgtga aagagtttct ggacgccggc    900
cagtacacct gccacaaggg cggcgagaca ctgagccaca gccacctgct gctgcacaag    960
aaagagaacg gcatctggtc caccgagatc ctgaagaact tcaagaacaa gaccttcctg   1020
aagtgcgagg cccccaacta cagcggccgg ttcacctgca gctggctggt gcagcggaac   1080
atggacctga agttcaacat caagagcagc agcagccccc ctgacagcag ggccgtgacc   1140
tgcggcatgg ccagcctgag cgccgagaag gtgaccctgg accagaggga ctacgagaag   1200
tacagcgtga gctgccagga agatgtcacc tgccccaccg ccgaggaaac cctgcccatc   1260
gagctggccc tggaagcccg gcagcagaac aagtacgaga actactctac cagcttcttc   1320
atccgggaca tcatcaagcc cgaccccccc aagaacctgc agatgaagcc cctgaagaac   1380
agccaggtgg aggtgtcctg ggagtaccct gacagctggt ccacccccag aagctacttc   1440
agcctgaagt tcttcgtgag aatccagcgg aagaaagaaa agatgaaaga gacagaggaa   1500
ggctgcaacc agaagggcgc cttcttcgtc gagaaaacca gcaccgaggt gcagtgcaag   1560
ggcggcaacg tgtgcgtgca ggcccaggac cggtactaca acagcagctg cagcaagtgg   1620
gcctgcgtgc cctgcagagt gcggtctggc ggcgacggct ctggcggcgg aggaagcggc   1680
ggagggggca gcagagtgat ccccgtgagc ggccctgccc ggtgcctgag ccagagccgg   1740
aacctgctga aaaccaccga cgacatggtg aaaaccgcca gagagaagct gaagcactac   1800
agctgcacag ccgaggacat cgaccacgag gacatcaccc gggaccagac cagcaccctg   1860
aaaacctgcc tgcccctgga actgcacaaa aacgagagct gcctggccac ccgggagaca   1920
agcagcacca cccggggcag ctgcctgcct ccccagaaaa cctccctgat gatgaccctg   1980
tgcctgggca gcatctacga ggacctgaag atgtaccaga ccgagttcca ggccatcaac   2040
gccgccctgc agaaccacaa tcaccagcag atcatcctgg acaagggcat gctggtcgcc   2100
atcgacgagc tgatgcagag cctgaaccac aacggcgaaa ccctgcggca gaaacccccc   2160
gtgggcgagg ccgaccccta ccgggtgaag atgaagctgt gcatcctgct gcacgccttc   2220
agcacccggg tggtgaccat caaccgggtg atgggctacc tgtcctctgc cgggggaggg   2280
ggatccggcg gaggtggctc tggcggtggc ggagaggtgc agctgttgga gtctggggga   2340
ggcttggtac agcctggggg gtccctgaga ctctcctgtg cagcctctgg attcaccttt   2400
agcagttttt cgatgagctg ggtccgccag gctccaggga aggggctgga gtgggtctca   2460
tctatttccg gtagttcggg taccacatac tacgcagact ccgtgaaggg ccggttcacc   2520
atctccagag acaattccaa gaacacgctg tatctgcaaa tgaacagcct gagagccgag   2580
gacacggccg tatattactg tgcgaaaccg tttccgtatt ttgactactg gggccaggga   2640
accctggtca ccgtctcgag tgctagcacc aagggcccat cggtcttccc cctggcaccc   2700
tcctccaaga gcacctctgg gggcacagcg gccctgggct gcctggtcaa ggactacttc   2760
cccgaaccgg tgacggtgtc gtggaactca ggcgccctga ccagcggcgt gcacaccttc   2820
ccggctgtcc tacagtcctc aggactctac tccctcagca gcgtggtgac cgtgccctcc   2880
agcagcttgg gcacccagac ctacatctgc aacgtgaatc acaagcccag caacaccaag   2940
gtggataaga aagttgagcc caaatcttgt gactga                              2976
```

<210> SEQ ID NO 118
<211> LENGTH: 2964
<212> TYPE: DNA
<213> ORGANISM: Artificial Sequence
<220> FEATURE:
<223> OTHER INFORMATION: Fab-IL12-Fab, L19 antibody, human scIL12, DNA

<400> SEQUENCE: 118
gaggtgcagc tgttggagtc tgggggaggc ttggtacagc ctggggggtc cctgagactc 60
tcctgtgcag cctctggatt cacctttagc agtttttcga tgagctgggt ccgccaggct 120
ccagggaagg ggctggagtg ggtctcatct attagaggta gttcgggtac cacatactac 180
gcagactccg tgaagggccg gttcaccatc tccagagaca attccaagaa cacgctgtat 240
ctgcaaatga acagcctgag agccgaggac acggccgtat attactgtgc gaaaccgttt 300
ccgtattttg actactgggg ccagggaacc ctggtcaccg tctcgagtgc tagcaccaag 360
ggcccatcgg tcttccccct ggcaccctcc tccaagagca cctctggggg cacagcggcc 420
ctgggctgcc tggtcaagga ctacttcccc gaaccggtga cggtgtcgtg gaactcaggc 480
gccctgacca gcggcgtgca caccttcccg gctgtcctac agtcctcagg actctactcc 540
ctcagcagcg tggtgaccgt gccctccagc agcttgggca cccagaccta catctgcaac 600
gtgaatcaca agcccagcaa caccaaggtg gataagaaag ttgagcccaa atcttgtgac 660
tccggcggag gagggagcgg cggaggtggc tccggagggg gcggaatctg ggagctgaag 720
aaagacgtgt acgtggtgga gctggactgg tatcccgacg cccctggcga gatggtggtg 780
ctgacctgcg acacccccga agaggacggc atcacctgga ccctggacca gagcagcgag 840
gtgctgggca gcggcaagac cctgaccatc caggtgaaag agttcggcga cgccggccag 900
tacacctgcc acaagggcgg cgaagtgctg tcccacagcc tgctgctgct gcacaagaaa 960
gaggatggca tctggtccac cgacatcctg aaggaccaga aagagcccaa gaacaagacc 1020
ttcctgcggt gcgaggccaa gaactacagc ggccggttca cctgttggtg gctgaccacc 1080
atcagcaccg acctgacctt cagcgtgaag agcagccggg gcagcagcga ccctcagggc 1140
gtgacctgcg gagccgccac cctgagcgcc gagagagtgc ggggcgacaa caaagagtac 1200
gagtacagcg tcgagtgcca ggaagatagc gcctgccctg ccgccgagga aagcctgccc 1260
atcgaggtga tggtggacgc cgtgcacaag ctgaagtacg agaactacac cagcagcttt 1320
ttcatccggg acatcatcaa gcccgacccc cccaagaacc tgcagctgaa gcccctgaag 1380
aacagccggc aggtggaggt gtcctgggag taccctgaca cctggtccac cccccacagc 1440
tacttcagcc tgacattctg tgtgcaggtg cagggcaaga gcaagcggga gaagaaagac 1500
cgggtgttca ccgacaagac cagcgccacc gtgatctgcc ggaagaacgc cagcatcagc 1560
gtgcgggccc aggaccggta ctacagcagc tcctggtccg agtgggccag cgtgccttgc 1620
agcggcggag gggctctgg cggcggagga tctgggggag gggcagccg gaacctgccc 1680
gtggccaccc ccgaccccgg catgttcccc tgcctgcacc acagccagaa cctgctgcgg 1740
gccgtgagca acatgctgca gaaggcccgg cagaccctgg aattctaccc ctgcaccagc 1800
gaggaaatcg accacgagga catcaccaag gataagacca gcaccgtgga ggcctgcctg 1860
cccctggaac tgaccaagaa cgagagctgc ctgaacagcc gggagacaag cttcatcacc 1920
aacggcagct gcctggccag cagaaagacc agcttcatga tggccctgtg cctgagcagc 1980
atctacgagg acctgaagat gtaccaggtg gagttcaaga ccatgaacgc caagctgctg 2040
atggacccca agcggcagat cttcctggat cagaacatgc tggccgtgat cgacgagctg 2100
atgcaggccc tgaacttcaa cagcgagaca gtgccccaga agtccagcct ggaagagccc 2160
gacttctaca agaccaagat caagctgtgc atcctgctgc acgccttcag aatccgggcc 2220
gtgaccatcg accgggtgat gagctacctg aacgccagcg gaggggggg atccggcgga 2280 ggtggctctg gcggtggcgg agaggtgcag ctgttggagt ctgggggagg cttggtacag 2340
cctggggggt ccctgagact ctcctgtgca gcctctggat tcacctttag cagtttttcg 2400
atgagctggg tccgccaggc tccagggaag gggctggagt gggtctcatc tattagaggt 2460
agttcgggta ccacatacta cgcagactcc gtgaagggcc ggttcaccat ctccagagac 2520
aattccaaga acacgctgta tctgcaaatg aacagcctga gagccgagga cacggccgta 2580
tattactgtg cgaaaccgtt tccgtatttt gactactggg gccagggaac cctggtcacc 2640
gtctcgagtg ctagcaccaa gggcccatcg gtcttccccc tggcaccctc ctccaagagc 2700
acctctgggg gcacagcggc cctgggctgc ctggtcaagg actacttccc cgaaccggtg 2760
acggtgtcgt ggaactcagg cgccctgacc agcggcgtgc acaccttccc ggctgtccta 2820
cagtcctcag gactctactc cctcagcagc gtggtgaccg tgccctccag cagcttgggc 2880
acccagacct acatctgcaa cgtgaatcac aagcccagca acaccaaggt ggataagaaa 2940
gttgagccca aatcttgtga ctga 2964

<210> SEQ ID NO 119
<211> LENGTH: 1794
<212> TYPE: DNA
<213> ORGANISM: Artificial Sequence
<220> FEATURE:
<223> OTHER INFORMATION: Fab-GMCSF-Fab, L19 antibody, human GM-CSF, DNA

<400> SEQUENCE: 119
gaggtgcagc tgttggagtc tgggggaggc ttggtacagc ctggggggtc cctgagactc 60
tcctgtgcag cctctggatt cacctttagc agtttttcga tgagctgggt ccgccaggct 120
ccagggaagg ggctggagtg ggtctcatct attagaggta gttcgggtac cacatactac 180
gcagactccg tgaagggccg gttcaccatc tccagagaca attccaagaa cacgctgtat 240
ctgcaaatga acagcctgag agccgaggac acggccgtat attactgtgc gaaaccgttt 300
ccgtattttg actactgggg ccagggaacc ctggtcaccg tctcgagtgc tagcaccaag 360
ggcccatcgg tcttccccct ggcaccctcc tccaagagca cctctggggg cacagcggcc 420
ctgggctgcc tggtcaagga ctacttcccc gaaccggtga cggtgtcgtg gaactcaggc 480
gccctgacca gcggcgtgca caccttcccg gctgtcctac agtcctcagg actctactcc 540
ctcagcagcg tggtgaccgt gccctccagc agcttgggca cccagaccta catctgcaac 600
gtgaatcaca agcccagcaa caccaaggtg gataagaaag ttgagcccaa atcttgtgac 660
tccggcggag gagggagcgg cggaggtggc tccggaggtg gcggagcacc cgcccgctcg 720
cccagcccca gcacgcagcc ctgggagcat gtgaatgcca tccaggaggc ccggcgtctc 780
ctgaacctga gtagagacac tgctgctgag atgaatgaaa cagtagaagt catctcagaa 840
atgtttgacc tccaggagcc gacctgccta cagacccgcc tggagctgta caagcagggc 900
ctgcggggca gcctcaccaa gctcaagggc cccttgacca tgatggccag ccactacaag 960
cagcactgcc ctccaacccc ggaaacttcc tgtgcaaccc agattatcac ctttgaaagt 1020
ttcaaagaga acctgaagga ctttctgctt gtcatcccct ttgactgctg ggagccagtc 1080
caggagtccg gcggaggagg atccggcgga ggtggctctg gcggtggcgg agaggtgcag 1140
ctgttggagt ctgggggagg cttggtacag cctggggggt ccctgagact ctcctgtgca 1200

```
gcctctggat tcacctttag cagtttttcg atgagctggg tccgccaggc tccagggaag   1260

gggctggagt gggtctcatc tattagaggt agttcgggta ccacatacta cgcagactcc   1320

gtgaagggcc ggttcaccat ctccagagac aattccaaga acacgctgta tctgcaaatg   1380

aacagcctga gagccgagga cacggccgta tattactgtg cgaaaccgtt tccgtatttt   1440

gactactggg gccagggaac cctggtcacc gtctcgagtg ctagcaccaa gggcccatcg   1500

gtcttccccc tggcaccctc ctccaagagc acctctgggg gcacagcggc cctgggctgc   1560

ctggtcaagg actacttccc cgaaccggtg acggtgtcgt ggaactcagg cgccctgacc   1620

agcggcgtgc acaccttccc ggctgtccta cagtcctcag gactctactc cctcagcagc   1680

gtggtgaccg tgccctccag cagcttgggc acccagacct acatctgcaa cgtgaatcac   1740

aagcccagca acaccaaggt ggataagaaa gttgagccca aatcttgtga ctga         1794
```

<210> SEQ ID NO 120
<211> LENGTH: 1911
<212> TYPE: DNA
<213> ORGANISM: Artificial Sequence
<220> FEATURE:
<223> OTHER INFORMATION: Fab-IFNa2-Fab, L19 antibody, DNA

<400> SEQUENCE: 120

```
gaggtgcagc tgttggagtc tgggggaggc ttggtacagc ctggggggtc cctgagactc     60

tcctgtgcag cctctggatt cacctttagc agtttttcga tgagctgggt ccgccaggct    120

ccagggaagg ggctggagtg ggtctcatct attagaggta gttcgggtac cacatactac    180

gcagactccg tgaagggccg gttcaccatc tccagagaca attccaagaa cacgctgtat    240

ctgcaaatga acagcctgag agccgaggac acggccgtat attactgtgc gaaaccgttt    300

ccgtattttg actactgggg ccagggaacc ctggtcaccg tctcgagtgc tagcaccaag    360

ggcccatcgg tcttccccct ggcaccctcc tccaagagca cctctggggg cacagcggcc    420

ctgggctgcc tggtcaagga ctacttcccc gaaccggtga cggtgtcgtg gaactcaggc    480

gccctgacca gcggcgtgca caccttcccg gctgtcctac agtcctcagg actctactcc    540

ctcagcagcg tggtgaccgt gccctccagc agcttgggca cccagaccta catctgcaac    600

gtgaatcaca agcccagcaa caccaaggtg gataagaaag ttgagcccaa atcttgtgac    660

tccggcggag gagggagcgg cggaggtggc tccggagggg gcggatgcga cctgccccag    720

acccacagcc tgggcaacag acgggccctg atcctgctgg cccagatgcg gcggatcagc    780

cccttcagct gcctgaagga ccggcacgac ttcggcttcc cccaggaaga gttcgacggc    840

aaccagttcc agaaggccca ggccatcagc gtgctgcacg agatgatcca gcagaccttc    900

aacctgttca gcaccaagga cagcagcgcc gcctgggacg agagcctgct ggaaaagttc    960

tacaccgagc tgtaccagca gctgaacgac ctggaagcct gcgtgatcca ggaagtgggc   1020

gtcgaggaaa cccccctgat gaacgtggac agcatcctgg ccgtgaagaa gtacttccag   1080

cggatcaccc tgtacctgac cgagaagaag tatagcccct gcgcctggga ggtggtgcgg   1140

gccgagatca tgcggagctt cagcctgagc accaacctgc aggaacggct gcggcggaaa   1200

gagagcggcg gaggggggatc cggcggaggt ggctctggcg gtggcggaga ggtgcagctg   1260

ttggagtctg gggggaggctt ggtacagcct gggggggtccc tgagactctc ctgtgcagcc   1320

tctggattca cctttagcag tttttcgatg agctgggtcc gccaggctcc agggaagggg   1380

ctggagtggg tctcatctat tagaggtagt tcgggtacca catactacgc agactccgtg   1440
```

```
aagggccggt tcaccatctc cagagacaat tccaagaaca cgctgtatct gcaaatgaac   1500

agcctgagag ccgaggacac ggccgtatat tactgtgcga aaccgtttcc gtattttgac   1560

tactggggcc agggaaccct ggtcaccgtc tcgagtgcta gcaccaaggg cccatcggtc   1620

ttcccctgg caccctcctc caagagcacc tctgggggca cagcggccct gggctgcctg   1680

gtcaaggact acttccccga accggtgacg gtgtcgtgga actcaggcgc cctgaccagc   1740

ggcgtgcaca ccttcccggc tgtcctacag tcctcaggac tctactccct cagcagcgtg   1800

gtgaccgtgc cctccagcag cttgggcacc cagacctaca tctgcaacgt gaatcacaag   1860

cccagcaaca ccaaggtgga taagaaagtt gagcccaaat cttgtgactg a            1911


<210> SEQ ID NO 121
<211> LENGTH: 108
<212> TYPE: PRT
<213> ORGANISM: Artificial Sequence
<220> FEATURE:
<223> OTHER INFORMATION: 19G1; VL

<400> SEQUENCE: 121

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105


<210> SEQ ID NO 122
<211> LENGTH: 324
<212> TYPE: DNA
<213> ORGANISM: Artificial Sequence
<220> FEATURE:
<223> OTHER INFORMATION: 19G1; VL

<400> SEQUENCE: 122

gaaatcgtgt taacgcagtc tccaggcacc ctgtctttgt ctccagggga aagagccacc     60

ctctcttgca gggccagtca gagtgttacc agtagctact tagcctggta ccagcagaaa    120

cctggccagg ctcccaggct cctcatcaat gtgggctccc gtagggccac tggcatccca    180

gacaggttca gtggcagtgg atccgggaca gacttcactc tcaccatcag cagactggag    240

cctgaagatt ttgcagtgta ttactgtcag cagggtatta tgcttccccc gacgttcggc    300

caggggacca aagtggaaat caaa                                           324


<210> SEQ ID NO 123
<211> LENGTH: 117
<212> TYPE: PRT
<213> ORGANISM: Artificial Sequence
<220> FEATURE:
<223> OTHER INFORMATION: 19G1; VH

<400> SEQUENCE: 123
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Ser Ser Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115


<210> SEQ ID NO 124
<211> LENGTH: 351
<212> TYPE: DNA
<213> ORGANISM: Artificial Sequence
<220> FEATURE:
<223> OTHER INFORMATION: 19G1; VH

<400> SEQUENCE: 124

gaggtgcaat tgttggagtc tgggggaggc ttggtacagc ctggggggtc cctgagactc      60

tcctgtgcag cctccggatt cacctttagc agttatgcga tgagctgggt ccgccaggct     120

ccagggaagg ggctggagtg ggtctcagcg attattagta gtggtggtct cacatactac     180

gcagactccg tgaagggccg gttcaccatc tccagagaca attccaagaa cacgctgtat     240

ctgcagatga acagcctgag agccgaggac acggccgtat attactgtgc gaaagggtgg     300

tttggtggtt ttaactactg gggccaagga accctggtca ccgtctcgtc c              351


<210> SEQ ID NO 125
<211> LENGTH: 108
<212> TYPE: PRT
<213> ORGANISM: Artificial Sequence
<220> FEATURE:
<223> OTHER INFORMATION: 20G8; VL

<400> SEQUENCE: 125

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105


<210> SEQ ID NO 126
```

<211> LENGTH: 324
<212> TYPE: DNA
<213> ORGANISM: Artificial Sequence
<220> FEATURE:
<223> OTHER INFORMATION: 20G8; VL

<400> SEQUENCE: 126

```
gaaatcgtgt taacgcagtc tccaggcacc ctgtctttgt ctccagggga aagagccacc     60

ctctcttgca gggccagtca gagtgttacc agtagctact tagcctggta ccagcagaaa    120

cctggccagg ctcccaggct cctcatcaat gtgggctccc gtagggccac tggcatccca    180

gacaggttca gtggcagtgg atccgggaca gacttcactc tcaccatcag cagactggag    240

cctgaagatt ttgcagtgta ttactgtcag cagggtatta tgcttccccc gacgttcggc    300

caggggacca aagtggaaat caaa                                           324
```

<210> SEQ ID NO 127
<211> LENGTH: 117
<212> TYPE: PRT
<213> ORGANISM: Artificial Sequence
<220> FEATURE:
<223> OTHER INFORMATION: 20G8; VH

<400> SEQUENCE: 127

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ser Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115
```

<210> SEQ ID NO 128
<211> LENGTH: 351
<212> TYPE: DNA
<213> ORGANISM: Artificial Sequence
<220> FEATURE:
<223> OTHER INFORMATION: 20G8; VH

<400> SEQUENCE: 128

```
gaggtgcaat tgttggagtc tgggggaggc ttggtacagc ctggggggtc cctgagactc     60

tcctgtgcag cctccggatt cacctttagc agttatgcaa tgagctgggt ccgccaggct    120

ccagggaagg ggctggagtg ggtctcagct attattggga gtggtagtcg tacatactac    180

gcagactccg tgaagggccg gttcaccatc tccagagaca attccaagaa cacgctgtat    240

ctgcagatga acagcctgag agccgaggac acggccgtat attactgtgc gaaagggtgg    300

tttggtggtt ttaactactg gggccaagga accctggtca ccgtctcgtc c             351
```

<210> SEQ ID NO 129
<211> LENGTH: 108

```
<212> TYPE: PRT
<213> ORGANISM: Artificial Sequence
<220> FEATURE:
<223> OTHER INFORMATION: 4B9; VL

<400> SEQUENCE: 129

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105


<210> SEQ ID NO 130
<211> LENGTH: 324
<212> TYPE: DNA
<213> ORGANISM: Artificial Sequence
<220> FEATURE:
<223> OTHER INFORMATION: 4B9; VL

<400> SEQUENCE: 130

gaaatcgtgt taacgcagtc tccaggcacc ctgtctttgt ctccagggga aagagccacc      60

ctctcttgca gggccagtca gagtgttacc agtagctact tagcctggta ccagcagaaa     120

cctggccagg ctcccaggct cctcatcaat gtgggctccc gtagggccac tggcatccca     180

gacaggttca gtggcagtgg atccgggaca gacttcactc tcaccatcag cagactggag     240

cctgaagatt ttgcagtgta ttactgtcag cagggtatta tgcttccccc gacgttcggc     300

caggggacca aagtggaaat caaa                                            324


<210> SEQ ID NO 131
<211> LENGTH: 117
<212> TYPE: PRT
<213> ORGANISM: Artificial Sequence
<220> FEATURE:
<223> OTHER INFORMATION: 4B9; VH

<400> SEQUENCE: 131

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
```

```
            100                 105                 110

Val Thr Val Ser Ser
        115


<210> SEQ ID NO 132
<211> LENGTH: 351
<212> TYPE: DNA
<213> ORGANISM: Artificial Sequence
<220> FEATURE:
<223> OTHER INFORMATION: 4B9; VH

<400> SEQUENCE: 132

gaggtgcaat tgttggagtc tgggggaggc ttggtacagc ctggggggtc cctgagactc      60

tcctgtgcag cctccggatt cacctttagc agttatgcta tgagctgggt ccgccaggct     120

ccagggaagg ggctggagtg ggtctcagct attattggta gtggtgctag cacatactac     180

gcagactccg tgaagggccg gttcaccatc tccagagaca attccaagaa cacgctgtat     240

ctgcagatga acagcctgag agccgaggac acggccgtat attactgtgc gaaagggtgg     300

tttggtggtt ttaactactg gggccaagga accctggtca ccgtctcgtc c              351


<210> SEQ ID NO 133
<211> LENGTH: 108
<212> TYPE: PRT
<213> ORGANISM: Artificial Sequence
<220> FEATURE:
<223> OTHER INFORMATION: 5B8; VL

<400> SEQUENCE: 133

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105


<210> SEQ ID NO 134
<211> LENGTH: 324
<212> TYPE: DNA
<213> ORGANISM: Artificial Sequence
<220> FEATURE:
<223> OTHER INFORMATION: 5B8; VL

<400> SEQUENCE: 134

gaaatcgtgt taacgcagtc tccaggcacc ctgtctttgt ctccagggga aagagccacc      60

ctctcttgca gggccagtca gagtgttacc agtagctact tagcctggta ccagcagaaa     120

cctggccagg ctcccaggct cctcatcaat gtgggctccc gtagggccac tggcatccca     180

gacaggttca gtggcagtgg atccgggaca gacttcactc tcaccatcag cagactggag     240

cctgaagatt ttgcagtgta ttactgtcag cagggtatta tgcttccccc gacgttcggc     300

caggggacca aagtggaaat caaa                                            324
```

<210> SEQ ID NO 135
<211> LENGTH: 117
<212> TYPE: PRT
<213> ORGANISM: Artificial Sequence
<220> FEATURE:
<223> OTHER INFORMATION: 5B8; VH

<400> SEQUENCE: 135

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Trp Gly Gly Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 136
<211> LENGTH: 351
<212> TYPE: DNA
<213> ORGANISM: Artificial Sequence
<220> FEATURE:
<223> OTHER INFORMATION: 5B8; VH

<400> SEQUENCE: 136
gaggtgcaat tgttggagtc tgggggaggc ttggtacagc ctggggggtc cctgagactc      60
tcctgtgcag cctccggatt cacctttagc agttatgcta tgagctgggt ccgccaggct     120
ccagggaagg ggctggagtg ggtctcagct atttggggtg gtggtcgtag cacatactac     180
gcagactccg tgaagggccg gttcaccatc tccagagaca attccaagaa cacgctgtat     240
ctgcagatga acagcctgag agccgaggac acggccgtat attactgtgc gaaagggtgg     300
tttggtggtt ttaactactg gggccaagga accctggtca ccgtctcgtc c              351

<210> SEQ ID NO 137
<211> LENGTH: 108
<212> TYPE: PRT
<213> ORGANISM: Artificial Sequence
<220> FEATURE:
<223> OTHER INFORMATION: 5F1; VL

<400> SEQUENCE: 137

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

-continued

```
Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105
```

<210> SEQ ID NO 138
<211> LENGTH: 324
<212> TYPE: DNA
<213> ORGANISM: Artificial Sequence
<220> FEATURE:
<223> OTHER INFORMATION: 5F1; VL

<400> SEQUENCE: 138

```
gaaatcgtgt taacgcagtc tccaggcacc ctgtctttgt ctccagggga aagagccacc     60

ctctcttgca gggccagtca gagtgttacc agtagctact tagcctggta ccagcagaaa    120

cctggccagg ctcccaggct cctcatcaat gtgggctccc gtagggccac tggcatccca    180

gacaggttca gtggcagtgg atccgggaca gacttcactc tcaccatcag cagactggag    240

cctgaagatt ttgcagtgta ttactgtcag cagggtatta tgcttccccc gacgttcggc    300

caggggacca aagtggaaat caaa                                           324
```

<210> SEQ ID NO 139
<211> LENGTH: 117
<212> TYPE: PRT
<213> ORGANISM: Artificial Sequence
<220> FEATURE:
<223> OTHER INFORMATION: 5F1; VH

<400> SEQUENCE: 139

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Ser Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115
```

<210> SEQ ID NO 140
<211> LENGTH: 351
<212> TYPE: DNA
<213> ORGANISM: Artificial Sequence
<220> FEATURE:
<223> OTHER INFORMATION: 5F1; VH

<400> SEQUENCE: 140

```
gaggtgcaat tgttggagtc tgggggaggc ttggtacagc ctggggggtc cctgagactc     60

tcctgtgcag cctccggatt cacctttagc agttatgcta tgagctgggt ccgccaggct    120
```

```
ccagggaagg ggctggagtg ggtctcagct attattagta gtggggctag cacatactac    180

gcagactccg tgaagggccg gttcaccatc tccagagaca attccaagaa cacgctgtat    240

ctgcagatga acagcctgag agccgaggac acggccgtat attactgtgc gaaagggtgg    300

tttggtggtt ttaactactg gggccaagga accctggtca ccgtctcgtc c             351


<210> SEQ ID NO 141
<211> LENGTH: 108
<212> TYPE: PRT
<213> ORGANISM: Artificial Sequence
<220> FEATURE:
<223> OTHER INFORMATION: 14B3; VL

<400> SEQUENCE: 141

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105


<210> SEQ ID NO 142
<211> LENGTH: 324
<212> TYPE: DNA
<213> ORGANISM: Artificial Sequence
<220> FEATURE:
<223> OTHER INFORMATION: 14B3; VL

<400> SEQUENCE: 142

gaaatcgtgt taacgcagtc tccaggcacc ctgtctttgt ctccagggga aagagccacc     60

ctctcttgca gggccagtca gagtgttacc agtagctact tagcctggta ccagcagaaa    120

cctggccagg ctcccaggct cctcatcaat gtgggctccc gtagggccac tggcatccca    180

gacaggttca gtggcagtgg atccgggaca gacttcactc tcaccatcag cagactggag    240

cctgaagatt ttgcagtgta ttactgtcag cagggtatta tgcttccccc gacgttcggc    300

caggggacca aagtggaaat caaa                                           324


<210> SEQ ID NO 143
<211> LENGTH: 117
<212> TYPE: PRT
<213> ORGANISM: Artificial Sequence
<220> FEATURE:
<223> OTHER INFORMATION: 14B3; VH

<400> SEQUENCE: 143

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Leu Ala Ser Gly Ala Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115
```

<210> SEQ ID NO 144
<211> LENGTH: 351
<212> TYPE: DNA
<213> ORGANISM: Artificial Sequence
<220> FEATURE:
<223> OTHER INFORMATION: 14B3; VH

<400> SEQUENCE: 144

```
gaggtgcaat tgttggagtc tggggggaggc ttggtacagc ctggggggtc cctgagactc     60

tcctgtgcag cctccggatt cacctttagc agttatgcta tgagctgggt ccgccaggct    120

ccagggaagg ggctggagtg ggtctcagct attttggcta gtggtgcgat cacatactac    180

gcagactccg tgaagggccg gttcaccatc tccagagaca attccaagaa cacgctgtat    240

ctgcagatga acagcctgag agccgaggac acggccgtat attactgtgc gaaagggtgg    300

tttggtggtt ttaactactg gggccaagga accctggtca ccgtctcgtc c             351
```

<210> SEQ ID NO 145
<211> LENGTH: 108
<212> TYPE: PRT
<213> ORGANISM: Artificial Sequence
<220> FEATURE:
<223> OTHER INFORMATION: 16F1; VL

<400> SEQUENCE: 145

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105
```

<210> SEQ ID NO 146
<211> LENGTH: 324
<212> TYPE: DNA
<213> ORGANISM: Artificial Sequence
<220> FEATURE:
<223> OTHER INFORMATION: 16F1; VL

<400> SEQUENCE: 146

```
gaaatcgtgt taacgcagtc tccaggcacc ctgtctttgt ctccagggga aagagccacc      60

ctctcttgca gggccagtca gagtgttacc agtagctact tagcctggta ccagcagaaa     120

cctggccagg ctcccaggct cctcatcaat gtgggctccc gtagggccac tggcatccca     180

gacaggttca gtggcagtgg atccgggaca gacttcactc tcaccatcag cagactggag     240

cctgaagatt ttgcagtgta ttactgtcag cagggtatta tgcttccccc gacgttcggc     300

caggggacca aagtggaaat caaa                                            324
```

```
<210> SEQ ID NO 147
<211> LENGTH: 117
<212> TYPE: PRT
<213> ORGANISM: Artificial Sequence
<220> FEATURE:
<223> OTHER INFORMATION: 16F1; VH

<400> SEQUENCE: 147

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ile Gly Ser Gly Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115
```

```
<210> SEQ ID NO 148
<211> LENGTH: 351
<212> TYPE: DNA
<213> ORGANISM: Artificial Sequence
<220> FEATURE:
<223> OTHER INFORMATION: 16F1; VH

<400> SEQUENCE: 148

gaggtgcaat tgttggagtc tgggggaggc ttggtacagc ctggggggtc cctgagactc      60

tcctgtgcag cctccggatt cacctttagc agttatgcta tgagctgggt ccgccaggct     120

ccagggaagg ggctggagtg ggtctcaggt attattggta gtggtggtat cacatactac     180

gcagactccg tgaagggccg gttcaccatc tccagagaca attccaagaa cacgctgtat     240

ctgcagatga acagcctgag agccgaggac acggccgtat attactgtgc gaaagggtgg     300

tttggtggtt ttaactactg gggccaagga accctggtca ccgtctcgtc c              351
```

```
<210> SEQ ID NO 149
<211> LENGTH: 108
<212> TYPE: PRT
<213> ORGANISM: Artificial Sequence
<220> FEATURE:
<223> OTHER INFORMATION: 16F8; VL

<400> SEQUENCE: 149

Glu Ile Val Leu Thr Gln Ser Pro Gly Thr Leu Ser Leu Ser Pro Gly
```

-continued

```
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105
```

<210> SEQ ID NO 150
<211> LENGTH: 324
<212> TYPE: DNA
<213> ORGANISM: Artificial Sequence
<220> FEATURE:
<223> OTHER INFORMATION: 16F8; VL

<400> SEQUENCE: 150

```
gaaatcgtgt taacgcagtc tccaggcacc ctgtctttgt ctccagggga aagagccacc     60

ctctcttgca gggccagtca gagtgttacc agtagctact tagcctggta ccagcagaaa    120

cctggccagg ctcccaggct cctcatcaat gtgggctccc gtagggccac tggcatccca    180

gacaggttca gtggcagtgg atccgggaca gacttcactc tcaccatcag cagactggag    240

cctgaagatt ttgcagtgta ttactgtcag cagggtatta tgcttccccc gacgttcggc    300

caggggacca aagtggaaat caaa                                           324
```

<210> SEQ ID NO 151
<211> LENGTH: 117
<212> TYPE: PRT
<213> ORGANISM: Artificial Sequence
<220> FEATURE:
<223> OTHER INFORMATION: 16F8; VH

<400> SEQUENCE: 151

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Leu Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115
```

<210> SEQ ID NO 152
<211> LENGTH: 351

<212> TYPE: DNA
<213> ORGANISM: Artificial Sequence
<220> FEATURE:
<223> OTHER INFORMATION: 16F8; VH

<400> SEQUENCE: 152
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attcttggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaagggtgg 300
tttggtggtt ttaactactg gggccaagga accctggtca ccgtctcgtc c 351

<210> SEQ ID NO 153
<211> LENGTH: 108
<212> TYPE: PRT
<213> ORGANISM: Artificial Sequence
<220> FEATURE:
<223> OTHER INFORMATION: O3C9; VL

<400> SEQUENCE: 153

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Thr Ser Ser
20 25 30

Tyr Leu Ala Trp Tyr Gln Gln Lys Pro Gly Gln Ala Pro Arg Leu Leu
35 40 45

Ile Asn Val Gly Ser Arg Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Ile Met Leu Pro
85 90 95

Pro Thr Phe Gly Gln Gly Thr Lys Val Glu Ile Lys
100 105

<210> SEQ ID NO 154
<211> LENGTH: 324
<212> TYPE: DNA
<213> ORGANISM: Artificial Sequence
<220> FEATURE:
<223> OTHER INFORMATION: O3C9; VL

<400> SEQUENCE: 154
gaaatcgtgt taacgcagtc tccaggcacc ctgtctttgt ctccagggga aagagccacc 60
ctctcttgca gggccagtca gagtgttacc agtagctact tagcctggta ccagcagaaa 120
cctggccagg ctcccaggct cctcatcaat gtgggctccc gtagggccac tggcatccca 180
gacaggttca gtggcagtgg atccgggaca gacttcactc tcaccatcag cagactggag 240
cctgaagatt ttgcagtgta ttactgtcag cagggtatta tgcttccccc gacgttcggc 300
caggggacca aagtggaaat caaa 324

<210> SEQ ID NO 155
<211> LENGTH: 117
<212> TYPE: PRT
<213> ORGANISM: Artificial Sequence
<220> FEATURE:
<223> OTHER INFORMATION: O3C9; VH

<400> SEQUENCE: 155

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ser Pro Gly Lys Gly Leu Glu Trp Val
        35                  40                  45

Ser Ala Ile Ile Gly Ser Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115
```

<210> SEQ ID NO 156
<211> LENGTH: 351
<212> TYPE: DNA
<213> ORGANISM: Artificial Sequence
<220> FEATURE:
<223> OTHER INFORMATION: O3C9; VH

<400> SEQUENCE: 156

```
gaggtgcaat tgttggagtc tgggggaggc ttggtacagc ctggggggtc cctgagactc      60

tcctgtgcag cctccggatt cacctttagc agttttgcca tgagctgggt ccgtcagtct     120

ccagggaagg ggctggagtg ggtctcagct attattggta gtggtagtaa cacatactac     180

gcagactccg tgaagggccg gttcaccatc tccagagaca attccaagaa cacgctgtat     240

ctgcagatga acagcctgag agccgaggac acggccgtat attactgtgc gaaagggtgg     300

tttggtggtt ttaactactg gggccaagga accctggtca ccgtctcgtc c              351
```

<210> SEQ ID NO 157
<211> LENGTH: 108
<212> TYPE: PRT
<213> ORGANISM: Artificial Sequence
<220> FEATURE:
<223> OTHER INFORMATION: O2D7; VL

<400> SEQUENCE: 157

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Thr Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ala Ile Met Leu Pro
                85                  90                  95

Pro Thr Phe Gly Gln Gly Thr Lys Val Glu Ile Lys
            100                 105
```

<210> SEQ ID NO 158
<211> LENGTH: 324
<212> TYPE: DNA
<213> ORGANISM: Artificial Sequence
<220> FEATURE:
<223> OTHER INFORMATION: O2D7; VL

<400> SEQUENCE: 158
gaaatcgtgt taacgcagtc tccaggcacc ctgtctttgt ctccagggga aagagccacc 60
ctctcttgca gggccagtca gagtgttacc agtagctact tagcctggta ccagcagaaa 120
cctggccagg ctcccaggct cctcatcaat gtgggctccc gtagggccac tggcacccca 180
gacaggttca gtggcagtgg atccgggaca gacttcactc tcaccatcag cagactggag 240
cctgaagatt ttgcagtgta ttactgtcag caggctatta tgcttcctcc gacgttcggc 300
caggggacca aagtggaaat caaa 324

<210> SEQ ID NO 159
<211> LENGTH: 117
<212> TYPE: PRT
<213> ORGANISM: Artificial Sequence
<220> FEATURE:
<223> OTHER INFORMATION: O2D7; VH

<400> SEQUENCE: 159

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115

<210> SEQ ID NO 160
<211> LENGTH: 351
<212> TYPE: DNA
<213> ORGANISM: Artificial Sequence
<220> FEATURE:
<223> OTHER INFORMATION: O2D7; VH

<400> SEQUENCE: 160
gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaagggtgg 300
tttggtggtt ttaactactg gggccaagga accctggtca ccgtctcgtc c 351

<210> SEQ ID NO 161
<211> LENGTH: 108
<212> TYPE: PRT
<213> ORGANISM: Artificial Sequence
<220> FEATURE:
<223> OTHER INFORMATION: 28H1; VL

<400> SEQUENCE: 161

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105
```

<210> SEQ ID NO 162
<211> LENGTH: 324
<212> TYPE: DNA
<213> ORGANISM: Artificial Sequence
<220> FEATURE:
<223> OTHER INFORMATION: 28H1; VL

<400> SEQUENCE: 162

```
gaaatcgtgt taacgcagtc tccaggcacc ctgtctttgt ctccagggga aagagccacc      60

ctctcttgca gggccagtca gagtgttagc cgcagctact tagcctggta ccagcagaaa     120

cctggccagg ctcccaggct cctcatcatt ggggcctcca ccagggccac tggcatccca     180

gacaggttca gtggcagtgg atccgggaca gacttcactc tcaccatcag cagactggag     240

cctgaagatt ttgcagtgta ttactgtcag cagggtcagg ttattccccc tacgttcggc     300

caggggacca aagtggaaat caaa                                            324
```

<210> SEQ ID NO 163
<211> LENGTH: 116
<212> TYPE: PRT
<213> ORGANISM: Artificial Sequence
<220> FEATURE:
<223> OTHER INFORMATION: 28H1; VH

<400> SEQUENCE: 163

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ala Ile Trp Ala Ser Gly Glu Gln Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
```

```
                85                  90                  95

Lys Gly Trp Leu Gly Asn Phe Asp Tyr Trp Gly Gln Gly Thr Leu Val
            100                 105                 110

Thr Val Ser Ser
        115


<210> SEQ ID NO 164
<211> LENGTH: 348
<212> TYPE: DNA
<213> ORGANISM: Artificial Sequence
<220> FEATURE:
<223> OTHER INFORMATION: 28H1; VH

<400> SEQUENCE: 164

gaggtgcaat tgttggagtc tgggggaggc ttggtacagc ctggggggtc cctgagactc     60

tcctgtgcag cctccggatt cacctttagc agtcatgcta tgagctgggt ccgccaggct    120

ccagggaagg ggctggagtg ggtctcagct atttgggcta gtggggagca atactacgca    180

gactccgtga agggccggtt caccatctcc agagacaatt ccaagaacac gctgtatctg    240

cagatgaaca gcctgagagc cgaggacacg gccgtatatt actgtgcgaa agggtggctg    300

ggtaattttg actactgggg ccaaggaacc ctggtcaccg tctcgagt                 348


<210> SEQ ID NO 165
<211> LENGTH: 108
<212> TYPE: PRT
<213> ORGANISM: Artificial Sequence
<220> FEATURE:
<223> OTHER INFORMATION: 22A3; VL

<400> SEQUENCE: 165

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105


<210> SEQ ID NO 166
<211> LENGTH: 324
<212> TYPE: DNA
<213> ORGANISM: Artificial Sequence
<220> FEATURE:
<223> OTHER INFORMATION: 22A3; VL

<400> SEQUENCE: 166

gaaatcgtgt taacgcagtc tccaggcacc ctgtctttgt ctccagggga aagagccacc     60

ctctcttgca gggccagtca gagtgttacc agtagctact tagcctggta ccagcagaaa    120

cctggccagg ctcccaggct cctcatcaat gtgggctccc gtagggccac tggcatccca    180

gacaggttca gtggcagtgg atccgggaca gacttcactc tcaccatcag cagactggag    240
```

```
cctgaagatt ttgcagtgta ttactgtcag cagggtatta tgcttccccc gacgttcggc    300

caggggacca aagtggaaat caaa                                           324


<210> SEQ ID NO 167
<211> LENGTH: 117
<212> TYPE: PRT
<213> ORGANISM: Artificial Sequence
<220> FEATURE:
<223> OTHER INFORMATION: 22A3; VH

<400> SEQUENCE: 167

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ser Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115


<210> SEQ ID NO 168
<211> LENGTH: 351
<212> TYPE: DNA
<213> ORGANISM: Artificial Sequence
<220> FEATURE:
<223> OTHER INFORMATION: 22A3; VH

<400> SEQUENCE: 168

gaggtgcaat tgttggagtc tgggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attattggta gtggtagtat cacatactac    180

gcagactccg tgaagggccg gttcaccatc tccagagaca attccaagaa cacgctgtat    240

ctgcagatga acagcctgag agccgaggac acggccgtat attactgtgc gaaagggtgg    300

tttggtggtt ttaactactg gggccaagga accctggtca ccgtctcgag t             351


<210> SEQ ID NO 169
<211> LENGTH: 108
<212> TYPE: PRT
<213> ORGANISM: Artificial Sequence
<220> FEATURE:
<223> OTHER INFORMATION: 29B11; VL

<400> SEQUENCE: 169

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45
```

-continued

```
Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys
            100                 105
```

<210> SEQ ID NO 170
<211> LENGTH: 324
<212> TYPE: DNA
<213> ORGANISM: Artificial Sequence
<220> FEATURE:
<223> OTHER INFORMATION: 29B11; VL

<400> SEQUENCE: 170

```
gaaatcgtgt taacgcagtc tccaggcacc ctgtctttgt ctccagggga aagagccacc      60

ctctcttgca gggccagtca gagtgttacc agtagctact tagcctggta ccagcagaaa     120

cctggccagg ctcccaggct cctcatcaat gtgggctccc gtagggccac tggcatccca     180

gacaggttca gtggcagtgg atccgggaca gacttcactc tcaccatcag cagactggag     240

cctgaagatt ttgcagtgta ttactgtcag cagggtatta tgcttccccc gacgttcggc     300

caggggacca aagtggaaat caaa                                            324
```

<210> SEQ ID NO 171
<211> LENGTH: 117
<212> TYPE: PRT
<213> ORGANISM: Artificial Sequence
<220> FEATURE:
<223> OTHER INFORMATION: 29B11; VH

<400> SEQUENCE: 171

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser
        115
```

<210> SEQ ID NO 172
<211> LENGTH: 351
<212> TYPE: DNA
<213> ORGANISM: Artificial Sequence
<220> FEATURE:
<223> OTHER INFORMATION: 29B11; VH

<400> SEQUENCE: 172

```
gaggtgcaat tgttggagtc tgggggaggc ttggtacagc ctggggggtc cctgagactc      60
```

```
tcctgtgcag cctccggatt cacctttagc agttatgcta tgagctgggt ccgccaggct    120

ccagggaagg ggctggagtg ggtctcagct attattggta gtggtggtat cacatactac    180

gcagactccg tgaagggccg gttcaccatc tccagagaca attccaagaa cacgctgtat    240

ctgcagatga acagcctgag agccgaggac acggccgtat attactgtgc gaaagggtgg    300

tttggtggtt ttaactactg gggccaagga accctggtca ccgtctcgag t             351
```

<210> SEQ ID NO 173
<211> LENGTH: 108
<212> TYPE: PRT
<213> ORGANISM: Artificial Sequence
<220> FEATURE:
<223> OTHER INFORMATION: 23C10; VL

<400> SEQUENCE: 173

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys
            100                 105
```

<210> SEQ ID NO 174
<211> LENGTH: 324
<212> TYPE: DNA
<213> ORGANISM: Artificial Sequence
<220> FEATURE:
<223> OTHER INFORMATION: 23C10; VL

<400> SEQUENCE: 174

```
gaaatcgtgt taacgcagtc tccaggcacc ctgtctttgt ctccagggga aagagccacc     60

ctctcttgca gggccagtca gagtgttagc cgcagctact tagcctggta ccagcagaaa    120

cctggccagg ctcccaggct cctcatcatt ggggcctcca ccagggccac tggcatccca    180

gacaggttca gtggcagtgg atccgggaca gacttcactc tcaccatcag cagactggag    240

cctgaagatt ttgcagtgta ttactgtcag cagggtcagg ttattccccc tacgttcggc    300

caggggacca aagtggaaat caaa                                           324
```

<210> SEQ ID NO 175
<211> LENGTH: 117
<212> TYPE: PRT
<213> ORGANISM: Artificial Sequence
<220> FEATURE:
<223> OTHER INFORMATION: 23C10; VH

<400> SEQUENCE: 175

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ser
            20                  25                  30
```

-continued

Ala Met Ser Trp Val Arg Gln Ala Pro Gly Lys Gly Leu Glu Trp Val
35 40 45

Ser Ala Ile Ser Thr Asn Gly Asn Tyr Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Trp Leu Gly Asn Phe Asp Tyr Trp Gly Gln Gly Thr Leu
100 105 110

Val Thr Val Ser Ser
115

<210> SEQ ID NO 176
<211> LENGTH: 351
<212> TYPE: DNA
<213> ORGANISM: Artificial Sequence
<220> FEATURE:
<223> OTHER INFORMATION: 23C10; VH

<400> SEQUENCE: 176
gaggtgcaat tgttggagtc tgggggaggc ttggtacagc ctggggggtc cctgagactc 60
tcctgtgcag cctccggatt cacctttagc agttctgcca tgagctgggt ccgccaggct 120
ccagggaagg ggctggagtg ggtctcagct attagtacta atggtaatta tacatactac 180
gcagactccg tgaagggccg gttcaccatc tccagagaca attccaagaa cacgctgtat 240
ctgcagatga acagcctgag agccgaggac acggccgtat attactgtgc gaaagggtgg 300
ctgggtaatt ttgactactg gggccaagga accctggtca ccgtctcgag t 351

<210> SEQ ID NO 177
<211> LENGTH: 107
<212> TYPE: PRT
<213> ORGANISM: Artificial Sequence
<220> FEATURE:
<223> OTHER INFORMATION: 2B10_C3B6; VL

<400> SEQUENCE: 177

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Asn Asp
20 25 30

Leu Gly Trp Tyr Gln Gln Lys Pro Gly Lys Ala Pro Lys Arg Leu Ile
35 40 45

Tyr Ala Ala Ser Ser Leu Gln Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Leu Gln Asn Gly Leu Gln Pro Ala
85 90 95

Thr Phe Gly Gln Gly Thr Lys Val Glu Ile Lys
100 105

<210> SEQ ID NO 178
<211> LENGTH: 321
<212> TYPE: DNA
<213> ORGANISM: Artificial Sequence
<220> FEATURE:
<223> OTHER INFORMATION: 2B10_C3B6; VL

<400> SEQUENCE: 178

```
gatatccaga tgacccagtc tccatcctcc ctgtctgcat ctgtcggaga ccgggtcacc      60

atcacctgcc gggcaagtca gggcattaga aatgatttag gctggtacca gcagaagcca     120

gggaaagccc ctaagcgcct gatctatgct gcatccagtt tgcagagtgg cgtcccatca     180

aggttcagcg gcagtggatc cgggacagag ttcactctca ccatcagcag cttgcagcct     240

gaagattttg ccacctatta ctgcttgcag aatggtctgc agcccgcgac gtttggccag     300

ggcaccaaag tcgagatcaa g                                               321
```

<210> SEQ ID NO 179
<211> LENGTH: 121
<212> TYPE: PRT
<213> ORGANISM: Artificial Sequence
<220> FEATURE:
<223> OTHER INFORMATION: 2B10_C3B6; VH

<400> SEQUENCE: 179

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ala Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120
```

<210> SEQ ID NO 180
<211> LENGTH: 363
<212> TYPE: DNA
<213> ORGANISM: Artificial Sequence
<220> FEATURE:
<223> OTHER INFORMATION: 2B10_C3B6; VH

<400> SEQUENCE: 180

```
caggtgcaat tggtgcagtc tggggctgag gtgaagaagc ctgggtcctc ggtgaaggtc      60

tcctgcaagg cctccggagg cacattcagc agctacgcta taagctgggt gcgacaggcc     120

cctggacaag ggctcgagtg gatgggagct atcatcccga tccttggtat cgcaaactac     180

gcacagaagt tccagggcag ggtcaccatt actgcagaca aatccacgag cacagcctac     240

atggagctga gcagcctgag atctgaggac accgccgtgt attactgtgc gagactgtac     300

ggttacgctt actacggtgc ttttgactac tggggccaag ggaccaccgt gaccgtctcc     360

tca                                                                   363
```

<210> SEQ ID NO 181
<211> LENGTH: 107
<212> TYPE: PRT
<213> ORGANISM: Artificial Sequence
<220> FEATURE:

<223> OTHER INFORMATION: 2B10_6A12; VL

<400> SEQUENCE: 181

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105
```

<210> SEQ ID NO 182
<211> LENGTH: 321
<212> TYPE: DNA
<213> ORGANISM: Artificial Sequence
<220> FEATURE:
<223> OTHER INFORMATION: 2B10_6A12; VL

<400> SEQUENCE: 182

```
gatatccaga tgacccagtc tccatcctcc ctgtctgcat ctgtcggaga ccgggtcacc      60

atcacctgcc gggcaagtca gggcattaga aatgatttag gctggtacca gcagaagcca     120

gggaaagccc ctaagcgcct gatctatgct gcatccagtt tgcagagtgg cgtcccatca     180

aggttcagcg gcagtggatc cgggacagag ttcactctca ccatcagcag cttgcagcct     240

gaagattttg ccacctatta ctgcttgcag aatggtctgc agcccgcgac gtttggccag     300

ggcaccaaag tcgagatcaa g                                               321
```

<210> SEQ ID NO 183
<211> LENGTH: 121
<212> TYPE: PRT
<213> ORGANISM: Artificial Sequence
<220> FEATURE:
<223> OTHER INFORMATION: 2B10_6A12; VH

<400> SEQUENCE: 183

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Val Ile Ile Pro Ile Leu Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
```

115 120

<210> SEQ ID NO 184
<211> LENGTH: 363
<212> TYPE: DNA
<213> ORGANISM: Artificial Sequence
<220> FEATURE:
<223> OTHER INFORMATION: 2B10_6A12; VH

<400> SEQUENCE: 184
caggtgcaat tggtgcagtc tggggctgag gtgaagaagc ctgggtcctc ggtgaaggtc 60
tcctgcaagg cctccggagg cacattcagc agctatgcta taagctgggt gcgacaggcc 120
cctggacaag ggctcgagtg gatgggagtg atcatcccta tccttggtac cgcaaactac 180
gcacagaagt tccagggcag ggtcaccatt actgcagaca aatccacgag cacagcctac 240
atggagctga gcagcctgag atctgaggac accgccgtgt attactgtgc gagactgtac 300
ggttacgctt actacggtgc ttttgactac tggggccaag ggaccaccgt gaccgtctcc 360
tca 363

<210> SEQ ID NO 185
<211> LENGTH: 107
<212> TYPE: PRT
<213> ORGANISM: Artificial Sequence
<220> FEATURE:
<223> OTHER INFORMATION: 2B10_C3A6; VL

<400> SEQUENCE: 185

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Asn Val
20 25 30

Leu Gly Trp Tyr Gln Gln Lys Pro Gly Lys Ala Pro Lys Arg Leu Ile
35 40 45

Tyr Asp Ser Ser Ser Leu Gln Ser Gly Val Pro Ser Arg Phe Ser Gly
50 55 60

Gly Gly Ser Gly Thr Glu Phe Thr Leu Thr Ile Ser Ser Leu Gln Pro
65 70 75 80

Glu Asp Phe Ala Thr Tyr Tyr Cys Leu Gln Asn Gly Leu Gln Pro Ala
85 90 95

Thr Phe Gly Gln Gly Thr Lys Val Glu Ile Lys
100 105

<210> SEQ ID NO 186
<211> LENGTH: 321
<212> TYPE: DNA
<213> ORGANISM: Artificial Sequence
<220> FEATURE:
<223> OTHER INFORMATION: 2B10_C3A6; VL

<400> SEQUENCE: 186
gacatccaga tgacccagtc tccttcctcc ctgtctgcat ctgtcggaga ccgggtcacc 60
atcacctgcc gggcaagtca gggcattcgt aatgttttag gctggtacca gcagaagcca 120
gggaaagccc ctaagcgcct gatctatgat tcgtccagtt tgcagagtgg cgtcccatca 180
aggttcagcg gcggtggatc cgggacagag ttcactctca ccatcagcag cttgcagcct 240
gaagattttg ccacctatta ctgcttgcag aatggtctgc agcccgcgac gtttggccag 300
ggcaccaaag tcgagatcaa g 321

<210> SEQ ID NO 187
<211> LENGTH: 121
<212> TYPE: PRT
<213> ORGANISM: Artificial Sequence
<220> FEATURE:
<223> OTHER INFORMATION: 2B10_C3A6; VH

<400> SEQUENCE: 187

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120
```

<210> SEQ ID NO 188
<211> LENGTH: 363
<212> TYPE: DNA
<213> ORGANISM: Artificial Sequence
<220> FEATURE:
<223> OTHER INFORMATION: 2B10_C3A6; VH

<400> SEQUENCE: 188

```
caggtgcaat tggtgcagtc tggggctgag gtgaagaagc ctgggtcctc ggtgaaggtc      60

tcctgcaagg cctccggagg cacattcagc agctacgcta taagctgggt gcgacaggcc     120

cctggacaag ggctcgagtg gatgggaggg atcatcccta tctttggtac agcaaactac     180

gcacagaagt tccagggcag ggtcaccatt actgcagaca aatccacgag cacagcctac     240

atggagctga gcagcctgag atctgaggac accgccgtgt attactgtgc gagactgtac     300

ggttacgctt actacggtgc ttttgactac tggggccaag ggaccaccgt gaccgtctcc     360

tca                                                                   363
```

<210> SEQ ID NO 189
<211> LENGTH: 107
<212> TYPE: PRT
<213> ORGANISM: Artificial Sequence
<220> FEATURE:
<223> OTHER INFORMATION: 2B10_D1A2_wt; VL

<400> SEQUENCE: 189

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Val
            20                  25                  30

Leu Gly Trp Tyr Gln Gln Lys Pro Gly Lys Ala Pro Lys Arg Leu Ile
        35                  40                  45

Tyr Asp Ala Tyr Ser Leu Gln Ser Gly Val Pro Ser Arg Phe Ser Gly
    50                  55                  60
```

Gly Gly Ser Gly Thr Glu Phe Thr Leu Thr Ile Ser Ser Leu Gln Pro
65 70 75 80

Glu Asp Phe Ala Thr Tyr Tyr Cys Leu Gln Asn Gly Leu Gln Pro Ala
85 90 95

Thr Phe Gly Gln Gly Thr Lys Val Glu Ile Lys
100 105

<210> SEQ ID NO 190
<211> LENGTH: 321
<212> TYPE: DNA
<213> ORGANISM: Artificial Sequence
<220> FEATURE:
<223> OTHER INFORMATION: 2B10_D1A2_wt; VL

<400> SEQUENCE: 190
gatatccaga tgacccagtc tccatcctcc ctgtctgcat ctgtcggaga ccgggtcacc 60
atcacctgcc gggcaagtca ggggattcgt aatgttttag gctggtacca gcagaagcca 120
gggaaagccc ctaagcgcct gatctatgat gcttacagct tgcagagtgg cgtcccatca 180
aggttcagcg gcggtggatc cgggacagag ttcactctca ccatcagcag cttgcagcct 240
gaagattttg ccacctatta ctgcttgcag aatggtctgc agcccgcgac gtttggccag 300
ggcaccaaag tcgagatcaa g 321

<210> SEQ ID NO 191
<211> LENGTH: 121
<212> TYPE: PRT
<213> ORGANISM: Artificial Sequence
<220> FEATURE:
<223> OTHER INFORMATION: 2B10_D1A2_wt; VH

<400> SEQUENCE: 191

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Leu Tyr Gly Tyr Ala Tyr Tyr Gly Ala Phe Asp Tyr Trp Gly
100 105 110

Gln Gly Thr Thr Val Thr Val Ser Ser
115 120

<210> SEQ ID NO 192
<211> LENGTH: 363
<212> TYPE: DNA
<213> ORGANISM: Artificial Sequence
<220> FEATURE:
<223> OTHER INFORMATION: 2B10_D1A2_wt; VH

<400> SEQUENCE: 192
caggtgcaat tggtgcagtc tggggctgag gtgaagaagc ctgggtcctc ggtgaaggtc 60
tcctgcaagg cctccggagg cacattcagc agctacgcta taagctgggt gcgacaggcc 120

-continued

```
cctggacaag ggctcgagtg gatgggaggg atcatcccta tctttggtac agcaaactac    180

gcacagaagt tccagggcag ggtcaccatt actgcagaca aatccacgag cacagcctac    240

atggagctga gcagcctgag atctgaggac accgccgtgt attactgtgc gagactgtac    300

ggttacgctt actacggtgc ttttgactac tggggccaag ggaccaccgt gaccgtctcc    360

tca                                                                  363
```

```
<210> SEQ ID NO 193
<211> LENGTH: 107
<212> TYPE: PRT
<213> ORGANISM: Artificial Sequence
<220> FEATURE:
<223> OTHER INFORMATION: 2B10_D1A2_VD; VL

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Asp Ala Tyr Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105
```

```
<210> SEQ ID NO 194
<211> LENGTH: 321
<212> TYPE: DNA
<213> ORGANISM: Artificial Sequence
<220> FEATURE:
<223> OTHER INFORMATION: 2B10_D1A2_VD; VL

<400> SEQUENCE: 194

gacatccaga tgacccagtc tccatcctcc ctgtctgcat ctgtcggaga ccgggtcacc     60

atcacctgcc gggcaagtca ggggattcgt aatgatttag gctggtacca gcagaagcca    120

gggaaagccc ctaagcgcct gatctatgat gcttacagct tgcagagtgg cgtcccatca    180

aggttcagcg gcggtggatc cgggacagag ttcactctca ccatcagcag cttgcagcct    240

gaagattttg ccacctatta ctgcttgcag aatggtctgc agcccgcgac gtttggccag    300

ggcaccaaag tcgagatcaa g                                              321
```

```
<210> SEQ ID NO 195
<211> LENGTH: 121
<212> TYPE: PRT
<213> ORGANISM: Artificial Sequence
<220> FEATURE:
<223> OTHER INFORMATION: 2B10_D1A2_VD; VH

<400> SEQUENCE: 195

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30
```

```
Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser
        115                 120
```

```
<210> SEQ ID NO 196
<211> LENGTH: 363
<212> TYPE: DNA
<213> ORGANISM: Artificial Sequence
<220> FEATURE:
<223> OTHER INFORMATION: 2B10_D1A2_VD; VH

<400> SEQUENCE: 196

caggtgcaat tggtgcagtc tggggctgag gtgaagaagc ctgggtcctc ggtgaaggtc     60

tcctgcaagg cctccggagg cacattcagc agctacgcta taagctgggt gcgacaggcc    120

cctggacaag ggctcgagtg gatgggaggg atcatcccta tctttggtac agcaaactac    180

gcacagaagt tccagggcag ggtcaccatt actgcagaca aatccacgag cacagcctac    240

atggagctga gcagcctgag atctgaggac accgccgtgt attactgtgc gagactgtac    300

ggttacgctt actacggtgc ttttgactac tggggccaag ggaccaccgt gaccgtctcc    360

tca                                                                   363
```

```
<210> SEQ ID NO 197
<211> LENGTH: 107
<212> TYPE: PRT
<213> ORGANISM: Artificial Sequence
<220> FEATURE:
<223> OTHER INFORMATION: 2B10_O7D8; VL

<400> SEQUENCE: 197

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Asn Val
            20                  25                  30

Leu Gly Trp Tyr Gln Gln Lys Pro Gly Lys Ala Pro Lys Arg Leu Ile
        35                  40                  45

Tyr Asp Val Ser Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105
```

```
<210> SEQ ID NO 198
<211> LENGTH: 321
<212> TYPE: DNA
<213> ORGANISM: Artificial Sequence
```

<220> FEATURE:
<223> OTHER INFORMATION: 2B10_O7D8; VL

<400> SEQUENCE: 198
gatatccaga tgacccagtc tccatcctcc ctgtctgcat ctgtcggaga ccgggtcacc 60
atcacctgcc gggcaagtca gagcattcgt aatgttttag gctggtacca gcagaagcca 120
gggaaagccc ctaagcgcct gatctatgat gtgtccagtt tgcagagtgg cgtcccatca 180
aggttcagcg gcggtggatc cgggacagag ttcactctca ccatcagcag cttgcagcct 240
gaagattttg ccacctatta ctgcttgcag aatggtctgc agcccgcgac gtttggccag 300
ggcaccaaag tcgagatcaa g 321

<210> SEQ ID NO 199
<211> LENGTH: 121
<212> TYPE: PRT
<213> ORGANISM: Artificial Sequence
<220> FEATURE:
<223> OTHER INFORMATION: 2B10_O7D8; VH

<400> SEQUENCE: 199

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Leu Tyr Gly Tyr Ala Tyr Tyr Gly Ala Phe Asp Tyr Trp Gly
100 105 110

Gln Gly Thr Thr Val Thr Val Ser Ser
115 120

<210> SEQ ID NO 200
<211> LENGTH: 363
<212> TYPE: DNA
<213> ORGANISM: Artificial Sequence
<220> FEATURE:
<223> OTHER INFORMATION: 2B10_O7D8; VH

<400> SEQUENCE: 200
caggtgcaat tggtgcagtc tggggctgag gtgaagaagc ctgggtcctc ggtgaaggtc 60
tcctgcaagg cctccggagg cacattcagc agctacgcta taagctgggt gcgacaggcc 120
cctggacaag ggctcgagtg gatgggaggg atcatcccta tctttggtac agcaaactac 180
gcacagaagt tccagggcag ggtcaccatt actgcagaca aatccacgag cacagcctac 240
atggagctga gcagcctgag atctgaggac accgccgtgt attactgtgc gagactgtac 300
ggttacgctt actacggtgc ttttgactac tggggccaag ggaccaccgt gaccgtctcc 360
tca 363

<210> SEQ ID NO 201
<211> LENGTH: 107
<212> TYPE: PRT

```
<213> ORGANISM: Artificial Sequence
<220> FEATURE:
<223> OTHER INFORMATION: 2B10_O1F7; VL

<400> SEQUENCE: 201

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Val
            20                  25                  30

Leu Gly Trp Tyr Gln Gln Lys Pro Gly Lys Ala Pro Lys Arg Leu Ile
        35                  40                  45

Tyr Asp Ala Ser Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105


<210> SEQ ID NO 202
<211> LENGTH: 321
<212> TYPE: DNA
<213> ORGANISM: Artificial Sequence
<220> FEATURE:
<223> OTHER INFORMATION: 2B10_O1F7; VL

<400> SEQUENCE: 202

gatatccaga tgacccagtc tccatcctcc ctgtctgcat ctgtcggaga ccgggtcacc     60

atcacctgcc gggcaagtca gggcattcgt aatgttttag gctggtacca gcagaagcca    120

gggaaagccc ctaagcgcct gatctatgat gcgtccagtt tgcagagtgg cgtcccatca    180

aggttcagcg gcggtggatc cgggacagag ttcactctca ccatcagcag cttgcagcct    240

gaagattttg ccacctatta ctgcctgcag aatggtctgc agcccgcgac gtttggccag    300

ggcaccaaag tcgagatcaa g                                              321


<210> SEQ ID NO 203
<211> LENGTH: 121
<212> TYPE: PRT
<213> ORGANISM: Artificial Sequence
<220> FEATURE:
<223> OTHER INFORMATION: 2B10_O1F7; VH

<400> SEQUENCE: 203

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110
```

```
Gln Gly Thr Thr Val Thr Val Ser Ser
        115                 120


<210> SEQ ID NO 204
<211> LENGTH: 363
<212> TYPE: DNA
<213> ORGANISM: Artificial Sequence
<220> FEATURE:
<223> OTHER INFORMATION: 2B10_O1F7; VH

<400> SEQUENCE: 204

caggtgcaat tggtgcagtc tggggctgag gtgaagaagc ctgggtcctc ggtgaaggtc     60

tcctgcaagg cctccggagg cacattcagc agctacgcta taagctgggt gcgacaggcc    120

cctggacaag ggctcgagtg gatgggaggg atcatcccta tctttggtac agcaaactac    180

gcacagaagt tccagggcag ggtcaccatt actgcagaca aatccacgag cacagcctac    240

atggagctga gcagcctgag atctgaggac accgccgtgt attactgtgc gagactgtac    300

ggttacgctt actacggtgc ttttgactac tggggccaag ggaccaccgt gaccgtctcc    360

tca                                                                   363


<210> SEQ ID NO 205
<211> LENGTH: 107
<212> TYPE: PRT
<213> ORGANISM: Artificial Sequence
<220> FEATURE:
<223> OTHER INFORMATION: 2B10_6H10; VL

<400> SEQUENCE: 205

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Val
            20                  25                  30

Leu Gly Trp Tyr Gln Gln Lys Pro Gly Lys Ala Pro Lys Arg Leu Ile
        35                  40                  45

Gln Ala Ala Thr Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys
            100                 105


<210> SEQ ID NO 206
<211> LENGTH: 321
<212> TYPE: DNA
<213> ORGANISM: Artificial Sequence
<220> FEATURE:
<223> OTHER INFORMATION: 2B10_6H10; VL

<400> SEQUENCE: 206

gacatccaga tgacccagtc tccatcctcc ctgtctgcat ctgtcggaga ccgggtcacc     60

atcacctgcc gggcaagtca gggcattcgt aatgttttag gctggtacca gcagaagcca    120

gggaaagccc ctaagcgcct gatccaggct gctaccagtt tgcagagtgg cgtcccatca    180

aggttcagcg gcggtggatc cgggacagag ttcactctca ccatcagcag cttgcagcct    240

gaagattttg ccacctatta ctgcttgcag aatggtctgc agcccgcgac gtttggccag    300
```

-continued ggcaccaaag tcgagatcaa g 321

<210> SEQ ID NO 207
<211> LENGTH: 121
<212> TYPE: PRT
<213> ORGANISM: Artificial Sequence
<220> FEATURE:
<223> OTHER INFORMATION: 2B10_6H10; VH

<400> SEQUENCE: 207

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Gly Ile Ile Pro Ile Phe Gly Thr Ala Asn Tyr Ala Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Leu Tyr Gly Tyr Ala Tyr Tyr Gly Ala Phe Asp Tyr Trp Gly
100 105 110

Gln Gly Thr Thr Val Thr Val Ser Ser
115 120

<210> SEQ ID NO 208
<211> LENGTH: 363
<212> TYPE: DNA
<213> ORGANISM: Artificial Sequence
<220> FEATURE:
<223> OTHER INFORMATION: 2B10_6H10; VH

<400> SEQUENCE: 208
caggtgcaat tggtgcagtc tggggctgag gtgaagaagc ctgggtcctc ggtgaaggtc 60
tcctgcaagg cctccggagg cacattcagc agctacgcta taagctgggt gcgacaggcc 120
cctggacaag ggctcgagtg gatgggaggg atcatcccta tctttggtac agcaaactac 180
gcacagaagt tccagggcag ggtcaccatt actgcagaca aatccacgag cacagcctac 240
atggagctga gcagcctgag atctgaggac accgccgtgt attactgtgc gagactgtac 300
ggttacgctt actacggtgc ttttgactac tggggccaag ggaccaccgt gaccgtctcc 360
tca 363

<210> SEQ ID NO 209
<211> LENGTH: 605
<212> TYPE: PRT
<213> ORGANISM: Artificial Sequence
<220> FEATURE:
<223> OTHER INFORMATION: 3F2 Fab-IL2-Fab (heavy chain cytokine fusion construct)

<400> SEQUENCE: 209

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

-continued

```
Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Ser Gly Gly
    210                 215                 220

Gly Gly Ser Gly Gly Gly Gly Ser Gly Gly Gly Gly Ala Pro Thr Ser
225                 230                 235                 240

Ser Ser Thr Lys Lys Thr Gln Leu Gln Leu Glu His Leu Leu Leu Asp
                245                 250                 255

Leu Gln Met Ile Leu Asn Gly Ile Asn Asn Tyr Lys Asn Pro Lys Leu
            260                 265                 270

Thr Arg Met Leu Thr Phe Lys Phe Tyr Met Pro Lys Lys Ala Thr Glu
        275                 280                 285

Leu Lys His Leu Gln Cys Leu Glu Glu Glu Leu Lys Pro Leu Glu Glu
    290                 295                 300

Val Leu Asn Leu Ala Gln Ser Lys Asn Phe His Leu Arg Pro Arg Asp
305                 310                 315                 320

Leu Ile Ser Asn Ile Asn Val Ile Val Leu Glu Leu Lys Gly Ser Glu
                325                 330                 335

Thr Thr Phe Met Cys Glu Tyr Ala Asp Glu Thr Ala Thr Ile Val Glu
            340                 345                 350

Phe Leu Asn Arg Trp Ile Thr Phe Ala Gln Ser Ile Ile Ser Thr Leu
        355                 360                 365

Thr Ser Gly Gly Gly Gly Ser Gly Gly Gly Gly Ser Gly Gly Gly Gly
    370                 375                 380

Glu Val Gln Leu Leu Glu Ser Gly Gly Gly Leu Val Gln Pro Gly Gly
385                 390                 395                 400

Ser Leu Arg Leu Ser Cys Ala Ala Ser Gly Phe Thr Phe Ser Ser Tyr
                405                 410                 415

Ala Met Ser Trp Val Arg Gln Ala Pro Gly Lys Gly Leu Glu Trp Val
            420                 425                 430

Ser Ala Ile Ser Gly Ser Gly Gly Ser Thr Tyr Tyr Ala Asp Ser Val
        435                 440                 445

Lys Gly Arg Phe Thr Ile Ser Arg Asp Asn Ser Lys Asn Thr Leu Tyr
    450                 455                 460
```

Leu Gln Met Asn Ser Leu Arg Ala Glu Asp Thr Ala Val Tyr Tyr Cys
465 470 475 480

Ala Lys Gly Trp Phe Gly Gly Phe Asn Tyr Trp Gly Gln Gly Thr Leu
485 490 495

Val Thr Val Ser Ser Ala Ser Thr Lys Gly Pro Ser Val Phe Pro Leu
500 505 510

Ala Pro Ser Ser Lys Ser Thr Ser Gly Gly Thr Ala Ala Leu Gly Cys
515 520 525

Leu Val Lys Asp Tyr Phe Pro Glu Pro Val Thr Val Ser Trp Asn Ser
530 535 540

Gly Ala Leu Thr Ser Gly Val His Thr Phe Pro Ala Val Leu Gln Ser
545 550 555 560

Ser Gly Leu Tyr Ser Leu Ser Ser Val Val Thr Val Pro Ser Ser Ser
565 570 575

Leu Gly Thr Gln Thr Tyr Ile Cys Asn Val Asn His Lys Pro Ser Asn
580 585 590

Thr Lys Val Asp Lys Lys Val Glu Pro Lys Ser Cys Asp
595 600 605

<210> SEQ ID NO 210
<211> LENGTH: 1818
<212> TYPE: DNA
<213> ORGANISM: Artificial Sequence
<220> FEATURE:
<223> OTHER INFORMATION: 3F2 Fab-IL2-Fab (heavy chain cytokine fusion construct)

<400> SEQUENCE: 210
gaggtgcaat tgttggagtc tggggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac acggccgtat attactgtgc gaaagggtgg 300
tttggtggtt ttaactactg gggccaagga accctggtca ccgtctcgag tgctagcacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggataaga aagttgagcc caaatcttgt 660
gactccggcg gaggagggag cggcggaggt ggctccggag gtggcggagc acctacttca 720
agttctacaa agaaaacaca gctacaactg gagcatttac tgctggattt acagatgatt 780
ttgaatggaa ttaataatta caagaatccc aaactcacca ggatgctcac atttaagttt 840
tacatgccca agaaggccac agaactgaaa catcttcagt gtctagaaga agaactcaaa 900
cctctggagg aagtgctaaa tttagctcaa agcaaaaact ttcacttaag acccagggac 960
ttaatcagca atatcaacgt aatagttctg gaactaaagg gatctgaaac aacattcatg 1020
tgtgaatatg ctgatgagac agcaaccatt gtagaatttc tgaacagatg gattaccttt 1080
gcccaaagca tcatctcaac actgacttcc ggcggaggag gatccggcgg aggtggctct 1140
ggcggtggcg gagaggtgca attgttggag tctgggggag gcttggtaca gcctgggggg 1200
tccctgagac tctcctgtgc agcctccgga ttcaccttta gcagttatgc catgagctgg 1260

```
gtccgccagg ctccagggaa ggggctggag tgggtctcag ctattagtgg tagtggtggt   1320

agcacatact acgcagactc cgtgaagggc cggttcacca tctccagaga caattccaag   1380

aacacgctgt atctgcagat gaacagcctg agagccgagg acacggccgt atattactgt   1440

gcgaaagggt ggtttggtgg ttttaactac tggggccaag gaaccctggt caccgtctcg   1500

agtgctagca ccaagggccc atcggtcttc cccctggcac cctcctccaa gagcacctct   1560

gggggcacag cggccctggg ctgcctggtc aaggactact tccccgaacc ggtgacggtg   1620

tcgtggaact caggcgccct gaccagcggc gtgcacacct tcccggctgt cctacagtcc   1680

tcaggactct actccctcag cagcgtggtg accgtgccct ccagcagctt gggcacccag   1740

acctacatct gcaacgtgaa tcacaagccc agcaacacca aggtggataa gaaagttgag   1800

cccaaatctt gtgactga                                                 1818
```

<210> SEQ ID NO 211
<211> LENGTH: 605
<212> TYPE: PRT
<213> ORGANISM: Artificial Sequence
<220> FEATURE:
<223> OTHER INFORMATION: 4G8 Fab-IL2-Fab (heavy chain cytokine fusion construct)

<400> SEQUENCE: 211

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Ser Gly Gly
    210                 215                 220

Gly Gly Ser Gly Gly Gly Gly Ser Gly Gly Gly Gly Ala Pro Thr Ser
225                 230                 235                 240

Ser Ser Thr Lys Lys Thr Gln Leu Gln Leu Glu His Leu Leu Leu Asp
                245                 250                 255
```

```
Leu Gln Met Ile Leu Asn Gly Ile Asn Asn Tyr Lys Asn Pro Lys Leu
            260                 265                 270

Thr Arg Met Leu Thr Phe Lys Phe Tyr Met Pro Lys Lys Ala Thr Glu
        275                 280                 285

Leu Lys His Leu Gln Cys Leu Glu Glu Glu Leu Lys Pro Leu Glu Glu
    290                 295                 300

Val Leu Asn Leu Ala Gln Ser Lys Asn Phe His Leu Arg Pro Arg Asp
305                 310                 315                 320

Leu Ile Ser Asn Ile Asn Val Ile Val Leu Glu Leu Lys Gly Ser Glu
                325                 330                 335

Thr Thr Phe Met Cys Glu Tyr Ala Asp Glu Thr Ala Thr Ile Val Glu
            340                 345                 350

Phe Leu Asn Arg Trp Ile Thr Phe Ala Gln Ser Ile Ile Ser Thr Leu
        355                 360                 365

Thr Ser Gly Gly Gly Gly Ser Gly Gly Gly Gly Ser Gly Gly Gly Gly
    370                 375                 380

Glu Val Gln Leu Leu Glu Ser Gly Gly Gly Leu Val Gln Pro Gly Gly
385                 390                 395                 400

Ser Leu Arg Leu Ser Cys Ala Ala Ser Gly Phe Thr Phe Ser Ser Tyr
                405                 410                 415

Ala Met Ser Trp Val Arg Gln Ala Pro Gly Lys Gly Leu Glu Trp Val
            420                 425                 430

Ser Ala Ile Ser Gly Ser Gly Gly Ser Thr Tyr Tyr Ala Asp Ser Val
        435                 440                 445

Lys Gly Arg Phe Thr Ile Ser Arg Asp Asn Ser Lys Asn Thr Leu Tyr
    450                 455                 460

Leu Gln Met Asn Ser Leu Arg Ala Glu Asp Thr Ala Val Tyr Tyr Cys
465                 470                 475                 480

Ala Lys Gly Trp Leu Gly Asn Phe Asp Tyr Trp Gly Gln Gly Thr Leu
                485                 490                 495

Val Thr Val Ser Ser Ala Ser Thr Lys Gly Pro Ser Val Phe Pro Leu
            500                 505                 510

Ala Pro Ser Ser Lys Ser Thr Ser Gly Gly Thr Ala Ala Leu Gly Cys
        515                 520                 525

Leu Val Lys Asp Tyr Phe Pro Glu Pro Val Thr Val Ser Trp Asn Ser
    530                 535                 540

Gly Ala Leu Thr Ser Gly Val His Thr Phe Pro Ala Val Leu Gln Ser
545                 550                 555                 560

Ser Gly Leu Tyr Ser Leu Ser Ser Val Val Thr Val Pro Ser Ser Ser
                565                 570                 575

Leu Gly Thr Gln Thr Tyr Ile Cys Asn Val Asn His Lys Pro Ser Asn
            580                 585                 590

Thr Lys Val Asp Lys Lys Val Glu Pro Lys Ser Cys Asp
        595                 600                 605
```

<210> SEQ ID NO 212
<211> LENGTH: 1818
<212> TYPE: DNA
<213> ORGANISM: Artificial Sequence
<220> FEATURE:
<223> OTHER INFORMATION: 4G8 Fab-IL2-Fab (heavy chain cytokine fusion construct)

<400> SEQUENCE: 212

```
gaggtgcaat tgttggagtc tgggggaggc ttggtacagc ctggggggtc cctgagactc     60
```

-continued

```
tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaagggtgg    300

ctgggtaatt ttgactactg gggccaagga accctggtca ccgtctcgag tgctagcacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggataaga aagttgagcc caaatcttgt    660

gactccggcg gaggagggag cggcggaggt ggctccggag gtggcggagc acctacttca    720

agttctacaa agaaaacaca gctacaactg gagcatttac tgctggattt acagatgatt    780

ttgaatggaa ttaataatta caagaatccc aaactcacca ggatgctcac atttaagttt    840

tacatgccca agaaggccac agaactgaaa catcttcagt gtctagaaga agaactcaaa    900

cctctggagg aagtgctaaa tttagctcaa agcaaaaact ttcacttaag acccagggac    960

ttaatcagca atatcaacgt aatagttctg gaactaaagg gatctgaaac aacattcatg   1020

tgtgaatatg ctgatgagac agcaaccatt gtagaatttc tgaacagatg gattaccttt   1080

gcccaaagca tcatctcaac actgacttcc ggcggaggag gatccggcgg aggtggctct   1140

ggcggtggcg gagaggtgca attgttggag tctgggggag gcttggtaca gcctgggggg   1200

tccctgagac tctcctgtgc agcctccgga ttcaccttta gcagttatgc catgagctgg   1260

gtccgccagg ctccagggaa ggggctggag tgggtctcag ctattagtgg tagtggtggt   1320

agcacatact acgcagactc cgtgaagggc cggttcacca tctccagaga caattccaag   1380

aacacgctgt atctgcagat gaacagcctg agagccgagg acacggccgt atattactgt   1440

gcgaaagggt ggctgggtaa ttttgactac tggggccaag gaaccctggt caccgtctcg   1500

agtgctagca ccaagggccc atcggtcttc cccctggcac cctcctccaa gagcacctct   1560

gggggcacag cggccctggg ctgcctggtc aaggactact tccccgaacc ggtgacggtg   1620

tcgtggaact caggcgccct gaccagcggc gtgcacacct tcccggctgt cctacagtcc   1680

tcaggactct actccctcag cagcgtggtg accgtgccct ccagcagctt gggcacccag   1740

acctacatct gcaacgtgaa tcacaagccc agcaacacca aggtggataa gaaagttgag   1800

cccaaatctt gtgactga                                                 1818
```

<210> SEQ ID NO 213
<211> LENGTH: 605
<212> TYPE: PRT
<213> ORGANISM: Artificial Sequence
<220> FEATURE:
<223> OTHER INFORMATION: 3D9 Fab-IL2-Fab (heavy chain cytokine fusion construct)

<400> SEQUENCE: 213

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Thr Pro Gly Lys Gly Leu Glu Trp Val
```

-continued

```
        35                  40                  45

Ser Ala Ile Gly Val Ser Thr Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Pro Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Ser Gly Gly
    210                 215                 220

Gly Gly Ser Gly Gly Gly Gly Ser Gly Gly Gly Gly Ala Pro Thr Ser
225                 230                 235                 240

Ser Ser Thr Lys Lys Thr Gln Leu Gln Leu Glu His Leu Leu Leu Asp
                245                 250                 255

Leu Gln Met Ile Leu Asn Gly Ile Asn Asn Tyr Lys Asn Pro Lys Leu
            260                 265                 270

Thr Arg Met Leu Thr Phe Lys Phe Tyr Met Pro Lys Lys Ala Thr Glu
        275                 280                 285

Leu Lys His Leu Gln Cys Leu Glu Glu Glu Leu Lys Pro Leu Glu Glu
    290                 295                 300

Val Leu Asn Leu Ala Gln Ser Lys Asn Phe His Leu Arg Pro Arg Asp
305                 310                 315                 320

Leu Ile Ser Asn Ile Asn Val Ile Val Leu Glu Leu Lys Gly Ser Glu
                325                 330                 335

Thr Thr Phe Met Cys Glu Tyr Ala Asp Glu Thr Ala Thr Ile Val Glu
            340                 345                 350

Phe Leu Asn Arg Trp Ile Thr Phe Ala Gln Ser Ile Ile Ser Thr Leu
        355                 360                 365

Thr Ser Gly Gly Gly Gly Ser Gly Gly Gly Gly Ser Gly Gly Gly Gly
    370                 375                 380

Glu Val Gln Leu Leu Glu Ser Gly Gly Gly Leu Val Gln Pro Gly Gly
385                 390                 395                 400

Ser Leu Arg Leu Ser Cys Ala Ala Ser Gly Phe Thr Phe Ser Ser Tyr
                405                 410                 415

Ala Met Ser Trp Val Arg Gln Thr Pro Gly Lys Gly Leu Glu Trp Val
            420                 425                 430

Ser Ala Ile Gly Val Ser Thr Gly Ser Thr Tyr Tyr Ala Asp Ser Val
        435                 440                 445

Lys Gly Arg Phe Thr Ile Ser Arg Asp Asn Ser Lys Asn Thr Leu Tyr
    450                 455                 460
```

```
Leu Gln Met Asn Ser Leu Arg Ala Glu Asp Thr Ala Val Tyr Tyr Cys
465                 470                 475                 480

Ala Lys Gly Trp Leu Gly Pro Phe Asp Tyr Trp Gly Gln Gly Thr Leu
                485                 490                 495

Val Thr Val Ser Ser Ala Ser Thr Lys Gly Pro Ser Val Phe Pro Leu
            500                 505                 510

Ala Pro Ser Ser Lys Ser Thr Ser Gly Gly Thr Ala Ala Leu Gly Cys
        515                 520                 525

Leu Val Lys Asp Tyr Phe Pro Glu Pro Val Thr Val Ser Trp Asn Ser
    530                 535                 540

Gly Ala Leu Thr Ser Gly Val His Thr Phe Pro Ala Val Leu Gln Ser
545                 550                 555                 560

Ser Gly Leu Tyr Ser Leu Ser Ser Val Val Thr Val Pro Ser Ser Ser
                565                 570                 575

Leu Gly Thr Gln Thr Tyr Ile Cys Asn Val Asn His Lys Pro Ser Asn
            580                 585                 590

Thr Lys Val Asp Lys Lys Val Glu Pro Lys Ser Cys Asp
        595                 600                 605


<210> SEQ ID NO 214
<211> LENGTH: 1818
<212> TYPE: DNA
<213> ORGANISM: Artificial Sequence
<220> FEATURE:
<223> OTHER INFORMATION: 3D9 Fab-IL2-Fab (heavy chain cytokine fusion
      construct)

<400> SEQUENCE: 214

gaggtgcaat tgttggagtc tggggggaggc ttggtacagc ctgggggggtc cctgagactc     60

tcctgtgcag cctccggatt cacctttagc agttatgcta tgagctgggt ccgccagact    120

ccagggaagg ggctggagtg ggtctcagct attggtgtta gtactggtag cacatactac    180

gcagactccg tgaagggccg gttcaccatc tccagagaca attccaagaa cacgctgtat    240

ctgcagatga acagcctgag agccgaggac acggccgtat attactgtgc gaaaggttgg    300

ctgggtcctt ttgactactg gggccaagga accctggtca ccgtctcgag tgctagcacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggataaga aagttgagcc caaatcttgt    660

gactccggcg gaggagggag cggcggaggt ggctccggag gtggcggagc acctacttca    720

agttctacaa agaaaacaca gctacaactg gagcatttac tgctggattt acagatgatt    780

ttgaatggaa ttaataatta caagaatccc aaactcacca ggatgctcac atttaagttt    840

tacatgccca agaaggccac agaactgaaa catcttcagt gtctagaaga agaactcaaa    900

cctctggagg aagtgctaaa tttagctcaa agcaaaaact ttcacttaag acccagggac    960

ttaatcagca atatcaacgt aatagttctg gaactaaagg gatctgaaac aacattcatg   1020

tgtgaatatg ctgatgagac agcaaccatt gtagaatttc tgaacagatg gattaccttt   1080

gcccaaagca tcatctcaac actgacttcc ggcggaggag gatccggcgg aggtggctct   1140

ggcggtggcg gagaggtgca attgttggag tctgggggag gcttggtaca gcctgggggg   1200
```

```
tccctgagac tctcctgtgc agcctccgga ttcaccttta gcagttatgc tatgagctgg   1260

gtccgccaga ctccagggaa ggggctggag tgggtctcag ctattggtgt tagtactggt   1320

agcacatact acgcagactc cgtgaagggc cggttcacca tctccagaga caattccaag   1380

aacacgctgt atctgcagat gaacagcctg agagccgagg acacggccgt atattactgt   1440

gcgaaaggtt ggctgggtcc ttttgactac tggggccaag gaaccctggt caccgtctcg   1500

agtgctagca ccaagggccc atcggtcttc cccctggcac cctcctccaa gagcacctct   1560

gggggcacag cggccctggg ctgcctggtc aaggactact tccccgaacc ggtgacggtg   1620

tcgtggaact caggcgccct gaccagcggc gtgcacacct tcccggctgt cctacagtcc   1680

tcaggactct actccctcag cagcgtggtg accgtgccct ccagcagctt gggcacccag   1740

acctacatct gcaacgtgaa tcacaagccc agcaacacca aggtggataa gaaagttgag   1800

cccaaatctt gtgactga                                                 1818
```

<210> SEQ ID NO 215
<211> LENGTH: 605
<212> TYPE: PRT
<213> ORGANISM: Artificial Sequence
<220> FEATURE:
<223> OTHER INFORMATION: 2F11 Fab-IL2-Fab (heavy chain cytokine fusion construct)

<400> SEQUENCE: 215

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Arg Trp Met Met Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Ser Gly Gly
    210                 215                 220

Gly Gly Ser Gly Gly Gly Gly Ser Gly Gly Gly Ala Pro Thr Ser
225                 230                 235                 240

Ser Ser Thr Lys Lys Thr Gln Leu Gln Leu Glu His Leu Leu Leu Asp
```

```
                245                 250                 255

Leu Gln Met Ile Leu Asn Gly Ile Asn Asn Tyr Lys Asn Pro Lys Leu
            260                 265                 270

Thr Arg Met Leu Thr Phe Lys Phe Tyr Met Pro Lys Lys Ala Thr Glu
        275                 280                 285

Leu Lys His Leu Gln Cys Leu Glu Glu Glu Leu Lys Pro Leu Glu Glu
    290                 295                 300

Val Leu Asn Leu Ala Gln Ser Lys Asn Phe His Leu Arg Pro Arg Asp
305                 310                 315                 320

Leu Ile Ser Asn Ile Asn Val Ile Val Leu Glu Leu Lys Gly Ser Glu
                325                 330                 335

Thr Thr Phe Met Cys Glu Tyr Ala Asp Glu Thr Ala Thr Ile Val Glu
            340                 345                 350

Phe Leu Asn Arg Trp Ile Thr Phe Ala Gln Ser Ile Ile Ser Thr Leu
        355                 360                 365

Thr Ser Gly Gly Gly Gly Ser Gly Gly Gly Gly Ser Gly Gly Gly Gly
    370                 375                 380

Glu Val Gln Leu Leu Glu Ser Gly Gly Gly Leu Val Gln Pro Gly Gly
385                 390                 395                 400

Ser Leu Arg Leu Ser Cys Ala Ala Ser Gly Phe Thr Phe Ser Ser Tyr
                405                 410                 415

Ala Met Ser Trp Val Arg Gln Ala Pro Gly Lys Gly Leu Glu Trp Val
            420                 425                 430

Ser Ala Ile Ser Gly Ser Gly Gly Ser Thr Tyr Tyr Ala Asp Ser Val
        435                 440                 445

Lys Gly Arg Phe Thr Ile Ser Arg Asp Asn Ser Lys Asn Thr Leu Tyr
    450                 455                 460

Leu Gln Met Asn Ser Leu Arg Ala Glu Asp Thr Ala Val Tyr Tyr Cys
465                 470                 475                 480

Ala Lys Trp Arg Trp Met Met Phe Asp Tyr Trp Gly Gln Gly Thr Leu
                485                 490                 495

Val Thr Val Ser Ser Ala Ser Thr Lys Gly Pro Ser Val Phe Pro Leu
            500                 505                 510

Ala Pro Ser Ser Lys Ser Thr Ser Gly Gly Thr Ala Ala Leu Gly Cys
        515                 520                 525

Leu Val Lys Asp Tyr Phe Pro Glu Pro Val Thr Val Ser Trp Asn Ser
    530                 535                 540

Gly Ala Leu Thr Ser Gly Val His Thr Phe Pro Ala Val Leu Gln Ser
545                 550                 555                 560

Ser Gly Leu Tyr Ser Leu Ser Ser Val Val Thr Val Pro Ser Ser Ser
                565                 570                 575

Leu Gly Thr Gln Thr Tyr Ile Cys Asn Val Asn His Lys Pro Ser Asn
            580                 585                 590

Thr Lys Val Asp Lys Lys Val Glu Pro Lys Ser Cys Asp
        595                 600                 605


<210> SEQ ID NO 216
<211> LENGTH: 1818
<212> TYPE: DNA
<213> ORGANISM: Artificial Sequence
<220> FEATURE:
<223> OTHER INFORMATION: 2F11 Fab-IL2-Fab (heavy chain cytokine fusion
      construct)

<400> SEQUENCE: 216
```

gaggtgcaat tgttggagtc tgggggaggc ttggtacagc ctggggggtc cctgagactc 60
tcctgtgcag cctccggatt cacctttagc agttatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcagatga acagcctgag agccgaggac accgccgtat attactgtgc gaaatggaga 300
tggatgatgt ttgactactg gggccaagga accctggtca ccgtctcgag tgctagcacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt gcacaccttc ccggctgtcc tacagtcctc aggactctac 540
tccctcagca gcgtggtgac cgtgccctcc agcagcttgg gcacccagac ctacatctgc 600
aacgtgaatc acaagcccag caacaccaag gtggataaga aagttgagcc caaatcttgt 660
gactccggcg gaggagggag cggcggaggt ggctccggag gtggcggagc acctacttca 720
agttctacaa agaaaacaca gctacaactg gagcatttac tgctggattt acagatgatt 780
ttgaatggaa ttaataatta caagaatccc aaactcacca ggatgctcac atttaagttt 840
tacatgccca agaaggccac agaactgaaa catcttcagt gtctagaaga agaactcaaa 900
cctctggagg aagtgctaaa tttagctcaa agcaaaaact ttcacttaag acccagggac 960
ttaatcagca atatcaacgt aatagttctg gaactaaagg gatctgaaac aacattcatg 1020
tgtgaatatg ctgatgagac agcaaccatt gtagaatttc tgaacagatg gattaccttt 1080
gcccaaagca tcatctcaac actgacttcc ggcggaggag gatccggcgg aggtggctct 1140
ggcggtggcg gagaggtgca attgttggag tctgggggag gcttggtaca gcctgggggg 1200
tccctgagac tctcctgtgc agcctccgga ttcaccttta gcagttatgc catgagctgg 1260
gtccgccagg ctccagggaa ggggctggag tgggtctcag ctattagtgg tagtggtggt 1320
agcacatact acgcagactc cgtgaagggc cggttcacca tctccagaga caattccaag 1380
aacacgctgt atctgcagat gaacagcctg agagccgagg acaccgccgt atattactgt 1440
gcgaaatgga gatggatgat gtttgactac tggggccaag gaaccctggt caccgtctcg 1500
agtgctagca ccaagggccc atcggtcttc cccctggcac cctcctccaa gagcacctct 1560
gggggcacag cggccctggg ctgcctggtc aaggactact tccccgaacc ggtgacggtg 1620
tcgtggaact caggcgccct gaccagcggc gtgcacacct tcccggctgt cctacagtcc 1680
tcaggactct actccctcag cagcgtggtg accgtgccct ccagcagctt gggcacccag 1740
acctacatct gcaacgtgaa tcacaagccc agcaacacca aggtggataa gaaagttgag 1800
cccaaatctt gtgactga 1818

<210> SEQ ID NO 217
<211> LENGTH: 605
<212> TYPE: PRT
<213> ORGANISM: Artificial Sequence
<220> FEATURE:
<223> OTHER INFORMATION: 4B3 Fab-IL2-Fab (heavy chain cytokine fusion construct)

<400> SEQUENCE: 217

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

```
Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Ser Gly Gly
    210                 215                 220

Gly Gly Ser Gly Gly Gly Gly Ser Gly Gly Gly Gly Ala Pro Thr Ser
225                 230                 235                 240

Ser Ser Thr Lys Lys Thr Gln Leu Gln Leu Glu His Leu Leu Leu Asp
                245                 250                 255

Leu Gln Met Ile Leu Asn Gly Ile Asn Asn Tyr Lys Asn Pro Lys Leu
            260                 265                 270

Thr Arg Met Leu Thr Phe Lys Phe Tyr Met Pro Lys Lys Ala Thr Glu
        275                 280                 285

Leu Lys His Leu Gln Cys Leu Glu Glu Glu Leu Lys Pro Leu Glu Glu
    290                 295                 300

Val Leu Asn Leu Ala Gln Ser Lys Asn Phe His Leu Arg Pro Arg Asp
305                 310                 315                 320

Leu Ile Ser Asn Ile Asn Val Ile Val Leu Glu Leu Lys Gly Ser Glu
                325                 330                 335

Thr Thr Phe Met Cys Glu Tyr Ala Asp Glu Thr Ala Thr Ile Val Glu
            340                 345                 350

Phe Leu Asn Arg Trp Ile Thr Phe Ala Gln Ser Ile Ile Ser Thr Leu
        355                 360                 365

Thr Ser Gly Gly Gly Gly Ser Gly Gly Gly Gly Ser Gly Gly Gly Gly
    370                 375                 380

Glu Val Gln Leu Leu Glu Ser Gly Gly Gly Leu Val Gln Pro Gly Gly
385                 390                 395                 400

Ser Leu Arg Leu Ser Cys Ala Ala Ser Gly Phe Thr Phe Ser Ser Tyr
                405                 410                 415

Ala Met Ser Trp Val Arg Gln Ala Pro Gly Lys Gly Leu Glu Trp Val
            420                 425                 430

Ser Ala Ile Ser Gly Ser Gly Gly Ser Thr Tyr Tyr Ala Asp Ser Val
        435                 440                 445

Lys Gly Arg Phe Thr Ile Ser Arg Asp Asn Ser Lys Asn Thr Leu Tyr
```

```
    450                 455                 460

Leu Gln Met Asn Ser Leu Arg Ala Glu Asp Thr Ala Val Tyr Tyr Cys
465                 470                 475                 480

Ala Lys Gly Trp Leu Gly Asn Phe Asp Tyr Trp Gly Gln Gly Thr Leu
                485                 490                 495

Val Thr Val Ser Ser Ala Ser Thr Lys Gly Pro Ser Val Phe Pro Leu
            500                 505                 510

Ala Pro Ser Ser Lys Ser Thr Ser Gly Gly Thr Ala Ala Leu Gly Cys
        515                 520                 525

Leu Val Lys Asp Tyr Phe Pro Glu Pro Val Thr Val Ser Trp Asn Ser
    530                 535                 540

Gly Ala Leu Thr Ser Gly Val His Thr Phe Pro Ala Val Leu Gln Ser
545                 550                 555                 560

Ser Gly Leu Tyr Ser Leu Ser Ser Val Val Thr Val Pro Ser Ser Ser
                565                 570                 575

Leu Gly Thr Gln Thr Tyr Ile Cys Asn Val Asn His Lys Pro Ser Asn
            580                 585                 590

Thr Lys Val Asp Lys Lys Val Glu Pro Lys Ser Cys Asp
        595                 600                 605


<210> SEQ ID NO 218
<211> LENGTH: 1818
<212> TYPE: DNA
<213> ORGANISM: Artificial Sequence
<220> FEATURE:
<223> OTHER INFORMATION: 4B3 Fab-IL2-Fab (heavy chain cytokine fusion
      construct)

<400> SEQUENCE: 218

gaggtgcaat tgttggagtc tggggggaggc ttggtacagc ctggggggtc cctgagactc     60

tcctgtgcag cctccggatt cacctttagc agttatgcca tgagctgggt ccgccaggct    120

ccagggaagg ggctggagtg ggtctcagct attagtggta gtggtggtag cacatactac    180

gcagactccg tgaagggccg gttcaccatc tccagagaca attccaagaa cacgctgtat    240

ctgcagatga acagcctgag agccgaggac acggccgtat attactgtgc gaaagggtgg    300

ctgggtaatt ttgactactg gggccaagga accctggtca ccgtctcgag tgctagcacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt gcacaccttc ccggctgtcc tacagtcctc aggactctac    540

tccctcagca gcgtggtgac cgtgccctcc agcagcttgg gcacccagac ctacatctgc    600

aacgtgaatc acaagcccag caacaccaag gtggataaga aagttgagcc caaatcttgt    660

gactccggcg gaggagggag cggcggaggt ggctccggag gtggcggagc acctacttca    720

agttctacaa agaaaacaca gctacaactg gagcatttac tgctggattt acagatgatt    780

ttgaatggaa ttaataatta caagaatccc aaactcacca ggatgctcac atttaagttt    840

tacatgccca agaaggccac agaactgaaa catcttcagt gtctagaaga agaactcaaa    900

cctctggagg aagtgctaaa tttagctcaa agcaaaaact ttcacttaag acccagggac    960

ttaatcagca atatcaacgt aatagttctg gaactaaagg gatctgaaac aacattcatg   1020

tgtgaatatg ctgatgagac agcaaccatt gtagaatttc tgaacagatg gattaccttt   1080

gcccaaagca tcatctcaac actgacttcc ggcggaggag gatccggcgg aggtggctct   1140

ggcggtggcg gagaggtgca attgttggag tctgggggag gcttggtaca gcctgggggg   1200
```

```
tccctgagac tctcctgtgc agcctccgga ttcaccttta gcagttatgc catgagctgg   1260

gtccgccagg ctccagggaa ggggctggag tgggtctcag ctattagtgg tagtggtggt   1320

agcacatact acgcagactc cgtgaagggc cggttcacca tctccagaga caattccaag   1380

aacacgctgt atctgcagat gaacagcctg agagccgagg acacggccgt atattactgt   1440

gcgaaagggt ggctgggtaa ttttgactac tggggccaag gaaccctggt caccgtctcg   1500

agtgctagca ccaagggccc atcggtcttc cccctggcac cctcctccaa gagcacctct   1560

gggggcacag cggccctggg ctgcctggtc aaggactact tccccgaacc ggtgacggtg   1620

tcgtggaact caggcgccct gaccagcggc gtgcacacct tcccggctgt cctacagtcc   1680

tcaggactct actccctcag cagcgtggtg accgtgccct ccagcagctt gggcacccag   1740

acctacatct gcaacgtgaa tcacaagccc agcaacacca aggtggataa gaaagttgag   1800

cccaaatctt gtgactga                                                 1818


<210> SEQ ID NO 219
<211> LENGTH: 993
<212> TYPE: PRT
<213> ORGANISM: Artificial Sequence
<220> FEATURE:
<223> OTHER INFORMATION: 4G8 Fab-IL12-Fab (murine IL-12; heavy chain
      cytokine fusion construct)

<400> SEQUENCE: 219

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Leu Gly Asn Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Ser Gly Gly
    210                 215                 220

Gly Gly Ser Gly Gly Gly Gly Ser Gly Gly Gly Gly Ala Met Trp Glu
225                 230                 235                 240
```

```
Leu Glu Lys Asp Val Tyr Val Val Glu Val Asp Trp Thr Pro Asp Ala
                245                 250                 255

Pro Gly Glu Thr Val Asn Leu Thr Cys Asp Thr Pro Glu Glu Asp Asp
            260                 265                 270

Ile Thr Trp Thr Ser Asp Gln Arg His Gly Val Ile Gly Ser Gly Lys
        275                 280                 285

Thr Leu Thr Ile Thr Val Lys Glu Phe Leu Asp Ala Gly Gln Tyr Thr
    290                 295                 300

Cys His Lys Gly Gly Glu Thr Leu Ser His Ser His Leu Leu Leu His
305                 310                 315                 320

Lys Lys Glu Asn Gly Ile Trp Ser Thr Glu Ile Leu Lys Asn Phe Lys
                325                 330                 335

Asn Lys Thr Phe Leu Lys Cys Glu Ala Pro Asn Tyr Ser Gly Arg Phe
            340                 345                 350

Thr Cys Ser Trp Leu Val Gln Arg Asn Met Asp Leu Lys Phe Asn Ile
        355                 360                 365

Lys Ser Ser Ser Ser Pro Pro Asp Ser Arg Ala Val Thr Cys Gly Met
    370                 375                 380

Ala Ser Leu Ser Ala Glu Lys Val Thr Leu Asp Gln Arg Asp Tyr Glu
385                 390                 395                 400

Lys Tyr Ser Val Ser Cys Gln Glu Asp Val Thr Cys Pro Thr Ala Glu
                405                 410                 415

Glu Thr Leu Pro Ile Glu Leu Ala Leu Glu Ala Arg Gln Gln Asn Lys
            420                 425                 430

Tyr Glu Asn Tyr Ser Thr Ser Phe Phe Ile Arg Asp Ile Ile Lys Pro
        435                 440                 445

Asp Pro Pro Lys Asn Leu Gln Met Lys Pro Leu Lys Asn Ser Gln Val
    450                 455                 460

Glu Val Ser Trp Glu Tyr Pro Asp Ser Trp Ser Thr Pro Arg Ser Tyr
465                 470                 475                 480

Phe Ser Leu Lys Phe Phe Val Arg Ile Gln Arg Lys Lys Glu Lys Met
                485                 490                 495

Lys Glu Thr Glu Glu Gly Cys Asn Gln Lys Gly Ala Phe Phe Val Glu
            500                 505                 510

Lys Thr Ser Thr Glu Val Gln Cys Lys Gly Gly Asn Val Cys Val Gln
        515                 520                 525

Ala Gln Asp Arg Tyr Tyr Asn Ser Ser Cys Ser Lys Trp Ala Cys Val
    530                 535                 540

Pro Cys Arg Val Arg Ser Gly Gly Asp Gly Ser Gly Gly Gly Gly Ser
545                 550                 555                 560

Gly Gly Gly Gly Ser Arg Val Ile Pro Val Ser Gly Pro Ala Arg Cys
                565                 570                 575

Leu Ser Gln Ser Arg Asn Leu Leu Lys Thr Thr Asp Asp Met Val Lys
            580                 585                 590

Thr Ala Arg Glu Lys Leu Lys His Tyr Ser Cys Thr Ala Glu Asp Ile
        595                 600                 605

Asp His Glu Asp Ile Thr Arg Asp Gln Thr Ser Thr Leu Lys Thr Cys
    610                 615                 620

Leu Pro Leu Glu Leu His Lys Asn Glu Ser Cys Leu Ala Thr Arg Glu
625                 630                 635                 640

Thr Ser Ser Thr Thr Arg Gly Ser Cys Leu Pro Pro Gln Lys Thr Ser
                645                 650                 655

Leu Met Met Thr Leu Cys Leu Gly Ser Ile Tyr Glu Asp Leu Lys Met
```

```
            660                 665                 670

Tyr Gln Thr Glu Phe Gln Ala Ile Asn Ala Ala Leu Gln Asn His Asn
        675                 680                 685

His Gln Gln Ile Ile Leu Asp Lys Gly Met Leu Val Ala Ile Asp Glu
    690                 695                 700

Leu Met Gln Ser Leu Asn His Asn Gly Glu Thr Leu Arg Gln Lys Pro
705                 710                 715                 720

Pro Val Gly Glu Ala Asp Pro Tyr Arg Val Lys Met Lys Leu Cys Ile
                725                 730                 735

Leu Leu His Ala Phe Ser Thr Arg Val Val Thr Ile Asn Arg Val Met
            740                 745                 750

Gly Tyr Leu Ser Ser Ala Gly Gly Gly Gly Ser Gly Gly Gly Gly Ser
        755                 760                 765

Gly Gly Gly Gly Glu Val Gln Leu Leu Glu Ser Gly Gly Gly Leu Val
    770                 775                 780

Gln Pro Gly Gly Ser Leu Arg Leu Ser Cys Ala Ala Ser Gly Phe Thr
785                 790                 795                 800

Phe Ser Ser Tyr Ala Met Ser Trp Val Arg Gln Ala Pro Gly Lys Gly
                805                 810                 815

Leu Glu Trp Val Ser Ala Ile Ser Gly Ser Gly Gly Ser Thr Tyr Tyr
            820                 825                 830

Ala Asp Ser Val Lys Gly Arg Phe Thr Ile Ser Arg Asp Asn Ser Lys
        835                 840                 845

Asn Thr Leu Tyr Leu Gln Met Asn Ser Leu Arg Ala Glu Asp Thr Ala
    850                 855                 860

Val Tyr Tyr Cys Ala Lys Gly Trp Leu Gly Asn Phe Asp Tyr Trp Gly
865                 870                 875                 880

Gln Gly Thr Leu Val Thr Val Ser Ser Ala Ser Thr Lys Gly Pro Ser
                885                 890                 895

Val Phe Pro Leu Ala Pro Ser Ser Lys Ser Thr Ser Gly Gly Thr Ala
            900                 905                 910

Ala Leu Gly Cys Leu Val Lys Asp Tyr Phe Pro Glu Pro Val Thr Val
        915                 920                 925

Ser Trp Asn Ser Gly Ala Leu Thr Ser Gly Val His Thr Phe Pro Ala
    930                 935                 940

Val Leu Gln Ser Ser Gly Leu Tyr Ser Leu Ser Ser Val Val Thr Val
945                 950                 955                 960

Pro Ser Ser Ser Leu Gly Thr Gln Thr Tyr Ile Cys Asn Val Asn His
                965                 970                 975

Lys Pro Ser Asn Thr Lys Val Asp Lys Lys Val Glu Pro Lys Ser Cys
            980                 985                 990

Asp
```

<210> SEQ ID NO 220
<211> LENGTH: 2982
<212> TYPE: DNA
<213> ORGANISM: Artificial Sequence
<220> FEATURE:
<223> OTHER INFORMATION: 4G8 Fab-IL12-Fab (murine IL-12; heavy chain cytokine fusion construct)

<400> SEQUENCE: 220

```
gaggtgcaat tgctggaaag cggcggagga ctggtgcagc ctggcggcag cctgagactg      60

agctgcgccg ccagcggctt caccttcagc agctacgcca tgtcttgggt ccgccaggcc     120
```

-continued

```
cctggaaagg gcctggaatg ggtgtccgcc atcagcggca gcggcggcag cacctactac    180
gccgacagcg tgaagggccg gttcaccatc agccgggaca acagcaagaa caccctgtac    240
ctgcagatga acagcctgag agccgaggac accgccgtgt actactgcgc caagggctgg    300
ctgggcaact tcgactactg gggccagggc actctggtca cagtgtctag cgctagcacc    360
aagggcccat cggtcttccc cctggcaccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggataaga aagttgagcc caaatcttgt    660
gactccggcg gaggagggag cggcggaggt ggctccggag gggcggagc catgtgggag    720
ctggaaaagg acgtgtacgt ggtggaggtg gactggaccc ccgacgcccc tggcgagaca    780
gtgaacctga cctgcgacac ccccgaagag gacgacatca cctggaccag cgaccagcgg    840
cacggcgtga tcggcagcgg caagaccctg accatcaccg tgaaagagtt tctggacgcc    900
ggccagtaca cctgccacaa gggcggcgag acactgagcc acagccacct gctgctgcac    960
aagaaagaga acggcatctg gtccaccgag atcctgaaga acttcaagaa caagaccttc   1020
ctgaagtgcg aggcccccaa ctacagcggc cggttcacct gcagctggct ggtgcagcgg   1080
aacatggacc tgaagttcaa catcaagagc agcagcagcc cccctgacag cagggccgtg   1140
acctgcggca tggccagcct gagcgccgag aaggtgaccc tggaccagag ggactacgag   1200
aagtacagcg tgagctgcca ggaagatgtc acctgcccca ccgccgagga aaccctgccc   1260
atcgagctgg ccctggaagc ccggcagcag aacaagtacg agaactactc taccagcttc   1320
ttcatccggg acatcatcaa gcccgacccc cccaagaacc tgcagatgaa gcccctgaag   1380
aacagccagg tggaggtgtc ctgggagtac cctgacagct ggtccacccc cagaagctac   1440
ttcagcctga agttcttcgt gagaatccag cggaagaaag aaaagatgaa agagacagag   1500
gaaggctgca accagaaggg cgccttcttc gtcgagaaaa ccagcaccga ggtgcagtgc   1560
aagggcggca acgtgtgcgt gcaggcccag gaccggtact acaacagcag ctgcagcaag   1620
tgggcctgcg tgccctgcag agtgcggtct ggcggcgacg gctctggcgg cggaggaagc   1680
ggcggagggg gcagcagagt gatccccgtg agcggccctg cccggtgcct gagccagagc   1740
cggaacctgc tgaaaaccac cgacgacatg gtgaaaaccg ccagagagaa gctgaagcac   1800
tacagctgca cagccgagga catcgaccac gaggacatca cccgggacca gaccagcacc   1860
ctgaaaacct gcctgcccct ggaactgcac aaaaacgaga gctgcctggc cacccgggag   1920
acaagcagca ccacccgggg cagctgcctg cctccccaga aaacctccct gatgatgacc   1980
ctgtgcctgg gcagcatcta cgaggacctg aagatgtacc agaccgagtt ccaggccatc   2040
aacgccgccc tgcagaacca caatcaccag cagatcatcc tggacaaggg catgctggtc   2100
gccatcgacg agctgatgca gagcctgaac cacaacggcg aaaccctgcg gcagaaaccc   2160
cccgtgggcg aggccgaccc ctaccgggtg aagatgaagc tgtgcatcct gctgcacgcc   2220
ttcagcaccc gggtggtgac catcaaccgg gtgatgggct acctgtcctc tgccggggga   2280
gggggatccg gcggaggtgg ctctggcggt ggcggagagg tgcaattgct ggaaagcggc   2340
ggaggactgg tgcagcctgg cggcagcctg agactgagct gcgccgccag cggcttcacc   2400
ttcagcagct acgccatgtc ttgggtccgc caggcccctg gaaagggcct ggaatgggtg   2460
tccgccatca gcggcagcgg cggcagcacc tactacgccg acagcgtgaa gggccggttc   2520
```

-continued accatcagcc gggacaacag caagaacacc ctgtacctgc agatgaacag cctgagagcc 2580
gaggacaccg ccgtgtacta ctgcgccaag ggctggctgg gcaacttcga ctactggggc 2640
cagggcactc tggtcacagt gtctagcgct agcaccaagg gcccatcggt cttcccctg 2700 gcaccctcct ccaagagcac ctctgggggc acagcggccc tgggctgcct ggtcaaggac 2760
tacttccccg aaccggtgac ggtgtcgtgg aactcaggcg ccctgaccag cggcgtgcac 2820
accttcccgg ctgtcctaca gtcctcagga ctctactccc tcagcagcgt ggtgaccgtg 2880
ccctccagca gcttgggcac ccagacctac atctgcaacg tgaatcacaa gcccagcaac 2940
accaaggtgg ataagaaagt tgagcccaaa tcttgtgact ga 2982

<210> SEQ ID NO 221
<211> LENGTH: 603
<212> TYPE: PRT
<213> ORGANISM: Artificial Sequence
<220> FEATURE:
<223> OTHER INFORMATION: 28H1 Fab-IL2-Fab (heavy chain cytokine fusion construct)

<400> SEQUENCE: 221

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser His
20 25 30

Ala Met Ser Trp Val Arg Gln Ala Pro Gly Lys Gly Leu Glu Trp Val
35 40 45

Ser Ala Ile Trp Ala Ser Gly Glu Gln Tyr Tyr Ala Asp Ser Val Lys
50 55 60

Gly Arg Phe Thr Ile Ser Arg Asp Asn Ser Lys Asn Thr Leu Tyr Leu
65 70 75 80

Gln Met Asn Ser Leu Arg Ala Glu Asp Thr Ala Val Tyr Tyr Cys Ala
85 90 95

Lys Gly Trp Leu Gly Asn Phe Asp Tyr Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Ser Gly Gly Gly
210 215 220

Gly Ser Gly Gly Gly Gly Ser Gly Gly Gly Gly Ala Pro Thr Ser Ser
225 230 235 240

Ser Thr Lys Lys Thr Gln Leu Gln Leu Glu His Leu Leu Leu Asp Leu
245 250 255

Gln Met Ile Leu Asn Gly Ile Asn Asn Tyr Lys Asn Pro Lys Leu Thr
260 265 270

-continued

```
Arg Met Leu Thr Phe Lys Phe Tyr Met Pro Lys Lys Ala Thr Glu Leu
        275                 280                 285

Lys His Leu Gln Cys Leu Glu Glu Glu Leu Lys Pro Leu Glu Glu Val
    290                 295                 300

Leu Asn Leu Ala Gln Ser Lys Asn Phe His Leu Arg Pro Arg Asp Leu
305                 310                 315                 320

Ile Ser Asn Ile Asn Val Ile Val Leu Glu Leu Lys Gly Ser Glu Thr
                325                 330                 335

Thr Phe Met Cys Glu Tyr Ala Asp Glu Thr Ala Thr Ile Val Glu Phe
            340                 345                 350

Leu Asn Arg Trp Ile Thr Phe Ala Gln Ser Ile Ile Ser Thr Leu Thr
        355                 360                 365

Ser Gly Gly Gly Gly Ser Gly Gly Gly Gly Ser Gly Gly Gly Gly Glu
    370                 375                 380

Val Gln Leu Leu Glu Ser Gly Gly Gly Leu Val Gln Pro Gly Gly Ser
385                 390                 395                 400

Leu Arg Leu Ser Cys Ala Ala Ser Gly Phe Thr Phe Ser Ser His Ala
                405                 410                 415

Met Ser Trp Val Arg Gln Ala Pro Gly Lys Gly Leu Glu Trp Val Ser
            420                 425                 430

Ala Ile Trp Ala Ser Gly Glu Gln Tyr Tyr Ala Asp Ser Val Lys Gly
        435                 440                 445

Arg Phe Thr Ile Ser Arg Asp Asn Ser Lys Asn Thr Leu Tyr Leu Gln
    450                 455                 460

Met Asn Ser Leu Arg Ala Glu Asp Thr Ala Val Tyr Tyr Cys Ala Lys
465                 470                 475                 480

Gly Trp Leu Gly Asn Phe Asp Tyr Trp Gly Gln Gly Thr Leu Val Thr
                485                 490                 495

Val Ser Ser Ala Ser Thr Lys Gly Pro Ser Val Phe Pro Leu Ala Pro
            500                 505                 510

Ser Ser Lys Ser Thr Ser Gly Gly Thr Ala Ala Leu Gly Cys Leu Val
        515                 520                 525

Lys Asp Tyr Phe Pro Glu Pro Val Thr Val Ser Trp Asn Ser Gly Ala
    530                 535                 540

Leu Thr Ser Gly Val His Thr Phe Pro Ala Val Leu Gln Ser Ser Gly
545                 550                 555                 560

Leu Tyr Ser Leu Ser Ser Val Val Thr Val Pro Ser Ser Ser Leu Gly
                565                 570                 575

Thr Gln Thr Tyr Ile Cys Asn Val Asn His Lys Pro Ser Asn Thr Lys
            580                 585                 590

Val Asp Lys Lys Val Glu Pro Lys Ser Cys Asp
        595                 600
```

<210> SEQ ID NO 222
<211> LENGTH: 1812
<212> TYPE: DNA
<213> ORGANISM: Artificial Sequence
<220> FEATURE:
<223> OTHER INFORMATION: 28H1 Fab-IL2-Fab (heavy chain cytokine fusion construct)

<400> SEQUENCE: 222

```
gaagtgcagc tgctggaatc cggcggaggc ctggtgcagc ctggcggatc tctgagactg      60

tcctgcgccg cctccggctt caccttctcc tcccacgcca tgtcctgggt ccgacaggct     120

cctggcaaag gcctggaatg ggtgtccgcc atctgggcct ccggcgagca gtactacgcc     180
```

gactctgtga agggccggtt caccatctcc cgggacaact ccaagaacac cctgtacctg 240
cagatgaact ccctgcgggc cgaggacacc gccgtgtact actgtgccaa gggctggctg 300
ggcaacttcg actactgggg acagggcacc ctggtcaccg tgtccagcgc tagcaccaag 360
ggaccctccg tgttccccct ggccccctcc agcaagtcta cctctggcgg caccgccgct 420
ctgggctgcc tggtcaagga ctacttcccc gagcccgtga ccgtgtcctg gaactctggc 480
gccctgacca gcggcgtcca cacctttcca gccgtgctgc agtcctccgg cctgtactcc 540
ctgtcctccg tcgtgaccgt gccctccagc tctctgggca cccagaccta catctgcaac 600
gtgaaccaca agccctccaa caccaaggtg gacaagaagg tggaacccaa gtcctgcgac 660
agtggtgggg gaggatctgg tggcggaggt tctggcggag gtggcgctcc tacatcctcc 720
agcaccaaga aaacccagct ccagctggaa catctcctgc tggatctgca gatgatcctg 780
aacggcatca acaactacaa gaaccccaag ctgacccgga tgctgacctt caagttctac 840
atgcccaaga aggccaccga gctgaaacat ctgcagtgcc tggaagagga actgaagcct 900
ctggaagagg tgctgaacct ggcccagtcc aagaacttcc acctgaggcc tcgggacctg 960
atctccaaca tcaacgtgat cgtgctggaa ctgaagggct ccgagacaac cttcatgtgc 1020
gagtacgccg acgagacagc taccatcgtg gaatttctga accggtggat caccttcgcc 1080
cagtccatca tctccaccct gacctccggt ggtggcggat ccgggggagg gggttctggc 1140
ggaggcggag aagtgcagct gctggaatcc ggcggaggcc tggtgcagcc tggcggatct 1200
ctgagactgt cctgcgccgc ctccggcttc accttctcct cccacgccat gtcctgggtc 1260
cgacaggctc caggcaaggg cctggaatgg gtgtccgcca tctgggcctc cggcgagcag 1320
tactacgccg actctgtgaa gggccggttc accatctccc gggacaactc caagaacacc 1380
ctgtacctgc agatgaactc cctgcgggcc gaggacaccg ccgtgtacta ctgtgccaag 1440
ggctggctgg gcaacttcga ctactggggc cagggcaccc tggtcaccgt gtcctccgcc 1500
tctaccaagg gcccctccgt gttccctctg gccccctcca gcaagtctac ctctggcggc 1560
accgccgctc tgggctgcct ggtcaaggac tacttccccg agcccgtgac cgtgtcctgg 1620
aactctggcg ccctgaccag cggcgtgcac acctttccag ccgtgctgca gtcctccggc 1680
ctgtactccc tgtcctccgt cgtgaccgtg ccctccagct ctctgggcac ccagacctac 1740
atctgcaacg tgaaccacaa gccctccaac accaaggtgg acaagaaggt ggaacccaag 1800
tcctgcgact ga 1812

<210> SEQ ID NO 223
<211> LENGTH: 605
<212> TYPE: PRT
<213> ORGANISM: Artificial Sequence
<220> FEATURE:
<223> OTHER INFORMATION: 29B11 Fab-IL2-Fab (heavy chain cytokine fusion construct)

<400> SEQUENCE: 223

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ile Gly Ser Gly Gly Ile Thr Tyr Tyr Ala Asp Ser Val
50 55 60

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Ser Gly Gly
    210                 215                 220

Gly Gly Ser Gly Gly Gly Gly Ser Gly Gly Gly Gly Ala Pro Thr Ser
225                 230                 235                 240

Ser Ser Thr Lys Lys Thr Gln Leu Gln Leu Glu His Leu Leu Leu Asp
                245                 250                 255

Leu Gln Met Ile Leu Asn Gly Ile Asn Asn Tyr Lys Asn Pro Lys Leu
            260                 265                 270

Thr Arg Met Leu Thr Phe Lys Phe Tyr Met Pro Lys Lys Ala Thr Glu
        275                 280                 285

Leu Lys His Leu Gln Cys Leu Glu Glu Glu Leu Lys Pro Leu Glu Glu
    290                 295                 300

Val Leu Asn Leu Ala Gln Ser Lys Asn Phe His Leu Arg Pro Arg Asp
305                 310                 315                 320

Leu Ile Ser Asn Ile Asn Val Ile Val Leu Glu Leu Lys Gly Ser Glu
                325                 330                 335

Thr Thr Phe Met Cys Glu Tyr Ala Asp Glu Thr Ala Thr Ile Val Glu
            340                 345                 350

Phe Leu Asn Arg Trp Ile Thr Phe Ala Gln Ser Ile Ile Ser Thr Leu
        355                 360                 365

Thr Ser Gly Gly Gly Gly Ser Gly Gly Gly Gly Ser Gly Gly Gly Gly
    370                 375                 380

Glu Val Gln Leu Leu Glu Ser Gly Gly Gly Leu Val Gln Pro Gly Gly
385                 390                 395                 400

Ser Leu Arg Leu Ser Cys Ala Ala Ser Gly Phe Thr Phe Ser Ser Tyr
                405                 410                 415

Ala Met Ser Trp Val Arg Gln Ala Pro Gly Lys Gly Leu Glu Trp Val
            420                 425                 430

Ser Ala Ile Ile Gly Ser Gly Gly Ile Thr Tyr Tyr Ala Asp Ser Val
        435                 440                 445

Lys Gly Arg Phe Thr Ile Ser Arg Asp Asn Ser Lys Asn Thr Leu Tyr
    450                 455                 460

Leu Gln Met Asn Ser Leu Arg Ala Glu Asp Thr Ala Val Tyr Tyr Cys
465                 470                 475                 480
```

```
Ala Lys Gly Trp Phe Gly Gly Phe Asn Tyr Trp Gly Gln Gly Thr Leu
                485                 490                 495

Val Thr Val Ser Ser Ala Ser Thr Lys Gly Pro Ser Val Phe Pro Leu
            500                 505                 510

Ala Pro Ser Ser Lys Ser Thr Ser Gly Gly Thr Ala Ala Leu Gly Cys
        515                 520                 525

Leu Val Lys Asp Tyr Phe Pro Glu Pro Val Thr Val Ser Trp Asn Ser
    530                 535                 540

Gly Ala Leu Thr Ser Gly Val His Thr Phe Pro Ala Val Leu Gln Ser
545                 550                 555                 560

Ser Gly Leu Tyr Ser Leu Ser Ser Val Val Thr Val Pro Ser Ser Ser
                565                 570                 575

Leu Gly Thr Gln Thr Tyr Ile Cys Asn Val Asn His Lys Pro Ser Asn
            580                 585                 590

Thr Lys Val Asp Lys Lys Val Glu Pro Lys Ser Cys Asp
        595                 600                 605


<210> SEQ ID NO 224
<211> LENGTH: 1818
<212> TYPE: DNA
<213> ORGANISM: Artificial Sequence
<220> FEATURE:
<223> OTHER INFORMATION: 29B11 Fab-IL2-Fab (heavy chain cytokine fusion
      construct)

<400> SEQUENCE: 224

gaagtgcagc tgctggaatc cggcggaggc ctggtgcagc ctggcggatc tctgagactg      60

tcctgcgccg cctccggctt caccttctcc tcctacgcca tgtcctgggt ccgacaggct     120

cctggcaaag gcctggaatg ggtgtccgcc atcatcggct ccggcggcat cacctactac     180

gccgactctg tgaagggccg gttcaccatc tcccgggaca actccaagaa caccctgtac     240

ctgcagatga actccctgcg ggccgaggac accgccgtgt actactgtgc caagggctgg     300

ttcggaggct tcaactactg gggacagggc accctggtca ccgtgtccag cgctagcacc     360

aagggaccct ccgtgttccc cctggccccc tccagcaagt ctacctctgg cggcaccgcc     420

gctctgggct gcctggtcaa ggactacttc cccgagcccg tgaccgtgtc ctggaactct     480

ggcgccctga ccagcggcgt ccacaccttt ccagccgtgc tgcagtcctc cggcctgtac     540

tccctgtcct ccgtcgtgac cgtgccctcc agctctctgg gcacccagac ctacatctgc     600

aacgtgaacc acaagccctc caacaccaag gtggacaaga aggtggaacc caagtcctgc     660

gacagtggtg ggggaggatc tggtggcgga ggttctggcg gaggtggcgc tcctacatcc     720

tccagcacca agaaaaccca gctccagctg gaacatctcc tgctggatct gcagatgatc     780

ctgaacggca tcaacaacta caagaacccc aagctgaccc ggatgctgac cttcaagttc     840

tacatgccca agaaggccac cgagctgaaa catctgcagt gcctggaaga ggaactgaag     900

cctctggaag aggtgctgaa cctggcccag tccaagaact tccacctgag gcctcgggac     960

ctgatctcca acatcaacgt gatcgtgctg gaactgaagg gctccgagac aaccttcatg    1020

tgcgagtacg ccgacgagac agctaccatc gtggaatttc tgaaccggtg gatcaccttc    1080

gcccagtcca tcatctccac cctgacctcc ggtggtggcg gatccggggg agggggttct    1140

ggcggaggcg gagaagtgca gctgctggaa tccggcggag gcctggtgca gcctggcgga    1200

tctctgagac tgtcctgcgc cgcctccggc ttcaccttct cctcctatgc catgtcctgg    1260

gtccgacagg ctccaggcaa gggcctggaa tgggtgtccg ccatcatcgg ctccggcggc    1320
```

-continued

```
atcacctact acgccgactc tgtgaagggc cggttcacca tctcccggga caactccaag   1380

aacaccctgt acctgcagat gaactccctg cgggccgagg acaccgccgt gtactactgt   1440

gccaagggct ggttcggagg cttcaactac tggggccagg gcaccctggt caccgtgtcc   1500

tccgcctcta ccaagggccc ctccgtgttc cctctggccc cctccagcaa gtctacctct   1560

ggcggcaccg ccgctctggg ctgcctggtc aaggactact tccccgagcc cgtgaccgtg   1620

tcctggaact ctggcgccct gaccagcggc gtgcacacct ttccagccgt gctgcagtcc   1680

tccggcctgt actccctgtc ctccgtcgtg accgtgccct ccagctctct gggcacccag   1740

acctacatct gcaacgtgaa ccacaagccc tccaacacca aggtggacaa gaaggtggaa   1800

cccaagtcct gcgactga                                                 1818
```

```
<210> SEQ ID NO 225
<211> LENGTH: 605
<212> TYPE: PRT
<213> ORGANISM: Artificial Sequence
<220> FEATURE:
<223> OTHER INFORMATION: 19G1 Fab-IL2-Fab (heavy chain cytokine fusion
      construct)

<400> SEQUENCE: 225

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Ser Ser Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Ser Gly Gly
    210                 215                 220

Gly Gly Ser Gly Gly Gly Gly Ser Gly Gly Gly Gly Ala Pro Thr Ser
225                 230                 235                 240

Ser Ser Thr Lys Lys Thr Gln Leu Gln Leu Glu His Leu Leu Leu Asp
                245                 250                 255

Leu Gln Met Ile Leu Asn Gly Ile Asn Asn Tyr Lys Asn Pro Lys Leu
            260                 265                 270
```

```
Thr Arg Met Leu Thr Phe Lys Phe Tyr Met Pro Lys Lys Ala Thr Glu
        275                 280                 285

Leu Lys His Leu Gln Cys Leu Glu Glu Glu Leu Lys Pro Leu Glu Glu
    290                 295                 300

Val Leu Asn Leu Ala Gln Ser Lys Asn Phe His Leu Arg Pro Arg Asp
305                 310                 315                 320

Leu Ile Ser Asn Ile Asn Val Ile Val Leu Glu Leu Lys Gly Ser Glu
                325                 330                 335

Thr Thr Phe Met Cys Glu Tyr Ala Asp Glu Thr Ala Thr Ile Val Glu
            340                 345                 350

Phe Leu Asn Arg Trp Ile Thr Phe Ala Gln Ser Ile Ile Ser Thr Leu
        355                 360                 365

Thr Ser Gly Gly Gly Gly Ser Gly Gly Gly Gly Ser Gly Gly Gly Gly
    370                 375                 380

Glu Val Gln Leu Leu Glu Ser Gly Gly Gly Leu Val Gln Pro Gly Gly
385                 390                 395                 400

Ser Leu Arg Leu Ser Cys Ala Ala Ser Gly Phe Thr Phe Ser Ser Tyr
                405                 410                 415

Ala Met Ser Trp Val Arg Gln Ala Pro Gly Lys Gly Leu Glu Trp Val
            420                 425                 430

Ser Ala Ile Ile Ser Ser Gly Gly Leu Thr Tyr Tyr Ala Asp Ser Val
        435                 440                 445

Lys Gly Arg Phe Thr Ile Ser Arg Asp Asn Ser Lys Asn Thr Leu Tyr
    450                 455                 460

Leu Gln Met Asn Ser Leu Arg Ala Glu Asp Thr Ala Val Tyr Tyr Cys
465                 470                 475                 480

Ala Lys Gly Trp Phe Gly Gly Phe Asn Tyr Trp Gly Gln Gly Thr Leu
                485                 490                 495

Val Thr Val Ser Ser Ala Ser Thr Lys Gly Pro Ser Val Phe Pro Leu
            500                 505                 510

Ala Pro Ser Ser Lys Ser Thr Ser Gly Gly Thr Ala Ala Leu Gly Cys
        515                 520                 525

Leu Val Lys Asp Tyr Phe Pro Glu Pro Val Thr Val Ser Trp Asn Ser
    530                 535                 540

Gly Ala Leu Thr Ser Gly Val His Thr Phe Pro Ala Val Leu Gln Ser
545                 550                 555                 560

Ser Gly Leu Tyr Ser Leu Ser Ser Val Val Thr Val Pro Ser Ser Ser
                565                 570                 575

Leu Gly Thr Gln Thr Tyr Ile Cys Asn Val Asn His Lys Pro Ser Asn
            580                 585                 590

Thr Lys Val Asp Lys Lys Val Glu Pro Lys Ser Cys Asp
        595                 600                 605
```

<210> SEQ ID NO 226
<211> LENGTH: 1818
<212> TYPE: DNA
<213> ORGANISM: Artificial Sequence
<220> FEATURE:
<223> OTHER INFORMATION: 19G1 Fab-IL2-Fab (heavy chain cytokine fusion construct)

<400> SEQUENCE: 226

```
gaggtgcagc tgctcgaaag cggcggagga ctggtgcagc ctggcggcag cctgagactg      60

tcttgcgccg ccagcggctt caccttcagc agctacgcca tgagctgggt ccgccaggcc     120
```

```
cctggcaagg gactggaatg ggtgtccgcc atcatcagct ctggcggcct gacctactac    180
gccgacagcg tgaagggccg gttcaccatc agccgggaca acagcaagaa caccctgtac    240
ctgcagatga acagcctgcg ggccgaggac accgccgtgt actactgcgc caagggatgg    300
ttcggcggct tcaactactg gggacagggc accctggtca cagtgtccag cgctagcacc    360
aagggaccca gcgtgttccc cctggccccc agcagcaaga gcacatctgg cggaacagcc    420
gccctgggct gcctggtcaa agactacttc cccgagcccg tgaccgtgtc ctggaacagc    480
ggagccctga ccagcggcgt gcacaccttt ccagccgtgc tgcagagcag cggcctgtac    540
agcctgagca gcgtggtcac cgtgcctagc tctagcctgg gcacccagac ctacatctgc    600
aacgtgaacc acaagcccag caacaccaag gtggacaaga aggtggaacc caagagctgc    660
gactccggcg gaggcggatc tggcggtgga ggctccggag gcggaggcgc tcctactagc    720
agctccacca agaaaaccca gctccagctg gaacatctgc tgctggatct gcagatgatc    780
ctgaacggca tcaacaacta caagaacccc aagctgaccc ggatgctgac cttcaagttc    840
tacatgccca agaaggccac cgaactgaaa catctgcagt gcctggaaga ggaactgaag    900
cctctggaag aggtgctgaa cctggcccag agcaagaact tccacctgag gcccagggac    960
ctgatcagca acatcaacgt gatcgtgctg gaactgaagg gcagcgagac aaccttcatg   1020
tgcgagtacg ccgacgagac agccaccatc gtggaatttc tgaaccggtg gatcaccttc   1080
gcccagagca tcatcagcac cctgacaagc ggaggcggcg gatccggcgg aggcggatct   1140
ggcggaggag gcgaggtcca gctgctcgaa agcggcggag gactggtgca gcctggcggc   1200
agcctgagac tgtcttgcgc cgccagcggc ttcaccttca gcagctacgc catgagctgg   1260
gtccgccagg cccctggcaa gggactggaa tgggtgtccg ccatcatcag ctctggcggc   1320
ctgacctact acgccgacag cgtgaagggc cggttcacca tcagccggga caacagcaag   1380
aacaccctgt acctgcagat gaacagcctg cgggccgagg acaccgccgt gtactactgc   1440
gccaagggat ggttcggcgg cttcaactac tggggacagg gcaccctggt cacagtgtcc   1500
agcgccagca ccaagggccc cagcgtgttc cccctggccc ccagcagcaa gagcacatct   1560
ggcggaacag ccgccctggg ctgcctggtc aaagactact tccccgagcc cgtgaccgtg   1620
tcctggaaca gcggagccct gaccagcggc gtgcacacct ttccagccgt gctgcagagc   1680
agcggcctgt acagcctgag cagcgtggtc accgtgccta gctctagcct gggcacccag   1740
acctacatct gcaacgtgaa ccacaagccc agcaacacca aggtggacaa gaaggtggaa   1800
cccaagagct gcgactga                                                 1818
```

```
<210> SEQ ID NO 227
<211> LENGTH: 605
<212> TYPE: PRT
<213> ORGANISM: Artificial Sequence
<220> FEATURE:
<223> OTHER INFORMATION: 20G8 Fab-IL2-Fab (heavy chain cytokine fusion
      construct)

<400> SEQUENCE: 227

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ile Gly Ser Gly Ser Arg Thr Tyr Tyr Ala Asp Ser Val
```

-continued

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Trp Phe Gly Gly Phe Asn Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Ser Gly Gly
    210                 215                 220

Gly Gly Ser Gly Gly Gly Gly Ser Gly Gly Gly Gly Ala Pro Thr Ser
225                 230                 235                 240

Ser Ser Thr Lys Lys Thr Gln Leu Gln Leu Glu His Leu Leu Leu Asp
                245                 250                 255

Leu Gln Met Ile Leu Asn Gly Ile Asn Asn Tyr Lys Asn Pro Lys Leu
            260                 265                 270

Thr Arg Met Leu Thr Phe Lys Phe Tyr Met Pro Lys Lys Ala Thr Glu
        275                 280                 285

Leu Lys His Leu Gln Cys Leu Glu Glu Glu Leu Lys Pro Leu Glu Glu
    290                 295                 300

Val Leu Asn Leu Ala Gln Ser Lys Asn Phe His Leu Arg Pro Arg Asp
305                 310                 315                 320

Leu Ile Ser Asn Ile Asn Val Ile Val Leu Glu Leu Lys Gly Ser Glu
                325                 330                 335

Thr Thr Phe Met Cys Glu Tyr Ala Asp Glu Thr Ala Thr Ile Val Glu
            340                 345                 350

Phe Leu Asn Arg Trp Ile Thr Phe Ala Gln Ser Ile Ile Ser Thr Leu
        355                 360                 365

Thr Ser Gly Gly Gly Gly Ser Gly Gly Gly Gly Ser Gly Gly Gly Gly
    370                 375                 380

Glu Val Gln Leu Leu Glu Ser Gly Gly Gly Leu Val Gln Pro Gly Gly
385                 390                 395                 400

Ser Leu Arg Leu Ser Cys Ala Ala Ser Gly Phe Thr Phe Ser Ser Tyr
                405                 410                 415

Ala Met Ser Trp Val Arg Gln Ala Pro Gly Lys Gly Leu Glu Trp Val
            420                 425                 430

Ser Ala Ile Ile Gly Ser Gly Ser Arg Thr Tyr Tyr Ala Asp Ser Val
        435                 440                 445

Lys Gly Arg Phe Thr Ile Ser Arg Asp Asn Ser Lys Asn Thr Leu Tyr
    450                 455                 460

Leu Gln Met Asn Ser Leu Arg Ala Glu Asp Thr Ala Val Tyr Tyr Cys
465                 470                 475                 480
```

```
Ala Lys Gly Trp Phe Gly Gly Phe Asn Tyr Trp Gly Gln Gly Thr Leu
                485                 490                 495

Val Thr Val Ser Ser Ala Ser Thr Lys Gly Pro Ser Val Phe Pro Leu
            500                 505                 510

Ala Pro Ser Ser Lys Ser Thr Ser Gly Gly Thr Ala Ala Leu Gly Cys
        515                 520                 525

Leu Val Lys Asp Tyr Phe Pro Glu Pro Val Thr Val Ser Trp Asn Ser
    530                 535                 540

Gly Ala Leu Thr Ser Gly Val His Thr Phe Pro Ala Val Leu Gln Ser
545                 550                 555                 560

Ser Gly Leu Tyr Ser Leu Ser Ser Val Val Thr Val Pro Ser Ser Ser
                565                 570                 575

Leu Gly Thr Gln Thr Tyr Ile Cys Asn Val Asn His Lys Pro Ser Asn
            580                 585                 590

Thr Lys Val Asp Lys Lys Val Glu Pro Lys Ser Cys Asp
        595                 600                 605


<210> SEQ ID NO 228
<211> LENGTH: 1818
<212> TYPE: DNA
<213> ORGANISM: Artificial Sequence
<220> FEATURE:
<223> OTHER INFORMATION: 20G8 Fab-IL2-Fab (heavy chain cytokine fusion
      construct)

<400> SEQUENCE: 228

gaggtgcagc tgctcgaaag cggcggagga ctggtgcagc ctggcggcag cctgagactg      60

tcttgcgccg ccagcggctt caccttcagc agctacgcca tgagctgggt ccgccaggcc     120

cctggcaagg gactggaatg ggtgtccgcc atcatcggct ctggcagccg gacctactac     180

gccgacagcg tgaagggccg gttcaccatc agccgggaca acagcaagaa caccctgtac     240

ctgcagatga acagcctgcg ggccgaggac accgccgtgt actactgcgc caagggatgg     300

ttcggcggct tcaactactg gggacagggc accctggtca cagtgtccag cgctagcacc     360

aagggaccca gcgtgttccc cctggccccc agcagcaaga gcacatctgg cggaacagcc     420

gccctgggct gcctggtcaa agactacttc cccgagcccg tgaccgtgtc ctggaacagc     480

ggagccctga ccagcggcgt gcacaccttt ccagccgtgc tgcagagcag cggcctgtac     540

agcctgagca gcgtggtcac cgtgcctagc tctagcctgg gcacccagac ctacatctgc     600

aacgtgaacc acaagcccag caacaccaag gtggacaaga aggtggaacc caagagctgc     660

gactccggcg gaggcggatc tggcggtgga ggctccggag gcggaggcgc tcctactagc     720

agctccacca agaaaaccca gctccagctg gaacatctgc tgctggatct gcagatgatc     780

ctgaacggca tcaacaacta caagaacccc aagctgaccc ggatgctgac cttcaagttc     840

tacatgccca agaaggccac cgaactgaaa catctgcagt gcctggaaga ggaactgaag     900

cctctggaag aggtgctgaa cctggcccag agcaagaact tccacctgag gcccagggac     960

ctgatcagca acatcaacgt gatcgtgctg gaactgaagg gcagcgagac aaccttcatg    1020

tgcgagtacg ccgacgagac agccaccatc gtggaatttc tgaaccggtg gatcaccttc    1080

gcccagagca tcatcagcac cctgacaagc ggaggcggcg gatccggcgg aggcggatct    1140

ggcggaggag gcgaggtcca gctgctcgaa agcggcggag gactggtgca gcctggcggc    1200

agcctgagac tgtcttgcgc cgccagcggc ttcaccttca gcagctacgc catgagctgg    1260

gtccgccagg cccctggcaa gggactggaa tgggtgtccg ccatcatcgg ctctggcagc    1320
```

```
cggacctact acgccgacag cgtgaagggc cggttcacca tcagccggga caacagcaag   1380

aacaccctgt acctgcagat gaacagcctg cgggccgagg acaccgccgt gtactactgc   1440

gccaagggat ggttcggcgg cttcaactac tggggacagg gcaccctggt cacagtgtcc   1500

agcgccagca ccaagggccc cagcgtgttc cccctggccc ccagcagcaa gagcacatct   1560

ggcggaacag ccgccctggg ctgcctggtc aaagactact tccccgagcc cgtgaccgtg   1620

tcctggaaca gcggagccct gaccagcggc gtgcacacct ttccagccgt gctgcagagc   1680

agcggcctgt acagcctgag cagcgtggtc accgtgccta gctctagcct gggcacccag   1740

acctacatct gcaacgtgaa ccacaagccc agcaacacca aggtggacaa gaaggtggaa   1800

cccaagagct gcgactga                                                  1818
```

<210> SEQ ID NO 229
<211> LENGTH: 215
<212> TYPE: PRT
<213> ORGANISM: Artificial Sequence
<220> FEATURE:
<223> OTHER INFORMATION: 3F2 light chain

<400> SEQUENCE: 229

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Asn Val Gly Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Ile Met Leu Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 230
<211> LENGTH: 648
<212> TYPE: DNA
<213> ORGANISM: Artificial Sequence
<220> FEATURE:
<223> OTHER INFORMATION: 3F2 light chain

<400> SEQUENCE: 230

```
gagatcgtgc tgacccagtc ccccggcacc ctgtctctga gccctggcga gagagccacc     60

ctgtcctgca gagcctccca gtccgtgacc tcctcctacc tcgcctggta tcagcagaag    120

cccggccagg cccctcggct gctgatcaac gtgggcagtc ggagagccac cggcatccct    180

gaccggttct ccggctctgg ctccggcacc gacttcaccc tgaccatctc ccggctggaa    240

cccgaggact tcgccgtgta ctactgccag cagggcatca tgctgccccc cacctttggc    300

cagggcacca aggtggaaat caagcgtacg gtggccgctc cctccgtgtt catcttccca    360

ccctccgacg agcagctgaa gtccggcacc gcctccgtcg tgtgcctgct gaacaacttc    420

taccccccgcg aggccaaggt gcagtggaag gtggacaacg ccctgcagtc cggcaactcc    480

caggaatccg tcaccgagca ggactccaag gacagcacct actccctgtc ctccaccctg    540

accctgtcca aggccgacta cgagaagcac aaggtgtacg cctgcgaagt gacccaccag    600

ggcctgtcca gccccgtgac caagtccttc aaccggggcg agtgctga                 648
```

<210> SEQ ID NO 231
<211> LENGTH: 215
<212> TYPE: PRT
<213> ORGANISM: Artificial Sequence
<220> FEATURE:
<223> OTHER INFORMATION: 4G8 light chain

<400> SEQUENCE: 231

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Ser
            20                  25                  30

Tyr Leu Ala Trp Tyr Gln Gln Lys Pro Gly Gln Ala Pro Arg Leu Leu
        35                  40                  45

Ile Ile Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 232
<211> LENGTH: 648

<212> TYPE: DNA
<213> ORGANISM: Artificial Sequence
<220> FEATURE:
<223> OTHER INFORMATION: 4G8 light chain

<400> SEQUENCE: 232
gagatcgtgc tgacccagtc cccggcacc ctgtctctga gccctggcga gagagccacc 60
ctgtcctgca gagcctccca gtccgtgtcc cggtcctacc tcgcctggta tcagcagaag 120
cccggccagg cccctcggct gctgatcatc ggcgcctcta ccagagccac cggcatccct 180
gaccggttct ccggctctgg ctccggcacc gacttcaccc tgaccatctc ccggctggaa 240
cccgaggact tcgccgtgta ctactgccag cagggccagg tcatccctcc cacctttggc 300
cagggcacca aggtggaaat caagcgtacg gtggccgctc cctccgtgtt catcttccca 360
ccctccgacg agcagctgaa gtccggcacc gcctccgtcg tgtgcctgct gaacaacttc 420
tacccccgcg aggccaaggt gcagtggaag gtggacaacg ccctgcagtc cggcaactcc 480
caggaatccg tcaccgagca ggactccaag gacagcacct actccctgtc ctccaccctg 540
accctgtcca aggccgacta cgagaagcac aaggtgtacg cctgcgaagt gacccaccag 600
ggcctgtcca gccccgtgac caagtccttc aaccggggcg agtgctga 648

<210> SEQ ID NO 233
<211> LENGTH: 215
<212> TYPE: PRT
<213> ORGANISM: Artificial Sequence
<220> FEATURE:
<223> OTHER INFORMATION: 3D9 light chain

<400> SEQUENCE: 233

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Leu Ile Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
```

210 215

<210> SEQ ID NO 234
<211> LENGTH: 648
<212> TYPE: DNA
<213> ORGANISM: Artificial Sequence
<220> FEATURE:
<223> OTHER INFORMATION: 3D9 light chain

<400> SEQUENCE: 234
gaaatcgtgt taacgcagtc tccaggcacc ctgtctttgt ctccagggga aagagccacc 60
ctctcttgca gggccagtca gagtgttagc agcagctact tagcctggta ccagcagaaa 120
cctggccagg ctcccaggct cctcatctat ggagcatcca gcagggccac tggcatccca 180
gacaggttca gtggcagtgg atccgggaca gacttcactc tcaccatcag cagactggag 240
cctgaagatt ttgcagtgta ttactgtcag cagggtcagc ttattccccc tacgttcggc 300
caggggacca aagtggaaat caaacgtacg gtggctgcac catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480
caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgttag 648

<210> SEQ ID NO 235
<211> LENGTH: 215
<212> TYPE: PRT
<213> ORGANISM: Artificial Sequence
<220> FEATURE:
<223> OTHER INFORMATION: 2F11 light chain

<400> SEQUENCE: 235

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Gly Gln Tyr Thr Pro
85 90 95

Pro Thr Phe Gly Gln Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

```
Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 236
<211> LENGTH: 648
<212> TYPE: DNA
<213> ORGANISM: Artificial Sequence
<220> FEATURE:
<223> OTHER INFORMATION: 2F11 light chain

<400> SEQUENCE: 236

gaaatcgtgt taacgcagtc tccaggcacc ctgtctttgt ctccagggga aagagccacc     60

ctctcttgca gggccagtca gagtgttagc agcagctact tagcctggta ccagcagaaa    120

cctggccagg ctcccaggct cctcatctat ggagcatcca gcagggccac tggcatccca    180

gacaggttca gtggcagtgg atccgggaca gacttcactc tcaccatcag cagactggag    240

cctgaagatt ttgcagtgta ttactgtcag cagggtcagt atactccccc cacgttcggc    300

caggggacca aagtggaaat caaacgtacg gtggctgcac catctgtctt catcttcccg    360

ccatctgatg agcagttgaa atctggaact gcctctgttg tgtgcctgct gaataacttc    420

tatcccagag aggccaaagt acagtggaag gtggataacg ccctccaatc gggtaactcc    480

caggagagtg tcacagagca ggacagcaag gacagcacct acagcctcag cagcaccctg    540

acgctgagca aagcagacta cgagaaacac aaagtctacg cctgcgaagt cacccatcag    600

ggcctgagct cgcccgtcac aaagagcttc aacaggggag agtgttag                 648


<210> SEQ ID NO 237
<211> LENGTH: 215
<212> TYPE: PRT
<213> ORGANISM: Artificial Sequence
<220> FEATURE:
<223> OTHER INFORMATION: 4B3 light chain

<400> SEQUENCE: 237

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Tyr Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Gln Val Ile Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160
```

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 238
<211> LENGTH: 648
<212> TYPE: DNA
<213> ORGANISM: Artificial Sequence
<220> FEATURE:
<223> OTHER INFORMATION: 4B3 light chain

<400> SEQUENCE: 238
gaaatcgtgt taacgcagtc tccaggcacc ctgtctttgt ctccagggga aagagccacc 60
ctctcttgca gggccagtca gagtgttagc agcaattact tagcctggta ccagcagaaa 120
cctggccagg ctcccaggct cctcatctat ggcgcctaca tcagggccac tggcatccca 180
gacaggttca gtggcagtgg atccgggaca gacttcactc tcaccatcag cagactggag 240
cctgaagatt ttgcagtgta ttactgtcag cagggtcagg ttattccccc tacgttcggc 300
caggggacca aagtggaaat caaacgtacg gtggctgcac catctgtctt catcttcccg 360
ccatctgatg agcagttgaa atctggaact gcctctgttg tgtgcctgct gaataacttc 420
tatcccagag aggccaaagt acagtggaag gtggataacg ccctccaatc gggtaactcc 480
caggagagtg tcacagagca ggacagcaag gacagcacct acagcctcag cagcaccctg 540
acgctgagca aagcagacta cgagaaacac aaagtctacg cctgcgaagt cacccatcag 600
ggcctgagct cgcccgtcac aaagagcttc aacaggggag agtgttag 648

<210> SEQ ID NO 239
<211> LENGTH: 613
<212> TYPE: PRT
<213> ORGANISM: Artificial Sequence
<220> FEATURE:
<223> OTHER INFORMATION: 2B10 Fab-IL2-Fab (heavy chain cytokine fusion
      construct)

<400> SEQUENCE: 239

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser Ala Ser Thr Lys Gly Pro Ser
        115                 120                 125

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Ser Gly Gly Gly Gly Ser Gly Gly Gly Gly Ser Gly Gly Gly Gly
225                 230                 235                 240

Ala Pro Thr Ser Ser Ser Thr Lys Lys Thr Gln Leu Gln Leu Glu His
                245                 250                 255

Leu Leu Leu Asp Leu Gln Met Ile Leu Asn Gly Ile Asn Asn Tyr Lys
            260                 265                 270

Asn Pro Lys Leu Thr Arg Met Leu Thr Phe Lys Phe Tyr Met Pro Lys
        275                 280                 285

Lys Ala Thr Glu Leu Lys His Leu Gln Cys Leu Glu Glu Glu Leu Lys
    290                 295                 300

Pro Leu Glu Glu Val Leu Asn Leu Ala Gln Ser Lys Asn Phe His Leu
305                 310                 315                 320

Arg Pro Arg Asp Leu Ile Ser Asn Ile Asn Val Ile Val Leu Glu Leu
                325                 330                 335

Lys Gly Ser Glu Thr Thr Phe Met Cys Glu Tyr Ala Asp Glu Thr Ala
            340                 345                 350

Thr Ile Val Glu Phe Leu Asn Arg Trp Ile Thr Phe Ala Gln Ser Ile
        355                 360                 365

Ile Ser Thr Leu Thr Ser Gly Gly Gly Gly Ser Gly Gly Gly Gly Ser
    370                 375                 380

Gly Gly Gly Gly Gln Val Gln Leu Val Gln Ser Gly Ala Glu Val Lys
385                 390                 395                 400

Lys Pro Gly Ser Ser Val Lys Val Ser Cys Lys Ala Ser Gly Gly Thr
                405                 410                 415

Phe Ser Ser Tyr Ala Ile Ser Trp Val Arg Gln Ala Pro Gly Gln Gly
            420                 425                 430

Leu Glu Trp Met Gly Gly Ile Ile Pro Ile Phe Gly Thr Ala Asn Tyr
        435                 440                 445

Ala Gln Lys Phe Gln Gly Arg Val Thr Ile Thr Ala Asp Lys Ser Thr
    450                 455                 460

Ser Thr Ala Tyr Met Glu Leu Ser Ser Leu Arg Ser Glu Asp Thr Ala
465                 470                 475                 480

Val Tyr Tyr Cys Ala Arg Leu Tyr Gly Tyr Ala Tyr Tyr Gly Ala Phe
                485                 490                 495

Asp Tyr Trp Gly Gln Gly Thr Thr Val Thr Val Ser Ser Ala Ser Thr
            500                 505                 510

Lys Gly Pro Ser Val Phe Pro Leu Ala Pro Ser Ser Lys Ser Thr Ser
        515                 520                 525

Gly Gly Thr Ala Ala Leu Gly Cys Leu Val Lys Asp Tyr Phe Pro Glu
    530                 535                 540

Pro Val Thr Val Ser Trp Asn Ser Gly Ala Leu Thr Ser Gly Val His
```

-continued

```
545                 550                 555                 560

Thr Phe Pro Ala Val Leu Gln Ser Ser Gly Leu Tyr Ser Leu Ser Ser
                565                 570                 575

Val Val Thr Val Pro Ser Ser Ser Leu Gly Thr Gln Thr Tyr Ile Cys
            580                 585                 590

Asn Val Asn His Lys Pro Ser Asn Thr Lys Val Asp Lys Lys Val Glu
        595                 600                 605

Pro Lys Ser Cys Asp
    610


<210> SEQ ID NO 240
<211> LENGTH: 1842
<212> TYPE: DNA
<213> ORGANISM: Artificial Sequence
<220> FEATURE:
<223> OTHER INFORMATION: 2B10 Fab-IL2-Fab (heavy chain cytokine fusion
      construct)

<400> SEQUENCE: 240

caggtgcaat tggtgcagtc tggggctgag gtgaagaagc ctgggtcctc ggtgaaggtc     60

tcctgcaagg cctccggagg cacattcagc agctacgcta taagctgggt gcgacaggcc    120

cctggacaag ggctcgagtg gatgggaggg atcatcccta tctttggtac agcaaactac    180

gcacagaagt tccagggcag ggtcaccatt actgcagaca aatccacgag cacagcctac    240

atggagctga gcagcctgag atctgaggac accgccgtgt attactgtgc gagactgtac    300

ggttacgctt actacggtgc ttttgactac tggggccaag ggaccaccgt gaccgtctcc    360

tcagctagca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggataa gaaagttgag    660

cccaaatctt gtgactccgg cggaggaggg agcggcggag gtggctccgg aggtggcgga    720

gcacctactt caagttctac aaagaaaaca cagctacaac tggagcattt actgctggat    780

ttacagatga ttttgaatgg aattaataat tacaagaatc ccaaactcac caggatgctc    840

acatttaagt tttacatgcc caagaaggcc acagaactga aacatcttca gtgtctagaa    900

gaagaactca aacctctgga ggaagtgcta aatttagctc aaagcaaaaa ctttcactta    960

agacccaggg acttaatcag caatatcaac gtaatagttc tggaactaaa gggatctgaa   1020

acaacattca tgtgtgaata tgctgatgag acagcaacca ttgtagaatt tctgaacaga   1080

tggattacct ttgcccaaag catcatctca acactgactt ccggcggagg aggatccggc   1140

ggaggtggct ctggcggtgg cggacaggtg caattggtgc agtctggggc tgaggtgaag   1200

aagcctgggt cctcggtgaa ggtctcctgc aaggcctccg gaggcacatt cagcagctac   1260

gctataagct gggtgcgaca ggcccctgga caagggctcg agtggatggg agggatcatc   1320

cctatctttg gtacagcaaa ctacgcacag aagttccagg gcagggtcac cattactgca   1380

gacaaatcca cgagcacagc ctacatggag ctgagcagcc tgagatctga ggacaccgcc   1440

gtgtattact gtgcgagact gtacggttac gcttactacg gtgcttttga ctactggggc   1500

caagggacca ccgtgaccgt ctcctcagct agcaccaagg gcccatcggt cttccccctg   1560

gcaccctcct ccaagagcac ctctgggggc acagcggccc tgggctgcct ggtcaaggac   1620
```

```
tacttccccg aaccggtgac ggtgtcgtgg aactcaggcg ccctgaccag cggcgtgcac   1680

accttcccgg ctgtcctaca gtcctcagga ctctactccc tcagcagcgt ggtgaccgtg   1740

ccctccagca gcttgggcac ccagacctac atctgcaacg tgaatcacaa gcccagcaac   1800

accaaggtgg ataagaaagt tgagcccaaa tcttgtgact ga                      1842
```

<210> SEQ ID NO 241
<211> LENGTH: 613
<212> TYPE: PRT
<213> ORGANISM: Artificial Sequence
<220> FEATURE:
<223> OTHER INFORMATION: C3B6 Fab-IL2-Fab (heavy chain cytokine fusion construct)

<400> SEQUENCE: 241

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ala Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Tyr Gly Tyr Ala Tyr Tyr Gly Ala Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Ser Gly Gly Gly Gly Ser Gly Gly Gly Gly Ser Gly Gly Gly Gly
225                 230                 235                 240

Ala Pro Thr Ser Ser Ser Thr Lys Lys Thr Gln Leu Gln Leu Glu His
                245                 250                 255

Leu Leu Leu Asp Leu Gln Met Ile Leu Asn Gly Ile Asn Asn Tyr Lys
            260                 265                 270

Asn Pro Lys Leu Thr Arg Met Leu Thr Phe Lys Phe Tyr Met Pro Lys
        275                 280                 285

Lys Ala Thr Glu Leu Lys His Leu Gln Cys Leu Glu Glu Glu Leu Lys
    290                 295                 300

Pro Leu Glu Glu Val Leu Asn Leu Ala Gln Ser Lys Asn Phe His Leu
305                 310                 315                 320
```

```
Arg Pro Arg Asp Leu Ile Ser Asn Ile Asn Val Ile Val Leu Glu Leu
                325                 330                 335

Lys Gly Ser Glu Thr Thr Phe Met Cys Glu Tyr Ala Asp Glu Thr Ala
            340                 345                 350

Thr Ile Val Glu Phe Leu Asn Arg Trp Ile Thr Phe Ala Gln Ser Ile
        355                 360                 365

Ile Ser Thr Leu Thr Ser Gly Gly Gly Gly Ser Gly Gly Gly Gly Ser
    370                 375                 380

Gly Gly Gly Gly Gln Val Gln Leu Val Gln Ser Gly Ala Glu Val Lys
385                 390                 395                 400

Lys Pro Gly Ser Ser Val Lys Val Ser Cys Lys Ala Ser Gly Gly Thr
                405                 410                 415

Phe Ser Ser Tyr Ala Ile Ser Trp Val Arg Gln Ala Pro Gly Gln Gly
            420                 425                 430

Leu Glu Trp Met Gly Ala Ile Ile Pro Ile Leu Gly Ile Ala Asn Tyr
        435                 440                 445

Ala Gln Lys Phe Gln Gly Arg Val Thr Ile Thr Ala Asp Lys Ser Thr
    450                 455                 460

Ser Thr Ala Tyr Met Glu Leu Ser Ser Leu Arg Ser Glu Asp Thr Ala
465                 470                 475                 480

Val Tyr Tyr Cys Ala Arg Leu Tyr Gly Tyr Ala Tyr Tyr Gly Ala Phe
                485                 490                 495

Asp Tyr Trp Gly Gln Gly Thr Thr Val Thr Val Ser Ser Ala Ser Thr
            500                 505                 510

Lys Gly Pro Ser Val Phe Pro Leu Ala Pro Ser Ser Lys Ser Thr Ser
        515                 520                 525

Gly Gly Thr Ala Ala Leu Gly Cys Leu Val Lys Asp Tyr Phe Pro Glu
    530                 535                 540

Pro Val Thr Val Ser Trp Asn Ser Gly Ala Leu Thr Ser Gly Val His
545                 550                 555                 560

Thr Phe Pro Ala Val Leu Gln Ser Ser Gly Leu Tyr Ser Leu Ser Ser
                565                 570                 575

Val Val Thr Val Pro Ser Ser Ser Leu Gly Thr Gln Thr Tyr Ile Cys
            580                 585                 590

Asn Val Asn His Lys Pro Ser Asn Thr Lys Val Asp Lys Lys Val Glu
        595                 600                 605

Pro Lys Ser Cys Asp
    610
```

<210> SEQ ID NO 242
<211> LENGTH: 1842
<212> TYPE: DNA
<213> ORGANISM: Artificial Sequence
<220> FEATURE:
<223> OTHER INFORMATION: C3B6 Fab-IL2-Fab (heavy chain cytokine fusion construct)

<400> SEQUENCE: 242

```
caggtgcaat tggtgcagtc tggggctgag gtgaagaagc ctgggtcctc ggtgaaggtc      60

tcctgcaagg cctccggagg cacattcagc agctacgcta taagctgggt gcgacaggcc     120

cctggacaag ggctcgagtg gatgggagct atcatcccga tccttggtat cgcaaactac     180

gcacagaagt tccagggcag ggtcaccatt actgcagaca aatccacgag cacagcctac     240

atggagctga gcagcctgag atctgaggac accgccgtgt attactgtgc gagactgtac     300

ggttacgctt actacggtgc ttttgactac tggggccaag ggaccaccgt gaccgtctcc     360
```

```
tcagctagca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggataa gaaagttgag    660

cccaaatctt gtgactccgg cggaggaggg agcggcggag gtggctccgg aggtggcgga    720

gcacctactt caagttctac aaagaaaaca cagctacaac tggagcattt actgctggat    780

ttacagatga ttttgaatgg aattaataat tacaagaatc ccaaactcac caggatgctc    840

acatttaagt tttacatgcc caagaaggcc acagaactga aacatcttca gtgtctagaa    900

gaagaactca aacctctgga ggaagtgcta aatttagctc aaagcaaaaa ctttcactta    960

agacccaggg acttaatcag caatatcaac gtaatagttc tggaactaaa gggatctgaa   1020

acaacattca tgtgtgaata tgctgatgag acagcaacca ttgtagaatt tctgaacaga   1080

tggattacct ttgcccaaag catcatctca acactgactt ccggcggagg aggatccggc   1140

ggaggtggct ctggcggtgg cggacaggtg caattggtgc agtctggggc tgaggtgaag   1200

aagcctgggt cctcggtgaa ggtctcctgc aaggcctccg gaggcacatt cagcagctac   1260

gctataagct gggtgcgaca ggcccctgga caagggctcg agtggatggg agctatcatc   1320

ccgatccttg gtatcgcaaa ctacgcacag aagttccagg gcagggtcac cattactgca   1380

gacaaatcca cgagcacagc ctacatggag ctgagcagcc tgagatctga ggacaccgcc   1440

gtgtattact gtgcgagact gtacggttac gcttactacg gtgcttttga ctactggggc   1500

caagggacca ccgtgaccgt ctcctcagct agcaccaagg gcccatcggt cttcccccctg   1560

gcaccctcct ccaagagcac ctctgggggc acagcggccc tgggctgcct ggtcaaggac   1620

tacttccccg aaccggtgac ggtgtcgtgg aactcaggcg ccctgaccag cggcgtgcac   1680

accttcccgg ctgtcctaca gtcctcagga ctctactccc tcagcagcgt ggtgaccgtg   1740

ccctccagca gcttgggcac ccagacctac atctgcaacg tgaatcacaa gcccagcaac   1800

accaaggtgg ataagaaagt tgagcccaaa tcttgtgact ga                      1842
```

<210> SEQ ID NO 243
<211> LENGTH: 613
<212> TYPE: PRT
<213> ORGANISM: Artificial Sequence
<220> FEATURE:
<223> OTHER INFORMATION: 6A12 Fab-IL2-Fab (heavy chain cytokine fusion construct)

<400> SEQUENCE: 243

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Val Ile Ile Pro Ile Leu Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Leu Tyr Gly Tyr Ala Tyr Tyr Gly Ala Phe Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Ser Gly Gly Gly Gly Ser Gly Gly Gly Gly Ser Gly Gly Gly Gly
225                 230                 235                 240

Ala Pro Thr Ser Ser Ser Thr Lys Lys Thr Gln Leu Gln Leu Glu His
                245                 250                 255

Leu Leu Leu Asp Leu Gln Met Ile Leu Asn Gly Ile Asn Asn Tyr Lys
            260                 265                 270

Asn Pro Lys Leu Thr Arg Met Leu Thr Phe Lys Phe Tyr Met Pro Lys
        275                 280                 285

Lys Ala Thr Glu Leu Lys His Leu Gln Cys Leu Glu Glu Glu Leu Lys
    290                 295                 300

Pro Leu Glu Glu Val Leu Asn Leu Ala Gln Ser Lys Asn Phe His Leu
305                 310                 315                 320

Arg Pro Arg Asp Leu Ile Ser Asn Ile Asn Val Ile Val Leu Glu Leu
                325                 330                 335

Lys Gly Ser Glu Thr Thr Phe Met Cys Glu Tyr Ala Asp Glu Thr Ala
            340                 345                 350

Thr Ile Val Glu Phe Leu Asn Arg Trp Ile Thr Phe Ala Gln Ser Ile
        355                 360                 365

Ile Ser Thr Leu Thr Ser Gly Gly Gly Gly Ser Gly Gly Gly Gly Ser
    370                 375                 380

Gly Gly Gly Gly Gln Val Gln Leu Val Gln Ser Gly Ala Glu Val Lys
385                 390                 395                 400

Lys Pro Gly Ser Ser Val Lys Val Ser Cys Lys Ala Ser Gly Gly Thr
                405                 410                 415

Phe Ser Ser Tyr Ala Ile Ser Trp Val Arg Gln Ala Pro Gly Gln Gly
            420                 425                 430

Leu Glu Trp Met Gly Val Ile Ile Pro Ile Leu Gly Thr Ala Asn Tyr
        435                 440                 445

Ala Gln Lys Phe Gln Gly Arg Val Thr Ile Thr Ala Asp Lys Ser Thr
    450                 455                 460

Ser Thr Ala Tyr Met Glu Leu Ser Ser Leu Arg Ser Glu Asp Thr Ala
465                 470                 475                 480

Val Tyr Tyr Cys Ala Arg Leu Tyr Gly Tyr Ala Tyr Tyr Gly Ala Phe
                485                 490                 495

Asp Tyr Trp Gly Gln Gly Thr Thr Val Thr Val Ser Ser Ala Ser Thr
            500                 505                 510
```

```
Lys Gly Pro Ser Val Phe Pro Leu Ala Pro Ser Ser Lys Ser Thr Ser
        515                 520                 525

Gly Gly Thr Ala Ala Leu Gly Cys Leu Val Lys Asp Tyr Phe Pro Glu
    530                 535                 540

Pro Val Thr Val Ser Trp Asn Ser Gly Ala Leu Thr Ser Gly Val His
545                 550                 555                 560

Thr Phe Pro Ala Val Leu Gln Ser Ser Gly Leu Tyr Ser Leu Ser Ser
                565                 570                 575

Val Val Thr Val Pro Ser Ser Ser Leu Gly Thr Gln Thr Tyr Ile Cys
            580                 585                 590

Asn Val Asn His Lys Pro Ser Asn Thr Lys Val Asp Lys Lys Val Glu
        595                 600                 605

Pro Lys Ser Cys Asp
    610


<210> SEQ ID NO 244
<211> LENGTH: 1842
<212> TYPE: DNA
<213> ORGANISM: Artificial Sequence
<220> FEATURE:
<223> OTHER INFORMATION: 6A12 Fab-IL2-Fab (heavy chain cytokine fusion
      construct)

<400> SEQUENCE: 244

caggtgcaat tggtgcagtc tggggctgag gtgaagaagc ctgggtcctc ggtgaaggtc     60

tcctgcaagg cctccggagg cacattcagc agctatgcta taagctgggt gcgacaggcc    120

cctggacaag ggctcgagtg gatgggagtg atcatcccta tccttggtac cgcaaactac    180

gcacagaagt tccagggcag ggtcaccatt actgcagaca aatccacgag cacagcctac    240

atggagctga gcagcctgag atctgaggac accgccgtgt attactgtgc gagactgtac    300

ggttacgctt actacggtgc ttttgactac tggggccaag ggaccaccgt gaccgtctcc    360

tcagctagca ccaagggccc atcggtcttc cccctggcac cctcctccaa gagcacctct    420

gggggcacag cggccctggg ctgcctggtc aaggactact tccccgaacc ggtgacggtg    480

tcgtggaact caggcgccct gaccagcggc gtgcacacct tcccggctgt cctacagtcc    540

tcaggactct actccctcag cagcgtggtg accgtgccct ccagcagctt gggcacccag    600

acctacatct gcaacgtgaa tcacaagccc agcaacacca aggtggataa gaaagttgag    660

cccaaatctt gtgactccgg cggaggaggg agcggcggag gtggctccgg aggtggcgga    720

gcacctactt caagttctac aaagaaaaca cagctacaac tggagcattt actgctggat    780

ttacagatga ttttgaatgg aattaataat tacaagaatc ccaaactcac caggatgctc    840

acatttaagt tttacatgcc caagaaggcc acagaactga aacatcttca gtgtctagaa    900

gaagaactca aacctctgga ggaagtgcta aatttagctc aaagcaaaaa ctttcactta    960

agacccaggg acttaatcag caatatcaac gtaatagttc tggaactaaa gggatctgaa   1020

acaacattca tgtgtgaata tgctgatgag acagcaacca ttgtagaatt tctgaacaga   1080

tggattacct ttgcccaaag catcatctca acactgactt ccggcggagg aggatccggc   1140

ggaggtggct ctggcggtgg cggacaggtg caattggtgc agtctggggc tgaggtgaag   1200

aagcctgggt cctcggtgaa ggtctcctgc aaggcctccg gaggcacatt cagcagctat   1260

gctataagct gggtgcgaca ggcccctgga caagggctcg agtggatggg agtgatcatc   1320

cctatccttg gtaccgcaaa ctacgcacag aagttccagg gcagggtcac cattactgca   1380

gacaaatcca cgagcacagc ctacatggag ctgagcagcc tgagatctga ggacaccgcc   1440
```

```
gtgtattact gtgcgagact gtacggttac gcttactacg gtgcttttga ctactggggc    1500

caagggacca ccgtgaccgt ctcctcagct agcaccaagg gcccatcggt cttccccctg    1560

gcaccctcct ccaagagcac ctctgggggc acagcggccc tgggctgcct ggtcaaggac    1620

tacttccccg aaccggtgac ggtgtcgtgg aactcaggcg ccctgaccag cggcgtgcac    1680

accttcccgg ctgtcctaca gtcctcagga ctctactccc tcagcagcgt ggtgaccgtg    1740

ccctccagca gcttgggcac ccagacctac atctgcaacg tgaatcacaa gcccagcaac    1800

accaaggtgg ataagaaagt tgagcccaaa tcttgtgact ga                        1842
```

<210> SEQ ID NO 245
<211> LENGTH: 214
<212> TYPE: PRT
<213> ORGANISM: Artificial Sequence
<220> FEATURE:
<223> OTHER INFORMATION: 2B10 light chain

<400> SEQUENCE: 245

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 246
<211> LENGTH: 645
<212> TYPE: DNA
<213> ORGANISM: Artificial Sequence
<220> FEATURE:
<223> OTHER INFORMATION: 2B10 light chain

<400> SEQUENCE: 246

```
gatatccaga tgacccagtc tccatcctcc ctgtctgcat ctgtcggaga ccgggtcacc    60
```

-continued

```
atcacctgcc gggcaagtca gggcattaga aatgatttag gctggtacca gcagaagcca    120

gggaaagccc ctaagcgcct gatctatgct gcatccagtt tgcagagtgg cgtcccatca    180

aggttcagcg gcagtggatc cgggacagag ttcactctca ccatcagcag cttgcagcct    240

gaagattttg ccacctatta ctgcttgcag aatggtctgc agcccgcgac gtttggccag    300

ggcaccaaag tcgagatcaa gcgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645
```

<210> SEQ ID NO 247
<211> LENGTH: 214
<212> TYPE: PRT
<213> ORGANISM: Artificial Sequence
<220> FEATURE:
<223> OTHER INFORMATION: D1A2 light chain

<400> SEQUENCE: 247

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Asp Ala Tyr Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 248
<211> LENGTH: 645
<212> TYPE: DNA
<213> ORGANISM: Artificial Sequence
<220> FEATURE:
<223> OTHER INFORMATION: D1A2 light chain

<400> SEQUENCE: 248

```
gacatccaga tgacccagtc tccatcctcc ctgtctgcat ctgtcggaga ccgggtcacc     60

atcacctgcc gggcaagtca ggggattcgt aatgatttag gctggtacca gcagaagcca    120

gggaaagccc ctaagcgcct gatctatgat gcttacagct tgcagagtgg cgtcccatca    180

aggttcagcg gcggtggatc cgggacagag ttcactctca ccatcagcag cttgcagcct    240

gaagattttg ccacctatta ctgcttgcag aatggtctgc agcccgcgac gtttggccag    300

ggcaccaaag tcgagatcaa gcgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645
```

<210> SEQ ID NO 249
<211> LENGTH: 214
<212> TYPE: PRT
<213> ORGANISM: Artificial Sequence
<220> FEATURE:
<223> OTHER INFORMATION: O7D8 light chain

<400> SEQUENCE: 249

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Asn Val
            20                  25                  30

Leu Gly Trp Tyr Gln Gln Lys Pro Gly Lys Ala Pro Lys Arg Leu Ile
        35                  40                  45

Tyr Asp Val Ser Ser Leu Gln Ser Gly Val Pro Ser Arg Phe Ser Gly
    50                  55                  60

Gly Gly Ser Gly Thr Glu Phe Thr Leu Thr Ile Ser Ser Leu Gln Pro
65                  70                  75                  80

Glu Asp Phe Ala Thr Tyr Tyr Cys Leu Gln Asn Gly Leu Gln Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 250

<211> LENGTH: 645
<212> TYPE: DNA
<213> ORGANISM: Artificial Sequence
<220> FEATURE:
<223> OTHER INFORMATION: 07D8 light chain

<400> SEQUENCE: 250

```
gatatccaga tgacccagtc tccatcctcc ctgtctgcat ctgtcggaga ccgggtcacc     60

atcacctgcc gggcaagtca gagcattcgt aatgttttag gctggtacca gcagaagcca    120

gggaaagccc ctaagcgcct gatctatgat gtgtccagtt tgcagagtgg cgtcccatca    180

aggttcagcg gcggtggatc cgggacagag ttcactctca ccatcagcag cttgcagcct    240

gaagattttg ccacctatta ctgcttgcag aatggtctgc agcccgcgac gtttggccag    300

ggcaccaaag tcgagatcaa gcgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645
```

<210> SEQ ID NO 251
<211> LENGTH: 615
<212> TYPE: PRT
<213> ORGANISM: Artificial Sequence
<220> FEATURE:
<223> OTHER INFORMATION: MHLG1 Fab-IL2-Fab (heavy chain cytokine fusion
      construct)

<400> SEQUENCE: 251

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Asn Phe Gly Arg Tyr Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Tyr Gly Asn Tyr Val Gly His Tyr Phe Asp His Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205
```

```
His Lys Pro Ser Asn Thr Lys Val Asp Lys Lys Val Glu Pro Lys Ser
    210                 215                 220

Cys Asp Ser Gly Gly Gly Gly Ser Gly Gly Gly Gly Ser Gly Gly Gly
225                 230                 235                 240

Gly Ala Pro Thr Ser Ser Ser Thr Lys Lys Thr Gln Leu Gln Leu Glu
                245                 250                 255

His Leu Leu Leu Asp Leu Gln Met Ile Leu Asn Gly Ile Asn Asn Tyr
            260                 265                 270

Lys Asn Pro Lys Leu Thr Arg Met Leu Thr Phe Lys Phe Tyr Met Pro
        275                 280                 285

Lys Lys Ala Thr Glu Leu Lys His Leu Gln Cys Leu Glu Glu Glu Leu
    290                 295                 300

Lys Pro Leu Glu Glu Val Leu Asn Leu Ala Gln Ser Lys Asn Phe His
305                 310                 315                 320

Leu Arg Pro Arg Asp Leu Ile Ser Asn Ile Asn Val Ile Val Leu Glu
                325                 330                 335

Leu Lys Gly Ser Glu Thr Thr Phe Met Cys Glu Tyr Ala Asp Glu Thr
            340                 345                 350

Ala Thr Ile Val Glu Phe Leu Asn Arg Trp Ile Thr Phe Ala Gln Ser
        355                 360                 365

Ile Ile Ser Thr Leu Thr Ser Gly Gly Gly Gly Ser Gly Gly Gly Gly
    370                 375                 380

Ser Gly Gly Gly Gly Glu Val Gln Leu Val Glu Ser Gly Gly Gly Leu
385                 390                 395                 400

Val Lys Pro Gly Gly Ser Leu Arg Leu Ser Cys Ala Ala Ser Gly Phe
                405                 410                 415

Thr Phe Ser Asn Tyr Trp Met Asn Trp Val Arg Gln Ala Pro Gly Lys
            420                 425                 430

Gly Leu Glu Trp Val Ala Glu Ile Arg Leu Lys Ser Asn Asn Phe Gly
        435                 440                 445

Arg Tyr Tyr Ala Ala Ser Val Lys Gly Arg Phe Thr Ile Ser Arg Asp
    450                 455                 460

Asp Ser Lys Asn Thr Leu Tyr Leu Gln Met Asn Ser Leu Lys Thr Glu
465                 470                 475                 480

Asp Thr Ala Val Tyr Tyr Cys Thr Thr Tyr Gly Asn Tyr Val Gly His
                485                 490                 495

Tyr Phe Asp His Trp Gly Gln Gly Thr Thr Val Thr Val Ser Ser Ala
            500                 505                 510

Ser Thr Lys Gly Pro Ser Val Phe Pro Leu Ala Pro Ser Ser Lys Ser
        515                 520                 525

Thr Ser Gly Gly Thr Ala Ala Leu Gly Cys Leu Val Lys Asp Tyr Phe
    530                 535                 540

Pro Glu Pro Val Thr Val Ser Trp Asn Ser Gly Ala Leu Thr Ser Gly
545                 550                 555                 560

Val His Thr Phe Pro Ala Val Leu Gln Ser Ser Gly Leu Tyr Ser Leu
                565                 570                 575

Ser Ser Val Val Thr Val Pro Ser Ser Ser Leu Gly Thr Gln Thr Tyr
            580                 585                 590

Ile Cys Asn Val Asn His Lys Pro Ser Asn Thr Lys Val Asp Lys Lys
        595                 600                 605

Val Glu Pro Lys Ser Cys Asp
    610                 615
```

<210> SEQ ID NO 252
<211> LENGTH: 1848
<212> TYPE: DNA
<213> ORGANISM: Artificial Sequence
<220> FEATURE:
<223> OTHER INFORMATION: MHLG1 Fab-IL2-Fab (heavy chain cytokine fusion construct)

<400> SEQUENCE: 252
gaagtgcagc tggtggagtc tggaggaggc ttggtcaagc ctggcgggtc cctgcggctc 60
tcctgtgcag cctccggatt cacatttagc aactattgga tgaactgggt gcggcaggct 120
cctggaaagg gcctcgagtg ggtggccgag atcagattga aatccaataa cttcggaaga 180
tattacgctg caagcgtgaa gggccggttc accatcagca gagatgattc caagaacacg 240
ctgtacctgc agatgaacag cctgaagacc gaggatacgg ccgtgtatta ctgtaccaca 300
tacggcaact acgttgggca ctacttcgac cactggggcc aagggaccac cgtcaccgtc 360
tccagtgcta gcaccaaggg cccatcggtc ttccccctgg caccctcctc caagagcacc 420
tctgggggca cagcggccct gggctgcctg gtcaaggact acttccccga accggtgacg 480
gtgtcgtgga actcaggcgc cctgaccagc ggcgtgcaca ccttcccggc tgtcctacag 540
tcctcaggac tctactccct cagcagcgtg gtgaccgtgc cctccagcag cttgggcacc 600
cagacctaca tctgcaacgt gaatcacaag cccagcaaca ccaaggtgga taagaaagtt 660
gagcccaaat cttgtgactc cggcggagga gggagcggcg gaggtggctc cggaggtggc 720
ggagcaccta cttcaagttc tacaaagaaa acacagctac aactggagca tttactgctg 780
gatttacaga tgattttgaa tggaattaat aattacaaga atcccaaact caccaggatg 840
ctcacattta agttttacat gcccaagaag gccacagaac tgaaacatct tcagtgtcta 900
gaagaagaac tcaaacctct ggaggaagtg ctaaatttag ctcaaagcaa aaactttcac 960
ttaagaccca gggacttaat cagcaatatc aacgtaatag ttctggaact aaagggatct 1020
gaaacaacat tcatgtgtga atatgctgat gagacagcaa ccattgtaga atttctgaac 1080
agatggatta cctttgccca aagcatcatc tcaacactga cttccggcgg aggaggatcc 1140
ggcggaggtg gctctggcgg tggcggagaa gtgcagctgg tggagtctgg aggaggcttg 1200
gtcaagcctg gcgggtccct gcggctctcc tgtgcagcct ccggattcac atttagcaac 1260
tattggatga actgggtgcg gcaggctcct ggaaagggcc tcgagtgggt ggccgagatc 1320
agattgaaat ccaataactt cggaagatat tacgctgcaa gcgtgaaggg ccggttcacc 1380
atcagcagag atgattccaa gaacacgctg tacctgcaga tgaacagcct gaagaccgag 1440
gatacggccg tgtattactg taccacatac ggcaactacg ttgggcacta cttcgaccac 1500
tggggccaag ggaccaccgt caccgtctcc agtgctagca ccaagggccc atcggtcttc 1560
cccctggcac cctcctccaa gagcacctct gggggcacag cggccctggg ctgcctggtc 1620
aaggactact tccccgaacc ggtgacggtg tcgtggaact caggcgccct gaccagcggc 1680
gtgcacacct tcccggctgt cctacagtcc tcaggactct actccctcag cagcgtggtg 1740
accgtgccct ccagcagctt gggcacccag acctacatct gcaacgtgaa tcacaagccc 1800
agcaacacca aggtggataa gaaagttgag cccaaatctt gtgactga 1848

<210> SEQ ID NO 253
<211> LENGTH: 214
<212> TYPE: PRT
<213> ORGANISM: Artificial Sequence
<220> FEATURE:

<223> OTHER INFORMATION: KV9 light chain

<400> SEQUENCE: 253

```
Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Gln Ala Pro Arg Pro Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 254
<211> LENGTH: 645
<212> TYPE: DNA
<213> ORGANISM: Artificial Sequence
<220> FEATURE:
<223> OTHER INFORMATION: KV9 light chain

<400> SEQUENCE: 254

```
gatatccagt tgacccagtc tccatccttc ctgtctgcat ctgtgggcga ccgggtcacc     60

atcacctgca aggccagtca gaatgtggat actaacgtgg cttggtacca gcagaagcca    120

gggcaggcac ctaggcctct gatctattcg gcatcctacc ggtacactgg cgtcccatca    180

aggttcagcg gcagtggatc cgggacagag ttcactctca caatctcaag cctgcaacct    240

gaagatttcg caacttacta ctgtcaacag tacaatagtt accctctgac gttcggcgga    300

ggtaccaagg tggagatcaa gcgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645
```

<210> SEQ ID NO 255
<211> LENGTH: 615
<212> TYPE: PRT
<213> ORGANISM: Artificial Sequence
<220> FEATURE:
<223> OTHER INFORMATION: MHLG Fab-IL2-Fab (heavy chain cytokine fusion construct)

<400> SEQUENCE: 255

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Asn Phe Gly Arg Tyr Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Tyr Gly Asn Tyr Val Gly His Tyr Phe Asp His Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Ser Gly Gly Gly Gly Ser Gly Gly Gly Gly Ser Gly Gly Gly
225                 230                 235                 240

Gly Ala Pro Thr Ser Ser Ser Thr Lys Lys Thr Gln Leu Gln Leu Glu
                245                 250                 255

His Leu Leu Leu Asp Leu Gln Met Ile Leu Asn Gly Ile Asn Asn Tyr
            260                 265                 270

Lys Asn Pro Lys Leu Thr Arg Met Leu Thr Phe Lys Phe Tyr Met Pro
        275                 280                 285

Lys Lys Ala Thr Glu Leu Lys His Leu Gln Cys Leu Glu Glu Glu Leu
    290                 295                 300

Lys Pro Leu Glu Glu Val Leu Asn Leu Ala Gln Ser Lys Asn Phe His
305                 310                 315                 320

Leu Arg Pro Arg Asp Leu Ile Ser Asn Ile Asn Val Ile Val Leu Glu
                325                 330                 335

Leu Lys Gly Ser Glu Thr Thr Phe Met Cys Glu Tyr Ala Asp Glu Thr
            340                 345                 350

Ala Thr Ile Val Glu Phe Leu Asn Arg Trp Ile Thr Phe Ala Gln Ser
        355                 360                 365
```

```
Ile Ile Ser Thr Leu Thr Ser Gly Gly Gly Gly Ser Gly Gly Gly Gly
    370                 375                 380

Ser Gly Gly Gly Gly Glu Val Gln Leu Val Glu Ser Gly Gly Gly Leu
385                 390                 395                 400

Val Gln Pro Gly Gly Ser Leu Arg Leu Ser Cys Ala Ala Ser Gly Phe
                405                 410                 415

Thr Phe Ser Asn Tyr Trp Met Asn Trp Val Arg Gln Ala Pro Gly Lys
            420                 425                 430

Gly Leu Glu Trp Val Ala Glu Ile Arg Leu Lys Ser Asn Asn Phe Gly
        435                 440                 445

Arg Tyr Tyr Ala Ala Ser Val Lys Gly Arg Phe Thr Ile Ser Arg Asp
    450                 455                 460

Asp Ser Lys Asn Thr Leu Tyr Leu Gln Met Asn Ser Leu Lys Thr Glu
465                 470                 475                 480

Asp Thr Ala Val Tyr Tyr Cys Thr Thr Tyr Gly Asn Tyr Val Gly His
                485                 490                 495

Tyr Phe Asp His Trp Gly Gln Gly Thr Thr Val Thr Val Ser Ser Ala
            500                 505                 510

Ser Thr Lys Gly Pro Ser Val Phe Pro Leu Ala Pro Ser Ser Lys Ser
        515                 520                 525

Thr Ser Gly Gly Thr Ala Ala Leu Gly Cys Leu Val Lys Asp Tyr Phe
    530                 535                 540

Pro Glu Pro Val Thr Val Ser Trp Asn Ser Gly Ala Leu Thr Ser Gly
545                 550                 555                 560

Val His Thr Phe Pro Ala Val Leu Gln Ser Ser Gly Leu Tyr Ser Leu
                565                 570                 575

Ser Ser Val Val Thr Val Pro Ser Ser Ser Leu Gly Thr Gln Thr Tyr
            580                 585                 590

Ile Cys Asn Val Asn His Lys Pro Ser Asn Thr Lys Val Asp Lys Lys
        595                 600                 605

Val Glu Pro Lys Ser Cys Asp
    610                 615
```

<210> SEQ ID NO 256
<211> LENGTH: 1848
<212> TYPE: DNA
<213> ORGANISM: Artificial Sequence
<220> FEATURE:
<223> OTHER INFORMATION: MHLG Fab-IL2-Fab (heavy chain cytokine fusion construct)

<400> SEQUENCE: 256

```
gaagtgcagc tggtggagtc tggaggaggc ttggtccagc ctggcgggtc cctgcggctc      60

tcctgtgcag cctccggatt cacatttagc aactattgga tgaactgggt gcggcaggct     120

cctggaaagg gcctcgagtg ggtggccgag atcagattga aatccaataa cttcggaaga     180

tattacgctg caagcgtgaa gggccggttc accatcagca gagatgattc caagaacacg     240

ctgtacctgc agatgaacag cctgaagacc gaggatacgg ccgtgtatta ctgtaccaca     300

tacggcaact acgttgggca ctacttcgac cactggggcc aagggaccac cgtcaccgtc     360

tccagtgcta gcaccaaggg cccatcggtc ttccccctgg caccctcctc caagagcacc     420

tctgggggca cagcggccct gggctgcctg gtcaaggact acttccccga accggtgacg     480

gtgtcgtgga actcaggcgc cctgaccagc ggcgtgcaca ccttcccggc tgtcctacag     540

tcctcaggac tctactccct cagcagcgtg gtgaccgtgc cctccagcag cttgggcacc     600
```

```
cagacctaca tctgcaacgt gaatcacaag cccagcaaca ccaaggtgga taagaaagtt    660
gagcccaaat cttgtgactc cggcggagga gggagcggcg gaggtggctc cggaggtggc    720
ggagcaccta cttcaagttc tacaaagaaa acacagctac aactggagca tttactgctg    780
gatttacaga tgattttgaa tggaattaat aattacaaga atcccaaact caccaggatg    840
ctcacattta agttttacat gcccaagaag gccacagaac tgaaacatct tcagtgtcta    900
gaagaagaac tcaaacctct ggaggaagtg ctaaatttag ctcaaagcaa aaactttcac    960
ttaagaccca gggacttaat cagcaatatc aacgtaatag ttctggaact aaagggatct   1020
gaaacaacat tcatgtgtga atatgctgat gagacagcaa ccattgtaga atttctgaac   1080
agatggatta cctttgccca aagcatcatc tcaacactga cttccggcgg aggaggatcc   1140
ggcggaggtg gctctggcgg tggcggagaa gtgcagctgg tggagtctgg aggaggcttg   1200
gtccagcctg gcgggtccct gcggctctcc tgtgcagcct ccggattcac atttagcaac   1260
tattggatga actgggtgcg gcaggctcct ggaaagggcc tcgagtgggt ggccgagatc   1320
agattgaaat ccaataactt cggaagatat tacgctgcaa gcgtgaaggg ccggttcacc   1380
atcagcagag atgattccaa gaacacgctg tacctgcaga tgaacagcct gaagaccgag   1440
gatacggccg tgtattactg taccacatac ggcaactacg ttgggcacta cttcgaccac   1500
tggggccaag ggaccaccgt caccgtctcc agtgctagca ccaagggccc atcggtcttc   1560
cccctggcac cctcctccaa gagcacctct gggggcacag cggccctggg ctgcctggtc   1620
aaggactact tccccgaacc ggtgacggtg tcgtggaact caggcgccct gaccagcggc   1680
gtgcacacct tcccggctgt cctacagtcc tcaggactct actccctcag cagcgtggtg   1740
accgtgccct ccagcagctt gggcacccag acctacatct gcaacgtgaa tcacaagccc   1800
agcaacacca aggtggataa gaaagttgag cccaaatctt gtgactga                1848
```

<210> SEQ ID NO 257
<211> LENGTH: 122
<212> TYPE: PRT
<213> ORGANISM: Artificial Sequence
<220> FEATURE:
<223> OTHER INFORMATION: MHLG1; VH

<400> SEQUENCE: 257

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Ala Glu Ile Arg Leu Lys Ser Asn Asn Phe Gly Arg Tyr Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Tyr Gly Asn Tyr Val Gly His Tyr Phe Asp His Trp
            100                 105                 110

Gly Gln Gly Thr Thr Val Thr Val Ser Ser
        115                 120
```

<210> SEQ ID NO 258
<211> LENGTH: 366

<212> TYPE: DNA
<213> ORGANISM: Artificial Sequence
<220> FEATURE:
<223> OTHER INFORMATION: MHLG1; VH

<400> SEQUENCE: 258
gaagtgcagc tggtggagtc tggaggaggc ttggtcaagc ctggcgggtc cctgcggctc 60
tcctgtgcag cctccggatt cacatttagc aactattgga tgaactgggt gcggcaggct 120
cctggaaagg gcctcgagtg ggtggccgag atcagattga aatccaataa cttcggaaga 180
tattacgctg caagcgtgaa gggccggttc accatcagca gagatgattc caagaacacg 240
ctgtacctgc agatgaacag cctgaagacc gaggatacgg ccgtgtatta ctgtaccaca 300
tacggcaact acgttgggca ctacttcgac cactggggcc aagggaccac cgtcaccgtc 360
tccagt 366

<210> SEQ ID NO 259
<211> LENGTH: 109
<212> TYPE: PRT
<213> ORGANISM: Artificial Sequence
<220> FEATURE:
<223> OTHER INFORMATION: MHLG KV9; VL

<400> SEQUENCE: 259

Asp Ile Gln Leu Thr Gln Ser Pro Ser Phe Leu Ser Ala Ser Val Gly
1 5 10 15

Asp Arg Val Thr Ile Thr Cys Lys Ala Ser Gln Asn Val Asp Thr Asn
20 25 30

Val Ala Trp Tyr Gln Gln Lys Pro Gly Gln Ala Pro Arg Pro Leu Ile
35 40 45

Tyr Ser Ala Ser Tyr Arg Tyr Thr Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Tyr Asn Ser Tyr Pro Leu
85 90 95

Thr Phe Gly Gly Gly Thr Lys Val Glu Ile Lys Arg Thr
100 105

<210> SEQ ID NO 260
<211> LENGTH: 327
<212> TYPE: DNA
<213> ORGANISM: Artificial Sequence
<220> FEATURE:
<223> OTHER INFORMATION: MHLG KV9; VL

<400> SEQUENCE: 260
gatatccagt tgacccagtc tccatccttc ctgtctgcat ctgtgggcga ccgggtcacc 60
atcacctgca aggccagtca gaatgtggat actaacgtgg cttggtacca gcagaagcca 120
gggcaggcac ctaggcctct gatctattcg gcatcctacc ggtacactgg cgtcccatca 180
aggttcagcg gcagtggatc cgggacagag ttcactctca caatctcaag cctgcaacct 240
gaagatttcg caacttacta ctgtcaacag tacaatagtt accctctgac gttcggcgga 300
ggtaccaagg tggagatcaa gcgtacg 327

<210> SEQ ID NO 261
<211> LENGTH: 122
<212> TYPE: PRT
<213> ORGANISM: Artificial Sequence

<220> FEATURE:
<223> OTHER INFORMATION: MHLG; VH

<400> SEQUENCE: 261

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Trp Met Asn Trp Val Arg Gln Ala Pro Gly Lys Gly Leu Glu Trp Val
35 40 45

Ala Glu Ile Arg Leu Lys Ser Asn Asn Phe Gly Arg Tyr Tyr Ala Ala
50 55 60

Ser Val Lys Gly Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Thr Thr Tyr Gly Asn Tyr Val Gly His Tyr Phe Asp His Trp
100 105 110

Gly Gln Gly Thr Thr Val Thr Val Ser Ser
115 120

<210> SEQ ID NO 262
<211> LENGTH: 366
<212> TYPE: DNA
<213> ORGANISM: Artificial Sequence
<220> FEATURE:
<223> OTHER INFORMATION: MHLG; VH

<400> SEQUENCE: 262
gaagtgcagc tggtggagtc tggaggaggc ttggtccagc ctggcgggtc cctgcggctc 60
tcctgtgcag cctccggatt cacatttagc aactattgga tgaactgggt gcggcaggct 120
cctggaaagg gcctcgagtg ggtggccgag atcagattga aatccaataa cttcggaaga 180
tattacgctg caagcgtgaa gggccggttc accatcagca gagatgattc caagaacacg 240
ctgtacctgc agatgaacag cctgaagacc gaggatacgg ccgtgtatta ctgtaccaca 300
tacggcaact acgttgggca ctacttcgac cactggggcc aagggaccac cgtcaccgtc 360
tccagt 366

<210> SEQ ID NO 263
<211> LENGTH: 214
<212> TYPE: PRT
<213> ORGANISM: Artificial Sequence
<220> FEATURE:
<223> OTHER INFORMATION: KV1 light chain

<400> SEQUENCE: 263

Asp Ile Gln Leu Thr Gln Ser Pro Ser Phe Leu Ser Ala Ser Val Gly
1 5 10 15

Asp Arg Val Thr Ile Thr Cys Arg Ala Ser Gln Asn Val Asp Thr Asn
20 25 30

Leu Ala Trp Tyr Gln Gln Lys Pro Gly Lys Ala Pro Lys Leu Leu Ile
35 40 45

Tyr Ser Ala Ser Tyr Arg Tyr Thr Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Tyr Asn Ser Tyr Pro Leu

```
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 264
<211> LENGTH: 645
<212> TYPE: DNA
<213> ORGANISM: Artificial Sequence
<220> FEATURE:
<223> OTHER INFORMATION: KV1 light chain

<400> SEQUENCE: 264

```
gatatccagt tgacccagtc tccatccttc ctgtctgcat ctgtgggcga ccgggtcacc     60

atcacctgca gggccagtca gaatgtggat actaacttag cttggtacca gcagaagcca    120

gggaaagcac ctaagctcct gatctattcg gcatcctacc gttacactgg cgtcccatca    180

aggttcagcg gcagtggatc cgggacagag ttcactctca caatctcaag cctgcaacct    240

gaagatttcg caacttacta ctgtcaacag tacaatagtt accctctgac gttcggcgga    300

ggtaccaagg tggagatcaa gcgtacggtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645
```

<210> SEQ ID NO 265
<211> LENGTH: 214
<212> TYPE: PRT
<213> ORGANISM: Artificial Sequence
<220> FEATURE:
<223> OTHER INFORMATION: KV7 light chain

<400> SEQUENCE: 265

```
Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Pro Leu Ile
        35                  40                  45

Tyr Ser Ala Ser Tyr Arg Tyr Thr Gly Val Pro Ser Arg Phe Ser Gly
    50                  55                  60
```

```
Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 266
<211> LENGTH: 645
<212> TYPE: DNA
<213> ORGANISM: Artificial Sequence
<220> FEATURE:
<223> OTHER INFORMATION: KV7 light chain

<400> SEQUENCE: 266

gatatccagt tgacccagtc tccatccttc ctgtctgcat ctgtgggcga ccgggtcacc      60

atcacctgca aggccagtca gaatgtggat actaacgtgg cttggtacca gcagaagcca     120

gggaaagcac ctaagcctct gatctattcg gcatcctacc ggtacactgg cgtcccatca     180

aggttcagcg gcagtggatc cgggacagag ttcactctca caatctcaag cctgcaacct     240

gaagatttcg caacttacta ctgtcaacag tacaatagtt accctctgac gttcggcgga     300

ggtaccaagg tggagatcaa gcgtacggtg gctgcaccat ctgtcttcat cttcccgcca     360

tctgatgagc agttgaaatc tggaactgcc tctgttgtgt gcctgctgaa taacttctat     420

cccagagagg ccaaagtaca gtggaaggtg gataacgccc tccaatcggg taactcccag     480

gagagtgtca cagagcagga cagcaaggac agcacctaca gcctcagcag caccctgacg     540

ctgagcaaag cagactacga gaaacacaaa gtctacgcct gcgaagtcac ccatcagggc     600

ctgagctcgc ccgtcacaaa gagcttcaac aggggagagt gttag                     645


<210> SEQ ID NO 267
<211> LENGTH: 107
<212> TYPE: PRT
<213> ORGANISM: Mus musculus

<400> SEQUENCE: 267

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Glu Pro Leu Leu
        35                  40                  45
```

Phe Ser Ala Ser Tyr Arg Tyr Thr Gly Val Pro Asp Arg Phe Thr Gly
50 55 60

Ser Gly Ser Gly Thr Asp Phe Thr Leu Thr Ile Ser Asn Val Gln Ser
65 70 75 80

Glu Asp Leu Ala Glu Tyr Phe Cys Gln Gln Tyr Asn Ser Tyr Pro Leu
85 90 95

Thr Phe Gly Gly Gly Thr Lys Leu Glu Ile Lys
100 105

<210> SEQ ID NO 268
<211> LENGTH: 122
<212> TYPE: PRT
<213> ORGANISM: Mus musculus

<400> SEQUENCE: 268

Gln Val Lys Leu Gln Gln Ser Gly Gly Gly Leu Val Gln Pro Gly Gly
1 5 10 15

Ser Met Lys Leu Ser Cys Val Val Ser Gly Phe Thr Phe Ser Asn Tyr
20 25 30

Trp Met Asn Trp Val Arg Gln Ser Pro Glu Lys Gly Leu Glu Trp Ile
35 40 45

Ala Glu Ile Arg Leu Lys Ser Asn Asn Phe Gly Arg Tyr Tyr Ala Glu
50 55 60

Ser Val Lys Gly Arg Phe Thr Ile Ser Arg Asp Asp Ser Lys Ser Ser
65 70 75 80

Ala Tyr Leu Gln Met Ile Asn Leu Arg Ala Glu Asp Thr Gly Ile Tyr
85 90 95

Tyr Cys Thr Ser Tyr Gly Asn Tyr Val Gly His Tyr Phe Asp His Trp
100 105 110

Gly Gln Gly Thr Thr Val Thr Val Ser Ser
115 120

<210> SEQ ID NO 269
<211> LENGTH: 109
<212> TYPE: PRT
<213> ORGANISM: Artificial Sequence
<220> FEATURE:
<223> OTHER INFORMATION: KV1; VL

<400> SEQUENCE: 269

Asp Ile Gln Leu Thr Gln Ser Pro Ser Phe Leu Ser Ala Ser Val Gly
1 5 10 15

Asp Arg Val Thr Ile Thr Cys Arg Ala Ser Gln Asn Val Asp Thr Asn
20 25 30

Leu Ala Trp Tyr Gln Gln Lys Pro Gly Lys Ala Pro Lys Leu Leu Ile
35 40 45

Tyr Ser Ala Ser Tyr Arg Tyr Thr Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Tyr Asn Ser Tyr Pro Leu
85 90 95

Thr Phe Gly Gly Gly Thr Lys Val Glu Ile Lys Arg Thr
100 105

<210> SEQ ID NO 270
<211> LENGTH: 327

<212> TYPE: DNA
<213> ORGANISM: Artificial Sequence
<220> FEATURE:
<223> OTHER INFORMATION: KV1; VL

<400> SEQUENCE: 270
gatatccagt tgacccagtc tccatccttc ctgtctgcat ctgtgggcga ccgggtcacc 60
atcacctgca gggccagtca gaatgtggat actaacttag cttggtacca gcagaagcca 120
gggaaagcac ctaagctcct gatctattcg gcatcctacc gttacactgg cgtcccatca 180
aggttcagcg gcagtggatc cgggacagag ttcactctca caatctcaag cctgcaacct 240
gaagatttcg caacttacta ctgtcaacag tacaatagtt accctctgac gttcggcgga 300
ggtaccaagg tggagatcaa gcgtacg 327

<210> SEQ ID NO 271
<211> LENGTH: 109
<212> TYPE: PRT
<213> ORGANISM: Artificial Sequence
<220> FEATURE:
<223> OTHER INFORMATION: KV7; VL

<400> SEQUENCE: 271

Asp Ile Gln Leu Thr Gln Ser Pro Ser Phe Leu Ser Ala Ser Val Gly
1 5 10 15

Asp Arg Val Thr Ile Thr Cys Lys Ala Ser Gln Asn Val Asp Thr Asn
20 25 30

Val Ala Trp Tyr Gln Gln Lys Pro Gly Lys Ala Pro Lys Pro Leu Ile
35 40 45

Tyr Ser Ala Ser Tyr Arg Tyr Thr Gly Val Pro Ser Arg Phe Ser Gly
50 55 60

Ser Gly Ser Gly Thr Glu Phe Thr Leu Thr Ile Ser Ser Leu Gln Pro
65 70 75 80

Glu Asp Phe Ala Thr Tyr Tyr Cys Gln Gln Tyr Asn Ser Tyr Pro Leu
85 90 95

Thr Phe Gly Gly Gly Thr Lys Val Glu Ile Lys Arg Thr
100 105

<210> SEQ ID NO 272
<211> LENGTH: 327
<212> TYPE: DNA
<213> ORGANISM: Artificial Sequence
<220> FEATURE:
<223> OTHER INFORMATION: KV7; VL

<400> SEQUENCE: 272
gatatccagt tgacccagtc tccatccttc ctgtctgcat ctgtgggcga ccgggtcacc 60
atcacctgca aggccagtca gaatgtggat actaacgtgg cttggtacca gcagaagcca 120
gggaaagcac ctaagcctct gatctattcg gcatcctacc ggtacactgg cgtcccatca 180
aggttcagcg gcagtggatc cgggacagag ttcactctca caatctcaag cctgcaacct 240
gaagatttcg caacttacta ctgtcaacag tacaatagtt accctctgac gttcggcgga 300
ggtaccaagg tggagatcaa gcgtacg 327

<210> SEQ ID NO 273
<211> LENGTH: 19
<212> TYPE: PRT
<213> ORGANISM: Artificial Sequence
<220> FEATURE:
<223> OTHER INFORMATION: leader sequence

<400> SEQUENCE: 273

Met Asp Trp Thr Trp Arg Ile Leu Phe Leu Val Ala Ala Ala Thr Gly
1 5 10 15

Ala His Ser

<210> SEQ ID NO 274
<211> LENGTH: 57
<212> TYPE: DNA
<213> ORGANISM: Artificial Sequence
<220> FEATURE:
<223> OTHER INFORMATION: leader sequence

<400> SEQUENCE: 274
atggactgga cctggagaat cctcttcttg gtggcagcag ccacaggagc ccactcc 57

<210> SEQ ID NO 275
<211> LENGTH: 57
<212> TYPE: DNA
<213> ORGANISM: Artificial Sequence
<220> FEATURE:
<223> OTHER INFORMATION: leader sequence

<400> SEQUENCE: 275
atggactgga cctggaggat cctcttcttg gtggcagcag ccacaggagc ccactcc 57

<210> SEQ ID NO 276
<211> LENGTH: 22
<212> TYPE: PRT
<213> ORGANISM: Artificial Sequence
<220> FEATURE:
<223> OTHER INFORMATION: leader sequence

<400> SEQUENCE: 276

Met Asp Met Arg Val Pro Ala Gln Leu Leu Gly Leu Leu Leu Leu Trp
1 5 10 15

Phe Pro Gly Ala Arg Cys
20

<210> SEQ ID NO 277
<211> LENGTH: 66
<212> TYPE: DNA
<213> ORGANISM: Artificial Sequence
<220> FEATURE:
<223> OTHER INFORMATION: leader sequence

<400> SEQUENCE: 277
atggacatga gggtccccgc tcagctcctg ggcctcctgc tgctctggtt cccaggtgcc 60
aggtgt 66

<210> SEQ ID NO 278
<211> LENGTH: 19
<212> TYPE: PRT
<213> ORGANISM: Artificial Sequence
<220> FEATURE:
<223> OTHER INFORMATION: leader sequence

<400> SEQUENCE: 278

Met Gly Trp Ser Cys Ile Ile Leu Phe Leu Val Ala Thr Ala Thr Gly
1 5 10 15

Val His Ser

<210> SEQ ID NO 279

-continued

<211> LENGTH: 57
<212> TYPE: DNA
<213> ORGANISM: Artificial Sequence
<220> FEATURE:
<223> OTHER INFORMATION: leader sequence

<400> SEQUENCE: 279
atgggatgga gctgtatcat cctcttcttg gtagcaacag ctaccggtgt gcattcc 57

<210> SEQ ID NO 280
<211> LENGTH: 57
<212> TYPE: DNA
<213> ORGANISM: Artificial Sequence
<220> FEATURE:
<223> OTHER INFORMATION: leader sequence

<400> SEQUENCE: 280
atgggctggt cctgcatcat cctgtttctg gtggctaccg ccactggagt gcattcc 57

<210> SEQ ID NO 281
<211> LENGTH: 57
<212> TYPE: DNA
<213> ORGANISM: Artificial Sequence
<220> FEATURE:
<223> OTHER INFORMATION: leader sequence

<400> SEQUENCE: 281
atgggctggt cctgcatcat cctgtttctg gtcgccacag ccaccggcgt gcactct 57